US012329768B2

(12) United States Patent
Aldous et al.

(10) Patent No.: US 12,329,768 B2
(45) Date of Patent: *Jun. 17, 2025

(54) COMPOSITIONS AND DOSAGE FORMS FOR TREATMENT OF HPV INFECTION AND HPV-INDUCED NEOPLASIA

(71) Applicant: Antiva Biosciences, Inc., Redwood City, CA (US)

(72) Inventors: Barry Aldous, Brisbane, CA (US); Ramakrishna Gadiraju, Brisbane, CA (US); Ankush Argade, Sunnyvale, CA (US); Zhengle Zhao, Shanghai (CN); Siyi Jiang, Shanghai (CN); Runyan Li, Shanghai (CN); Chao Liu, Shanghai (CN); Minyan Liu, Shanghai (CN)

(73) Assignee: Antiva Biosciences, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/385,766

(22) Filed: Oct. 31, 2023

(65) Prior Publication Data

US 2024/0150381 A1  May 9, 2024

Related U.S. Application Data

(63) Continuation of application No. PCT/US2023/028218, filed on Jul. 20, 2023.

(60) Provisional application No. 63/412,143, filed on Sep. 30, 2022, provisional application No. 63/400,661, filed on Aug. 24, 2022, provisional application No. 63/391,283, filed on Jul. 21, 2022.

(30) Foreign Application Priority Data

Sep. 30, 2022 (CN) .......................... 202211206517.7

(51) Int. Cl.
| | |
|---|---|
| *C07F 9/36* | (2006.01) |
| *A61K 9/00* | (2006.01) |
| *A61K 9/06* | (2006.01) |
| *A61K 9/14* | (2006.01) |
| *A61K 9/20* | (2006.01) |
| *A61K 31/675* | (2006.01) |
| *A61K 47/12* | (2006.01) |
| *A61K 47/14* | (2017.01) |
| *A61K 47/18* | (2017.01) |
| *A61K 47/32* | (2006.01) |
| *A61K 47/36* | (2006.01) |
| *A61K 47/38* | (2006.01) |
| *A61K 47/44* | (2017.01) |
| *A61P 15/02* | (2006.01) |
| *A61P 35/00* | (2006.01) |
| *A61P 43/00* | (2006.01) |
| *C07F 9/6561* | (2006.01) |

(52) U.S. Cl.
CPC .......... *A61K 31/675* (2013.01); *A61K 9/0036* (2013.01); *A61K 9/06* (2013.01); *A61K 9/145* (2013.01); *A61K 9/146* (2013.01); *A61K 9/2013* (2013.01); *A61K 9/2018* (2013.01); *A61K 9/2027* (2013.01); *A61K 9/2054* (2013.01); *A61K 9/2059* (2013.01); *A61K 47/12* (2013.01); *A61K 47/14* (2013.01); *A61K 47/183* (2013.01); *A61K 47/32* (2013.01); *A61K 47/36* (2013.01); *A61K 47/38* (2013.01); *A61K 47/44* (2013.01); *A61P 15/02* (2018.01); *A61P 35/00* (2018.01); *A61P 43/00* (2018.01); *C07F 9/36* (2013.01); *C07F 9/65616* (2013.01)

(58) Field of Classification Search
CPC .................................................. C07F 9/65616
See application file for complete search history.

(56) References Cited

U.S. PATENT DOCUMENTS

| | | |
|---|---|---|
| 4,409,239 A | 10/1983 | Yu |
| 4,410,545 A | 10/1983 | Yu et al. |
| 4,522,811 A | 6/1985 | Eppstein et al. |
| 4,659,825 A | 4/1987 | Holy et al. |
| 4,724,233 A | 2/1988 | De Clercq et al. |
| 4,808,716 A | 2/1989 | Holy et al. |
| 4,921,951 A | 5/1990 | Shuto et al. |
| 5,484,809 A | 1/1996 | Hostetler et al. |
| 5,532,225 A | 7/1996 | Reist et al. |
| 5,641,763 A | 6/1997 | Holy et al. |
| 5,650,510 A | 7/1997 | Webb, II et al. |
| 5,656,745 A | 8/1997 | Bischofberger et al. |
| 5,663,159 A | 9/1997 | Starrett, Jr. et al. |

(Continued)

FOREIGN PATENT DOCUMENTS

| | | |
|---|---|---|
| CN | 1034365 C | 3/1997 |
| CN | 1426418 A | 6/2003 |

(Continued)

OTHER PUBLICATIONS

Korn et al, Compound selection for development—is salt formation the ultimate answer? Experiences with an extended concept of the "100 mg approach", 2014, European Journal of Pharmaceutical Sciences, vol. 57, p. 257-263. (Year: 2014).*

(Continued)

*Primary Examiner* — Kamal A Saeed
*Assistant Examiner* — Karen Cheng
(74) *Attorney, Agent, or Firm* — McNeill PLLC

(57) ABSTRACT

A pharmaceutically acceptable salt of an acyclic nucleotide phosphoramidate to treat HPV and related conditions including neoplasia, as well as pharmaceutical compositions, morphic forms and dosage forms thereof.

10 Claims, 126 Drawing Sheets

(56) References Cited

U.S. PATENT DOCUMENTS

| | | |
|---|---|---|
| 5,696,277 A | 12/1997 | Hostetler et al. |
| 5,717,095 A | 2/1998 | Arimilli et al. |
| 5,726,174 A | 3/1998 | Kim et al. |
| 5,733,896 A | 3/1998 | Holy et al. |
| 5,798,340 A | 8/1998 | Bischofberger et al. |
| 5,817,647 A | 10/1998 | Casara et al. |
| 5,827,831 A | 10/1998 | Hostetler et al. |
| 5,840,716 A | 11/1998 | Ubasawa et al. |
| 5,854,228 A | 12/1998 | Webb, II et al. |
| 5,869,467 A | 2/1999 | Holy et al. |
| 5,877,166 A | 3/1999 | Reist et al. |
| 5,886,179 A | 3/1999 | Arimilli et al. |
| 5,922,696 A | 7/1999 | Casara et al. |
| 5,955,610 A | 9/1999 | Nguyen-Ba et al. |
| 5,977,061 A | 11/1999 | Holy et al. |
| 6,005,107 A | 12/1999 | Nguyen-Ba et al. |
| 6,037,335 A | 3/2000 | Takashima et al. |
| 6,057,305 A | 5/2000 | Holy et al. |
| 6,127,540 A | 10/2000 | Nquyen-Ba et al. |
| 6,197,775 B1 | 3/2001 | Ubasawa et al. |
| 6,225,460 B1 | 5/2001 | Bischofberger et al. |
| 6,444,656 B1 | 9/2002 | Nguyen-Ba et al. |
| 6,448,392 B1 | 9/2002 | Hostetler et al. |
| 6,599,887 B2 | 7/2003 | Hostetler et al. |
| 6,653,296 B1 | 11/2003 | Holy et al. |
| 6,686,462 B2 | 2/2004 | Rosowsky et al. |
| 6,716,825 B2 | 4/2004 | Hostetler et al. |
| 6,767,900 B2 | 7/2004 | Ubasawa et al. |
| 7,034,014 B2 | 4/2006 | Hostetler et al. |
| 7,094,772 B2 | 8/2006 | Hostetler et al. |
| 7,098,197 B2 | 8/2006 | Hostetler et al. |
| 7,452,898 B2 | 11/2008 | Hostetler et al. |
| 7,452,901 B2 | 11/2008 | Boojamra et al. |
| 7,517,858 B1 | 4/2009 | Hostetler et al. |
| 7,652,001 B2 | 1/2010 | Hostetler et al. |
| 7,687,480 B2 | 3/2010 | Hostetler et al. |
| 7,749,983 B2 | 7/2010 | Hostetler et al. |
| 7,790,703 B2 | 9/2010 | Hostetler et al. |
| 7,994,143 B2 | 8/2011 | Hostetler et al. |
| 8,008,308 B2 | 8/2011 | Hostetler et al. |
| 8,088,754 B2 | 1/2012 | Cheng et al. |
| 8,101,745 B2 | 1/2012 | Hostetler et al. |
| 8,163,718 B2 | 4/2012 | Birkus et al. |
| 8,193,167 B2 | 6/2012 | Hostetler et al. |
| 8,309,565 B2 | 11/2012 | Hostetler et al. |
| 8,318,700 B2 | 11/2012 | Hostetler et al. |
| 8,569,321 B2 | 10/2013 | Ware et al. |
| 8,609,627 B2 | 12/2013 | Cho et al. |
| 8,614,200 B2 | 12/2013 | Painter et al. |
| 8,710,030 B2 | 4/2014 | Hostetler et al. |
| 8,754,065 B2 | 6/2014 | Liu et al. |
| 8,835,630 B1 | 9/2014 | Hostetler et al. |
| 8,846,643 B2 | 9/2014 | Hostetler et al. |
| 8,889,658 B2 | 11/2014 | Hostetler et al. |
| 8,962,829 B1 | 2/2015 | Ware, Jr. et al. |
| 8,993,542 B2 | 3/2015 | Lanier et al. |
| 9,006,218 B2 | 4/2015 | Almond et al. |
| 9,095,599 B2 | 8/2015 | Chang et al. |
| 9,156,867 B2 | 10/2015 | Hostetler et al. |
| 9,156,874 B2 | 10/2015 | Chang et al. |
| 9,206,208 B2 | 12/2015 | Hostetler et al. |
| 9,387,217 B2 | 7/2016 | Hostetler et al. |
| 9,475,832 B2 | 10/2016 | Hostetler et al. |
| 9,493,493 B2 | 11/2016 | Hostetler et al. |
| 9,629,860 B2 | 4/2017 | Hostetler et al. |
| 9,775,852 B2 | 10/2017 | Hostetler et al. |
| 9,801,884 B2 | 10/2017 | Hostetler et al. |
| 10,213,430 B2 | 2/2019 | Hostetler et al. |
| 10,377,782 B2 | 8/2019 | Hostetler et al. |
| 10,702,532 B2 | 7/2020 | Hostetler et al. |
| 11,014,950 B2 | 5/2021 | Hostetler et al. |
| 11,344,555 B2 | 5/2022 | Hostetler et al. |
| 2003/0109498 A1 | 6/2003 | Yuasa et al. |
| 2004/0019232 A1 | 1/2004 | Hostetler et al. |
| 2004/0023921 A1 | 2/2004 | Hong et al. |
| 2004/0023928 A1 | 2/2004 | Colacino |
| 2004/0127735 A1 | 7/2004 | Hostetler et al. |
| 2005/0176673 A1 | 8/2005 | Hostetler et al. |
| 2005/0182019 A1 | 8/2005 | Hostetler et al. |
| 2005/0192241 A1 | 9/2005 | Hostetler et al. |
| 2005/0192246 A1 | 9/2005 | Hostetler et al. |
| 2006/0281706 A1 | 12/2006 | Hostetler et al. |
| 2007/0003608 A1 | 1/2007 | Almond et al. |
| 2007/0161602 A1 | 7/2007 | Hostetler et al. |
| 2008/0103115 A1 | 5/2008 | Hostetler et al. |
| 2008/0221061 A1 | 9/2008 | Hostetler et al. |
| 2009/0105513 A1 | 4/2009 | Smith, Jr. et al. |
| 2009/0149400 A1 | 6/2009 | Cheng et al. |
| 2009/0232768 A1 | 9/2009 | Birkus et al. |
| 2009/0291922 A1 | 11/2009 | Cheng et al. |
| 2010/0173870 A1 | 7/2010 | Hostetler et al. |
| 2010/0273742 A1 | 10/2010 | Hostetler et al. |
| 2012/0058975 A1 | 3/2012 | Hostetler et al. |
| 2012/0116067 A1 | 5/2012 | Meier et al. |
| 2012/0122818 A1 | 5/2012 | Hostetler et al. |
| 2012/0164104 A1 | 6/2012 | Lanier et al. |
| 2013/0029940 A1 | 1/2013 | Hostetler et al. |
| 2013/0045950 A1 | 2/2013 | Hostetler et al. |
| 2014/0045794 A1 | 2/2014 | Hostetler et al. |
| 2014/0274959 A1 | 9/2014 | Hostetler et al. |
| 2014/0364397 A1 | 12/2014 | Hostetler et al. |
| 2015/0011488 A1 | 1/2015 | Preston et al. |
| 2015/0051174 A1 | 2/2015 | Hostetler et al. |
| 2015/0080344 A1 | 3/2015 | Hostetler et al. |
| 2015/0141375 A1 | 5/2015 | Painter et al. |
| 2015/0141575 A1 | 5/2015 | Kataoka et al. |
| 2016/0015726 A1 | 1/2016 | Hostetler et al. |
| 2016/0303147 A1 | 10/2016 | Painter et al. |
| 2017/0002033 A1 | 1/2017 | Hostetler et al. |
| 2017/0096441 A1 | 4/2017 | Hostetler et al. |
| 2017/0189430 A1 | 7/2017 | Hostetler et al. |
| 2017/0304330 A1 | 10/2017 | Hostetler et al. |
| 2018/0015095 A1 | 1/2018 | Hostetler et al. |
| 2018/0064737 A1 | 3/2018 | Hostetler et al. |
| 2018/0071323 A1 | 3/2018 | Hostetler et al. |
| 2019/0388442 A1 | 12/2019 | Hostetler et al. |
| 2020/0316076 A1 | 10/2020 | Hostetler et al. |
| 2021/0246153 A1 | 12/2021 | Hostetler et al. |
| 2022/0062289 A1 | 3/2022 | Hostetler et al. |
| 2022/0072004 A1 | 3/2022 | Hostetler et al. |
| 2022/0395510 A1 | 12/2022 | Hostetler et al. |

FOREIGN PATENT DOCUMENTS

| | | |
|---|---|---|
| CN | 1805966 A | 7/2006 |
| CN | 101089004 A | 12/2007 |
| CN | 102532199 A | 7/2012 |
| CN | 103435672 A | 12/2013 |
| CN | 103980318 A | 8/2014 |
| CN | 106188192 A | 12/2016 |
| CN | 107286190 A | 10/2017 |
| CS | 263953 B1 | 5/1989 |
| CS | 263955 B1 | 5/1989 |
| CS | 263956 B1 | 5/1989 |
| CZ | 292199 | 8/2003 |
| EP | 0262876 A2 | 9/1987 |
| EP | 0481214 A1 | 6/1998 |
| EP | 0481214 B1 | 6/1998 |
| RU | 2187509 C | 8/2002 |
| WO | WO 1991/19726 A | 12/1991 |
| WO | WO 1992/03462 A1 | 3/1992 |
| WO | WO 1992/07065 A1 | 4/1992 |
| WO | WO 1993/15187 A1 | 8/1993 |
| WO | WO 1993/019075 A1 | 9/1993 |
| WO | WO 1995/032984 A1 | 12/1995 |
| WO | WO 1996/005309 A1 | 2/1996 |
| WO | WO 1996/039831 A1 | 12/1996 |
| WO | WO 1998/038202 A1 | 9/1998 |
| WO | WO 1998/042351 A1 | 10/1998 |
| WO | WO 1999/062921 A1 | 12/1999 |
| WO | WO 2000/029414 A1 | 5/2000 |
| WO | WO 2001/039724 A1 | 6/2001 |
| WO | WO 2001/064693 A1 | 9/2001 |
| WO | WO 2002/008241 A2 | 1/2002 |

(56) References Cited

FOREIGN PATENT DOCUMENTS

| | | |
|---|---|---|
| WO | WO 2002/057288 A1 | 7/2002 |
| WO | WO 2002/087465 A2 | 11/2002 |
| WO | WO 2003/002580 A1 | 1/2003 |
| WO | WO 2003/050129 A1 | 6/2003 |
| WO | WO 2003/090691 A1 | 11/2003 |
| WO | WO 2003/099294 A1 | 12/2003 |
| WO | WO 2004/096235 A1 | 11/2004 |
| WO | WO 2004/096286 A1 | 11/2004 |
| WO | WO 2004/111064 A1 | 12/2004 |
| WO | WO 2005/066189 A1 | 7/2005 |
| WO | WO 2005/087788 A1 | 9/2005 |
| WO | WO 2006/066074 A1 | 6/2006 |
| WO | WO 2006/076015 A1 | 7/2006 |
| WO | WO 2006/114064 A1 | 11/2006 |
| WO | WO 2006/114065 A1 | 11/2006 |
| WO | WO 2007/002808 A1 | 1/2007 |
| WO | WO 2007/002912 A1 | 4/2007 |
| WO | WO 2007/130783 A1 | 11/2007 |
| WO | WO 2008/104408 A1 | 9/2008 |
| WO | WO 2008/133966 A1 | 11/2008 |
| WO | 20090105513 | 2/2009 |
| WO | WO 2009/094190 A1 | 7/2009 |
| WO | WO 2009/105513 A2 | 8/2009 |
| WO | WO 2010/091386 A1 | 8/2010 |
| WO | WO 2010/135520 A1 | 11/2010 |
| WO | WO 2011/011519 A1 | 1/2011 |
| WO | WO 2011/011710 A1 | 1/2011 |
| WO | WO 2011/017253 A1 | 2/2011 |
| WO | WO 2011/053812 A1 | 5/2011 |
| WO | WO 2011/130557 A1 | 10/2011 |
| WO | WO 2018/126994 A1 | 7/2012 |
| WO | WO 2014/143643 A1 | 9/2014 |
| WO | WO 2016/044281 A1 | 3/2016 |
| WO | WO 2016/195522 A1 | 12/2016 |
| WO | WO 2017/048956 A1 | 3/2017 |
| WO | WO 2018/082503 A1 | 5/2018 |

OTHER PUBLICATIONS

U.S. Appl. No. 18/385,771, Aldous et al., filed Oct. 31, 2023.
U.S. Appl. No. 18/385,778, Aldous et al., filed Oct. 31, 2023.
Aldern et al., "Update and Metabolism of Cidofovir and Oleyloxyethyl-cidofovir in Human Papillomavirus Positive ME-180 Human Cervical Cancer Cells" Abstract 173 Antiviral Res 74(3):A83, 2007.
Australia New Zealand Clinical Trial Registry, "Part A: A Study of ABI-2280 Vaginal Tablet in Participants with Cervical Intraepithelial Neoplasia" Published Aug. 2, 2022.
Australia New Zealand Clinical Trial Registry, "A single and multiple dose escalation study in healthy participants to evaluate safety, tolerability, and pharmacokinetics of ABI-2280 vaginal gel and tablets" Nov. 11, 2021.
Balzarini et al., "9-[(2R5)-3-Fluoro-2-phosphonylmethoxypropyl] derivatives of purines: A class of highly selective antiretroviral agents in vitro and in vivo." Proc. Natl. Acad. Sci., vol. 88, pp. 4961-4965, Jun. 1991.
Beadle et al., "Alkoxyalkyl esters of cidofovir and cyclic cidofovir exhibit multiple-log enhancement of antiviral activity against cytomegalovirus and herpesvirus replication in vitro," Antimicrob Agents Chemother 46(8):2381-2386, Aug. 2002.
Beadle et al., "Synthesis and Antiviral Evaluation of Alkoxyalkyl Derivatives of 9-(S)-(3-Hydroxy-2-phosphonomethoxypropyl)adenine against Cytomegalovirus", Journal of Medicinal Chemistry, 49:2010-2015, Feb. 18, 2006.
Benzaria et al., "Synthesis, in vitro antiviral evaluation, and stability studies of bis(S-acyl-2-thioethyl) ester derivatives of 9-[2-(phosphonomethoxy)ethyl]adenine (PMEA) as potential PMEA prodrugs with improved oral bioavailability.," J. Med. Chem. 39(25):4958-4965, Dec. 6, 1996.
Berge et al., "Pharmaceutical Salts", Journal of Pharmaceutical Sciences, 66: 1-19, Jan. 1977.
Bronson et al., Nucleotide Analogues as Antiviral Agents, Chapter 5, p. 72-87, ACS Symposium Series, vol. 401, 1989.
Brown, N.A., "Progress towards improving antiviral therapy for hepatitis C with hepatitis C virus polymerase inhibitors. Part 1: Nucleoside analogues," Expert Opinion on investigational Drugs 18(6):709-725, 2009.
Buller et al., "Efficacy of oral active ether lipid analogs of cidofovir in a lethal mousepox model", Virology, 318(2), 474-481, Jan. 20, 2004.
Callebaut et al., "In Vitro Virology Profile of Tenofovir Alafenamide, a Novel Oral Prodrug of Tenofovir with Improved Antiviral Activity Compared to That of Tenofovir Disoproxil Fumarate" Antimicrobial Agents and Chemotherapy, vol. 59(10) Oct. 2015.
Cundy, K.C., "Clinical Pharmacokinetics of the Antiviral Nucleotide Analogues Cidofovir and Adefovir", Clinical Pharmacokinetics, 36:127-143, Feb. 1999.
De Clercq, E., "Acyclic nucleoside phosphonates: Past, present and future Bridging chemistry to HIV, HBV, HCV, HPV, adeno-, herpes-, and poxvirus infections: The phosphonate bridge", Biochemical Pharmacology, 73:911-922, 2007.
Figlerowicz et al., "Genetic Variability: The Key Problem in the Prevention and Therapy of RNA-Based Virus Infections." Medicinal Research Reviews 23(4):488-518, 2003.
Franchetti et al., "8-Aza-analogues of PMEA and PMEG: Synthesis and In Vitro Anti-HIV Activity," Nucleosides & Nucleotides 13(8):1707-1719, Sep. 1994.
Haynes et al., "Syntheses of 9-(2'-monoethylphosphonomethoxyethyl)-8-[14C]guanine ([14C]-EPMG) and 9-(2'-phosphonomethoxyethyl)-8-[14C]guanine ([14C]-PMEG)," Journal of Labelled Compounds and Radiopharmaceuticals 33(8):795-799, Aug. 1993.
Holy, A., "Antiviral acyclic nucleoside phosphonates structure activity studies," Antiviral Research 71 :248-253, 2006.
Holy et al., "Structure-Antiviral Activity Relationship in the Series of Pyrimidine and Purine N-[2-(2-Phosphonomethyoxy)ethyl] Nucleotide Analogues. 1. Derivatives Substituted at the Carbon Atoms of the base" J. Med. Chem., 42(12):2064-2086, Jun. 17, 1999.
Holy, A et al., "Synthesis of 9-(2-Phosphonylmethoxyethyl) Adenine and Related Compounds," Collection Czechoslovak Chem Commun. 52:2801-2809, 1987.
Hostetler et al., "Lipid prodrugs of phosphonoacids: greatly enhanced antiviral activity of 1-O-octadecyl-sn-glycero-3-phosphonoformate in HIV-1, HSV-1 and HCMV-infected cells, in vitro", Antiviral Research, 31(1-2), 59-67, Jun. 1996.
Hostetler et al., "Alkoxyalkyl Esters of (S)-9-[3-Hydroxy-2-(Phosphonomethoxy)propyl]Adenine Are Potent Inhibitors of the Replication of Wild-Type and Drug-Resistant Human Immunodeficiency Virus Type 1 In Vitro", Antimicrobial Agents and Chemotherapy, American Society for Microbiology, 50(8):2857-2859, 2006.
Hostetler et al., "Enhanced anti proliferative effects of alkoxyalkyl esters of cidofovir in human cervical cancer cells in vitro" Mo—Cancer Ther, 51 (1):156-158, 2006.
Hostetler et al., "Oral 1-O-octadecyl-2-O-benzyl-sn-glycero-3-cidofovir targets the lung and is effective against a lethal respiratory challenge with ectromelia virus in mice", Antiviral Research, 73(3), 212-218, Mar. 2007.
International Search Report mailed on Dec. 4, 2015, for PCT Application No. PCT-US2015-050202, filed Sep. 15, 2015, 5 pages.
International Search Report mailed Dec. 13, 2023, for PCT Application No. PCT-US2023-028218, filed Jul. 20, 2023, 10 pages.
Jansa et al., "A novel and efficient one-pot synthesis of symmetrical diamide (bis-amidate) prod rugs of acyclic nucleoside phosphonates and evaluation of their biological activities," European Journal of Medicinal Chemistry, 46(9):3748-3754, Sep. 2011, e-published May 23, 2011.
Jindrich et al., "Synthesis of N-(3-Fluoro-2-Phosphonomethoxypropyl) (FPMP) Derivatives of Heterocyclic Bases", Collect. Czech. Chem. Commun., 58:1645-1667, 1993.
Keough et al., "Inhibition of hypoxanthine-guanine phosphoribosyltransferase by acyclic nucleoside phosphonates: a new class of antimalarial therapeutics," J Med Chem 52(14):4391-4399, Jul. 23, 2009.

(56) References Cited

OTHER PUBLICATIONS

Kramata et al., "Votruba I, Otova B, Holy A. Different inhibitory potencies of acyclic phosphonomethoxyalkyl nucleotide analogs toward DNA polymerases alpha, delta and epsilon," Mol Pharmacol. 49(6):1005-1011, Jun. 1996.

Kramata et al., "Incorporation and excision of 9-(2 phosphonylmethoxyethyl)guanine (PMEG) by DNA polymerase delta and epsilon in vitro," J Biol. Chem. 273(34):21966-21971, Aug. 21, 1998.

Meier et al., cycloSal-PMEA and cycloAmb-PMEA: potentially new phosphonate prodrugs based on the cycloSal-pronucleotide approach, J. Med. Chem. 48(25):8079-8086, Dec. 15, 2005.

Merta et al., "Phosphorylation of 9-(2-phosphonomethoxyethyl) adenine and 9-(S)-(3-hydroxy-2-phosphonomethoxypropyl)adenine by AMP (dAMP) kinase from L 121 O cells", Biochemical Pharmacology, Elsevier, 44(10):2067-2077, 1992.

Naesens et al., "In vivo Antiretroviral Efficacy of Oral bis(POM)-PMEA, the bis(Pivaloyloxymethyl)prodrug of 9-(2-Phosphonylmethoxyethyl) adenine (PMEA)," Nucleosides & Nucleotides 14(3-5):767-770, 1995, published online Feb. 16, 2007.

Pertusati et al., "Medicinal chemistry of nucleoside phosphonate prod rugs for antiviral therapy." Antiviral Chemistry & Chemotherapy, vol. 22, pp. 181-203, 2012.

Pertusati et al., PMPA and PMEA prodrugs for the treatment of HIV infections and human papillomavirus (HPV) associated neoplasia and cancer, 2014, European Journal of Medicinal Chemistry, 78, 259-268, 2014.

Pradere et al., "Synthesis of Nucleoside and Phosphonate Prodrugs," Chemical Reviews 114(18):9154-9218, Sep. 24, 2014, e-published Aug. 21, 2014.

Ruiz et al., "Synthesis, metabolic stability and antiviral evaluation of various alkoxyalkyl esters of cidofovir and (S)-[3-Hydroxy-2-(Phosphonomethoxy)Propyl]Adenine", Bioorg. Med. Chem. 19(9), 2950-2958, 2011.

South African National Clinical Trials Registry, "An Open-Label, Single and Multiple-dose Study to Evaluate Safety, Tolerability and Efficacy of ABI-2280 Vaginal Tablet in Participants with Cervical Squamous Intraepithelial Lesions" Dec. 13, 2022.

Srivasta et al., "Bioreversible Phosphate Protective Groups: Synthesis and Stability of Model Acyloxymethyl Phosphates," Bioorg. Chem12:118-129, 1984.

Starrett et al., "Synthesis, oral bioavailability determination, and in vitro evaluation of prodrugs of the antiviral agent 9-[2-(phosphonomethoxy)ethyl]adenine (Pmea).," J. Med. Chem. 37:1857-1864, Jun. 10, 1994.

Tichy et al., "New prodrugs of Adefovir and Cidofovir," Bioorg. & Med. Chem. 19(11):3527-3539, Jun. 1, 2011, e-published Apr. 22, 2011.

United States Clinical Trials Registry, "A study of ABI-2280 Vaginal Tablet in Participants with Cervical Intraepithelial Neoplasia", Published Aug. 16, 2022.

Valiaeva et al., "Antiproliferative Effects of Octadecyloxyethyl 9-[2-(Phosphonomethoxy)Ethyl] Guanine against Me-180 Human Cervical Cancer Cells in vitro and in vivo", Chemotherapy, 56(1):54-59, Mar. 8, 2010.

Valiaeva et al., "Antiviral evaluation of octadecyloxyethyl esters of (S)-3-hydroxy-2-(-(phosphonomethoxy)propyl nucleosides against herpesviruses and orthopoxviruses", Antiviral Research, vol. 84, pp. 254-259, 2009.

Valiaeva et al., "Synthesis and antiviral evaluation of alkoxyalkyl esters of acyclic purine and pyrimidine nucleoside phosphonates against HIV-1 in vitro", Antiviral Research, 72:10-19, 2006.

Valiaeva et al., "Synthesis and antiviral evaluation of 9-(S)-[3-alkoxy-2-(phosphonomethoxy)-propyl] nucleoside alkoxyalkyl esters: Inhibitors of hepatitis C virus and HIV-1 replication", Bioorganic & Medicinal Chemistry, 19:4616-4625, 2011.

Votruba et al., "Inhibition of human purine nucleoside phosphorylase by tenofovir phosphate congeners", Collection of Czechoslovak Chemical Communications, 75(12), 1249-1257, Nov. 23, 2010.

Vrbkova et al., "Synthesis of phosphonomethoxyethyl or 1,3-bis(phosphonomethyox)propan-2-yl lipophilic esters of acyclic nucleoside phosphonates" Tetrahedron, 63:11391-11398, 2007.

Wyles et al., "The Octadecyloxyethyl Ester of (S)-9-[3-Hydroxy-2-(Phosphonomethoxy)Propyl]Adenine Is a Potent and Selective Inhibitor of Hepatitus C Virus Replication in Genotype 1A, 1 B, and 2A Replicons", Antimicrobial Agents and Chemotherapy, American Society for Microbiology, 53:2660-2662, Jun. 2009.

Yokota et al., "Inhibitory effects of acyclic nucleoside phosphonate analogs on hepatitis B virus DNA synthesis in HB611 cells", Antiviral Chemistry and Chemotherapy, 5(2):57-63, 1994.

Yu et al., "Synthesis and antiviral activity of methyl derivatives of 9-[2-(phosohonomethoxy)ethvllauanine," J Med Chem 35(16):2958-2969, Aug. 1992.

Koh Y-H.,c et al., "Design, Synthesis, and Antiviral Activity of Adenosine 5'-phosphonate Analogues as Chain Terminators Against Hepatitis C virus", Journal of Medicinal Chemistry, 2005, vol. 48(8), pp. 2867-2875. Abstract Only.

Korba B.E. and Gerin J.L., "Use of a Standardized Cell Culture Assay to assess activities of Nucleoside Analogs Against Hepatitis B Virus Replication," Antiviral Research, 1992, vol. 19,pp. 55-70. Abstract Only.

Magee W,C., et al., "Mechanism of Inhibition of Vaccinia Virus DNA Polymerase by Cidofovir Diphosphate", Antimicrobial Agents and Chemotherapy, American Society for Microbiology, 2005, vol. 49(8),pp. 3153-3162.

Maloisel J., et al., "Neoglycolipid Conjugates of Foscarnet With Enhanced Antiviral Activity in Cells Infected With Human Cytomegalovirus and Herpes Simplex Virus Type 1," Antiviral Chemistry and Chemotherapy, 1999, vol. 10(6), pp. 333-345.

McKimm-Breschkin J.L., et al., "Tethered Neuraminidase Inhibitors That Bind an Influenza Virus: a First Step Towards a Diagnostic Method for Influenza," Angewandte Chemie, 2003, vol. 42(27), pp. 3118-3121. Abstract Only.

Nucleotides, Nucleosides, and Nucleobases (Molecular Biology), located at:http://what-when-how.com/molecular-biology/nucleotides-nucleosides-and-nucleobasesmolecular-biology.

Painter et al., "Evaluation of Hexadecyloxypropyi-9-R-[2-(Phosphomethoxy)Proply]-Adenine, CMX157, as a Potential Treatment for Human Immunodeficiency Virus Type 1 and Hepatitis B Virus Infections," Antimicrobial Agents and Chemotherapy, 2007, 51 :3505-3509.

Pomeisl K., et al., "Pyrimidine Acyclic Nucleoside Phosphonates and Phosphorylated Analogs (Part 2): Syntheses and Investigation of Their Inhibitory Effects Towards Human Thymidine Phosphorylase", Nucleic Acids Symposium Series, 2008, vol. 52(1), pp. 657-658.

Prichard M.N., et al., "Inhibition of Herpesvirus Replication by Hexadecyloxypropyl Esters of Purine- and Pyrimidine-Based Phosphonomethoxyethyl Nucleoside Phosphonates", Antimicrobial Agents and Chemotherapy, 2008, vol. 52, pp. 4326-4330.

Puech, F. et al. (Oct. 1993). "Intracellular Delivery of Nucleoside Monophosphates through a Reductase-Mediated Activation Process," Antiviral Research 22:155-174.

Quenelle D.C., et al., "Oral Treatment of Cowpox and Vaccinia Virus Infections in Mice with Ether Lipid Esters of Cidofovir," Antimicrobial Agents Chemotherapy, 2004, vol. 48, pp. 404-412.

Reddy, K.R. et al. (Feb. 14, 2008, e-published Jan. 4, 2008). "Pradefovir: a prodrug that targets adefovir to the liver for the treatment of hepatitis B," Journal of Medicinal Chemistry. 51 (3):666-676.

Rosenberg, I., et al., "Phosphonylmethoxyalkyl and Phosphonylalkyl Derivatives of Adenine*," Collection Czechoslovak Chem. Commun, 1988, vol. 53, pp. 2753-2777.

Saudek C.D., et al., "A Preliminary Trial of the Programmable Implantable Medication System for Insulin Delivery," The New England Journal of Medicine, 1989, vol. 321(9), pp. 574-579.

Sefton M.V., "Implantable pumps," Critical reviews in Biomedical Engineering, 1987, vol. 14(3), pp. 201-240. Abstract Only.

Sheng, X.C., et al., "Discovery of Novel Phosphonate Derivatives as Hepatitis C Virus NS3 Protease Inhibitors," Bioorganic & Medicinal Chemistry Letters, 2009, vol. 19, pp. 3453-3457.

(56) References Cited

OTHER PUBLICATIONS

Tobias S.C., et al., "Synthesis and Biological Evaluation of a Cytarabine Phosphoramidate Prodrug," Molecular Pharmaceutics, 2003, vol. 1(2), pp. 112-116.

Trahan et al., "Antiproliferative Effects of Octadecyloxyethyl-Phosphonomethoxyethylguanine (ODE-PMEG) on the Growth of Human Papilloma Virus Positive Cervical Carcinoma (ME-180) Cells In Vitro and Solid Tumors in Athymic Nude Mice" Abstract 85 Antiviral Research (2009) 82(2):A42.

Watson et al., "Burden of Cervical Cancer in the United States, 1998-2003" Cancer, 2008 (Supplement), pp. 2855-2864.

Webb R.R., "The Bis-Trityl Route to (S)-HPMPA", Nucleosides & Nucleotides, 1989, vol. 8(4), pp. 619-624.

Written Opinion mailed on Dec. 4, 2015, for PCT Application No. PCT/US2015/050202, filed Sep. 15, 2015, 4 pages.

Written Opinion mailed on Dec. 7, 2016, for PCT Application No. PCT/US2016/51942, filed Sep. 15, 2016, 12 pages.

Heidel, K.M., et al. "Phosphonate Prodrugs: an Overview and Recent Advances," Future Medicinal Chemistry, vol. 11 (13), pp. 1625-1643, 2019.

Wiemer, D.F., et al. "Prodrugs of Phosphonates and Phosphates: Crossing the Membrane Barrier," Top Curr. Chem, 360, pp. 115-160, 2015.

Alexander R.L., et al., "Synthesis and Cytotoxic Activity of Two Novel 1-dodecylthio-2-decyloxypropyl-3-phosphatidic Acid Conjugates With Gemcitabine and Cytosine Arabinoside," Journal of Medical Chemistry, 2003, vol. 46(19), pp. 4205-4208.

American Chemical Society. STN Database. RN 1022982-83-7, May 27, 2008, 1 page.

American Chemical Society. STN Database. RN 1204478-95-4, Feb. 3, 2010, 1 page.

American Chemical Society. STN Database. RN 123156-16-1, Oct. 13, 1989.

American Chemical Society. STN Database. RN 183107-05-3, Nov. 14, 1996, 1 page.

American Chemical Society. STN Database. RN 278611-52-2, Jul. 19, 2000, 1 page.

American Chemical Society. STN Database. RN 913356-63-5, Nov. 16, 2006, 1 page.

Baker R.O., et al., "Potential Antiviral Therapeutics for Smallpox, Monkeypox and Other Orthopoxvirus Infections," Antiviral Research, 2003, vol. 57(1-2), pp. 13-23.

Bronson J.J., et al., "Synthesis and Antiviral Activity of the Nucleotide Analog (S)-1-[3-hydroxy-2-(Phosphonylmethoxy)propyl]cystosine," Journal of Medicinal Chemistry, 1989, vol. 32(7), pp. 1457-1463.

Buchwald P., et al., "Long-term, Continuous Intravenous Heparin Administration by an Implantable Infusion Pump in Ambulatory Patients With Recurrent Venous Thrombosis," Surgery, 1980, vol. 88(4), pp. 507-516.

Campagne J., et al., "Synthesis of Mixed Phosphonate Diester Analogues of Dipeptides using BOP or PyBOP Reagents," Tetrahedron Letters, 1993, vol. 34(42), pp. 6743-6744.

CAS RN:278611-19-1, Registry. Jul. 19, 2000, 1 page.

CAS RN:278611-52-2, Registry. Jul. 19, 2000, 1 paqe.

Chand P., "Recent Advances in the Discovery and Synthesis of Neuraminidase Inhibitors," Expert Opinion on Therapeutic Patents, 2005, vol. 15(8), pp. 1009-1025.

Chinese OA for CN Application No. 201810387212.8 mailed Feb. 24, 2020, with translation (18 pp).

Chinese Office Action for CN Application No. 202110079522.5, mailed Jun. 6, 2023, with translation.

Database Caplus [Online] Chemical Abstracts Service, Columbus, Ohio, US; Otmar, Miroslav et al: "An alternative synthesis of HPMPC and HPMPA diphosphoryl derivatives", retrieved from STN Database accession No. 2000:234286; & Otmar, Miroslav et al.: "An alternative synthesis of HPMPC and HPMPA diphosphoryl derivatives", Collection Symposium Series, 2(Chemistry of Nucleic Acid Components), 252-254 CODEN: CSYSFN, 1999, 2 pages.

Database Caplus [Online] Chemical Abstracts Service, Columbus, Ohio, US; Votruba, Ivan et al: "Inhibition of human purine nucleoside phosphorylase by tenofovir phosphate congeners", retrieved from STN Database accession No. 2010:1628491 ; & Votruba, Ivan et al: "Inhibition of human purine nucleoside phosphorylase by tenofovir phosphate congeners", Collection of Czechoslovak Chemical Communications, 75(12), 1249-1257 CODEN: CCCCAK; ISSN: 0010-0765,2010, 1 paqe.

De Clercq E., "Vaccinia Virus Inhibitors as a Paradigm for the Chemotherapy of Poxvirus Infections," Clinical Microbiology Reviews, 2001, vol. 14(2), pp. 382-397.

El-Faham A., et al., "Peptide Coupling Reagents, More Than a Letter Soup," Chemical Reviews, 2011, vol. 111(11), pp. 6557-6602.

European Office Action for EP Application No. 16847300.7 mailed Dec. 17, 2019 (4 pages).

European Search Report for EP Application No. 16847300.7 mailed Feb. 14, 2019 (7 pages).

Extended European Search Report dated Oct. 10, 2013 for European Application No. EP11769615.3, 12 pages.

File History of U.S. Appl. No. 14/854,897, filed Sep. 15, 2015, Inventors Karl Y. Hostetler, et al., available on Patent Center.

File History of U.S. Appl. No. 15/171,935, filed Jun. 2, 2016, Inventors Karl Y. Hostetler, et al., available on Patent Center.

File History of U.S. Appl. No. 15/718,898, filed Sep. 28, 2017 Inventors Karl Y. Hostetler, et al., available on Patent Center.

File History of U.S. Appl. No. 16/242,336, filed Jan. 8, 2019, Inventors Karl Y. Hostetler, et al., available on Patent Center.

File History of U.S. Appl. No. 16/908,183, filed Jun. 22, 2020, Inventors Karl Y. Hostetler, et al., available on Patent Center.

File History of U.S. Appl. No. 17/523,806, filed Nov. 10, 2021, Inventors Karl Y. Hostetler, et al., available on Patent Center.

File History of U.S. Appl. No. 17/524,334, filed Nov. 11, 2021, Inventors Karl Y, Hostetler, et al., available on Patent Center.

File History of U.S. Appl. No. 17/829, 147, filed May 31, 2022, Inventors Karl Y. Hostetler, et al., available on Patent Center.

File History of U.S. Appl. No. 18/385,766, filed Oct. 31, 2023, Inventors Barry Aldous, et al., available on Patent Center.

File History of U.S. Appl. No. 18/385,771, filed Oct. 31, 2023, Inventors Barry Aldous, et al., available on Patent Center.

File History of U.S. Appl. No. 18/385,778, filed Oct. 31, 2023, Inventors Barry Aldous, et al., available on Patent Center.

Fingl, E. & Woodbury, D.M., "The Pharmacological Basis of Therapeutics," Fifth Edition, Chapter 1, Section 1, 1975, pp. 1-47.

Heijtink, R.A et al. "Inhibitory Effects of Acyclic Nucleoside Phosphonates on Human Hepatitis B Virus and Duck Hepatitis B Virus Infections in Tissue Culture," Antimicrobial agents and chemotherapy, 1994, vol. 38(9), pp. 2180-2182.

File History of U.S. Appl. No. 17/236,590, filed Apr. 21, 2021, Inventors Hostetler et al., available on Patent Center.

Cervical Cancer Overview located at https://www.nccc-online.org/hpvcervical-cancer/cervical-cancer-overview/.

Huggins J.W., et al., "Orally Active Ether Lipid Prodrugs of Cidofovir for the Treatment of Smallpox," Antiviral Research, 2002, vol. 53, pp. A66 (104).

International Preliminary Report on Patentability and Written Opinion dated Jun. 19, 2007 for International PCT Application No. PCT/US2005/045579, 8 pages.

International Preliminary Report on Patentability and Written Opinion dated Oct. 16, 2012 for International Application No. PCT/US2011/032558, 7 pages.

International Search Report and Written Opinion dated May 29, 2014 for International Application No. PCT/US2014/027005, 8 pages.

International Search report dated Jan. 18, 2012 for International Application No. PCT/US2011/032558, 5 pages.

International Search Report dated Jul. 19, 2006 for International PCT Application No. PCT/US2005/045579, 4 pages.

International Search Report mailed on Dec. 7, 2016, for PCT Application No. PCT/US2016/51942, filed Sep. 15, 2016, 4 pages.

Iyer et al., "Phosphorothioate Di- and Trinucleotides as a Novel Class of Anti-Hepatitis B Virus Agents," Antimicrobial Agents and Chemotherapy, 2004, vol. 48(6) pp. 2199-2205.

(56) References Cited

OTHER PUBLICATIONS

Jansa et al., "Microwave-Assisted Hydrolysis of Phosphonate Diesters: an Efficient Protocol for the Preparation of Phosphonic Acids," Green Chemistry, 2012, vol. 14, pp. 2282-2288 (supporting information only).

Japanese Office Action for JP Application No. 2018-242188 mailed Nov. 26, 2019 (20 pages).

Keith K.A., et al., "Inhibitory Activity of Alkoxyalkyl and Alkyl Esters of Cidofovir and Cyclic Cidofovir Against Orthopoxvirus Replication in Vitro, "Antimicrobial Agents and Chemotherapy, 2004, vol. 48:5, pp. 1869-1871.

Kern, E.R., et al., "Enhanced Inhibition of Orthopoxvirus Replication In Vitro by Alkoxyalkyl Esters of Cidofovir and Cyclic Cidofovir," Antimicrobial Agents and Chemotherapy, 2002, vol. 46(4), pp. 991-995.

\* cited by examiner

Compound I Monofumarate

Compound II

Compound III

COMPOSITIONS AND DOSAGE FORMS FOR TREATMENT OF HPV INFECTION AND HPV-INDUCED NEOPLASIA

CROSS-REFERENCE TO RELATED APPLICATIONS

This application is a continuation of International Patent Application No. PCT/US2023/028218, filed in the U.S. Receiving Office on Jul. 20, 2023, which claims the benefit of U.S. Provisional Application No. 63/391,283, filed Jul. 21, 2022; U.S. Provisional Application No. 63/400,661, filed Aug. 24, 2022; Chinese Patent Application No. 202211206517.7, filed Sep. 30, 2022; and U.S. Provisional Application No. 63/412,143, filed Sep. 30, 2022. The entirety of each of these applications is incorporated herein by reference for all purposes.

FIELD OF THE INVENTION

The present invention provides compositions, advantageous salts, prodrugs, stereoisomers, morphic forms, dosage forms, and uses thereof to treat human papilloma virus (HPV) infection or a related disorder such as HPV-induced neoplasia in a host in need thereof.

BACKGROUND OF THE INVENTION

According to the U.S. Center for Disease Control, there is no direct cure for human papilloma virus. In 2018, over 43 million people were infected, and there were over 13 million new infections.

The current therapeutic options for HPV infection are adjunctive only and are limited. They all suffer from significant drawbacks. Commonly used drug therapies include salicylic acid, trichloroacetic acid, imiquimod and podofilox. Both trichloroacetic acid and salicylic acid chemically burn the wart tissue as a means of removing the virus, frequently causing skin irritation, sores and pain in the process. Further, salicylic acid is not used to treat HPV infections of the anogenital area. Imiquimod (Aldara™, Zyclara™) stimulates the immune system to clear the infection through toll-like receptor signaling and causes redness and swelling. Podofilox (Condylox™) destroys tissues by destabilizing microtubules which prevents host cell replication.

Even more problematic are the HPV infections that have caused cellular transformations in the human patient that have not yet progressed to cancer but have reached the stage of neoplasia. Forms of HPV-induced neoplasia include cervical intraepithelial neoplasia ("CIN"), anal intraepithelial neoplasia ("AIN"), perianal intraepithelial neoplasia ("PAIN"), vulvar intraepithelial neoplasia ("VIN"), penile intraepithelial neoplasia ("PIN") and vaginal intraepithelial neoplasia ("VAIN"). Cancers caused by HPV include cervical, anal, perianal, penile, vaginal, vulvar, and oropharyngeal cancer.

It is critical to identify and treat HPV-induced neoplasia before it advances to cancer that may not be treatable. Nearly all cases of cervical cancer are caused by infection with sexually transmitted oncogenic types of HPV. The primary goal of early screening, such as the Papanicolaou test (Pap smear), is to identify abnormal cervical cells with severe cell changes so they can be removed or destroyed.

Cervical intraepithelial neoplasia is most often treated by observation (the wait and see approach) or by excision or ablation of the cervical transformation zone. Techniques include cryotherapy, laser therapy, loop electrosurgical procedure (LEEP) and cone biopsy. All of these surgical procedures damage the affected areas and can lead to scarring. The most common intervention, LEEP, is effective in 60-90% of cases, however, it is associated with a significantly increased risk of miscarriage, ectopic pregnancies, and negative psychological outcomes. Despite extensive research, no drug has been approved to replace or combine with these surgical methods.

Papillomaviruses are a group of non-enveloped DNA viruses, which in humans infect keratinocytes of skin and mucous membranes including in the anogenital area. They are known to cause skin warts, genital warts, respiratory papillomatosis and cancer. Several species of the alpha-papillomavirus genus contain high risk types of HPV which are more likely to lead to human neoplasia and then cancer. Most of the cancer-causing HPV types are from the alpha-7 and alpha-9 species and include types 16, 18, 31, 33, 35, 39, 45, 51, 52, 56, 58, 59, 68, 73, and 82. The most common cancer-causing HPV types are 16 and 18. HPV-16 and -18 are the cause of the majority of cervical cancers. The majority of venereal warts are caused by the low-risk HPV types 6 and 11. Vaccines have been developed for HPV 6, 11, 16 and 18, which may be effective if administered prior to sexual debut. However, the HPV vaccines may provide little benefit in sexually active women who have already been infected with HPV.

Specific preventative vaccines available include Gardasil 9 (HPV 9 valent vaccine; HPV 6, 11, 16, 18, 31, 33, 45, 52 and 58), Gardasil 4 (quadrivalent) and Cervarix (bivalent). These are useful if the person is vaccinated prior to viral contact, which typically means prior to sexual activity. Preventative vaccines are designed to produce neutralizing antibodies which clear the virus before it can infect a cell. In contrast, therapeutic vaccines are vaccines designed to mount a CD4+ and/or CD8+ T-cell-based response to clear HPV infected cells. Exemplary antigens for therapeutic vaccines include E6 and E7. There are currently no therapeutic vaccines which are approved. Nonlimiting examples of therapeutic vaccines being studied in clinical trials include VGX-3100 (INOVIO), GGX-188E (Genexine, Inc.), and ADXS11-001 (Advaxis, Inc.).

Cervical intraepithelial neoplasia (CIN) is a precursor to cervical cancer. As many as 20% of women infected with HPV have CIN (Rozendaal, L. et al. "PCR-based high-risk HPV test in cervical cancer screening gives objective risk assessment of women with cytomorphologically normal cervical smears" 1996, *Int J Cancer,* 68, 766-769). CIN is graded on the Bethesda scale from mild Grade 1 to the serious Grade 3. When a woman is diagnosed with Grade 1 CIN, the "wait and watch" approach is usually taken. Only when the CIN is Grade 2-3 is treatment recommended, due to the adverse side effects of the surgical approaches.

The cervical epithelium is composed of several layers of tissue and is referred to as stratified squamous epithelium. The layers are the superficial cell layer, the intermediate cell layer, the parabasal cell layer and the basal cell layer. It is essential that a topical drug for the treatment of cervical intraepithelial neoplasia be able to penetrate these multiple layers of tissue to adequately reach and treat the transformed cells. This is a formidable task because the cells are tightly bound and without blood vessels.

In 1996, a National Cancer Institute consensus panel identified a need for nonsurgical interventions for cervical intraepithelial neoplasia (National Institutes of Health Consensus Development Conference statement on cervical cancer. Apr. 1-3, 1996. *J Women's Health,* 1996, 1, 1-38). Since that guidance was issued, many different approaches to treat HPV and CIN have been explored, including immunomodulators, antiproliferative medicines, antivirals, and hormones. However, there are still no FDA-approved treatment options with proven efficacy in clinical trials for HPV infection or CIN (Desravines, N. et al. "Topical therapies for the treatment of cervical intraepithelial neoplasia (CIN) 2-3: A narrative review" Gynecol Oncol Rep. 2020, 33, 100608).

The Regents of the University of California, with Karl Hostetler, et. al, as named inventors, has filed a series of patents on various acyclic nucleotide derivatives to treat papilloma infections, including (i) U.S. Pat. Nos. 8,835,603; 9,629,860; 9,156,867; 10,449,207; 10,195,222; 10,076,533; 10,076,532; 9,775,852; 9,387,217 with a priority date of Mar. 15, 2013; (ii) U.S. Pat. Nos. 10,702,532; 10,213,430; 9,493,493; and 9,801,884, with a priority date of Sep. 15, 2014; and (iii) U.S. Pat. Nos. 11,014,950 and 10,377,782 with a priority date of Sep. 15, 2015. Some of these patents are licensed to Antiva Biosciences, Inc., which is developing novel therapeutics to treat pre-cancerous lesions caused by HPV.

Antiva Biosciences carried out human clinical trials with the phosphonate ABI-1968 to assess its ability to adequately penetrate the various layers of cervical epithelium and release the antiviral agent PMEG ((9-[2-phosphonomethyoxy)ethyl)guanine]). PMEG is then phosphorylated to PMEGpp (PMEG polyphosphate), which is the active compound. It was determined that ABI-1968, when used even up to a 3% dose, does not reach 15 ng/mg of tissue concentration for ABI-1968, (See Bar F and G in FIG. 116) and thus is not suitable as a topical drug to treat cervical intraepithelial neoplasia. It is a formidable challenge to topically dose HPV-infected epithelial stratified tissue in an effective manner that destroys the neoplasia cells in the multiple epithelial layers. The drug must be lipophilic enough to pass through the tissue layers and be metabolized if necessary to the active agent in a sufficient concentration to kill the pathogenic cells.

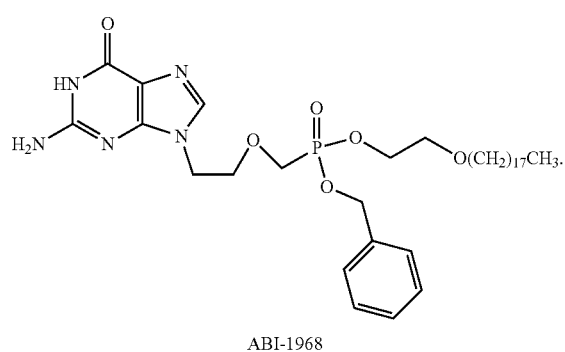

ABI-1968

Articles have been published that discuss various topical drug delivery strategies including semi-solid dosage forms, gels, tablets, film, and pessaries See, for example, Keshari Sahoo, C. et al. "Intra vaginal Drug Delivery System: An Overview", 2013, *American Journal of Advanced Drug Delivery*, 1, 43-55; da Neves, J. et al. "Gels as vaginal drug delivery systems", 2006, *International Journal of Pharmaceutics*, 318 (2) 1-14; Cencia Rohan, L. et al. "Vaginal Drug Delivery Systems for HIV Prevention", 2009, *AAPS*, 11 (78); Kast, C. E. et al. "Design and in vitro evaluation of a novel bioadhesive vaginal drug delivery system for clotrimazole" *Journal of Controlled Release*, 2002, 81 (3) 347-354; Acarturk, F. "Mucoadhesive vaginal drug delivery systems", *Recent Pat Drug Deliv Formul.*, 2009, 3 (3) 193-205; and Sonal, G. et al. "Exploring Novel Approaches to Vaginal Drug Delivery", *Recent Patents on Drug Delivery and Formulation*, 2011, 5 (2) 82-94.

It is an object of the present invention to provide an effective pharmaceutical composition and treatment for HPV infection and related conditions such as HPV-induced neoplasia in a host in need thereof, including but not limited to cervical intraepithelial neoplasia (CIN), anal intraepithelial neoplasia (AIN), vulvar intraepithelial neoplasia (VIN), penile intraepithelial neoplasia (PIN), perianal intraepithelial neoplasia (PAIN) and vaginal intraepithelial neoplasia (VAIN).

SUMMARY OF THE INVENTION

It has been discovered that an effective composition for the treatment of HPV infection and related diseases including HPV-induced neoplasia, such as cervical intraepithelial neoplasia, anal intraepithelial neoplasia, perianal intraepithelial neoplasia, penile intraepithelial neoplasia, vulvar intraepithelial neoplasia, and vaginal intraepithelial neoplasia, requires the combination of the selection of a number of aspects that work together to achieve the desired results. It was essential to select the right compound with advantageous lipophilic and tissue penetrating properties combined with a selected pharmaceutically acceptable salt optionally in an advantageous morphic form to achieve the long-sought ability to penetrate the epithelial stratified tissues in an effective amount to deliver the active agent. It required years of research to solve this problem, after many failures, to the benefit of patients globally suffering from interepithelial neoplasia that may become cancerous.

Specifically, it was discovered that the key compound is a specific salt of:

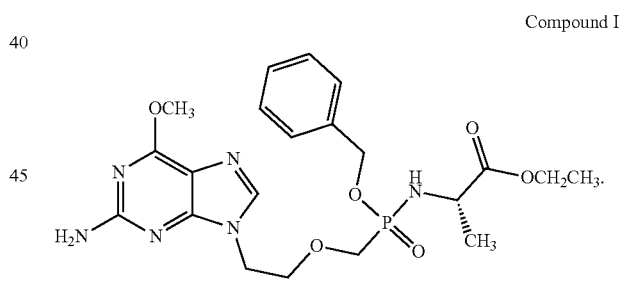

Compound I

Compound I is (ethyl(((2-(2-amino-6-methoxy-9H-purin-9-yl)ethoxy)methyl)(benzyloxy)-phosphoryl)-L-alaninate).

U.S. Pat. Nos. 9,801,884 and 11,344,555 assigned to the Regents of the University of California claim Compound I and pharmaceutically acceptable salts generally, as well as methods of using the same for treating a papillomavirus infection. Compound I is an acyclic nucleotide phosphonate that metabolizes to a known potent antiviral compound (PMEG; ((9-[2-phosphonomethyoxy)ethyl)guanine])), but PMEG has poor cellular permeability and use-limiting systemic toxicity. The assignee has discovered how to improve the prodrug to be delivered topically in a manner that it is rapidly taken up into epithelial cells, a challenging task to date and one that ABI-1968 failed.

Compound I (ethyl (-((2-(2-amino-6-methoxy-9H-purin-9-yl)ethoxy)methyl)-(benzyloxy)phosphoryl)-L-alaninate) has two chiral centers, one at the phosphorus atom and one in the amino acid moiety, either of which can be in the R or S stereoconfiguration. Therefore, Compound I exists as four stereoisomers, or two diastereomeric pairs: $(R_P, S_C)/(S_P, S_C)$ and $(R_P, R_C)/(S_P, R_C)$. While U.S. Pat. Nos. 9,801,884 and 11,344,555 describe Compound I generally, the patents do not address the potential stereochemistry of the phosphorus atom. It has been discovered that the stereoisomer of Compound I with R-stereochemistry at the phosphorus and S-stereochemistry at the amino acid carbon has advantageous properties over the other three stereoisomers, as discussed further herein.

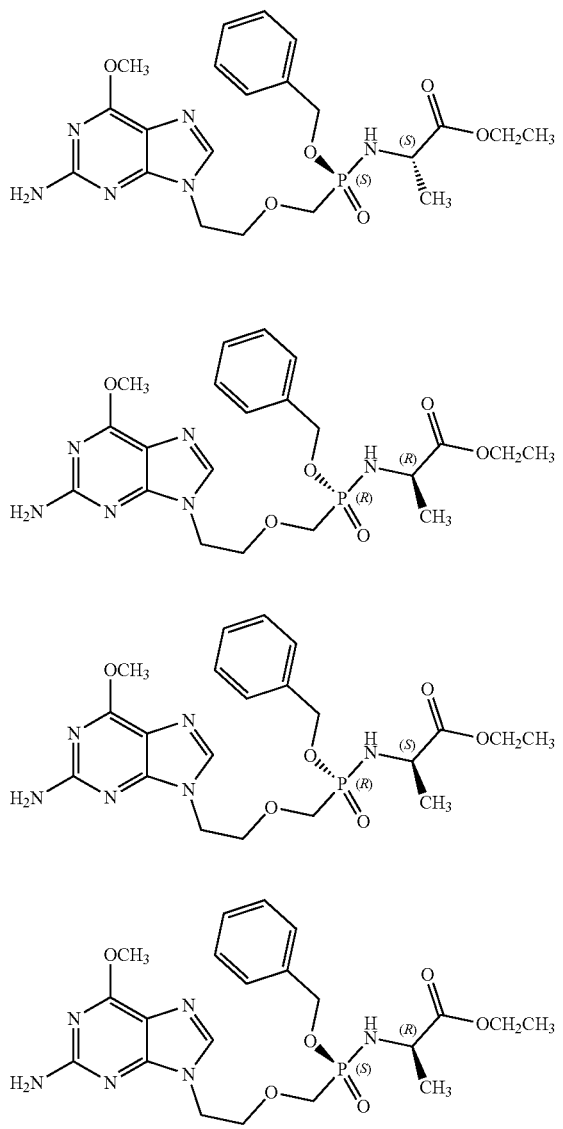

In a non-limiting embodiment, the advantageous salt (for example fumarate) of Compound I is used as a mixture of (R,S) and (S,S) diastereomers, wherein the first R/S designates the stereochemistry at the phosphorus atom and the second S is the stereochemistry of the carbon in the amino acid moiety (corresponding to the L-alanine residue having S-configuration). While any ratio of the diastereomers can be used that provides the desired results, the (R,S) diastereomer stands out. In other embodiments, the ratio is approximately 1:1 of the R to S enantiomer at the phosphorus atom. In aspects, the compound is enantiomerically enriched with the R chirality at the phosphorus atom, wherein the amount of R by weight is for example, greater than about 50%, or equal to or greater than about 60%, 70%, 75%, 80%, or even 85% or more.

The S-stereoconfiguration at the chiral carbon corresponding to the natural amino acid configuration is advantageous in the present invention. In certain aspects, the amount of S by weight is for example, greater than about 50%, or equal to or greater than about 60%, 70%, 75%, 80%, or even 85% or more. In alternative embodiments, the compound is used with R-stereoconfiguration at the chiral carbon and wherein the R-stereoconfiguration is greater than about 50%, or equal to or greater than about 60%, 70%, 75%, 80%, or even 85% or more.

The enantiomerically pure ($R_p,S_c$, or simply "R,S") version of Compound I is a principal embodiment. Unless described otherwise, an enantiomerically pure Compound II is at least 90% free of the opposite enantiomer. Surprisingly, the compound is an oil, not a solid, and thus would not have been selected as the active ingredient for the topical formulation. This is especially true because the racemic mixture or enantiomerically enriched R,S with S,S as a free base is a solid. Further, the S,S isomer has medium crystallinity as can be seen in FIG. 120. However, when formed as the fumarate salt, the R,S enantiomerically pure Compound I becomes a highly crystalline material and the most advantageous for intraepithelial topical administration. Thus, the monofumarate salt of Compound I exhibits unexpected stability, processability, and thus has therapeutic advantages over the free base Compound I.

The monofumarate of the R,S isomer can be readily crystallized from isopropanol and heptanes. This morphic form is an anhydrate with a melting point of about 140° C. (Example 15). This morphic form has been reproduced not only on milligram scale but also multigram scale.

While the S,S isomer was more easily handled as a free base, the monofumarate salt of the S,S isomer is polymorphic and has a lower melting point of about 105° C. Four morphic forms of the S,S monofumarate salt were identified (Example 15). In certain experiments, dissociation of the S,S monofumarate into the hemifumarate was observed. Synthesis of this pattern was not reproducible when performed on larger scales.

It has been surprisingly discovered that certain pharmaceutical composition dosage forms prepared from Compound I monofumarate, and its morphic form Pattern 1, have advantageous properties. Tablets prepared from Compound I free base substantially degrade within one month at 40° C. and 75% RH, but in contrast, tablets prepared from Compound I monofumarate experience far less degradation (Example 25), significantly increasing the shelf life.

Compound II as referred to herein and illustrated below is the enantiomerically enriched or pure embodiment that has predominately R-stereochemistry at the phosphorus atom and S-stereochemistry at the amino acid carbon atom. In an enantiomerically pure form, Compound II exhibits superior stability properties over its stereoisomer, ethyl ((S)-((2-(2-amino-6-methoxy-9H-purin-9-yl)ethoxy)methyl)(benzyloxy) phosphoryl)-L-alaninate monofumarate (Compound III). This is important for the success of the topical application to the cervix, vagina, vulva, perianal region, anus or penis.

Compound II

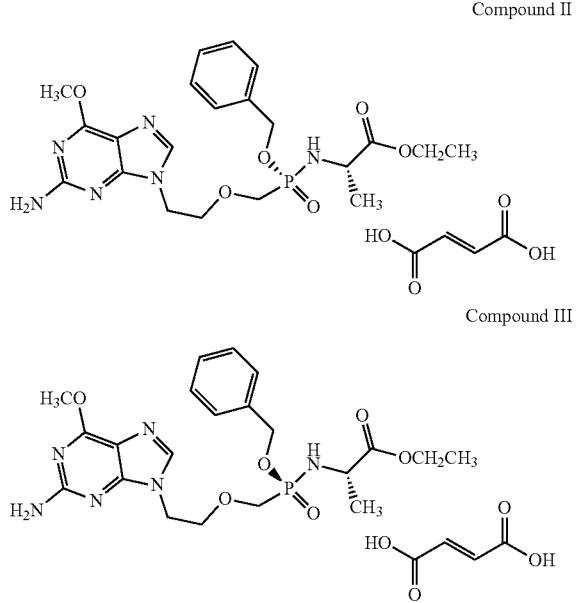

Compound III

Other advantageous salts of Compound I that have been discovered include the hemifumarate salts ethyl ((R)-((2-(2-amino-6-methoxy-9H-purin-9-yl)ethoxy)methyl)(benzyloxy)phosphoryl)-L-alaninate hemifumarate (Compound IV) and ethyl ((S)-((2-(2-amino-6-methoxy-9H-purin-9-yl)ethoxy)methyl)(benzyloxy)phosphoryl)-L-alaninate hemifumarate (Compound V).

Compound IV

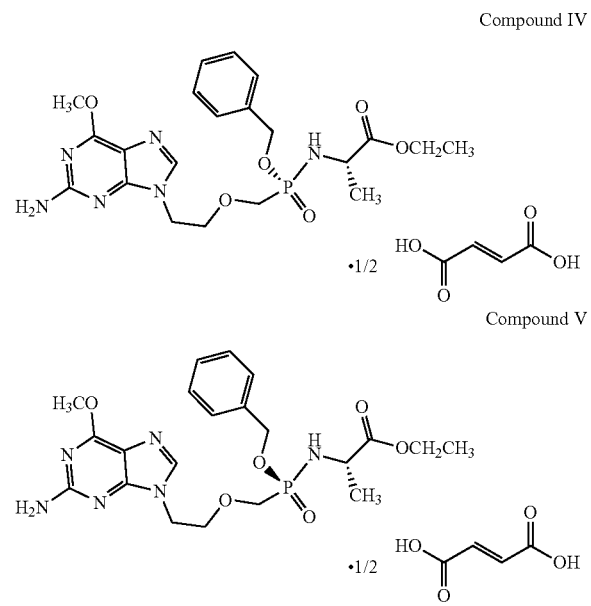

Compound V

It has been discovered that Compound II has high tissue penetration and is surprisingly stable, crystalline, and non-hygroscopic. Compound II and its advantageous morphic form Pattern 1 can be used to treat HPV infection, or a disease associated with HPV infection, such as intraepithelial neoplasia, including but not limited to cervical intraepithelial neoplasia, anal intraepithelial neoplasia, vulvar intraepithelial neoplasia, penile intraepithelial neoplasia, perianal intraepithelial and vaginal intraepithelial neoplasia to prevent the transition to cancer.

There are many strains of HPV, some of which are strongly associated with the development of cancer and are known as high-risk strains. Compound I fumarate or Compound II can be used to treat the high-risk types of HPV, including HPV-16 and HPV-18. Thus, the present invention in certain aspects provides Compound II and the isolated morphic form Compound II Patten 1, pharmaceutical compositions containing such compound, methods of treating an HPV infection or intraepithelial neoplasia related to HPV infection using the selected morphic form described herein, and methods of preparing such compound and morphic form.

In particular, it has been surprisingly discovered that the monofumarate salt of ethyl ((R)-((2-(2-amino-6-methoxy-9H-purin-9-yl)ethoxy)methyl)(benzyloxy)phosphoryl)-L-alaninate (Compound II) has very high tissue penetration when administered topically to the target tissue. Topical administration avoids toxicity associated with systemic administration of the drug. Because precancerous and/or cancerous cells that are infected with HPV are several layers into the epithelium, the compound must have high penetration into the tissue to reach and treat these affected cells.

Compound I monofumarate has superior tissue permeation and penetration in both porcine and human vaginal tissues over ABI-1968, which failed in clinical trials despite also being a phosphonate ester of an acyclic purine nucleoside. Compound I monofumarate reaches concentrations of 40-85 ng/mL in vaginal tissue for a 0.1% dose. ABI-1968, even when used in a 3% dose does not reach even 15 ng/mL concentration (See FIG. 116). The significant improvement in tissue penetration, especially considering the decrease in dose, could not have been predicted in advance.

Compound II is surprisingly stable in comparison to its corresponding $S_P$ isomer (Compound III). As shown in Example 7, Table 9, Compound II has a melting point of about 140° C.±10° C., for example at 141.5° C., whereas Compound III has a melting point of about 100° C.+10° C., for example 106.4° C. Compound II is also much more crystalline than Compound III, as can be seen from the XRPD data comparing the monofumarate salts of both compounds (See Example 13, Table 37 and FIG. 71 compared to Example 15, Table 40 and FIG. 77).

Careful selection of each aspect of the invention was crucial to achieve the desired results. One important aspect is the formulation. Topical formulations as used herein include semisolid dosage forms such as gels, creams, ointments, liquids or a solid dosage form. Nonlimiting examples of a solid dosage form includes a tablet, which can be inserted into the affected area.

It has been discovered that Compound I monofumarate, Compound II or Compound III can be prepared in a solid dosage form for topical administration. In some embodiments, the tablet formulation provides similar tissue penetration of the gel formulation (55-85 ng/mg for gel and 44-79 ng/mg for the tablet, FIG. 121).

High crystallinity can facilitate isolation and processing of pharmaceutical compounds. Compound II displays surprisingly little hygroscopicity compared to Compound III. When exposed to a cycle of 40-0-95-0-45% relative humidity, Compound II retains about 0.25% water content, and the XRPD pattern does not change (Example 21, Table 46). Exposed to the same conditions, Compound III retains about 10% water content, a 40-fold increase. These conditions also cause the XRPD pattern to lose one of the peaks, indicating that Compound III is changing morphic forms in response to humidity changes. The hygroscopicity and stability benefits of Compound II over Compound III are surprising and could not be predicted in advance.

Compound II Pattern 1 can be produced, for example, by recrystallizing Compound II (Example 13, Table 37) and equilibration in a suitable solvent (Example 22). In certain embodiments, Compound II can be dissolved in an alcoholic solvent, for example isopropanol, and crystallized as Pattern 1 by the addition of an aliphatic solvent, for example heptane. In certain embodiments, Compound II can be dissolved in an alcoholic solvent, for example, ethanol, and crystallized as Pattern 1 by the addition of an aliphatic solvent, for example heptane. Compound II Pattern I may also be prepared by equilibration in isopropanol, heptane, water, acetone, isopropanol:heptane (3:10), isopropanol: MTBE (1:3), and ethyl acetate:toluene (1:3).

Compound III Pattern I can be prepared in multiple steps (see Example 15). First, Compound III free base was dissolved in isopropanol. One equivalent of fumaric acid was added, inducing precipitation. After addition of heptanes, the mixture was stirred at elevated temperature, for example 50° C., for 20 hours then cooled. A further 0.2 equivalent of fumaric acid was added along with heptane and the mixture stirred at elevated temperature for at least about 13 hours. The suspension was then cooled slowly until reaching less than about 5° C. and stirred at that temperature for at least about 2 days. The resulting solid, Compound III Pattern I, was collected by filtration.

Compound I (i.e., a mixture of R and S enantiomers at the phosphorus atom and the S stereoisomer at the amino acid carbon) monofumarate Pattern 1 can be produced, for example, by recrystallizing Compound I monofumarate (Example 12, Table 31), equilibration of Compound I monofumarate in a suitable solvent, or crystallization by slow evaporation of solvent (Example 12, Table 32). In certain embodiments, Compound I monofumarate can be dissolved in an alcoholic solvent, for example isopropanol, and crystallized as Pattern 1 by the addition of an aliphatic solvent, for example heptanes. In certain embodiments, Compound I monofumarate can be dissolved in an alcoholic solvent, for example, isopropanol, and crystallized as Pattern 1 by the addition of an ethereal solvent, for example methyl tert-butyl ether. In certain embodiments, Compound I monofumarate Pattern 1 can be produced by equilibration in a mixture of an ethereal solvent, for example tetrahydrofuran, and an aliphatic solvent, for example heptane. In certain embodiments, Compound I monofumarate Pattern 1 can be produced by crystallization by slow evaporation of solvent at room temperature. Suitable solvents for slow evaporation crystallization of Compound I monofumarate Pattern 1 include but are not limited to, acetone, methyl ethyl ketone, ethyl acetate, methanol, ethanol, isopropanol, and tetrahydrofuran. In certain embodiments, Compound I monofumarate Pattern 1 is characterized by an XRPD pattern comprising at least three 2theta values selected from 6.0±0.2°, 8.9±0.2°, 9.6±0.2°, 11.1±0.2°, 11.9±0.2°, 14.8±0.2°, 15.3±0.2°, 18.1±0.2°, 20.2±0.2°, 23.1±0.2°, 25.2±0.2°, and 27.0±0.2° (see Example 7).

Other morphic forms of Compound I monofumarate were prepared, including Pattern 2, Pattern 3, and Pattern 4. However, these morphic forms are sometimes unstable and result in the hemifumarate (a mixture of Compound IV and Compound V), even when prepared from the monofumarate.

Recrystallization of Compound I monofumarate in methyl ethyl ketone; acetone; acetone and heptanes; methyl ethyl ketone and heptanes; and ethanol and methyl tertbutyl ether all result in the hemifumarate Pattern 2. The ratio of Compound I as a free base to fumarate measured by $^1$H NMR is about 1:0.5, for example 1:0.52. In one embodiment, Pattern 2 is characterized by an XRPD pattern comprising at least three 2theta values selected from 4.3±0.2°, 6.2 0.2°, 9.0±0 0.2°, 13.0±0.2°, 17.7±0.2°, 18.7±0.2°, and 25.3±0.2° (see Example 12).

Recrystallization of Compound I monofumarate in acetonitrile or acetonitrile and water provides the hemifumarate Pattern 3. The ratio of Compound I as a free base to fumarate measured by $^1$H NMR after isolation by filtration is about 1:0.95, but after washing with water the ratio decreases to about 1:0.76. In one embodiment, Pattern 3 is characterized by an XRPD pattern comprising at least three 2theta values selected from 3.5±0.2°, 5.1±0.2°, 6.2 0.2°, 6.9±0.2°, 10.2±0.2°, 15.3±0.2°, 17.6±0.2°, 21.2±0.2°, and 28.9±0.2° (see Example 12). Recrystallization of Compound I monofumarate in acetone and toluene provided the hemifumarate Pattern 4. The ratio of Compound I as a free base to fumarate measured by $^1$H NMR is about 1:0.7, for example 1:0.69. In one embodiment, Pattern 4 is characterized by an XRPD pattern comprising at least three 2theta values selected from 4.0±0.2°, 6.0±0.2°, 11.8±0.2°, 13.2±0.2°, 14.8±0.2°, 17.7±0.2°, 20.4±0.2°, and 25.2±0.2° (See Example 12). Due to the superior properties of the monofumarate over the hemifumarate, Compound I monofumarate Pattern 1 was selected for further study due to its surprising stability and crystallinity.

In exemplary non-limiting embodiments, a method for the treatment of HPV-induced intraepithelial neoplasia is provided that includes administering an effective amount of one or a combination of the active compounds as described herein in a topical formulation that is sufficient to treat the neoplasia.

In an exemplary embodiment, a formulation for the treatment of intraepithelial neoplasia is a dosage form containing of from 0.005 mg to 50 mg, from 0.05 mg to 40 mg, from 0.1 mg to 30 mg, from 0.5 mg to 20 mg, from 1 mg to 20 mg, from 1 mg to 15 mg, from 1 mg to 10 mg of Compound I monofumarate, Compound II or Compound III.

In certain embodiments, a formulation for the treatment of intraepithelial neoplasia is a dosage form containing of from about 0.001 to about 20 mg, from about 0.005 to about 10 mg, from about 0.01 mg to about 5 mg, from about 0.03 mg to about 1 mg, from about 0.05 mg to about 0.3 mg, from about 0.03 mg to about 0.07 mg, from about 0.05 mg to about 0.15 mg, or from about 0.15 mg to about 0.45 mg of Compound I monofumarate, Compound II or Compound III.

In certain embodiments, a formula for the treatment of intraepithelial neoplasia is a dosage form containing from about 0.001 milligrams to about 0.005 milligrams, from about 0.005 milligrams to about 0.01 milligram, from about 0.01 milligram to about 0.03 milligram, from about 0.03 milligrams to about 0.25 milligrams, from about 0.20 milligrams to about 0.5 milligrams, from about 0.4 milligrams to about 1 milligram, from about 0.75 milligram to about 3 milligrams, from about 1 milligram to about 10 milligrams, from about or 5 milligrams to about 20 milligrams. In certain embodiments, a formulation for the treatment of intraepithelial neoplasia is a dosage form contains about or at least 0.005, 0.01, 0.03, 0.05, 0.1 mg, 0.3 mg. 0.5 mg, 0.7 mg, 1 mg, 1.5 mg, 2 mg, 2.5 mg, 3 mg, 4 mg, 5 mg, 10 mg, 15 mg, 20 mg, 25 mg, 30 mg, 35 mg, 40 mg, 45 mg or 50 mg of Compound I monofumarate, Compound II or Compound III.

A particular dosage is 0.05 mg, 0.1 mg, 0.2 mg, or 0.3 mg of Compound I monofumarate, Compound II or Compound III. In certain embodiments, the 0.05 mg, 0.1 mg, 0.2 mg, or 0.3 mg dosage of Compound I monofumarate, Compound II or Compound III is administered once, twice, or three times per week as needed. In certain embodiments the 0.05 mg dosage of Compound I monofumarate, Compound II or Compound III is administered for the prescribed time instructed by the healthcare provider, including daily dosing.

In certain embodiments, the topical formulation is administered twice a day, once a day, or several days a week (such as 2 or 3 days a week), as long as necessary to achieve the desired results. In certain embodiments, the topical formulation is administered on a weekly schedule for one, two, three, four, five, six or more weeks. In certain aspects, the topical formulation is administered on a schedule of three dosages a week for two, three four, five or six weeks.

In certain embodiments, the compound can be administered in one or more therapeutic cycles comprising a treatment cycle and a rest cycle, wherein the treatment cycle comprises administering the compound as described herein, followed by a rest cycle (comprising a period of no treatment) before the next treatment cycle. In certain embodiments, the rest cycle is from about one day to about six months. In certain embodiments the rest cycle is one, two, three, four, five, six, seven, eight or more weeks before the next treatment cycle. In certain embodiments, multiple therapeutic cycles are administered, for example one, two, three, four, five, or six therapeutic cycles.

Dosage forms which do not adhere well to the target site may be dislodged, interfering with treatment. Dosage forms have been discovered that adhere to the target site and dissolve rapidly in low fluid volumes. Adhesion to the target site also prevents exposure to non-target tissues, which may limit toxicity, unwanted systemic exposure, and side effects. Dosage forms which soften, break down, and/or disintegrate quickly in low fluid volumes are advantageous to cause a rapid release of the active compound to the target tissue. Dosage forms that disintegrate in, for example, less than about 50 µL, less than about 100 µL, less than about 125 µL, less than about 150 µL, less than about 175 µL, less than about 200 µL, less than about 250 µL, less than about 500 µL, less than about 1 mL, or less than about 2 mL fluid facilitate drug penetration into the target site.

In certain embodiments, the dosage form is a semisolid such as a gel or cream. In certain embodiments, the dosage form is a tablet. In certain embodiments, the dosage form disintegrates in about one to about ten seconds. In certain embodiments, the dosage form disintegrates in about ten seconds to one minute, in certain embodiments, the dosage form disintegrates in about one minute to about one hour. In certain embodiments, the dosage form disintegrates in one to six hours.

The physical dimensions of the dosage form can impact the effectiveness of the dosage form. A tablet that is thinner provides a greater surface area to volume ratio and may degrade quicker and cover the target area better. In certain embodiments the dosage form is less than 3 millimeters thick in its smallest dimension.

The formulation of the dosage form is very important for adequate administration of the active agent into the intraepithelial tissue. The formulation for example, can be prepared for use as a tablet, a reconstituted powder, a dry powder, a semi solid dosage form, a film or a pessary (i.e., a vaginal suppository).

Tablet formulation should display the properties of mucoadhesion and substantivity and include excipients that have solubilizing, erosion-generating (for disintegration), porosity (for water uptake) and viscosity enhancing (to keep the drug at the target site) properties.

Examples of excipients that will cause rapid disintegration of a solid dosage form to cover the cervix, anal, penile, perianal, vulvar, or vaginal areas include, but are not limited to mannitol, microcrystalline cellulose, lactose, sucrose, calcium phosphate, sodium phosphate, sodium bicarbonate, citric acid, maleic acid, adipic acid or fumaric acid. Examples of excipients that can enhance disintegration and coverage of the affected area include but are not limited to sodium starch glycollate, pregelatinized starch, crospovidone and croscarmellose sodium. Mucoadhesive excipients that are useful in the present invention include but are not limited to microcrystalline cellulose, polycarbophil, hydroxymethyl cellulose, hypromellose, hydroxypropyl cellulose, and PVP.

A nonlimiting example of a tablet formulation includes, but is not limited to, microcrystalline cellulose, crospovidone, magnesium stearate, silicon dioxide, polyethylene oxide and mannitol. Another non-limiting example of a tablet formulation has microcrystalline cellulose, magnesium stearate and mannitol.

Alternative formulations are reconstituted powders or dry powders. These formulations can include excipients described above and in certain embodiments xanthan gum can be added. As a non-limiting example, a dry powder formulation can include, but is not limited to, xanthan gum, mannitol, silicon dioxide and sodium benzoate.

Semi solid dosage forms may include, for example, a mucoadhesive polymer, a solubility/penetration enhancer, a lipophilic solubilizer and a penetration enhancer. The mucoadhesive polymer, for example, may be, but is not limited to, a carbomer, polyethylene glycol, crospovidone, hypromellose, polycarbophil and/or hydroxyethyl cellulose. The solubility/penetration enhancer can be, for example, but not limited to, a mixture of polyoxyl 6 stearate Type I, ethylene glycol stearates and polyoxy 32 stearate Type I, cetyl alcohol, stearyl alcohol, polysorbate 80, sodium lauryl sulphate, mono and di-glycerides, sorbitan monostearate, glyceryl isostearate, polyoxy 15 hydroxystearate, poly15 hydroxystearate, polyoxy 40 hydrogenated castor oil, octyl dodecanol, and/or soybean lecithin. Lipophilic solubilizers include, but are not limited to light mineral oil, mineral oil, white wax and silicone fluid. Penetration enhancers include but are not limited to propylene glycol, transcutol, oleic acid, isopropyl myristate, propylene glycol glycerol monooleate, propylene glycol monocaprylate, PEG-8 Bees wax, cetyl alcohol, stearic acid, cetyl palmitate and/or cetostearyl alcohol.

A non-limiting example of a semi-solid formulation includes, for example, a carbomer, propylene glycol, sorbic acid, EDTA and water. Another non-limiting example of a semi solid formulation includes a carbomer, mineral oil, a mixture of polyoxy 6 stearate Type I, ethylene glycol stearate, polyoxy 32 stearate Type I, parabens, propylene glycol, EDTA and/or water.

Films can be produced, for example, with, but not limited to, hypromellose, polyethylene glycol, polymethacrylates, microcrystalline cellulose, xanthan gum, guar gum and/or polyvinylpyrrolidone.

A pessary (vaginal suppository) can be formulated with, for example but not limited to, hard fat (such as Ovucire, Witepsol, Supposi-Base), polyethylene glycol, macrogols, cocoa butter and glycerol. A non-limiting example of a pessary can be made from Witepsol H 15 or Ovucire WL 3264.

Therefore, the present invention includes at least the following features:

(i) Compound I monofumarate;
(ii) Compound II;
(iii) Compound III;
(iv) Compound IV;
(v) Compound V;
(vi) The Compound of (i), (ii), (iii), (iv) or (v) in enantiomerically enriched or enantiomerically pure form;
(vii) The Compound of (ii) wherein the amount of R by weight is for example, greater than about 50%, or equal to or greater than about 60%, 70%, 75%, 80%, or even 85% or more;
(viii) The Compound of (vii) wherein the amount of the S-stereoconfiguration at the chiral carbon is greater than about 50%, or equal to or greater than about 60%, 70%, 75%, 80%, or even 85% or more;
(ix) Enantiomerically pure (R,S) Compound I;
(x) Enantiomerically pure (S,S) Compound I;
(xi) The R,S enantiomerically pure Compound II in a highly crystalline form;
(xii) Compound II Pattern 1;
(xiii) Morphic forms described more specifically in Section III;
(xiv) Topical pharmaceutical compositions comprising an effective amount of an active compound as described herein or a morphic form thereof and a pharmaceutically acceptable carrier;
(xv) The topical formulation of (xiv) in the form of a tablet;
(xvi) The tablet dosage form of (xv), comprising Compound I monofumarate, mannitol, polycrystalline cellulose and magnesium stearate;
(xvii) The tablet dosage form of (xv), comprising Compound II, mannitol, polycrystalline cellulose and magnesium stearate;
(xviii) The topical formulation of (xiv) in the form of a semi-solid dosage form;
(xix) The semi-solid dosage form of (xviii), comprising Compound I monofumarate, light mineral oil, propylparaben, Tefose® 63, water, EDTA, methylparaben and Carbopol® 974P;
(xx) The semi-solid dosage form of (xviii), comprising Compound I monofumarate, water, EDTA, methyl paraben, Carbopol® 974P, propylene glycol and optionally sorbic acid;
(xxi) The semi-solid dosage form of (xviii), comprising Compound II, light mineral oil, propylparaben, Tefose® 63, water, EDTA, methylparaben and Carbopol® 974P;
(xxii) The semi-solid dosage form of (xviii), comprising Compound II, water, EDTA, methyl paraben, Carbopol® 974P, propylene glycol and optionally sorbic acid;
(xxiii) The topical formulation of (xiv) in the form of a reconstituted powder;
(xxiv) The topical formulation of (xiv) in the form of a dry powder dosage form;
(xxv) The topical formulation of (xiv) in the form of a film;
(xxvi) The topical formulation of (xiv) in the form of a pessary;
(xxvii) Advantageous dosage forms of (xv)-(xxvi) for delivery to the cervix, vagina, vulva, penis, perianal region, and/or anus;
(xxviii) A method to treat an HPV-induced infection or an associated condition, including but not limited to intraepithelial neoplasia such as cervical, vaginal, vulvar, perianal, anal or penile, comprising administering to a host in need thereof an effective amount of a compound, morphic form, or pharmaceutical composition of any one of embodiments above to a host in need thereof;
(xxix) Use of any of the embodiments above in the manufacture of a medicament for the treatment of HPV infection or an associated condition, including but not limited to intraepithelial neoplasia such as cervical, penile, vulvar, perianal, anal or vaginal, in a host in need thereof;
(xxx) Embodiments (i)-(xxvii) for use to treat HPV infection or an associated condition, including but not limited to intraepithelial neoplasia, such as cervical, penile, vulvar, perianal, anal or vaginal, in a host in need thereof;
(xxxi) Any one of above embodiments, wherein the host is a human;
(xxxii) Any of the topical formulations described above, for the treatment of intraepithelial neoplasia that provides a dosage form containing of from 0.005 mg to 50 mg, from 0.05 mg to 40 mg, from 0.1 mg to 30 mg, from 0.05 to 0.3 mg, from 0.5 mg to 20 mg, from 1 mg to 20 mg, from 1 mg to 15 mg, from 1 mg to 10 mg of a compound of embodiments (i)-(v) and in certain embodiments about or at least 0.005, 0.01, 0.03, 0.05, 0.1 mg, 0.3 mg. 0.5 mg, 0.7 mg, 1 mg, 1.5 mg, 2 mg, 2.5 mg, 3 mg, 4 mg, 5 mg, 10 mg, 15 mg, 20 mg, 25 mg, 30 mg, 35 mg, 40 mg, 45 mg or 50 mg;
(xxxiii) Any of the topical formulations described above, for the treatment of intraepithelial neoplasia that provides a dosage form containing from about 0.001 to about 20 mg, from about 0.005 to about 10 mg, from about 0.01 mg to about 5 mg, from about 0.03 mg to about 1 mg, from about 0.05 mg to about 0.3 mg, from about 0.03 mg to about 0.07 mg, from about 0.05 to about 0.15 mg, or from about 0.15 mg to about 0.45 mg of a compound of embodiments (i)-(v).
(xxxiv) The topical formulation of embodiments (xiv) to (xxvii) administered twice a day, once a day, or several days a week (such as 2 or 3 days a week), or as long as necessary to achieve the desired results;
(xxxv) The topical formulation of embodiments (xiv) to (xxvii) that are administered on a weekly schedule for one, two, three, four, five, six or more weeks;
(xxxvi) The method of (xxviii), further including applying a lubricant to the dosage form or epithelial tissue before inserting the dosage form in the affected area;
(xxxvii) The method of (xxxvi), wherein the lubricant is selected from water, a glycerol based lubricant and a hydroxyethylcellulose-based lubricant; and
(xxxviii) Process for the preparation of the topical formulations of embodiments of (xiv) to (xxviii);
(xxxix) A method to treat an HPV-induced infection or an associated condition, including but not limited to intraepithelial neoplasia such as cervical, penile, vulvar, perianal, anal or vaginal, comprising administering an effective amount of embodiments (i)-(xxii) to a host in need thereof, in combination with surgical treatment of the target tissue before, during or after administration of the compound;
(xl) The method of (xxxix) comprising a surgical treatment of the target tissue followed by administering an effective amount of embodiments (i)-(xxii) to a host in need thereof;

(xli) The method of (xxxiv) comprising administering an effective amount of embodiments (i)-(xxii) to a host in need thereof, followed by surgical treatment of the target tissue;

(xlii) The method of (xxxiv) comprising administering an effective amount of embodiments (i)-(xxii) to a host in need thereof, around or at approximately the same time as surgical treatment of the target tissue;

(xliii) The method of embodiments (xxxiv)-(xxxvii) wherein the surgical treatment of the target tissue is excision;

(xliv) The method of embodiments (xxxiv)-(xxxvii) wherein the surgical treatment of the target tissue is ablation;

(xlv) The method of (xliii) wherein the excision is a loop electrosurgical excision procedure (LEEP);

(xlvi) The method of (xliii) wherein the excision is a large loop excision of the transformation zone (LLETZ);

(xlvii) The method of (xliii) wherein the excision is a knife cone biopsy;

(xlviii) The method of (xliii) wherein the excision is laser conization;

(xlix) The method of (xliv) wherein the ablation is laser ablation; and (l) The method of (xliv) wherein the ablation is cryoablation.

(li) Processes for the manufacture of Compound II, as described herein; and (lii) Processes for the manufacture of the morphic forms described herein.

Figure 116:
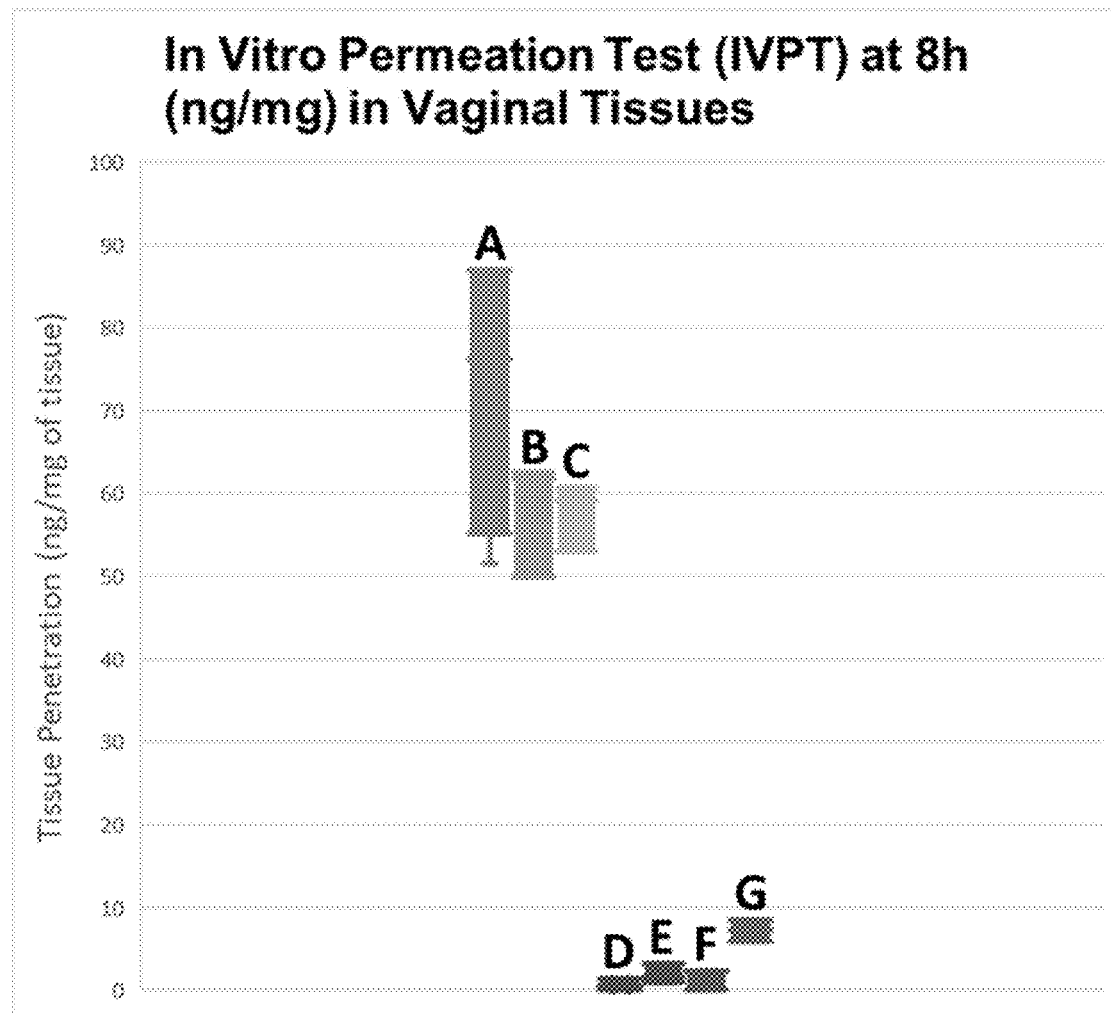

FIG. 116 is an in vitro tissue permeation test in vaginal tissue comparing Compound II to ABI-1968. Bar A shows the tissue penetration of a 0.1% Compound II gel in porcine vaginal tissue. Bars B and C show the tissue penetration of a 0.1% Compound II gel in human cervical tissue. Bar D shows the tissue penetration of a 1% formulation of ABI-1968 in 6% NMP into porcine vaginal tissue. Bar E shows the tissue penetration of a 1% nanosuspension of ABI-1968 in porcine vaginal tissue. Bar F shows the tissue penetration of a 3% formulation of ABI-1968 in 6% NMP into porcine vaginal tissue. Bar G shows the tissue penetration of a 3% formulation of ABI-1968 in 20% NMP into porcine vaginal tissue. ABI-1968 penetrates the tissue to a substantially smaller degree, which hinders the ability of the compound to reach the cells which are infected with HPV. This may be a contributing factor to the performance of ABI-1968 in clinical studies. Surprisingly, Compound II displays high tissue penetration in both porcine and human tissues. High tissue penetration may lead to high activity against HPV. This is described in Example 41.

Figure 117:
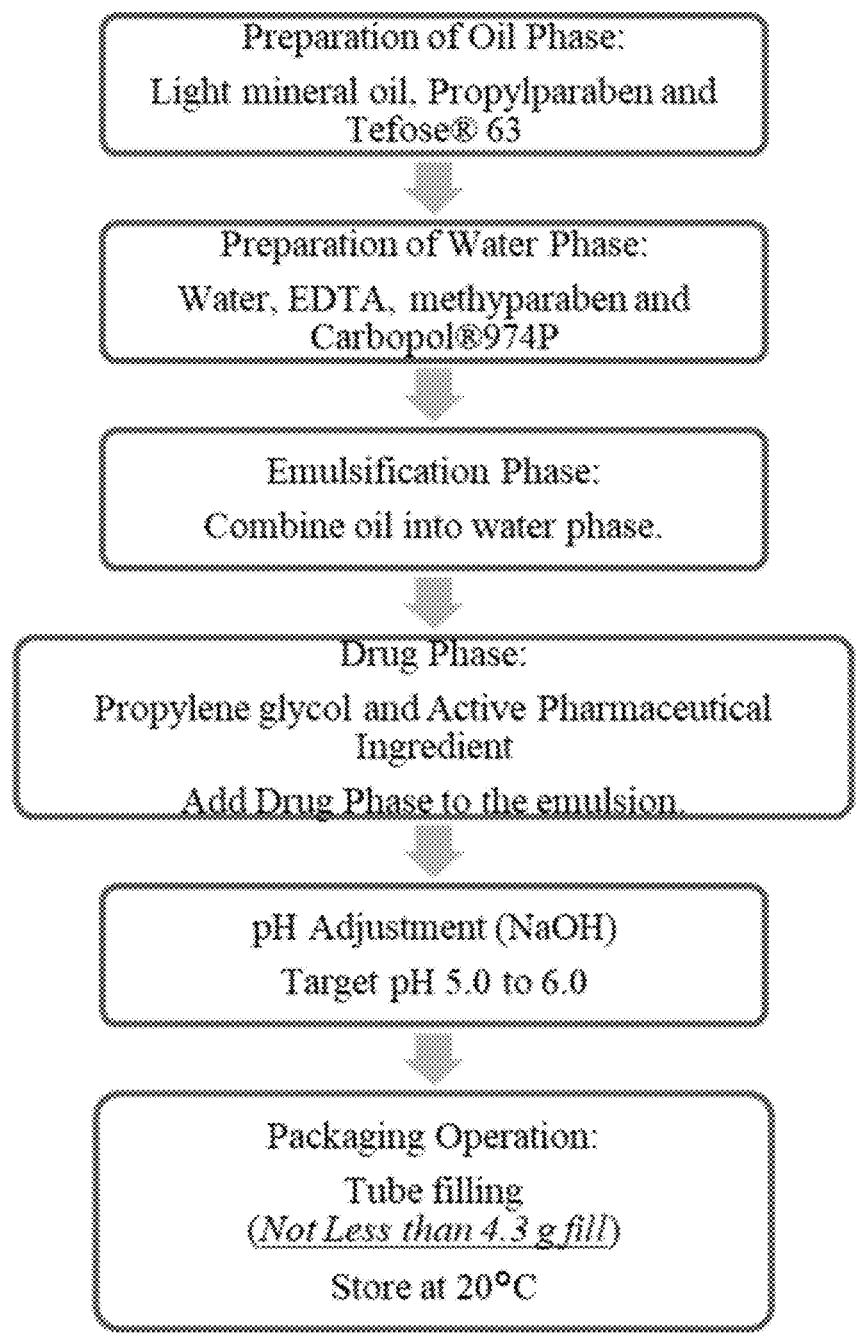

FIG. 117 shows a flow diagram for the process of preparing a topical cream formulation described in Example 29.

Figure 118:
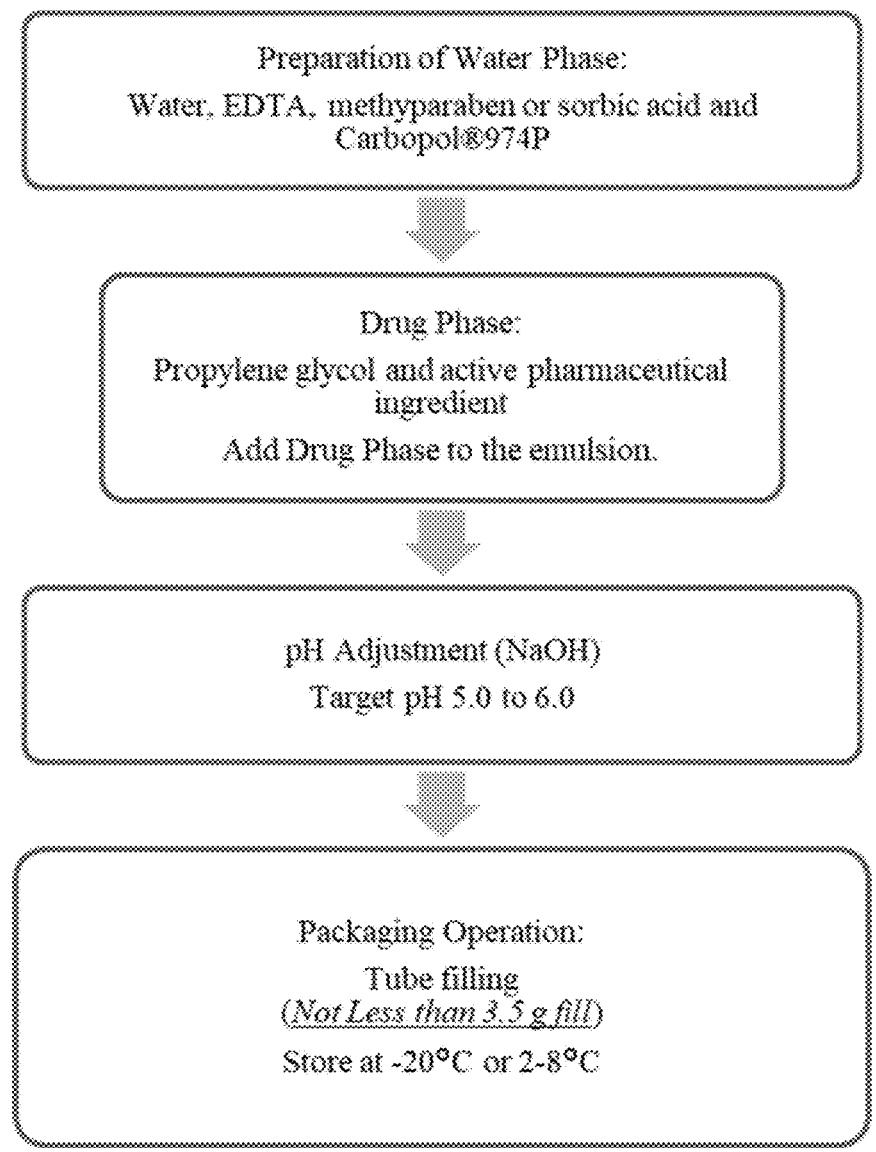

FIG. 118 shows a flow diagram for the process of preparing a topical gel formulation described in Example 29.

Figure 119:
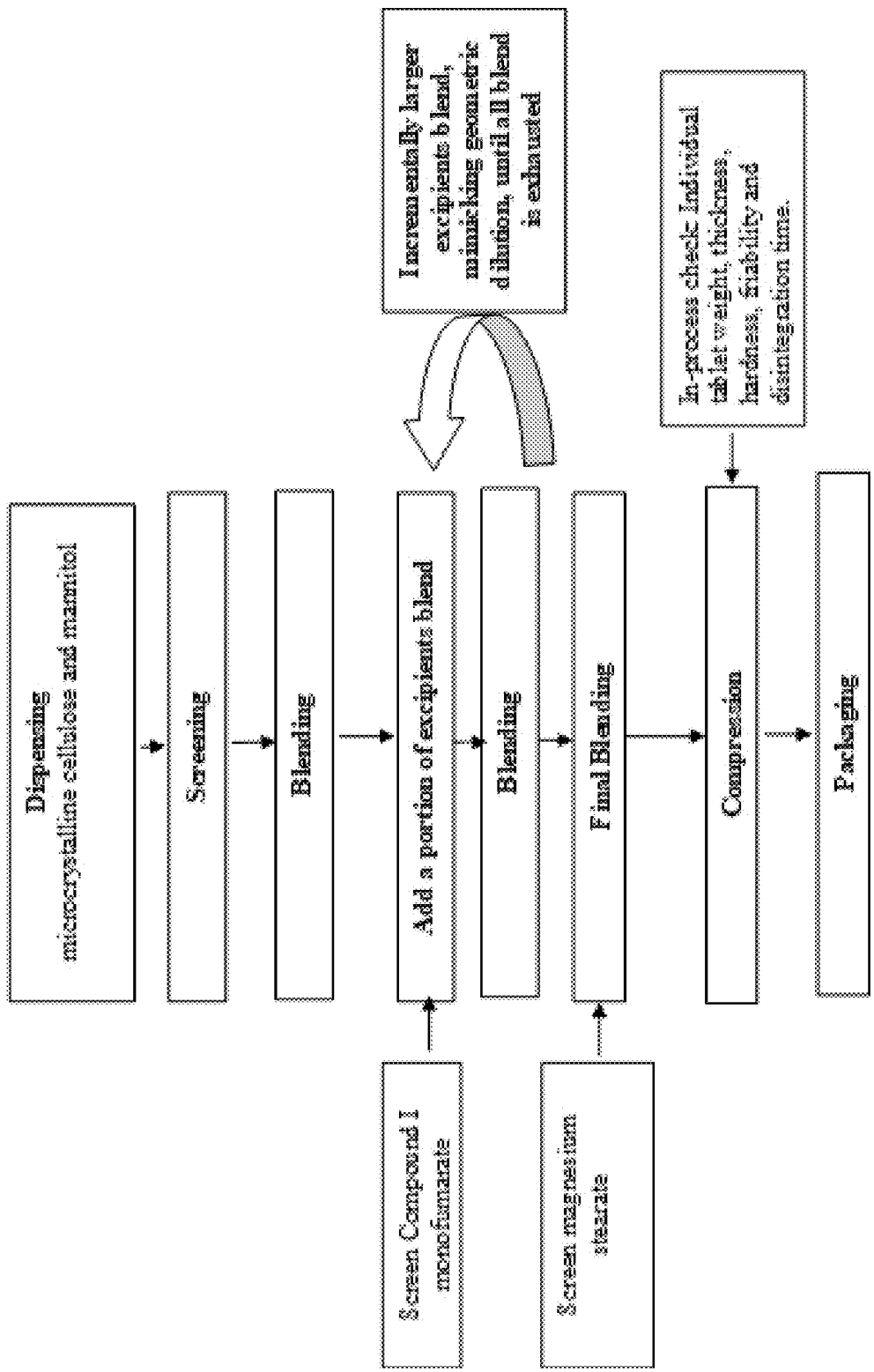

FIG. 119 shows a flow diagram for the process of preparing a tablet formulation described in Example 30.

Figure 120:
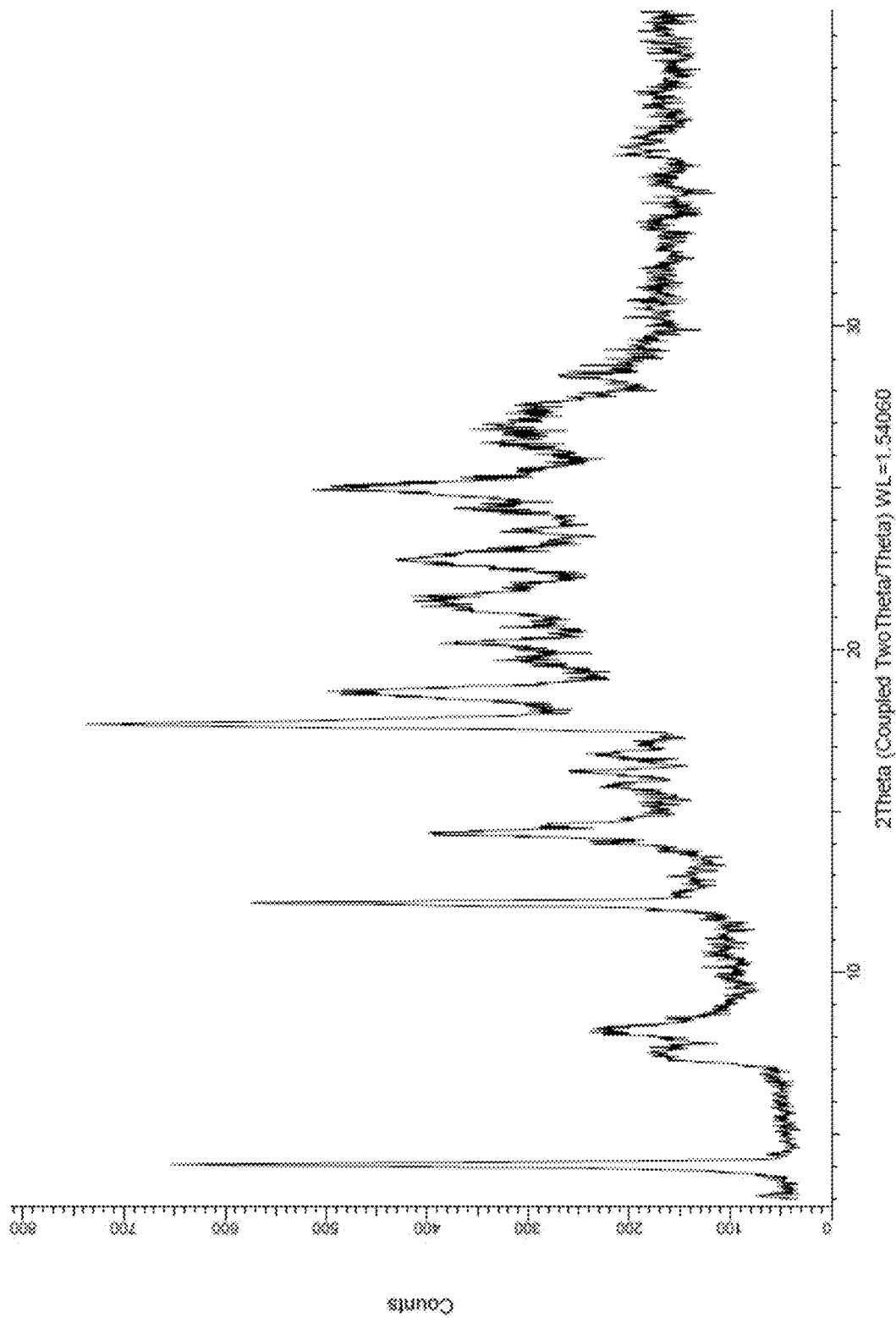

FIG. 120 is an XRPD diffractogram of (S,S)-Compound I with medium crystallinity as described in Example 12.

Figure 121:
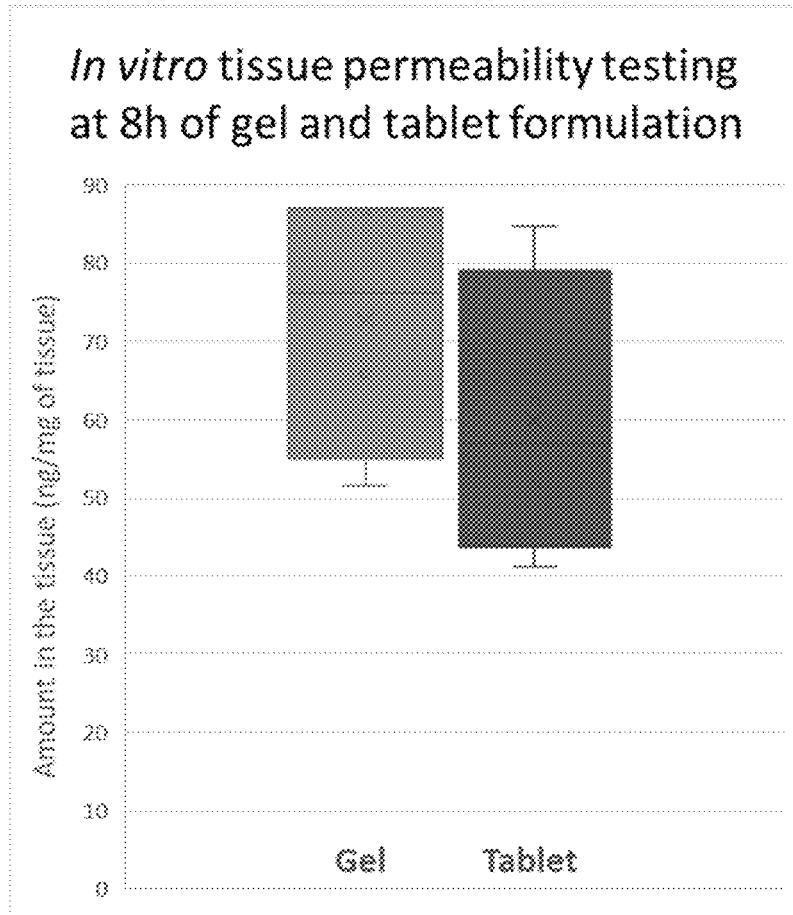

FIG. 121 is a bar graph comparing the tissue penetration of a topical gel and a topical tablet dosage form as described in Example 41. The tablet dosage form produces similar tissue penetration to the topical gel, with an average of 58 ng/mg of compound in the tissue.

Figure 122:
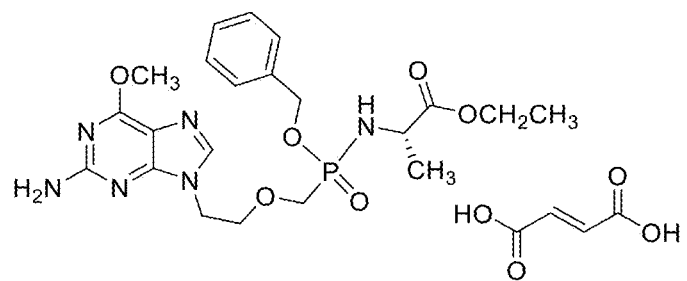
Figure 122:
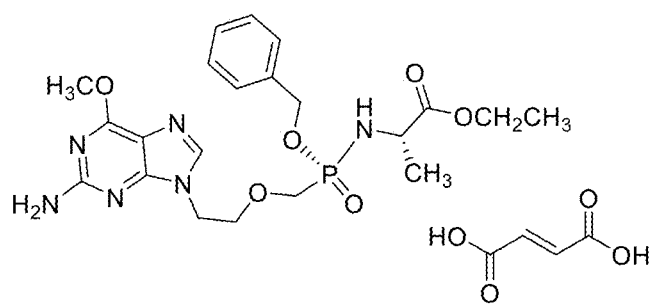
Figure 122:
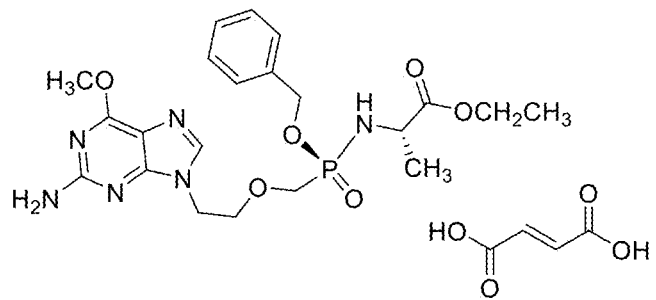

FIG. 122 depicts the structures of Compound I monofumarate, Compound II and Compound III. The synthesis of these compounds can be found in Examples 26-28.

DETAILED DESCRIPTION OF THE INVENTION

It has been discovered that an effective composition for the treatment of HPV infection or a disease or condition related to HPV infection such as HPV-induced neoplasia, including but not limited to cervical intraepithelial neoplasia, perianal intraepithelial neoplasia, penile intraepithelial neoplasia, vulvar intraepithelial neoplasia, anal intraepithelial neoplasia, and vaginal intraepithelial neoplasia, requires the combination of the selection a number of aspects that work together to achieve the desired results. It was essential to select the right compound with advantageous lipophilic and tissue penetrating properties combined with a selected pharmaceutically acceptable salt optionally in advantageous morphic forms to achieve the long-sought ability to penetrate the epithelial stratified tissues in an effective amount to deliver the active agent. It required years of research to solve this problem, after many failures, to the benefit of patients globally suffering from interepithelial neoplasia that may become cancerous.

Specifically, it was discovered that the key compound for delivery of the active agent is a specific salt of:

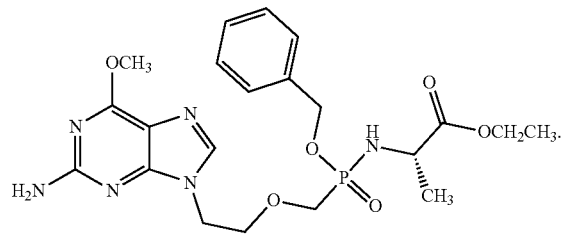

Compound I

Compound I is (ethyl(((2-(2-amino-6-methoxy-9H-purin-9-yl)ethoxy)methyl)(benzyloxy)-phosphoryl)-L-alaninate).

U.S. Pat. Nos. 9,801,884 and 11,344,555 assigned to the Regents of the University of California claim Compound I and pharmaceutically acceptable salts generally, as well as methods of using the same for treating a papillomavirus infection. Compound I is an acyclic nucleotide phosphonate that metabolizes to a known potent antiviral compound (PMEG; ((9-[2-phosphonomethyoxy)ethyl)guanine])) but has poor cellular permeability and use-limiting systemic toxicity. The assignee has discovered how to improve the prodrug to be delivered topically in a manner that it is rapidly taken up into epithelial cells, a challenging task to date and one that ABI-1968 failed.

Compound I (ethyl (-((2-(2-amino-6-methoxy-9H-purin-9-yl)ethoxy)methyl)-(benzyloxy)phosphoryl)-L-alaninate) has two chiral centers, one at the phosphorus atom and one in the amino acid moiety, either of which can be in the R or S stereoconfiguration. Therefore, Compound I has four stereoisomers. While U.S. Pat. Nos. 9,801,884 and 11,344,555 describe Compound I generally, the patents do not address the potential stereochemistry of the phosphorus atom. It has been discovered that the stereoisomer of Compound I with R-stereochemistry at the phosphorus and S-stereochemistry at the amino acid carbon has advantageous properties over the other three stereoisomers, as discussed further herein.

In a non-limiting embodiment, the advantageous salt (for example fumarate) of Compound I is used as a mixture of (R,S) and (S,S) diastereomers, wherein the first R/S designates the stereochemistry at the phosphorus atom and the second S is the stereochemistry of the carbon in the amino acid moiety (corresponds to the L-alanine residue having S-configuration). While any ratio of the diastereomers can be used that provides the desired results, the (R,S) diastereomer stands out. In other embodiments, the ratio is approximately 1:1 of the R to S enantiomer at the phosphorus atom. In certain aspects, the compound is enantiomerically enriched with the R enantiomer at the phosphorus atom, wherein the amount of R by weight is for example, greater than about 50%, or equal to or greater than about 60%, 70%, 75%, 80%, or even 85% or more.

The S-stereoconfiguration at the chiral carbon corresponding to the natural amino acid configuration is advantageous in the present invention. In other aspects, the amount of S by weight is for example, greater than about 50%, or equal to or greater than about 60%, 70%, 75%, 80%, or even 85% or more. In alternative embodiments, the R-stereoconfiguration of the chiral carbon is predominant and is greater than about 50%, or equal to or greater than about 60%, 70%, 75%, 80%, or even 85% or more, In principal aspects, therefore, the invention includes the administration of an effective amount of the fumarate salt of $(R_P, S_C)$ ethyl (((2-(2-amino-6-methoxy-9H-purin-9-yl)ethoxy)methyl)(benzyloxy)-phosphoryl)-L-alaninate (Compound II) as described herein, optionally in a pharmaceutically acceptable carrier. The present invention provides a pharmaceutical salt of an acyclic nucleotide, methods, compositions, and dosage forms for the treatment of diseases associated with human papilloma virus (HPV).

Compound II

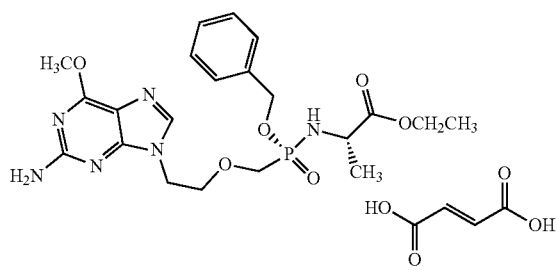

The compound, compositions, and dosage forms can also be used to treat conditions related to or occurring as a result of an HPV viral exposure or infection. For example, the active compound can be used to treat precancerous cervical lesions, cervical intraepithelial neoplasia, vaginal, vulvar, penile, perianal, and anal intraepithelial neoplasia, cervical cancer, rectal cancer, penile cancer, vaginal cancer, and oropharyngeal cancer.

The active compounds and compositions can also be used to treat an infection caused by the range of HPV types. Most of the cancer-causing HPV types are from the alpha-7 and alpha-9 species including types 16, 18, 31, 33, 35, 39, 45, 51, 52, 56, 58, 59, 68, 73, and 82. The most common cancer-causing HPV types are 16 and 18. HPV-16 and HPV-18 are reported to be the cause of 50% of cervical cancers; and 90% of venereal warts are caused by HPV-6 and HPV-11 (World Health Organization, "Cervical Cancer" https://www.who.int/news-room/fact-sheets/detail/cervical-cancer). Infection with one type of genotype does not preclude a later infection with a different genotype.

In one embodiment, Compound I monofumarate, Compound II or Compound III is used to treat HPV-16. In one embodiment, Compound I monofumarate, Compound II or Compound III is used to treat HPV-18. In one embodiment, Compound I monofumarate, Compound II or Compound III is used to treat a high risk HPV infection. In one embodiment, Compound I monofumarate, Compound II or Compound III is used to treat HPV type 31, 33, 35, 39, 45, 51, 52, 56, 58, 59, 68, 73, or 82.

In one embodiment, the compound, formulations, or solid dosage forms that include the compound can also be used prophylactically to prevent or retard the progression of clinical illness in individuals who are HPV positive or who have been exposed to HPV.

In particular, it has been discovered that Compound II exhibits superior drug-like and pharmacological properties.

Figure 114:
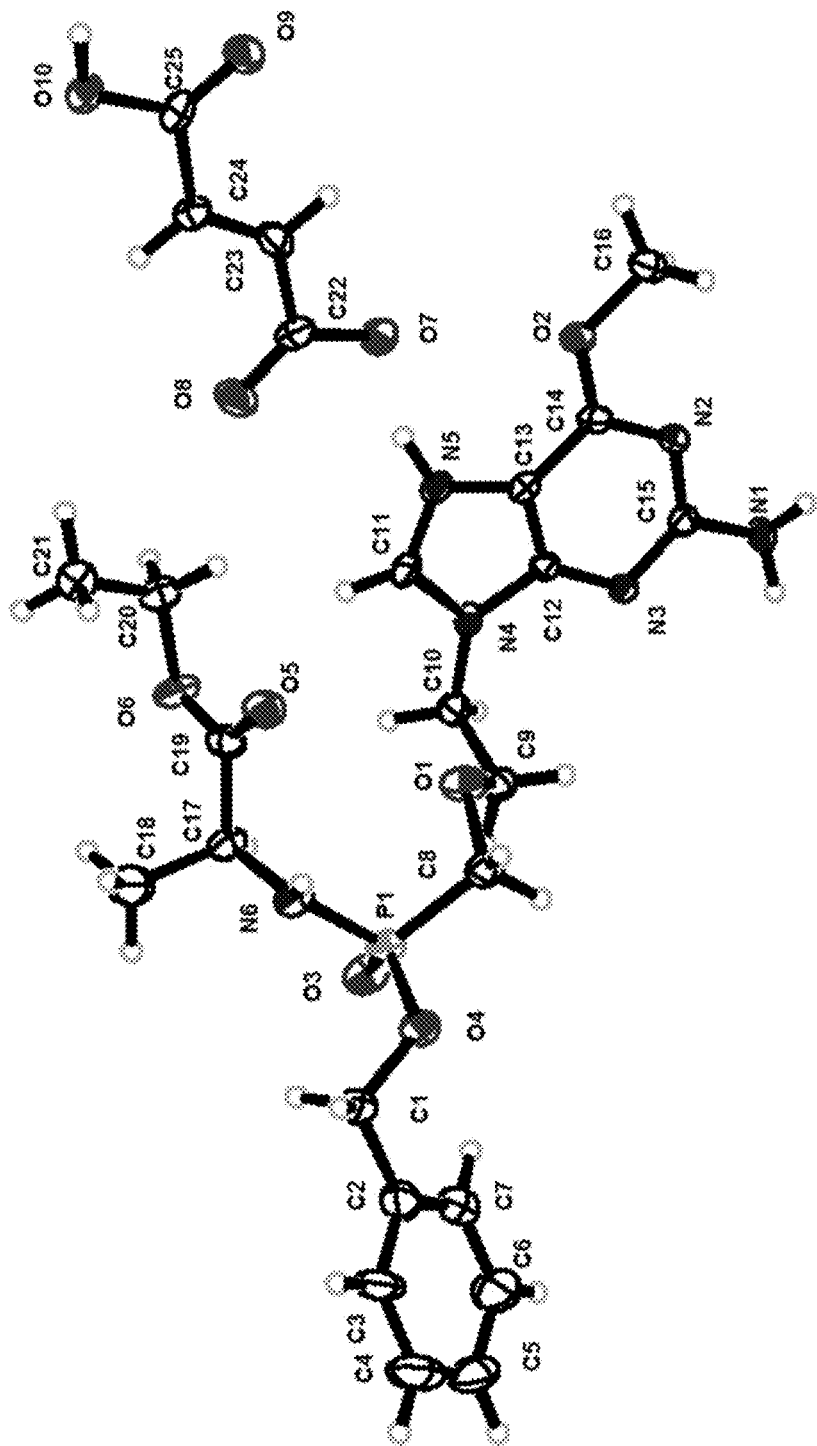
FIG. 114 is the molecular structure of Compound II Pattern 1 as determined by the single crystal X-ray diffraction analysis of Example 25.
Figure 115:
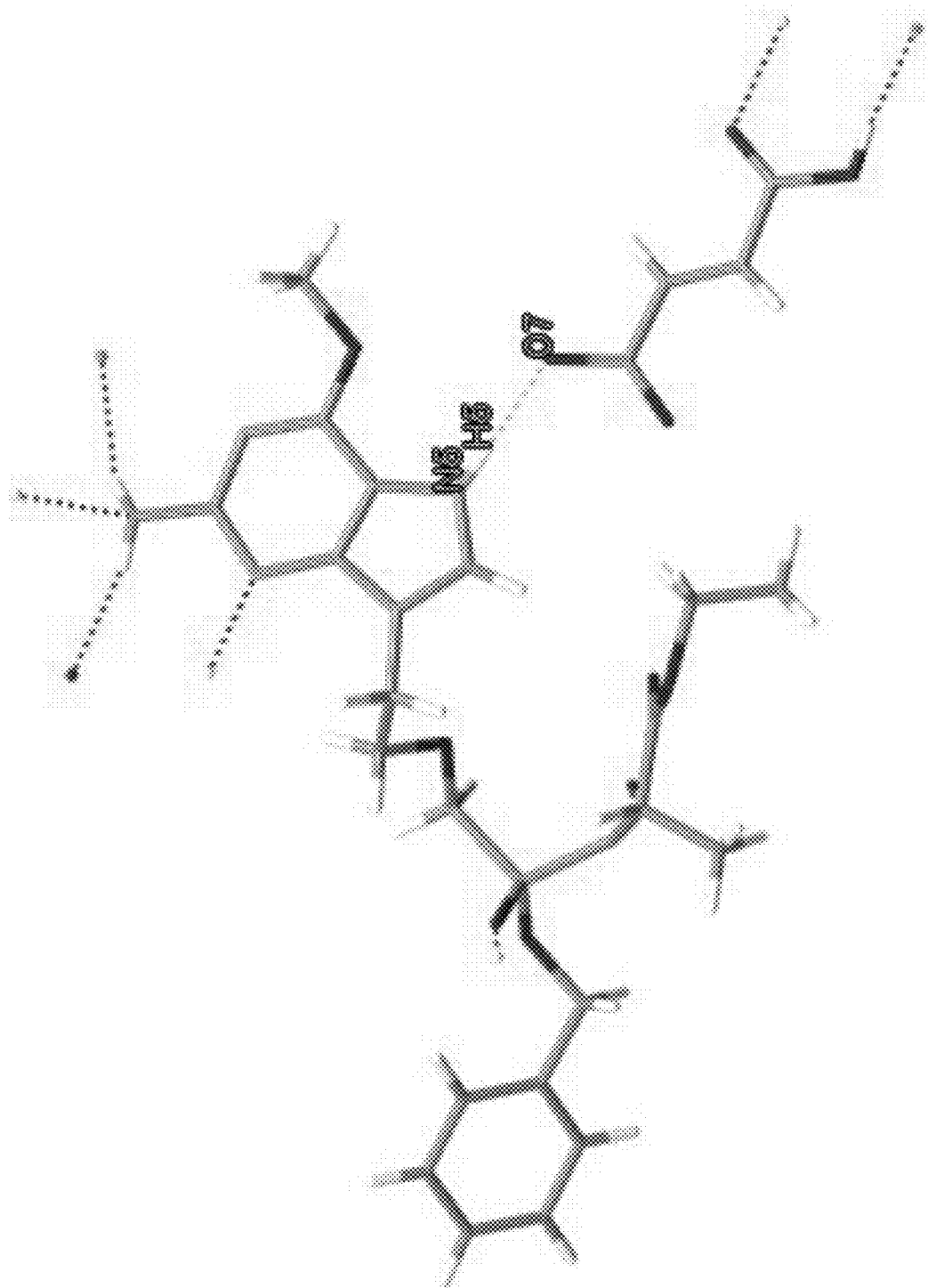
FIG. 115 is the molecular structure of Compound II Pattern 1 as determined by the single crystal X-ray diffraction analysis of Example 25. There exists an intermolecular interaction between protonated N5-atom of free base and O7-atom of fumaric acid anion (N(5)-H(5) . . . O(7)) in the single-crystal form of Pattern 1.

Compound II has R-stereochemistry at the phosphorus atom which has been confirmed with X-ray crystallography (Example 25, see FIG. 114 and FIG. 115). In alternative embodiments, Compound II can be used in the form of any desired ratio of phosphorus R- and S-enantiomers, including up to pure enantiomers. In some embodiments, Compound II is used in a form that is at least 90% free of the opposite enantiomer, and can be at least 98%, 99%, or even 100% free of the opposite enantiomer. Unless described otherwise, an enantiomerically pure Compound II is at least 90% free of the opposite enantiomer. In certain embodiments Compound II is used as a racemic mixture of isomers. In addition, in an alternative embodiment, the amino acid of the phosphonamidate can be in the D- or L-configuration, or a mixture thereof, including a racemic mixture.

Where a phosphonamidate exhibits chirality, it can be provided as an R or S chiral phosphorus derivative or a mixture thereof, including an enantiomerically enriched form including a racemic mixture. All of the combinations of these stereoconfigurations are alternative embodiments in the invention described herein. In another embodiment, at least one of the hydrogen atoms of Compound I, Compound II, or Compound III can be replaced with deuterium.

In certain embodiments, Compound I may be:

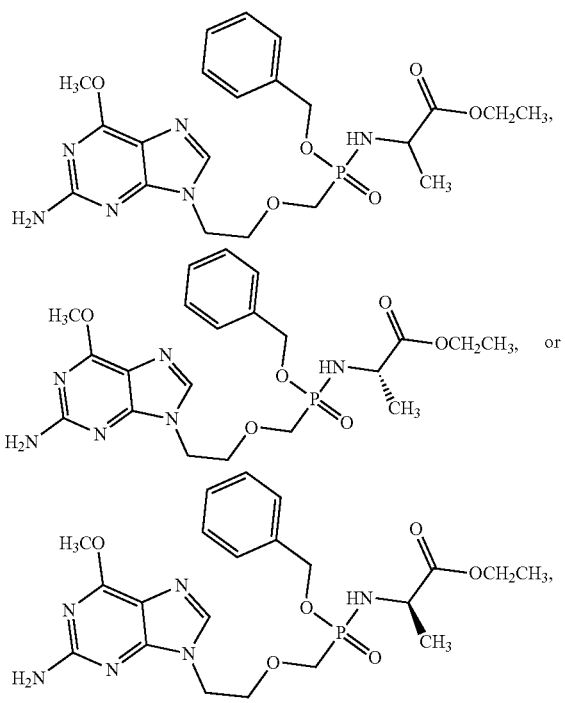

or a pharmaceutically acceptable salt thereof.

In certain embodiments Compound II may be

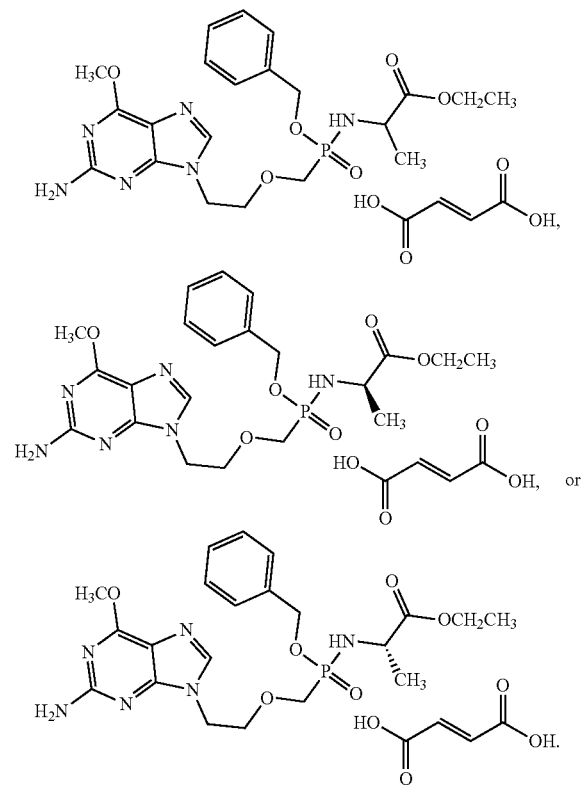

In certain embodiments, Compound III may be

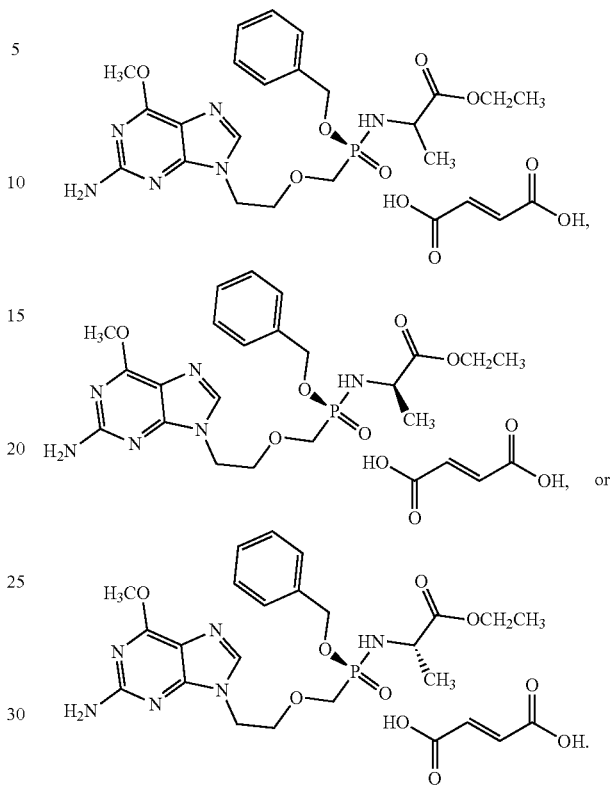

I. Fumarate salt of ($R_P$, $S_C$) ethyl (((2-(2-amino-6-methoxy-9H-purin-9-yl)ethoxy)methyl)(benzyloxy)phosphoryl)-L-alaninate (Compound II)

In certain embodiments, the active compound of the invention is Compound II, which can be provided in a pharmaceutically acceptable composition or solid dosage form thereof. In an embodiment, Compound II is an amorphous solid. In yet a further embodiment, Compound II is a crystalline solid.

Synthesis of Compound II

The present invention further includes a non-limiting illustrative process for the preparation of a fumarate salt of Compound I such as Compound II that includes (i) a first step of dissolving Compound I, $R_P$, $S_C$ isomer in an organic solvent, for example, acetone, methanol, ethanol, isopropanol, dichloromethane, tetrahydrofuran or acetonitrile or the like, in a flask or container;

(ii) adding fumaric acid at a specific molar ratio (for example 0.5:1.0, 1.0:1.0, or 1.5:1) to the solution of $R_P$, $S_C$ Compound I of step (i) at ambient or slightly increased or decreased temperature (for example 23-55° C.);

(iii) stirring the reaction of step (ii) at ambient or slightly increased or decreased temperature;

(iv) optionally seeding the solution of step (iii) with crystals of Compound II;

(v) adding a second organic solvent to induce crystallization, for example, pentane, n-hexane, heptanes, petroleum ether, methyl tert-butyl ether, diethyl ether or water;

(vi) optionally stirring the resulting solution at ambient or slightly increased or decreased temperature;

(vii) cooling the resulting solution to a decreased temperature, for example about 0-10° C., then stirring the solution at that temperature
(viii) filtering the resulting solids; and
(ix) optionally drying the solids at a reduced pressure and increased temperature, for example at or at least 30° C., 35° C., 40° C., 45° C., or 50° C.;

In certain embodiments, step (i) above is carried out in isopropanol. Further, the second organic solvent in step (v) may be for example heptanes.

In one embodiment, Compound I $R_P$, $S_C$ isomer is dissolved in ethanol in step (i). In one embodiment, Compound I $R_P$, $S_C$ isomer is dissolved in methanol in step (i). In one embodiment, Compound I $R_P$, $S_C$ isomer is dissolved in acetonitrile in step (i). In an additional embodiment, Compound I $R_P$, $S_C$ isomer is dissolved in tetrahydrofuran in step (i).

In one embodiment, the second organic solvent in step (v) is pentane. In one embodiment, the second organic solvent in step (v) is hexane. In one embodiment, the second organic solvent in step (v) is methyl tert-butyl ether. In one embodiment, the second organic solvent in step (v) is water.

The present invention further includes a non-limiting illustrative process for the preparation of Compound III that includes
(x) a first step of dissolving Compound I, $S_P$, $S_C$ isomer in an organic solvent, for example, acetone, methanol, ethanol, isopropanol, dichloromethane, tetrahydrofuran or acetonitrile or the like, in a flask or container;
(xi) adding fumaric acid at a specific molar ratio (for example 0.5:1.0, 1.0:1.0, or 1.5:1) to the solution of Compound I of step (i) at ambient or slightly increased or decreased temperature (for example about 23-55° C.);
(xii) stirring the reaction of step (ii) at ambient or slightly increased or decreased temperature;
(xiii) optionally seeding the solution of step (iii) with crystals of Compound II;
(xiv) adding a second organic solvent to induce crystallization, for example, pentane, n-hexane, heptanes, petroleum ether, methyl tert-butyl ether, diethyl ether or water;
(xv) optionally stirring the resulting solution at ambient or slightly increased or decreased temperature;
(xvi) cooling the resulting solution to a decreased temperature, for example about 0-10° C., then stirring the solution at that temperature
(xvii) filtering the resulting solids; and
(xviii) optionally drying the solids at a reduced pressure and increased temperature, for example at or at least 30° C., 35° C., 40° C., 45° C., or 50° C.

In certain embodiments, step (i) above is carried out in isopropanol. Further, the second organic solvent in step (v) may be for example heptanes.

In one embodiment, Compound I $S_P$, $S_C$ isomer is dissolved in ethanol in step (i). In one embodiment, Compound I $S_P$, $S_C$ isomer is dissolved in methanol in step (i). In one embodiment, Compound I $S_P$, $S_C$ isomer is dissolved in acetonitrile in step (i). In an additional embodiment, Compound I $S_P$, $S_C$ isomer is dissolved in tetrahydrofuran in step (i).

In one embodiment, the second organic solvent in step (v) is pentane. In one embodiment, the second organic solvent in step (v) is hexane. In one embodiment, the second organic solvent in step (v) is methyl tert-butyl ether. In one embodiment, the second organic solvent in step (v) is water.

In certain embodiments, the monofumarate salt is synthesized from the sesquifumarate (1.5 equivalents of fumaric acid). The sesquifumarate can be washed with a solvent, for example methyl tert butyl ether, to remove excess fumaric acid, to provide in the monofumarate.

II. Salts of Compound I

In certain embodiments, the present invention provides Compound I, $R_P$ Compound I, and $S_P$ Compound I as a monofumarate salt. In certain embodiments, the present invention provides Compound I, $R_P$ Compound I, and $S_P$ Compound I as a hemifumarate salt. In certain embodiments, the present invention provides Compound I, $R_P$ Compound I, and $S_P$ Compound I as a sesquifumarate salt. In certain embodiments, the present invention provides $R_P$ Compound I and $S_P$ Compound I as a sulfate salt. In certain embodiments, the present invention $R_P$ Compound I and $S_P$ Compound I as a hydrochloride salt. In certain embodiments, the present invention provides Compound I, $R_P$ Compound I, and $S_P$ Compound I as a benzenesulfonate salt. In certain embodiments, the present invention provides $R_P$ Compound I and $S_P$ Compound I as a tosylate salt. In certain embodiments, the present invention provides $R_P$ Compound I and $S_P$ Compound I as a succinate salt.

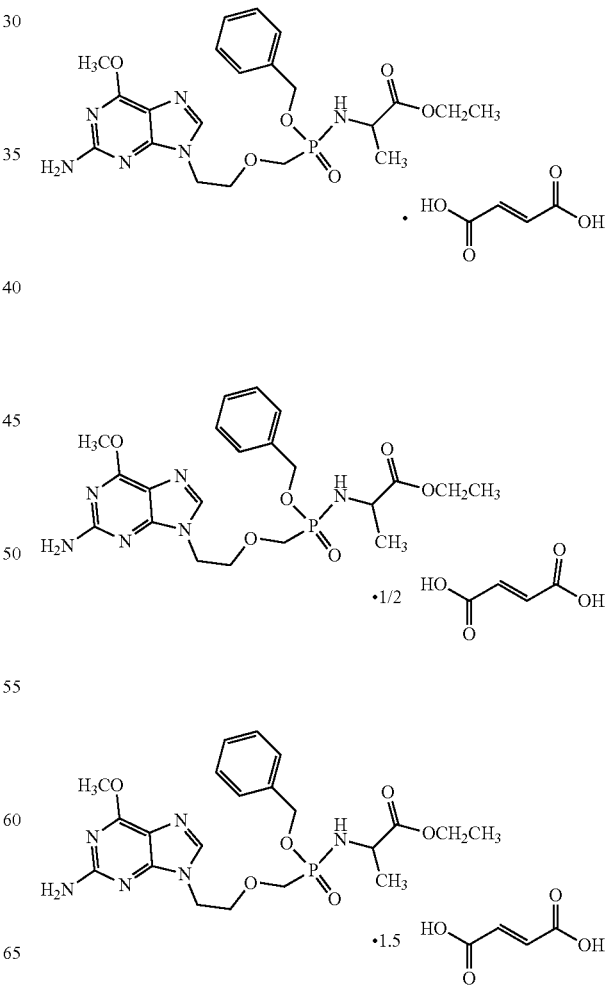

R$_P$ Salts of Compound I
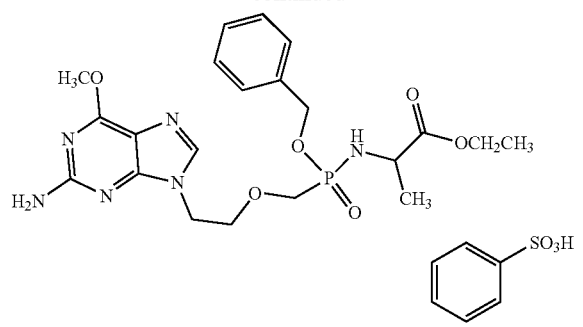
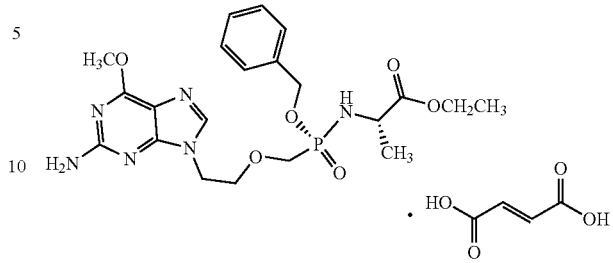
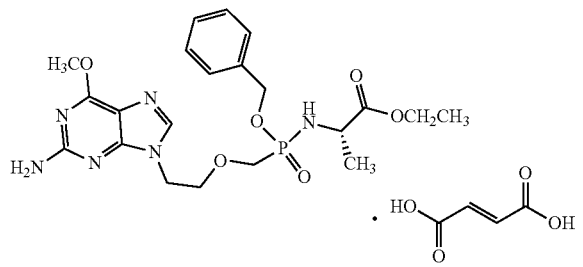
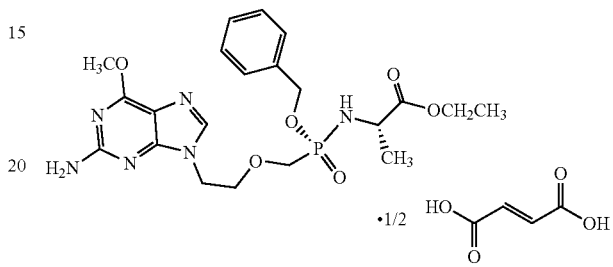
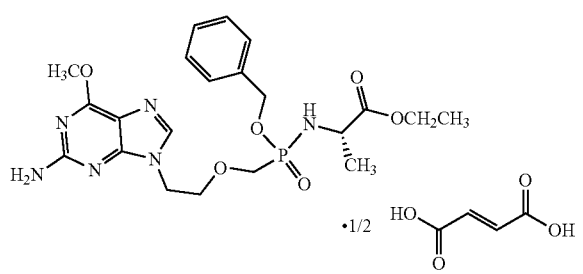
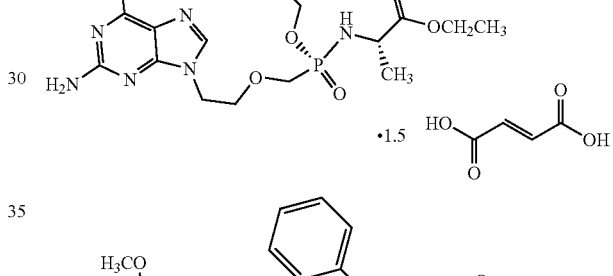
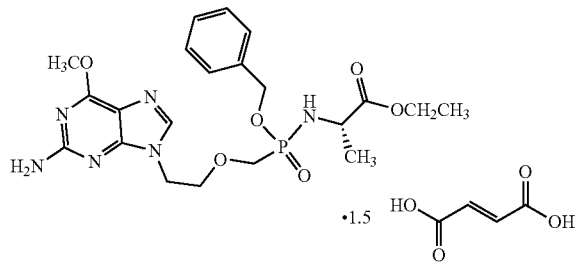
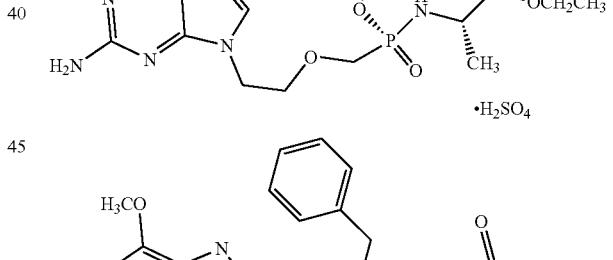
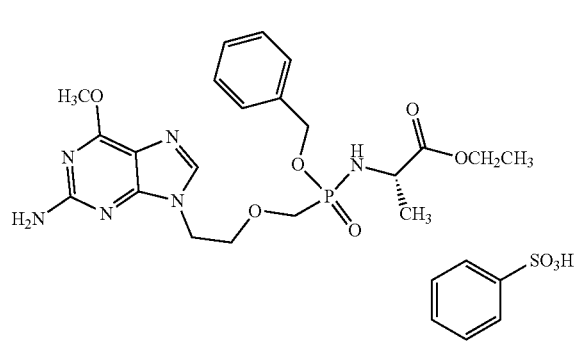
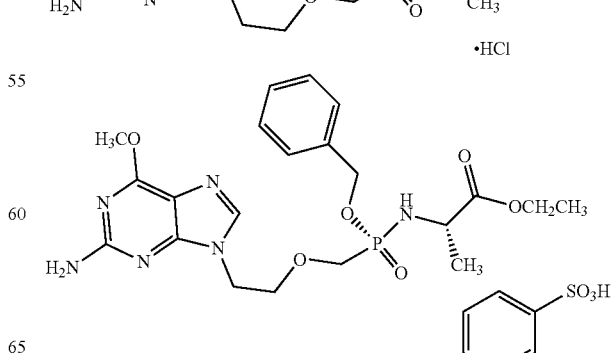

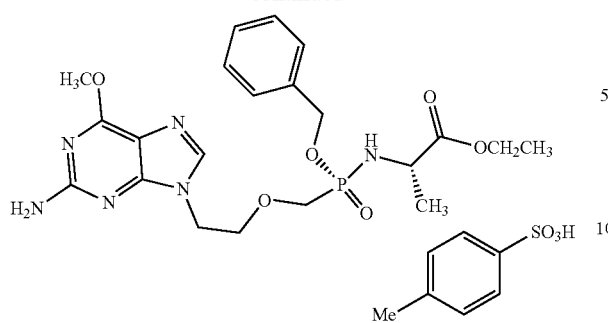
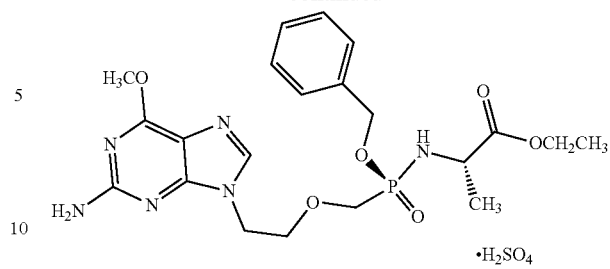

$S_P$ Salts of Compound I

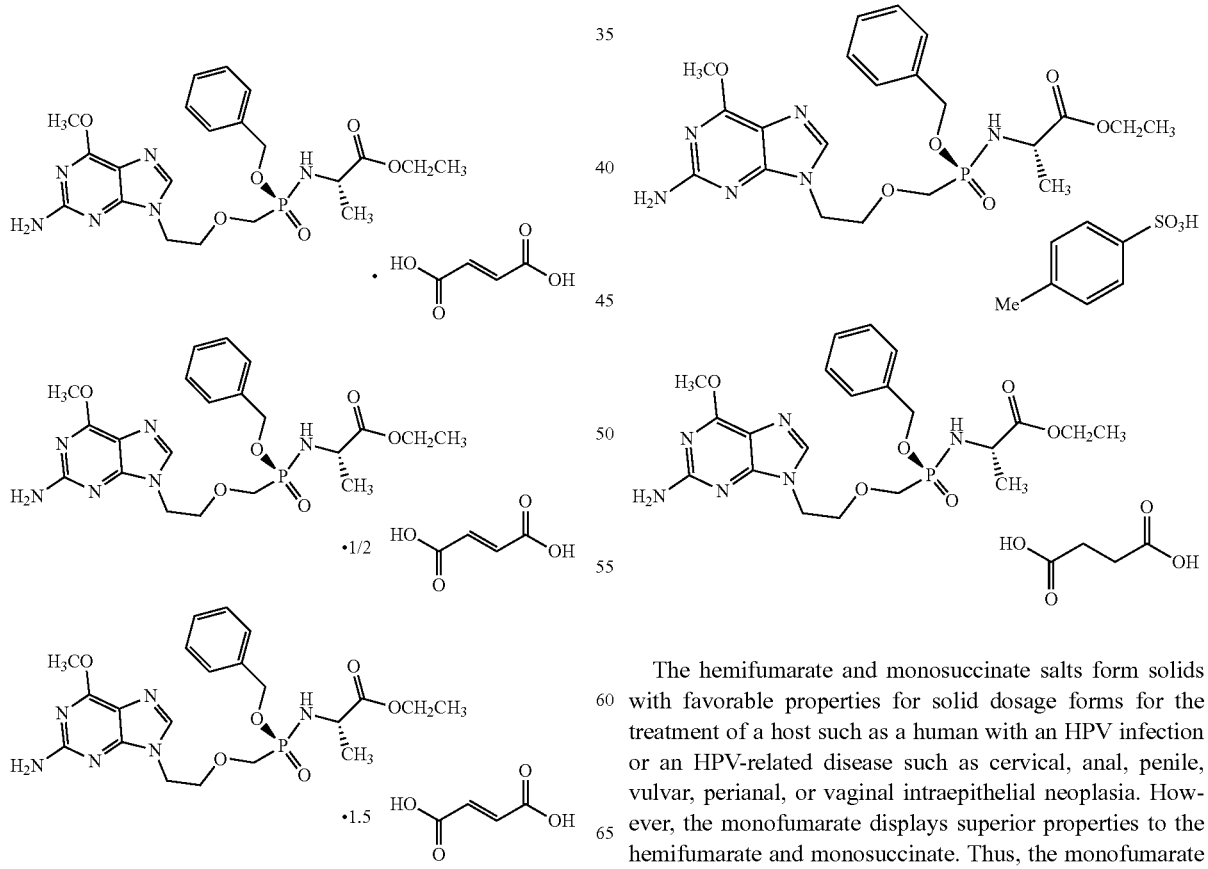

The hemifumarate and monosuccinate salts form solids with favorable properties for solid dosage forms for the treatment of a host such as a human with an HPV infection or an HPV-related disease such as cervical, anal, penile, vulvar, perianal, or vaginal intraepithelial neoplasia. However, the monofumarate displays superior properties to the hemifumarate and monosuccinate. Thus, the monofumarate salt remains a desired salt form of Compound I.

Additional Embodiments of the Present Invention

In certain embodiments, the present invention includes at least:

1. A compound of the formula:

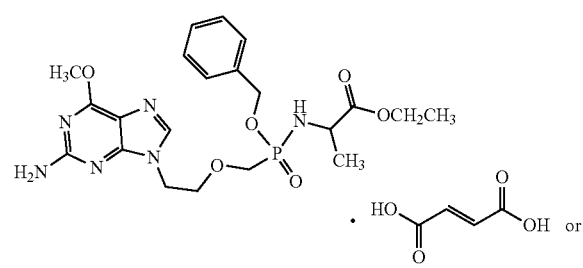

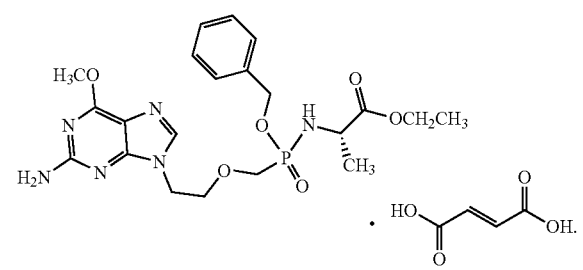

2. A compound of the formula:

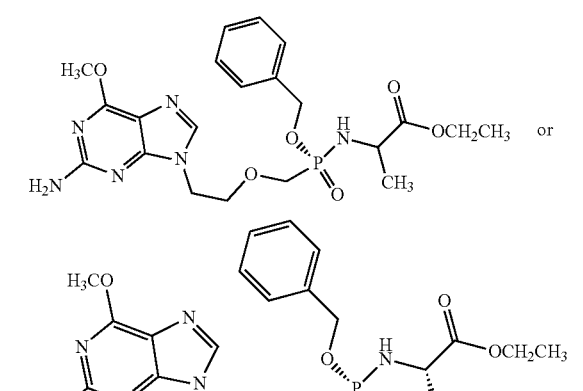

or a pharmaceutically acceptable salt thereof.

3. A compound of the formula:

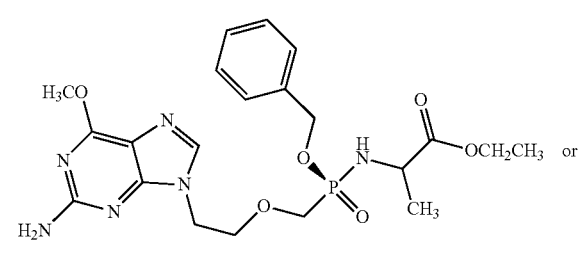

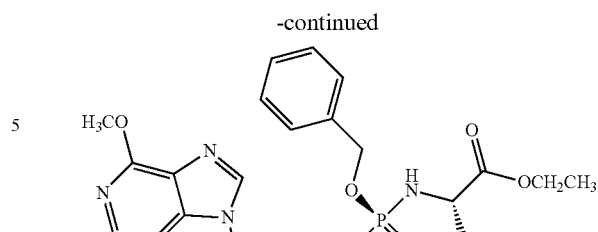

or a pharmaceutically acceptable salt thereof.

4. The compound of embodiment 2 of the formula:

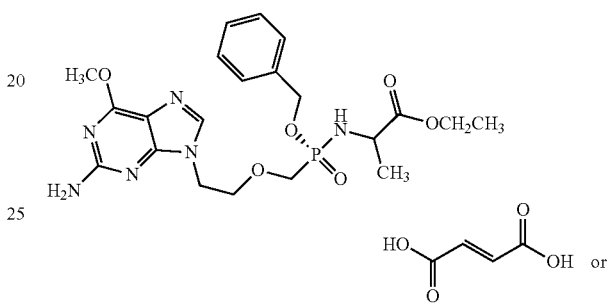

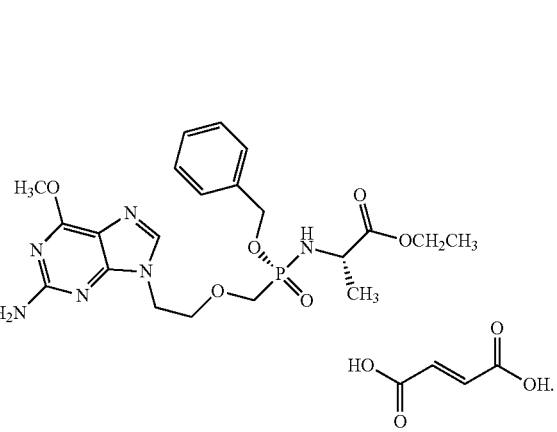

5. The compound of embodiment 3 of the formula:

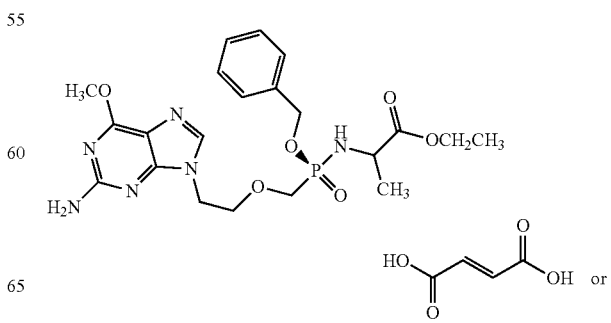

-continued

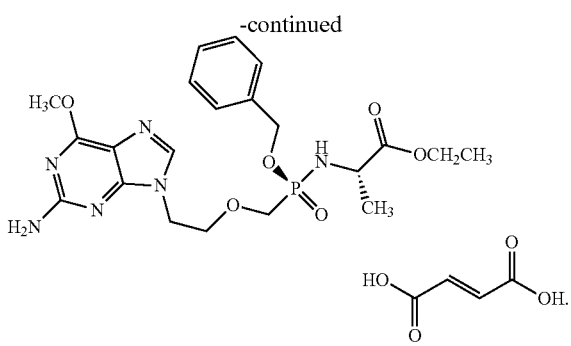

6. An isolated morphic form of the compound of the formula

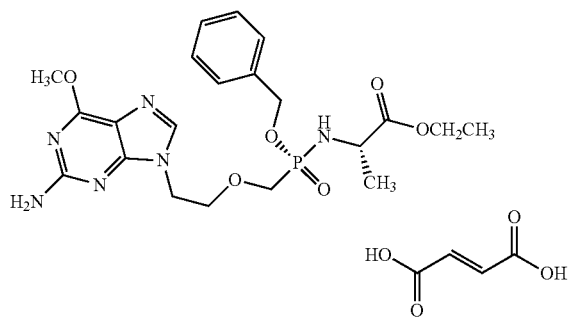 [SMILES: CCOC(=O)[C@H](C)N[P@@](=O)(COCCn1cnc2c(OC)nc(N)nc21)OCc1ccccc1 ; O=C(O)/C=C/C(=O)O]

wherein the isolated morphic form is characterized by an XRPD pattern comprising peaks independently selected from at least 3, 4, 5, or 6 of the following 2theta values 3.08±0.2°, 9.30±0.2°, 12.08±0.2°, 14.92±0.2°, 15.10±0.2°, 20.14±0.2°, 25.14±0.2°, and 28.82±0.2°.

7. An isolated morphic form of the compound of the formula

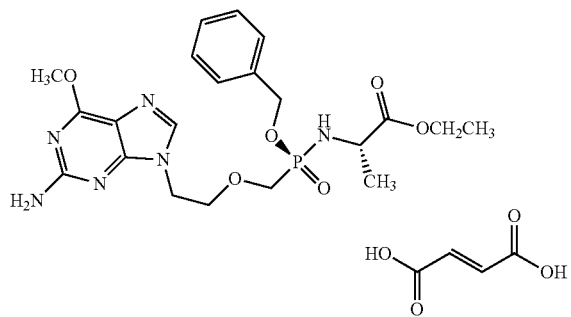 [SMILES: CCOC(=O)[C@H](C)N[P@](=O)(COCCn1cnc2c(OC)nc(N)nc21)OCc1ccccc1 ; O=C(O)/C=C/C(=O)O]

wherein the isolated morphic form is characterized by an XRPD pattern comprising peaks independently selected from at least 3, 4, 5, 6, 7, 8 or 9 of the following 2theta values 9.53±0.2°, 10.04±0.2°, 11.60±0.2°, 14.57±0.2°, 17.22±0.2°, 17.50±0.2°, 20.04±0.2°, 20.36±0.2°, 22.34±0.2°, 23.73±0.2°, 25.48±0.2°, 26.06±0.2°, 27.38±0.2°, and 32.20±0.2°.

8. An isolated morphic form of the compound of the formula

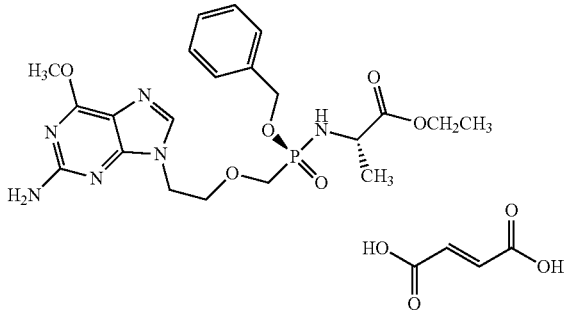 [SMILES: CCOC(=O)[C@H](C)N[P@](=O)(COCCn1cnc2c(OC)nc(N)nc21)OCc1ccccc1 ; O=C(O)/C=C/C(=O)O]

wherein the isolated morphic form is characterized by an XRPD pattern comprising peaks independently selected from at least 3, 4, 5, 6, 7, 8 or 9 of the following 2theta values 8.94±0.2°, 9.89±0.2°, 9.91±0.2°, 11.66±0.2°, 12.11±0.2°, 15.13±0.2°, 17.85±0.2°, 18.15±0.2°, 19.90±0.2°, 20.38±0.2°, 22.94±0.2°, 25.09±0.2°, 26.54±0.2°, 26.90±0.2°, 27.38±0.2°, 28.28±0.2°, 28.95±0.2°, 29.64±0.2°, and 38.07±0.2°.

9. An isolated morphic form of the compound of the formula

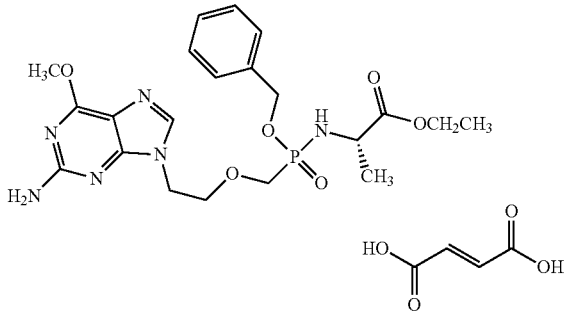 [SMILES: CCOC(=O)[C@H](C)NP(=O)(COCCn1cnc2c(OC)nc(N)nc21)OCc1ccccc1 ; O=C(O)/C=C/C(=O)O]

wherein the isolated morphic form is characterized by an XRPD pattern comprising peaks independently selected from at least 3, 4, 5, or 6 of the following 2theta values 3.08±0.2°, 9.30±0.2°, 12.08±0.2°, 14.92±0.2°, 15.10±0.2°, 20.14±0.2°, 25.14±0.2°, and 28.82±0.2°.

10. A pharmaceutical composition comprising the compound of any one of embodiments 1-5, and a pharmaceutically acceptable carrier.

11. A pharmaceutical composition comprising the morphic form of any one of embodiments 6-9, in a pharmaceutically acceptable carrier.

12. The pharmaceutical composition of embodiments 10-11, in a solid dosage form.

13. The pharmaceutical composition of embodiments 10-11, in a semi-solid dosage form.

14. The pharmaceutical composition of embodiments 10-11, in the form of a reconstitution powder.

15. The pharmaceutical composition of embodiments 10-11, in the form of a dry powder dosage form.

16. The pharmaceutical composition of embodiments 10-11, in the form of a film.

17. The pharmaceutical composition of embodiments 10-11, in the form of a pessary.

18. The pharmaceutical composition of embodiment 12, in the form of a tablet.

19. The pharmaceutical composition of embodiment 13, in the form of a cream.
20. The pharmaceutical composition of embodiment 13, in the form of a gel.
21. The pharmaceutical composition of any one of embodiments 10-20, formulated for topical administration.
22. The pharmaceutical composition of any one of embodiments 10-21, for delivery to the cervix.
23. The pharmaceutical composition of any one of embodiments 10-21, for delivery to the vagina.
24. The pharmaceutical composition of any one of embodiments 10-21, for delivery to the vulva.
25. The pharmaceutical composition of any one of embodiments 10-21, for delivery to the perianal region.
26. The pharmaceutical composition of any one of embodiments 10-21, for delivery to the anus.
27. The pharmaceutical composition of any one of embodiments 10-21, for delivery to the penis.
28. The pharmaceutical composition of embodiment 18, wherein the tablet is a bilayer tablet.
29. The pharmaceutical composition of embodiment 18, wherein the tablet disintegrates in less than about 250 µL of fluid.
30. The pharmaceutical composition of embodiment 18, wherein the table disintegrated in less than about 150 µL of fluid.
31. The pharmaceutical composition of any one of embodiments 10-30, comprising from about 0.001 to about 20 mg, from about 0.005 to about 10 mg, from about 0.01 mg to about 5 mg, from about 0.03 mg to about 1 mg, or from about 0.05 mg to about 0.3 mg of the compound.
32. The pharmaceutical composition of any one of embodiments 10-30 comprising from about 0.005 mg to about 50 mg of the compound.
33. The pharmaceutical composition of embodiment 32, comprising from about 0.05 mg to about 40 mg of the compound.
34. The pharmaceutical composition of embodiment 32, comprising from about 0.1 mg to about 30 mg of the compound.
35. The pharmaceutical composition of embodiment 32, comprising at least about 0.1 mg of the compound.
36. The pharmaceutical composition of embodiment 32, comprising at least about 0.3 mg of the compound.
37. The pharmaceutical composition of embodiment 32, comprising at least about 1 mg of the compound.
38. The pharmaceutical composition of embodiment 32, comprising at least 1.5 mg of the compound.
39. The pharmaceutical composition of embodiment 32, comprising at least about 2 mg of the compound.
40. The pharmaceutical composition of any one of embodiments 19-29, comprising from about 0.001% to about 10% of the compound.
41. The pharmaceutical composition of embodiment 40, comprising from about 0.01% to 0.5% of the compound.
42. The pharmaceutical composition of embodiment 40, comprising from about 0.1% to 5% of the compound.
43. The pharmaceutical composition of any one of embodiments 10-42, comprising mucoadhesive polymer.
44. The pharmaceutical composition of embodiment 43, comprising from about 5% to about 20% mucoadhesive polymer.
45. The pharmaceutical composition of embodiment 43, comprising from about 10% to about 50% mucoadhesive polymer.
46. The pharmaceutical composition of embodiment 43, comprising from about 50% to about 90% mucoadhesive polymer.
47. The pharmaceutical composition of any one of embodiments 10-42, comprising a disintegration enhancing excipient.
48. The pharmaceutical composition of any one of embodiments 10-42, comprising a penetration enhancing excipient.
49. The pharmaceutical composition of any one of embodiments 10-42, comprising an excipient which allows for the controlled release of the active compound.
50. The pharmaceutical composition of embodiment 19, wherein the pharmaceutically acceptable carrier is comprised of light mineral oil, propylparaben, Tefose 63, water, EDTA, methylparaben and Carbopol 974P.
51. The pharmaceutical composition of embodiment 20, wherein the pharmaceutically acceptable carrier is comprised of water, EDTA, methyl paraben, Carbopol 974P, propylene glycol and sorbic acid.
52. The pharmaceutical composition of embodiment 18, wherein the tablet is comprised of mannitol, polycrystalline cellulose and magnesium stearate.
53. A method to treat an infection of human papillomavirus comprising administering to a host in need thereof an effective amount of the compound of any one of embodiments 1-5, optionally in a pharmaceutically acceptable carrier.
54. A method to treat a condition caused by a human papillomavirus infection comprising administering to a host in need thereof an effective amount of the compound of any one of embodiments 1-5, optionally in a pharmaceutically acceptable carrier.
55. The method of embodiment 54, wherein the condition caused by a human papillomavirus infection is intraepithelial neoplasia.
56. The method of embodiment 55, wherein the condition caused by a human papillomavirus is atypical squamous cells of undetermined significance (ASC-US).
57. The method of embodiment 55, wherein the condition caused by a human papillomavirus is atypical glandular cells (AGC).
58. The method of embodiment 55, wherein the condition caused by a human papillomavirus is low-grade squamous intraepithelial lesions (LSIL).
59. The method of embodiment 55, wherein the condition caused by a human papillomavirus is atypical squamous cells, cannot exclude high grade squamous intraepithelial lesion (ASC-H).
60. The method of embodiment 55, wherein the condition caused by a human papillomavirus is high grade squamous intraepithelial lesions (HSIL).
61. The method of embodiment 54, wherein the condition caused by a human papillomavirus is adenocarcinoma in situ (AIS).
62. The method of embodiment 55, wherein the intraepithelial neoplasia is cervical intraepithelial neoplasia.
63. The method of embodiment 62, wherein the cervical intraepithelial neoplasia is Grade 1 cervical intraepithelial neoplasia.
64. The method of embodiment 62, wherein the cervical intraepithelial neoplasia is Grade 2 cervical intraepithelial neoplasia.

65. The method embodiment 62, wherein the cervical intraepithelial neoplasia is Grade 3 cervical intraepithelial neoplasia.

66. The method of embodiment 55, wherein the intraepithelial neoplasia is vaginal intraepithelial neoplasia.

67. The method of embodiment 55, wherein the intraepithelial neoplasia is vulvar intraepithelial neoplasia.

68. The method of embodiment 55, wherein the intraepithelial neoplasia is anal intraepithelial neoplasia.

69. The method of embodiment 55, wherein the intraepithelial neoplasia is perianal intraepithelial neoplasia.

70. The method of embodiment 55, wherein the intraepithelial neoplasia is penile intraepithelial neoplasia.

71. The method of any one of embodiments 53-70, wherein the host is a human.

72. The method of any one of embodiments 53-71, wherein the compound is administered topically.

73. The method of any one of embodiments 52-71, wherein from about 0.05 milligrams to about 40 milligrams of compound is administered.

74. The method of any one of embodiments 52-71, wherein from about 0.1 milligrams to about 30 milligrams is administered.

75. The method of any one of embodiments 52-71, wherein from about 0.001 to about 20 mg, from about 0.005 to about 10 mg, from about 0.01 mg to about 5 mg, from about 0.03 mg to about 1 mg, from about 0.05 mg to about 0.3 mg, from about 0.03 mg to about 0.07 mg, from about 0.05 mg to about 0.15 mg, or from about 0.15 mg to about 0.45 mg of the compound is administered.

76. The method of embodiment 75, wherein from about 0.05 mg to about 0.3 mg of the compound is administered.

77. The method of any one of embodiments 52-76, further including applying a lubrication means to the epithelial tissue before inserting the dosage form in the affected area.

78. The method of any one of embodiments 52-76, further including applying a lubrication means to the dosage form before inserting the dosage form in the affected area.

79. The method of embodiment 77 or 78 wherein the lubrication means is selected from water, a glycerol based lubricant and a hydroxyethylcellulose-based lubricant.

80. The method of any one of embodiments 52-79, wherein the compound is administered once per day.

81. The method of any one of embodiments 52-79, administered twice per day.

82. The method of any one of embodiments 52-79, administered twice per week.

83. The method of any one of embodiments 52-79, administered three times or more per week.

84. The method of any one of embodiments 52-83, administered for about one week.

85. The method of any one of embodiments 52-83, administered for about two weeks.

86. The method of any one of embodiments 52-83, administered for about three weeks.

87. The method of any one of embodiments 52-83, administered for about four weeks.

88. The method of any one of embodiments 52-83, administered for about five weeks.

89. The method of any one of embodiments 52-83, administered for about six weeks.

90. The method of any one of embodiments 52-89, wherein the compound is administered in a therapeutic cycle comprising:
   a. a treatment cycle comprising administering the compound, and
   b. a rest cycle, comprising a period of no treatment.

91. The method of embodiment 90, wherein the rest cycle is about one week.

92. The method of embodiment 90, wherein the rest cycle is about two weeks.

93. The method of embodiment 90, wherein the rest cycle is about three weeks.

94. The method of any one of embodiments 52-79, wherein the compound is administered daily.

95. The method of embodiment 94, wherein from about 0.01 mg to about 0.5 mg is administered.

96. The method of embodiment 95, wherein from about 0.05 to about 0.3 mg is administered.

97. The method of any one of embodiments 90-93, wherein two therapeutic cycles are administered.

98. The method of any one of embodiments 90-93, wherein three therapeutic cycles are administered.

99. The method of any one of embodiments 90-93, wherein four therapeutic cycles are administered.

100. The method of any one of embodiments 90-93, wherein five therapeutic cycles are administered.

101. The method of any one of embodiments 90-93, wherein six therapeutic cycles are administered.

102. The method of any one of embodiments 52-101, wherein human papillomavirus is HPV-16.

103. The method of any one of embodiments 52-101, wherein the human papillomavirus is HPV-18.

104. The method of any one of embodiments 52-103, wherein the compound is administered in combination with another antiviral compound.

105. The method of embodiment 104, wherein the antiviral compound is selected from the group consisting of a protease inhibitor, another DNA polymerase inhibitor, an inhibitor of E6 or E6AP, an inhibitor of E7, an inhibitor of E1, an inhibitor of E2, an inhibitor of the E1-E2 protein interaction, L2 lipopeptides, an inhibitor of L1, an inhibitor of L2, a degrader of L1, and a degrader of L2.

106. The method of any one of embodiments 52-103, wherein the compound is administered in combination with an anticancer compound.

107. The method of embodiments 106, wherein the anticancer compound is selected from the group consisting of an HDAC inhibitor, a degrader of tetraspanins, an immune checkpoint inhibitor, a T-cell therapy, and an antiproliferative drug.

108. The method of any one of embodiments 52-103, wherein the compound is administered in combination with a surgical procedure.

109. The method of embodiment 108, wherein the compound is administered before the surgical procedure.

110. The method of embodiment 108, wherein the compound is administered after the surgical procedure.

111. The method of embodiment 108, wherein the surgical procedure is performed during the administration of the compound.

112. The method of any one of embodiments 108-111, wherein the surgical procedure is an excision of the diseased tissue.

113. The method of embodiment 112, wherein the excision is a loop electrosurgical excision procedure (LEEP).

114. The method of embodiment 112, wherein the excision is a large loop excision of the transformation zone (LLETZ).
115. The method of embodiment 112, wherein the excision is a knife conization.
116. The method of embodiment 112, wherein the excision is laser conization.
117. The method of any one of embodiments 108-111, wherein the surgical procedure is an ablation of the diseased tissue.
118. The method of embodiment 117, wherein the ablation is laser ablation.
119. The method of embodiment 117, wherein the ablation is cryoablation.
120. The use of a compound of embodiments 1-5, optionally in a pharmaceutically acceptable carrier, in the manufacture of a medicament for the treatment of a human papillomavirus infection, in a host in need thereof.
121. The use of a compound of embodiments 1-5, optionally in a pharmaceutically acceptable carrier, in the manufacture of a medicament for the treatment of a condition caused by a human papillomavirus infection, in a host in need thereof.
122. The use of embodiment 121, wherein the condition caused by a human papillomavirus infection is intraepithelial neoplasia.
123. The use of embodiment 122, wherein the intraepithelial neoplasia is vaginal intraepithelial neoplasia.
124. The use of embodiment 122, wherein the intraepithelial neoplasia is vulvar intraepithelial neoplasia.
125. The use of embodiment 122, wherein the intraepithelial neoplasia is cervical intraepithelial neoplasia.
126. The use of embodiment 122, wherein the intraepithelial neoplasia is anal intraepithelial neoplasia.
127. The use of embodiment 122, wherein the intraepithelial neoplasia is perianal intraepithelial neoplasia.
128. The use of embodiment 122, wherein the intraepithelial neoplasia is penile intraepithelial neoplasia.
129. The use of embodiments 120-128, wherein the host is a human.
130. The use of embodiments 120-129, for topical administration.
131. The compound of any one of embodiments 1-5, optionally in a pharmaceutically acceptable carrier, for use to treat a human papillomavirus infection in a host in need thereof.
132. The compound of any one of embodiments 1-5, optionally in a pharmaceutically acceptable carrier, for use to treat a condition caused by a human papillomavirus infection, in a host in need thereof.
133. The compound for use of embodiment 132, wherein the condition caused by a human papillomavirus infection is intraepithelial neoplasia.
134. The compound for use of embodiment 133, wherein the intraepithelial neoplasia is vaginal intraepithelial neoplasia.
135. The compound for use of embodiment 133, wherein the intraepithelial neoplasia is vulvar intraepithelial neoplasia.
136. The compound for use of embodiment 133, wherein the intraepithelial neoplasia is cervical intraepithelial neoplasia.
137. The compound for use of embodiment 133, wherein the intraepithelial neoplasia is anal intraepithelial neoplasia.
138. The compound for use of embodiment 133, wherein the intraepithelial neoplasia is perianal intraepithelial neoplasia.
139. The compound for use of embodiment 133, wherein the intraepithelial neoplasia is penile intraepithelial neoplasia.
140. The compound for use of embodiments 131-139, wherein the host is a human.
141. The compound for use of embodiments 131-140, wherein the compound is administered topically.
142. A process for the preparation of the morphic form of embodiment 4 comprising:
   a. Dissolving $R_P$ Compound I in an alcoholic solvent;
   b. Stirring at a temperature from about 20° C. to about 70° C.;
   c. Adding 1.0 equivalent of fumaric acid;
   d. Adding an aliphatic solvent;
   e. Cooling the mixture;
   f. Stirring the cooled solution; and
   g. Isolating and drying the solids.
143. The process of embodiment 142, wherein the alcoholic solvent of step (a) is ethanol or isopropanol.
144. The process of embodiments 142-143, wherein the alcoholic solvent of step (a) is isopropanol.
145. The process of embodiment 142, wherein the solution of step (b) is stirred at about 45° C. to about 55° C.
146. The process of embodiment 142, wherein the aliphatic solvent is hexane or heptane.
147. The process of embodiments 142 and 146, wherein the aliphatic solvent is heptane.
148. The process of embodiment 142, wherein the mixture is cooled to less than about 20° C.
149. The process of embodiment 142, wherein the mixture is cooled to less than about 10° C.
150. The process of embodiment 142, wherein the mixture is cooled to less than about 5° C.
151. The process of embodiment 142, wherein the mixture is cooled to about 5° C. to 0° C.

III. Morphic Forms

Isolated morphic form Pattern 1 of Compound I monofumarate is provided in this invention. In certain embodiments, Compound I monofumarate pattern 1 is characterized by an XRPD pattern in or substantially similar to that in FIG. 23.

1. In one embodiment, Compound I monofumarate pattern 1 is characterized by an XRPD pattern comprising at least about 3, 4, or 5 2theta values selected from 6.0±0.2°, 8.9±0.2°, 9.3±0.2°, 9.7±0.2°, 11.9±0.2°, 14.8±0.2°, 18.0±0.2°, 20.0±0.2°, 23.4±0.2°, 25.2±0.2°, 25.9±0.2°, 26.8±0.2°, and 28.0±0.2°.
2. In one embodiment, Compound I monofumarate pattern 1 is characterized by an XRPD pattern comprising at least twelve of the 2theta values selected from 6.0±0.2°, 8.9±0.2°, 9.3±0.2°, 9.7±0.2°, 11.9±0.2°, 14.8±0.2°, 18.0±0.2°, 20.0±0.2°, 23.4±0.2°, 25.2±0.2°, 25.9±0.2°, 26.8±0.2°, and 28.0±0.2°.
3. In one embodiment, Compound I monofumarate pattern 1 is characterized by an XRPD pattern comprising at least eleven of the 2theta values selected from 6.0±0.2°, 8.9±0.2°, 9.3±0.2°, 9.7±0.2°, 11.9±0.2°, 14.8±0.2°, 18.0±0.2°, 20.0±0.2°, 23.4±0.2°, 25.2±0.2°, 25.9±0.2°, 26.8±0.2°, and 28.0±0.2°.
4. In one embodiment, Compound I monofumarate pattern 1 is characterized by an XRPD pattern comprising at least ten of the 2theta values selected from 6.0±0.2°, 8.9±0.2°, 9.3±0.2°, 9.7±0.2°, 11.9±0.2°, 14.8±0.2°, 18.0±0.2°, 20.0±0.2°, 23.4±0.2°, 25.2±0.2°, 25.9±0.2°, 26.8±0.2°, and 28.0±0.2°.

5. In one embodiment, Compound I monofumarate pattern 1 is characterized by an XRPD pattern comprising at least nine of the 2theta values selected from 6.0±0.2°, 8.9±0.2°, 9.3±0.2°, 9.7±0.2°, 11.9±0.2°, 14.8±0.2°, 18.0±0.2°, 20.0±0.2°, 23.4±0.2°, 25.2±0.2°, 25.9±0.2°, 26.8±0.2°, and 28.0±0.2°.

6. In one embodiment, Compound I monofumarate pattern 1 is characterized by an XRPD pattern comprising at least eight of the 2theta values selected from 6.0±0.2°, 8.9±0.2°, 9.3±0.2°, 9.7±0.2°, 11.9±0.2°, 14.8±0.2°, 18.0±0.2°, 20.0±0.2°, 23.4±0.2°, 25.2±0.2°, 25.9±0.2°, 26.8±0.2°, and 28.0±0.2°.

7. In one embodiment, Compound I monofumarate pattern 1 is characterized by an XRPD pattern comprising at least seven of the 2theta values selected from 6.0±0.2°, 8.9±0.2°, 9.3±0.2°, 9.7±0.2°, 11.9±0.2°, 14.8±0.2°, 18.0±0.2°, 20.0±0.2°, 23.4±0.2°, 25.2±0.2°, 25.9±0.2°, 26.8±0.2°, and 28.0±0.2°.

8. In one embodiment, Compound I monofumarate pattern 1 is characterized by an XRPD pattern comprising at least six of the 2theta values selected from 6.0±0.2°, 8.9±0.2°, 9.3±0.2°, 9.7±0.2°, 11.9±0.2°, 14.8±0.2°, 18.0±0.2°, 20.0±0.2°, 23.4±0.2°, 25.2±0.2°, 25.9±0.2°, 26.8±0.2°, and 28.0±0.2°.

9. In one embodiment, Compound I monofumarate pattern 1 is characterized by an XRPD pattern comprising at least five of the 2theta values selected from 6.0±0.2°, 8.9±0.2°, 9.3±0.2°, 9.7±0.2°, 11.9±0.2°, 14.8±0.2°, 18.0±0.2°, 20.0±0.2°, 23.4±0.2°, 25.2±0.2°, 25.9±0.2°, 26.8±0.2°, and 28.0±0.2°.

10. In one embodiment, Compound I monofumarate pattern 1 is characterized by an XRPD pattern comprising at least four of the 2theta values selected from 6.0±0.2°, 8.9±0.2°, 9.3±0.2°, 9.7±0.2°, 11.9±0.2°, 14.8±0.2°, 18.0±0.2°, 20.0±0.2°, 23.4±0.2°, 25.2±0.2°, 25.9±0.2°, 26.8±0.2°, and 28.0±0.2°.

11. In one embodiment, Compound I monofumarate pattern 1 is characterized by an XRPD pattern comprising at least three of the 2theta values selected from 6.0±0.2°, 8.9±0.2°, 9.3±0.2°, 9.7±0.2°, 11.9±0.2°, 14.8±0.2°, 18.0±0.2°, 20.0±0.2°, 23.4±0.2°, 25.2±0.2°, 25.9±0.2°, 26.8±0.2°, and 28.0±0.2°.

Compound I monofumarate pattern 1 can be produced, for example, by crystallization from isopropyl alcohol and heptane, as described in Example 7. Compound I free base and about 1.0 equivalents of fumaric acid can for example be dissolved in isopropanol at a concentration from about 25% to about 40% w/v and stirred at an elevated temperature, for example about 45° C., about 50° C., about 55° C. The solution is stirred at this temperature until some solids form and is then optionally seeded with Compound I monofumarate Pattern 1 crystalline solids. The mixture is stirred and cooled to a lower temperature to facilitate crystallization, for example less than about 40° C., less than about 30° C., less than about 25° C., less than about 20° C., or less than about 15° C. The mixture is then stirred while heptane is added in an amount ranging from about 1 mL per mL of isopropanol to about 5 mL per mL of isopropanol, such as about 4 mL per mL isopropanol. The resulting suspension is stirred while the product crystallizes, for example for at least about 24 hours at 25° C. Next, the suspension is cooled to facilitate crystallization further. The solution can be cooled to less than about 10° C., less than about 5° C., less than about 0° C., or less than about −5° C. The solution is stirred at the decreased temperature to allow time for additional product to crystallize, such as for at least about one day, and then the solids are collected by filtration. The collected solids are dried under reduced pressure and optionally at elevated temperature to provide Compound I monofumarate pattern 1.

Isolated morphic form Pattern 1 of Compound II is provided in this invention. In one embodiment, Pattern 1 is characterized by an XRPD pattern in or substantially similar to that in FIG. 71.

1. In one embodiment, Compound II Pattern 1 is characterized by an XRPD pattern comprising at least three, four or five 2theta values selected from 3.08±0.2°, 9.30±0.2°, 12.08±0.2°, 14.92±0.2°, 15.10±0.2°, 20.14±0.2°, 25.14±0.2°, and 28.82±0.2°.

2. Compound II Pattern 1 of embodiment 1, characterized by an XRPD pattern comprising at least seven 2theta values selected from 3.08±0.2°, 9.30±0.2°, 12.08±0.2°, 14.92±0.2°, 15.10±0.2°, 20.14±0.2°, 25.14±0.2°, and 28.82±0.2°.

3. Compound II Pattern 1 of embodiment 1, characterized by an XRPD pattern comprising at least six 2theta values selected from 3.08±0.2°, 9.30±0.2°, 12.08±0.2°, 14.92±0.2°, 15.10±0.2°, 20.14±0.2°, 25.14±0.2°, and 28.82±0.2°.

4. Compound II Pattern 1 of embodiment 1, characterized by an XRPD pattern comprising at least five 2theta values selected from 3.08±0.2°, 9.30±0.2°, 12.08±0.2°, 14.92±0.2°, 15.10±0.2°, 20.14±0.2°, 25.14±0.2°, and 28.82±0.2°.

5. Compound II Pattern 1 of embodiment 1, characterized by an XRPD pattern comprising at least four 2theta values selected from 3.08±0.2°, 9.30±0.2°, 12.08±0.2°, 14.92±0.2°, 15.10±0.2°, 20.14±0.2°, 25.14±0.2°, and 28.82±0.2°.

6. Compound II Pattern 1 of embodiment 1, characterized by an XRPD pattern comprising at least three 2theta values selected from 3.08±0.2°, 9.30±0.2°, 12.08±0.2°, 14.92±0.2°, 15.10±0.2°, 20.14±0.2°, 25.14±0.2°, and 28.82±0.2°.

7. Compound II Pattern 1 of embodiment 1, characterized by an XRPD pattern comprising at least two 2theta values selected from 3.08±0.2°, 9.30±0.2°, 12.08±0.2°, 14.92±0.2°, 15.10±0.2°, 20.14±0.2°, 25.14±0.2°, and 28.82±0.2°.

8. Compound II Pattern 1 of embodiment 1, characterized by an XRPD pattern comprising at least one 2theta values selected from 3.08±0.2°, 9.30±0.2°, 12.08±0.2°, 14.92±0.2°, 15.10±0.2°, 20.14±0.2°, 25.14±0.2°, and 28.82±0.2°.

9. In one embodiment, Compound II Pattern 1 is characterized by an XRPD pattern comprising at least three, four, or five 2theta values selected from 3.08±0.2°, 9.30±0.2°, 10.66±0.2°, 12.08±0.2°, 14.92±0.2°, 15.10±0.2°, 17.45±0.2°, 18.13±0.2°, 19.78±0.2°, 20.14±0.2°, 22.91±0.2°, 23.34±0.2°, 25.14±0.2°, 25.33±0.2°, 25.86±0.2°, 26.78±0.2°, 27.99±0.2°, and 28.82±0.2°.

10. Compound II Pattern 1 of embodiment 9, characterized by an XRPD pattern comprising at least fifteen 2theta values selected from 3.08±0.2°, 9.30±0.2°, 10.66±0.2°, 12.08±0.2°, 14.92±0.2°, 15.10±0.2°, 17.45±0.2°, 18.13±0.2°, 19.78±0.2°, 20.14±0.2°, 22.91±0.2°, 23.34±0.2°, 25.14±0.2°, 25.33±0.2°, 25.86±0.2°, 26.78±0.2°, 27.99±0.2°, and 28.82±0.2°.

11. Compound II Pattern 1 of embodiment 9, characterized by an XRPD pattern comprising at least fourteen 2theta values selected from 3.08±0.2°, 9.30±0.2°, 10.66±0.2°, 12.08±0.2°, 14.92±0.2°, 15.10±0.2°, 17.45±0.2°, 18.13±0.2°, 19.78±0.2°, 20.14±0.2°, 22.91±0.2°, 23.34±0.2°, 25.14±0.2°, 25.33±0.2°, 25.86±0.2°, 26.78±0.2°, 27.99±0.2°, and 28.82±0.2°.

12. Compound II Pattern 1 of embodiment 9, characterized by an XRPD pattern comprising at least thirteen 2theta values selected from 3.08±0.2°, 9.30±0.2°, 10.66±0.2°, 12.08±0.2°, 14.92±0.2°, 15.10±0.2°, 17.45±0.2°, 18.13±0.2°, 19.78±0.2°, 20.14±0.2°, 22.91±0.2°, 23.34±0.2°, 25.14±0.2°, 25.33±0.2°, 25.86±0.2°, 26.78±0.2°, 27.99±0.2°, and 28.82±0.2°.

13. Compound II Pattern 1 of embodiment 9, characterized by an XRPD pattern comprising at least twelve 2theta values selected from 3.08±0.2°, 9.30±0.2°, 10.66±0.2°, 12.08±0.2°, 14.92±0.2°, 15.10±0.2°, 17.45±0.2°, 18.13±0.2°, 19.78±0.2°, 20.14±0.2°, 22.91±0.2°, 23.34±0.2°, 25.14±0.2°, 25.33±0.2°, 25.86±0.2°, 26.78±0.2°, 27.99±0.2°, and 28.82±0.2°.

14. Compound II Pattern 1 of embodiment 9, characterized by an XRPD pattern comprising at least eleven 2theta values selected from 3.08±0.2°, 9.30±0.2°, 10.66±0.2°, 12.08±0.2°, 14.92±0.2°, 15.10±0.2°, 17.45±0.2°, 18.13±0.2°, 19.78±0.2°, 20.14±0.2°, 22.91±0.2°, 23.34±0.2°, 25.14±0.2°, 25.33±0.2°, 25.86±0.2°, 26.78±0.2°, 27.99±0.2°, and 28.82±0.2°.

15. Compound II Pattern 1 of embodiment 9, characterized by an XRPD pattern comprising at least ten 2theta values selected from 3.08±0.2°, 9.30±0.2°, 10.66±0.2°, 12.08±0.2°, 14.92±0.2°, 15.10±0.2°, 17.45±0.2°, 18.13±0.2°, 19.78±0.2°, 20.14±0.2°, 22.91±0.2°, 23.34±0.2°, 25.14±0.2°, 25.33±0.2°, 25.86±0.2°, 26.78±0.2°, 27.99±0.2°, and 28.82±0.2°.

16. Compound II Pattern 1 of embodiment 9, characterized by an XRPD pattern comprising at least nine 2theta values selected from 3.08±0.2°, 9.30±0.2°, 10.66±0.2°, 12.08±0.2°, 14.92±0.2°, 15.10±0.2°, 17.45±0.2°, 18.13±0.2°, 19.78±0.2°, 20.14±0.2°, 22.91±0.2°, 23.34±0.2°, 25.14±0.2°, 25.33±0.2°, 25.86±0.2°, 26.78±0.2°, 27.99±0.2°, and 28.82±0.2°.

17. Compound II Pattern 1 of embodiment 9, characterized by an XRPD pattern comprising at least eight 2theta values selected from 3.08±0.2°, 9.30±0.2°, 10.66±0.2°, 12.08±0.2°, 14.92±0.2°, 15.10±0.2°, 17.45±0.2°, 18.13±0.2°, 19.78±0.2°, 20.14±0.2°, 22.91±0.2°, 23.34±0.2°, 25.14±0.2°, 25.33±0.2°, 25.86±0.2°, 26.78±0.2°, 27.99±0.2°, and 28.82±0.2°.

18. In certain embodiments, Compound II Pattern 1 is characterized by an XRPD pattern comprising at least three, four, or five 2theta values selected from 3.08±0.2°, 6.07±0.2°, 8.80±0.2°, 9.30±0.2°, 10.66±0.2°, 12.08±0.2°, 12.60±0.2°, 14.92±0.2°, 15.10±0.2°, 17.45±0.2°, 17.838±0.2°, 18.13±0.2°, 18.63±0.2°, 18.89±0.2°, 19.78±0.2°, 20.14±0.2°, 20.81±0.2°, 21.24±0.2°, 21.59±0.2°, 21.89±0.2°, 22.91±0.2°, 23.34±0.2°, 24.23±0.2°, 25.14±0.2°, 25.33±0.2°, 25.86±0.2°, 26.78±0.2°, 27.13±0.2°, 27.59±0.2°, 27.99±0.2°, 28.82±0.2°, 29.23±0.2°, 29.45±0.2°, 30.39±0.2°, 31.18±0.2°, 31.66±0.2°, 32.27±0.2°, 32.69±0.2°, 33.43±0.2°, 34.06±0.2°, 34.34±0.2°, 34.69±0.2°, 35.58±0.2°, 36.19±0.2°, 36.62±0.2°, 37.41±0.2°, 38.30±0.2°, 38.77±0.2°, and 39.24±0.2°.

19. Compound II Pattern 1 of embodiment 18, characterized by an XRPD pattern comprising at least forty-five 2theta values selected from 3.08±0.2°, 6.07±0.2°, 8.80±0.2°, 9.30±0.2°, 10.66±0.2°, 12.08±0.2°, 12.60±0.2°, 14.92±0.2°, 15.10±0.2°, 17.45±0.2°, 17.838±0.2°, 18.13±0.2°, 18.63±0.2°, 18.89±0.2°, 19.78±0.2°, 20.14±0.2°, 20.81±0.2°, 21.24±0.2°, 21.59±0.2°, 21.89±0.2°, 22.91±0.2°, 23.34±0.2°, 24.23±0.2°, 25.14±0.2°, 25.33±0.2°, 25.86±0.2°, 26.78±0.2°, 27.13±0.2°, 27.59±0.2°, 27.99±0.2°, 28.82±0.2°, 29.23±0.2°, 29.45±0.2°, 30.39±0.2°, 31.18±0.2°, 31.66±0.2°, 32.27±0.2°, 32.69±0.2°, 33.43±0.2°, 34.06±0.2°, 34.34±0.2°, 34.69±0.2°, 35.58±0.2°, 36.19±0.2°, 36.62±0.2°, 37.41±0.2°, 38.30±0.2°, 38.77±0.2°, and 39.24±0.2°.

20. Compound II Pattern 1 of embodiment 18, characterized by an XRPD pattern comprising at least forty 2theta values selected from 3.08±0.2°, 6.07±0.2°, 8.80±0.2°, 9.30±0.2°, 10.66±0.2°, 12.08±0.2°, 12.60±0.2°, 14.92±0.2°, 15.10±0.2°, 17.45±0.2°, 17.838±0.2°, 18.13±0.2°, 18.63±0.2°, 18.89±0.2°, 19.78±0.2°, 20.14±0.2°, 20.81±0.2°, 21.24±0.2°, 21.59±0.2°, 21.89±0.2°, 22.91±0.2°, 23.34±0.2°, 24.23±0.2°, 25.14±0.2°, 25.33±0.2°, 25.86±0.2°, 26.78±0.2°, 27.13±0.2°, 27.59±0.2°, 27.99±0.2°, 28.82±0.2°, 29.23±0.2°, 29.45±0.2°, 30.39±0.2°, 31.18±0.2°, 31.66±0.2°, 32.27±0.2°, 32.69±0.2°, 33.43±0.2°, 34.06±0.2°, 34.34±0.2°, 34.69±0.2°, 35.58±0.2°, 36.19±0.2°, 36.62±0.2°, 37.41±0.2°, 38.30±0.2°, 38.77±0.2°, and 39.24±0.2°.

21. Compound II Pattern 1 of embodiment 18, characterized by an XRPD pattern comprising at least thirty-five 2theta values selected from 3.08±0.2°, 6.07±0.2°, 8.80±0.2°, 9.30±0.2°, 10.66±0.2°, 12.08±0.2°, 12.60±0.2°, 14.92±0.2°, 15.10±0.2°, 17.45±0.2°, 17.838±0.2°, 18.13±0.2°, 18.63±0.2°, 18.89±0.2°, 19.78±0.2°, 20.14±0.2°, 20.81±0.2°, 21.24±0.2°, 21.59±0.2°, 21.89±0.2°, 22.91±0.2°, 23.34±0.2°, 24.23±0.2°, 25.14±0.2°, 25.33±0.2°, 25.86±0.2°, 26.78±0.2°, 27.13±0.2°, 27.59±0.2°, 27.99±0.2°, 28.82±0.2°, 29.23±0.2°, 29.45±0.2°, 30.39±0.2°, 31.18±0.2°, 31.66±0.2°, 32.27±0.2°, 32.69±0.2°, 33.43±0.2°, 34.06±0.2°, 34.34±0.2°, 34.69±0.2°, 35.58±0.2°, 36.19±0.2°, 36.62±0.2°, 37.41±0.2°, 38.30±0.2°, 38.77±0.2°, and 39.24±0.2°.

22. Compound II Pattern 1 of embodiment 18, characterized by an XRPD pattern comprising at least thirty 2theta values selected from 3.08±0.2°, 6.07±0.2°, 8.80±0.2°, 9.30±0.2°, 10.66±0.2°, 12.08±0.2°, 12.60±0.2°, 14.92±0.2°, 15.10±0.2°, 17.45±0.2°, 17.838±0.2°, 18.13±0.2°, 18.63±0.2°, 18.89±0.2°, 19.78±0.2°, 20.14±0.2°, 20.81±0.2°, 21.24±0.2°, 21.59±0.2°, 21.89±0.2°, 22.91±0.2°, 23.34±0.2°, 24.23±0.2°, 25.14±0.2°, 25.33±0.2°, 25.86±0.2°, 26.78±0.2°, 27.13±0.2°, 27.59±0.2°, 27.99±0.2°, 28.82±0.2°, 29.23±0.2°, 29.45±0.2°, 30.39±0.2°, 31.18±0.2°, 31.66±0.2°, 32.27±0.2°, 32.69±0.2°, 33.43±0.2°, 34.06±0.2°, 34.34±0.2°, 34.69±0.2°, 35.58±0.2°, 36.19±0.2°, 36.62±0.2°, 37.41±0.2°, 38.30±0.2°, 38.77±0.2°, and 39.24±0.2°.

23. Compound II Pattern 1 of embodiment 18, characterized by an XRPD pattern comprising at least twenty-five 2theta values selected from 3.08±0.2°, 6.07±0.2°, 8.80±0.2°, 9.30±0.2°, 10.66±0.2°, 12.08±0.2°, 12.60±0.2°, 14.92±0.2°, 15.10±0.2°, 17.45±0.2°, 17.838±0.2°, 18.13±0.2°, 18.63±0.2°, 18.89±0.2°, 19.78±0.2°, 20.14±0.2°, 20.81±0.2°, 21.24±0.2°, 21.59±0.2°, 21.89±0.2°, 22.91±0.2°, 23.34±0.2°, 24.23±0.2°, 25.14±0.2°, 25.33±0.2°, 25.86±0.2°, 26.78±0.2°, 27.13±0.2°, 27.59±0.2°, 27.99±0.2°, 28.82±0.2°, 29.23±0.2°, 29.45±0.2°, 30.39±0.2°, 31.18±0.2°, 31.66±0.2°, 32.27±0.2°, 32.69±0.2°, 33.43±0.2°, 34.06±0.2°, 34.34±0.2°, 34.69±0.2°, 35.58±0.2°, 36.19±0.2°, 36.62±0.2°, 37.41±0.2°, 38.30±0.2°, 38.77±0.2°, and 39.24±0.2°.

24. Compound II Pattern 1 of embodiment 18, characterized by an XRPD pattern comprising at least twenty 2theta values selected from 3.08±0.2°, 6.07±0.2°, 8.80±0.2°, 9.30±0.2°, 10.66±0.2°, 12.08±0.2°, 12.60±0.2°, 14.92±0.2°, 15.10±0.2°, 17.45±0.2°, 17.838±0.2°, 18.13±0.2°, 18.63±0.2°, 18.89±0.2°, 19.78±0.2°, 20.14±0.2°, 20.81±0.2°, 21.24±0.2°, 21.59±0.2°, 21.89±0.2°, 22.91±0.2°, 23.34±0.2°, 24.23±0.2°, 25.14±0.2°, 25.33±0.2°, 25.86±0.2°, 26.78±0.2°, 27.13±0.2°, 27.59±0.2°, 27.99±0.2°, 28.82±0.2°, 29.23±0.2°, 29.45±0.2°, 30.39±0.2°, 31.18±0.2°, 31.66±0.2°, 32.27±0.2°, 32.69±0.2°, 33.43±0.2°, 34.06±0.2°, 34.34±0.2°, 34.69±0.2°, 35.58±0.2°, 36.19±0.2°, 36.62±0.2°, 37.41±0.2°, 38.30±0.2°, 38.77±0.2°, and 39.24±0.2°.

25. Compound II Pattern 1 of embodiment 18, characterized by an XRPD pattern comprising at least fifteen 2theta values selected from 3.08±0.2°, 6.07±0.2°, 8.80±0.2°, 9.30±0.2°, 10.66±0.2°, 12.08±0.2°, 12.60±0.2°, 14.92±0.2°, 15.10±0.2°, 17.45±0.2°, 17.838±0.2°, 18.13±0.2°, 18.63±0.2°, 18.89±0.2°, 19.78±0.2°, 20.14±0.2°, 20.81±0.2°, 21.24±0.2°, 21.59±0.2°, 21.89±0.2°, 22.91±0.2°, 23.34±0.2°, 24.23±0.2°, 25.14±0.2°, 25.33±0.2°, 25.86±0.2°, 26.78±0.2°, 27.13±0.2°, 27.59±0.2°, 27.99±0.2°, 28.82±0.2°, 29.23±0.2°, 29.45±0.2°, 30.39±0.2°, 31.18±0.2°, 31.66±0.2°, 32.27±0.2°, 32.69±0.2°, 33.43±0.2°, 34.06±0.2°, 34.34±0.2°, 34.69±0.2°, 35.58±0.2°, 36.19±0.2°, 36.62±0.2°, 37.41±0.2°, 38.30±0.2°, 38.77±0.2°, and 39.24±0.2°.

26. Compound II Pattern 1 of any one of embodiments 1-25, wherein the ratio of Compound II to fumaric acid is approximately 1:1 by $^1$H NMR.

Compound II Pattern 1 can be produced, for example, by recrystallizing Compound II (Example 12, Table 31), equilibration of Compound II in a suitable solvent, or crystallization by slow evaporation of solvent (Example 12, Table 32). The invention thus includes at least the following features:

1. In certain embodiments Compound II Pattern 1 is prepared by recrystallization of Compound II.
2. In certain embodiments Compound II Pattern 1 is prepared by equilibration of Compound II in a solvent.
3. In certain embodiments Compound II Pattern 1 is prepared by slow evaporation of solvent from a solution of Compound II.
4. The process of embodiment 1, wherein Compound II is dissolved in an alcoholic solvent and crystallized as Pattern 1 by the addition of an ethereal solvent.
5. The process of embodiment 1, wherein Compound II is dissolved in an alcoholic solvent and crystallized as Pattern 1 by the addition of an aliphatic solvent.
6. The process of embodiment 1, wherein Compound II is dissolved in an ethereal solvent and crystallized as Pattern 1 by the addition of an aliphatic solvent.
7. The process of embodiment 4 or 5, wherein the alcoholic solvent is or comprises methanol.
8. The process of embodiment 4 or 5, wherein the alcoholic solvent is or comprises ethanol.
9. The process of embodiment 4 or 5, wherein the alcoholic solvent is or comprises isopropanol.
10. The process of embodiment 4 or 5, wherein the alcoholic solvent is or comprises n-propanol.
11. The process of embodiment 4 or 5, wherein the alcoholic solvent is or comprises n-butanol.
12. The process of embodiment 4 or 5, wherein the alcoholic solvent is or comprises isoamyl alcohol.
13. The process of embodiment 4 or 5, wherein the alcoholic solvent is or comprises cyclohexanol.
14. The process of embodiment 4 or 6, wherein the ethereal solvent is or comprises diethyl ether.
15. The process of embodiment 4 or 6, wherein the ethereal solvent is or comprises dibutyl ether.
16. The process of embodiment 4 or 6, wherein the ethereal solvent is or comprises methyl tert-butyl ether.
17. The process of embodiment 4 or 6, wherein the ethereal solvent is or comprises cyclopropyl methyl ether.
18. The process of embodiment 4 or 6, wherein the ethereal solvent is or comprises glyme.
19. The process of embodiment 4 or 6, wherein the ethereal solvent is or comprises tetrahydrofuran.
20. The process of embodiment 4 or 6, wherein the ethereal solvent is 2-methyl tetrahydrofuran.
21. The process of embodiment 4 or 6, wherein the ethereal solvent is or comprises dioxane.
22. The process of any one of embodiments 5-21, wherein the aliphatic solvent is or comprises pentane.
23. The process of any one of embodiments 5-21, wherein the aliphatic solvent is or comprises n-hexane.
24. The process of any one of embodiments 5-21, wherein the aliphatic solvent is or comprises heptane.
25. The process of any one of embodiments 5-21, wherein the aliphatic solvent is or comprises petroleum ether.
26. The process of any one of embodiments 5-21, wherein the aliphatic solvent is or comprises octane.
27. The process of any one of embodiments 5-21, wherein the aliphatic solvent is or comprises cyclohexane.
28. The process of any one of embodiments 5-21, wherein the aliphatic solvent is or comprises a mixture of hexane isomers.
29. The process of any one of embodiments 4-28, wherein the solids are collected by filtration.
30. The process of any one of embodiments 4-28, wherein the solution is cooled after addition of the aliphatic solvent.
31. The process of embodiment 30, wherein the solution is cooled to less than about 10° C.
32. The process of embodiment 30, wherein the solution is cooled to about or less than about 5° C.
33. The process of any one of embodiments 4-32, wherein the solution, suspension or slurry is stirred until crystallization occurs.
34. The process of embodiment 33, wherein the solution, suspension or slurry is stirred for at least about one day.
35. The process of embodiment 33, wherein the solution, suspension or slurry is stirred for at least about one week.
36. The process of embodiment 33, wherein the solution, suspension or slurry is stirred for at least about two weeks.
37. The process of embodiment 33, wherein the solution, suspension or slurry is stirred for at least about three weeks.
38. The process of embodiment 2, wherein Compound II is dissolved in an equilibration solvent at 25° C. and stirred for a period of time from about 2 weeks to about 3 weeks.

39. The process of embodiment 2, wherein the equilibration solvent is a binary mixture of solvents.
40. The process of embodiment 2, wherein the equilibration solvent is isopropanol.
41. The process of embodiment 39, wherein the equilibration solvent is about one part tetrahydrofuran to about three parts heptanes.
42. The process of embodiment 39, wherein the equilibration solvent is about one part ethanol to about three parts heptanes.
43. The process of embodiment 39, wherein the equilibration solvent is about one part ethyl acetate to about three parts toluene.
44. The process of embodiment 39, wherein the equilibration solvent is about one part isopropanol to about one part heptanes.
45. The process of embodiment 39, wherein the equilibration solvent is about one part isopropanol to about one part toluene.
46. The process of embodiment 39, wherein the equilibration solvent is about one part isopropanol to about three parts methyl tert-butyl ether.
47. The process of embodiment 39, wherein the equilibration solvent is about one part isopropanol to about four parts heptanes.
48. The process of embodiment 39, wherein the equilibration solvent is about one part ethanol to about one parts toluene.
49. The process of embodiment 3, wherein Compound II was dissolved in an appropriate solvent, filtered through a 0.45 μM filter, then maintained at 23° C. and one atmosphere of pressure until the solvent evaporated.
50. The process of embodiment 49, wherein the solvent is or comprises acetone.
51. The process of embodiment 49, wherein the solvent is or comprises methyl ethyl ketone.
52. The process of embodiment 49, wherein the solvent is or comprises ethyl acetate.
53. The process of embodiment 49, wherein the solvent is or comprises methanol.
54. The process of embodiment 49, wherein the solvent is or comprises ethanol.
55. The process of embodiment 49, wherein the solvent is or comprises isopropanol.
56. The process of embodiment 49, wherein the solvent is or comprises tetrahydrofuran.

Isolated morphic forms Pattern 1 and Pattern 2 of Compound III are provided in this invention. In one embodiment, Pattern 1 is characterized by an XRPD pattern in or substantially similar to that in FIG. 77.

1. In one embodiment, Compound III Pattern 1 is characterized by an XRPD pattern comprising independently at least 2, 3, 4, 5, or 6 of the 2theta values selected from 9.53±0.2°, 10.04±0.2°, 11.60±0.2°, 14.57±0.2°, 17.22±0.2°, 17.50±0.2°, 20.04±0.2°, 20.36±0.2°, 22.34±0.2°, 23.73±0.2°, 25.48±0.2°, 26.06±0.2°, 27.38±0.2°, and 32.20±0.2°.
2. Compound III Pattern 1 of embodiment 1, characterized by an XRPD pattern comprising at least twelve 2theta values selected from 9.53±0.2°, 10.04±0.2°, 11.60±0.2°, 14.57±0.2°, 17.22±0.2°, 17.50±0.2°, 20.04±0.2°, 20.36±0.2°, 22.34±0.2°, 23.73±0.2°, 25.48±0.2°, 26.06±0.2°, 27.38±0.2°, and 32.20±0.2°.
3. Compound III Pattern 1 of embodiment 1, characterized by an XRPD pattern comprising at least eleven 2theta values selected from 9.53±0.2°, 10.04±0.2°, 11.60±0.2°, 14.57±0.2°, 17.22±0.2°, 17.50±0.2°, 20.04±0.2°, 20.36±0.2°, 22.34±0.2°, 23.73±0.2°, 25.48±0.2°, 26.06±0.2°, 27.38±0.2°, and 32.20±0.2°.
4. Compound III Pattern 1 of embodiment 1, characterized by an XRPD pattern comprising at least ten 2theta values selected from 9.53±0.2°, 10.04±0.2°, 11.60±0.2°, 14.57±0.2°, 17.22±0.2°, 17.50±0.2°, 20.04±0.2°, 20.36±0.2°, 22.34±0.2°, 23.73±0.2°, 25.48±0.2°, 26.06±0.2°, 27.38±0.2°, and 32.20±0.2°.
5. Compound III Pattern 1 of embodiment 1, characterized by an XRPD pattern comprising at least nine 2theta values selected from 9.53±0.2°, 10.04±0.2°, 11.60±0.2°, 14.57±0.2°, 17.22±0.2°, 17.50±0.2°, 20.04±0.2°, 20.36±0.2°, 22.34±0.2°, 23.73±0.2°, 25.48±0.2°, 26.06±0.2°, 27.38±0.2°, and 32.20±0.2°.
6. Compound III Pattern 1 of embodiment 1, characterized by an XRPD pattern comprising at least eight 2theta values selected from 9.53±0.2°, 10.04±0.2°, 11.60±0.2°, 14.57±0.2°, 17.22±0.2°, 17.50±0.2°, 20.04±0.2°, 20.36±0.2°, 22.34±0.2°, 23.73±0.2°, 25.48±0.2°, 26.06±0.2°, 27.38±0.2°, and 32.20±0.2°.
7. Compound III Pattern 1 of embodiment 1, characterized by an XRPD pattern comprising at least seven 2theta values selected from 9.53±0.2°, 10.04±0.2°, 11.60±0.2°, 14.57±0.2°, 17.22±0.2°, 17.50±0.2°, 20.04±0.2°, 20.36±0.2°, 22.34±0.2°, 23.73±0.2°, 25.48±0.2°, 26.06±0.2°, 27.38±0.2°, and 32.20±0.2°.
8. Compound III Pattern 1 of embodiment 1, characterized by an XRPD pattern comprising at least six 2theta values selected from 9.53±0.2°, 10.04±0.2°, 11.60±0.2°, 14.57±0.2°, 17.22±0.2°, 17.50±0.2°, 20.04±0.2°, 20.36±0.2°, 22.34±0.2°, 23.73±0.2°, 25.48±0.2°, 26.06±0.2°, 27.38±0.2°, and 32.20±0.2°.
9. Compound III Pattern 1 of embodiment 1, characterized by an XRPD pattern comprising at least five 2theta values selected from 9.53±0.2°, 10.04±0.2°, 11.60±0.2°, 14.57±0.2°, 17.22±0.2°, 17.50±0.2°, 20.04±0.2°, 20.36±0.2°, 22.34±0.2°, 23.73±0.2°, 25.48±0.2°, 26.06±0.2°, 27.38±0.2°, and 32.20±0.2°.
10. In one embodiment, Compound III Pattern 2 is characterized by an XRPD pattern comprising independently at least 3, 4, 5, or 6 of the 2theta values selected from 8.94±0.2°, 9.89±0.2°, 9.91±0.2°, 11.66±0.2°, 12.11±0.2°, 15.13±0.2°, 17.85±0.2°, 18.15±0.2°, 19.90±0.2°, 20.38±0.2°, 22.94±0.2°, 25.09±0.2°, 26.54±0.2°, 26.90±0.2°, 27.38±0.2°, 28.28±0.2°, 28.95±0.2°, 29.64±0.2°, and 38.07±0.2°.
11. Compound III Pattern 2 of embodiment 10, characterized by an XRPD pattern comprising at least twelve of the 2theta values selected from 8.94±0.2°, 9.89±0.2°, 9.91±0.2°, 11.66±0.2°, 12.11±0.2°, 15.13±0.2°, 17.85±0.2°, 18.15±0.2°, 19.90±0.2°, 20.38±0.2°, 22.94±0.2°, 25.09±0.2°, 26.54±0.2°, 26.90±0.2°, 27.38±0.2°, 28.28±0.2°, 28.95±0.2°, 29.64±0.2°, and 38.07±0.2°.
12. Compound III Pattern 2 of embodiment 10, characterized by an XRPD pattern comprising independently at least 3, 4, 5, or 6 of the 2theta values selected from 8.94±0.2°, 9.89±0.2°, 9.91±0.2°, 11.66±0.2°, 12.11±0.2°, 15.13±0.2°, 17.85±0.2°, 18.15±0.2°, 19.90±0.2°, 25.09±0.2°, 29.64±0.2°, and 38.07±0.2°.
13. Compound III Pattern 2 of embodiment 10, characterized by an XRPD pattern comprising at least eleven of the 2theta values selected from 8.94±0.2°, 9.89±0.2°, 9.91±0.2°, 11.66±0.2°, 12.11±0.2°, 15.13±0.2°, 17.85±0.2°, 18.15±0.2°, 19.90±0.2°, 25.09±0.2°, 29.64±0.2°, and 38.07±0.2°.

14. Compound III Pattern 2 of embodiment 10, characterized by an XRPD pattern comprising at least ten of the 2theta values selected from 8.94±0.2°, 9.89±0.2°, 9.91±0.2°, 11.66±0.2°, 12.11±0.2°, 15.13±0.2°, 17.85±0.2°, 18.15±0.2°, 19.90±0.2°, 25.09±0.2°, 29.64±0.2°, and 38.07±0.2°.

15. Compound III Pattern 2 of embodiment 10, characterized by an XRPD pattern comprising at least nine of the 2theta values selected from 8.94±0.2°, 9.89±0.2°, 9.91±0.2°, 11.66±0.2°, 12.11±0.2°, 15.13±0.2°, 17.85±0.2°, 18.15±0.2°, 19.90±0.2°, 25.09±0.2°, 29.64±0.2°, and 38.07±0.2°.

16. Compound III Pattern 2 of embodiment 10, characterized by an XRPD pattern comprising at least eight of the 2theta values selected from 8.94±0.2°, 9.89±0.2°, 9.91±0.2°, 11.66±0.2°, 12.11±0.2°, 15.13±0.2°, 17.85±0.2°, 18.15±0.2°, 19.90±0.2°, 25.09±0.2°, 29.64±0.2°, and 38.07±0.2°.

17. Compound III Pattern 2 of embodiment 10, characterized by an XRPD pattern comprising at least seven of the 2theta values selected from 8.94±0.2°, 9.89±0.2°, 9.91±0.2°, 11.66±0.2°, 12.11±0.2°, 15.13±0.2°, 17.85±0.2°, 18.15±0.2°, 19.90±0.2°, 25.09±0.2°, 29.64±0.2°, and 38.07±0.2°.

18. Compound III Pattern 2 of embodiment 10, characterized by an XRPD pattern comprising at least six of the 2theta values selected from 8.94±0.2°, 9.89±0.2°, 9.91±0.2°, 11.66±0.2°, 12.11±0.2°, 15.13±0.2°, 17.85±0.2°, 18.15±0.2°, 19.90±0.2°, 25.09±0.2°, 29.64±0.2°, and 38.07±0.2°.

19. Compound III Pattern 2 of embodiment 10, characterized by an XRPD pattern comprising at least five of the 2theta values selected from 8.94±0.2°, 9.89±0.2°, 9.91±0.2°, 11.66±0.2°, 12.11±0.2°, 15.13±0.2°, 17.85±0.2°, 18.15±0.2°, 19.90±0.2°, 25.09±0.2°, 29.64±0.2°, and 38.07±0.2°.

Compound III Pattern 1 can be produced, for example, by precipitation from isopropanol and heptanes (Example 15, Table 40). In certain nonlimiting embodiments, Compound III Pattern 1 was prepared by dissolving $S_P$-Compound I free base in isopropanol, for example about 100 mg of $S_P$-Compound I in about 0.25 mL to about 0.5 mL of isopropanol. To this solution was added about 1.0 eq of fumaric acid, and the mixture stirred at ambient or elevated temperature, for example about 25° C. to about 60° C. Next, about two to about five times as much heptanes was added as isopropanol. The resulting mixture was stirred at ambient or elevated temperature, for example about 25° C. to about 60° C., and then cooled gradually, for example about 0.01° C./min to 1° C./min the solids isolated by filtration and then dried at ambient or reduced pressure.

IV. Definitions

Unless defined otherwise, all technical and scientific terms used herein have the same meaning as is commonly understood by one of ordinary skill in the art. All patents, applications, and published applications referenced herein are incorporated by reference in their entirety unless stated otherwise. In the event that there are a plurality of definitions for a term herein, those in this section prevail unless stated otherwise.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "alcoholic solvent" as used herein refers to a solvent with a free hydroxyl group that is a liquid at either room temperature or the temperature of use. Nonlimiting examples of alcoholic solvents include methanol, ethanol, ethanediol, isopropanol, n-propanol, glycerol, n-butanol, iso-butanol, tert-butanol, 2-butanol, n-pentanol (n-amyl alcohol), iso-pentanol (isoamyl alcohol), neopentyl alcohol, hexanol, cyclohexanol, cyclohexane diol, phenol, benzyl alcohol, propargyl alcohol, diethylene glycol, 1,2-propane diol, heptanol, octanol, nonanol, and decanol.

The term "aliphatic solvent" as used herein refers to a hydrocarbon solvent that is a liquid at room temperature or the temperature of use. Nonlimiting examples of an aliphatic solvent include pentane, isopentane, cyclopentane, n-hexane, hexanes (mixture of isomers), cyclohexane, 2-hexene, 3-hexene, methyl cyclohexane, heptanes, octanes, isooctane, petroleum ether, naphtha, mineral spirits, nonane, decane, undecane, dodecane.

The term "ethereal solvent" as used herein refers to a solvent that contains at least one ether linkage and is a liquid at room temperature or the temperature of use. Examples of an ethereal solvent include but are not limited to diethyl ether, diisopropyl ether, methyl tert-butyl ether, dibutyl ether, tert-amyl ethyl ether, cyclopentyl methyl ether, ditert-butyl ether, ethyl tert-butyl ether, propylene glycol methyl ether, ethylene glycol ethyl ether, glyme, diglyme, glycol ethers, dioxane, tetrahydrofuran, 2-methyl tetrahydrofuran, 4-methyl tetrahydrofuran, and tetrahydropyran.

Where a range of values is provided, it is understood that the upper and lower limit, and each intervening value between the upper and lower limit of the range is encompassed within the embodiments.

As used herein, "about" refers to a range that includes up to 10% less than and up to 10% greater than the stated value. For example, "about 100 milligrams" includes all values from 90 milligrams to 110 milligrams.

The terms "therapeutically effective amount" and "effective amount" are used to indicate an amount of an active compound, or pharmaceutical agent, or its metabolite, that elicits a desired treatment effect. For example, an effective amount of compound can be the amount needed to prevent, alleviate or ameliorate symptoms of disease or prolong the survival of the subject such as a human being treated. This response may occur in a tissue, system, animal or human and includes alleviation of the signs or symptoms of the disease being treated.

Isotopic Substitution

The present invention includes but is not limited to compounds, pharmaceutical compositions, and the use of any of the active compounds described herein, including but not limited to Compound I monofumarate, Compound II or Compound III, with desired isotopic substitutions of atoms at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2H$) and tritium (H) may be used anywhere in described structures. Alternatively, or in addition, isotopes of carbon, e.g., $^{13}C$ and $^{14}C$, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect). Achillion Pharmaceuticals, Inc. (WO/2014/169278 and WO/2014/169280) describes deuteration of nucleotides to improve their pharmacokinetic or pharmacodynamic, including at the 5-position of the molecule.

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break-down can reduce the rate of or eliminate the metabolism at that bond. At any position of the compound that a hydrogen atom may be present, the hydrogen atom can be any isotope of hydrogen, including protium ($^1H$), deuterium ($^2H$) and tritium ($^3H$). Thus, reference herein to a compound encompasses all potential isotopic forms unless the context clearly dictates otherwise.

The term "isotopically-labeled" analog refers to an analog that is a "deuterated analog", a "$^{13}C$-labeled analog," or a "deuterated/$^{13}C$-labeled analog." The term "deuterated analog" means a compound described herein, whereby a H-isotope, i.e., hydrogen/protium (H), is substituted by a H-isotope, i.e., deuterium ($^2H$). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location. Unless indicated to the contrary, the deuteration is at least 80% at the selected location. Deuteration of the nucleoside can occur at any replaceable hydrogen that provides the desired results.

V. Treatment or Prophylaxis of HPV-Induced Intraepithelial Neoplasia

In exemplary non-limiting embodiments, a method for the treatment of HPV infection or HPV-induced intraepithelial neoplasia is provided that includes administering an effective amount of one or a combination of the active compounds as described herein in a topical formulation that is sufficient to treat the neoplasia or the resulting effects thereof, as described further herein. Types of HPV-induced intraepithelial neoplasia include but are not limited to cervical, vaginal, vulvar, penile, perianal and anal.

In an exemplary embodiment, a formulation for the treatment of intraepithelial neoplasia is a dosage form containing from about 0.005 mg to about 50 mg, from about 0.05 mg to about 40 mg, from about 0.1 mg to about 30 mg, from about 0.5 mg to about 20 mg, from about 1 mg to about 20 mg, from about 1 mg to about 15 mg, or from about 1 mg to about 10 mg of any of the active compounds described herein including but not limited to Compound I monofumarate, Compound II or Compound III. In certain embodiments, a formulation for the treatment of intraepithelial neoplasia is a dosage form that contains from about 0.01 mg to about 10 mg, from about 0.05 to about 5 mg, from about 0.05 to about 0.15 mg, from about 0.15 mg to about 0.45 mg, or from about 0.5 to about 1.5 mg of any of the active compounds described herein including but not limited to Compound I monofumarate, Compound II or Compound III. In certain embodiments, a formulation for the treatment of intraepithelial neoplasia is a dosage form that contains about or at least 0.005, 0.01, 0.03, 0.05, 0.1 mg, 0.3 mg. 0.5 mg, 0.7 mg, 1 mg, 1.5 mg, 2 mg, 2.5 mg, 3 mg, 4 mg, 5 mg, 10 mg, 15 mg, 20 mg, 25 mg, 30 mg, 35 mg, 40 mg, 45 mg or 50 mg of Compound I monofumarate, Compound II or Compound III.

In certain embodiments, a formulation for the treatment of intraepithelial neoplasia is a dosage form containing of from about 0.001 to about 20 mg, from about 0.005 to about 10 mg, from about 0.01 mg to about 5 mg, from about 0.03 mg to about 1 mg, or from about 0.05 mg to about 0.3 mg of Compound I monofumarate, Compound II or Compound III In certain embodiments, the topical formulation is administered twice a day, once a day, or several days a week (such as 2 or 3 days a week), as long as necessary to achieve the desired results. In certain embodiments, the topical formulation is administered on a weekly schedule for one, two, three, four, five, six or more weeks. In certain aspects, the topical formulation is administered on a schedule of three dosages a week for two, three, four, five, or six weeks.

In certain embodiments, the compound can be administered in one or more therapeutic cycles comprising a treatment cycle and a rest cycle, wherein the treatment cycle comprises administering the compound as described herein, followed by a rest cycle (comprising a period of no treatment) before the next treatment cycle. In certain embodiments, the rest cycle is from about one day to about six months. In certain embodiments the rest cycle is one, two, three, four, five, six, seven, eight or more weeks before the next treatment cycle. In certain embodiments, multiple therapeutic cycles are administered, for example one, two, three, four, five, or six therapeutic cycles.

Dosage forms which do not adhere well to the target site may be dislodged, interfering with treatment. Dosage forms have been discovered that adhere to the target site and dissolve rapidly in low fluid volumes. Adhesion to the target site also prevents exposure to healthy tissues, which may limit toxicity and side effects. Dosage forms which soften, break down, and/or disintegrate quickly in low fluid volumes are advantageous to cause a rapid release of the active compound to the target tissue. Dosage forms that disintegrate in, for example, less than about 50 µL, less than about 100 µL, less than about 125 µL, less than about 150 µL, less than about 175 µL, less than about 200 µL, or less than about 250 µL fluid particularly facilitate drug penetration into the target site.

In certain embodiments, the dosage form is a gel. In certain embodiments, the dosage form is a cream. In certain embodiments, the dosage form is a tablet. In certain embodiments, the dosage form disintegrates in about one to about ten seconds. In certain embodiments, the dosage form disintegrates in about ten seconds to one minute. In certain embodiments, the dosage form disintegrates in about one minute to about one hour. In certain embodiments, the dosage form disintegrates in about one to six hours.

The physical dimensions of the dosage form can impact the effectiveness of the dosage form. A tablet that is thinner provides a greater surface area to volume ratio and may degrade quicker and cover the target area better. In certain embodiments the dosage form is less than about 6, 5, 4, 3, or 2 millimeters thick in its smallest dimension.

The formulation of the dosage form is important for adequate administration of the active agent into the intraepithelial tissue. The formulation for example, can be prepared for use as a tablet, a reconstituted powder, a dry powder, a semi solid dosage form, a film or a pessary (i.e., a vaginal suppository).

Some embodiments disclosed herein include the use of an effective amount of Compound I monofumarate, Compound II or Compound III, in the manufacture of a medicament for ameliorating or treating a human papillomavirus infection, wherein the infection can be ameliorated or treated by inhibiting viral replication by inhibiting the synthesis of viral DNA. Other embodiments disclosed herein include the use of an effective amount of any of the active compounds described herein including but not limited to Compound I monofumarate, Compound II or Compound III, for ameliorating or treating a human papillomavirus infection, wherein the human papillomavirus infection can be ameliorated or treated by inhibiting viral replication by inhibiting the synthesis of viral DNA.

Certain nonlimiting embodiments disclosed herein include a method for ameliorating or treating a human papillomavirus infection that can include contacting a cell infected with the human papillomavirus in a subject with an effective amount of any of the active compounds described herein including but not limited to Compound I monofumarate, Compound II or Compound III, wherein the infection is ameliorated or treated by inhibiting the synthesis of viral DNA. Yet still other embodiments disclosed herein include a method for ameliorating or treating a human papillomavirus infection that can include administering to a subject infected with the human papillomavirus an effective amount of Compound I monofumarate, Compound II or Compound III, wherein the human papillomavirus infection can be ameliorated or treated by inhibiting viral replication by inhibiting the synthesis of viral DNA. Some embodiments disclosed herein relate Compound I monofumarate, Compound II or Compound III, for use in ameliorating or treating a human papillomavirus infection, wherein the human papillomavirus infection can be ameliorated or treated by inhibiting viral replication by inhibiting the synthesis of viral DNA.

In some embodiments, the human papillomavirus can be a high-risk human papillomavirus, such as those described herein. For example, the high-risk human papillomavirus can be selected from HPV-16, HPV-18, HPV-31, HPV-33, HPV-35, HPV-39, HPV-45, HPV-51, HPV-52, HPV-56, HPV-58, HPV-59, HPV-68, HPV-73 and HPV-82. In some embodiments, the human papillomavirus can be HPV-16. In some embodiments, the human papillomavirus can be HPV-11. In some embodiments, the human papillomavirus can be HPV-18. In some embodiments, the human papillomavirus can be one or more of the following high-risk types: HPV-31, HPV-33, HPV-35, HPV-39, HPV-45, HPV-51, HPV-52, HPV-56, HPV-58, HPV-59, HPV-68, HPV-73 and HPV-82. As described herein, the presence of an HPV infection can be detected using the Papanicolaou test (Pap smear) and/or DNA probe testing (for example, HPV DNA probe testing for one or more high-risk HPV types). Therefore, in some embodiments, an effective amount of Compound I monofumarate, Compound II or Compound III, can be provided to a subject diagnosed with an HPV infection, for example a high-risk HPV infection, by a DNA test. In some embodiments, an effective amount of Compound I monofumarate, Compound II or Compound III can be provided to a subject diagnosed with an HPV infection, or a disease associated with HPV infection, as identified by a Papanicolaou test.

In certain embodiments, an effective amount of Compound I monofumarate, Compound II, or Compound III may be provided to a subject with a Papanicolaou test result that does not indicate the disease has progressed to cervical cancer. The Bethesda system is a standardized scoring system for reporting pap smear test results and assigns a grade of 1-3 based on severity. Grade 1 CIN (CIN 1) indicates mild dysplasia. Grades 2 and 3 CIN (CIN 2, CIN 3) are more serious and typically require intervention. In certain embodiments, Compound I monofumarate, Compound II or Compound III is used to treat CIN 1 (Grade 1 cervical intraepithelial neoplasia). In certain embodiments, Compound I monofumarate, Compound II or Compound III is used to treat CIN 2 (Grade 2 cervical intraepithelial neoplasia). In certain embodiments, Compound I monofumarate, Compound II or Compound III is used to treat CIN 3 (Grade 3 cervical intraepithelial neoplasia).

In certain embodiments, a pharmaceutical composition comprising Compound I monofumarate, Compound II or Compound III, is used in the manufacture of a medicament for the treatment of CIN 1 (Grade 1 cervical intraepithelial neoplasia). In certain embodiments, a pharmaceutical composition comprising Compound I monofumarate, Compound II or Compound III, is used in the manufacture of a medicament for the treatment of CIN 2 (Grade 2 cervical intraepithelial neoplasia). In certain embodiments, a pharmaceutical composition comprising Compound I monofumarate, Compound II or Compound III, is used in the manufacture of a medicament for the treatment of CIN 3 (Grade 3 cervical intraepithelial neoplasia).

In certain embodiments, Compound I monofumarate, Compound II or Compound III, optionally in a pharmaceutically acceptable carrier, is used to treat a condition selected from the group consisting of atypical squamous cells of undetermined significance (ASC-US), atypical glandular cells (AGC), low-grade squamous intraepithelial lesions (LSIL), atypical squamous cells (cannot exclude high grade squamous intraepithelial lesion) (ASC-H), high grade squamous intraepithelial lesions (HSIL), adenocarcinoma in situ (AIS), and cervical cancer (e.g. squamous cell carcinoma or adenocarcinoma).

In certain embodiments, an effective amount of Compound II may be provided to a subject with a Papanicolaou test result that does not indicate the disease has progressed to cervical cancer. In certain embodiments, Compound II is used to treat CIN 1 (Grade 1 cervical intraepithelial neoplasia). In certain embodiments, Compound II is used to treat CIN 2 (Grade 2 cervical intraepithelial neoplasia). In certain embodiments, Compound II is used to treat CIN 3 (Grade 3 cervical intraepithelial neoplasia).

In certain embodiments, a pharmaceutical composition comprising Compound II is used in the manufacture of a medicament for the treatment of CIN 1 (Grade 1 cervical intraepithelial neoplasia). In certain embodiments, a pharmaceutical composition comprising Compound II is used in the manufacture of a medicament for the treatment of CIN 2 (Grade 2 cervical intraepithelial neoplasia). In certain embodiments, a pharmaceutical composition comprising Compound II is used in the manufacture of a medicament for the treatment of CIN 3 (Grade 3 cervical intraepithelial neoplasia).

In certain embodiments, Compound II optionally in a pharmaceutically acceptable carrier, is used to treat a condition selected from the group consisting of atypical squamous cells of undetermined significance (ASC-US), atypical glandular cells (AGC), low-grade squamous intraepithelial lesions (LSIL), atypical squamous cells (cannot exclude high grade squamous intraepithelial lesion) (ASC-H), high grade squamous intraepithelial lesions (HSIL), adenocarcinoma in situ (AIS), and cervical cancer (e.g. squamous cell carcinoma or adenocarcinoma).

In certain embodiments, Compound I monofumarate, Compound II or Compound III is used in the manufacture of a medicament for the treatment of anal intraepithelial neoplasia. In certain embodiments, Compound I monofumarate, Compound II or Compound III is used in the manufacture of a medicament for the treatment of perianal intraepithelial neoplasia. In certain embodiments, Compound I monofumarate, Compound II or Compound III is used in the manufacture of a medicament for the treatment of vulvar intraepithelial neoplasia. In certain embodiments, Compound I monofumarate, Compound II or Compound III is used in the manufacture of a medicament for the treatment of penile intraepithelial neoplasia. In certain embodiments, Compound I monofumarate, Compound II or Compound III is used in the manufacture of a medicament for the treatment of vaginal intraepithelial neoplasia.

In certain embodiments, Compound I monofumarate, Compound II or Compound III is used to treat anal intraepithelial neoplasia. In certain embodiments, Compound I monofumarate, Compound II or Compound III is used to treat perianal intraepithelial neoplasia. In certain embodiments, Compound I monofumarate, Compound II or Compound III is used to treat vulvar intraepithelial neoplasia. In certain embodiments, Compound I monofumarate, Compound II or Compound III is used to treat penile intraepithelial neoplasia. In certain embodiments, Compound I monofumarate, Compound II or Compound III is used to treat vaginal intraepithelial neoplasia.

In some embodiments, the human papillomavirus can be a low-risk human papillomavirus, including those described herein. In some embodiments, the human papillomavirus can be HPV-6. In some embodiments, the human papillomavirus can be HPV-11.

Compound I monofumarate, Compound II or Compound III, can be used to ameliorate and/or treat an infection caused by one or more types of human papillomaviruses. For example, Compound I monofumarate, Compound II or Compound III, can be used to ameliorate and/or treat an infection of HPV-16 and/or HPV-18. In certain embodiments, Compound I monofumarate, Compound II or Compound III can be used to treat a high-risk HPV infection. In certain embodiments, Compound I monofumarate, Compound II or Compound III can be used to treat a related disease or condition occurring as a result of a high-risk HPV infection. In some embodiments, Compound I monofumarate, Compound II or Compound III, can be used to ameliorate and/or treat an infection comprising both high-risk and low-risk HPV.

Compound I monofumarate, Compound II or Compound III, can be used in the manufacture of a medicament for use to ameliorate and/or treat an infection caused by one or more types of human papillomaviruses. For example, Compound I monofumarate, Compound II or Compound III, can be used in the manufacture of a medicament for use to ameliorate and/or treat an infection of HPV-16 and/or HPV-18. In certain embodiments, Compound I monofumarate, Compound II or Compound III can be used in the manufacture of a medicament for use to treat a high-risk HPV infection. In certain embodiments, Compound I monofumarate, Compound II or Compound III can be used in the manufacture of a medicament for use to treat a related disease or condition occurring as a result of a high-risk HPV infection. In some embodiments, Compound I monofumarate, Compound II or Compound III, can be used in the manufacture of a medicament for use to ameliorate and/or treat an infection comprising both high-risk and low-risk HPV.

As will be readily apparent to one skilled in the art, the useful in vivo dosage to be administered and the particular mode of administration will vary depending upon the age, weight, the severity of the affliction, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

In certain embodiments, a pharmaceutical composition comprising Compound II is used to treat conditions related to or occurring as a result of exposure to or an infection of HPV. In certain embodiments, a pharmaceutical composition comprising Compound II is used to treat precancerous cervical lesions. In certain embodiments, a pharmaceutical composition comprising Compound II is used to treat cervical intraepithelial neoplasia. In certain embodiments, a pharmaceutical composition comprising Compound II is used to treat vaginal and anal intraepithelial neoplasia. In certain embodiments, a pharmaceutical composition comprising Compound II is used to treat cervical cancer. In certain embodiments, a pharmaceutical composition comprising Compound II is used to treat rectal cancer. In certain embodiments, a pharmaceutical composition comprising Compound II is used to treat penile cancer. In certain embodiments, a pharmaceutical composition comprising Compound II is used to treat vaginal cancer. In certain embodiments, a pharmaceutical composition comprising Compound II is used to treat oropharyngeal cancer.

In certain embodiments, a pharmaceutical composition comprising Compound II is used in the manufacture of a medicament for the treatment of conditions related to or occurring as a result of exposure to or an infection of HPV. In certain embodiments, a pharmaceutical composition comprising Compound II is used in the manufacture of a medicament for the treatment of precancerous cervical lesions. In certain embodiments, a pharmaceutical composition comprising Compound II is used in the manufacture of a medicament for the treatment of cervical intraepithelial neoplasia. In certain embodiments, a pharmaceutical composition comprising Compound II is used in the manufacture of a medicament for the treatment of vaginal and anal intraepithelial neoplasia. In certain embodiments, a pharmaceutical composition comprising Compound II is used in the manufacture of a medicament for the treatment of cervical cancer. In certain embodiments, a pharmaceutical composition comprising Compound II is used in the manufacture of a medicament for the treatment of rectal cancer. In certain embodiments, a pharmaceutical composition comprising Compound II is used in the manufacture of a medicament for the treatment of penile cancer. In certain embodiments, a pharmaceutical composition comprising Compound II is used in the manufacture of a medicament for the treatment of vaginal cancer. In certain embodiments, a pharmaceutical composition comprising Compound II is used in the manufacture of a medicament for the treatment of oropharyngeal cancer.

It is advantageous for the dosage form to be easily applied to the target site. Direct application to the target site prevents systemic exposure and toxicity. To place the dosage form on the target site, the dosage form may be applied with an applicator. In certain embodiments the dosage form is applied with a vaginal applicator. In certain embodiments the dosage form is applied without an applicator. In certain embodiments, additional fluid (such as a lubricant) is delivered along with the dosage form, applied to the dosage form, or applied to the target site or surrounding tissues.

In certain embodiments, a lubricating fluid is administered in combination with the dosage form to enhance the coverage of the cervix, vagina, vulva, anus, perianal region or penis. In certain embodiments, water is used as the fluid administered with the dosage form. In certain embodiments, a lubricating glycerol- or hydroxyethylcellulose-based, water soluble fluid is used in combination with the dosage form. In certain embodiments the dosage form is administered without additional fluid. In certain embodiments, the dosage form will soften, disintegrate, and/or dissolve in less than about 5 milliliters of fluid. In certain embodiments, the dosage form will soften, disintegrate, and/or dissolve in less than about 4 milliliters of fluid. In certain embodiments, the dosage form will soften, disintegrate, and/or dissolve in less than about 3 milliliters of fluid. In certain embodiments, the dosage form will soften, disintegrate, and/or dissolve in less than about 2 milliliters of fluid. In certain embodiments, the dosage form will soften, disintegrate, and/or dissolve in less than about 1 milliliter of fluid. In certain embodiments, the dosage form will soften, disintegrate, and/or dissolve in less than about 0.75 milliliter of fluid. In certain embodiments, the dosage form will soften, disintegrate, and/or dissolve in less than about 0.5 milliliter of fluid. In certain embodiments, the dosage form will soften, disintegrate, and/or dissolve in less than about 0.25 milliliter of fluid. In certain embodiments, the dosage form will soften, disintegrate, and/or dissolve in less than about 0.2 milliliter of fluid. In certain embodiments, the dosage form will soften, disintegrate, and/or dissolve in less than about 0.15 milliliter of fluid. In certain embodiments, the dosage form will soften, disintegrate, and/or dissolve in less than about 0.125 milliliter of fluid. In certain embodiments, the dosage form will soften, disintegrate, and/or dissolve in less than about 0.1 milliliter of fluid.

In certain embodiments, the dosage form will soften, disintegrate, and/or dissolve in from about 10 microliters to about 100 microliters of fluid. In certain embodiments, the dosage form will soften, disintegrate, and/or dissolve in from about 75 microliters to about 250 microliters of fluid. In certain embodiments, the dosage form will soften, disintegrate, and/or dissolve in from about 200 microliters to about 500 microliters of fluid. In certain embodiments, the dosage form will soften, disintegrate, and/or dissolve in from about 400 microliters to about 750 microliters of fluid. In certain embodiments, the dosage form will soften, disintegrate, and/or dissolve in from about 700 microliters to about 1,000 microliters of fluid. In certain embodiments, the dosage form will soften, disintegrate, and/or dissolve in from about 1 milliliter to about 2 milliliters of fluid. In certain embodiments, the dosage form will soften, disintegrate, and/or dissolve in from about 2 milliliters to about 3 milliliters of fluid. In certain embodiments, the dosage form will soften, disintegrate, and/or dissolve in from about 3 milliliters to about 4 milliliters of fluid. In certain embodiments, the dosage form will soften, disintegrate, and/or dissolve in from about 4 milliliters to about 5 milliliters of fluid.

In certain embodiments, Compound II is administered for at least 1, 2, 3, 4, 5, or 6 consecutive or nonconsecutive days.

In certain embodiments, Compound II is administered once a week. In certain embodiments, Compound II is administered once a week for up to 12 weeks. In certain embodiments, Compound II is administered once a week for up to 10 weeks. In certain embodiments, Compound II is administered once a week for up to 8 weeks. In certain embodiments, Compound II is administered once a week for up to 6 weeks. In certain embodiments, Compound II is administered once a week for up to 4 weeks. In certain embodiments, Compound II is administered once a week for up to 2 weeks. In certain embodiments, Compound II is administered once a week for up to 1 week.

In certain embodiments, Compound II is administered twice a week. In certain embodiments, Compound II is administered twice a week for up to 12 weeks. In certain embodiments, Compound II is administered twice a week for up to 10 weeks. In certain embodiments, Compound II is administered twice a week for up to 8 weeks. In certain embodiments, Compound II is administered twice a week for up to 6 weeks. In certain embodiments, Compound II is administered twice a week for up to 4 weeks. In certain embodiments, Compound II is administered twice a week for up to 2 weeks. In certain embodiments, Compound II is administered twice a week for up to 1 week.

In certain embodiments, Compound II is administered three times a week. In certain embodiments, Compound II is administered three times a week for up to 12 weeks. In certain embodiments, Compound II is administered three times a week for up to 10 weeks. In certain embodiments, Compound II is administered three times a week for up to 8 weeks. In certain embodiments, Compound II is administered three times a week for up to 6 weeks. In certain embodiments, Compound II is administered three times a week for up to 4 weeks. In certain embodiments, Compound II is administered three times a week for up to 2 weeks. In certain embodiments, Compound II is administered three times a week for up to 1 week.

In certain embodiments, Compound II is administered daily. In certain embodiments, Compound II is administered daily for up to 12 weeks or indefinitely as instructed by a healthcare provider. In certain embodiments, Compound II is administered daily for up to 10 weeks. In certain embodiments, Compound II is administered daily for up to 8 weeks. In certain embodiments, Compound II is administered daily for up to 6 weeks. In certain embodiments, Compound II is administered daily for up to 4 weeks. In certain embodiments, Compound II is administered daily for up to 2 weeks. In certain embodiments, Compound II is administered daily for up to 1 week. In certain embodiments, from about 0.05 mg to about 0.3 mg of Compound II is administered daily for one, two, three, four, five, six, or more weeks, as instructed by a healthcare provider.

In certain embodiments, Compound I monofumarate is administered three times a week. In certain embodiments, Compound I monofumarate is administered three times a week for up to 12 weeks. In certain embodiments, Compound I monofumarate is administered three times a week for up to 10 weeks. In certain embodiments Compound I monofumarate is administered three times a week for up to 8 weeks. In certain embodiments, Compound I monofumarate is administered three times a week for up to 6 weeks. In certain embodiments, Compound I monofumarate is administered three times a week for up to 4 weeks. In certain embodiments, Compound I monofumarate is administered three times a week for up to 2 weeks. In certain embodiments, Compound I monofumarate is administered three times a week for up to 1 week.

In certain embodiments, Compound I monofumarate is administered daily. In certain embodiments, Compound I monofumarate is administered daily for up to 12 weeks or indefinitely as instructed by a healthcare provider. In certain embodiments, Compound I monofumarate is administered daily for up to 10 weeks. In certain embodiments, Compound I monofumarate is administered daily for up to 8 weeks. In certain embodiments, Compound I monofumarate is administered daily for up to 6 weeks. In certain embodiments, Compound I monofumarate is administered daily for up to 4 weeks. In certain embodiments, Compound I monofumarate is administered daily for up to 2 weeks. In certain embodiments, Compound I monofumarate is administered daily for up to 1 week.

In certain embodiments, Compound I monofumarate, Compound II or Compound III may be administered three, four, five or six times a week. In certain embodiments, Compound I monofumarate, Compound II or Compound III may be administered once per day. In certain embodiments, Compound I monofumarate, Compound II or Compound III may be administered twice per day. In certain embodiments, Compound I monofumarate, Compound II or Compound III may be administered three, four, or more times per day. In certain embodiments, Compound I monofumarate, Compound II or Compound III may be administered daily.

In certain embodiments, the compound can be administered in one or more therapeutic cycles comprising a treatment cycle and a rest cycle, wherein the treatment cycle comprises administering the compound as described herein, followed by a rest cycle (comprising a period of no treatment) before the next treatment cycle. In certain embodiments, the rest cycle is from about one day to about six months. In certain embodiments the rest cycle is one, two, three, four, five, six, seven, eight or more weeks before the next treatment cycle. In certain embodiments, multiple therapeutic cycles are administered, for example one, two, three, four, five, or six therapeutic cycles.

As described above, a number of compounds have been investigated for the treatment of HPV-induced neoplasia, however none has been approved yet. For non-limiting examples of investigated approaches, see Ahn W. S., et al. Protective effects of green tea extracts (polyphenon E and EGCG) on human cervical lesions *Eur. J. Cancer Prev.* 2003 12:383-390; Ashrafian L, et al. Double-blind randomized placebo-controlled multicenter clinical trial (phase IIa) on diindolymethane's efficacy and safety in the treatment of CIN: implications for cervical cancer prevention. *EPMA J.* 2015:6:doi: 10.1186/s13167-13015-10048-13169; Bossens M., et al. Safety and tolerance of cidofovir as a 2% gel for local application in high-grade cervical intraepithelial neoplasia: A phase I investigation. *Int. J. Clin. Pharmacol.* 2018; 56:134-141; Chen F. P. Efficacy of imiquimod 5% cream for persistent human papillomavirus in genital intraepithelial neoplasm. *Taiwanese J. Obstetrics Gynecol.* 2013; 52(4):475-478; Choo Y., et al. Intravaginal application of leukocyte interferon gel in the treatment of cervical intraepithelial neoplasia (CIN) *Arch Gynecol.* 1985; 237:51-54; de Witte C. J et al. Imiquimod in cervical, vaginal and vulvar intraepithelial neoplasia: a review. *Gynecol. Oncol.* 2015; 139:377-384; Desravines N, et al. Low dose 5-fluorouracil intravaginal therapy for the treatment of cervical intraepithelial neoplasia 2/3: A case series. *J. Gynecol. Surg.* 2020; 36; DiSilvestro P. A., et al. Treatment of cervical intraepithelial neoplasia levels 2 and 3 with adapalene, a retinoid-related molecule. *J. Low Genit Tract. Dis.* 2001; 5:33-37; Graham V., et al. Phase II trial of beta-all-transretinoic acid for cervical intraepithelial neoplasia via a collagen sponge and cervical cap. *West. J. Med.* 1986; 145:192-195; Grimm C., et al. Treatment of cervical intraepithelial neoplasia with topical imiquimod: a randomized controlled trial. *Obstet. Gynecol.* 2012; 120(1):152-159; Hampson L., et al. A single-arm, proof-of-concept trial of lopimune (lopinavir/ritonavir) as treatment for HPV-related pre-invasive cervical disease, PLoS ONE. 2016; 11; Helm C. W. et al. Retinoids for preventing the progression of cervical intra-epithelial neoplasia. *Cochrane Systematic Review.* 2013; Hubert P., et al. Local applications of GM-CSF induce the recruitment of immune cells in cervical low-grade squamous intraepithelial lesions. *Am. J Reprod. Immunol.* 2010; 64:126-136; Koeneman M M, et al. Topical Imiquimod treatment of high-grade Cervical intraepithelial neoplasia (TOPIC trial): study protocol for a randomized controlled trial. *BMC Cancer.* 2016:doi: 10.1186/s12885-12016-12187-12883; Krause S., et al. Interferon and cervical dysplasia: CIN III treated with local interferon application. *Colposcopy Gynecologic Laser Surgery.* 1987; 3:195-198; Krebs H. B., et al. Chronic ulcerations following topical therapy with 5-fluorouracil for vaginal human papillomavirus-associated lesions. *Obstet. Gynecol.* 1991; 78(2):205-208; Laccetta G. et al. Effect of the treatment with beta-glucan in women with cervical cytologic report of atypical squamous cells of undetermined significance (ASCUS) and low-grade intraepithelial lesions (L-SIL) *Minerva Ginecol.* 2015; 67:113-120; Meyskens F. L., et al. A phase I trial of beta-all-transretinoic acid delivered via a collagen sponge and a cervical cap for mild or moderate intraepithelial cervical neoplasia. *J. Natl Cancer Inst.* 1983; 71:921-925; Niwa K., et al. Topical vidarabine of 5-fluoruracil treatment against persistent HPV in genital (pre)cancerous lesions. *Oncol Reports.* 2003; 10:1437-1441; Pachman D R, et al. Randomized clinical trial of imiquimod: an adjunct to treating cervical dysplasia. *Am. J Obstet. Gynecol.* 2012; 206(1):42 e41-47; Rahangdale L et al. Topical 5-fluorouracil for treatment of Cervical Intraepithelial Neoplasia 2: a randomized controlled trial. *Am. J. Obstet. Gynecol.* 2014; 210:e1-e8; Schneider A., et al. Efficacy trial of topically administered Interferon gamma-1beta gel in comparison to laser treatment in cervical intraepithelial neoplasia. *Arch. Gynecol Obste.* 1995; 256: 75-83; Silman F. H., et al. 5-fluorouracil/chemosurgery for intraepithelial neoplasia of the lower genital tract. Obstet. Gynecol 1981; 58:356-360; Snoeck R., Noel J. C., Muller C., Clercq De, Bsossens M. Cidofovir, a new approach for the treatment of cervix intraepithelial neoplasia III (CIN III) J. Med. Virol. 2000; 60:205-209; Stentella P., Biamonti A., Carraro C. Efficacy of carboxymethyl beta-glucan in cervical intraepithelial neoplasia: a retrospective, case-control study. Minerva Ginecol. 2017; 69:425-430; Suh-Burgmann E., Sivret J., Duska L. R., Del Carmen M., Seiden M. V. Long-term administration of intravaginal dehydroepiandrosterone on regression of low-grade cervical dysplasia—a pilot study. Gynecol. Obstet. Invest. 2003; 55:25-31; Valencia M. H., Pacheco A. C., Quijano T. H., Giron A. V., Lopez C. V. Clinical response to glycyrrhizinic acid in genital infection due to human papillomavirus and low-grade squamous intraepithelial lesion. Clin. Pract. 2011 1(e93); van de Sande A., Koeneman M., Gerestein C, Kruse A., van Kemenade F., van Beekhuizen H. Topical Imiquimod treatment of residual or recurrent cervical intraepithelial neoplasia (TOPIC-2 trial): a study protocol for a randomized controlled trial. BMC Cancer. 2018; 18:4510-4517; and Van Pachterbeke C., Bucella D., Rozenberg S. Topical treatment of CIN 2+ by cidofovir: Results of a phase II, double-blind, prospective, placebo-controlled study. Gynecol Onc. 2009; 115:69-74.

VI. Pharmaceutical Compositions and Dosage Forms

In an aspect of the invention, pharmaceutical compositions according to the present invention comprise an anti-HPV effective amount of any of the active compounds described herein including but not limited to Compound I monofumarate, Compound II or Compound III as described herein, optionally in combination with a pharmaceutically acceptable carrier, additive, or excipient, and/or in combination or alternation with at least one other active compound. In one embodiment, the invention includes a solid dosage form of Compound II in a pharmaceutically acceptable carrier. In certain embodiments, the pharmaceutical composition is administered directly to the cervix, vagina, vulva, perianal region, anus, or penis. In certain embodiments, the dosage forms adhere to the cervix, vagina, vulva, perianal region, anus, or penis.

In an aspect of the invention, pharmaceutical compositions according to the present invention comprise an anti-HPV effective amount of Compound II described herein, optionally in combination with a pharmaceutically acceptable carrier, additive, or excipient, further optionally in combination with at least one other antineoplastic agent or antiviral agent, such as an anti-HPV agent. In certain embodiments the pharmaceutical composition includes Compound II in combination with a second antiviral drug. In certain embodiments the pharmaceutical composition includes Compound II in combination with an anticancer drug.

The invention includes pharmaceutical compositions that include an effective amount to treat an HPV infection of any of the active compounds described herein including but not limited to Compound I monofumarate, Compound II, or Compound III of the present invention, in a pharmaceutically acceptable carrier or excipient. In an alternative embodiment, the invention includes pharmaceutical compositions that include an effective amount to prevent an HPV infection of Compound I monofumarate or Compound II of the present invention or prodrug, in a pharmaceutically acceptable carrier or excipient.

One of ordinary skill in the art will recognize that a therapeutically effective amount will vary with the infection or condition to be treated, its severity, the treatment regimen to be employed, the pharmacokinetic of the agent used, as well as the patient or subject (animal or human) to be treated, and such therapeutic amount can be determined by the attending physician or specialist.

Compound I monofumarate, Compound II, or Compound III, or any of the active compounds described herein according to the present invention can be formulated in a mixture with a pharmaceutically acceptable carrier. To treat HPV infection, it is preferable to administer the pharmaceutical composition directly to the cervix, vagina, vulva, perianal region, anus or penis.

In certain pharmaceutical dosage forms, the prodrug form of the compounds, especially including acylated (acetylated or other), and ether (alkyl and related) derivatives, phosphate esters, thiophosphonamidates, phosphonamidates, and various salt forms of the present compounds, may be used to achieve the desired effect. One of ordinary skill in the art will recognize how to readily modify the present compounds to prodrug forms to facilitate delivery of active compounds to a targeted site within the host organism or patient. The person of ordinary skill in the art also will take advantage of favorable pharmacokinetic parameters of the prodrug forms, where applicable, in delivering the present compounds to a targeted site within the host organism or patient to maximize the intended effect of the compound.

The amount of any of the active compounds described herein including but not limited to Compound I monofumarate, Compound II, or Compound III included within the therapeutically active formulation according to the present invention is an effective amount to achieve the desired outcome according to the present invention, for example, for treating the HPV infection, reducing the likelihood of a HCV infection or the inhibition, reduction, and/or abolition of HPV or its secondary effects, including disease states, conditions, and/or complications which occur secondary to HPV infection.

Often, to treat, prevent or delay the onset of these infections and/or to reduce the likelihood of an HPV virus infection, or a secondary disease state, condition or complication of HPV, a dosage form containing any of the active compounds described herein including but not limited to Compound I monofumarate, Compound II, or Compound III are administered in an amount ranging from about 0.001 milligrams to about 100 milligrams. In certain embodiments, the solid dosage form comprises from about 0.001 milligrams to about 0.005 milligrams, from about 0.005 milligrams to about 0.01 milligram, from about 0.01 milligram to about 0.03 milligram, from about 0.03 milligrams to about 0.25 milligrams, from about 0.20 milligrams to about 0.5 milligrams, from about 0.4 milligrams to about 1 milligram, from about 0.75 milligram to about 3 milligrams, from about 1 milligram to about 10 milligrams, from about or 5 milligrams to about 20 milligrams. In certain embodiments, the solid dosage form comprises at least about 0.001, 0.003, 0.005 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3, 4, 5, 10, 20, 30, 40, or 50 milligrams or more of any of the active compounds described herein including but not limited to Compound I monofumarate, Compound II, or Compound III.

In certain embodiments, to treat or delay the onset of these infections and/or to reduce the likelihood of an HPV virus infection, or a secondary disease state, condition or complication of HPV, a dosage form containing any of the active compounds described herein including but not limited to Compound I monofumarate, Compound II, or Compound III are administered in an amount ranging from about 0.001 to about 20 mg, from about 0.005 to about 10 mg, from about 0.01 mg to about 5 mg, from about 0.03 mg to about 1 mg, or from about 0.05 mg to about 0.3 mg of Compound I monofumarate, Compound II or Compound III. The dosage can be administered 1, 2, 3, or more times a week, up to daily administration, typically in a dose ranging between 0.05 and 0.3 mg of Compound I monofumarate, Compound II or Compound III.

In certain embodiments, to treat an infection of a high-risk strain of HPV, a dosage form containing any of the active compounds described herein including but not limited to Compound I monofumarate, Compound II, or Compound III are administered in an amount ranging from about 0.001 to about 20 mg, from about 0.005 to about 10 mg, from about 0.01 mg to about 5 mg, from about 0.03 mg to about 1 mg, or from about 0.05 mg to about 0.3 mg of Compound I monofumarate, Compound II or Compound III. The dosage for treating a high-risk strain of HPV can be administered 1, 2, 3, or more times a week, up to daily administration, typically in a dose ranging between 0.05 and 0.3 mg of Compound I monofumarate, Compound II or Compound III.

In certain embodiments, Compound I monofumarate, Compound II, or Compound III may be administered in a gel. In certain embodiments the gel contains from about 0.001% to about 10%, from about 0.01% to about 10%, from about 0.05% to about 5%, from about 0.1 to about 3% from about 0.1 to about 2% Compound I monofumarate, Compound II, or Compound III (weight/weight). In certain embodiments the gel contains from about 0.001% to about 0.05% Compound I monofumarate, Compound II, or Compound III. In certain embodiments, the gel contains from about 0.01% to about 0.5% Compound I monofumarate, Compound II, or Compound III. In certain embodiments, the gel contains from about 0.1% to about 5% Compound I monofumarate, Compound II, or Compound III.

In a certain non-limiting embodiments, any of the active compounds described herein including but not limited to Compound I monofumarate, Compound II, or Compound III is administered topically. More generally, Compound I monofumarate, Compound II, or Compound III can be administered in a tablet, capsule, suspension, liquid, emulsion, implant, particle, sphere, cream, ointment, suppository, pessary, transdermal form, gel, mucosal, and the like. The dosage form may also be a bilayer tablet, in which the full dose of active compound is released one direction (for example towards the target tissue).

In certain embodiments, the dosage form can soften, disintegrate, and/or release the drug in low fluid volumes. In certain embodiments, the dosage form softens and begins to release the drug immediately. In certain embodiments, the dosage form softens and begins to release the drug gradually. In certain embodiments, the dosage form softens and begins to release the drug within one hour. In certain embodiments, the dosage form softens and begins to release the drug within two hours. The dosage form may be prepared to maximize surface area, facilitating disintegration. In certain embodiments, the dosage form is a round tablet. In certain embodiments, the dosage form is an oval tablet. In certain embodiments, the dosage form is a caplet. The tablet width is the largest dimension, and the tablet thickness is the smaller dimension. In certain embodiments, the dosage form is twice as wide as it is thick. In certain embodiments, the dosage form is three times as wide as it is thick. In certain embodiments, the dosage form is four or more times as wide as it is thick. In certain embodiments the dosage form is from about 0.1 mm thick to about 5 mm thick. In certain embodiments, the dosage form is from about 1 mm to about 2 mm thick. In certain embodiments, the dosage form is from about 2 mm to about 3 mm thick. In certain embodiments, the dosage form is from about 3 mm to about 4 mm thick. In certain embodiments the dosage form is from about 4 mm to about 5 mm thick. In certain embodiments the tablet is from about 5 mm to about 15 mm thick. In certain embodiments, the dosage form is less than 5 grams. In certain embodiments, the dosage form is from about 0.05 gram to about 0.15 gram. In certain embodiments, the dosage form is from about 0.1 to about 1 gram. In certain embodiments, the dosage form is from about 0.75 grams to about 2 grams. In certain embodiments, the dosage form is from about 1 gram to about 5 grams.

In certain embodiments, the dose form is not easily removed, dislodged, or moved from the target site. These desirable properties may be achieved by inclusion of a mucoadhesive polymer into the pharmaceutical composition. In certain embodiments, the pharmaceutical composition comprises a mucoadhesive polymer or mucoadhesive excipient. Nonlimiting examples of mucoadhesive polymers and excipients include: Hypromellose, lectin, thiolated polymers (e.g. chitosan-iminothiolane, poly(acrylic acid)-cysteine, poly(acrylic acid)-homocysteine, chitosan-thioglycolic acid, chitosan-thioethylamidine, alginate-cysteine, poly (methacrylic acid)-cysteine and sodium carboxymethylcellulose-cysteine), polyethylene glycol, polyvinyl alcohol, polyvinyl pyrrolidinone, polyacrylic acid (Carbopol®), polyheroxyethyl methacrylate, chitosan, hydroxyethyl cellulose, hydroxypropyl cellulose, hydroxypropyl methyl cellulose, methylcellulose, sodium carboxymethyl cellulose, aminated corn starch, cellulose derivatives, poly (acrylic acid) polymers, poly (hydroxyethyl methylacrylate), poly (ethylene oxide), poly (vinyl pyrrolidone), poly (vinyl alcohol), tragacanth, sodium alginate, karaya gum, guar gum, xanthan gum, soluble starch, gelatin, pectin, chitosan, methyl cellulose, hyaluronic acid, hydroxy propyl methylcellulose, hydroxy propyl cellulose, gellan gum, carrageenan, cationic hydroxyethyl celluloses, hydrogel, dihydroxyphenylalanine, and alginate-polyethylene glycol acrylate. In certain embodiments, the pharmaceutical composition comprises from about 0 to about 10% mucoadhesive polymer excipients selected from the list consisting of carbomer, polyethylene glycol, crospovidone, polycarbophil, hypromellose, and hydroxyethyl cellulose.

In certain embodiments, the pharmaceutical composition comprises from at least about 0.1% to about 90, about 92%, about 93%, about 95%, about 98% about 97%, about 98%, or about 99% mucoadhesive polymer. In certain embodiments, the pharmaceutical composition comprises from about 0.1% to about 1% mucoadhesive polymer. In certain embodiments, the pharmaceutical composition comprises from about 0.5% to about 5% mucoadhesive polymer. In certain embodiments, the pharmaceutical composition comprises from about 1% to about 10% mucoadhesive polymer. In certain embodiments, the pharmaceutical composition comprises from about 5% to about 20% mucoadhesive polymer. In certain embodiments, the pharmaceutical composition comprises from about 10% to about 50% mucoadhesive polymer. In certain embodiments, the pharmaceutical composition comprises from about 20% to about 75% mucoadhesive polymer. In certain embodiments, the pharmaceutical composition comprises from about 50% to about 90% mucoadhesive polymer. In certain embodiments, the pharmaceutical composition comprises from about 75% to about 99% mucoadhesive polymer. In certain embodiments, the pharmaceutical composition comprises at least about 0.1, 0.25, 0.5, 0.75, 1, 2, 3, 5, 10, 15, 20, 25, 30, 35, 40, 45, 50, 55, 60, 65, 70, 75, 80, 85, 90 or 95 percent mucoadhesive polymer. In certain embodiments, the pharmaceutical composition comprises no more than about 0.1, 0.25, 0.5, 0.75, 1, 2, 3, 5, 10, 15, 20, 25, 30, 35, 40, 45, 50, 55, 60, 65, 70, 75, 80, 85, 90 or 95 percent mucoadhesive polymer. In certain embodiments, the pharmaceutical composition comprises 0% mucoadhesive polymer. In this instance, the adhesion to the target site is achieved by use of other pharmaceutically acceptable excipients.

To prepare the pharmaceutical compositions according to the present invention, a therapeutically effective amount of any of the active compounds described herein including but not limited to Compound I monofumarate, Compound II, or Compound III according to the present invention is often admixed with a pharmaceutically acceptable carrier according to conventional pharmaceutical compounding techniques to produce a dose. A carrier may take a wide variety of forms depending on the form of preparation desired for administration, e.g., topical, oral, or parenteral. In preparing pharmaceutical compositions in topical dosage form, any of the usual pharmaceutical media may be used. Thus, for liquid or semi-solid topical preparations such as gels, creams, ointments, suspensions, elixirs, and solutions, suitable carriers and additives including water, glycols, oils, alcohols, preservatives, and the like may be used. In certain embodiments, the pharmaceutical composition comprises propylene glycol. In certain embodiments, the pharmaceutical composition comprises carboxypolymethylene. In certain embodiments, the pharmaceutical composition comprises ethylenediaminetetraacetic acid (EDTA). In certain embodiments, the pharmaceutical composition comprises sorbic acid. In certain embodiments, the pharmaceutical composition comprises carbomer. In certain embodiments, the pharmaceutical composition comprises hydroxyethyl cellulose. In certain embodiments, the pharmaceutical composition comprises polyethylene glycol.

For solid topical preparations such as powders, tablets, capsules, and for solid preparations such as suppositories, suitable carriers and additives including starches, sugar carriers, such as dextrose, mannitol, lactose, and related carriers, diluents, granulating agents, lubricants, binders, mucoadhesive polymer, disintegrating agents, and the like may be used. If desired, the tablets or capsules may be coated or sustained release by standard techniques. The use of these dosage forms may significantly enhance the bioavailability of the compounds in the patient. In certain embodiments, the pharmaceutical composition comprises mannitol. In certain embodiments, the pharmaceutical composition comprises magnesium stearate. In certain embodiments, the pharmaceutical composition comprises microcrystalline cellulose. In certain embodiments, the pharmaceutical composition comprises polycarbophil. In certain embodiments, the pharmaceutical composition comprises polyethylene oxide. In certain embodiments, the pharmaceutical composition comprises colloidal silicon dioxide. In certain embodiments, the pharmaceutical composition comprises povidone. In certain embodiments, the pharmaceutical composition comprises isopropyl alcohol. In certain embodiments, the pharmaceutical composition comprises sodium starch glycolate. In certain embodiments, the pharmaceutical composition comprises croscarmellose sodium. In certain embodiments, the pharmaceutical composition comprises crospovidone. In certain embodiments, the pharmaceutical composition comprises hydroxypropylmethylcellulose. In certain embodiments, the pharmaceutical composition comprises lactose. In certain embodiments, a powder pharmaceutical composition comprises one or more excipient from the group consisting of xanthan gum, microcrystalline cellulose, polyethylene oxide, hydroxypropylmethylcellulose, hydroxypropylcellulose, carboxymethylcellulose sodium, povidone, mannitol, colloidal silicon dioxide, sodium benzoate, sodium starch glycolate, sodium lauryl sulfate, poloxamer 407, polyoxypropylene-polyoxyethylene copolymers, and the like.

In certain embodiments, the pharmaceutical composition comprising an effective amount of a fumarate salt of any of the active compounds described herein including but not limited to Compound I, further comprises a pharmaceutically acceptable excipient selected from the list consisting of Acacia, agar, alginic acid, ascorbyl palmitate, bentonite, benzoic acid, butylated hydroxyanisole, butylated hydroxytoluene, butylene glycol, calcium acetate, calcium hydroxide, canola oil, carob bean gum, carrageenan, castor oil, cellulose, corn starch, disodium edetate, erythorbic acid, ethyl lactate, ethylcellulose, glycerin, glyceryl behenate, glyceryl monooleate, glyceryl monostearate, hydroxyethylmethyl cellulose, hydroxypropyl cellulose, hypromellose, lactic acid, lauric acid, lecithin, linoleic acid, medium chain triglycerides, methyl paraben, methylcellulose, microcrystalline cellulose, microcrystalline wax, myristic acid, oleic acid, palmitic acid, peanut oil, pectin, phosphoric acid, polycarbophil, potassium alginate, propionic acid, propyl gallate, propyl paraben, propylene glycol, propylene glycol alginate, silicon dioxide, simethicone, sodium alginate, sodium benzoate, sodium bicarbonate, sodium carboxymethylcellulose, sodium chloride, sodium citrate, sodium lactate, sodium lauryl sulfate, sodium metabisulfate, sodium phosphate, sodium sulfite, sodium thiosulfate, sorbic acid, stearic acid, talc, tapioca starch, tartaric acid, thymol, urea, vitamin E polyethylene succinate, beeswax, xanthan gum, and zinc acetate.

In certain embodiments, the pharmaceutical composition comprises pharmaceutically acceptable excipients for use as a pessary. In certain embodiments, the pharmaceutical composition comprising any of the active compounds described herein, including but not limited to Compound I monofumarate, Compound II or Compound III further comprises up to 99.9% pessary excipient selected from the group consisting of hard fat, PEG, macrogols, cocoa butter, and glycerol. Non limiting examples of hard fat include Ovucire® (mono-, di- and triglyceride esters of fatty acids ($C_{10}$ to $C_{18}$), the triester fraction being predominant and ethoxylated fatty alcohols), Witepsol® (glycerol esters of vegetable saturated fatty acids, such as lauric acid), and Supposi-base™ (a blend of saturated polyglycolysed glycerides).

In certain embodiments, the pharmaceutical composition comprising an effective amount of any of the active compounds described herein, including but not limited to Compound I monofumarate, Compound II or Compound III further comprises a pharmaceutically acceptable excipient that enhances the penetration, disintegration, film forming and/or controlled release properties of the composition.

In certain embodiment, the pharmaceutical composition comprising any of the active compounds described herein, including but not limited to Compound I monofumarate, Compound II or Compound III further comprises a penetration enhancing excipient. In certain embodiments, the penetration enhancing excipient is selected from the group consisting of oleic acid, eucalyptol, Caprylol, Labrafil, Labrasol, Lauroglycol, diethylene glycol monomethyl ether (Transcutol), propylene glycol, sodium laurate, sodium lauryl sulfate, cetyltrimethylammonium bromide, poloxamer (231, 182, 184), Tween 20, 40, 60, 80, fatty acids and fatty acid esters, isostearic acid, glycerin, and chitosan. In certain embodiments, the pharmaceutical composition comprising a fumarate salt of Compound I contains from 0% to about 20% penetration enhancing excipients selected from the group consisting of cetyl alcohol, propylene glycol, transcutol P, oleic acid, isopropyl myristate, propylene glycol dicaprylate, glyceryl monooleate, propylene glycol monocaprylate, PEG-8 bees wax, cetyl alcohol, stearic acid, cetyl palmitate, and cetosteryl alcohol. In certain embodiments, the pharmaceutical composition comprises from about 0 to about 25% penetration enhancing excipients selected from the list consisting of stearyl alcohol, polysorbate 80, sodium lauryl sulfate, mono and diglycerides, sorbitan monostearate, glyceryl isostearate, polyoxyl 15 hydroxystearate, polyoxyl 40 hydrogenated castor oil, octyl dodecanol, and soybean lecithin.

In certain embodiments, the pharmaceutical composition comprising any of the active compounds described herein, including but not limited to Compound I monofumarate, Compound II or Compound III further comprises a film forming excipient. In certain embodiments, the pharmaceutical composition comprising any of the active compounds described herein including but not limited to Compound I monofumarate, Compound II or Compound III contains from 0% to about 99% film forming excipients selected from the group consisting of hypromellose, polyethylene glycol, polymethacrylates, microcrystalline cellulose, guar gum, xanthan gum, and polyvinylpyrrolidone.

In certain embodiments, the pharmaceutical composition comprising any of the active compounds described herein, including but not limited to Compound I monofumarate, Compound II or Compound III further comprises and excipient which allows for controlled release of the active compound. In certain embodiments, the controlled release pharmaceutical composition comprises ethylcellulose, hypromellose, microcrystalline wax, polycarbophil, beeswax.

Percentage ranges of excipients and other components of the pharmaceutical composition are given as a percent by weight, unless otherwise specified.

In certain embodiments, the pharmaceutical composition comprising any of the active compounds described herein, including but not limited to Compound I monofumarate, Compound II or Compound III further comprises a disintegration enhancing excipient. In certain embodiments, the disintegration enhancing excipient is selected from the group consisting of cellulose, guar gum, crospovidone, polyplasdone, soy polysaccharides, calcium silicate, gelatin, cation exchange resins, bentonite, citrus pulp, alginic acid, calcium alginate, methylcellulose, microcrystalline cellulose, sodium carboxymethylcellulose, croscarmellose, solka floc, corn starch, sodium starch glycolate (Explotab, Primojel), glycine, hydroxypropyl starch, and starch 1500. In certain embodiments, the pharmaceutical composition comprises up to about 99% disintegration enhancing excipient such as mannitol and/or microcrystalline cellulose. In certain embodiments, the pharmaceutical composition comprises from about 0 to about 70% disintegration enhancing excipients selected from the list consisting of lactose, sucrose, and calcium phosphate. In certain embodiments, the pharmaceutical composition comprises from about 0 to about 50% disintegration enhancing excipients selected from the list consisting of sodium bicarbonate, citric acid, maleic acid, adipic acid, and fumaric acid. In certain embodiments, the pharmaceutical composition comprises from about 0 to about 20% disintegration enhancing excipients selected from the list consisting of sodium starch glycollate, pregelatinized starch, crospovidone, and croscarmellose sodium.

In certain embodiments, the pharmaceutical composition comprising any of the active compounds described herein including but not limited to Compound I monofumarate, Compound II or Compound III further comprises from 0 to about 70% mannitol, including but not limited to any amount that achieves the desired results, for example up to about 5%, about 10%, about 20%, about 30% about 40%, about 50%, about 60% or about 70%. In certain embodiments, the pharmaceutical composition comprising a fumarate salt of Compound I further comprises from 0 to about 70% lactose, including but not limited to any amount that achieves the desired results, for example up to about 5%, about 10%, about 20%, about 30% about 40%, about 50%, about 60% or about 70%. In certain embodiments, the pharmaceutical composition comprising any of the active compounds described herein, including but not limited to Compound I monofumarate, Compound II or Compound III further comprises from about 0 to about 70% sucrose, including but not limited to any amount that achieves the desired results, for example up to about 5%, about 10%, about 20%, about 30% about 40%, about 50%, about 60% or about 70%. In certain embodiments, the pharmaceutical composition comprising any of the active compounds described herein, including but not limited to Compound I monofumarate, Compound II or Compound III further comprises from about 0 to about 70% microcrystalline cellulose, including but not limited to any amount that achieves the desired results, for example up to about 5%, about 10%, about 20%, about 30% about 40%, about 50%, about 60% or about 70%. In certain embodiments, the pharmaceutical composition comprising any of the active compounds described herein, including but not limited to Compound I monofumarate, Compound II or Compound III further comprises from 0 to about 20% sodium starch glycolate, including but not limited to any amount that achieves the desired results, for example up to about 1%, about 2%, about 3%, about 5% about 7%, about 10%, about 12%, about 15% or about 20%. In certain embodiments, the pharmaceutical composition comprising any of the active compounds described herein, including but not limited to Compound I monofumarate, Compound II or Compound III further comprises from about 0 to about 20% pregelatinized starch, including but not limited to any amount that achieves the desired results, for example up to about 1%, about 2%, about 3%, about 5% about 7%, about 10%, about 12%, about 15% or about 20%. In certain embodiments, the pharmaceutical composition comprising any of the active compounds described herein, including but not limited to Compound I monofumarate, Compound II or Compound III further comprises from about 0 to about 20% crospovidone, including but not limited to any amount that achieves the desired results, for example up to about 1%, about 2%, about 3%, about 5% about 7%, about 10%, about 12%, about 15% or about 20%. In certain embodiments, the pharmaceutical composition comprising any of the active compounds described herein, including but not limited to Compound I monofumarate, Compound II or Compound III further comprises from about 0 to about 20% croscarmellose sodium, including but not limited to any amount that achieves the desired results, for example up to about 1%, about 2%, about 3%, about 5% about 7%, about 10%, about 12%, about 15% or about 20%. In certain embodiments, the pharmaceutical composition comprising any of the active compounds described herein, including but not limited to Compound I monofumarate, Compound II or Compound III further comprises from 0 to about 50% xanthan gum, including but not limited to any amount that achieves the desired results, for example up to about 5%, about 10%, about 15%, about 20% about 25%, about 30%, about 35%, about 40% or about 45%. In certain embodiments, the pharmaceutical composition comprising any of the active compounds described herein, including but not limited to Compound I monofumarate, Compound II or Compound III further comprises from 0 to about 50% polycarbophil, including but not limited to any amount that achieves the desired results, for example up to about 5%, about 10%, about 15%, about 20% about 25%, about 30%, about 35%, about 40% or about 45%. In certain embodiments, the pharmaceutical composition comprising any of the active compounds described herein, including but not limited to Compound I monofumarate, Compound II or Compound III further comprises from 0 to about 50% polyethylene oxide, including but not limited to any amount that achieves the desired results, for example up to about 5%, about 10%, about 15%, about 20% about 25%, about 30%, about 35%, about 40% or about 45%. In certain embodiments, the pharmaceutical composition comprising any of the active compounds described herein, including but not limited to Compound I monofumarate, Compound II or Compound III further comprises from 0 to about 50% hydroxyethylmethyl cellulose, including but not limited to any amount that achieves the desired results, for example up to about 5%, about 10%, about 15%, about 20% about 25%, about 30%, about 35%, about 40% or about 45%. In certain embodiments, the pharmaceutical composition comprising any of the active compounds described herein, including but not limited to Compound I monofumarate, Compound II or Compound III further comprises from 0 to about 50% hydroxyethyl cellulose, including but not limited to any amount that achieves the desired results, for example up to about 5%, about 10%, about 15%, about 20% about 25%, about 30%, about 35%, about 40% or about 45%. In certain embodiments, the pharmaceutical composition comprising any of the active compounds described herein, including but not limited to Compound I monofumarate, Compound II or Compound III further comprises from 0 to about 50% hypromellose, including but not limited to any amount that achieves the desired results, for example up to about 5%, about 10%, about 15%, about 20% about 25%, about 30%, about 35%, about 40% or about 45%. In certain embodiments, the pharmaceutical composition comprising any of the active compounds described herein, including but not limited to Compound I monofumarate, Compound II or Compound III further comprises from 0 to about 50% hydroxypropyl cellulose, including but not limited to any amount that achieves the desired results, for example up to about 5%, about 10%, about 15%, about 20% about 25%, about 30%, about 35%, about 40% or about 45%. In certain embodiments, the pharmaceutical composition comprising any of the active compounds described herein, including but not limited to Compound I monofumarate, Compound II or Compound III further comprises from 0 to about 50% PVP, including but not limited to any amount that achieves the desired results, for example up to about 5%, about 10%, about 15%, about 20% about 25%, about 30%, about 35%, about 40% or about 45%. In certain embodiments, the pharmaceutical composition comprising any of the active compounds described herein, including but not limited to Compound I monofumarate, Compound II or Compound III further comprises from 0 to about 50% microcrystalline cellulose, including but not limited to any amount that achieves the desired results, for example up to about 5%, about 10%, about 15%, about 20% about 25%, about 30%, about 35%, about 40% or about 45%.

In typical embodiments according to the present invention, any of the active compounds described herein, including but not limited to Compound I monofumarate, Compound II or Compound III and the compositions described are used to treat, prevent, or delay an HPV infection or a secondary disease state, condition, or complication of HPV.

In certain embodiments, a tablet used to treat, prevent, or delay an HPV infection or a secondary disease state, condition, or complication of HPV comprising any of the active compounds described herein, including but not limited to Compound I monofumarate, Compound II or Compound III further comprises about 250 mg of microcrystalline cellulose, about 20 mg of crospovidone, about 5 mg of magnesium stearate, about 5 mg of silicon dioxide, about 5 mg of polyethylene oxide, and about 100 mg of mannitol. In certain embodiments, a tablet used to treat, prevent, or delay an HPV infection or a secondary disease state, condition, or complication of HPV further comprises about 155 mg microcrystalline cellulose, about 1.75 mg of magnesium stearate, and about 17.5 mg of mannitol.

In certain embodiments, a semi-solid formulation used to treat, prevent, or delay an HPV infection or a secondary disease state, condition, or complication of HPV comprising any of the active compounds described herein, including but not limited to Compound I monofumarate, Compound II or Compound III further comprises about 15 mg of carbomer, about 50 mg of propylene glycol, about 10 mg of sorbic acid, about 5 mg of EDTA, and about 920 mg of water. In certain embodiments, a semi-solid formulation used to treat, prevent, or delay an HPV infection or a secondary disease state, condition, or complication of HPV comprising any of the active compounds described herein, including but not limited to Compound I monofumarate, Compound II or Compound III further comprises about 20 mg of carbomer; about 70 mg of mineral oil; about 80 mg of a mixture of polyoxyl 6 stearate Type I, ethylene glycol stearates and polyoxyl 32 stearate type 1; about 5 mg parabens; about 60 mg propylene glycol; about 5 mg EDTA; and about 760 mg water.

In certain embodiments, a dry powder for reconstitution is used to treat, prevent, or delay an HPV infection or a secondary disease state, condition, or complication of HPV comprising any of the active compounds described herein, including but not limited to Compound I monofumarate, Compound II or Compound III further comprises about 15.5 mg xanthan gum, about 19.8 mg mannitol, about 5 mg silicon dioxide, and about 0.5 mg sodium benzoate.

VII. Combination and Alternation Therapy

The treatments described herein for intraepithelial neoplasia can be combined with conventional approaches such as, but not limited to, excision or ablation of the transformed zone. Techniques include cryotherapy, laser therapy, loop electrosurgical procedure (LEEP) and cone biopsy. All of these surgical procedures damage the affected areas and can lead to scarring. The most common intervention for cervical intraepithelial neoplasia, LEEP, is effective in 60-90% of cases, however, it has been associated with a significantly increased risk of miscarriage, ectopic pregnancies, and negative psychological outcomes. In certain embodiments, the treatments described herein are used to lessen, ameliorate or substitute for the use of these conventional practices.

In certain embodiments, the treatments described herein can be used in combination with a surgical technique. In certain embodiments, a patient in need thereof can receive surgery before, during and/or after administration of an effective amount of a compound described herein. In certain embodiments, the surgical procedure can be an excision of the target and/or diseased tissue, including but not limited to loop electrosurgical excision procedure (LEEP), large loop excision of the transformation zone (LLETZ), knife conization, cold knife conization, knife cone biopsy, or laser conization. In certain embodiments, the surgical procedure can be ablation, including but not limited to laser ablation or cryoablation.

The efficacy of a drug against an HPV infection, may be prolonged, augmented, or restored by administering the compound in combination or alternation with another, and perhaps even two or three other, antiviral compounds that induce a different mutation or act through a different pathway, from that of the principal drug. Alternatively, the pharmacokinetic, biodistribution, half-life, or other parameter of the drug can be altered by such combination therapy (which may include alternation therapy if considered concerted). Furthermore, since HPV is associated with several types of cancer, combination therapy with anticancer therapeutics can provide better outcomes for patients. Since the disclosed Compound II is a DNA Polymerase inhibitor, it may be useful to administer the compound to a host in need thereof in combination with, for example:

a) a protease inhibitor;
  b) another DNA polymerase inhibitor;
  c) an inhibitor of E6 or E6AP such as MEDI0457, luteolin, CAF-24 or gossypetin;
  d) an inhibitor of E7;
  e) an inhibitor of E1 or E2, including inhibitors of the E1-E2 protein interaction;
  f) L2 lipopeptides;

g) an inhibitor or degrader of L1 or L2;
h) an HDAC inhibitor such as vorinostat;
i) degraders of tetraspanins such as CD9, CD63 or CD151;
j) immunotherapeutics such as T-cell therapies (including adoptive T-cell therapies) and checkpoint inhibitors;
k) anti-proliferative drugs;
l) a therapeutic vaccine;
m) a prophylactic vaccine;
n) trichloroacetic acid;
o) salicylic acid;
p) imiquimod;
q) podofilox;
r) Gardasil® 9;
s) Gardasil® 4;
t) Cervarix;
u) VGX-3100;
v) GGX-188E; and/or
w) ADXS11-001.

EXAMPLES

General Remarks

The following instrumental methods were used in characterization of morphic forms of the present invention.

X-Ray Powder Diffraction (XRPD)

| Instrument | Bruker D8 Advance |
|---|---|
| Detector | LYNXEYE_XE_T(1D mode) |
| Open angle | 2.94° |
| Scan mode | Continuous PSD fast |
| Radiation | Cu/K-Alpha1 (λ = 1.5418 Å) |
| X-ray generator power | 40 kV, 40 mA |
| Step size | 0.02° |
| Time per step | 0.12 second per step |
| Scan range | 3° to 40° |
| Primary beam path slits | Twin_Primary motorized slit 10.0 mm by sample length; SollerMount axial soller 2.5° |
| Secondary beam path slits | Detector OpticsMount soller slit 2.5°; Twin_Secondary motorized slit 5.2 mm |
| Sample rotation speed | 15 rpm |

Differential Scanning Calorimetry (DSC)

| Instrument | TA Discovery 2500 or Q2000 |
|---|---|
| Sample pan | Tzero pan and Tzero hermetic lid with a pin hole |
| Temperature range | 0 to 250° C. or before decomposition |
| Heating rate | 2° C./min and 10° C./min |
| Nitrogen flow | 50 mL/min |
| Sample mass | ~0.5-2 mg |

Thermal Gravimetric Analysis (TGA)

| Instrument | Discovery 5500 or Q5000 |
|---|---|
| Sample pan | Aluminum, open |
| Nitrogen flow | Balance 10 mL/min; sample 25 mL/min |
| Start temperature | Ambient condition (below 35° C.) |
| Final temperature | 300° C. or abort next segment if weight <80% (w/w) (The weight loss of the compound is no more than 20% (w/w)) |
| Heating rate | 10° C./min |
| Sample mass | ~2-10 mg |

Dynamic Vapor Sorption (DVS)

| Instrument | Intrinsic, Advantage |
|---|---|
| Total gas flow | 200 sccm |
| Oven temperature | 25° C. |
| Solvent | Water |
| Method | Cycle: 40-0-95-0-40% RH |
| | Stage Step: 10% |
| | Equilibrium: 0.002 dm/dt (%/min) |
| | Minimum dm/dt stability duration: 60 min |
| | Maximum dm/dt stage time: 360 min |

Karl Fischer Water Determination

Instrument: Mettler Toledo Coulometric KF Titrator C30

Method: Coulometric

Polarized Light Microscopy (PLM)

| Instrument | OLYMPUS BX53LED |
|---|---|
| Method | Crossed polarizer, silicone oil added |
| Hot-stage | Heating from 25° C. to 90° C., 10K/min, heating from 90 to 130° C., 2K/min |
| Objective lens | 10X/20X/40X |

Nuclear Magnetic Resonance (NMR)

| Instrument | Bruker Avance-AV 400M |
|---|---|
| Frequency | 400 MHz |
| Probe | 5 mm PABBO BB-1H/D |
| Number of scans | 8 |
| Temperature | 297.6K |
| Relaxation delay | 1 second |

Fourier Transform Infrared Spectroscopy (FT-IR)

| Instrument | Fourier Transform Infrared Spectroscopy (Nicolet 6700, Thermo Scientific) |
|---|---|
| No. of sample scans | 32 |
| No. of background scans | 32 |
| Resolution | 4 |
| Wavelength range | 4000 to 525 cm$^{-1}$ |
| Baseline correction | Yes |
| Optical velocity | 0.4747 |
| Aperture | 150 |
| Window | Diamond |

High Performance Liquid Chromography (HPLC)

1. Stability Studies

| Instrument | Shimadzu | |
|---|---|---|
| HPLC method for stability samples | Wavelength: | 220 nm |
| | Column: | Agilent Zorbax SB-C18 4.6 mm*150 mm 5 μm |
| | Detector: | DAD |
| | Column temperature: | 40° C. |
| | Flow rate: | 1.2 mL/min |
| | Mobile phase A: | 0.1% TFA in water |
| | Mobile phase B: | CAN |
| | Diluent: | Acetonitrile:water = 8:2, v/v |
| | Injection volume: | 5 μL |

Gradient Program:

| Time (min) | Mobile Phase A (%) | Mobile Phase B (%) |
|---|---|---|
| 0 | 95 | 5 |
| 0.01 | 95 | 5 |
| 9.0 | 5 | 95 |
| 13.0 | 5 | 95 |
| 13.1 | 95 | 5 |
| 17.0 | 95 | 5 |

2. Chiral Purity

| Instrument | Agilent 1290 U-HPLC system with DAD Detector or equivalent |
|---|---|
| HPLC method chiral purity | Wavelength: 210 nm |
| | Column: Waters ACQUITY UPLC BEH C18 100 × 2.1 mm, 1.7 µm, PN: 186002352 |
| | Column temperature: 25° C. |
| | Sampler temperature: 5° C. |
| | Needle wash: MeOH |
| | Flow rate: 0.3 mL/min |
| | Injection volume: 2 µL |
| | Mobile phase A: 0.1% TFA in water |
| | Mobile phase B: 0.1% TFA in MeOH |
| | Diluent: MeOH |

Gradient Program:

| Time (min) | Mobile Phase A (%) | Mobile Phase B (%) |
|---|---|---|
| 0 | 95 | 5 |
| 35.0 | 60 | 40 |
| 45.0 | 55 | 45 |
| 50.0 | 10 | 90 |
| 55.0 | 10 | 90 |
| 55.5 | 95 | 5 |
| 60.0 | 95 | 5 |

Abbreviations

DMF: N,N-Dimethylformamide;
DCM: Dichloromethane, Methylene dichloride;
MeOH: Methanol, Methyl alcohol;
ACN: Acetonitrile;
EtOH: Ethanol; ethyl alcohol;
IPAc: iso-propyl acetate;
IPA: iso-Propyl alcohol, iso-Propanol;
THF: tetrahydrofuran;
MEK: Methyl ethyl ketone;
DIAD: diisopropyl azodicarboxylate;
DEAD: diethyl azodicarboxylate;
MTBE: Methyl tert-butyl ether;
DMSO-d6: Deuterated dimethyl sulfoxide;
$Cs_2CO_3$: Cesium carbonate;
TMSBr: Trimethylsilyl bromide;
NaOMe: Sodium methoxide;
TEA: Triethylamine;
$Ph_3P$: Triphenylphosphine;
$Na_2SO_4$: Sodium sulfate;
NaOH: Sodium hydroxide;
HCl: Hydrochloric acid;
$H_2SO_4$: Sulfuric acid;
BsOH: Benzenesulfonic acid;
p-TsOH: para-Toluenesulfonic acid;
MsOH: Methanesulfonic acid;
$^1$H NMR: Proton Nuclear Magnetic Resonance;
LCMS: Liquid chromatography Mass Spectrophotometer;
HPLC: High Pressure Liquid Chromatography;
$^1$H NMR section: s=singlet, bs=broad singlet, d=doublet, dd=doublet of doublets, t=triplet, m=multiplet, J=spin-spin coupling constant Example 1: Approximate Solubility of Compound I Free Base at 25° C.

About 2 mg of Compound I free form was weighed in a 2 mL glass vial and an aliquot of 20 µL of each solvent (Table 1) was added to determine solubility at 25° C. In the second set of experiments, about 10 mg of Compound I free form was added into a 2 mL glass vial and an aliquot of 20 µL of each solvent was added to determine solubility at 50° C. The maximum volume of each solvent added was 1 mL. Approximate solubility was determined by visual observation. The results are presented in Table 1.

TABLE 1

Approximate solubility of Compound I free form at 25° C. and 50° C.

| | | Solubility (mg/mL) | |
|---|---|---|---|
| Experiment | Solvent | 25° C. | 50° C. |
| 1 | Water | 20-25 | 25-27 |
| 2 | Methanol | >100 | >500 |
| 3 | Ethanol | >100 | >500 |
| 4 | Isopropanol (IPA) | >100 | >500 |
| 5 | Acetone | >100 | >500 |
| 6 | Methyl ethyl ketone | >100 | >500 |
| 7 | Ethyl acetate (EA) | >100 | >500 |
| 8 | Isopropyl acetate | >100 | >500 |
| 9 | Acetonitrile | >100 | >500 |
| 10 | Dichloromethane | >100 | >500 |
| 11 | Heptanes | <2 | <10 |
| 12 | Methyl t-butyl ether (MTBE) | <2 | <10 |
| 13 | Tetrahydrofuran | >100 | 167-250 |

Example 2: Crystallization Screening for Compound I Free Base Form

Equilibration with Solvents at 25° C.

About 30 mg of Compound I free base was equilibrated in a suitable amount of solvent as indicated in Table 2 at 25° C. for 1 week at stirring on a stirring plate. At the eighth day of the study, no precipitated solids were observed, and all the ten samples were stirred at 5° C. for about 3 days. In Experiment 10, the suspension in heptanes was filtered. The solid material (wet cake) obtained in Experiment 10 was investigated by XRPD, DSC, TGA, and NMR.

TABLE 2

Equilibration with solvents at 25° C. for 1 week

| Experiment | Solvent | Physical appearance |
|---|---|---|
| 1 | 1:1 Methanol/MTBE | Clear solution |
| 2 | 1:1 Ethanol/water | Clear solution |
| 3 | 1:1 Acetone/water | Clear solution |
| 4 | 1:1 Acetonitrile/water | Clear solution |
| 5 | 1:1 Ethanol/heptanes | Clear solution |

TABLE 2-continued

Equilibration with solvents at 25° C. for 1 week

| Experiment | Solvent | Physical appearance |
|---|---|---|
| 6 | 1:1 Dichloromethane/MTBE | Clear solution |
| 7 | 1:1 THF/heptanes | Gel |
| 8 | Water | Gel |
| 9 | MTBE | Gel |
| 10 | Heptanes | Gel |

Figure 1:
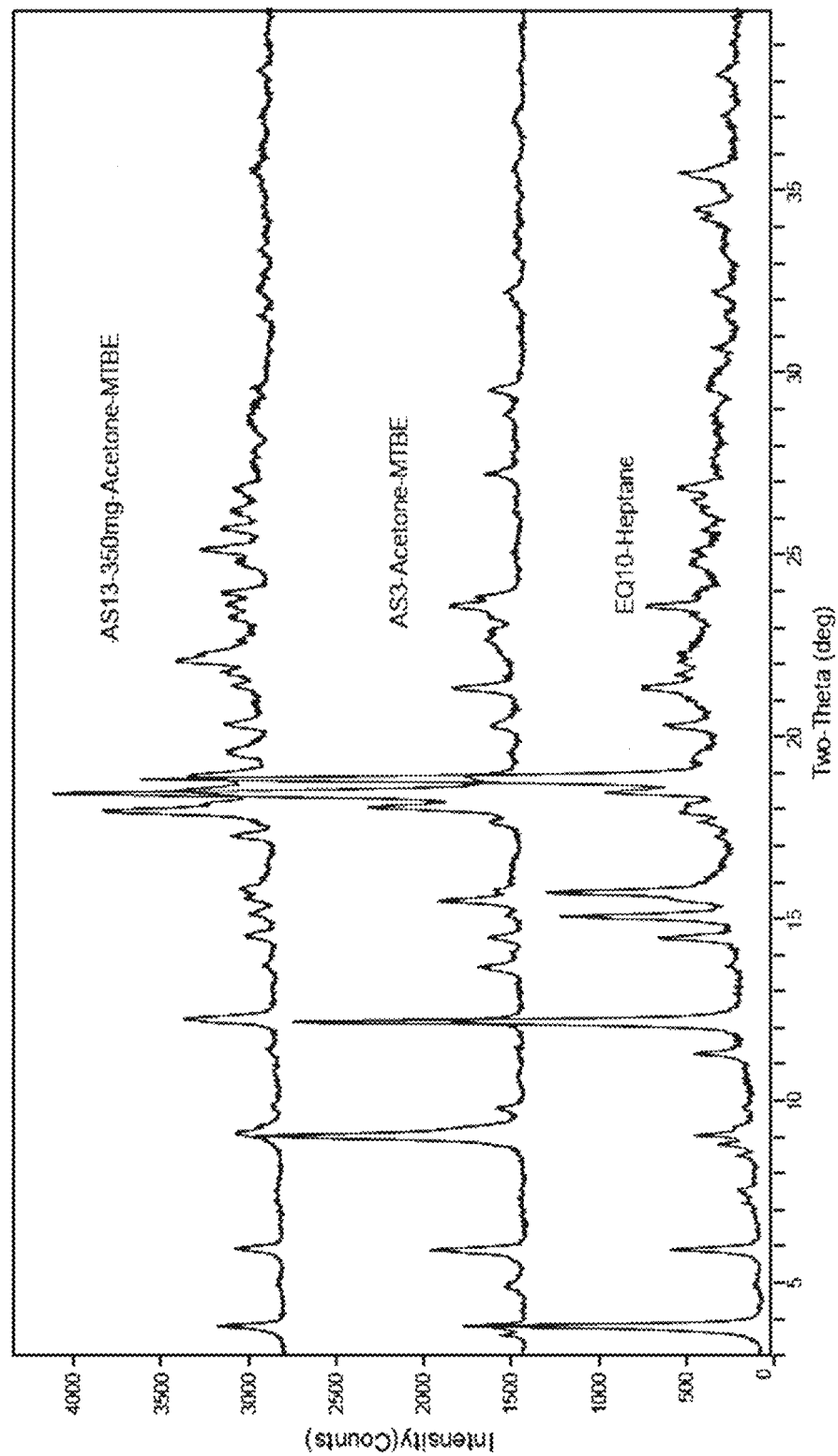
FIG. 1 is a comparison of XRPD diffractograms of Compound I Pattern 1 obtained in equilibration experiment in heptane (Example 2, Table 2, Experiment EQ10), anti-solvent precipitation in acetone/methyl tertbutyl ether (MTBE) system (Example 2, Table 3, Experiment AS3), and in scale-up preparation of Compound I Pattern 1 as described in Example 3.
Figure 2:
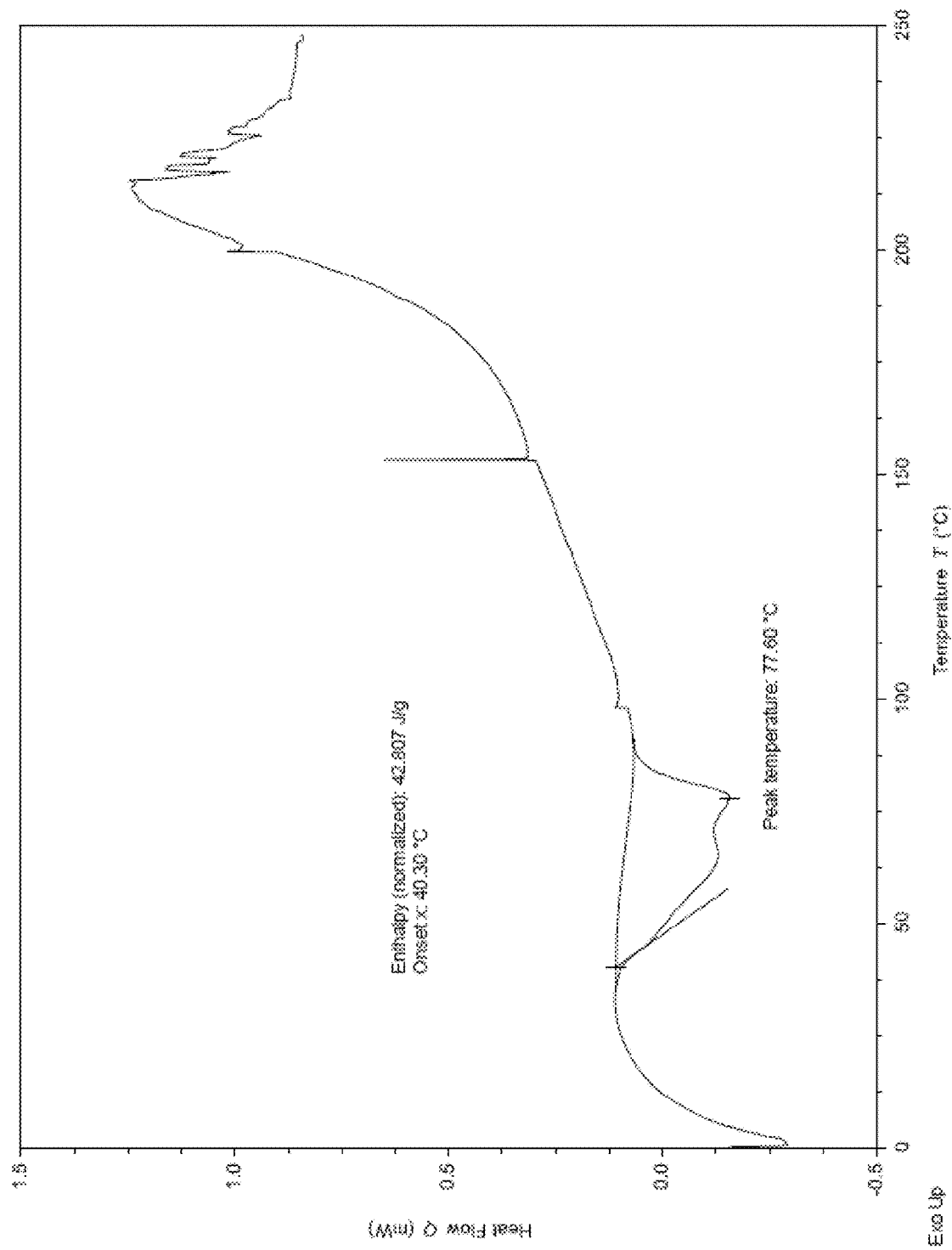
FIG. 2 is a DSC thermogram of Compound I Pattern 1 obtained in equilibration experiment in heptanes (Example 2, Table 2, Experiment EQ10).
Figure 3:
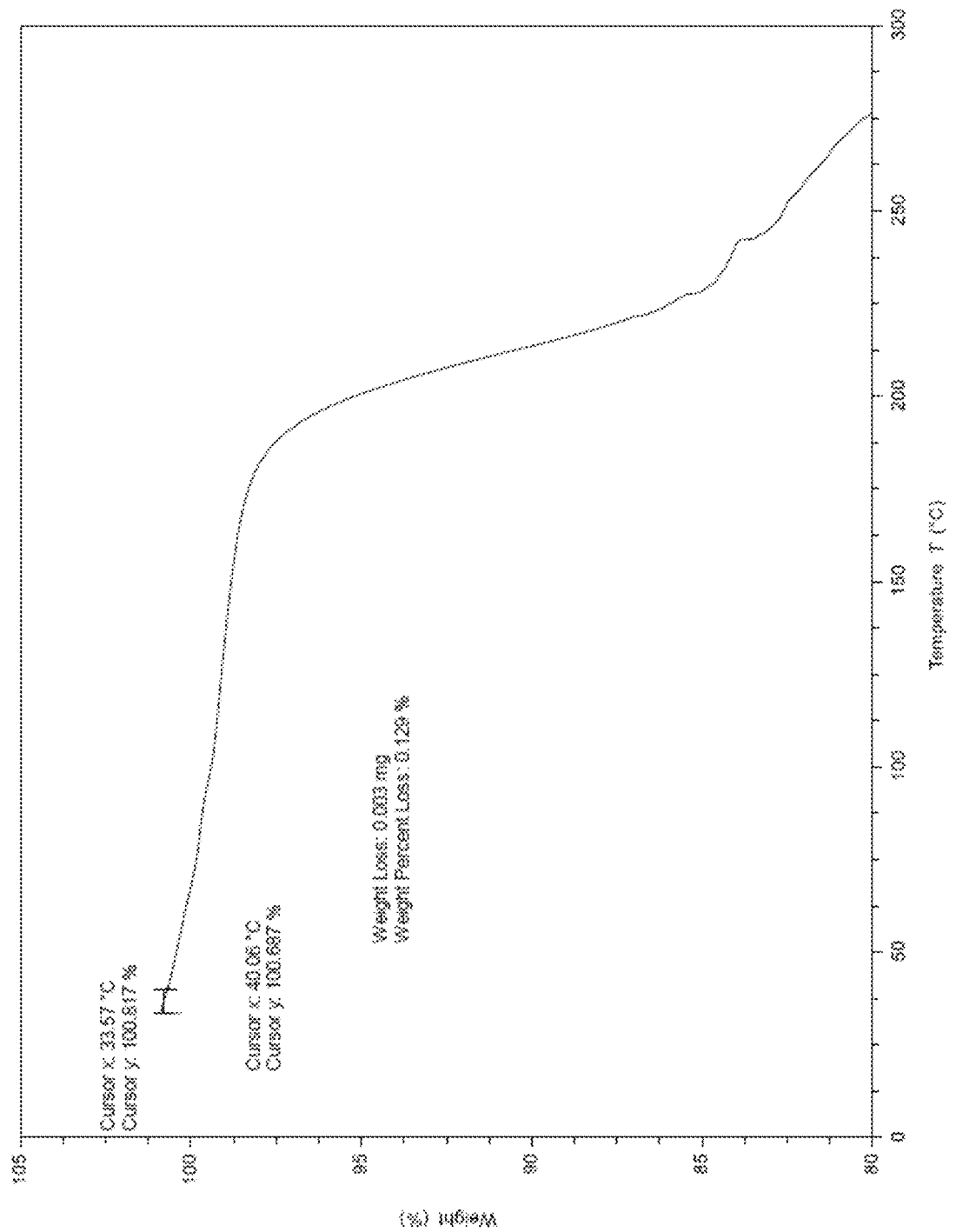
FIG. 3 is a TGA thermogram of Compound I Pattern 1 obtained in equilibration experiment in heptanes (Example 2, Table 2, Experiment EQ10).
Figure 4:
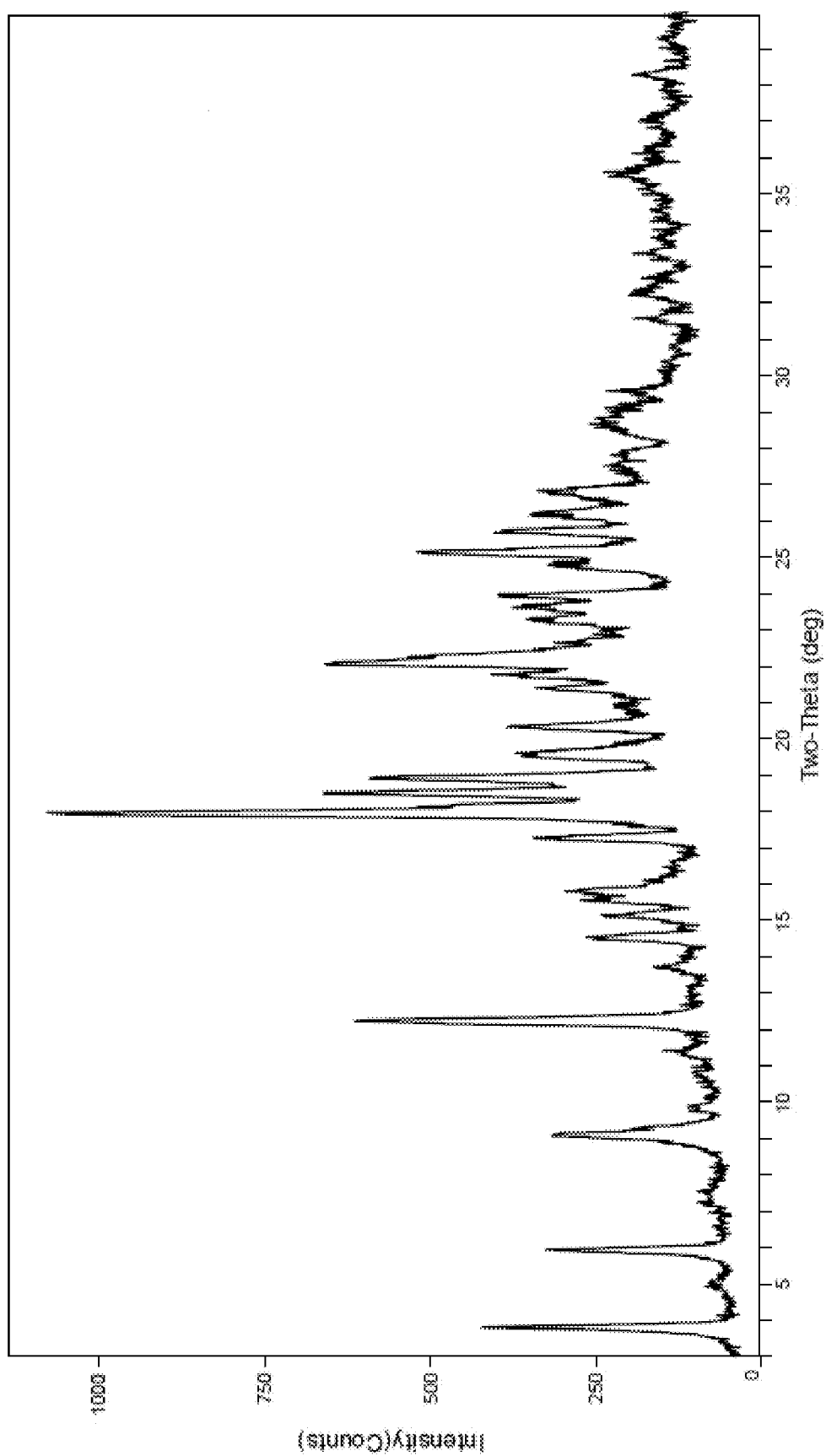
FIG. 4 is a XRPD diffractogram of Compound I Pattern 1 prepared in Example 3.
Figure 5:
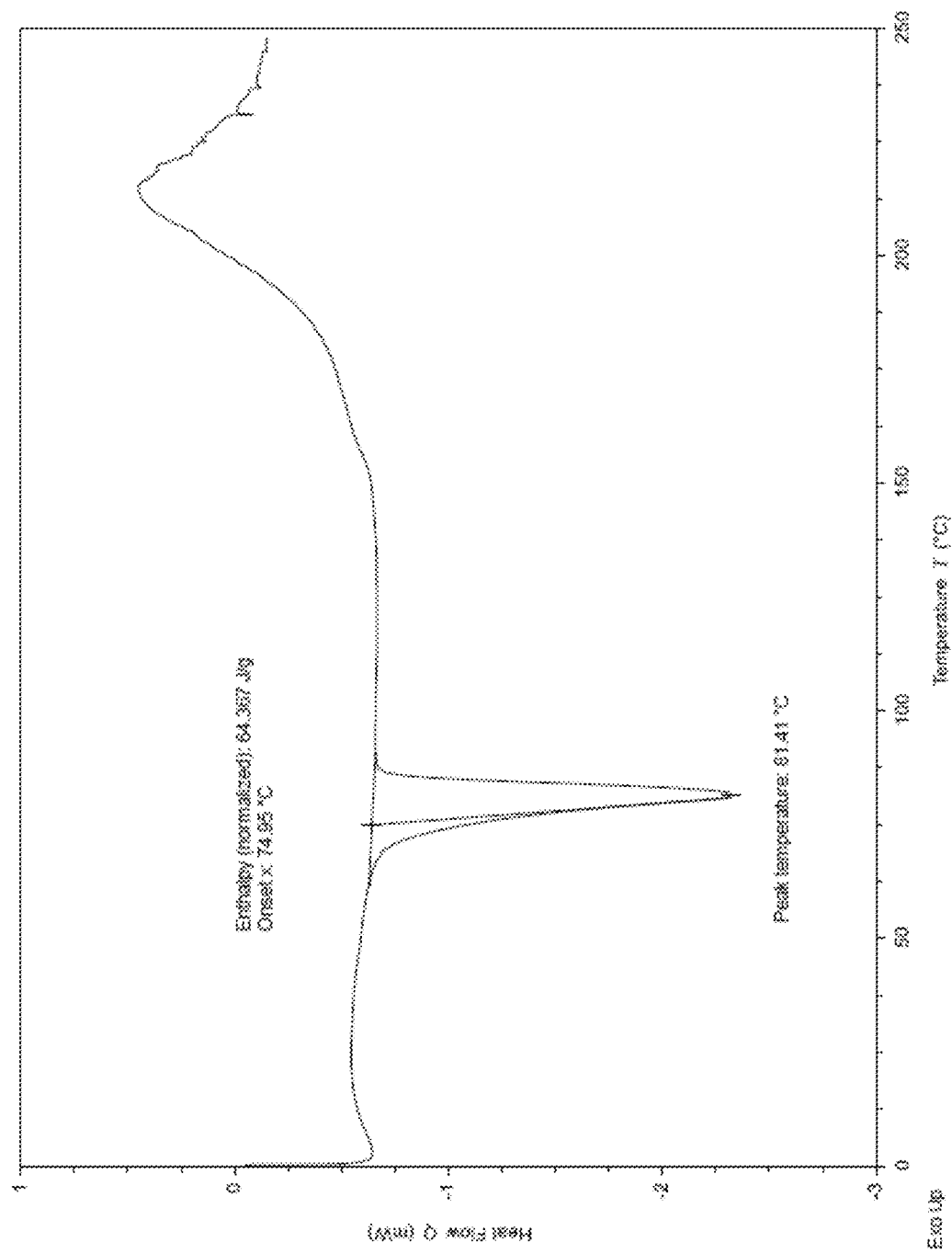
FIG. 5 is a DSC thermogram of Compound I Pattern 1 prepared in Example 3.
Figure 6:
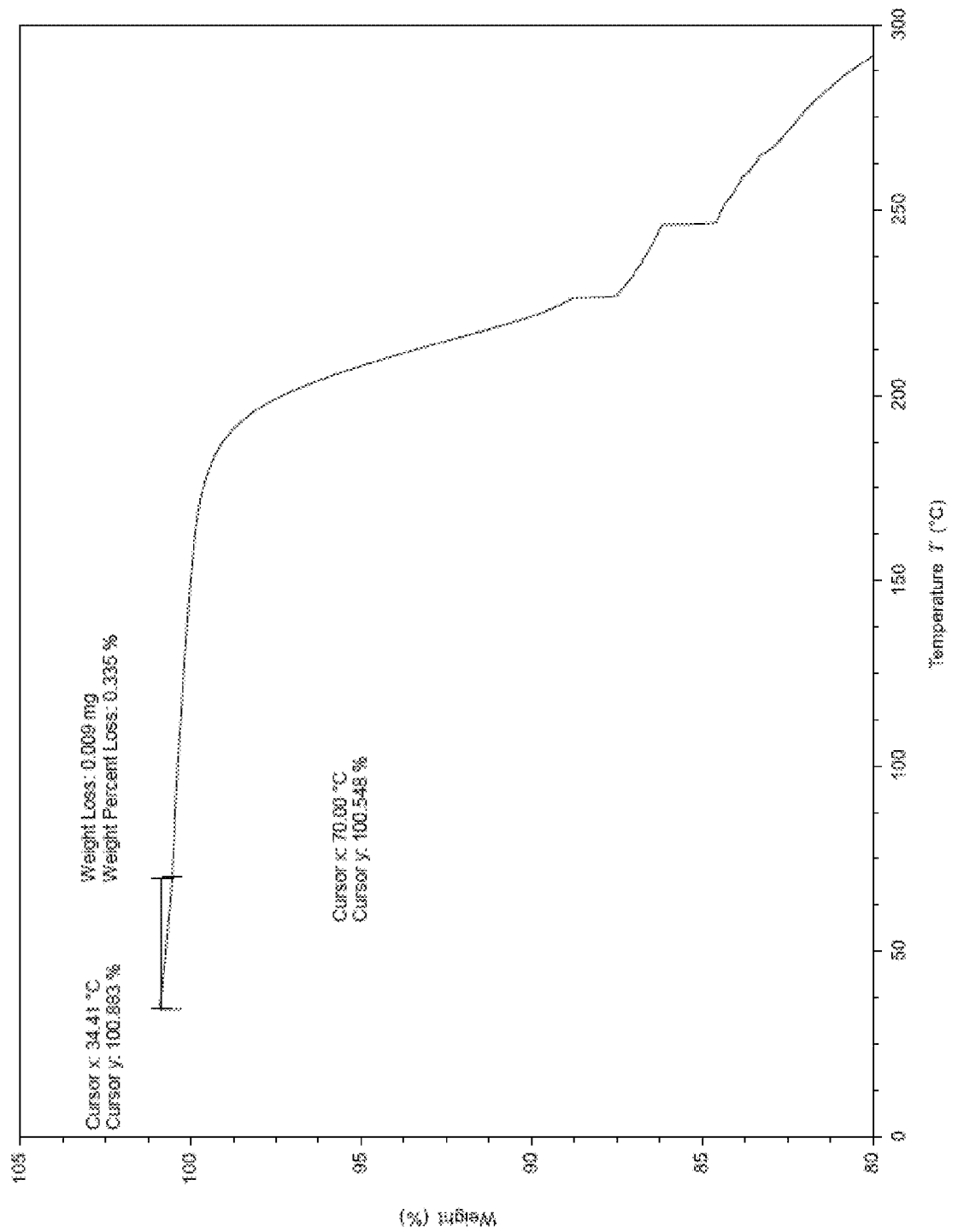
FIG. 6 is a TGA thermogram of Compound I Pattern 1 prepared in Example 3.

According to the XRPD measurements (FIG. 1) solid material obtained in Experiment 10 formed Compound I free form Pattern 1. This pattern was characterized by DSC (FIG. 2) as having a melting onset temperature of 40.3° C. (with a transition enthalpy of 43 J/g), and by TGA (FIG. 3) as having a 0.1% weight loss of 0.1% at 40° C. The material contained 0.2% of residual heptanes according to $^1$H NMR.

Precipitation by Addition of Antisolvent

About 30 mg of Compound I free base was dissolved in the solvent listed below (Table 3). Antisolvent was added into the obtained solutions slowly. Precipitate in Experiment 3 was collected by filtration and analyzed by XRPD.

TABLE 3

Results of precipitation by addition of antisolvent

| Experiment | Solvent | Antisolvent | Physical appearance |
|---|---|---|---|
| 1 | Isopropanol | Water | Gel |
| 2 | Dichloromethane | Heptanes | Gel |
| 3 | Acetone | MTBE | Solid |
| 4 | THF | Water | Clear solution |
| 5 | Ethanol | Heptanes | Oil |
| 6 | Acetonitrile | MTBE | Gel |
| 7 | 1:1 Methanol/MTBE | MTBE | Clear solution |
| 8 | 1:1 Ethanol/water | Water | Clear solution |
| 9 | 1:1 Acetone/water | Water | Clear solution |
| 10 | 1:1 Acetonitrile/water | Water | Clear solution |
| 11 | 1:1 Ethanol/heptanes | Heptanes | Oil |
| 12 | 1:1 Dichloromethane/MTBE | MTBE | Clear solution |

According to the XRPD data (FIG. 1), solid material formed as shown in Experiment 3, Table 3 is Compound I free form Pattern 1.

One crystalline free form, Compound I free form Pattern 1, was obtained from equilibration experiment in heptanes and antisolvent experiment in acetone/MTBE.

Example 3: Synthesis of Salts of Compound I

Compound I Sulfate

Two methods were used to synthesize the sulfate salt of Compound I.

Method A

To a solution of Compound I (0.049 g, 0.1 mmol) in dry THF (1 mL) at 0-10° C. was added a solution of sulfuric acid (1N in THF) slowly. During the addition of sulfuric acid solution, the pink colored, clear THE solution of Compound I free base was changed to an off-white semisolid. The reaction mixture was brought to room temperature over 20-30 minutes and shaken. After allowing the solid material to settle, the supernatant was decanted carefully. The resulting semi-solids were washed with an additional amount of dry THE (2×2 mL), and the resulting solids were dried under high vacuum to yield 0.053 g of Compound I Sulfate Salt-1 as an off-white solid.

Method B

To a solution of Compound I (0.024 g, 0.05 mmol) in dry ethyl acetate (EtOAc, 0.5 mL) at 0-10° C. was added a solution of sulfuric acid (1N in EtOAc) slowly. During the addition of sulfuric acid solution, the pink colored EtOAc clear solution of Compound I free base was changed to an off-white colored solid. The reaction mixture was brought to room temperature over 20-30 min and shaken well. After allowing the solid material to settle, the supernatant was decanted carefully. The off-white solids were washed with an additional amount of EtOAc (2×2 mL). The resulting off-white solids were dried under high vacuum to yield 0.023 g of Compound I Sulfate Salt-2.

Compound I Methanesulfonate

Two methods were used to synthesize the methanesulfonate salt of Compound I.

Method A

To a solution of Compound I (0.049 g, 0.1 mmol) in dry EtOAc (1 mL) at 0-10° C. was added neat methanesulfonic acid (MSA; MW=96.11; d=1.47; 0.007 mL; 0.11 mmol) dropwise. During the addition of MSA solution, the pink colored EtOAc clear solution of Compound I free base was changed in to an off-white semi-solid (glue like). The heterogeneous mixture was brought to room temperature in 20-30 min and shaken well. After allowing semi-solid material to settle down, the supernatant was decanted carefully. The resulting semi-solid (glue like) was washed with methyl tert-butyl ether (MTBE; 2×2 mL) and was dried under high vacuum to yield 0.054 g of Compound I Methanesulfonate Salt-1.

Method B

To a solution of Compound I (0.049 g, 0.1 mmol) in dry IPA (1 mL) at 0-10° C. was added methanesulfonic acid solution (1N in THF; 0.11 mmol; 0.110 mL) dropwise. During the addition of MSA solution, the pink colored EtOAc clear solution of Compound I free base was changed in to an off-white solid. The heterogeneous mixture was brought to room temperature in 20-30 min and shaken well. After allowing solid material to settle down, the supernatant was decanted carefully. The resulting solid was washed with methyl tert-butyl ether (MTBE; 2×2 mL) and was dried under high vacuum to yield 0.049 g of Compound I Methanesulfonate Salt-2.

Compound I Hydrochloride Salt

To a solution of Compound I (MW=492; 0.049 g, 0.1 mmol) in dry EtOAc (1 mL) at 0-10° C. was added HCl solution (4N in dioxane; 0.11 mmole; 0.027 mL) dropwise. During the addition of HCl solution, the pink colored EtOAc clear solution of Compound I free base was changed in to an off-white solid. This heterogeneous mixture was brought to room temperature in 20-30 min and shaken well. After allowing solid material to settle down, the supernatant was decanted carefully. The resulting solid was washed with methyl tert-butyl ether (MTBE; 2×2 mL) and was dried under high vacuum to yield 0.045 g of Compound I HCl Salt.

Compound I Monofumarate

To a solution of Compound I (0.035 g, 0.071 mmol) in dry iso-propanol (0.1 mL) at 0-10° C. was added a fumaric acid (MW=116; 12.3 mg; 0.106 mmol; 1.5 equivalents). The reaction mixture was brought to the room temperature then heated at 60° C. for 30 min and stirred at room temperature for 12 h. The reaction mixture was filtered, and the filtrate was concentrated under a reduced pressure at 40° C. The mixture was diluted with MTBE (2 mL), shaken well and the MTBE was decanted carefully. The colorless solid was washed with an additional amount of MTBE (2 mL) and dried under high vacuum to yield 0.022 g of Compound I sesquifumarate salt. Compound I monofumarate salt can be synthesized by washing Compound I sesquifumarate salt with additional MTBE and drying under high vacuum.

Compound I Benzenesulfonic Acid Salt

To a solution of Compound I (0.057 g, 0.115 mmol) in dry EtOAc (1.0 mL) at 0-10° C. was added a solution of benzenesulfonic acid (BsOH, MW=158; 0.020 g; 0.127 mmol in 0.2 mL of EtOAc) dropwise. During the addition of BsOH solution, the pink colored EtOAc clear solution of Compound I free base precipitated as a colorless solid. The reaction mixture was brought to room temperature in 20-30 min, shaken well. After allowing solid material to settle, the supernatant was decanted carefully. The colorless solid was washed with an additional amount of MTBE (2×2 mL). The resulting solid was dried under high vacuum to yield 0.064 g of Compound I Besylate Salt.

Compound I Tosylate Salt

To a solution of Compound I (0.024 g, 0.05 mmol) in dry EtOAc (0.5 mL) at 0-10° C. was added a solution of p-toluenesulfonic acid (p-TsOH, 0.055 mL; 0.055 mmol; 1N in EtOAc) dropwise. During the addition of p-TsOH solution, the pink colored EtOAc clear solution of Compound I free base precipitated as a colorless solid. The reaction mixture was brought to room temperature in 20-30 min and shaken well. After allowing solid material to settle, the supernatant was decanted carefully. The colorless solid was washed with an additional amount of MTBE (2×2 mL). The resulting solid was dried under high vacuum to yield 0.027 g of Compound I Tosylate Salt.

Melting points of salts of Compound I obtained in this example were determined by differential scanning calorimetry. The results are presented in Table 4. The monofumarate salt, produced by washing of the sesquifumarate salt has the highest melting point of the salts tested.

TABLE 4

Melting points of salts of Compound I

| Compound I salt | Onset of melting (° C.) |
|---|---|
| Sulfate-1 | 85 |
| Sulfate-2 | None observed |
| Methanesulfonate-1 | None observed |
| Methanesulfonate-2 | 50 |
| Hydrochloride | 75 |
| Fumarate | 100 |
| Benzenesulfonate | 70 |
| Tosylate | None observed |

Example 5: Salt Screening for Compound I Free Base

Eight acids (fumaric acid, citric acid, L-malic acid, L-tartaric acid, succinic acid, benzenesulfonic acid, oxalic acid, and maleic acid) and two co-formers (L-proline and nicotinamide) were selected for screening for potential salt and/or cocrystal formation. Compound I was used as a mixture of two diastereomers ($^1$H NMR purity of about 98-99%). Isopropanol (IPA), ethanol and ethyl acetate (EA) were selected as screening solvents. Slurry equilibration, antisolvent addition, and slow evaporation and were applied as screening methods.

Salt Screening by Slurry Equilibration

Compound I free base as a mixture of diastereomers (about 30 mg) was added into a suitable solvent, followed by addition of 1 or 0.5 molar equivalents (as indicated in Table 5 below) of an acid (Experiments RC2 to RC10) or co-former (Experiments RC11 and RC12) under stirring at 50° C. The mixtures were stirred for 2 hours at 50° C. and then at 25° C. for at least 12 hours. For those Experiments where clear solutions formed, half volume was evaporated in a fume hood and the rest was treated by antisolvents addition. Obtained suspensions were taken out and centrifuged. Solids obtained in Experiments RC2 (Sample RC2-EA), RC3 (Sample RC3-EA), RC7 (Samples RC7-IPA and RC7-EA), and RC11 (Sample RC11-EA) were analyzed by XRPD. The results are presented in Table 5.

TABLE 5

Salt (cocrystal) screening by slurry equilibration

| Exp. | Acid/co-former to form counter-ion | Screening results in different solvents | | |
|---|---|---|---|---|
| | | IPA | EtOH | EA |
| RC1 | No acid added | Clear solution | Clear solution | Clear solution |
| RC2 | Fumaric acid (1 eq.) | Deliquescent material | Clear solution | Similar to hemi-fumarate Pattern 1 + fumaric acid |
| RC3 | Fumaric acid (0.5 eq.) | Clear solution | Clear solution | Similar to hemi-fumarate Pattern 1 |
| RC4 | Citric acid | Clear solution | Clear solution | Gel |
| RC5 | L-malic acid | Clear solution | Clear solution | Oil |
| RC6 | L-tartaric acid | Clear solution | Clear solution | Gel |
| RC7 | Succinic acid | Similar to sample obtained in Exp. AS7 | Clear solution | Similar to sample obtained in Exp. AS7 |
| RC8 | Benzenesulfonic acid | Clear solution | Clear solution | Gel |
| RC9 | Oxalic acid | Clear solution | Clear solution | Gel |
| RC10 | Maleic acid | Clear solution | Clear solution | Oil |
| RC11 | L-Proline | Cloudy | Cloudy | Mixture of L-proline and free form Pattern 1 |
| RC12 | Nicotinamide | Clear solution | Clear solution | Clear solution |

Figure 7:
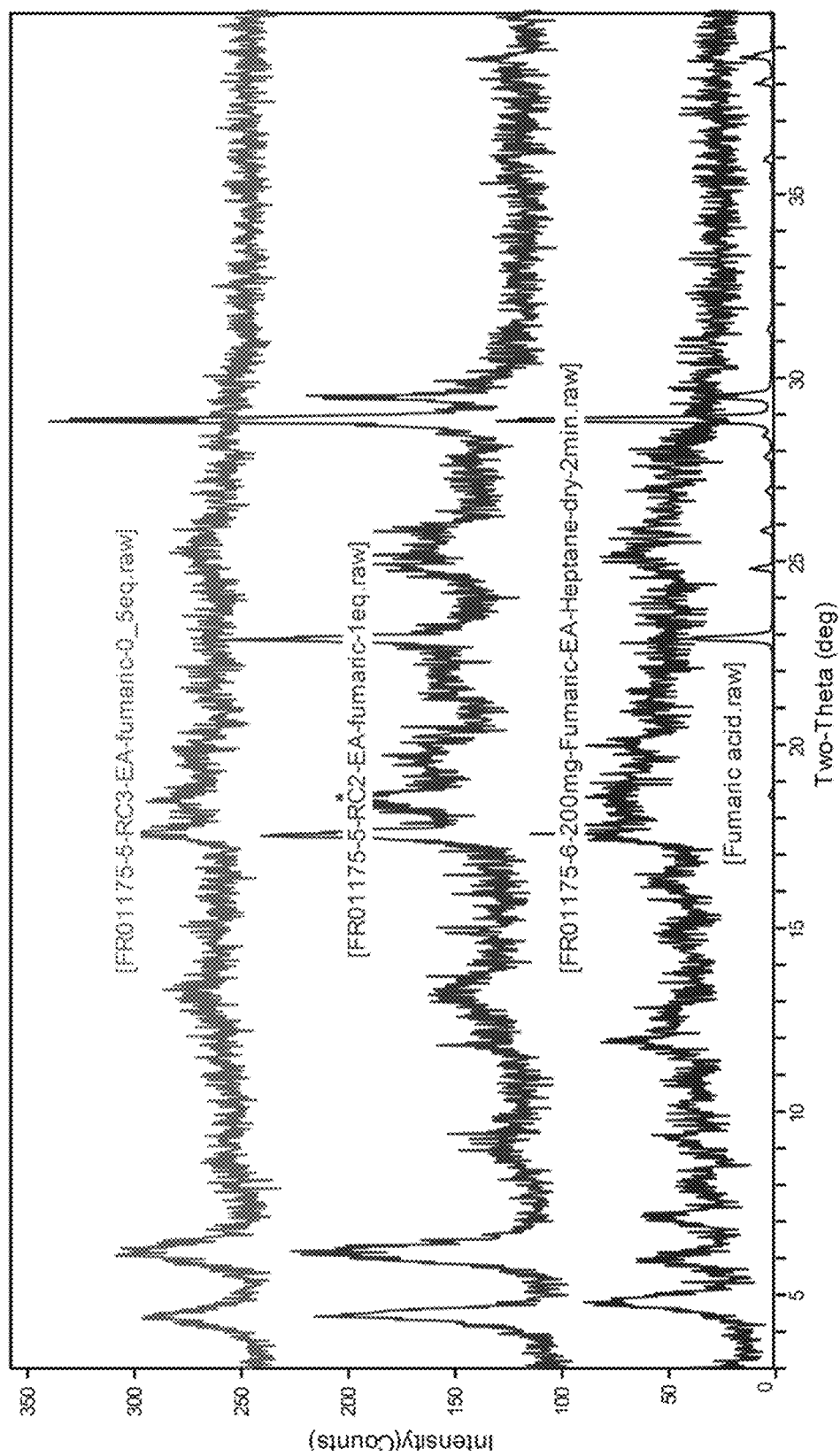
FIG. 7 is a comparison of XRPD diffractograms of fumaric acid pattern, Compound IV Pattern 1 (obtained in Example 7), Compound IV Pattern 1 in mixture with fumaric acid patter (Sample RC2-EA, obtained in Example 5, Experiment RC2) and Compound IV Pattern 1 (Example 5, Sample RC3-EA).
Figure 8:
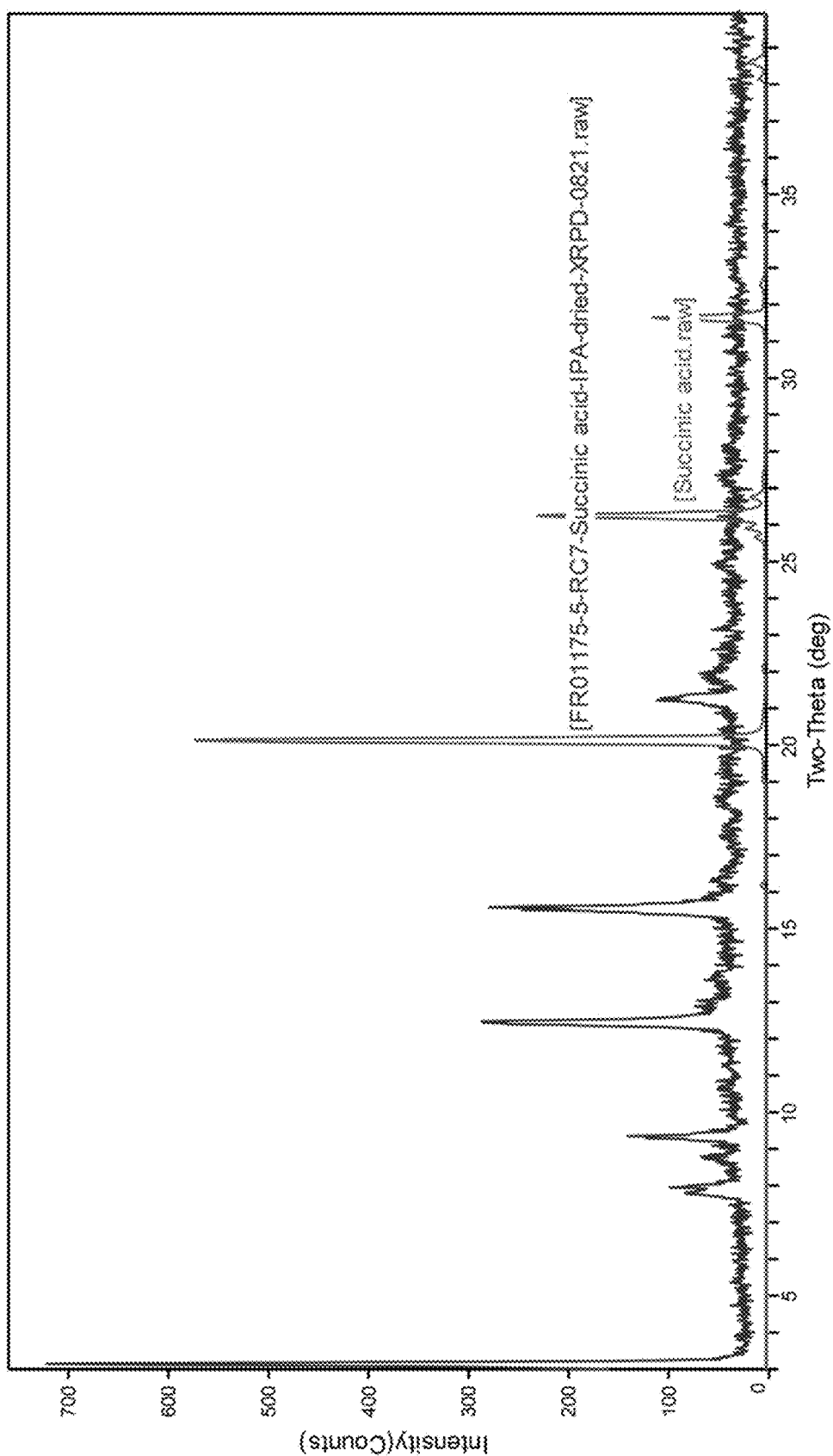
FIG. 8 is a comparison of XRPD diffractograms of Compound I mono-succinate Pattern 1 (Example 5, Sample RC7-IPA) and succinic acid pattern.
Figure 9:
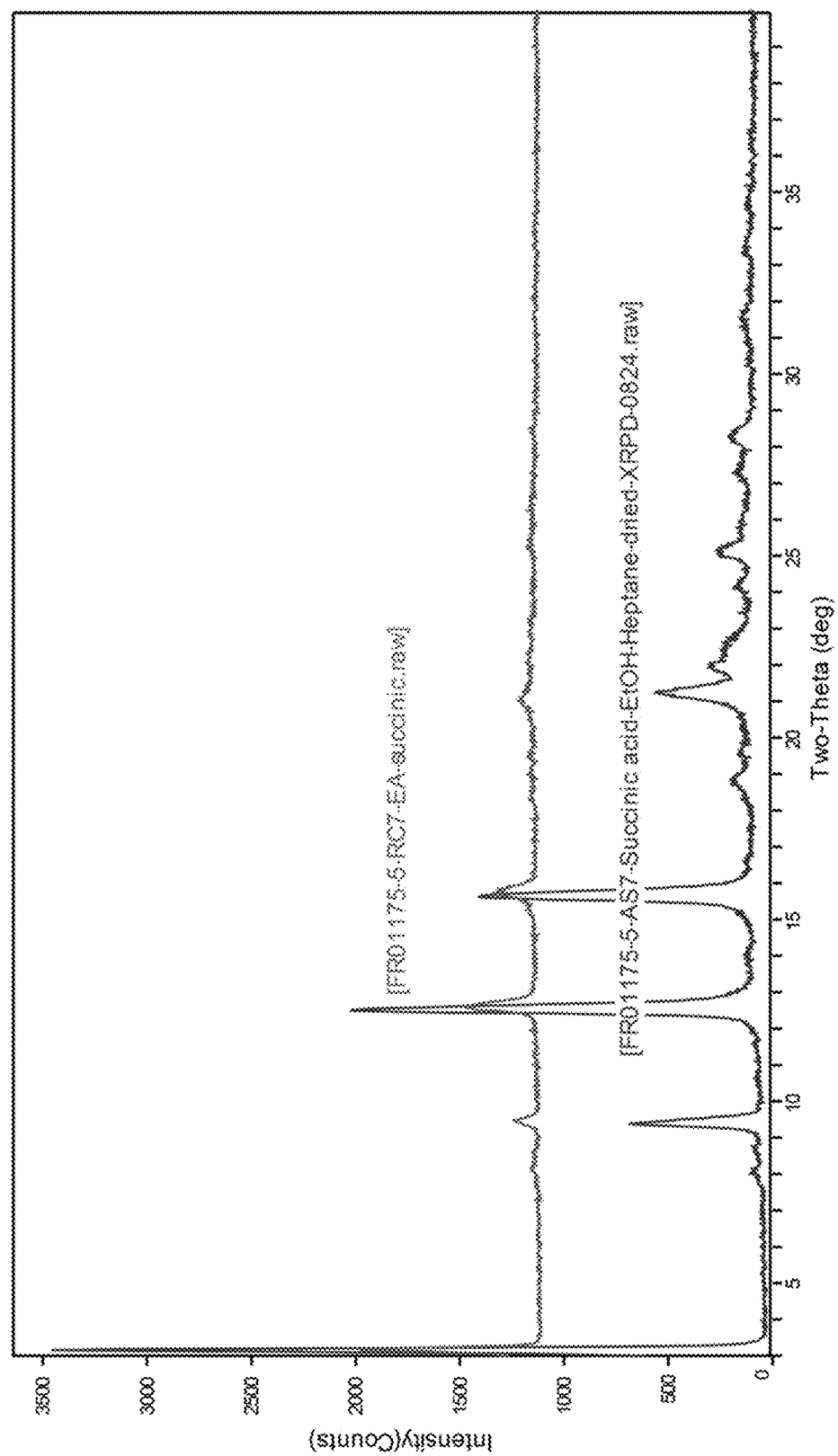
FIG. 9 is a comparison of XRPD diffractograms of Compound I mono-succinate Pattern 1 of Sample RC7-EA (Example 5, Table 5) and Compound I mono-succinate Pattern 1 of Sample AS7-B (Example 5, Table 6).
Figure 10:
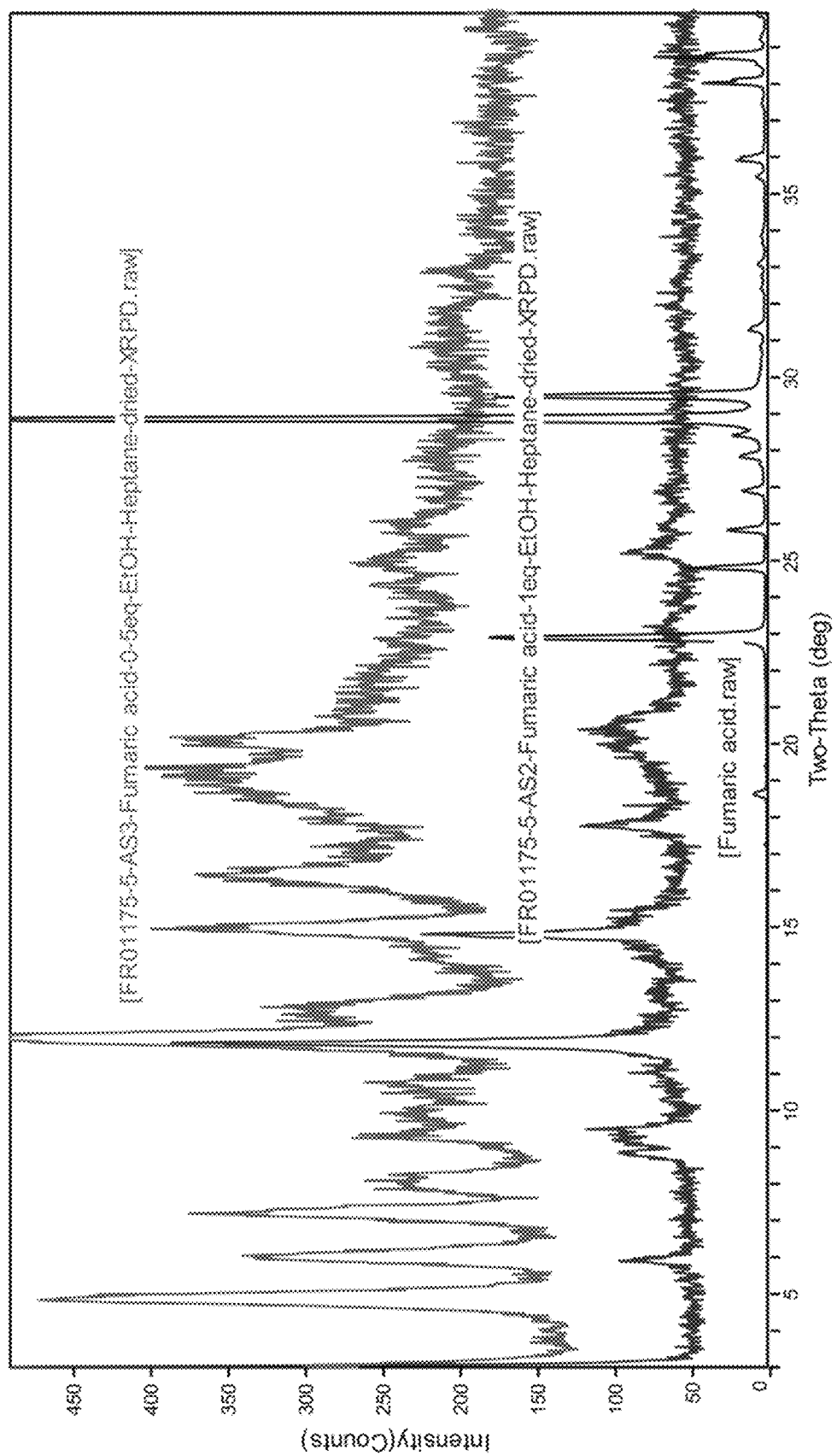
FIG. 10 is a comparison of XRPD diffractograms of fumaric acid pattern, Compound I mono-fumarate Pattern 1 (Example 5, Table 6, Sample AS2-B), and Compound IV Pattern 1 (Example 5, Sample AS3-B).

In Experiment RC2, solid material obtained in EA (Sample RC2-EA) was shown to be a mixture of fumaric acid and a phase similar to hemi-fumarate Pattern 1 (Sample AS3-B in Table 6) according to XRPD (FIG. 7 and FIG. 10). In Experiment RC3, solid material obtained in EA (Sample RC3-EA) was shown to be a phase similar hemi-fumarate Pattern 1 according to XRPD data (FIG. 7). In Experiment RC11, solid material obtained in EA was shown to be a mixture of L-proline co-former and free form Pattern 1. In Experiment RC7, solid material obtained from isopropanol (Sample RC7-IPA, FIG. 8) and ethyl acetate (Sample RC7-EA, FIG. 9) was characterized by XRPD as a phase similar to mono-succinate Pattern 1 (see below, Table 6, Experiment AS7, Sample AS7-B).

Salt Screening Results by Antisolvent Addition

To the clear solutions obtained in Experiments of Table 5, antisolvent (methyl tert-butyl ether (MTBE) or heptane) was added slowly (Experiments AS1 to AS12 in Table 6). In the case of Experiments AS2, AS3, and AS7, addition of heptane antisolvent to the solutions in EtOH resulted in precipitation of solid materials AS2-B, AS3-B, and AS7-B, which were characterized by XRPD.

Next, to clear solutions (from Experiments AS1, AS3, and AS12) and a sample AS5-A containing a small amount of solid material obtained after antisolvent has been added, 0.5, 1 or 1.5 molar amounts of acid or co-former were added under stirring at 25° C., and the mixtures were stirred for at least 12 hours at this temperature. No solid phases formed in Experiments AS13 to AS17. The results are summarized in Table 6.

Figure 11:
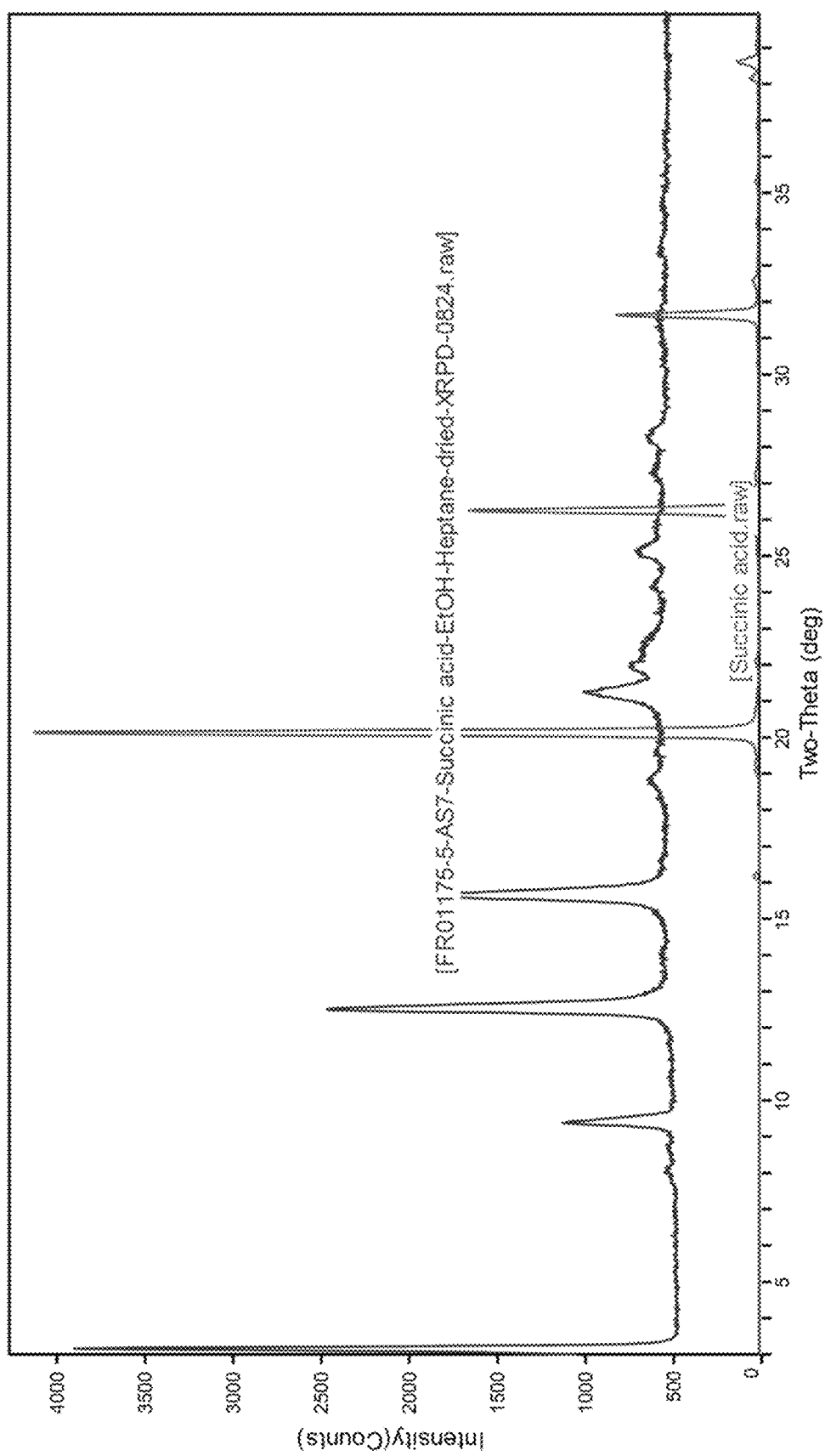
FIG. 11 is a comparison of XRPD diffractograms of Compound I mono-succinate Pattern 1 (Example 5, Sample AS7-B) and free succinic acid pattern.

Addition of heptane antisolvent to clear solution obtained from Experiment RC2 (ethanol as a solvent, 1 molar equivalent of fumaric acid) resulted in formation of mono-fumarate Pattern 1 characterized by XRPD (Sample AS2-1B, FIG. 10). The composition of this material as a mono-fumarate was established by $^1$H NMR (ratio of free base form to fumaric acid=1:0.98); no free fumaric acid phase was found in this sample according to XRPD. Addition of heptane antisolvent to clear solution obtained from Experiment RC3 (ethanol as a solvent, 0.5 molar equivalent of fumaric acid) resulted in formation of hemi-fumarate Pattern 1 characterized by XRPD (Sample AS3-B, FIG. 10). The composition of this material as a hemi-fumarate was established by $^1$H NMR (ratio of free base form to fumaric acid=1:0.54); no free fumaric acid phase was found in this sample according to XRPD. Addition of heptane antisolvent to clear solution obtained from Entry RC7 (ethanol as a solvent, 1 molar equivalent of succinic acid) resulted in formation of mono-succinate Pattern 1 characterized by XRPD (Sample AS7-B, FIG. 11). The composition of this material as a mono-succinate was established by $^1$H NMR (ratio of free base form to succinic acid=1:1.06); no free succinic acid phase was found in this sample according to XRPD.

Re-Equilibration Experiments

From gel-like or oily samples obtained in the above-described salt screening by antisolvent addition, solvents were evaporated. Residual mixtures were slurried in MTBE or heptanes at 25° C. as indicated in Table 7. Results of the experiments are given in Table 7.

TABLE 6

Salt screening results by antisolvent addition

| Experiment | Acid/co-former to form counter-ion | Screening results in different solvents | |
|---|---|---|---|
| | | Solvent A (IPA/MTBE) | Solvent B (EtOH/heptanes) |
| AS1 | No acid added | Clear solution | Clear solution |
| AS2 | Fumaric acid (1 eq.) | n/a | Mono-fumarate Pattern 1 |
| AS3 | Fumaric acid (0.5 eq.) | Clear solution | Hemi-fumarate Pattern 1 |
| AS4 | Citric acid (1 eq.) | Gel | Gel |
| AS5 | L-malic acid (1 eq.) | Small amount of solids | Oil |
| AS6 | L-tartaric acid (1 eq.) | Gel | Gel |
| AS7 | Succinic acid (1 eq.) | n/a | Mono-succinate Pattern 1 |
| AS8 | Benzenesulfonic acid (1 eq.) | Sticky material | Sticky material |
| AS9 | Oxalic acid (1 eq.) | Gel | Gel |
| AS10 | Maleic acid (1 eq.) | Gel | Oil |
| AS11 | L-Proline (1 eq.) | L-Proline by XRPD | L-Proline by XRPD |
| AS12 | Nicotinamide (1 eq.) | Clear solution | Oil |
| AS13 | Fumaric acid (1.5 eq.) | (obtained from solution AS1-A) Mushy sample | n/a |
| AS14 | Benzenesulfonic acid (1.5 eq.) | n/a | (obtained from solution AS1-B) Oil |
| AS15 | Fumaric acid (1.5 eq.) | (obtained from solution AS3-A) Mushy sample | n/a |
| AS16 | L-malic acid (1.5 eq.) | (obtained from solution AS5-A) Clear solution | n/a |
| AS17 | Nicotinamide (1.5 eq.) | (obtained from solution AS12-A) Clear solution | n/a |

TABLE 7

Re-equilibration results

| Experiment | Acid/co-former to form counter-ion | Solvent | XRRD | Sample from antisolvent addition experiments |
|---|---|---|---|---|
| 1 | Citric acid | MTBE | Gel | AS4 (IPA-MTBE) |
| 2 | Citric acid | Heptane | Amorphous | AS4 (EtOH-Heptanes) |
| 3 | L-malic acid | MTBE | Gel | AS5 (EtOH-Heptanes) |
| 4 | L-tartaric acid | MTBE | Amorphous | AS6 (IPA-MTBE) |
| 5 | L-tartaric acid | Heptane | Amorphous | AS6 (EtOH-Heptanes) |
| 6 | Oxalic acid | MTBE | Gel | AS9 (IPA-MTBE) |
| 7 | Oxalic acid | Heptane | Gel | AS9 (EtOH-Heptanes) |
| 8 | Maleic acid | MTBE | Gel | AS10 (IPA-MTBE) |
| 9 | Maleic acid | Heptane | Gel | AS10 (EtOH-Heptanes) |
| 10 | Nicotinamide | MTBE | Gel | AS12 (EtOH-Heptane) |

Citric acid, L-malic acid, L-tartaric acid, oxalic acid, maleic acid, and nicotinamide did not form crystalline phases with Compound I in re-equilibration experiments.

Example 6: Compound I Salt Formation by Slurry Crystallization

Figure 12:
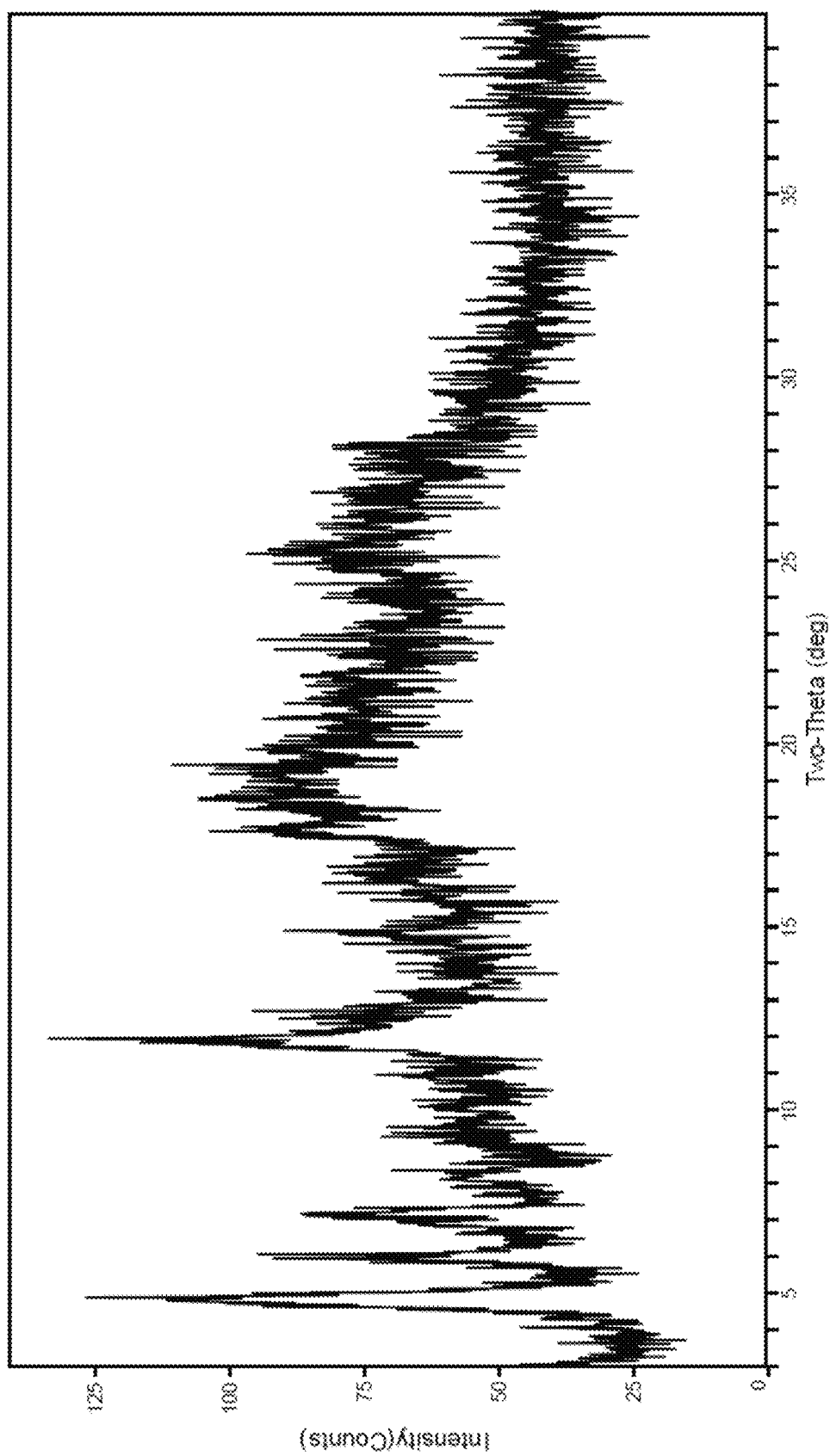
FIG. 12 is a XRPD diffractogram of Compound I hemifumarate Pattern 1 (Example 6, Sample RC13).
Figure 13:
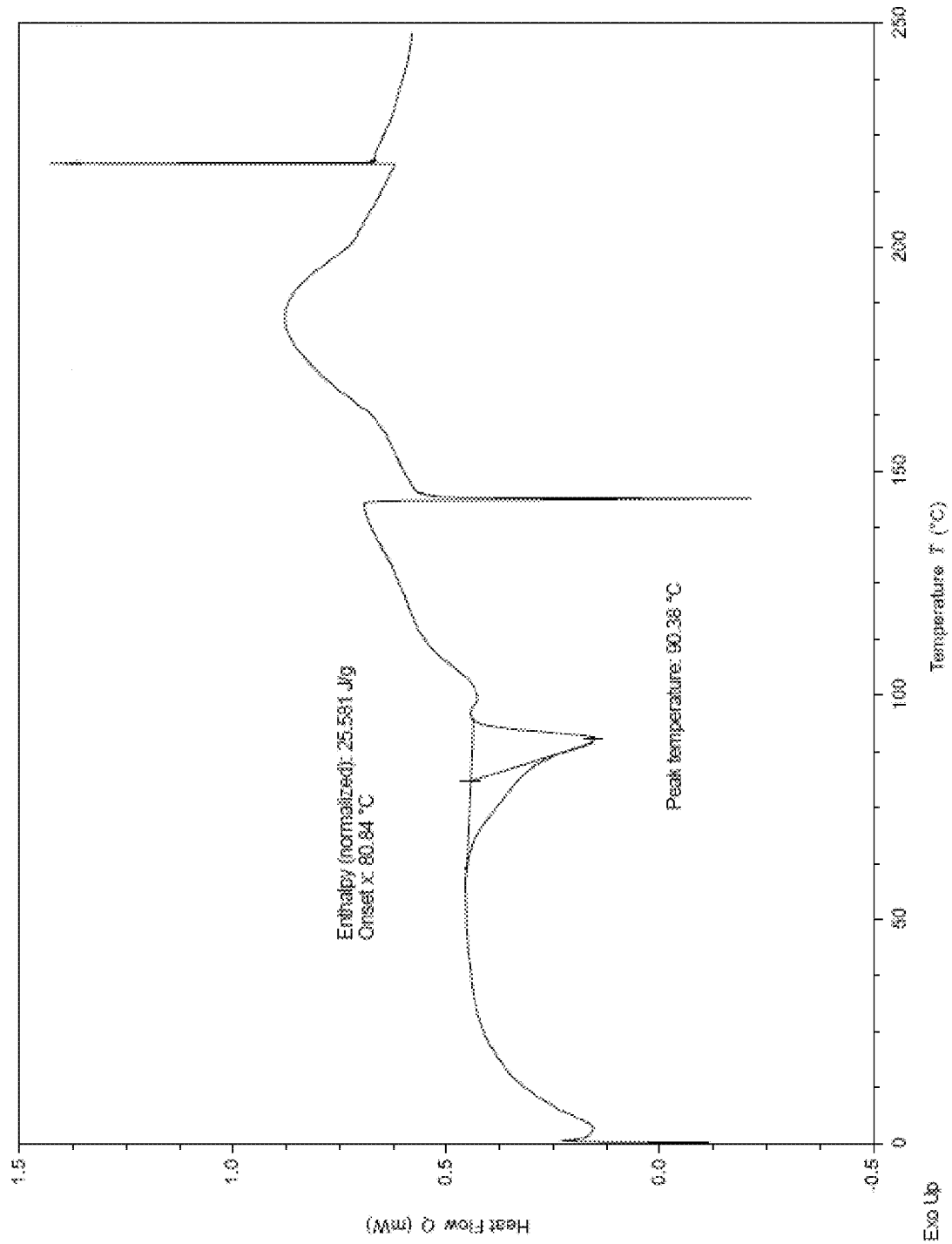
FIG. 13 is a DSC thermogram of Compound I hemifumarate Pattern 1 (Example 6, Sample RC13).
Figure 14:
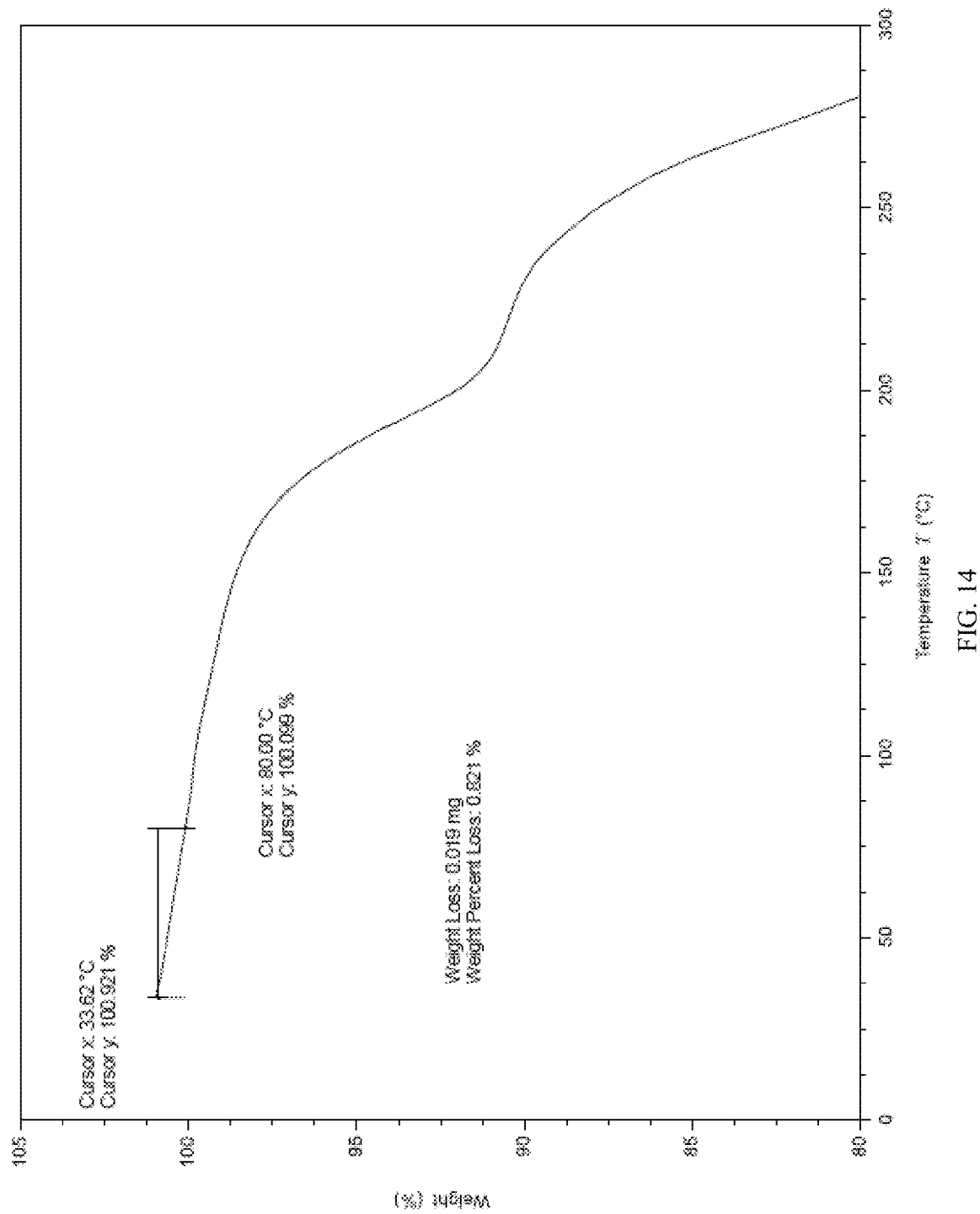
FIG. 14 is a TGA thermogram of Compound I hemifumarate Pattern 1 (Example 6, Sample RC13).

In Experiment RC13, about 50 mg of Compound I free base was added to EtOH, and 0.5 molar amount of fumaric acid was added under stirring at 50° C. for 2 hours and then at 25° C. for at least 12 hours. Seeds of Sample AS3-B were added, and heptanes (0.4 mL) was added as antisolvent. Obtained mixture was stirred at 5° C. for about 3 days. Then the suspension was taken out and centrifuged. Solids obtained were dried in oven at 50° C. for about 1 hour under vacuum, and analyzed by XRPD (FIG. 12), NMR, DSC (FIG. 13), and TGA (FIG. 14).

Figure 15:
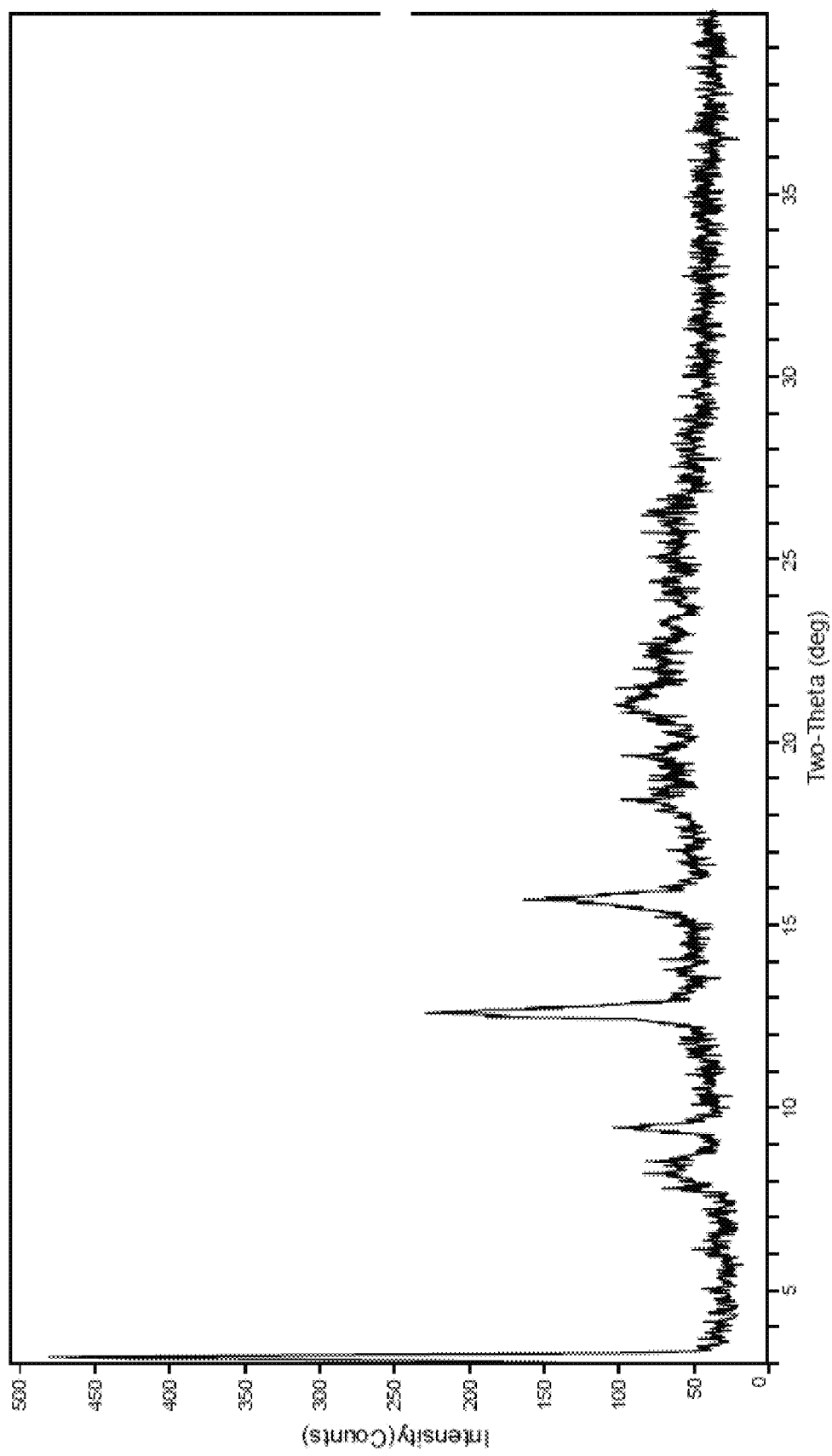
FIG. 15 is a XRPD diffractogram of Compound I monosuccinate Pattern 1 (Example 6, Sample RC14).
Figure 16:
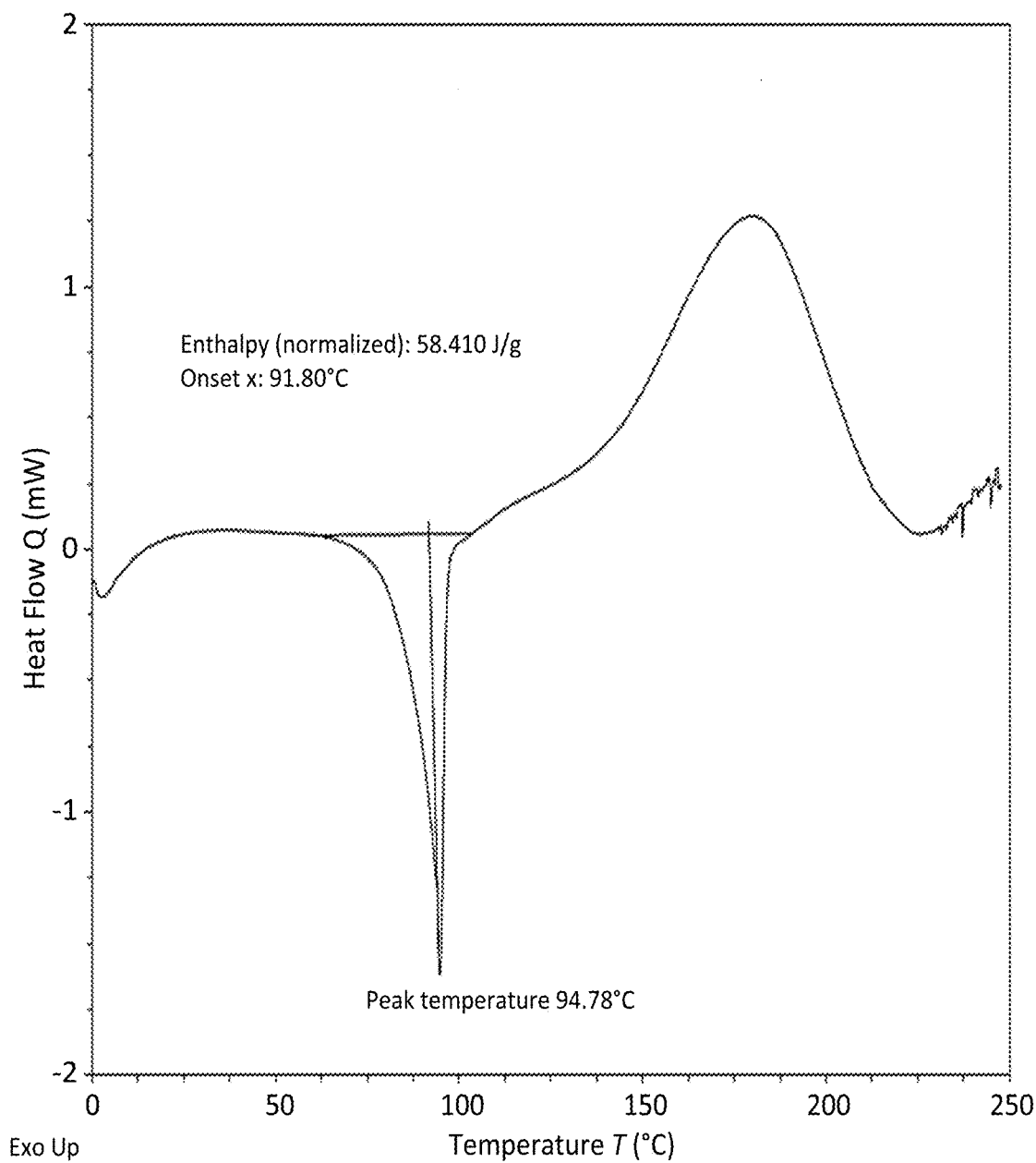
FIG. 16 is a DSC thermogram of Compound I monosuccinate Pattern 1 (Example 6, Sample RC14).
Figure 17:
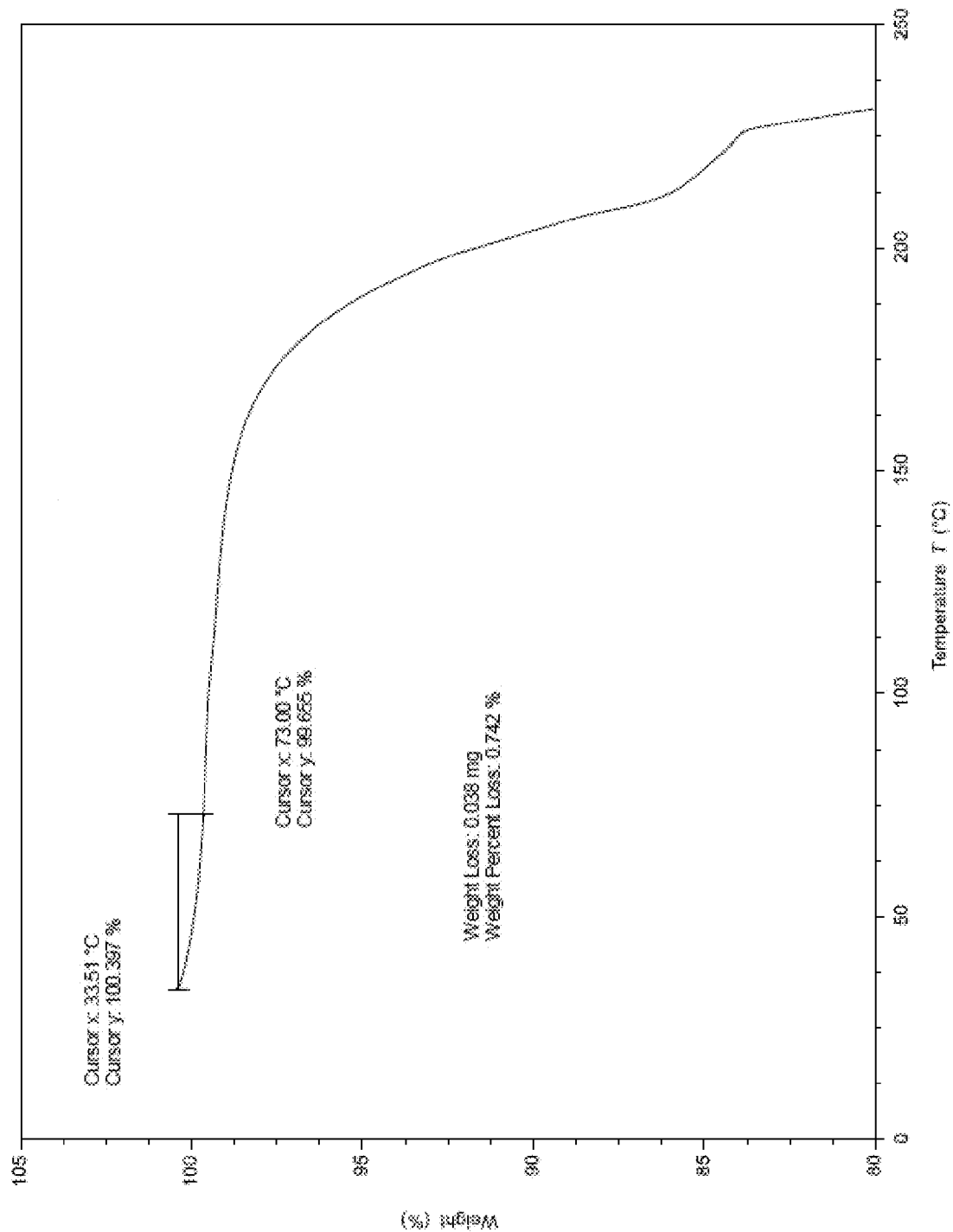
FIG. 17 is a TGA thermogram of Compound I monosuccinate Pattern 1 (Example 6, Sample RC14).

In Experiment RC14, about 50 mg of Compound I free base was added to EtOH and equimolar amount of succinic acid was added under stirring at 50° C. for 2 hours and then at 25° C. for at least 12 hours. Seeds of Sample AS7-B were added, and heptane (0.2 mL) was added as antisolvent. Obtained suspension was taken out and centrifuged. Solids obtained were dried in oven at 50° C. for about 1 hour under vacuum, and analyzed by XRPD (FIG. 15), NMR, DSC (FIG. 16), and TGA (FIG. 17).

In Experiment RC15, about 50 mg of Compound I free base was added in 0.1 mL of EtOH. Equimolar amount of benzenesulfonic acid was dissolved in 0.2 mL of EtOH. Then solution of benzenesulfonic acid was added to the free base solution dropwise at 25° C. MTBE (0.8 mL) as antisolvent was added, and the mixture was stirred at 5° C. with some solid formation.

Figure 18:
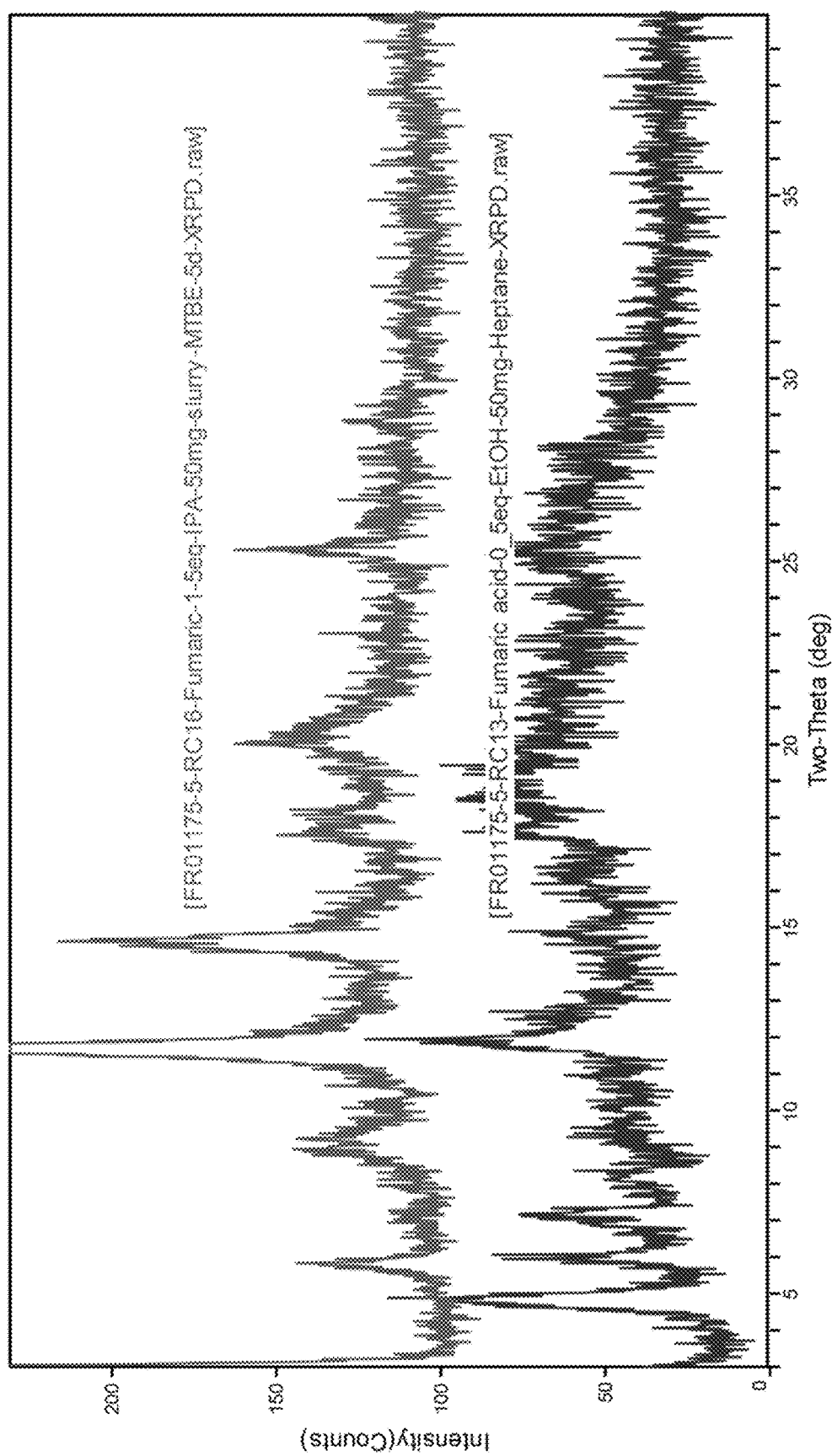
FIG. 18 is a comparison of XRPD diffractograms of Compound I monofumarate Pattern 1 (Example 6, Sample RC16) and Compound I hemi-fumarate Pattern 1 (Example 6, Sample RC-13).

In Experiment RC16, about 50 mg of Compound I free base was added in 0.1 mL of IPA. 1.5 molar amount of fumaric acid was added to the mixture and the mixture was stirred at 25° C. After about 3 hours, the sample was too sticky, 0.1 mL additional IPA was added and kept stirring at 25° C. for about 22 hours. Sticky sample was obtained and dried in a vacuum oven at 50° C. for about 2 hours, and reslurried in 1.0 mL of MTBE at 25° C. for about 5 days. Obtained suspension was taken out and centrifuged. Solids obtained were dried in oven at 40° C. under vacuum for about 1 hour, and analyzed by XRPD (FIG. 18) and NMR. Residual solids were added in RC18 as seeds.

Figure 19:
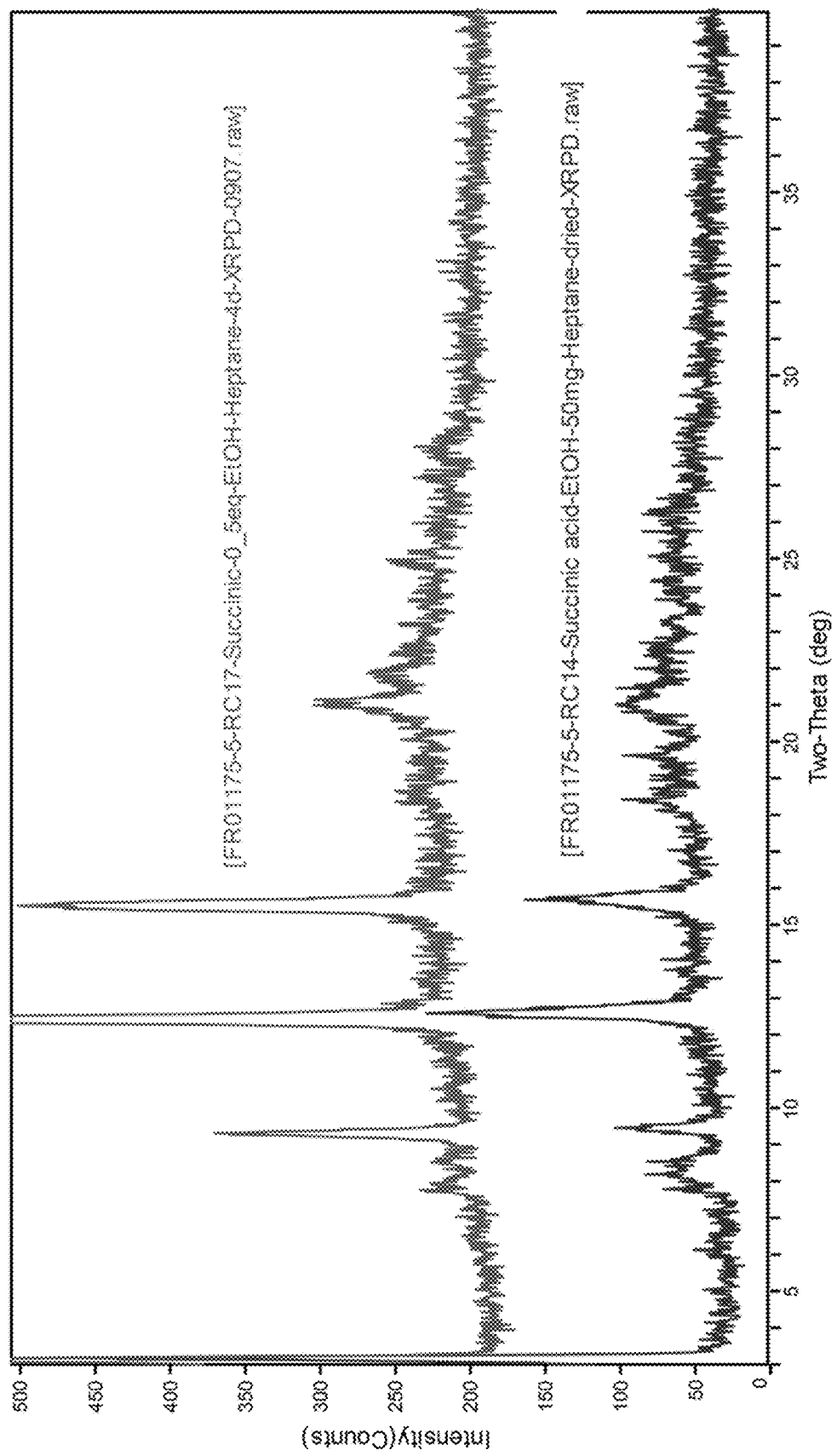
FIG. 19 is a comparison of XRPD diffractograms of Compound I hemi-succinate Pattern 1 (Example 6, Sample RC17) and Compound I mono-succinate Pattern 1 (Example 6, Sample RC-14).
Figure 20:
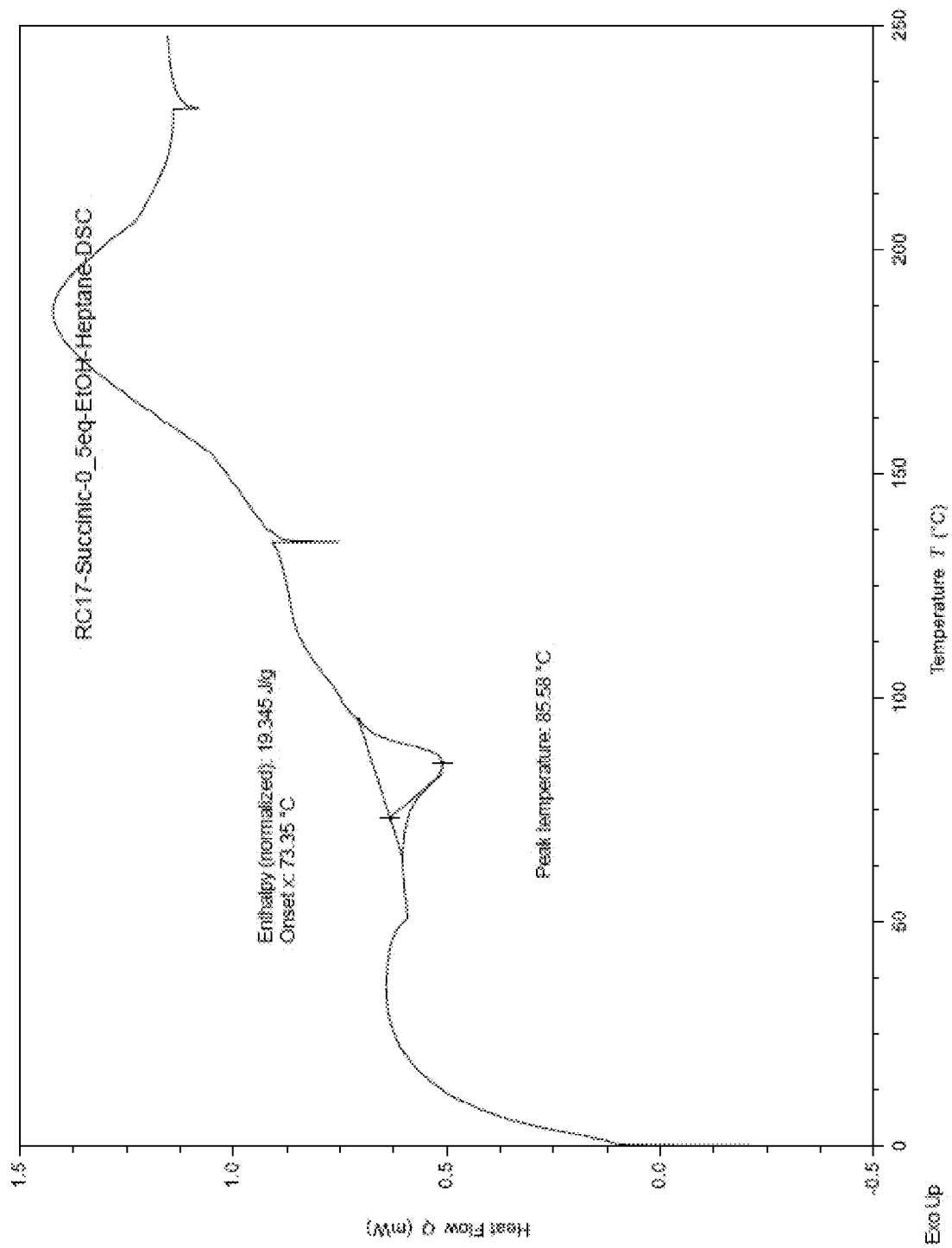
FIG. 20 is a DSC thermogram of Compound I hemisuccinate Pattern 1 (Example 6, Sample RC17).
Figure 21:
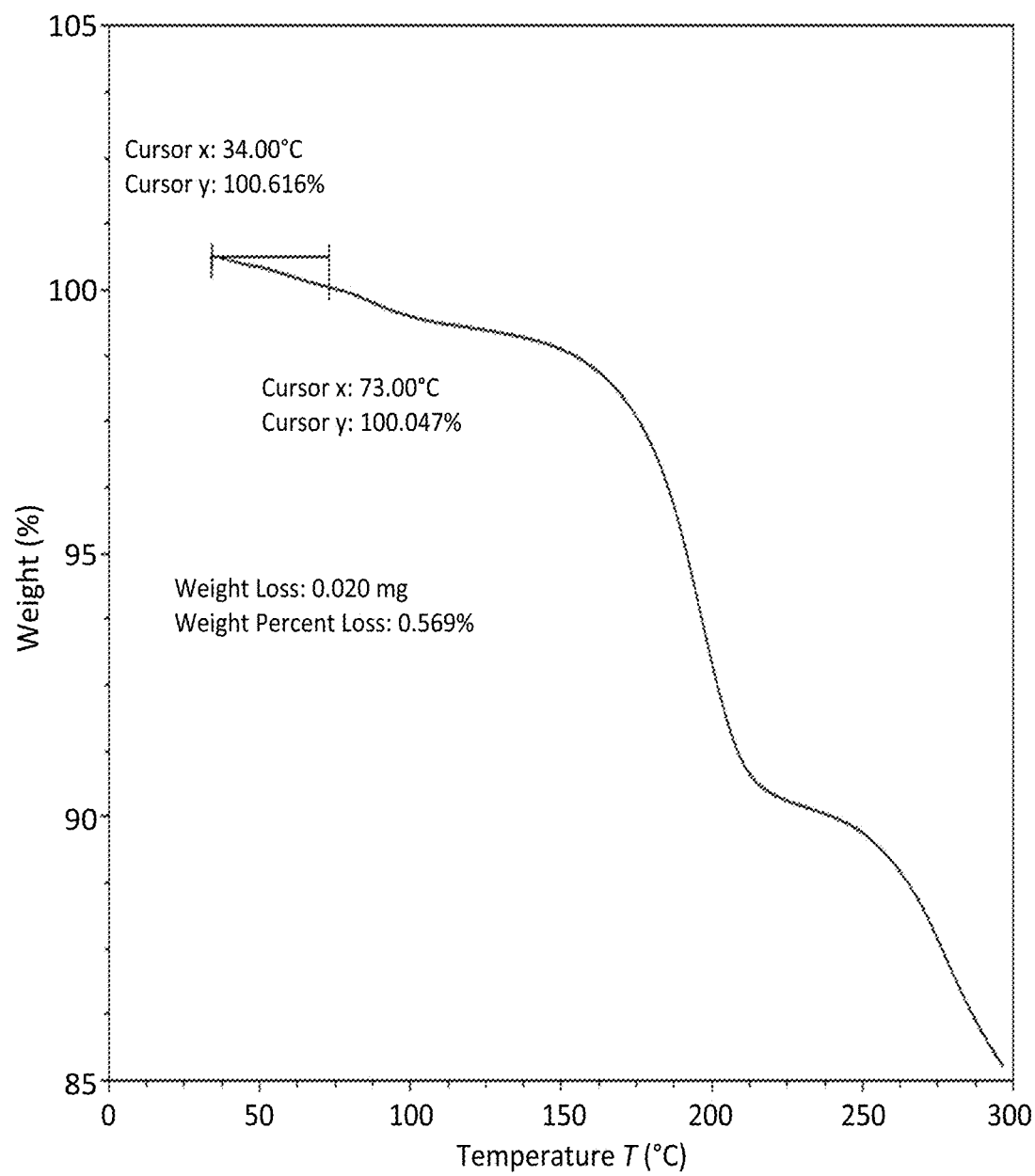
FIG. 21 is a TGA thermogram of Compound I hemisuccinate Pattern 1 (Example 6, Sample RC17).

In Experiment RC17, about 30 mg of Compound I free base was added in 0.1 mL of EtOH. 0.5 molar amount of succinic acid was added to the mixture under stirring at 50° C. for 2 hours and a clear solution was obtained. Heptanes (0.3 mL) as antisolvent was added. Oil was obtained and the mixture was stirred at 25° C. for about 5 days. Obtained suspension was taken out and centrifuged. Solids obtained were dried in oven at 40° C. under vacuum for about 1 hour, and analyzed by XRPD (FIG. 19), NMR, DSC (FIG. 20), and TGA (FIG. 21).

Figure 22:
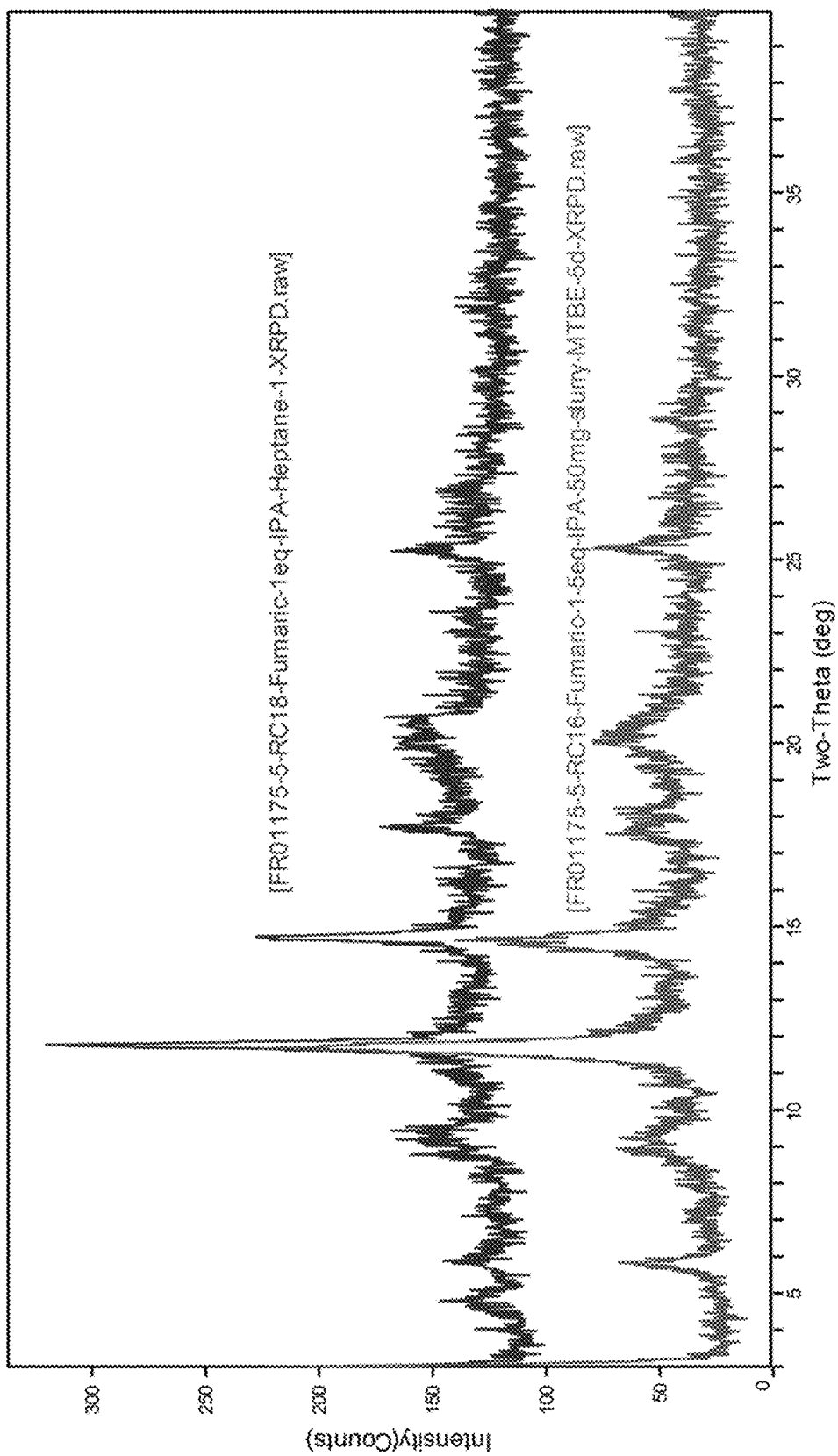
FIG. 22 is a comparison of XRPD diffractograms of Compound I mono-fumarate Pattern 1 (Example 6, Sample RC18) and Compound I mono-fumarate Pattern 1 (Example 6, Sample RC-16).

In Experiment RC18, about 30 mg of Compound I free base was added to 0.1 mL of IPA. Equimolar amount of fumaric acid was added to the mixture under stirring at 50° C. for 2 hours, a yellow clear solution was obtained, and 0.3 mL of heptane was added as antisolvent. Some seeds from RC16 were added. Suspension was obtained and it was stirred at 25° C. for at least 12 hours. Obtained suspension was taken out and centrifuged and analyzed by XRPD (FIG. 22). Mono-fumarate Pattern 1 was obtained and was added into scale up sample as seeds.

TABLE 8

Results of salt screening by slurry crystallization

| Exp. | Counterion | Solvent/Antisolvent | Salt ratio and residual solvent content* | DSC melting onset, ° C. (and enthalpy, J/g) | Weight loss by TGA | XRPD |
|---|---|---|---|---|---|---|
| RC13 | Fumarate (0.5 eq) | EtOH/heptanes | 1:0.5 0.7% EtOH, 1.1% heptanes | 80.8 (26) | 0.8% at 80° C. | Hemi-fumarate Pattern 1 |
| RC14 | Succinate (1.0 eq) | EtOH/heptanes | 1:1.0 0.9% EtOH, 1.1% heptanes | 91.8 (58) | 0.7% at 100° C. | Mono-succinate Pattern 1 |
| RC15 | Benzene sulfonate (1.0 eq) | EtOH/MTBE | | ND** | | ND |
| RC16 | Fumarate (1.5 eq) | IPA/MTBE | 1:1.09 5.7% MTBE | ND | ND | Mono-fumarate Pattern 1 |
| RC17 | Succinate (0.5 eq) | EtOH/heptanes | 1:0.67 0.5% EtOH 1.2% heptanes | 73.4 (19) | 0.6% at 73° C. | Hemi-succinate Pattern 1 |

TABLE 8-continued

Results of salt screening by slurry crystallization

| Exp. | Counterion | Solvent/ Antisolvent | Salt ratio and residual solvent content* | DSC melting onset, ° C. (and enthalpy, J/g) | Weight loss by TGA | XRPD |
|---|---|---|---|---|---|---|
| RC18 | Fumarate (1.0 eq) | IPA/heptane | ND | ND | ND | Mono-fumarate Pattern 1 |

Notes:
*Salt ratio is the ratio of Compound I free base:counterion as determined by proton integration in the $^1$H NMR spectra;
**ND: data not collected.

From the salt screening experiments, 4 patterns were identified, hemi-fumarate Pattern 1, mono-fumarate Pattern 1, hemi-succinate Pattern 1 and mono-succinate Pattern 1. The four Patterns show comparable properties, such as low to medium crystallinity, relative low melting point.

Example 7: Preparation of Fumarate Salts

Preparation of Compound I Hemifumarate Pattern 1

Figure 23:
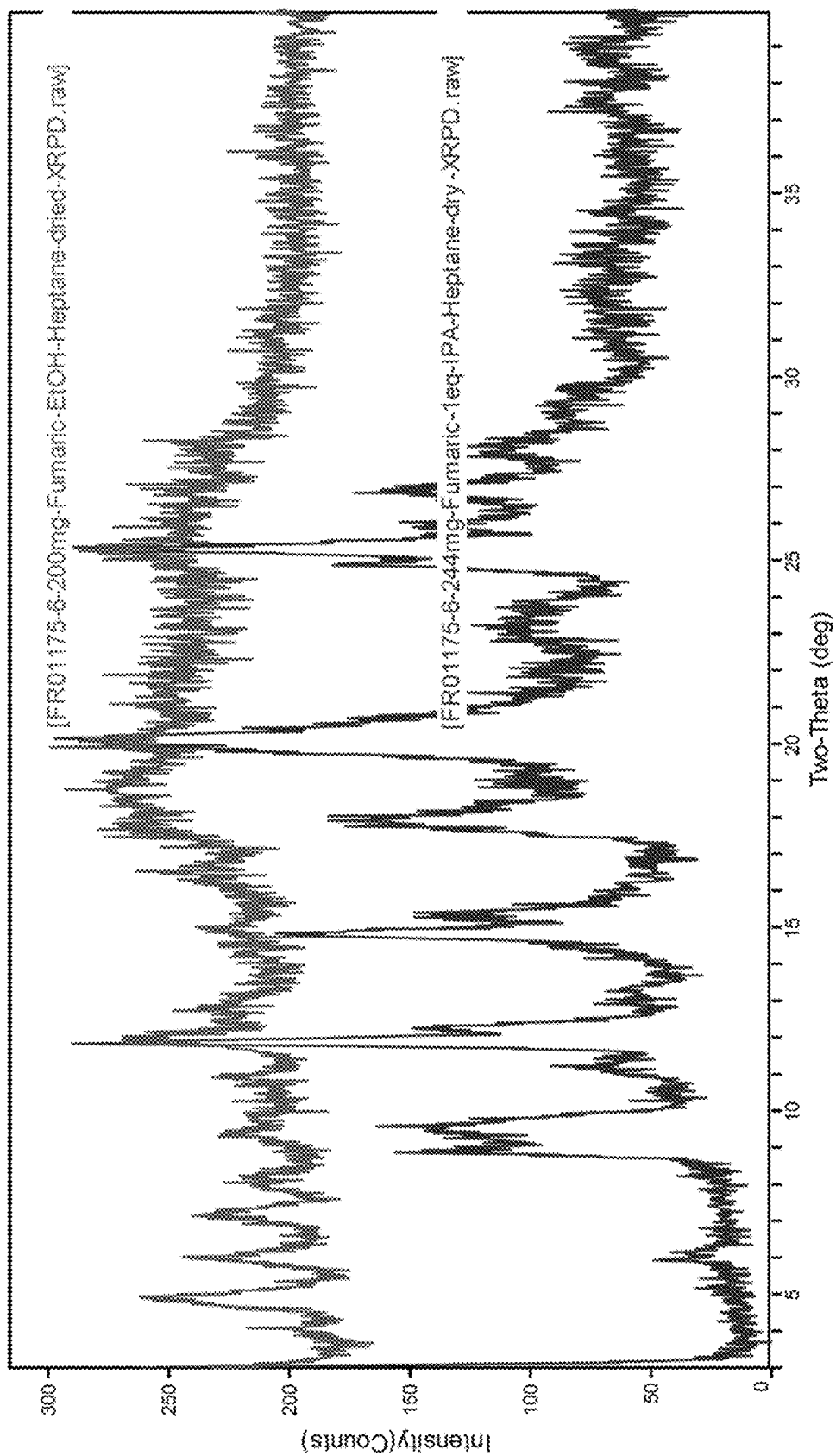
FIG. 23 is a comparison of XRPD diffractograms of Compound I hemifumarate Pattern 1 and Compound I monofumarate Pattern 1 (small scale preparation) obtained in Example 7.
Figure 24:
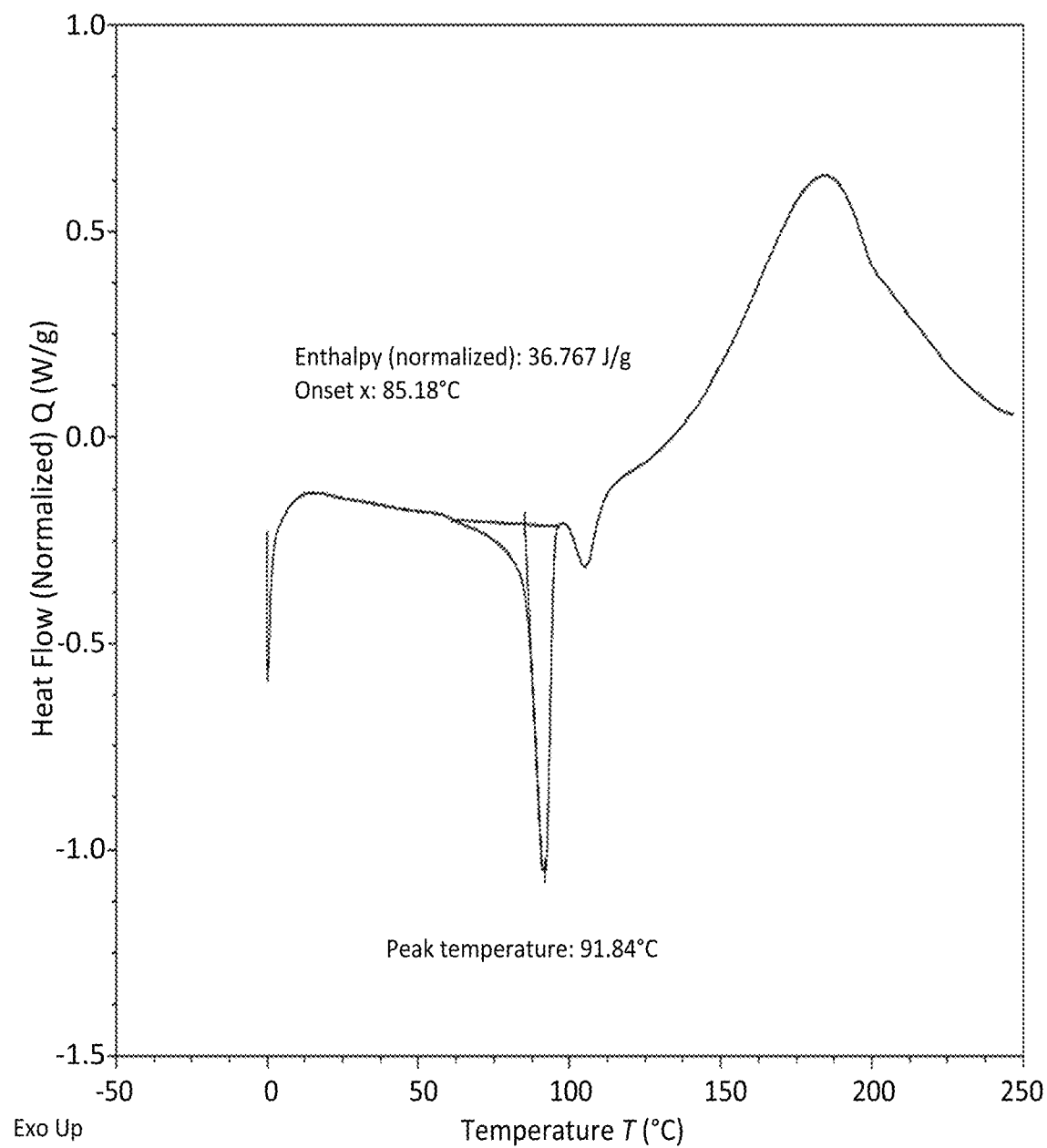
FIG. 24 is a DSC thermogram of Compound I hemifumarate Pattern 1 obtained in Example 7.
Figure 25:
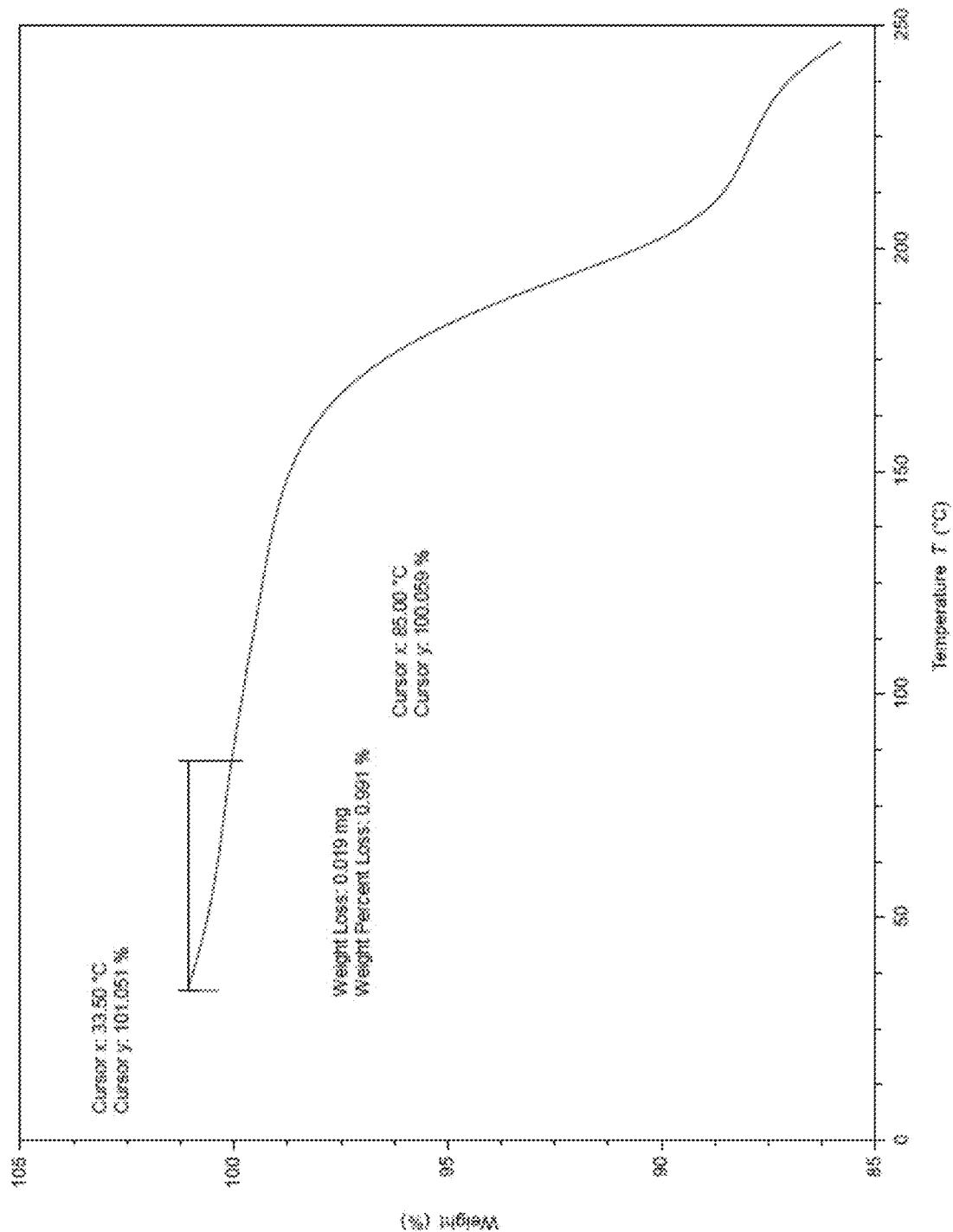
FIG. 25 is a TGA thermogram of Compound I hemifumarate Pattern 1 obtained in Example 7.

About 200 mg of Compound I free base was added to 0.5 mL of EtOH. While stirring, 0.5 molar amount of fumaric acid was added at 50° C. and the mixture was stirred for 2 hours. A clear solution was obtained. The solution was then cooled to 25° C. within 1 hour. Hemi-fumarate seeds of Sample RC13 (Example 5, Table 7) were added, followed by addition of 2.5 mL of heptanes to induce precipitation. An oil was obtained and stirred at 25° C. for about 4 days. After 4 days, the resulting suspension was cooled to 5° C. After stirred at 5° C. for about 4 days, the precipitated solids were collected by filtration and dried at 40° C. under vacuum for about 3 hours. As a result, 116 mg of light-orange hemi-fumarate Pattern 1 were obtained in yield of 52%. XRPD is shown in FIG. 23; DSC is shown in FIG. 24; and TGA is shown in FIG. 25.

Preparation of Compound I Monofumarate Pattern 1 (Small Scale Preparation)

Figure 26A:
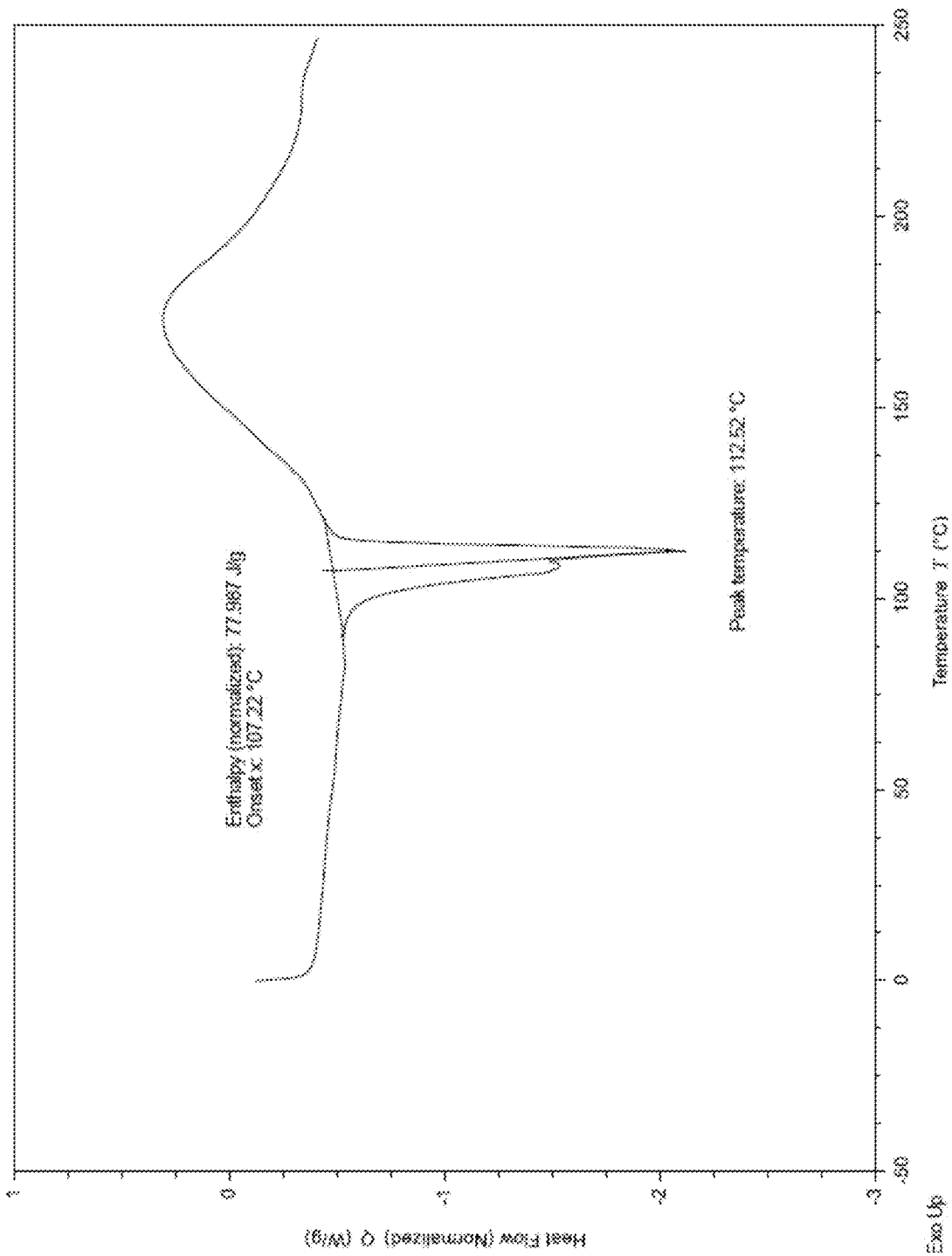
FIG. 26A is a DSC thermogram of Compound I monofumarate Pattern 1 (small scale preparation, Example 7), recorder at heating rate of 10° C./min.
Figure 26B:
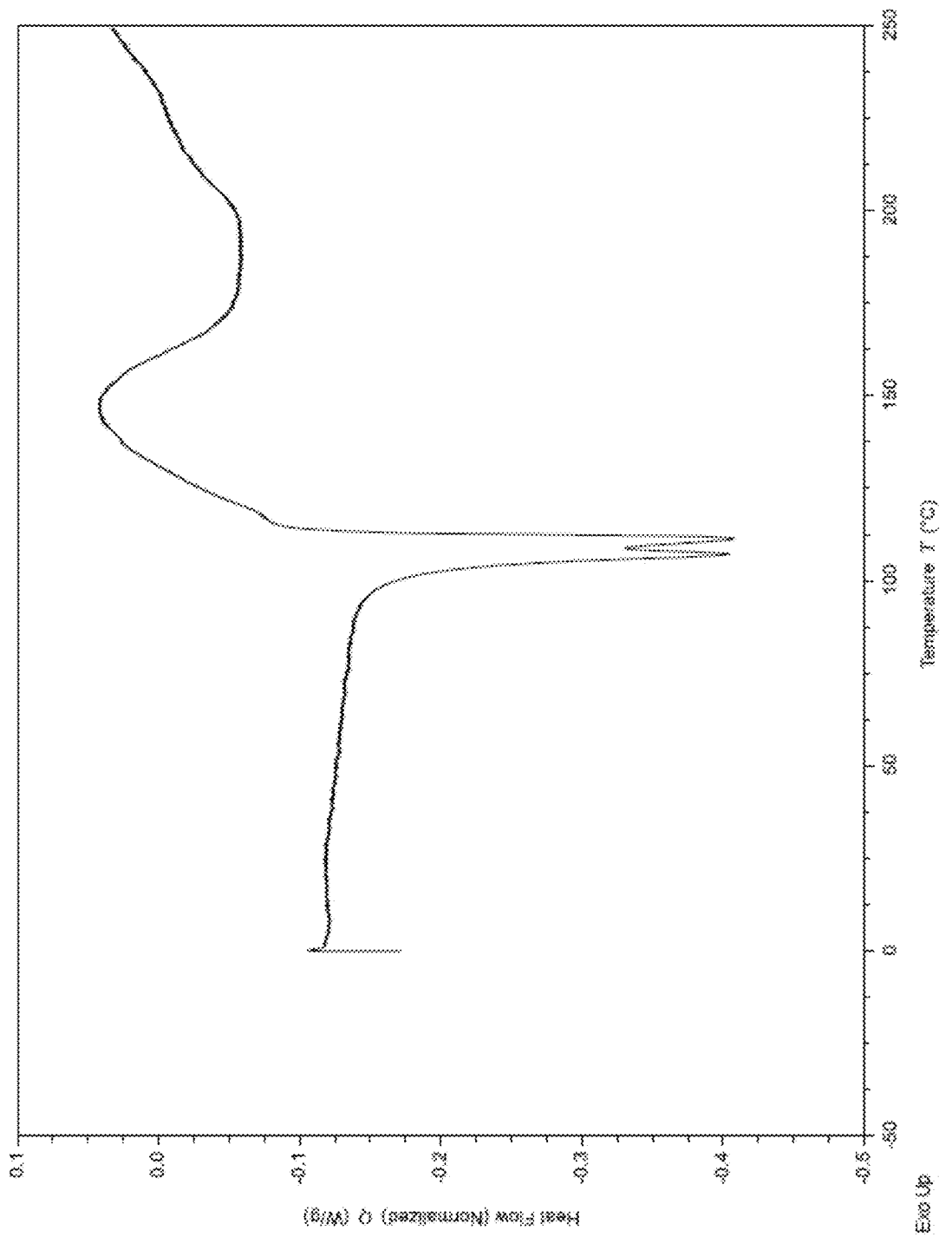
FIG. 26B is a DSC thermogram of Compound I monofumarate Pattern 1 (small scale preparation, Example 7), recorder at heating rate of 2° C./min.
Figure 26C:
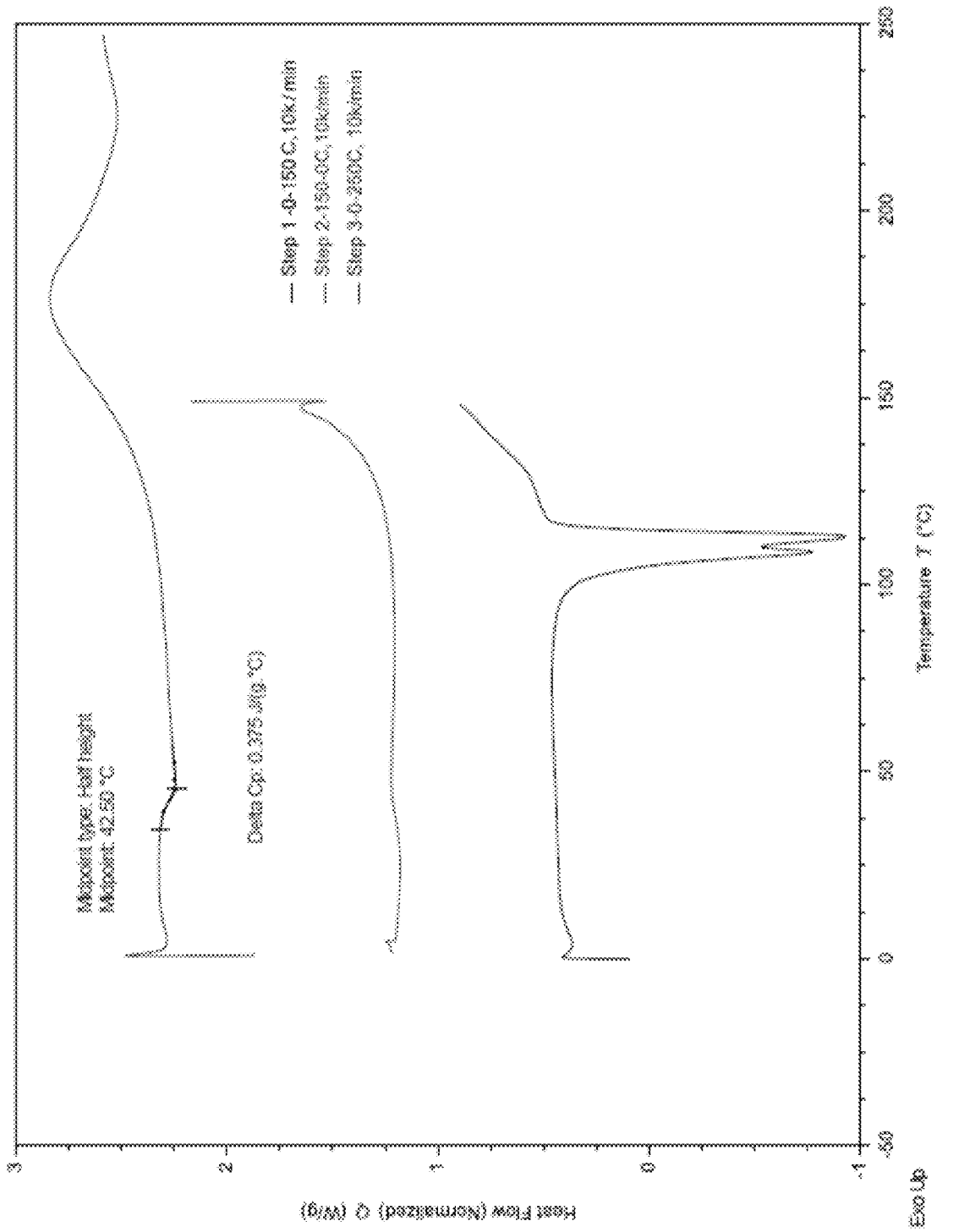
FIG. 26C is a DSC cycle of Compound I mono-fumarate Pattern 1 (DSC cycle, 0-150° C., 150-0° C., 0-250° C., 10° C./min) for the small-scale preparation sample (Example 7).
Figure 27:
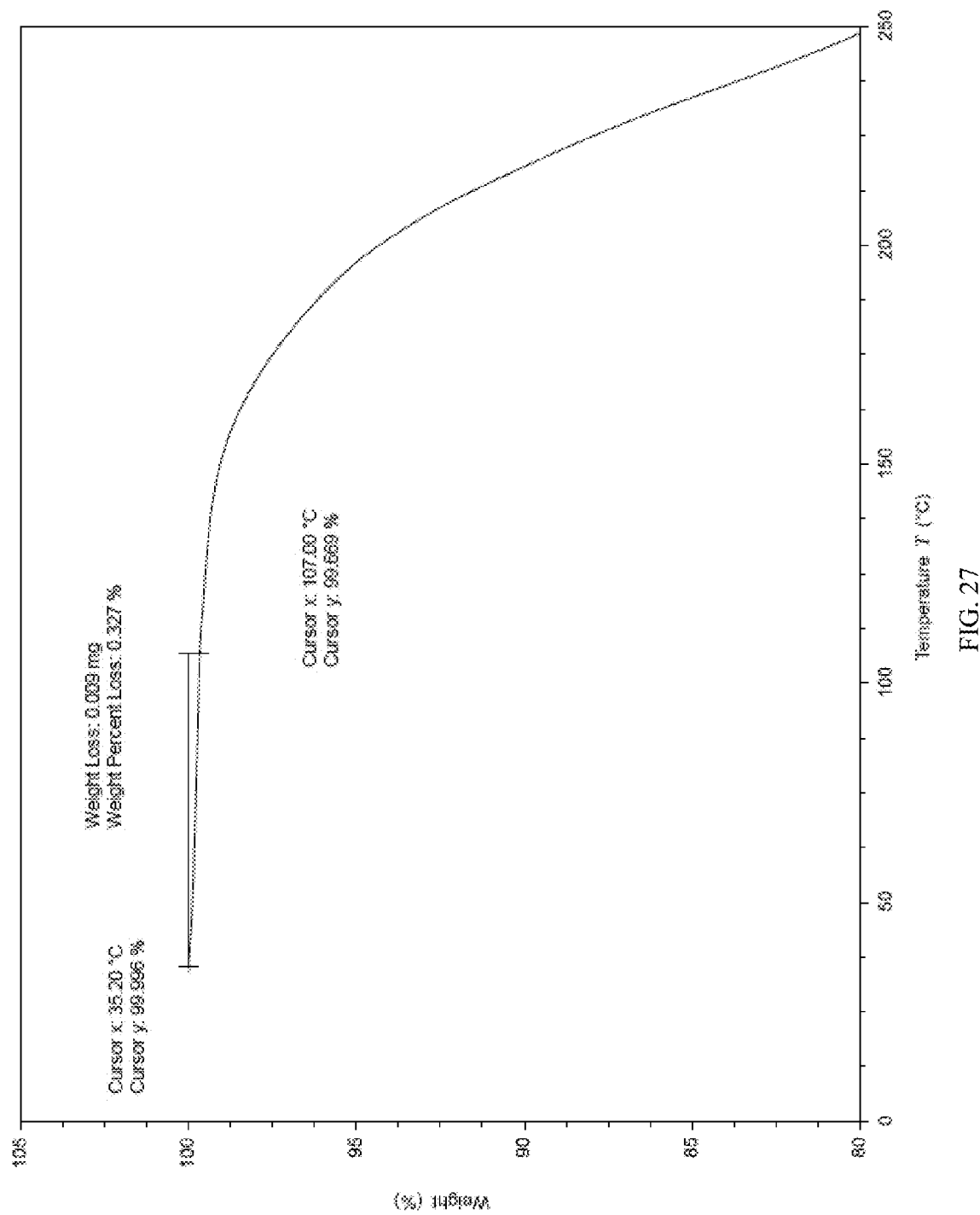
FIG. 27 is TGA thermogram of Compound I monofumarate Pattern 1 for the small-scale preparation sample (Example 7).

About 244 mg of Compound I free base was added into 0.8 mL of IPA. Then, 1.0 eq. of fumaric acid was added with stirring at 50° C. for about 1.5 hours. The yellow clear solution obtained was cooled to 25° C. and stirred for about 5 minutes. Mono-fumarate seeds of Sample RC 18 (Table 7) were added to the mixture, followed by addition of 4 mL of heptanes as an antisolvent. The mixture was stirred at 25° C. for 4 days. The precipitated material was collected by filtration and dried at 40° C. under vacuum for about 2 hours. As a result, 208 mg of mono-fumarate Pattern 1 solids were obtained in yield of 69%. XRPD is shown in FIG. 23. DSC at 10° C./min is shown in FIG. 26A, DSC at 2° C./min is shown in FIG. 26B. DSC cycle results are shown in FIG. 26C. TGA is shown in FIG. 27.

TABLE 9

Characterization of Compound I free base pattern and its mono- and hemifumarate patterns

| Parameter | Compound I free base Pattern 1 | Compound I Hemifumarate Pattern 1 | Compound I Monofumarate Pattern 1 (small-scale preparation) |
|---|---|---|---|
| Chemical Purity (HPLC area %) | 98.7% | 97.8% | 98.6% |
| Salt Ratio ($^1$H NMR) | N/A | 1:0.5 | 1:1.0 |
| Residual Solvent ($^1$H NMR) | 0.7% MTBE | 0.7% EtOH, 0.7% heptanes | 1.8% isopropanol, 2.2% heptanes |
| Water (KF titration) | 1.7% | 1.7% | 1.2% |
| Crystallinity (XRPD) | High | Medium | Medium |
| Melting point (DSC), ° C. | 75.0 | 85.2 | 107.2 |
| Melting enthalpy, J/g | 64 | 37 | 78 |
| TGA (% weight lost at given temperature) | 0.3% at 70° C. | 1.0% at 85° C. | 0.3% at 107° C. |

Compound I Pattern 1 is in high crystallinity. The hemi-fumarate and monofumarate Patterns are in medium crystallinity.

Compound I Pattern 1 is an anhydrate and has a melting peak at $T_{onset}$ of 75.0° C. with an enthalpy of about 64 J/g. It shows about 0.3% weight loss at about 70° C. KF shows it contains about 1.7% of water. About 0.7% of MTBE (by weight) residue was detected by $^1$H NMR.

Compound I hemifumarate Pattern 1 is an anhydrate. The stoichiometry of free form: fumaric acid is about 1:0.5 based on $^1$H NMR result. It has a melting peak at $T_{onset}$ of 85.2° C. with an enthalpy of about 37 J/g. It shows about 1.0% weight loss at about 85° C. KF shows it contains about 1.7% of water. About 0.7% of EtOH and 0.7% of heptanes (by weight residual) was detected by $^1$H NMR.

Compound I monofumarate Pattern 1 is an anhydrate. The stoichiometry of free form: fumaric acid is about 1:1.0 based on $^1$H NMR result. It has the melting peak at $T_{onset}$ of 107.2° C. with split peaks and with an enthalpy of about 78 J/g. The two thermal events cannot be resolved with 2 K/min and 0.5 K/min heating rate by DSC as well. It shows about 0.3% weight loss at about 107° C. KF shows it contains about 1.2% of water. About 0.7% of IPA and 2.2% of heptanes (by weight) residue was detected by $^1$H NMR.

Example 8. Stability of Compound I Free Base Pattern 1, Compound I Monofumarate Pattern 1 and Compound I Hemifumarate Pattern 1

Initial chemical purity: Initial purities of Compound I free base Pattern 1, Compound I monofumarate Pattern 1 and Compound I hemifumarate Pattern 1 are 98.7%, 98.6% and 97.8%, respectively.

Figure 28:
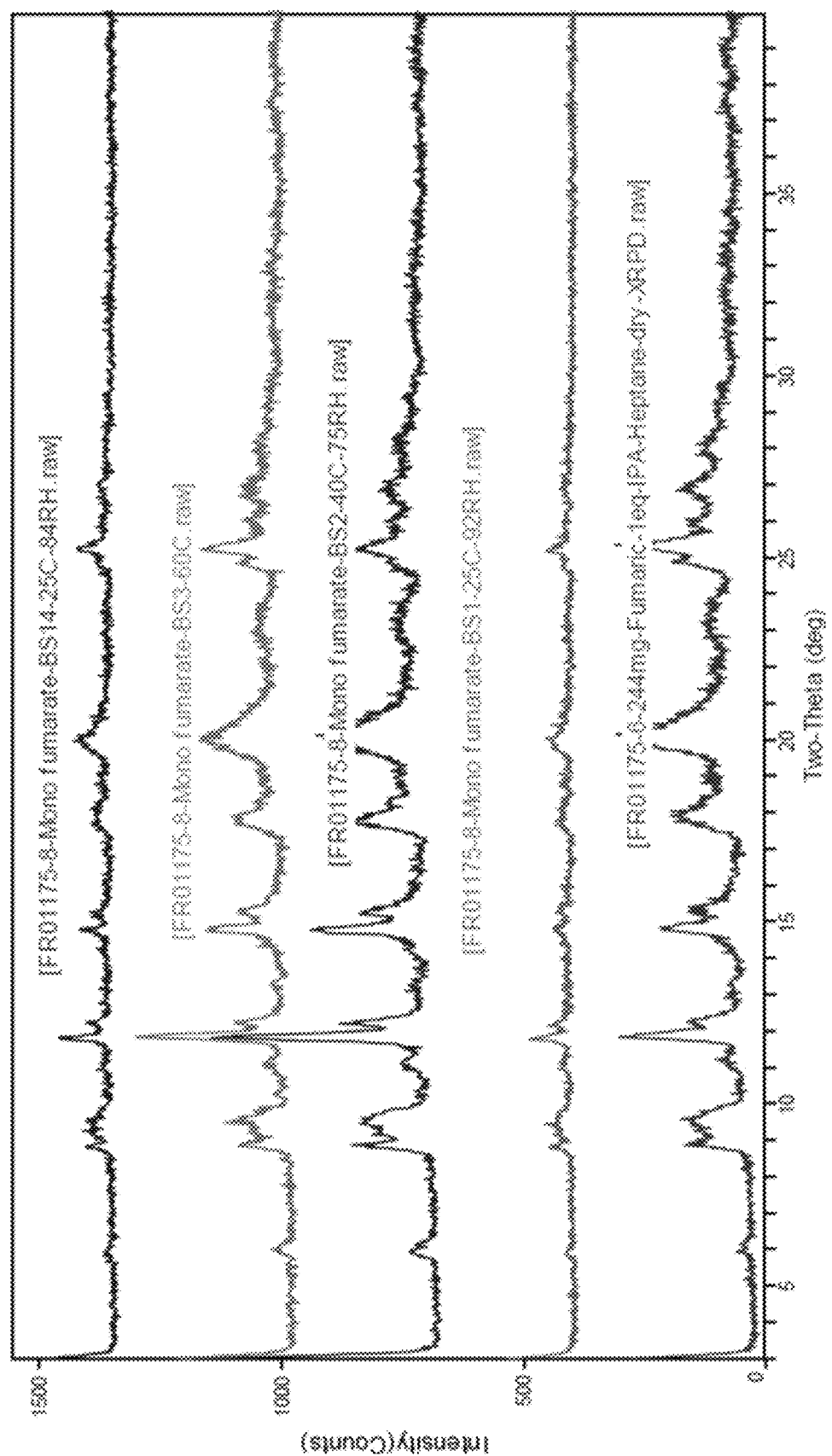
FIG. 28 is a comparison of XRPD diffractograms of Compound I monofumarate Pattern 1 obtained in stability test experiments at 25° C./84% RH (2 days, open container), 25° C./92% RH (1 week, open container), 40° C./75% RH (1 week, open container), and 60° C. (1 week, tight container) as described in Example 8 with original sample of Compound I monofumarate Pattern 1 before the test.
Figure 29:
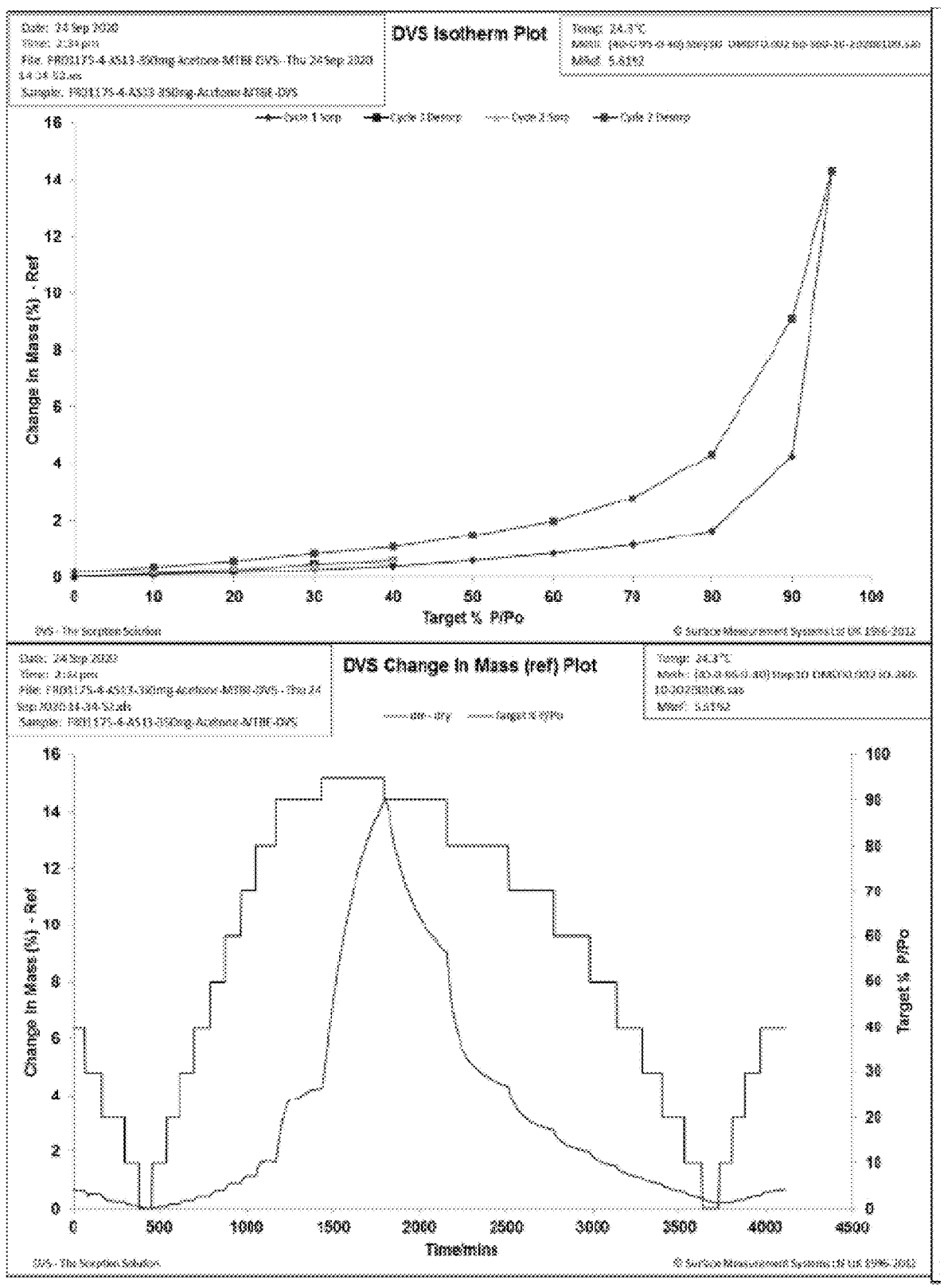
FIG. 29 is a Dynamic Vapor Sorption (DVS) plot and DVS change in mass plot for Compound I Pattern 1 (Example 10).
Figure 30:
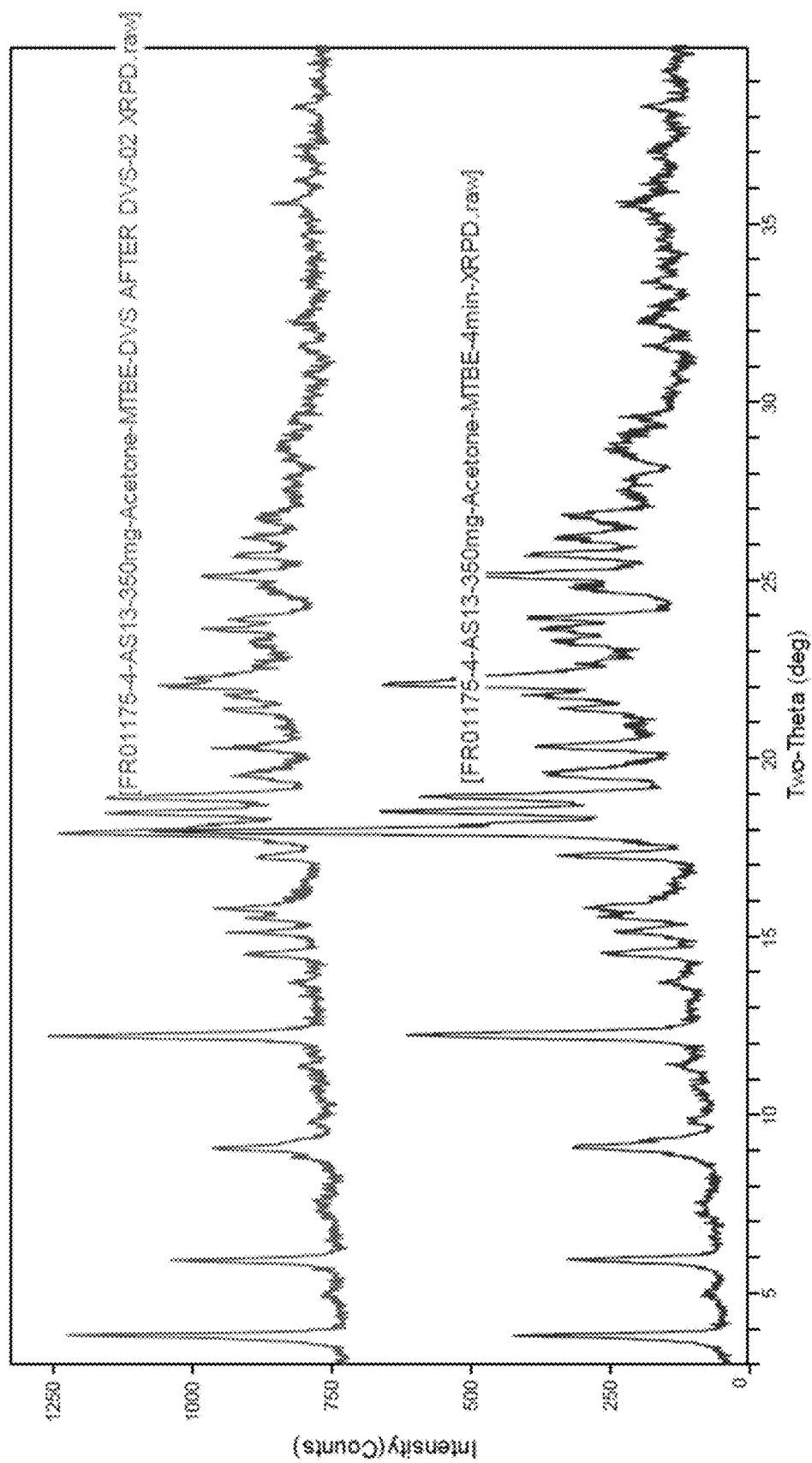
FIG. 30 is a comparison of XRPD diffractograms of Compound I Pattern 1 (obtained in Example 3) before and after DVS study (Example 10).
Figure 31:
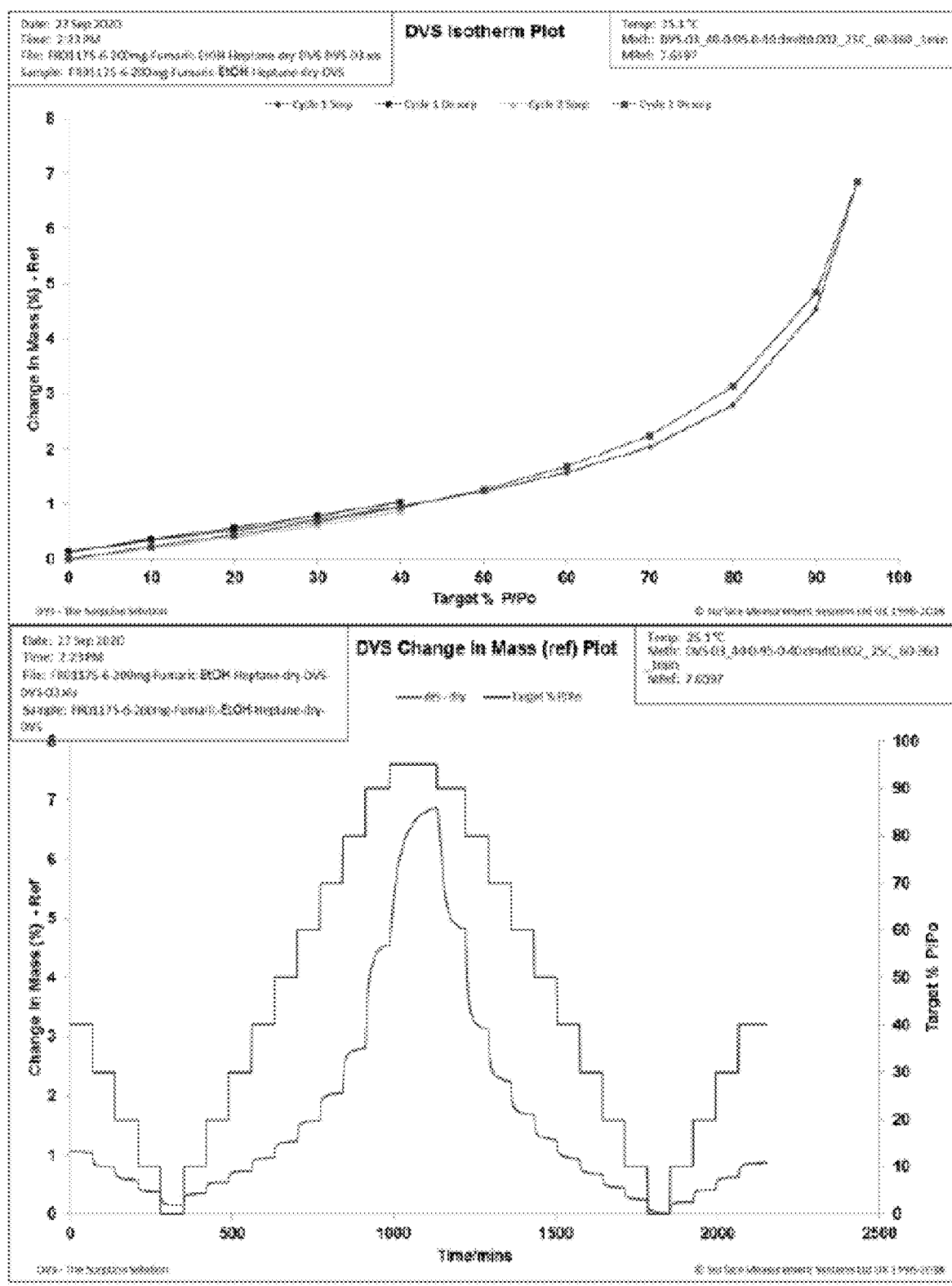
FIG. 31 is a Dynamic Vapor Sorption (DVS) plot and DVS change in mass plot for Compound I hemifumarate Pattern 1 (Example 10).
Figure 32:
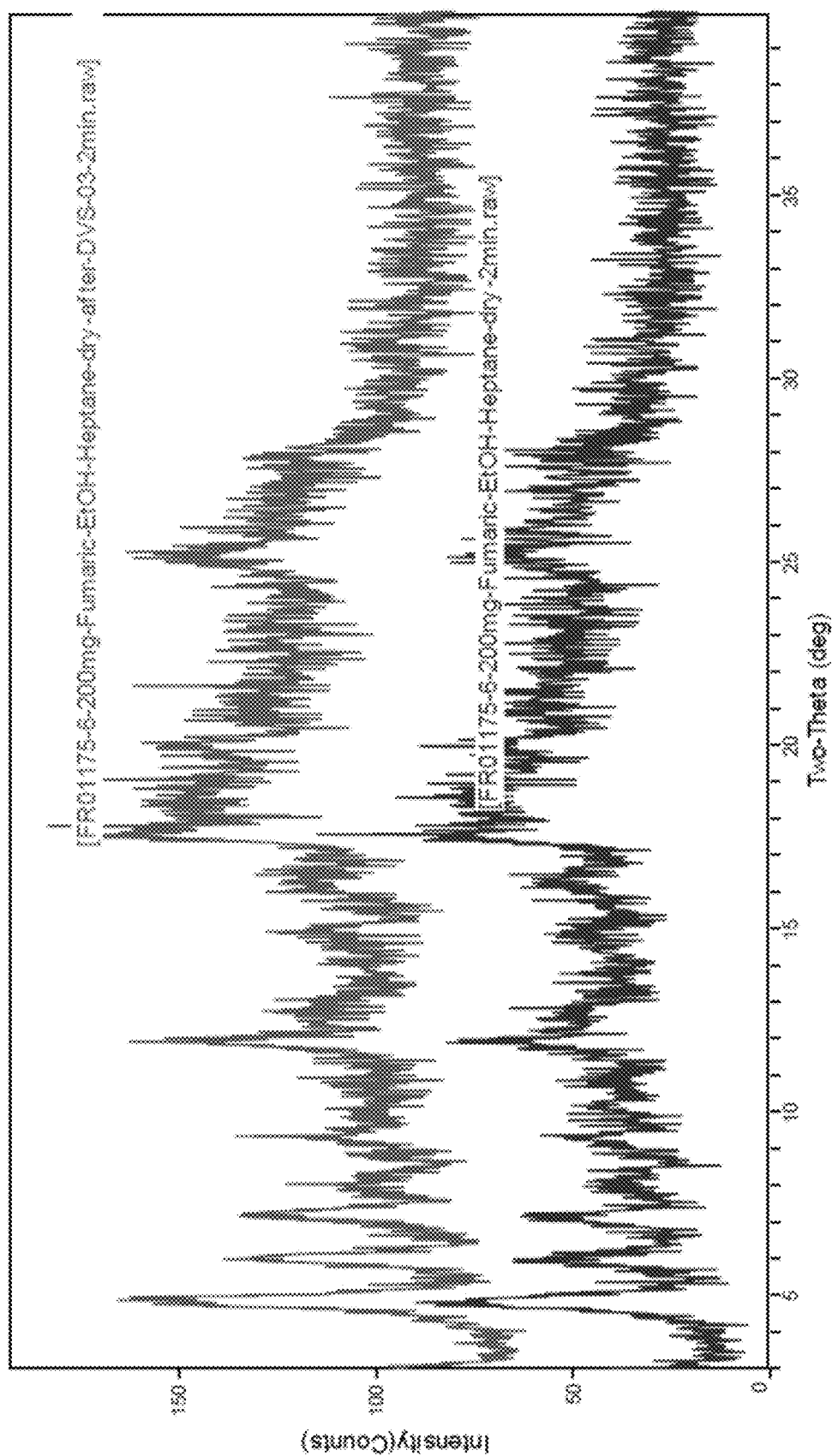
FIG. 32 is a comparison of XRPD diffractograms of Compound I hemifumarate Pattern 1 (obtained in Example 7) before and after DVS study (Example 10).
Figure 33:
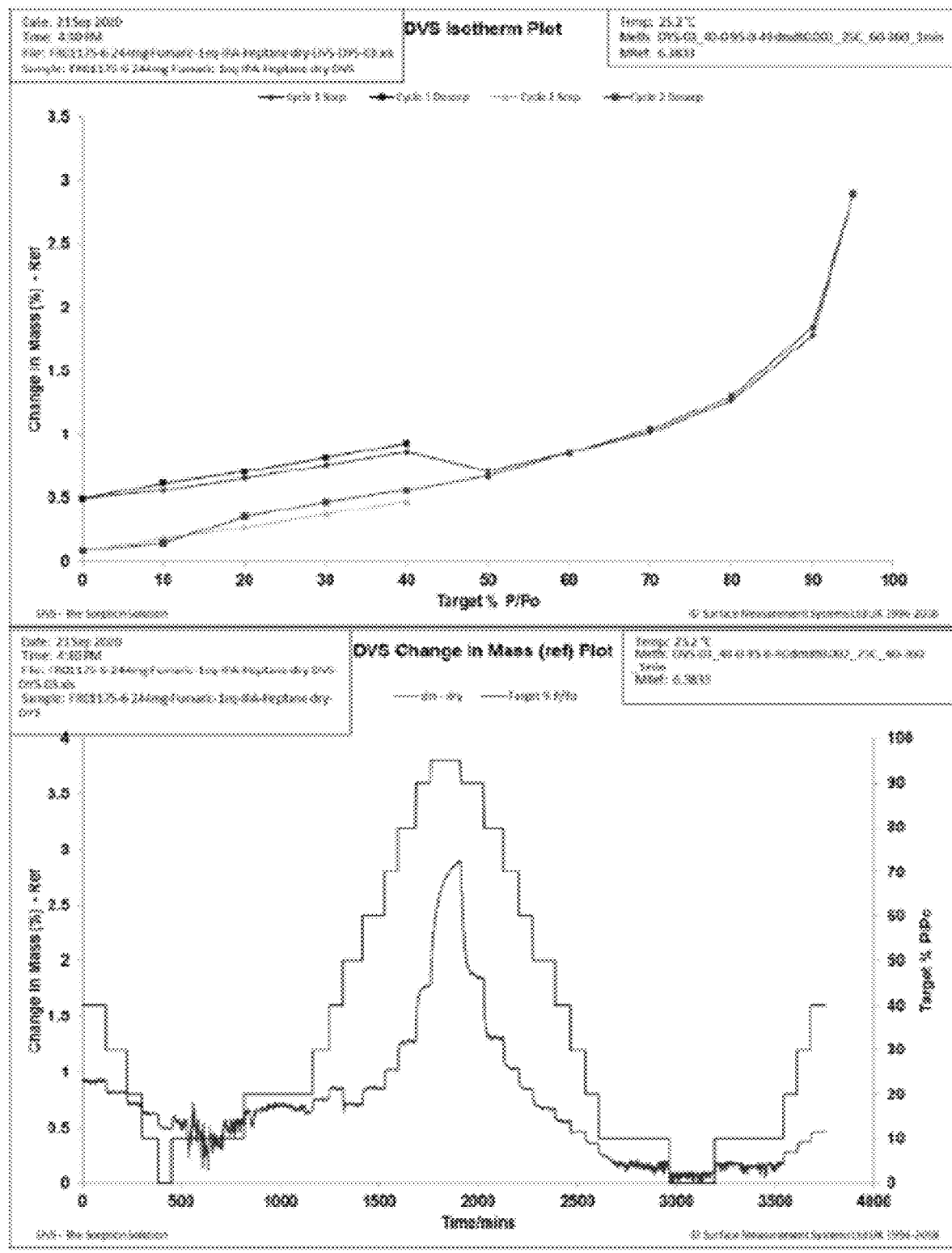
FIG. 33 is a Dynamic Vapor Sorption (DVS) plot and DVS change in mass plot for Compound I monofumarate Pattern 1 (Example 10).
Figure 34:
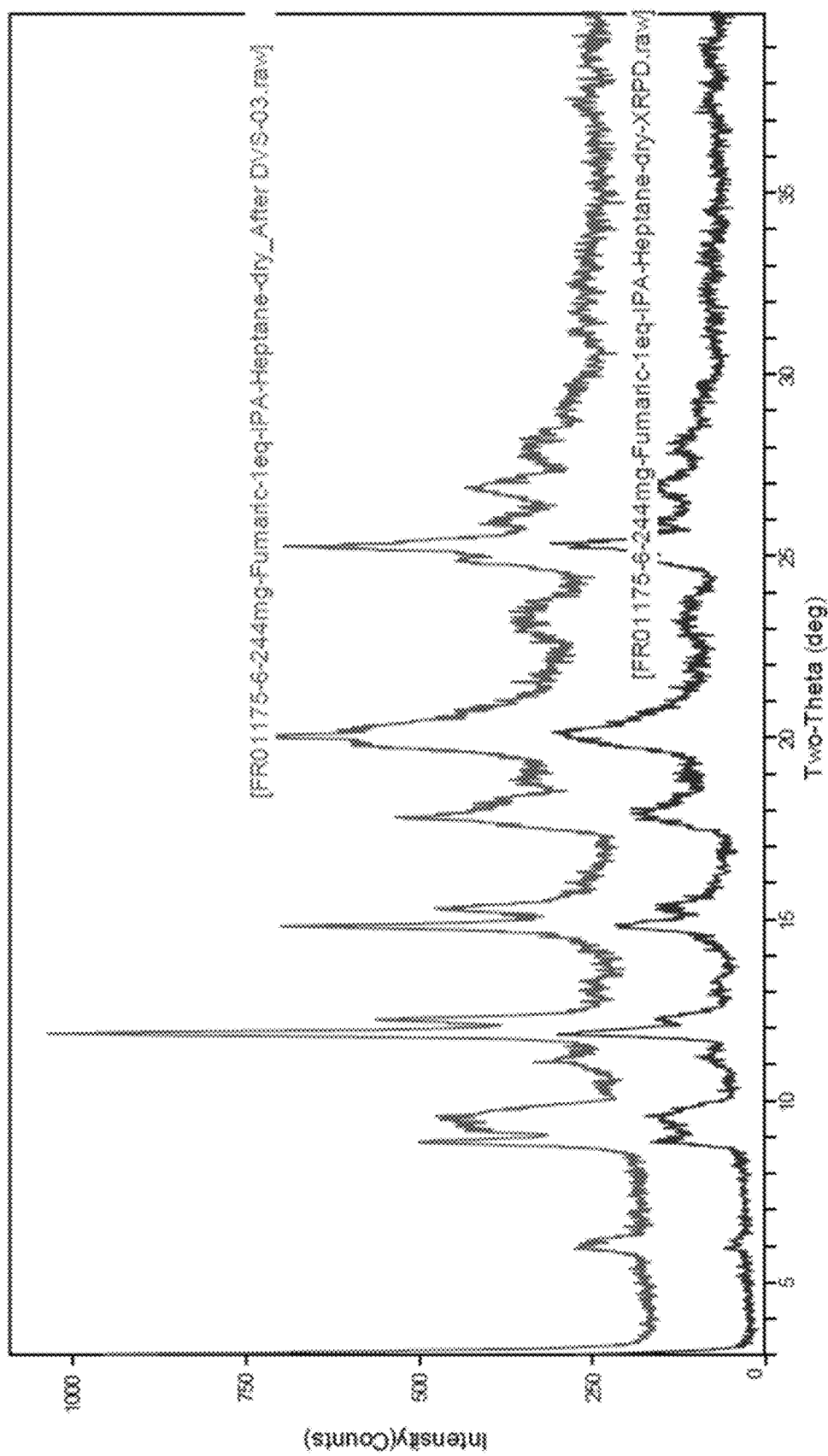
FIG. 34 is a comparison of XRPD diffractograms of Compound I monofumarate Pattern 1 (obtained in Example 7) before and after DVS study (Example 10).

Bulk stability: Accelerated stability experiments were conducted at 25° C./92% RH and 40° C./75% RH in an open container, 60° C. in a tight container for one week. Results are presented in Table 10. Results for Compound I monofumarate Pattern 1 are also presented in FIG. 28.

All the three candidates showed good physically stability after exposure to the three conditions. They all show some degradation after exposure to 40° C./75% RH for one week, and two are not stable at high temperature (60° C. for one week). Compound I hemifumarate Pattern 1 tends to degrade more than Compound I monofumarate Pattern 1 in the two conditions mentioned above.

TABLE 10

Bulk stability of Compound I free base Pattern 1, Compound I monofumarate Pattern 1 and Compound I hemifumarate Pattern 1

| Storage Conditions | | Compound I free base Pattern 1 | Compound I Hemifumarate Pattern 1 | Compound I Monofumarate Pattern 1 |
|---|---|---|---|---|
| Initial | HPLC | 98.7% | 97.8% | 98.6% |
| 25° C., 92% RH, open container | HPLC | 98.5% | 97.0% | 98.2% |
| | XRPD | No change | No change | No change |
| 40° C., 75% RH, open container | HPLC | 95.2% | 90.9% | 95.6% |
| | XRPD | No change | No change | No change |
| 60° C., tight container | HPLC | 98.5% | 82.3% | 95.5% |
| | XRPD | No change | No change | No change |
| 25° C., 84% RH, open container, 2 days | XRPD | No change | No change | No change |

Example 9. Solubility of Compound I Free Base Pattern 1, Compound I Monofumarate Pattern 1 and Compound I Hemifumarate Pattern 1

About 4 mg of Compound I Pattern 1 was added into 2 mL of buffer solution. For Compound I hemifumarate Pattern 1 and Compound I monofumarate Pattern 1, about 4 mg was added into 1.8 mL and 1.6 mL buffer solution, respectively. pH value was adjusted in simulated vaginal fluid with 0.2N NaOH. After stirring at 37° C. for 0.5 hour and 2 hours, clear solution was obtained for all the three candidates.

TABLE 11

Solubility of Compound I free base Pattern 1, Compound I monofumarate Pattern 1 and Compound I hemifumarate Pattern 1

| | Compound I free base Pattern 1 | | Compound I Hemifumarate Pattern 1 | | Compound I Monofumarate Pattern 1 | |
|---|---|---|---|---|---|---|
| Media | 0.5 hrs | 2 hrs (pH) | 0.5 hrs | 2 hrs (pH) | 0.5 hrs | 2 hrs (pH) |
| pH 3.0 100 mM citrate buffer | >2 | >2 (2.98) | >2 | >2 (3.07) | >2 | >2 (3.05) |
| pH 4.5 50 mM acetate buffer | >2 | >2 (4.50) | >2 | >2 (4.45) | >2 | >2 (4.36) |
| pH 6.8 50 mM phosphate buffer | >2 | >2 (6.81) | >2 | >2 (6.68) | >2 | >2 (6.49) |
| Water | >2 | >2 (7.55) | >2 | >2 (3.38) | >2 | >2 (3.11) |
| Simulated vaginal fluid (pH adjusted with 0.2N NaOH) | >2 | >2 (5.53) | >2 | >2 (5.30) | >2 | >2 (5.39) |

Solubility was tested in five media, pH 3.0 citrate buffer, pH 4.5 acetate buffer, pH 6.8 phosphate buffer, water, simulated vaginal fluid (pH 4.2) at 37° C. for 0.5 h and 2 h. All the three candidates are highly soluble in the media (>2 mg/mL).

Example 10: Hygroscopicity of Compound I Free Base Pattern 1, Compound I Hemifumarate Pattern 1, and Compound I Monofumarate Pattern 1

Hygroscopicity was investigated by DVS at 25° C., using the following method:

Method: 40-0-95-0-40% RH, dm/dt=0.002

The results are presented in Table 12 and in FIGS. 29 to 34.

TABLE 12

Hygroscopicity of Compound I free base Pattern 1, Compound I hemifumarate Pattern 1, and Compound I monofumarate Pattern 1

| % RH | Compound I free base Pattern 1 | | | | Compound I Hemifumarate Pattern 1 | | | | Compound I Monofumarate Pattern 1 | | | |
|---|---|---|---|---|---|---|---|---|---|---|---|---|
| | D. (%) Cycle 1 | S. (%) Cycle 1 | D. (%) Cycle 2 | S. (%) Cycle 2 | D. (%) Cycle 1 | S. (%) Cycle 1 | D. (%) Cycle 2 | S. (%) Cycle 2 | D. (%) Cycle 1 | S. (%) Cycle 1 | D. (%) Cycle 2 | S. (%) Cycle 2 |
| 0% | 0.00 | 0.00 | 0.19 | 0.19 | 0.13 | 0.13 | 0.00 | 0.00 | 0.49 | 0.49 | 0.09 | 0.09 |
| 10% | 0.11 | 0.08 | 0.37 | 0.22 | 0.36 | 0.34 | 0.23 | 0.20 | 0.62 | 0.56 | 0.15 | 0.18 |
| 20% | 0.23 | 0.17 | 0.57 | 0.30 | 0.56 | 0.53 | 0.44 | 0.40 | 0.71 | 0.66 | 0.35 | 0.27 |
| 30% | 0.47 | 0.28 | 0.83 | 0.44 | 0.79 | 0.73 | 0.68 | 0.61 | 0.81 | 0.76 | 0.47 | 0.37 |
| 40% | 0.60 | 0.41 | 1.09 | 0.62 | 1.04 | 0.96 | 0.94 | 0.87 | 0.93 | 0.86 | 0.56 | 0.47 |
| 50% | | 0.61 | 1.48 | | | 1.22 | 1.26 | | | 0.71 | 0.67 | |
| 60% | | 0.85 | 1.96 | | | 1.57 | 1.68 | | | 0.85 | 0.85 | |
| 70% | | 1.14 | 2.78 | | | 2.04 | 2.25 | | | 1.02 | 1.04 | |
| 80% | | 1.64 | 4.33 | | | 2.80 | 3.14 | | | 1.27 | 1.30 | |
| 90% | | 4.27 | 9.10 | | | 4.54 | 4.84 | | | 1.78 | 1.84 | |
| 95% | | 14.32 | 14.32 | | | 6.87 | 6.87 | | | 2.89 | 2.89 | |
| XRPD after DVS test | No form change, FIG. 30 | | | | No form change, FIG. 32 | | | | No form change, FIG. 34 | | | |

Note:
D.—Desorption; S.—Sorption

Hygroscopicity was investigated by DVS at 25° C. All three Patterns are moderately hygroscopic. Compound I Pattern 1 shows about 4.3% water uptake up to 90% RH, but absorbs about 14.3% water in 95% RH. For Compound I monofumarate Pattern 1 and Compound I hemifumarate Pattern 1, they show about 2.9% and 6.9% water uptake in up to 95% RH. There is no form change after the DVS tests.

Example 11: Large Scale Preparation of Mono-Fumarate Pattern 1

Figure 35:
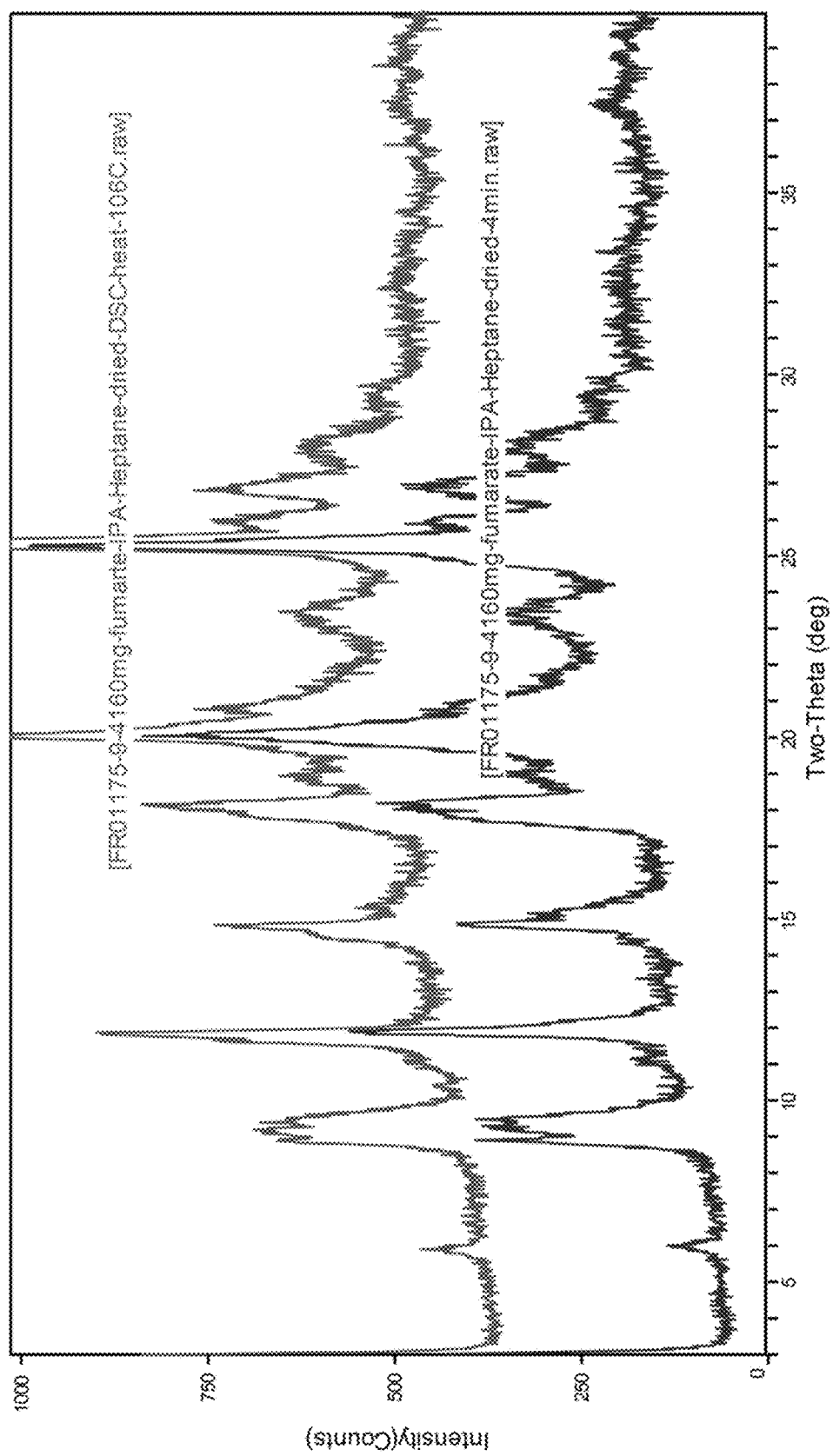
FIG. 35 is a comparison of XRPD diffractograms of Compound I monofumarate Pattern 1 obtained in Example 11 (large scale) before and after heating to 106° C.
Figure 36A:
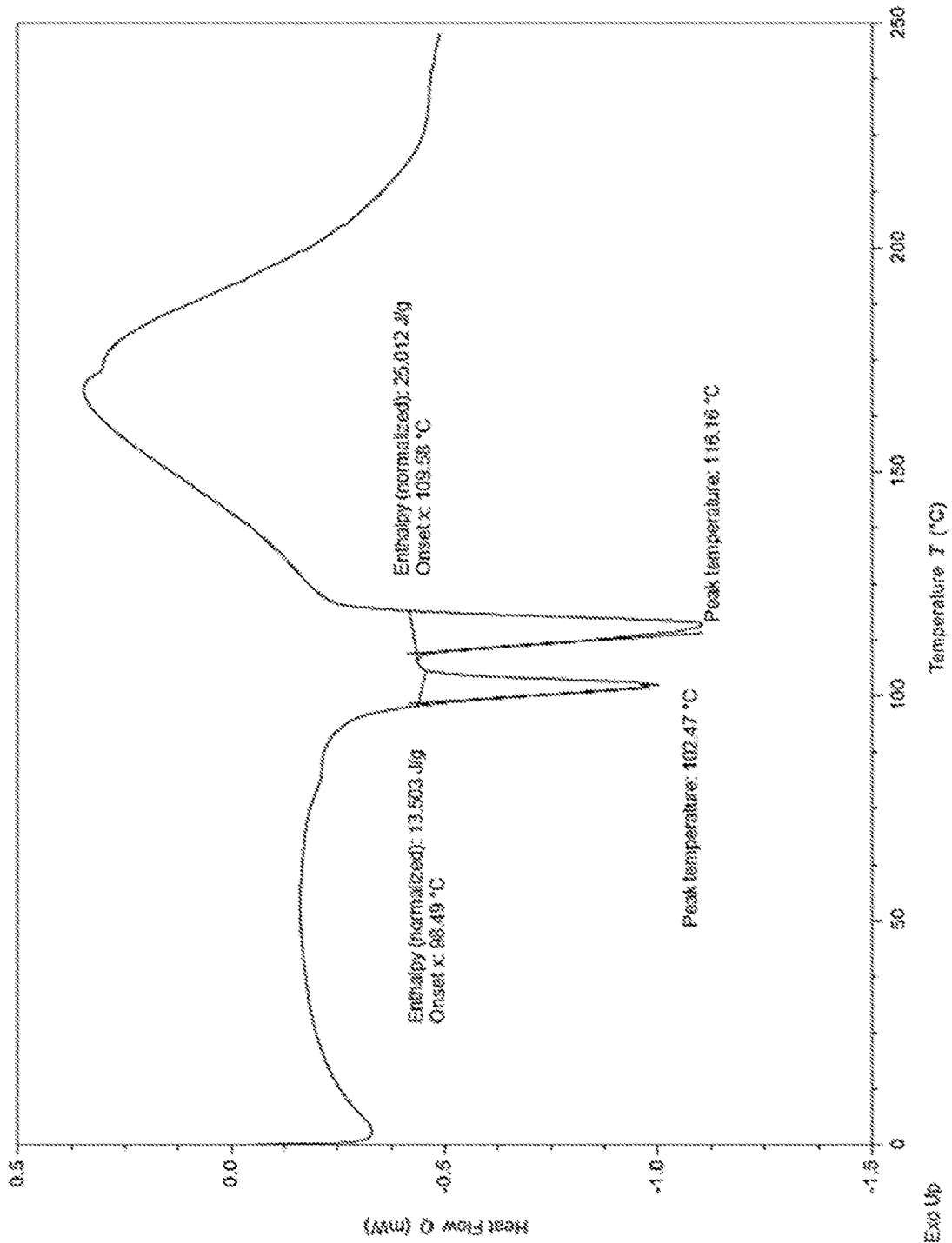
FIG. 36A is a DSC thermogram of Compound I monofumarate Pattern 1 (Example 11), recorded at heating rate of 10° C./min.
Figure 36B:
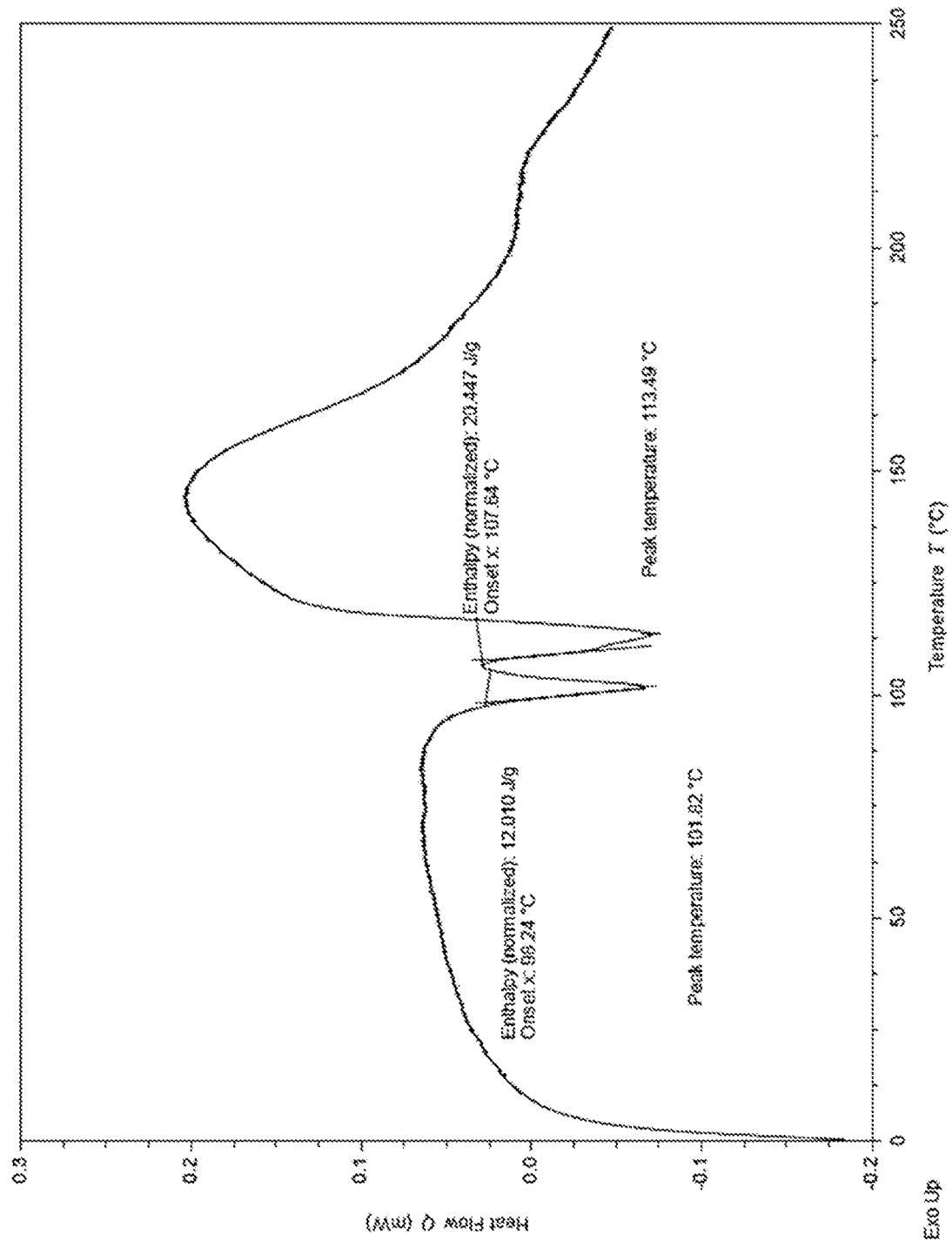
FIG. 36B is a DSC thermogram of Compound I monofumarate Pattern 1 (large scale preparation, Example 11), recorded at heating rate of 2° C./min.
Figure 36C:
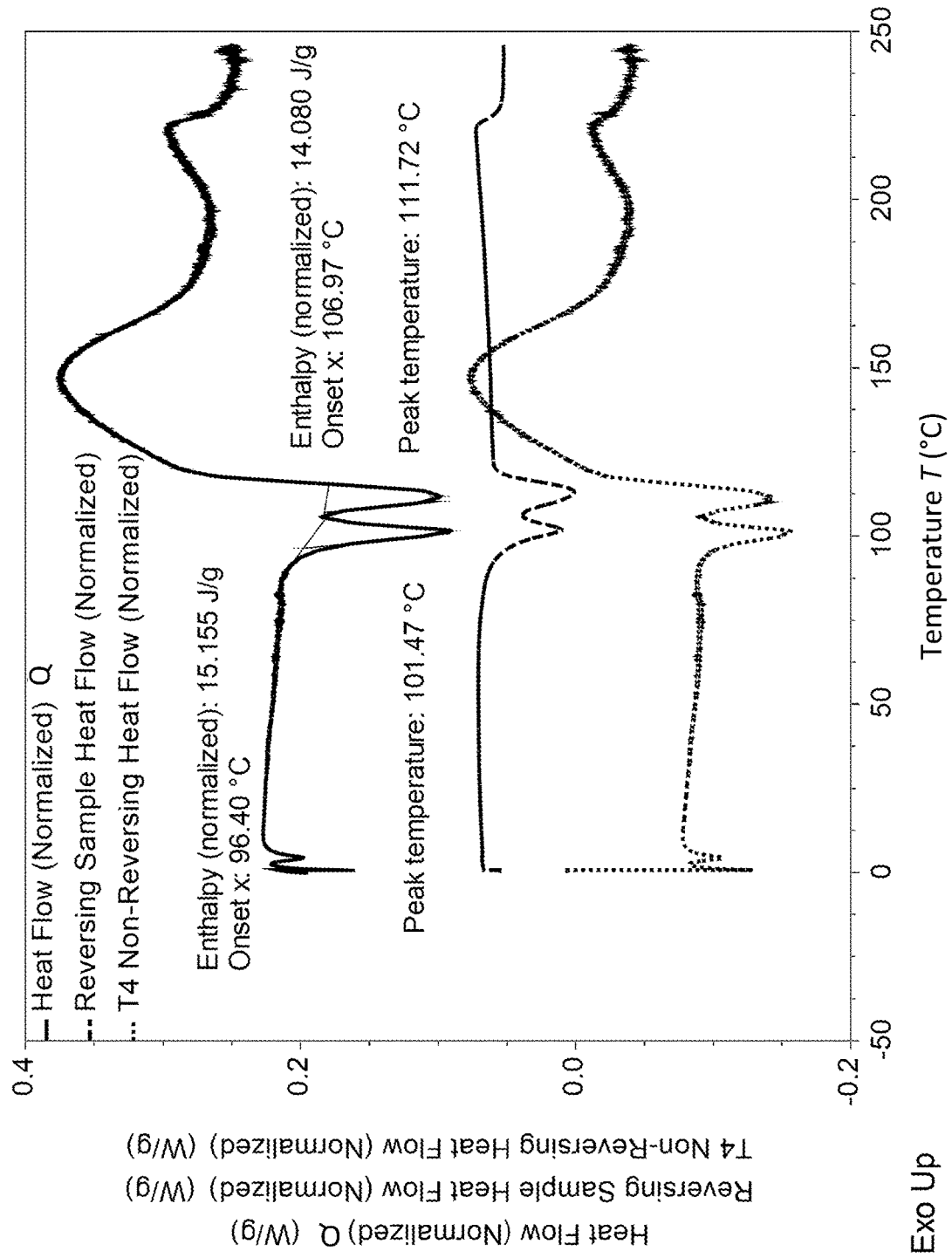
FIG. 36C is a DSC thermogram of Compound I monofumarate Pattern 1 (obtained in Example 11).
Figure 37:
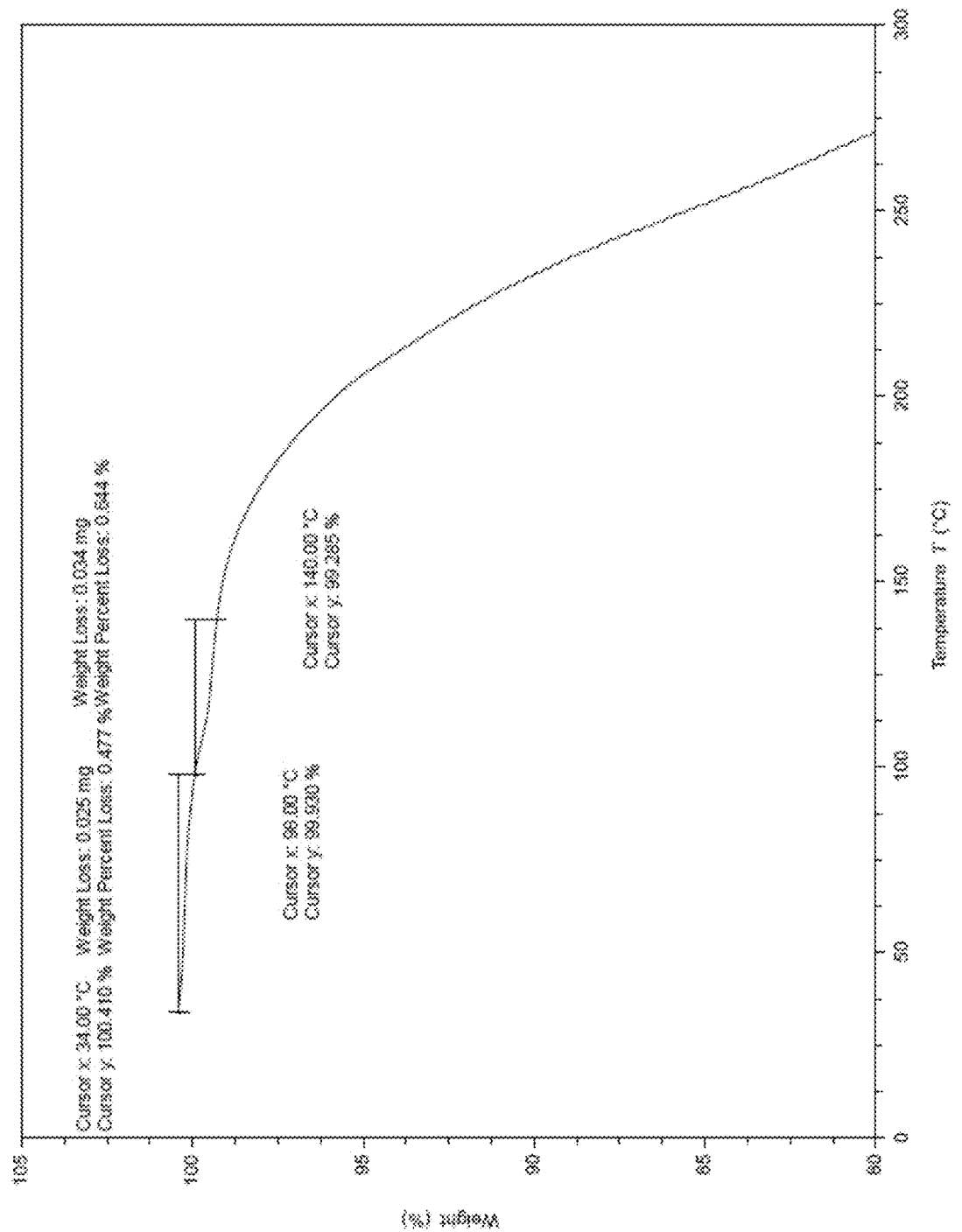
FIG. 37 is TGA thermogram of Compound I monofumarate Pattern 1 (obtained in Example 11).

About 4.16 g of Compound I free base was dissolved in 11 mL of IPA. Then, 1.0 eq. of fumaric acid was added to the yellow clear solution under stirring at 50° C. After about 1 hour, some solids precipitated out. Then, 10 mg seeds of mono-fumarate (from the above 'Small scale preparation') were added. The mixture was stirred at 50° C. for about 1.5 hours and cooled to 25° C., then it was stirred at 25° C. for about 10 min. Then, 40 mL of heptanes was added as antisolvent. Obtained suspension was stirred at 25° C. for about 24 hours, then cooled to 5° C. at a rate of 0.1° C./min and stirred at 5° C. for about 1 day. The solids were collected by filtration and dried in the oven at 40° C. for about 2 hours under vacuum. About 4.1 g of light pink solids were obtained in a yield of 81.2%. XRPD is shown in FIG. 35; DSC at 10° C./min rate is shown in FIG. 36a; DSC at 2° C./min rate is shown in FIG. 36b; mDSC thermogram is shown in FIG. 36c; TGA is shown in FIG. 37.

TABLE 13

Properties of Compound I Monofumarate Pattern 1

| Parameter | Method | Result |
|---|---|---|
| Purity | HPLC | 99.3% |
| X-ray diffraction | XRPD: 3-40° (2 theta) | Pattern 1 with medium crystallinity; After heating to 106° C. by DSC: Pattern 1 with medium crystallinity |
| Melting onset (enthalpy) | DSC: 10° C./min and 2° C./min | Heating rate 10K/min: Onset: 98.5° C. (14 J/g) Onset: 109.6° C. (25 J/g) Heating rate 2K/min: Onset: 98.2° C. (12 J/g) Onset: 107.6° C. (20 J/g) mDSC: Onset: 96.4° C. (15 J/g) Onset: 107.0° C. (14 J/g) |
| Thermogravimetry | TGA: 10° C./min | Weight loss: ~ 0.5% @ 98° C.; ~0.6% from 98° C. to 140° C. |
| Stoichiometry | $^1$H NMR | Free base form/fumaric acid = 1:0.96 |
| Residual solvent | $^1$H NMR (DMSO-$d_6$) | 1.0% (by weight) heptanes and 0.2% (by weight) IPA residue |
| Water content | KF | 1.3% by weight |
| Particle size and morphology | PLM | Irregular particles |

Example 12: Polymorph Screening Study of Compound I Fumarate Salts

The polymorph screening study was performed for fumarate salts of Compound I (mixture of diastereomers). Their polymorphic behaviors were investigated by equilibration, precipitation by addition of antisolvent, slow cooling, fast cooling and slow evaporation experiments.

Approximate Solubility of the Compound I Monofumarate Pattern 1 at 25° C. and 50° C.

About 2 mg of Compound I monofumarate Pattern 1 (Example 11) was weighed to a 2 mL glass vial, and a 20 μL aliquot of each solvent (as shown in Table 14) was added to determine solubility at 25° C. About 10 mg of Compound I monofumarate Pattern 1 (Example 11) was weighed to a 2 mL glass vial and aliquot of 20 μL of each solvent (as shown in Table 14 below) was added to determine solubility at 50° C. Maximum volume of each solvent added was 1 mL. Approximate solubility was determined by visual observation.

TABLE 14

Approximate solubility of Compound I monofumarate Pattern 1 at 25° C. and 50° C.

| | | Solubility (mg/mL) | |
|---|---|---|---|
| Experiment | Solvent | 25° C. | 50° C. |
| 1 | Water | 14-17 | 22-25 |
| 2 | MeOH | >100 | >500 |
| 3 | EtOH | >100 | 250-500 |
| 4 | IPAc | <2 | <10 |
| 5 | Acetone | 50-100 | 125-167 |
| 6 | MTBE | <2 | <10 |
| 7 | THF | >100 | 250-500 |
| 8 | ACN | 20-25 | 20-33 |
| 9 | DCM | <2 | <10 |
| 10 | EA | <2 | <10 |
| 11 | MEK | 20-25 | 22-25 |
| 12 | Toluene | <2 | <10 |
| 13 | IPA | 50-100 | 71-84 |
| 14 | Heptanes | <2 | <10 |

Equilibration with Solvents at 25° C. for 2 Weeks and 3 Weeks

About 30 mg of Compound I monofumarate Pattern 1 (obtained in Example 11) was equilibrated in suitable amount of solvent at 25° C. for 2 weeks and 3 weeks with a stirring plate. Obtained suspension was filtered. The solid part (wet cake) was investigated by XRPD. When differences were observed, additional studies were performed (e.g., NMR, DSC, TGA, HPLC, and PLM). The results are presented in Tables 15-30 and in FIGS. 38-60.

TABLE 15

Results of equilibration with water for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ1 (water) | Pattern D | DSC, onset (enthalpy): 41.4° C. (67 J/g); 72.1° C. (29 J/g) TGA, weight loss: ~0.6% at 41° C.; ~8.5% at 41-178° C. | Pattern D | DSC, onset (enthalpy): 48.8° C. (18 J/g); 89.0° C. (54 J/g) TGA, weight loss: ~2.2% at 48° C.; ~7.8% at 48-88° C.; ~7.3% at 88-194° C. |

Figure 38:
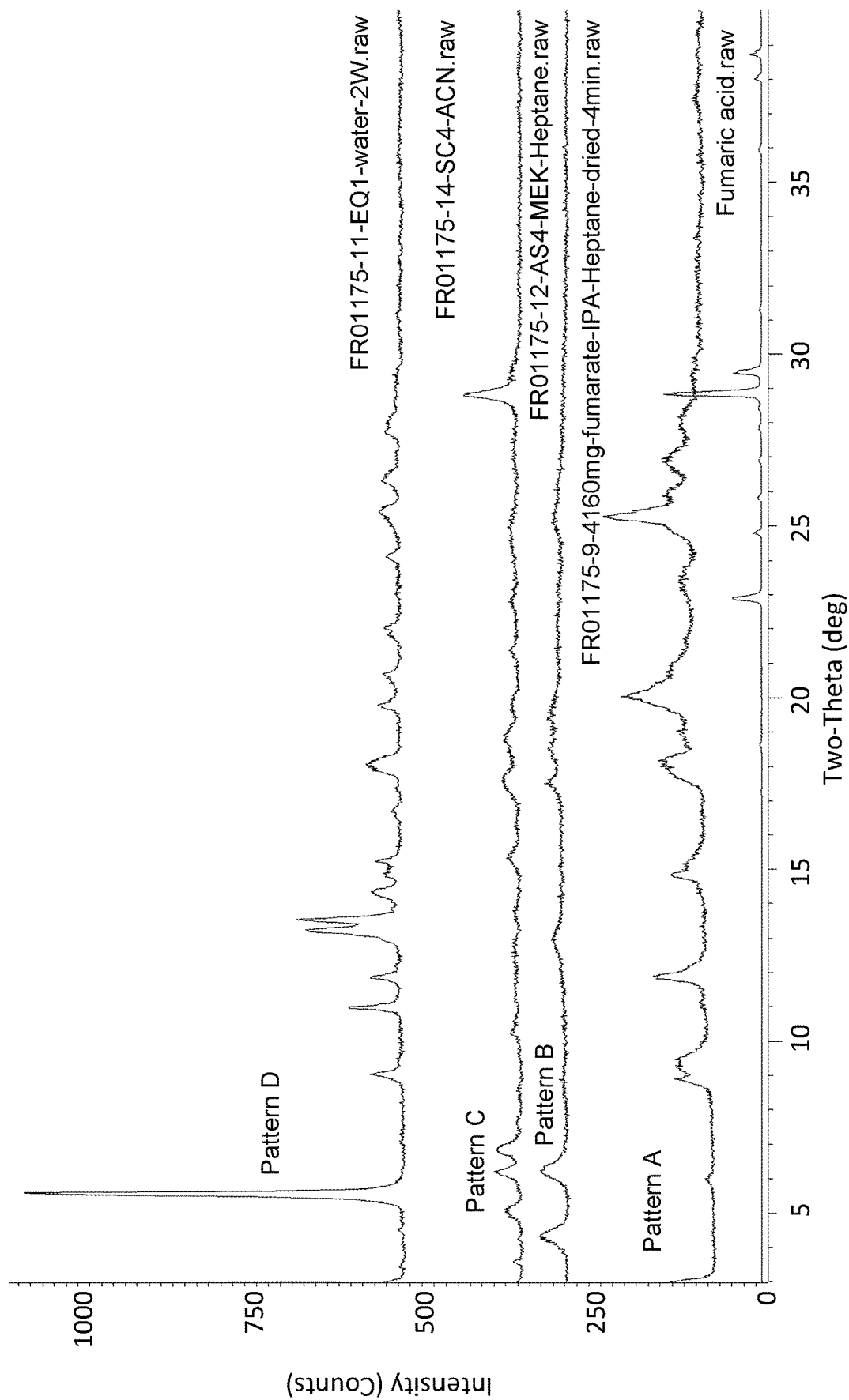
FIG. 38 is a comparison of XRPD diffractograms of Compound I mono-fumarate Pattern 1, hemi-fumarate Pattern 2, hemi-fumarate Pattern 3, Pattern 4 obtained from equilibration experiment in water at 25° C. for 2 weeks and fumaric acid pattern (obtained in Example 12).
Figure 39:
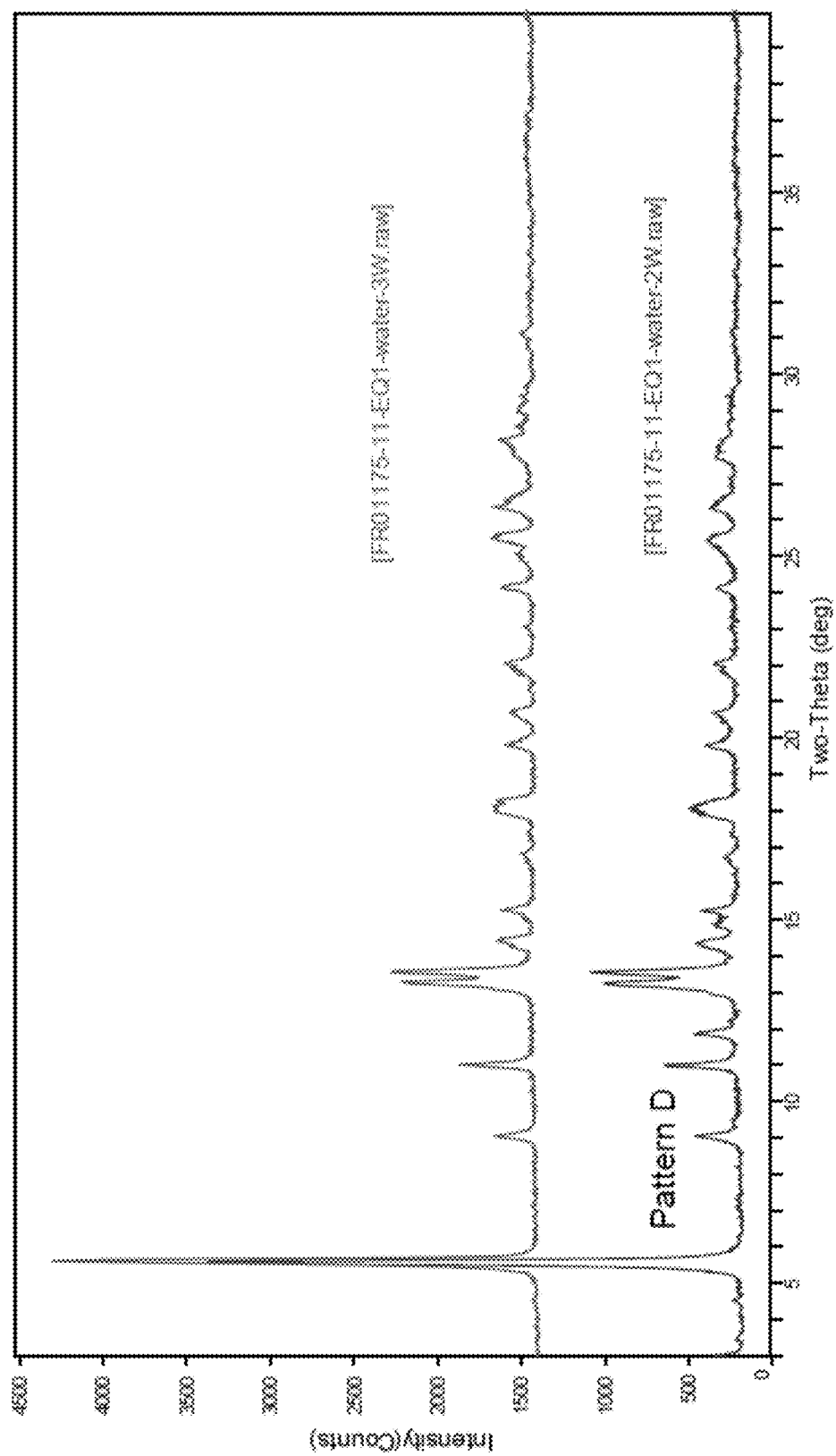
FIG. 39 is a comparison of XRPD diffractograms of Compound I Pattern 4 obtained from equilibration experiment in water at 25° C. for 2 and 3 weeks (obtained in Example 12).
Figure 40:
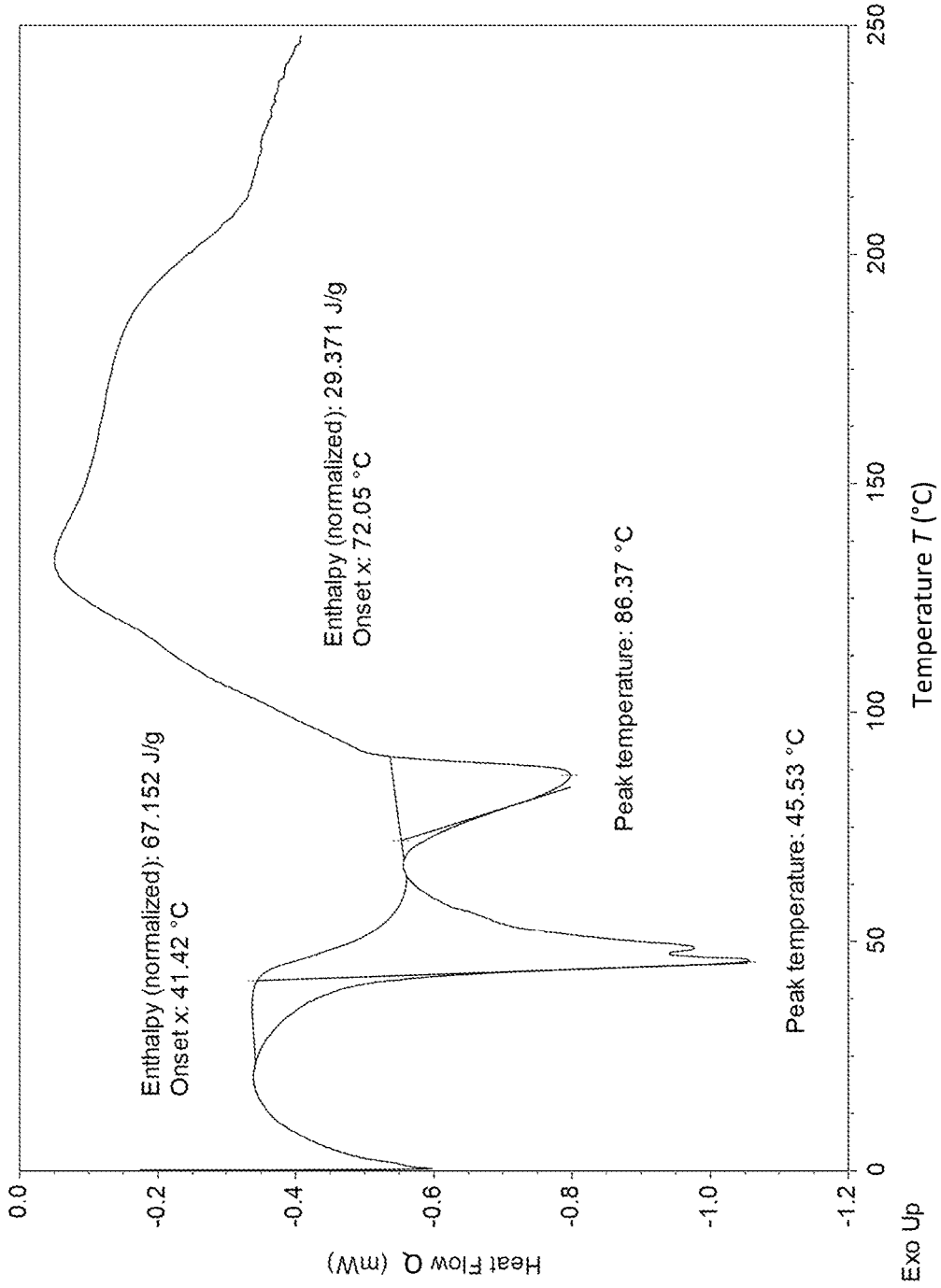
FIG. 40 is a DSC thermogram of Compound I Pattern 4 obtained from equilibration experiment in water at 25° C. for 2 weeks (obtained in Example 12).
Figure 41:
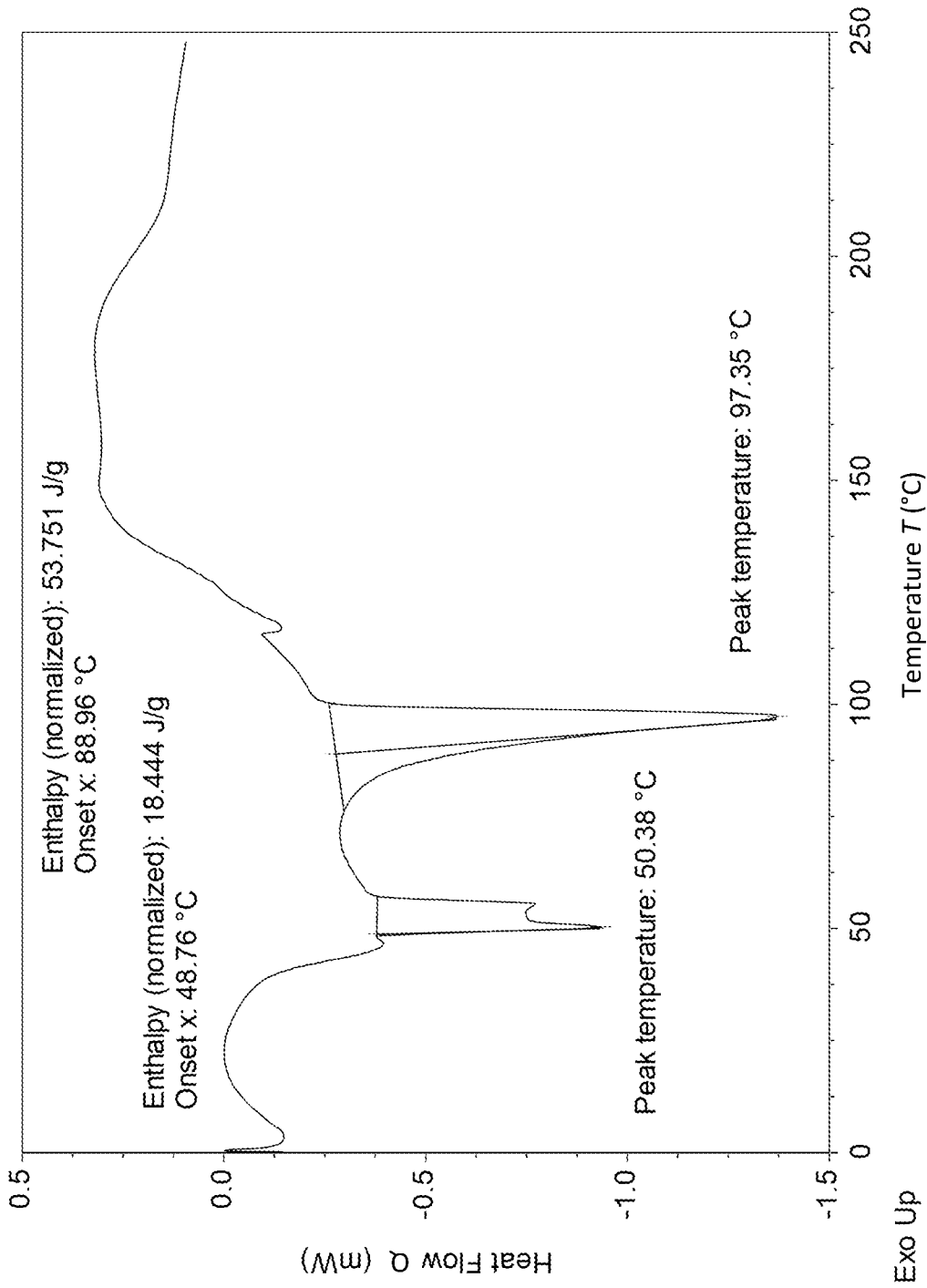
FIG. 41 is a DSC thermogram of Compound I Pattern 4 obtained from equilibration experiment in water at 25° C. for 3 weeks (obtained in Example 12).
Figure 42:
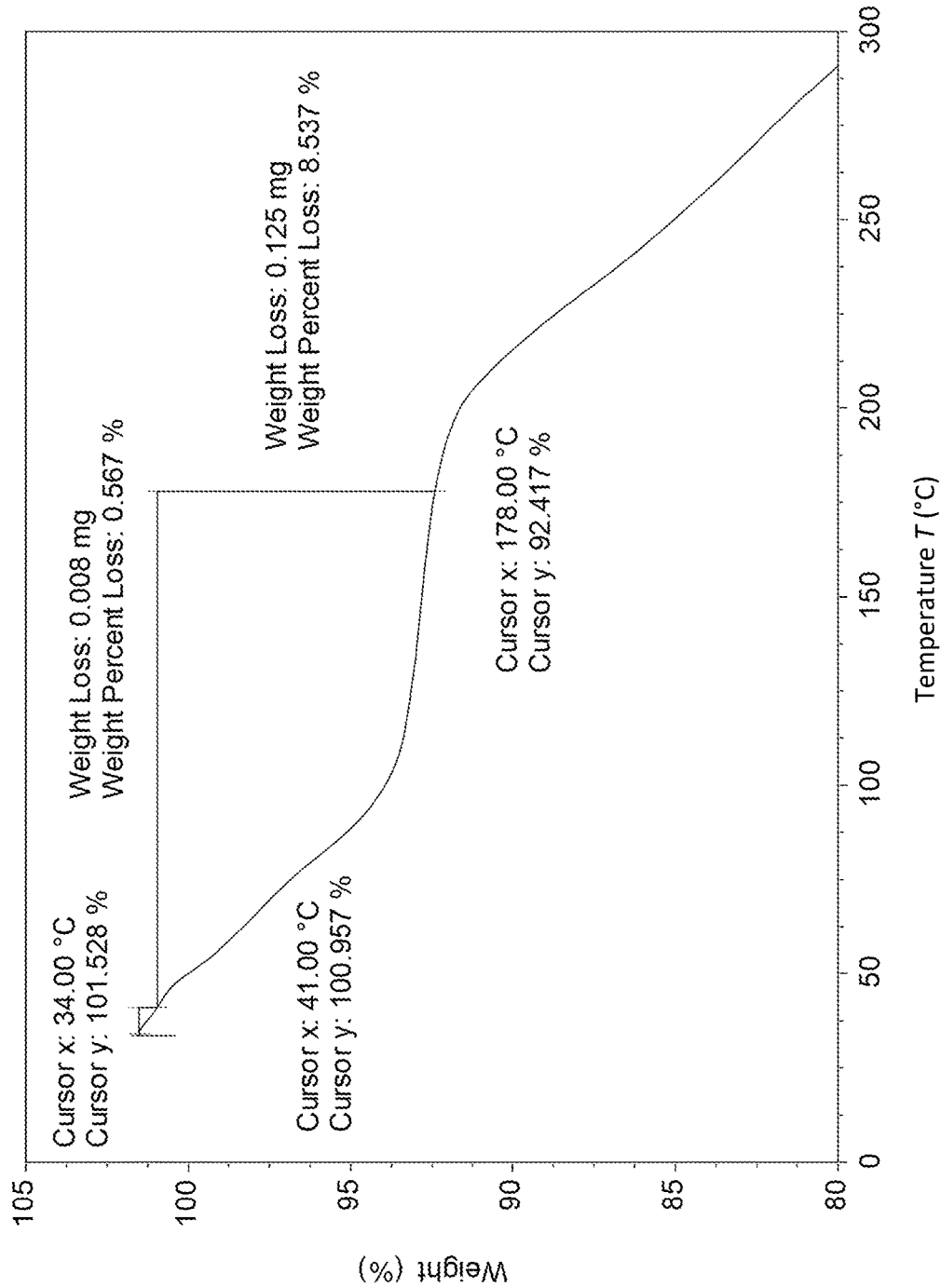
FIG. 42 is a TGA thermogram of Compound I Pattern 4 obtained from equilibration experiment in water at 25° C. for 2 weeks (obtained in Example 12).
Figure 43:
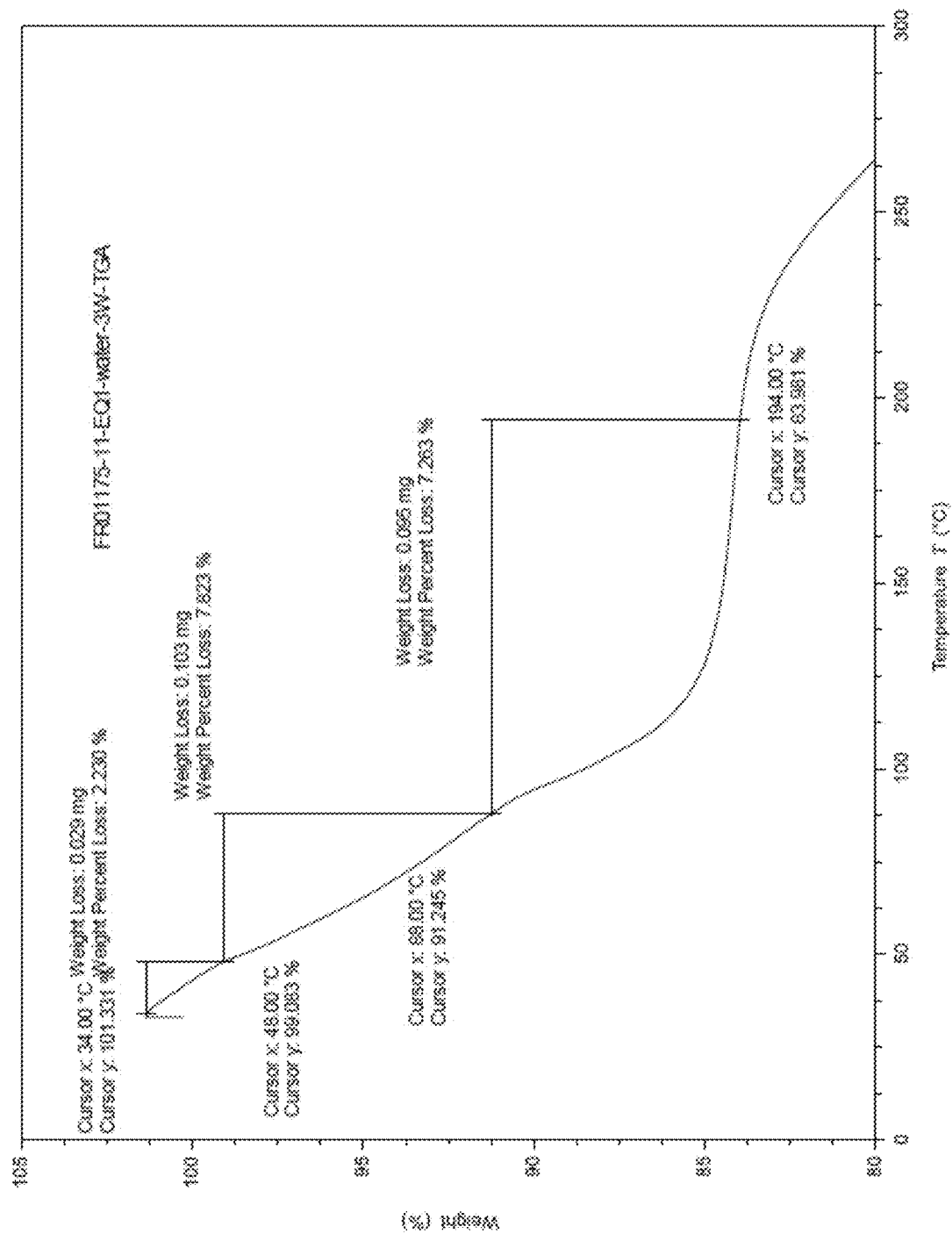
FIG. 43 is a TGA thermogram of Compound I Pattern 4 obtained from equilibration experiment in water at 25° C. for 3 weeks (obtained in Example 12).

For Pattern D, XRPD diffractograms are shown in FIG. 38 and FIG. 39; DSC thermograms are shown in FIG. 40 and FIG. 41; TGA thermograms are shown in FIG. 42 and FIG. 43.

TABLE 16

Results of equilibration with acetonitrile for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ2 (ACN) | Pattern C, medium crystallinity + fumaric acid | Salt ratio = 1:0.91; Residual solvent: 2.2% ACN (by weight); DSC, onset (enthalpy): 75.0° C. (92 J/g); 103.7° C. (13 J/g) | Pattern C, medium crystallinity + fumaric acid | n/a |

TABLE 16-continued

Results of equilibration with acetonitrile for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| | | TGA, weight loss: ~0.4% at 75° C.; ~1.8% at 75-134° C. HPLC Purity: 99.4% | | |

Note:
Salt ratio is free base form:fumaric acid ratio

Figure 44:
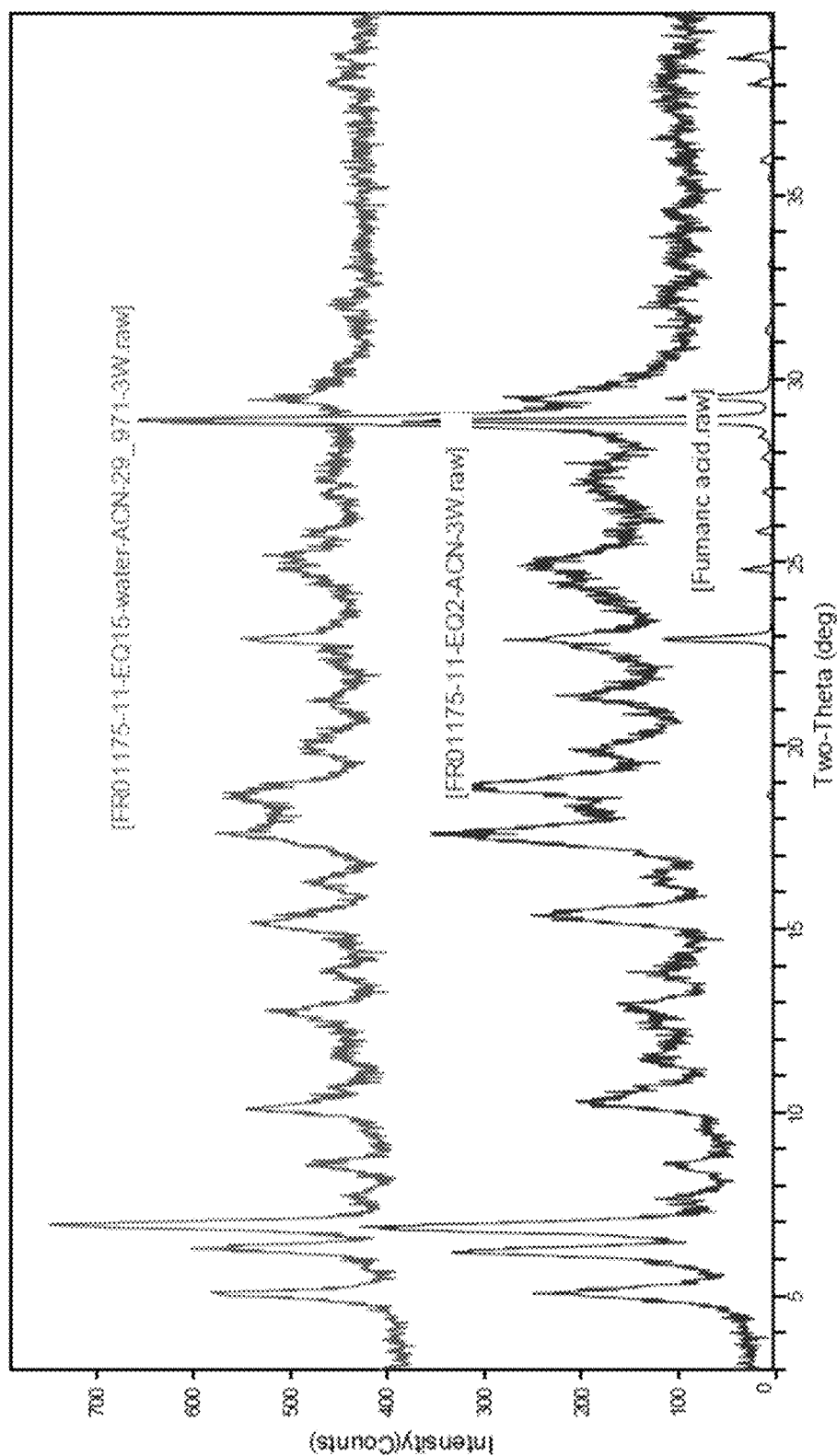
FIG. 44 is a comparison of XRPD diffractograms of fumaric acid pattern and Compound I hemifumarate Pattern C obtained in equilibration experiment EQ2 (in acetonitrile) and EQ15 (in 2.9:97.1 v/v water/acetonitrile) at 25° C. for 3 weeks (obtained in Example 12).
Figure 45:
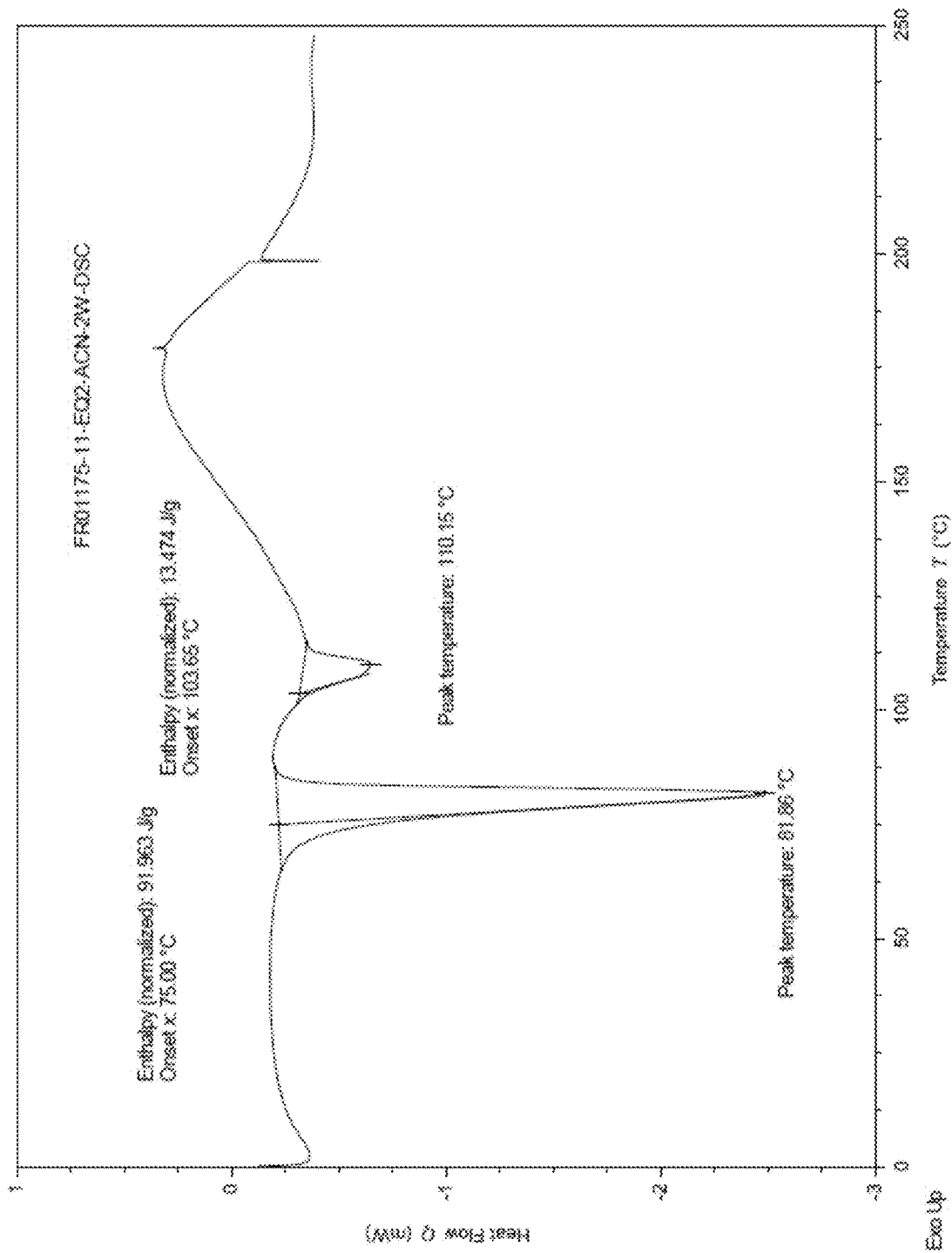
FIG. 45 is a DSC thermogram of Compound I hemifumarate Pattern C obtained from equilibration experiment in acetonitrile at 25° C. for 2 weeks (obtained in Example 12).
Figure 46:
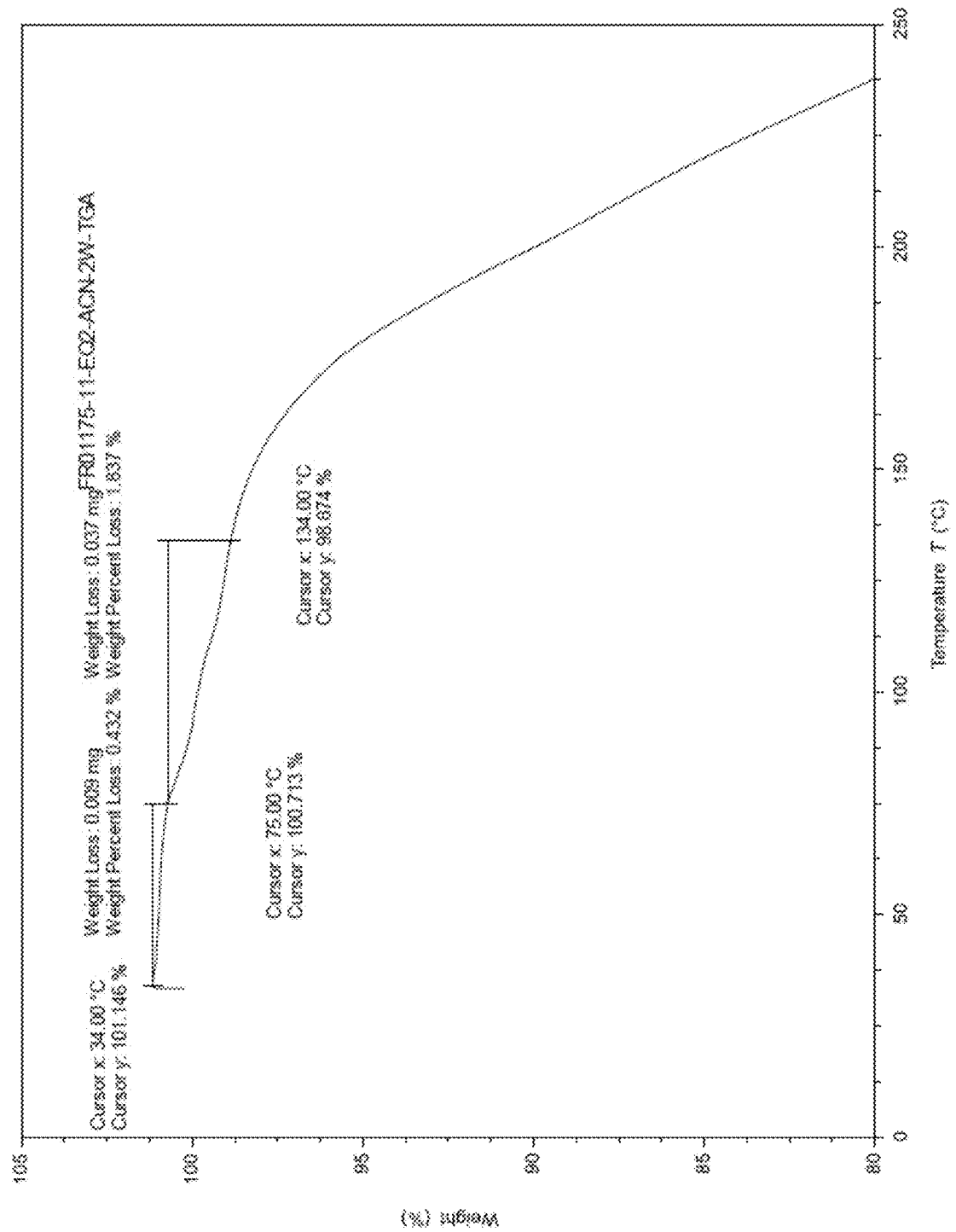
FIG. 46 is a TGA thermogram of Compound I hemifumarate Pattern C obtained from equilibration experiment in acetonitrile at 25° C. for 2 weeks (obtained in Example 12).

For Pattern C, XRPD diffractogram is shown in FIG. 44; DSC thermogram is shown in FIG. 45; and TGA thermogram is shown in FIG. 46.

TABLE 17

Results of equilibration with MEK for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ3 (MEK) | Pattern B, medium crystallinity | Salt ratio = 1:0.52; Residual solvent: 4.6% MEK (by weight) DSC, onset (enthalpy): 77.4° C. (71 J/g); 88.4° C. (18 J/g); TGA, weight loss: ~0.7% at 77° C. ~4.2% at 77-130° C. HPLC Purity: 99.6% | Pattern B, medium crystallinity | n/a |

Note:
Salt ratio is free base form:fumaric acid ratio

Figure 47:
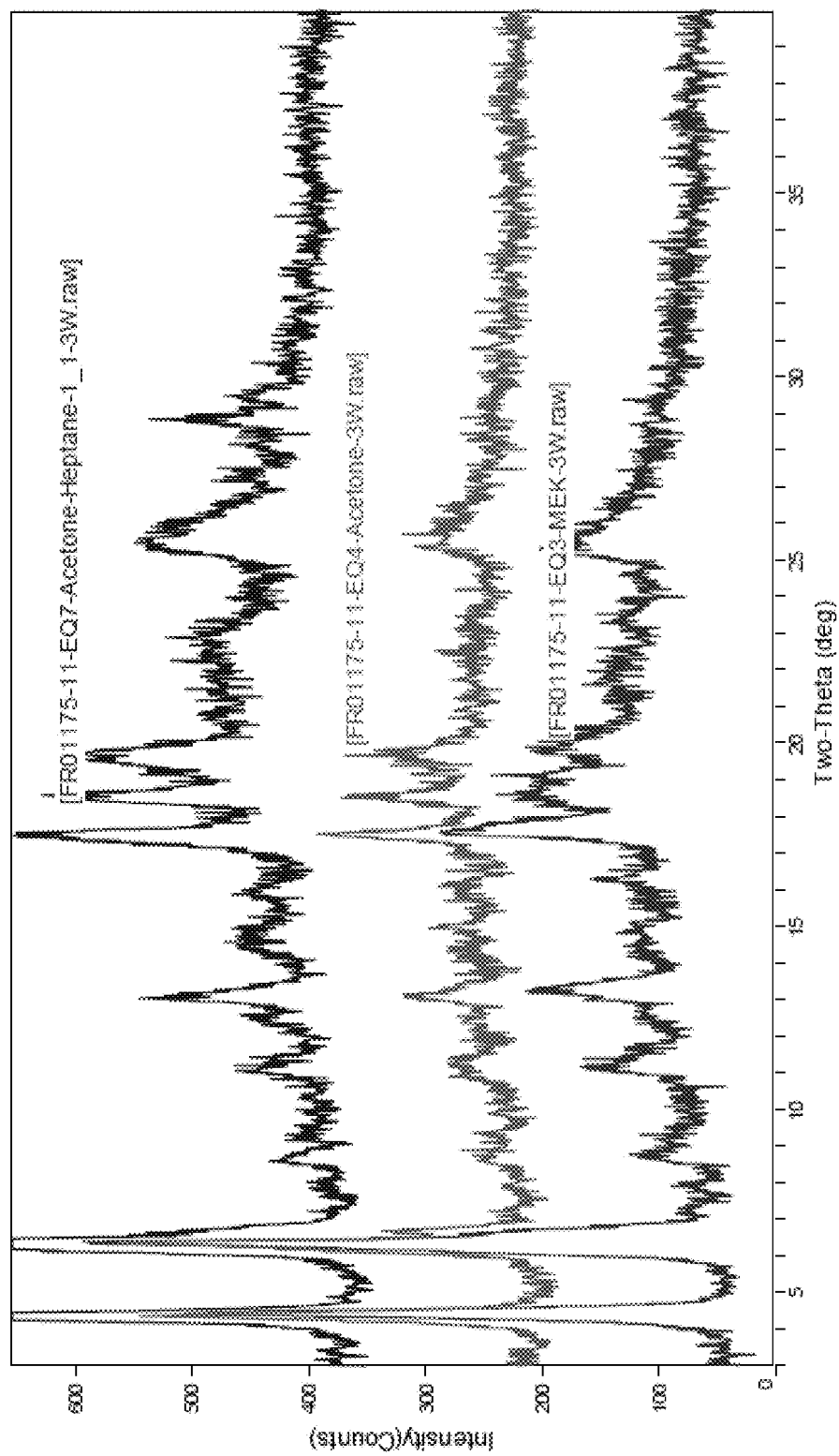
FIG. 47 is a comparison of XRPD diffractograms of Compound I hemi-fumarate Pattern 2 obtained in equilibration experiments EQ3 (in methyl ethyl ketone), EQ4 (in acetone), and EQ7 (in 1:1 v/v acetone/heptane) at 25° C. for 3 weeks (obtained in Example 12).
Figure 48:
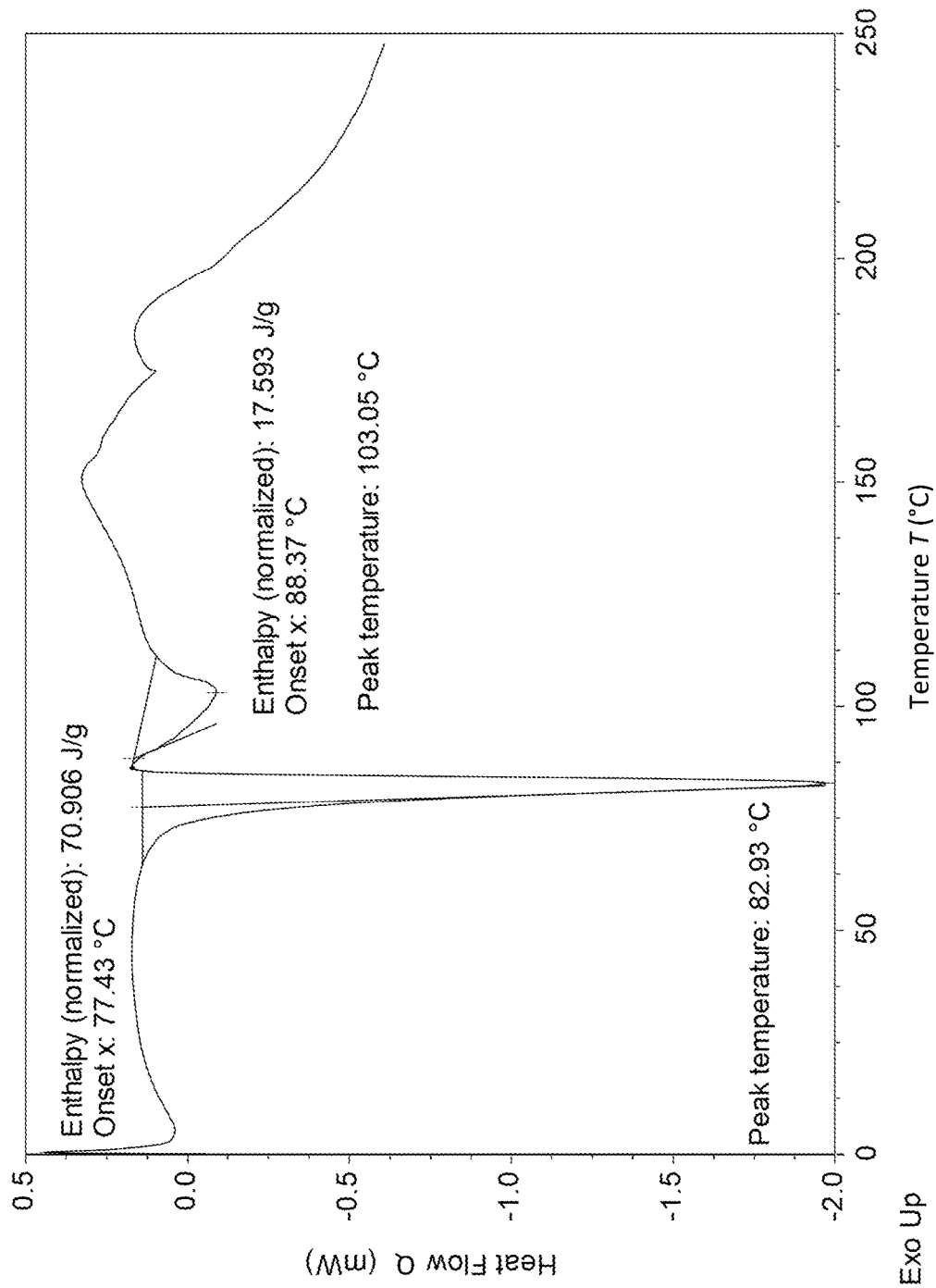
FIG. 48 is a DSC thermogram of Compound I hemifumarate Pattern 2 obtained in equilibration experiment in methyl ethyl ketone at 25° C. for 2 weeks (obtained in Example 12).
Figure 49:
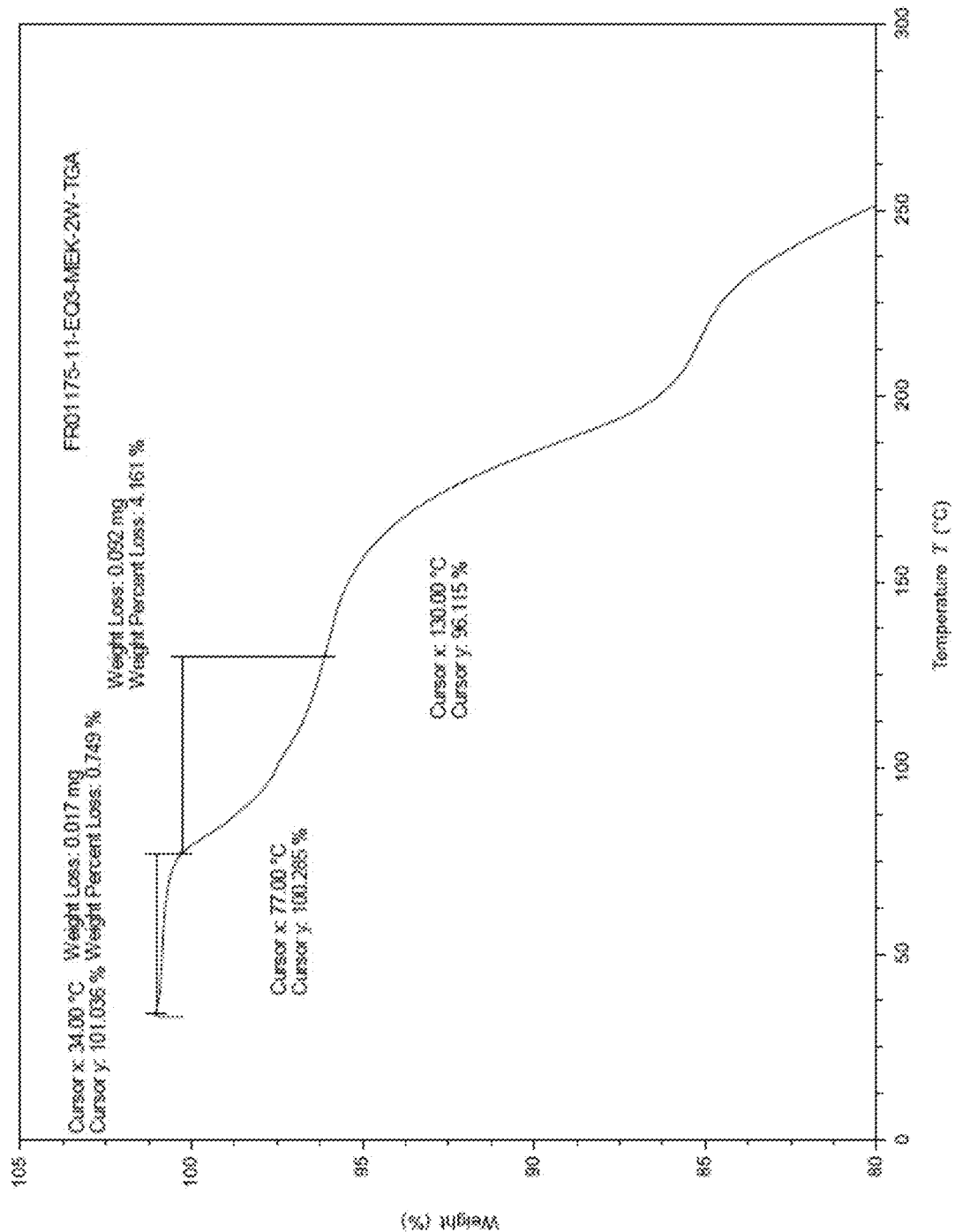
FIG. 49 is a TGA thermogram of Compound I hemifumarate Pattern 3 obtained in equilibration experiment in methyl ethyl ketone at 25° C. for 2 weeks (obtained in Example 12).

For Pattern B, XRPD diffractogram is shown in FIG. 47; DSC thermogram is shown in FIG. 48; and TGA thermogram is shown in FIG. 49.

TABLE 18

Results of equilibration with acetone for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ4 (acetone) | Pattern B, medium crystallinity | n/a | Pattern B, medium crystallinity | n/a |

XRPD diffractogram is shown in FIG. 47 (3 weeks).

TABLE 19

Results of equilibration with isopropanol for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ5 (IPA) | Mixture of Pattern 1 + unknown pattern | Salt ratio = 1:0.62; Residual solvent: 1.7% IPA (by weight) DSC, onset (enthalpy): 85.9° C. (53 J/g); 103.9° C. (12 J/g); | Mixture of Pattern 1 + unknown pattern | n/a |

TABLE 19-continued

Results of equilibration with isopropanol for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| | | TGA, weight loss: ~0.8% at 85° C. ~1.8% at 85-138° C. | | |

Note:
Salt ratio is free base form:fumaric acid ratio

Figure 50:
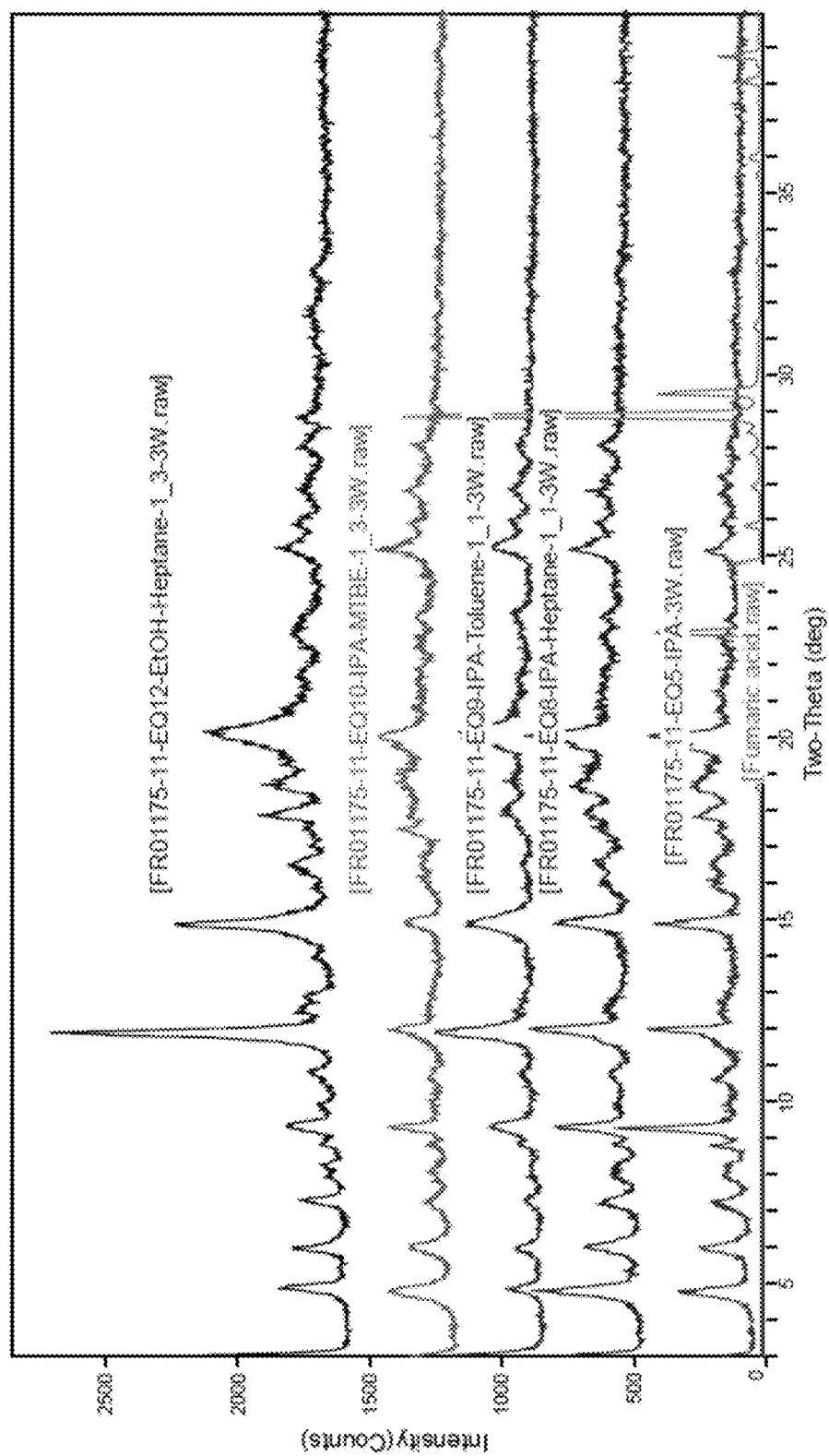
FIG. 50 is a comparison of XRPD diffractograms of fumaric acid and a mixture of Compound I monofumarate Pattern 1 and unknown pattern obtained in equilibration experiments EQ5 (in isopropanol), EQ8 (in 1:1 v/v isopropanol/heptane), EQ9 (in 1:1 v/v isopropanol/toluene), EQ10 (in 1:3 v/v isopropanol/methyl tertbutyl ether), and EQ12 (in 1:3 v/v ethanol/heptanes) at 25° C. for 3 weeks (obtained in Example 12).
Figure 51:
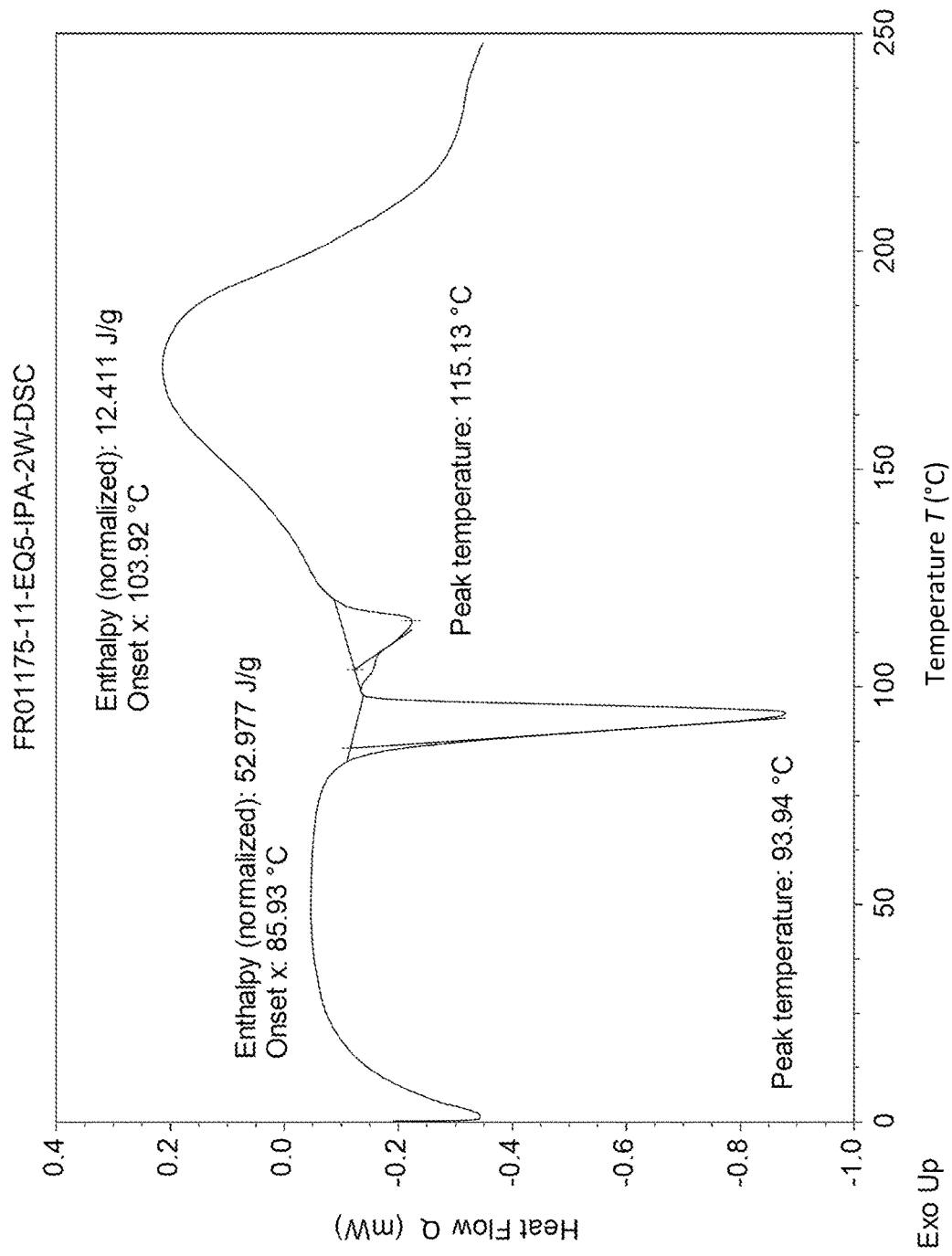
FIG. 51 is a DSC thermogram of a mixture of Compound I mono-fumarate Pattern 1 and unknown pattern obtained in equilibration experiment EQ5 in isopropanol at 25° C. for 2 weeks (obtained in Example 12).
Figure 52:
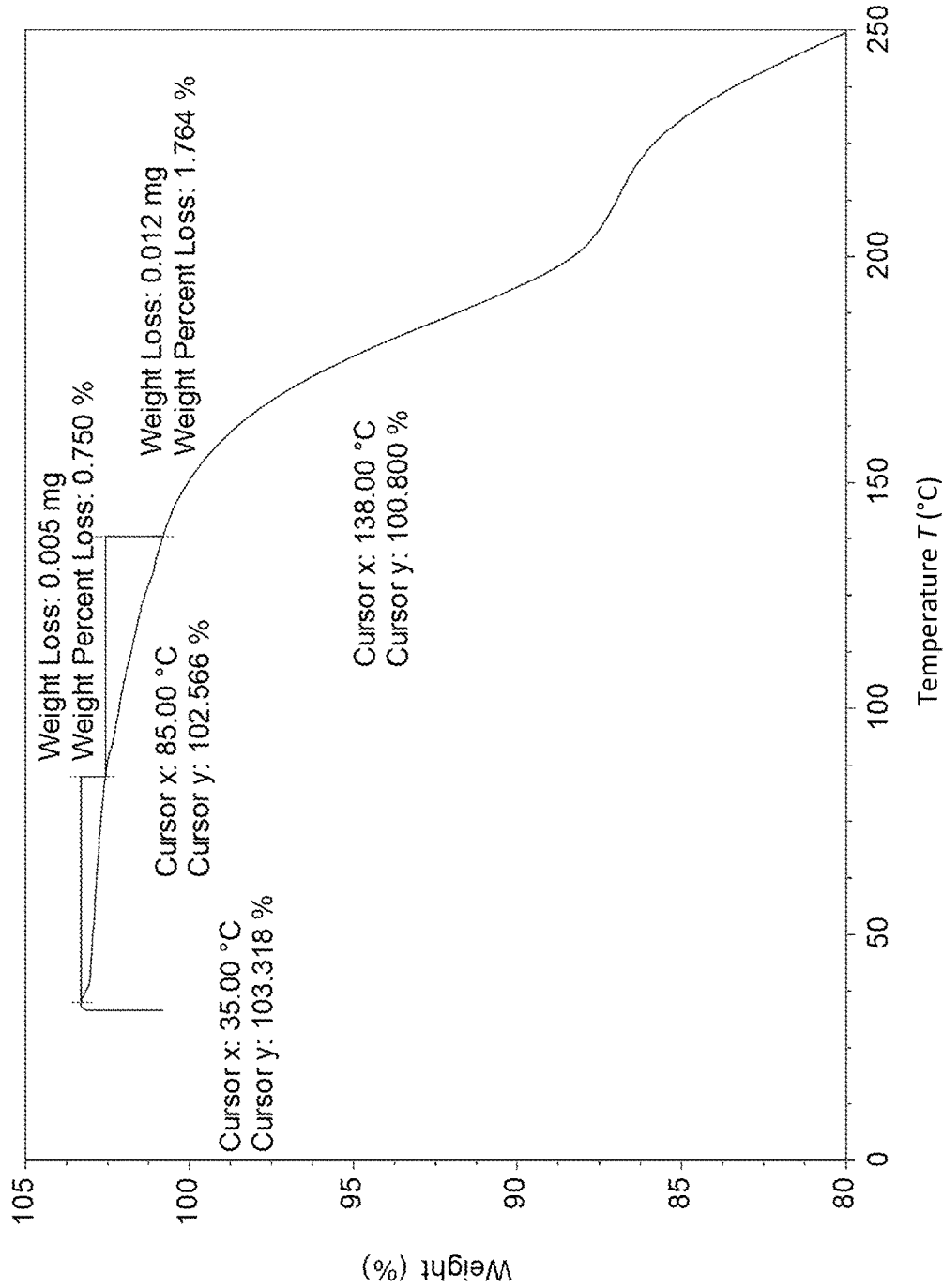
FIG. 52 is a TGA thermogram of a mixture of Compound I mono-fumarate Pattern 1 and unknown pattern obtained in equilibration experiment EQ5 in isopropanol at 25° C. for 2 weeks (obtained in Example 12).

For Pattern 1, XRPD diffractogram is shown in FIG. 50; DSC thermogram is shown in FIG. 51; and TGA thermogram is shown in FIG. 52.

TABLE 20

Results of equilibration with acetone/toluene (1:1 v/v) for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ6 (acetone/ toluene, 1:1 v/v) | Pattern E | Salt ratio = 1:0.69 Residual solvent: 0.9% (by weight) toluene and 0.4% (by weight) acetone DSC, onset (enthalpy): 55.3° C. (18 J/g); 100.5° C. (45 J/g) TGA, weight loss: ~0.8% at 55° C. ~1.8% at 55-100° C. | Pattern E | Salt ratio = 1:0.67 Residual solvent: 0.6% (by weight) acetone DSC, onset (enthalpy): 53.1° C. (33 J/g) 96.5° C. (34 J/g) TGA, weight loss: ~1.0% at 53° C. ~3.6% at 53-96° C. PLM: Irregular particles HPLC Purity: 98.9% |

Figure 53:
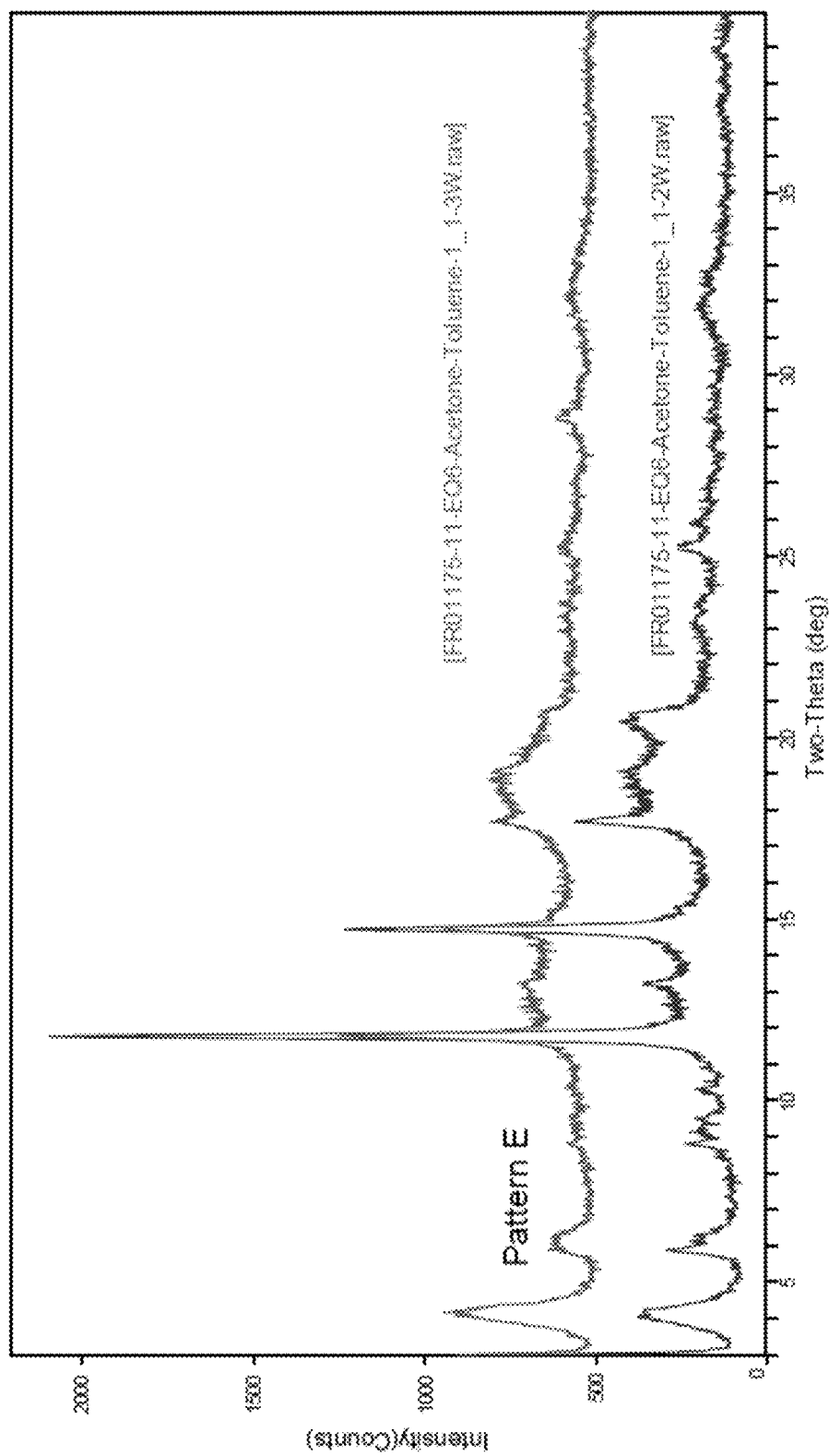
FIG. 53 is a comparison of XRPD diffractograms of Compound I hemi-fumarate Pattern 5 obtained in equilibration experiment EQ6 (in 1:1 v/v acetone/toluene) at 25° C. for 2 and 3 weeks (obtained in Example 12).
Figure 54:
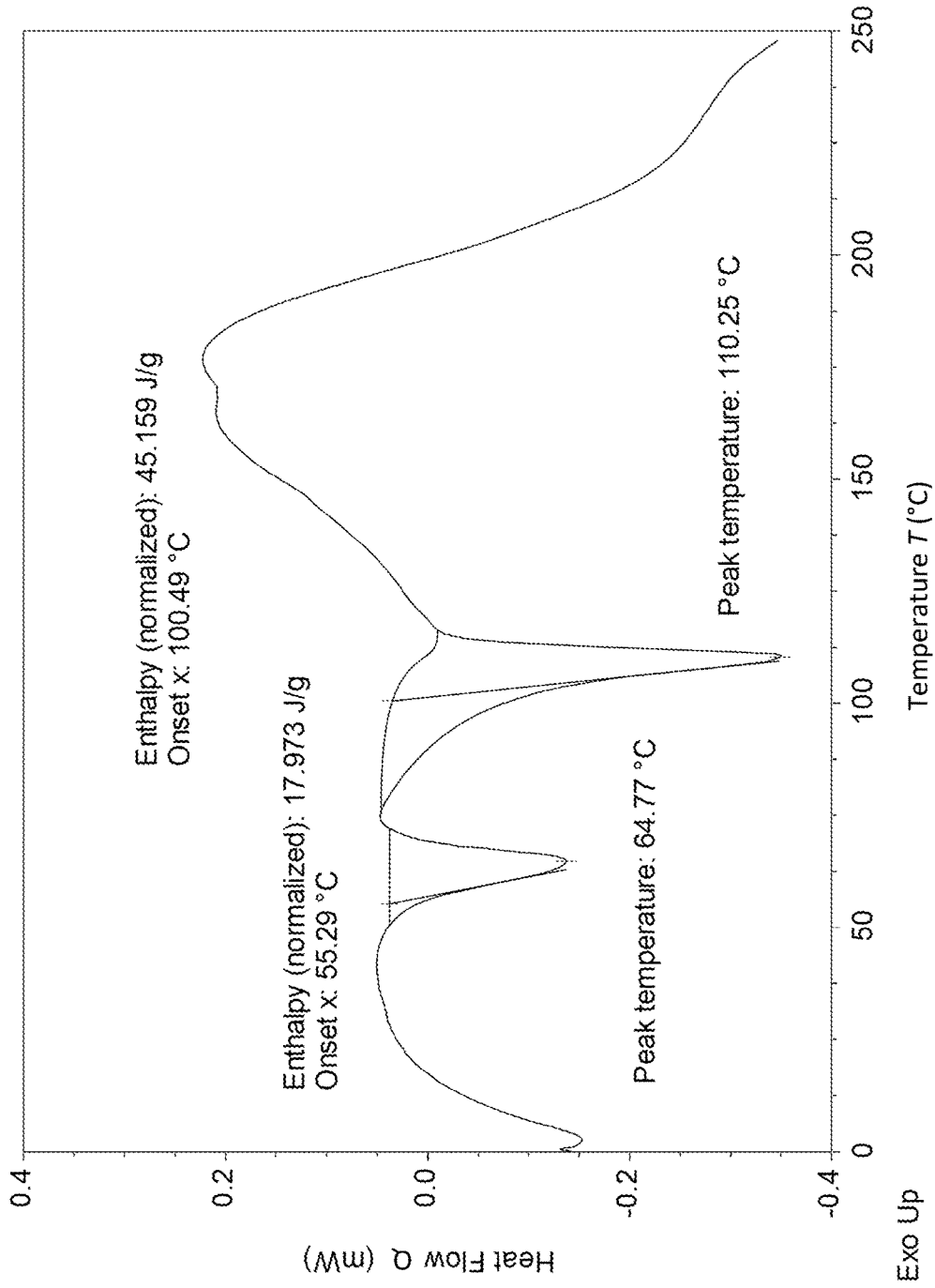
FIG. 54 is a DSC thermogram of Compound I hemifumarate Pattern 5 obtained in equilibration experiment EQ6 (in 1:1 v/v acetone/toluene) at 25° C. for 2 weeks (obtained in Example 12).
Figure 55:
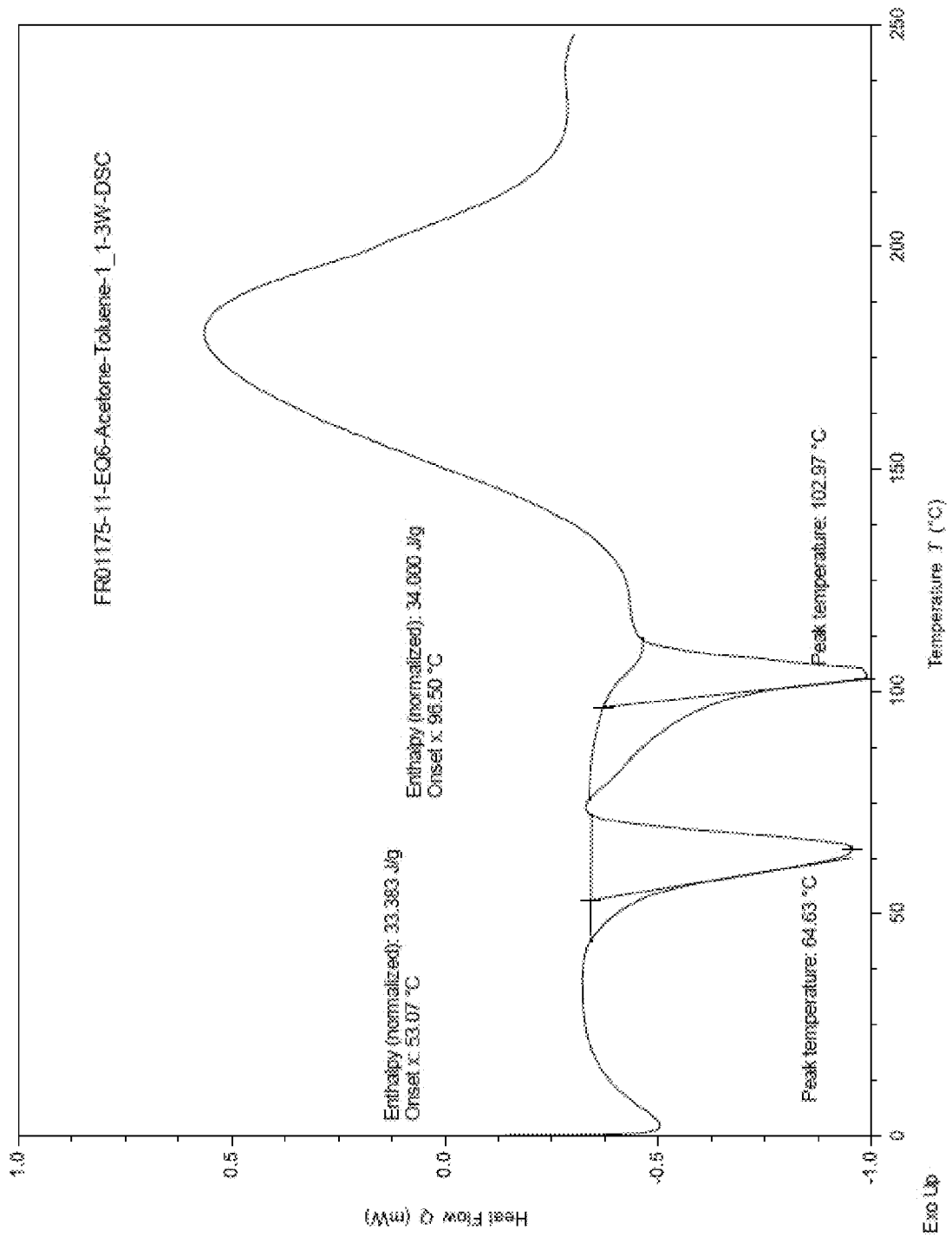
FIG. 55 is a DSC thermogram of Compound I hemifumarate Pattern 5 obtained in equilibration experiment EQ6 (in 1:1 v/v acetone/toluene) at 25° C. for 3 weeks (obtained in Example 12).
Figure 56:
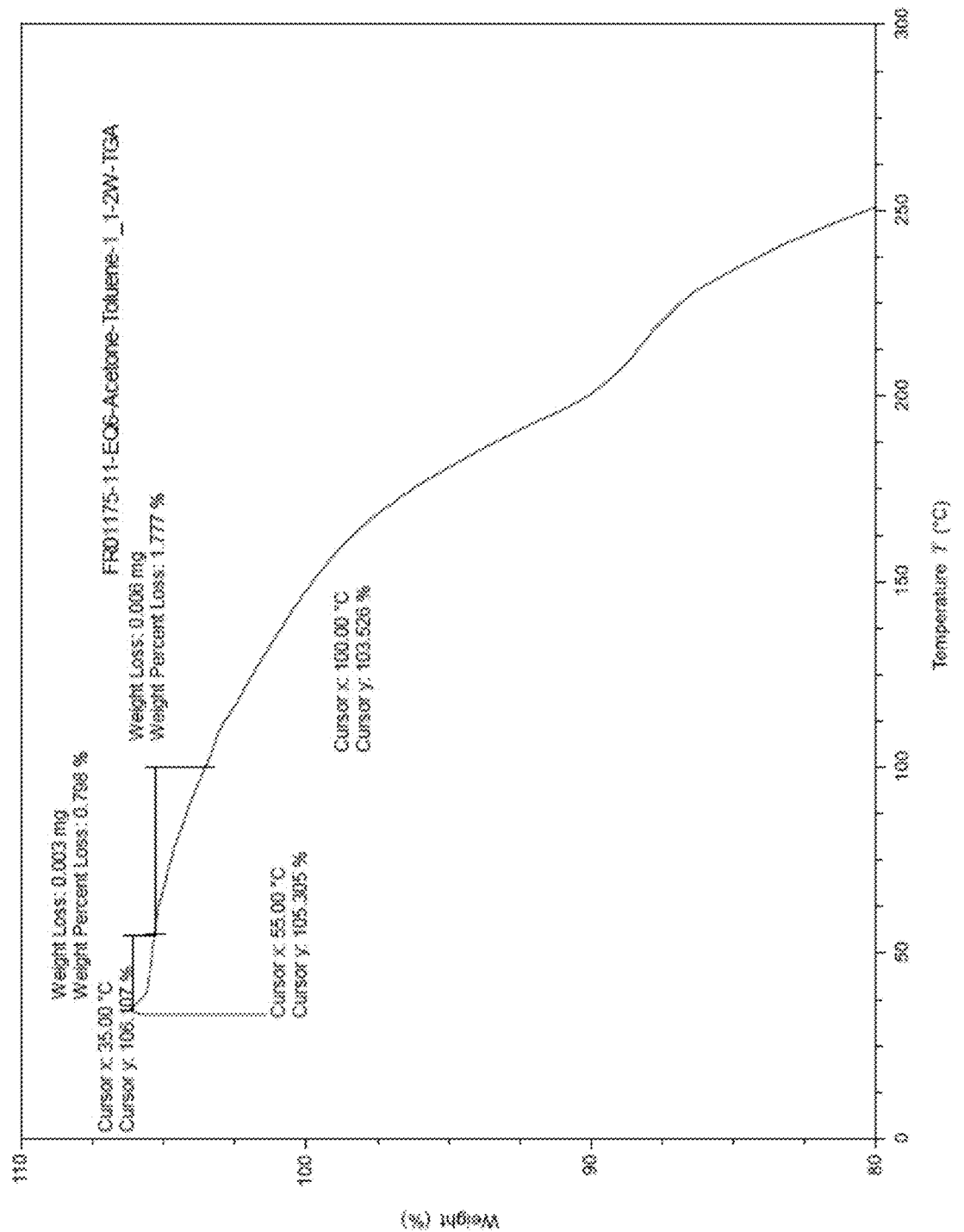
FIG. 56 is a TGA thermogram of Compound I hemifumarate Pattern 5 obtained in equilibration experiment EQ6 (in 1:1 v/v acetone/toluene) at 25° C. for 2 weeks (obtained in Example 12).
Figure 57:
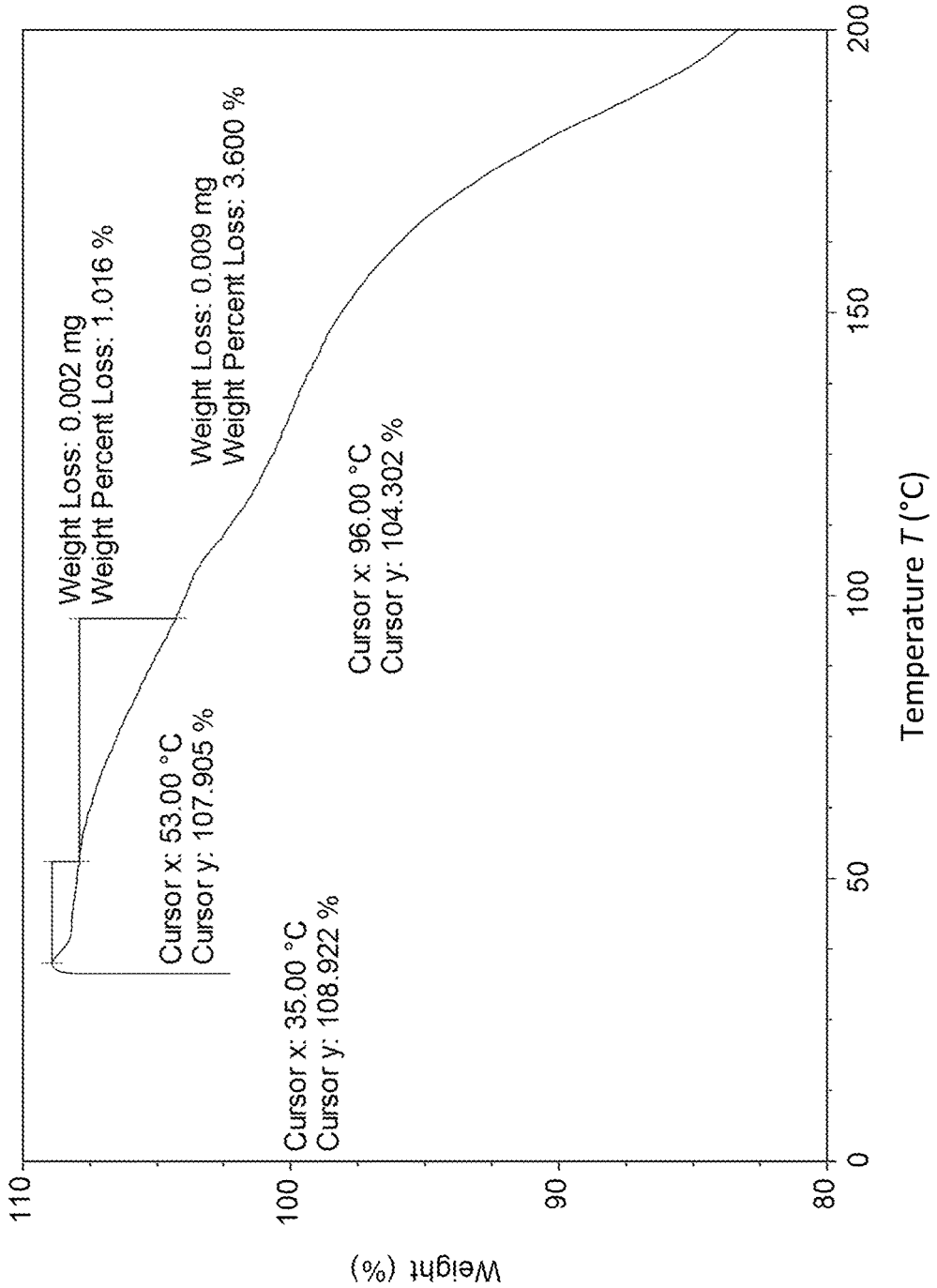
FIG. 57 is a TGA thermogram of Compound I hemifumarate Pattern 5 obtained in equilibration experiment EQ6 (in 1:1 v/v acetone/toluene) at 25° C. for 3 weeks (obtained in Example 12).

For Pattern E, XRPD diffractogram is shown in FIG. 53; DSC thermograms are shown in FIG. 54 and FIG. 55; and TGA thermograms are shown in FIG. 56 and FIG. 57.

TABLE 21

Results of equilibration with acetone/heptane (1:1 v/v) for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ7 (acetone/ heptane, 1:1 v/v) | Similar to Pattern B, medium crystallinity | Salt ratio = 1:0.56 Residual solvent: 3.3% (by weight) heptane and 0.6% (by weight) acetone Purity: 99.2% | Similar to Pattern B, medium crystallinity and one peak disappeared | Salt ratio = 1:0.62 Residual solvent: 3.0% (by weight) heptane and 0.2% (by weight) acetone Purity: 99.2% |

Note:
Salt ratio is free base form:fumaric acid ratio

XRPD diffractogram is shown in FIG. 47 (3 weeks).

TABLE 22

Results of equilibration with IPA/heptane (1:1 v/v) for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ8 (IPA/ heptane, 1:1 v/v) | Mixture of Pattern 1 + unknown pattern | Salt ratio = 1:0.60 Residual solvent: 0.9% (by weight) heptane and 0.6% (by weight) IPA DSC, onset (enthalpy): 81.6° C. (48 J/g); | Mixture of Pattern 1 + unknown pattern | n/a |

TABLE 22-continued

Results of equilibration with IPA/heptane (1:1 v/v) for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| | | 102.2° C. (16 J/g) TGA, weight loss: ~0.4% at 81° C. ~1.2% at 81-136° C. | | |

Note:
Salt ratio is free base form:fumaric acid ratio

XRPD diffractogram is shown in FIG. 50.

TABLE 23

Results of equilibration with IPA/toluene (1:1 v/v) for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ9 (IPA/toluene, 1:1 v/v) | Mixture of Pattern 1 + unknown pattern | Salt ratio = 1:0.91 Residual solvent: 0.3% (by weight) toluene and 0.7% (by weight) IPA DSC, onset (enthalpy): 88.3° C. (8 J/g) 112.3° C. (57 J/g) TGA, weight loss: ~1.2% at 112° C. | Mixture of Pattern 1 + unknown pattern | n/a |

Note:
Salt ratio is free base form:fumaric acid ratio

XRPD diffractogram is shown in FIG. 50.

TABLE 24

Results of equilibration with IPA/MTBE (1:3 v/v) for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ10 (IPA/MTBE, 1:3 v/v) | Mixture of Pattern 1 + unknown pattern | Salt ratio = 1:0.65 Residual solvent: 0.9% (by weight) MTBE and 0.8% (by weight) IPA DSC, onset (enthalpy); 80.4° C. (46 J/g) 103.7° C. (11 J/g) TGA, weight loss: ~0.3% at 80° C. ~1.4% at 80-135° C. Purity: 99.2% | Mixture of Pattern 1 + unknown pattern | n/a |

Note:
Salt ratio is free base form:fumaric acid ratio

XRPD diffractogram is shown in FIG. 50.

TABLE 25

Results of equilibration with THF/heptanes (1:3 v/v) for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ11 (THF/ | Pattern 1, medium | Salt ratio = 1:0.87 Residual solvent: No | Pattern 1, medium | |

TABLE 25-continued

Results of equilibration with THF/heptanes (1:3 v/v) for Compound
I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| heptane, 1:3 v/v) | crystallinity + one peak | Purity: 99.1% | crystallinity + one peak | |

Note:
Salt ratio is free base form:fumaric acid ratio

Figure 58:
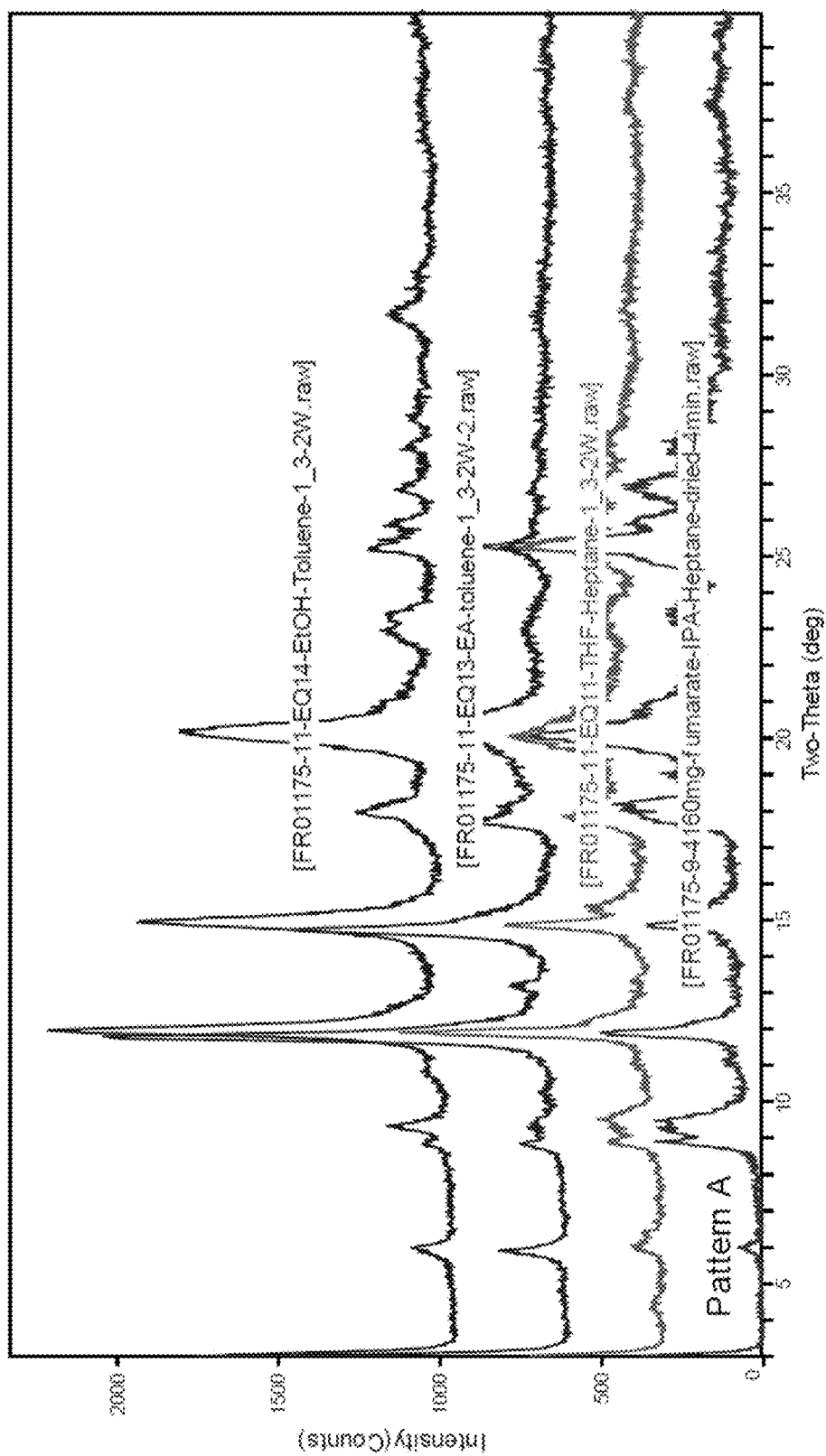
FIG. 58 is a comparison of XRPD diffractograms of Compound I monofumarate Pattern 1 obtained in equilibration experiments (procedure in Example 12) EQ11 (in 1:3 v/v tetrahydrofuran/heptane), EQ13 (in 1:3 v/v ethyl acetate/toluene), EQ14 (in 1:3 v/v ethanol/toluene) at 25° C. for 2 weeks and Compound I monofumarate Pattern 1 (material obtained in Example 7).
Figure 59:
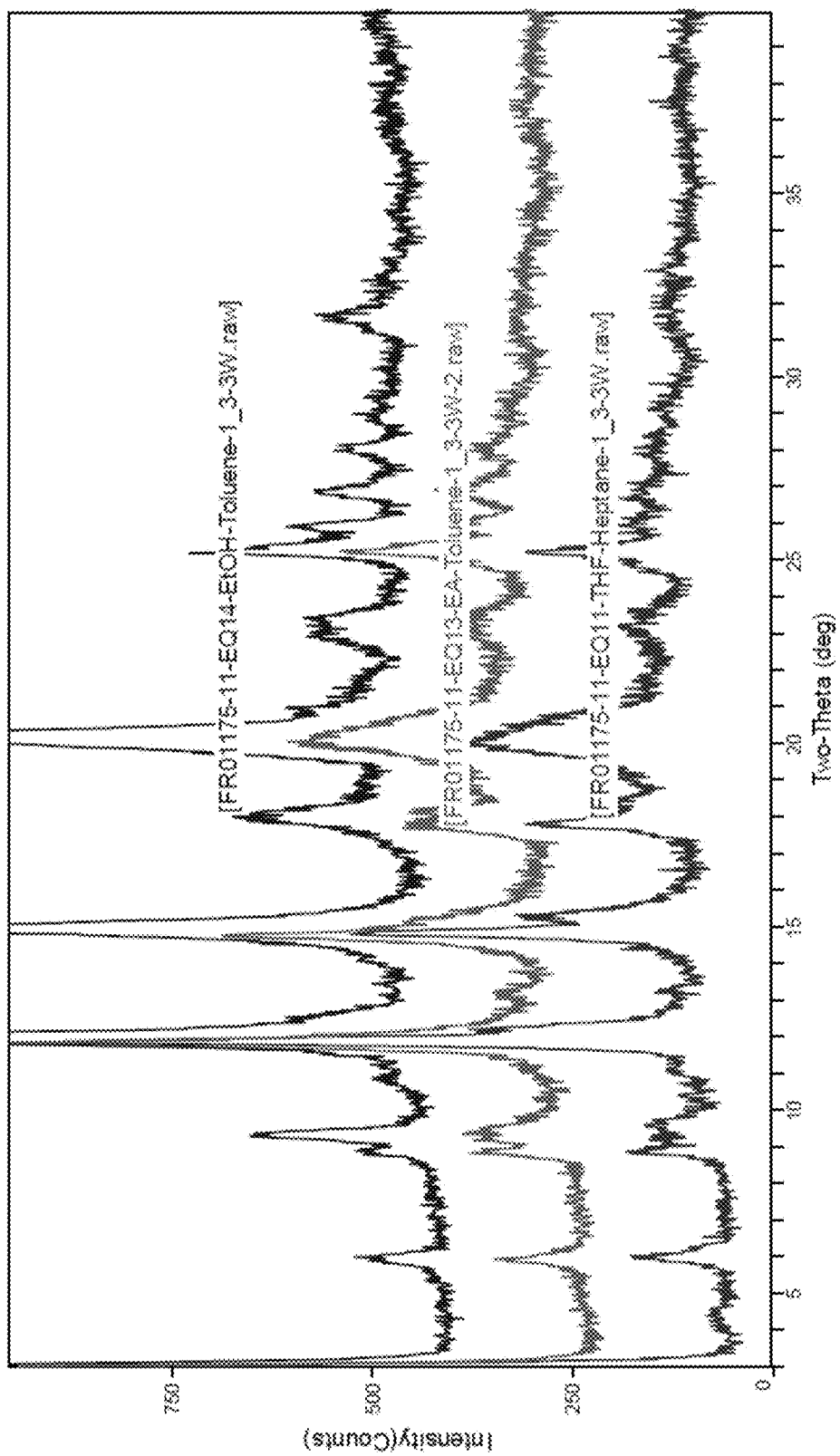
FIG. 59 is a comparison of XRPD diffractograms of Compound I monofumarate Pattern 1 obtained in equilibration experiments EQ11 (in 1:3 v/v tetrahydrofuran/heptane), EQ13 (in 1:3 v/v EA/toluene), EQ14 (in 1:3 v/v ethanol/toluene) at 25° C. for 3 weeks (obtained in Example 12).

XRPD is shown in FIG. 58 and FIG. 59.

TABLE 26

Results of equilibration with EtOH/heptanes (1:3 v/v) for Compound
I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ12 (EtOH/ heptanes, 1:3 v/v) | Mixture of Pattern 1 + unknown pattern + fumaric acid | Salt ratio = 1:1.05 Residual solvent: 0.4% (by weight) EtOH and 2.4% (by weight) heptanes DSC, onset (enthalpy): 95.4° C. (31 J/g) 109.8° C. (23 J/g) TGA, weight loss: ~0.7% at 95° C. ~1.9% at 95-145° C. | Mixture of Pattern 1 + unknown pattern + fumaric acid | Salt ratio = 1:0.79 Residual solvent: 2.1% (by weight) heptanes |

Note:
Salt ratio is free base form:fumaric acid ratio

XRPD diffractogram is shown in FIG. 50.

TABLE 27

Results of equilibration with EA/toluene(1:3 v/v) for Compound
I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ13 (EA/toluene, 1:3 v/v) | Pattern 1, medium crystallinity + one peak | Salt ratio = 1:0.95 Residual solvent: No | Pattern 1, medium crystallinity | n/a |

Note:
Salt ratio is free base form:fumaric acid ratio

XRPD is shown in FIG. 58 and FIG. 59

TABLE 28

Results of equilibration with EtOH/toluene (1:3 v/v) for Compound
I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ14 (EtOH/toluene, 1:3 v/v) | Pattern 1, medium crystallinity + one peak | Salt ratio = 1:0.91 Residual solvent: 0.6% (by weight) toluene | Pattern 1, medium crystallinity + one peak | n/a |

Note:
Salt ratio is free base form:fumaric acid ratio

XRPD is shown in FIG. 58 and FIG. 59

TABLE 29

Results of equilibration with water/ACN (2.9:97.1 v/v) for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ15 (water/ACN, 2.9:97.1 v/v) | Pattern C, medium crystallinity + fumaric acid | Salt ratio = 1:0.61 Residual solvent: 1.8% (by weight) ACN | Pattern C, medium crystallinity + fumaric acid | n/a |

Note:
Salt ratio is free base form:fumaric acid ratio

XRPD diffractogram is shown in FIG. 44.

TABLE 30

Results of equilibration with IPA/heptanes (1:4 v/v) for Compound I monofumarate Pattern 1 at 25° C. for 2 weeks and 3 weeks

| Exp. (Solvent) | XRPD (2 weeks) | Additional test (2 weeks) | XRPD (3 weeks) | Additional test (3 weeks) |
|---|---|---|---|---|
| EQ16 (IPA/heptane, 1:4 v/v) | Mixture of Pattern 1 + unknown pattern | Salt ratio = 1:0.76 Residual solvent: 1.5% (by weight) heptane and 0.7% (by weight) IPA DSC, onset (enthalpy): 89.9° C. (22 J/g) 105.0° C. (41 J/g) TGA, weight loss: ~0.2% at 89° C. ~0.1% at 89-105° C. | n/a | n/a |

Note:
Salt ratio is free base form:fumaric acid ratio

Figure 60:
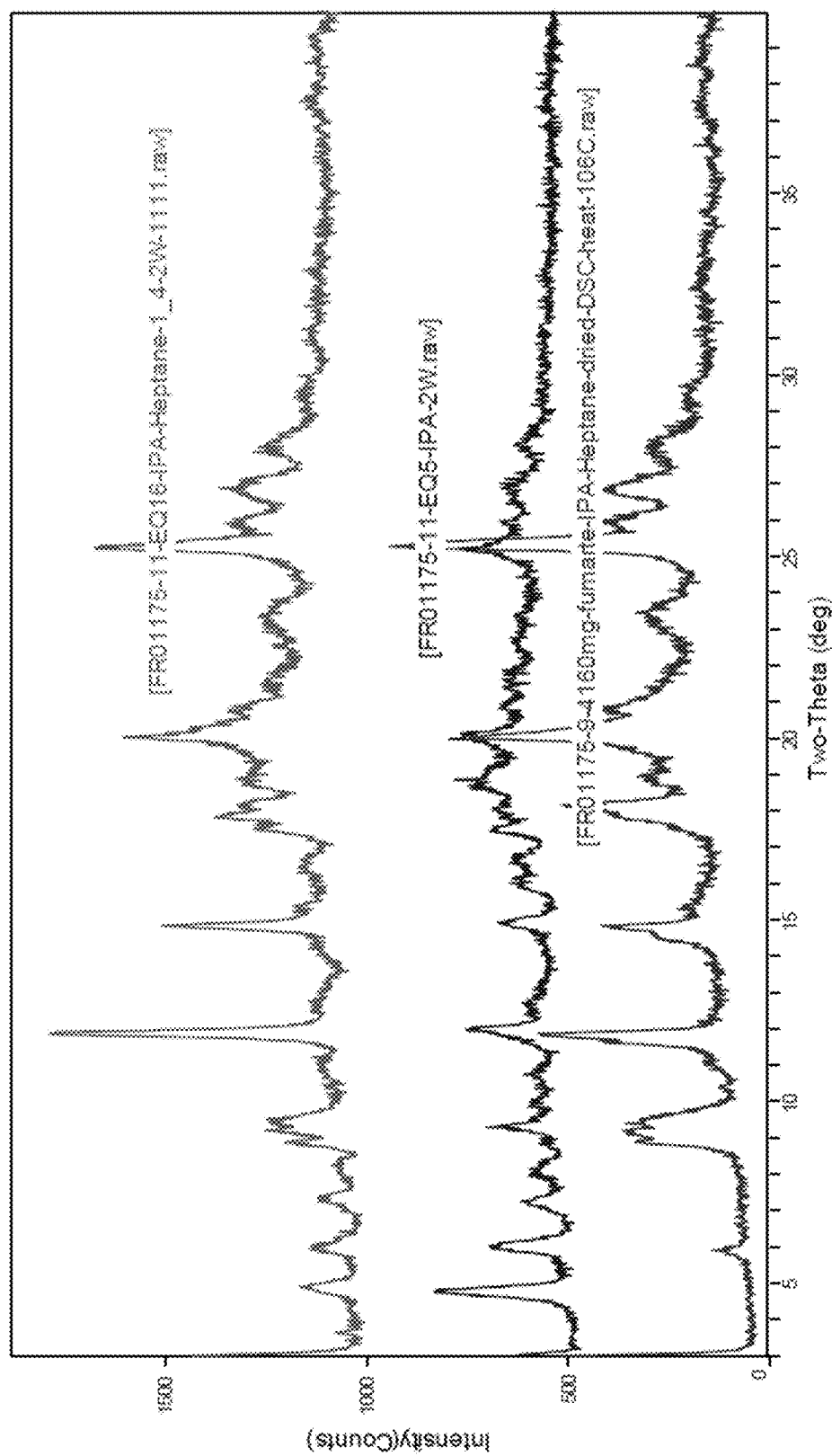
FIG. 60 is a comparison of XRPD diffractograms of a mixture of Compound I monofumarate Pattern 1 and unknown pattern obtained in equilibration experiments EQ16 (in 1:4 v/v isopropanol/heptane), EQ5 (in isopropanol) at 25° C. for 2 weeks and Compound I monofumarate Pattern 1 obtained in Example 7 (obtained in Example 12).

XRPD diffractogram is shown in FIG. 60.

Precipitation by Addition of Antisolvent

About 30 mg of Compound I monofumarate Pattern 1 (Example 7) was dissolved in a good solvent. Antisolvent was added into the obtained solutions slowly. Precipitates were collected by filtration. The solid part (wet cake) was investigated by XRPD. When differences were observed, additional investigations were performed (e.g., NMR, DSC, TGA). If no precipitation was obtained, the solutions were cooled to 5° C. for crystallization. After stirred at 5° C. for about 23 days, no precipitation was obtained, the solutions were put in a −20° C. freezer for crystallization.

Figure 61:
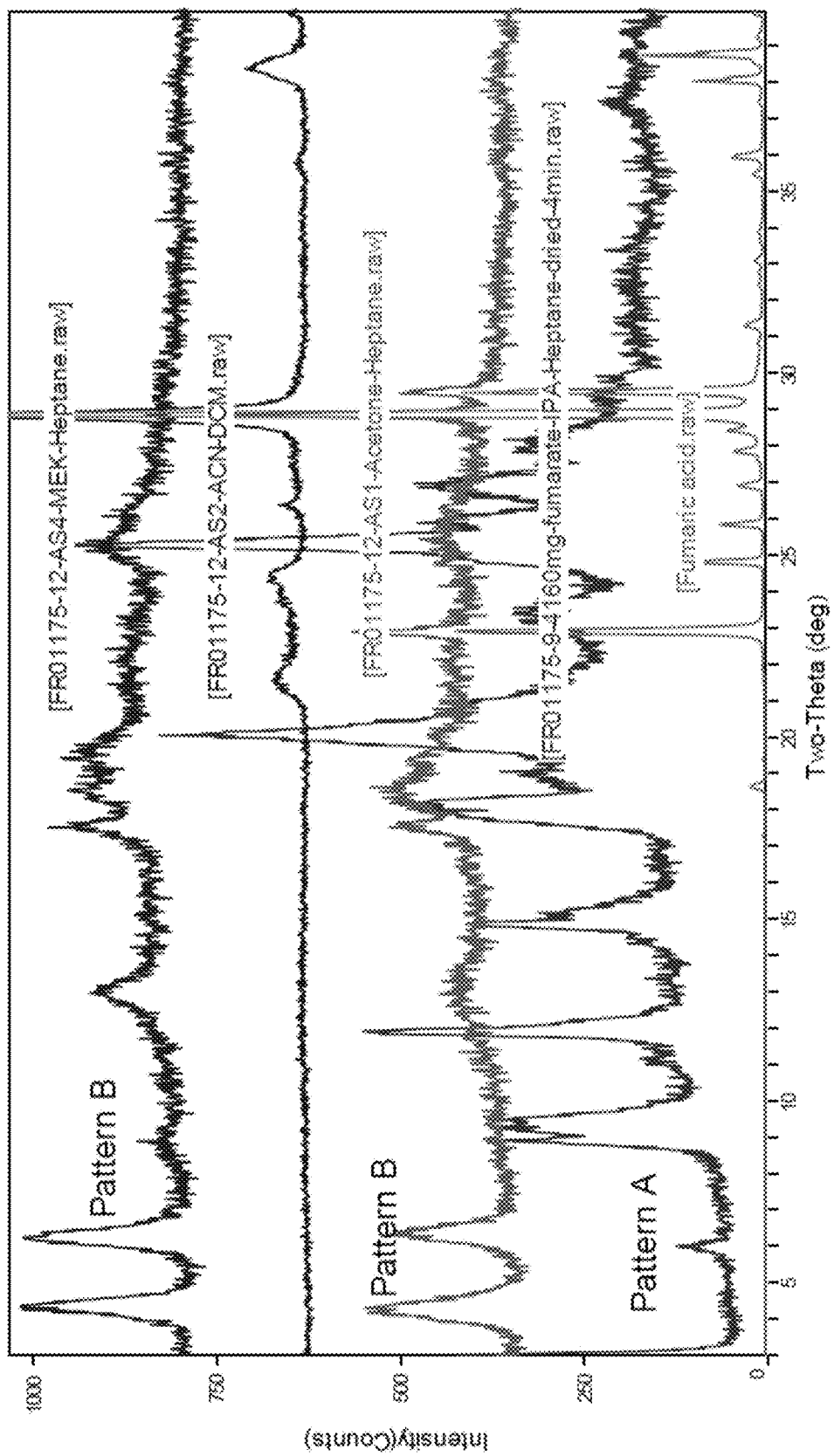
FIG. 61 is a comparison of XRPD diffractograms of reference fumaric acid pattern, Compound I monofumarate Pattern 1 (Example 7), Compound I monofumarate Pattern 2 (obtained by precipitation from acetone solution with heptane antisolvent in Experiment AS1, Example 12), Compound I monofumarate Pattern 2 (obtained by precipitation from methyl ethyl ketone solution with heptane antisolvent in Experiment AS4, Example 12), and fumaric acid pattern obtained in Experiment AS2, Example 12.
Figure 62:
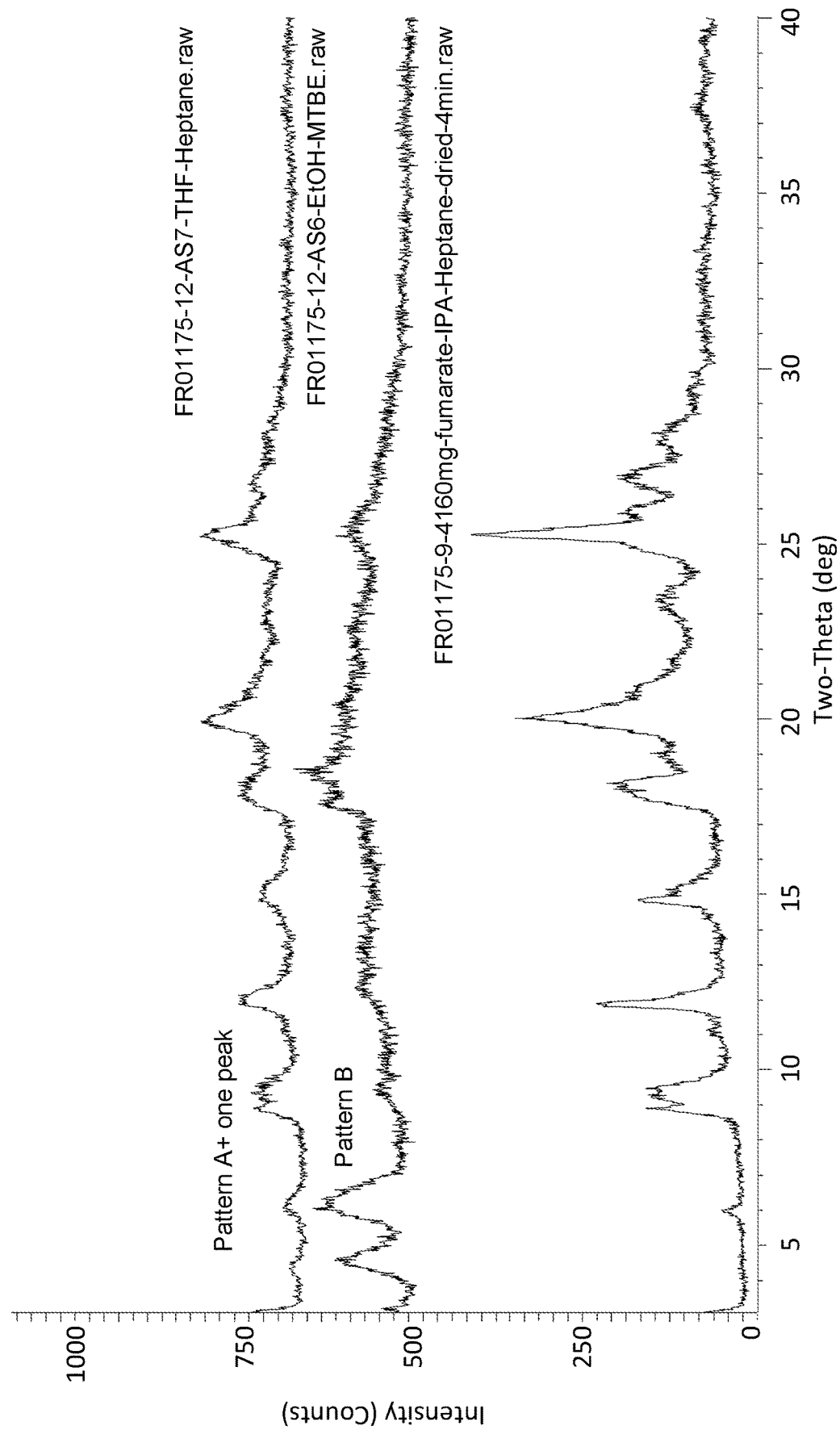
FIG. 62 is a comparison of XRPD diffractograms of Compound I monofumarate Pattern 1 (Example 7), Compound I monofumarate Pattern 2 (obtained by precipitation from ethanol solution with heptanes antisolvent in Experiment AS6, Example 12) and Compound I monofumarate Pattern 2 (obtained by precipitation from tetrahydrofuran solution with heptane antisolvent in Experiment AS7, Example 12).

Results are presented in Table 31. XRPD diffractograms are shown in FIG. 61 and FIG. 62.

TABLE 31

Precipitation of Compound I fumarate salts by addition of antisolvent

| Exp. | Solvent | Antisolvent | XRPD | Comments |
|---|---|---|---|---|
| AS1 | Acetone | Heptanes | Pattern B + fumaric acid | Salt ratio = 1:0.89 Residual solvent: 1.6% (by weight) heptanes DSC, onset (enthalpy): 59.3° C. (35 J/g); 95.5° C. (1 J/g); and 104.9° C. (3 J/g) TGA, weight loss: ~1.4% at 59° C.; ~0.9% at 59-119° C. |
| AS2 | ACN | DCM | Fumaric acid | After stirring at 5° C. for about 3 days |
| AS3 | IPA | Toluene | n/a | After storage at −20° C. for about 21 days, the sample was a clear solution |
| AS4 | MEK | Heptanes | Pattern B, low crystallinity | Salt ratio = 1:0.53 Residual solvent: 0.5% (by weight) MEK and 1.3% (by weight) heptane DSC, onset (enthalpy): 57.8° C. (44 J/g); 86.1° C. (0.4 J/g); 95.7° C. (6 J/g); TGA, weight loss: ~0.6% at 57° C.; ~0.8% at 57-129° C. |
| AS5 | EtOH | Toluene | n/a | After storage at −20° C. for about 21 days, a little flocculent sample appeared |
| AS6 | EtOH | MTBE | Pattern B, low crystallinity | After stirring at 5° C. for about 8 days |
| AS7 | THF | Heptanes | Pattern 1, medium crystallinity + one extra peak | Salt ratio = 1:0.87 Residual solvent: 1.6% (by weight) heptanes solvent |

TABLE 31-continued

Precipitation of Compound I fumarate salts by addition of antisolvent

| Exp. | Solvent | Antisolvent | XRPD | Comments |
|---|---|---|---|---|
| AS8 | IPA | MTBE | n/a | DSC, onset (enthalpy): 70.0° C. (5 J/g); 99.1° C. (46 J/g); TGA, weight loss: ~0.4% at 70° C.; ~0.7% at 70-99° C.; ~3.4% at 99-144° C. After storage at −20° C. for about 21 days, the sample was a clear solution |

Crystallization at Room Temperature by Slow Evaporation

Combined with approximate solubility experiment, solubility samples were filtered through a 0.45 μm nylon filter. Obtained solutions were slow evaporated at ambient condition. Solid residues were examined for their polymorphic form.

Figure 63:
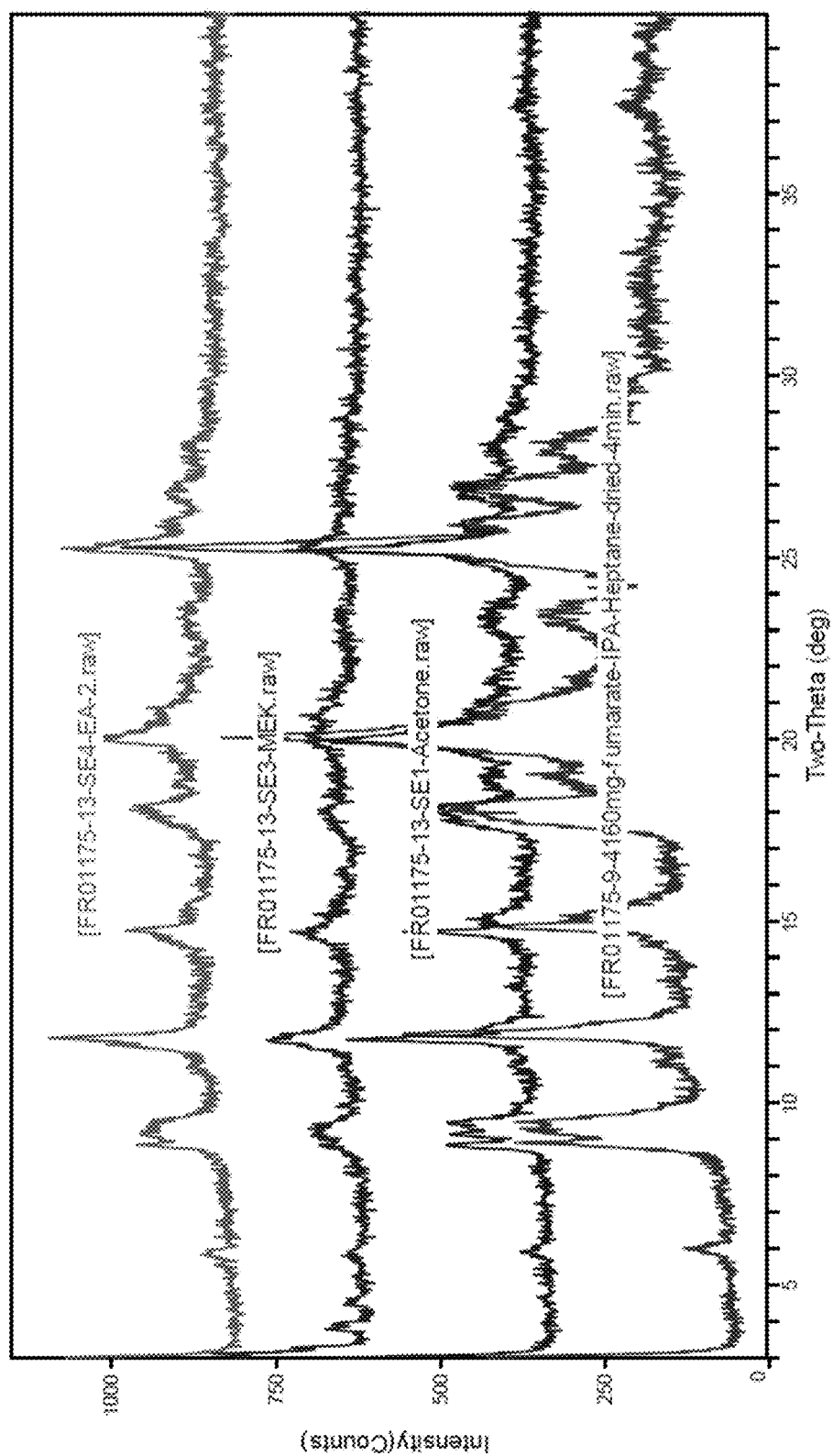
FIG. 63 is a comparison of XRPD diffractograms of Compound I monofumarate Pattern 1 (Example 7) and Compound I monofumarate Pattern 1 obtained by crystallization at room temperature by slow evaporation from acetone, methylethylketone and ethyl acetate as described in Example 12, Table 32.
Figure 64:
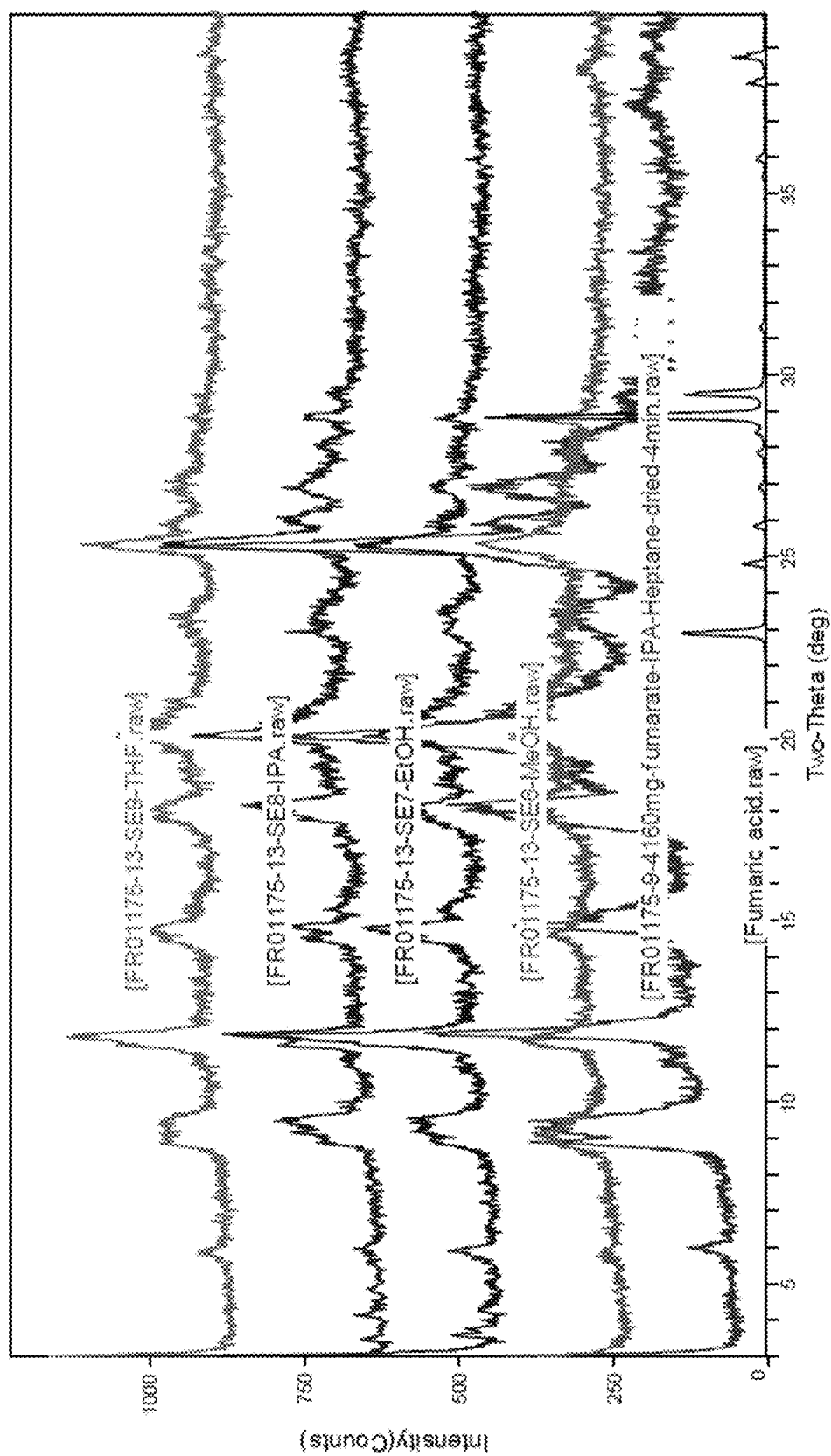
FIG. 64 is a comparison of XRPD diffractograms of Compound I monofumarate Pattern 1 (Example 7) and Compound I monofumarate Pattern 1 obtained by crystallization at room temperature by slow evaporation from methanol, ethanol, isopropanol and tetrahydrofuran as described in Example 12, Table 32.

Results are presented in Table 32. XRPD diffractograms are shown in FIG. 63 and FIG. 64.

TABLE 32

Crystallization at room temperature by slow evaporation

| Exp. | Solvent | XRPD |
|---|---|---|
| 1 | Acetone | Pattern 1 with medium crystallinity |
| 2 | ACN | Gel |
| 3 | MEK | Pattern 1 with medium crystallinity |
| 4 | EA | Pattern 1 with medium crystallinity |
| 5 | Acetone/water (75/25 v/v) | Clear solution |
| 6 | MeOH | Pattern 1 with medium crystallinity + fumaric acid |
| 7 | EtOH | Pattern 1 with medium crystallinity |
| 8 | IPA | Pattern 1 with medium crystallinity + fumaric acid |
| 9 | THF | Pattern 1 with medium crystallinity |
| 10 | EA/heptanes (1/1 v/v) | Clear solution |

Crystallization from Hot Saturated Solutions by Slow Cooling

About 30 mg of Compound I monofumarate Pattern 1 (Example 7) was dissolved in the minimal amount of selected solvents at 50° C. Obtained solutions were cooled to 5° C. at the rate of 0.1° C./min. Precipitates were collected by filtration. The solid part (wet cake) was investigated by XRPD. When differences were observed, additional investigations were performed (e.g., NMR, DSC, TGA). If no precipitation was obtained, the solutions were put in a −20° C. freezer for crystallization. After storing in −20° C. freezer for about 5 days, no precipitation was obtained, heptane was added as antisolvent. Precipitates were collected by filtration. The solid part (wet cake) was investigated by XRPD.

Figure 65:
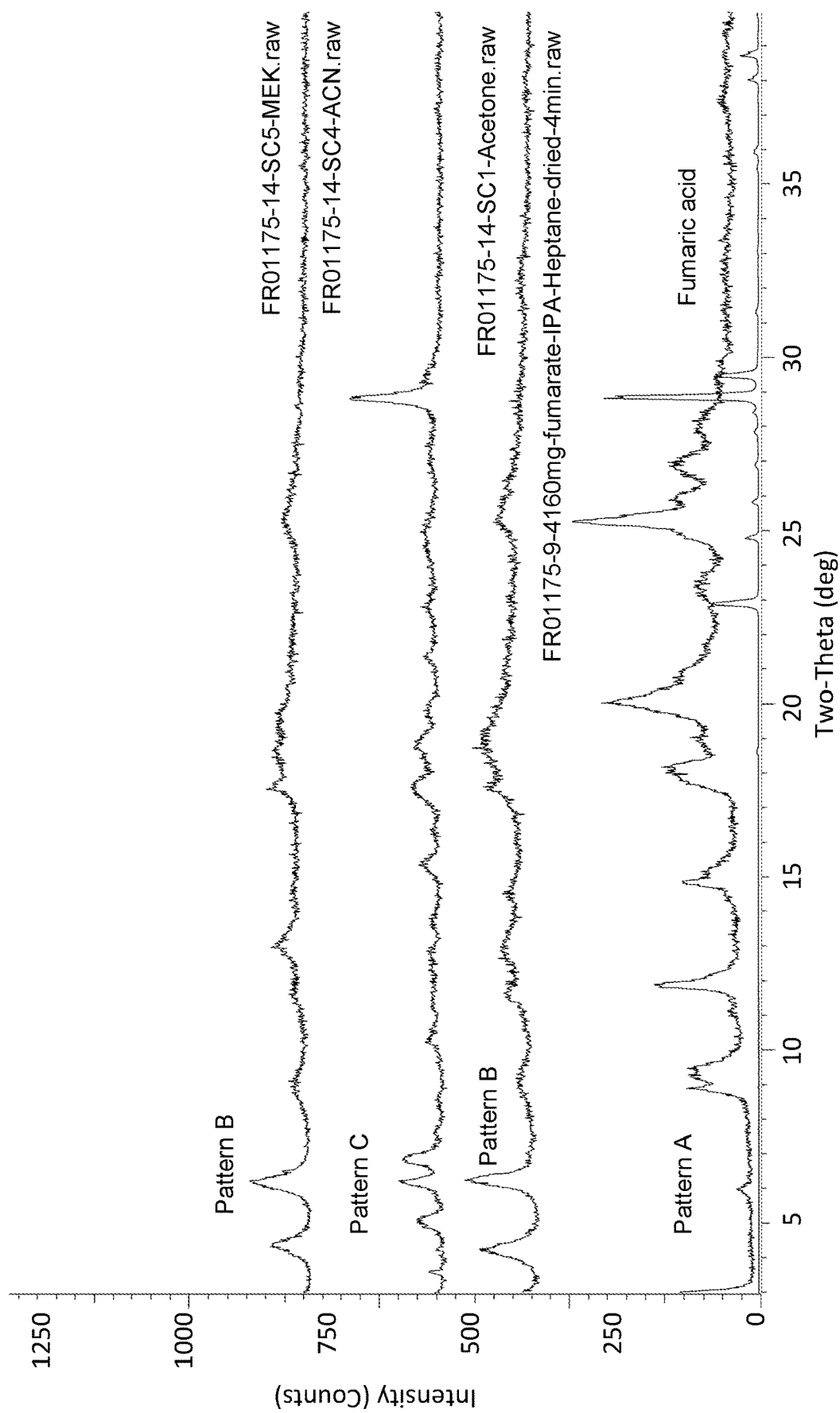
FIG. 65 is a comparison of XRPD diffractograms of reference fumaric acid pattern, Compound I monofumarate Pattern 1 (Example 7) and Compound I monofumarate Pattern 2 obtained by crystallization from hot methyl ethyl ketone saturated solution by slow cooling, Compound I monofumarate Pattern 2 obtained by crystallization from acetone hot saturated solution by slow cooling and Compound I monofumarate Pattern 3 obtained by crystallization from acetonitrile hot saturated solution by slow cooling.
Figure 66:
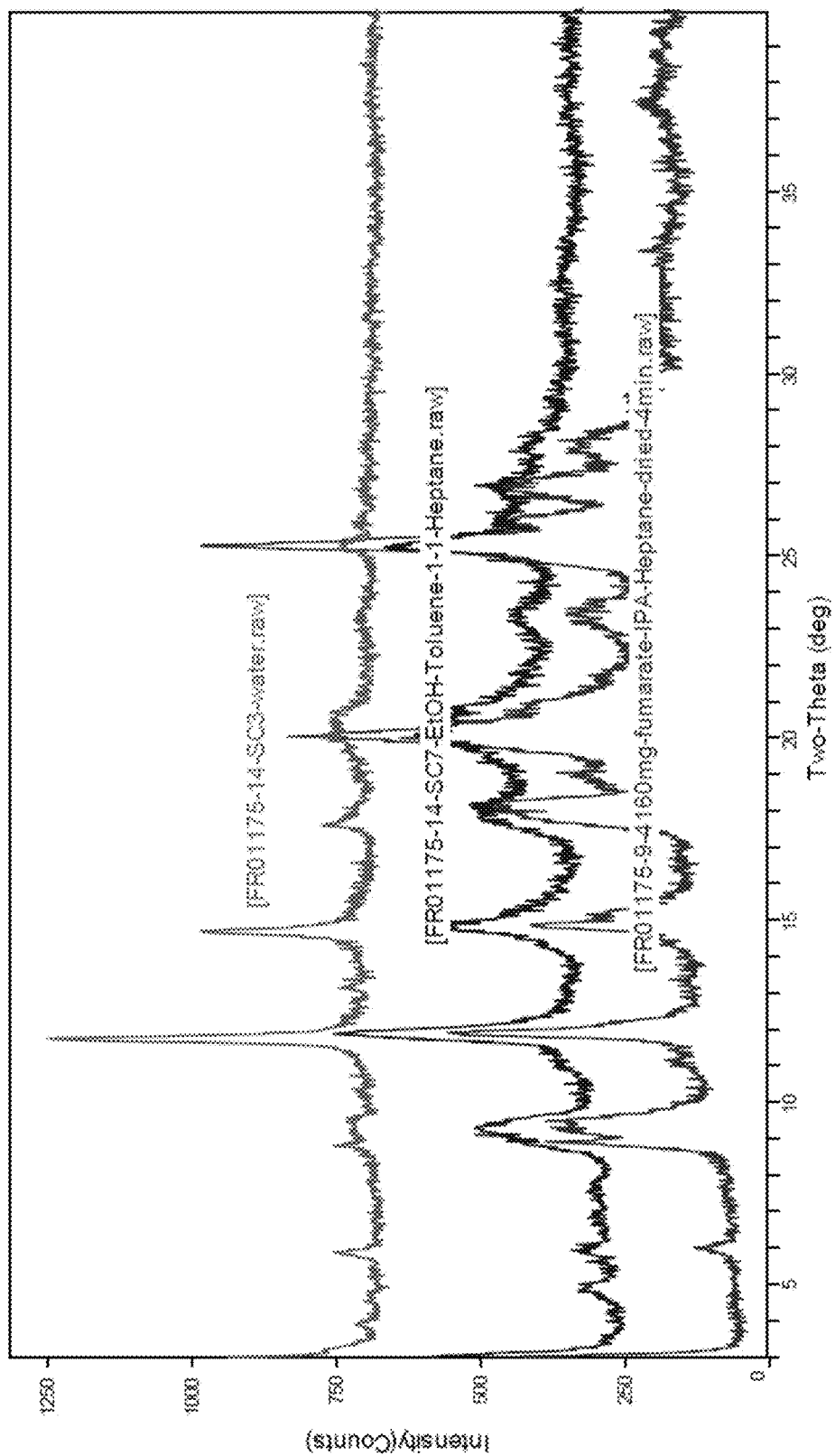
FIG. 66 is a comparison of XRPD diffractograms of Compound I monofumarate Pattern 1 (Example 7), Compound I monofumarate Pattern 1 obtained by crystallization from hot water saturated solution by slow cooling, and Compound I monofumarate Pattern 1 obtained by crystallization from hot saturated solution in ethanol/toluene (1/1 v/v) by slow cooling (Example 12, Table 33).

Results are presented in Table 33. XRPD diffractograms are shown in FIG. 65 and FIG. 66.

TABLE 33

Crystallization from hot saturated solutions by slow cooling

| Exp. | Solvent | XRPD | Comments |
|---|---|---|---|
| 1 | Acetone | Pattern B with medium crystallinity | Salt ratio = 1:0.66; Residual solvent: 1.5% (by weight) acetone |
| 2 | IPA | Deliquescent | n/a |
| 3 | Water | Pattern 1 with medium crystallinity | n/a |
| 4 | ACN | Pattern C with medium crystallinity + fumaric acid | Salt ratio = 1:0.95; Residual solvent: 2.0% (by weight) ACN solvent DSC, onset (enthalpy): 74.0° C. (89 J/g); 90.6° C. (15 J/g); TGA, weight loss: ~0.4% at 73° C.; ~2.1% at 73-144° C. After washing with water: Salt ratio = 1:0.76; Residual solvent: 1.3% (by weight) ACN solvent |
| 5 | MEK | Pattern B with medium crystallinity | n/a |
| 6 | Acetone/water (75/25 v/v) | n/a | After storage at −20° C. for about 5 days: clear solution |
| 7 | EtOH/toluene (1/1 v/v) | Pattern 1 with medium crystallinity + one peak | After storage at −20° C. for about 5 days: clear solution; added 0.8 mL of heptane |

Crystallization from Hot Saturated Solutions by Fast Cooling

About 30 mg of Compound I monofumarate Pattern 1 (Example 7) was dissolved in the minimal amount of selected solvents at 50° C. Obtained solutions were put into an ice bath and agitated. Precipitates were collected by filtration. The solid part (wet cake) was investigated by XRPD. When differences were observed, additional investigations were performed (e.g., NMR, DSC, TGA). If no precipitation was obtained, the solutions were put in −20° C. freezer for crystallization. After storing in −20° C. freezer for about 7 days, no precipitation was obtained, heptanes was added as antisolvent. Precipitates were collected by filtration. The solid part (wet cake) was investigated by XRPD.

Figure 67:
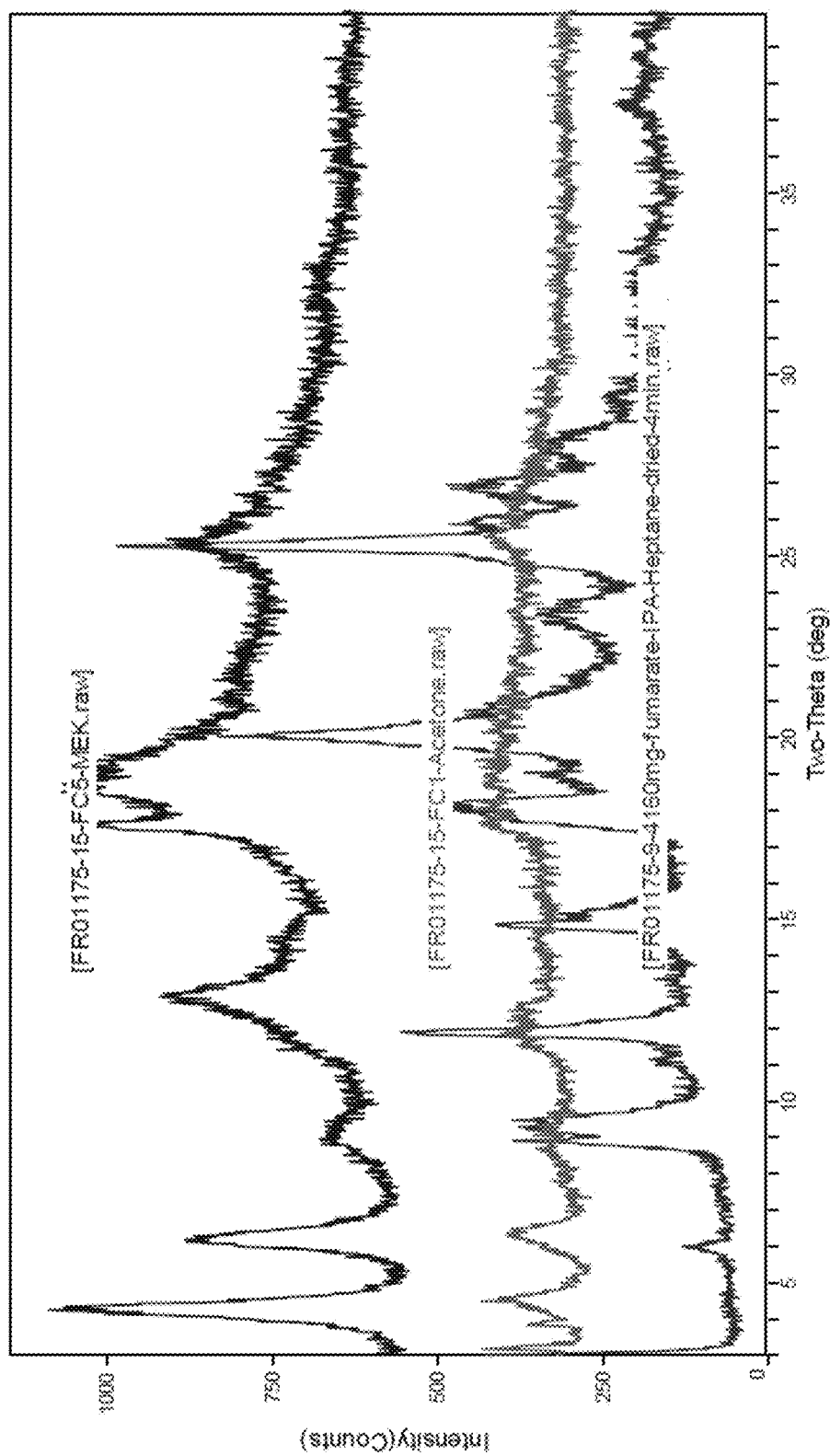
FIG. 67 is a comparison of XRPD diffractograms of Compound I monofumarate Pattern 1 (Example 7), Compound I monofumarate Pattern 2 obtained by crystallization from hot acetone saturated solution by fast cooling, and Compound I monofumarate Pattern 2 obtained by crystallization from hot saturated solution in methyl ethyl ketone by fast cooling (Example 12, Table 34).
Figure 68:
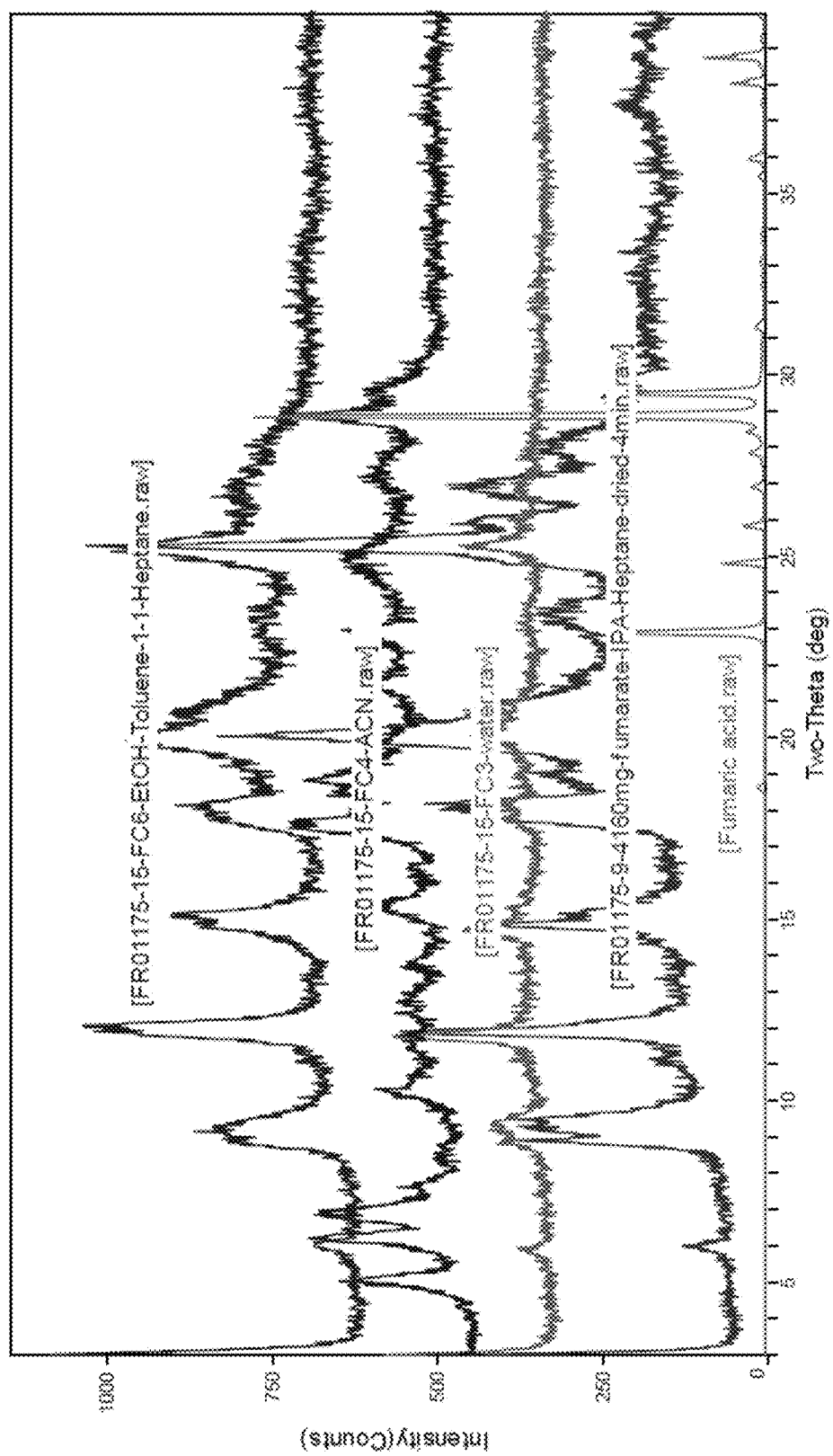
FIG. 68 is a comparison of XRPD diffractograms of reference fumaric acid pattern, Compound I monofumarate Pattern 1 (Example 7), Compound I monofumarate Pattern 1 obtained by crystallization from hot water saturated solution by fast cooling, Compound I monofumarate Pattern 3 obtained by crystallization from hot saturated solution in acetonitrile by fast cooling, and Compound I monofumarate Pattern 1 obtained by crystallization from hot saturated solution in ethanol/toluene (1/1 v/v) by fast cooling (Example 12).

Results are presented in Table 34. XRPD diffractograms are shown in FIG. 67 and FIG. 68.

TABLE 34

Crystallization from hot saturated solutions by fast cooling

| Exp. | Solvent | XRPD | Comments |
|---|---|---|---|
| 1 | Acetone | Pattern B with low crystallinity | Free base form:fumaric acid = 1:0.66; 1.0% (by weight) acetone residue |
| 2 | IPA | n/a | Clear solution |
| 3 | Water | Pattern 1 with medium crystallinity | Free base form:fumaric acid = 1:0.91; No residual solvent |
| 4 | ACN | Pattern C with medium crystallinity + fumaric acid | Free base form:fumaric acid = 1:0.76; 1.4% (by weight) ACN solvent residue |
| 5 | MEK | Pattern B with medium crystallinity | Free base form:fumaric acid = 1:0.64; 3.0% (by weight) MEK solvent residue |
| 6 | EtOH/toluene (1/1 v/v) | Pattern 1 with medium crystallinity | After storage at −20° C. for about 5 days: clear solution; added 0.8 mL of heptane |

Behavior of Compound I Monofumarate Pattern 1 Under Heating and Cooling

Polymorphic behavior of Compound I monofumarate Pattern was investigated by two different heating-cooling cycle of DSC.

Cycle 1: 0° C. to 106° C. at 10° C./min; 106° C. to 0° C. at 10° C./min; reheat from 0° C. to 250° C. at 10° C./min.

Cycle 2: 0° C. to 130° C. at 10° C./min; 130° C. to 0° C. at 10° C./min; reheat from 0° C. to 250° C. at 10° C./min.

Figure 69:
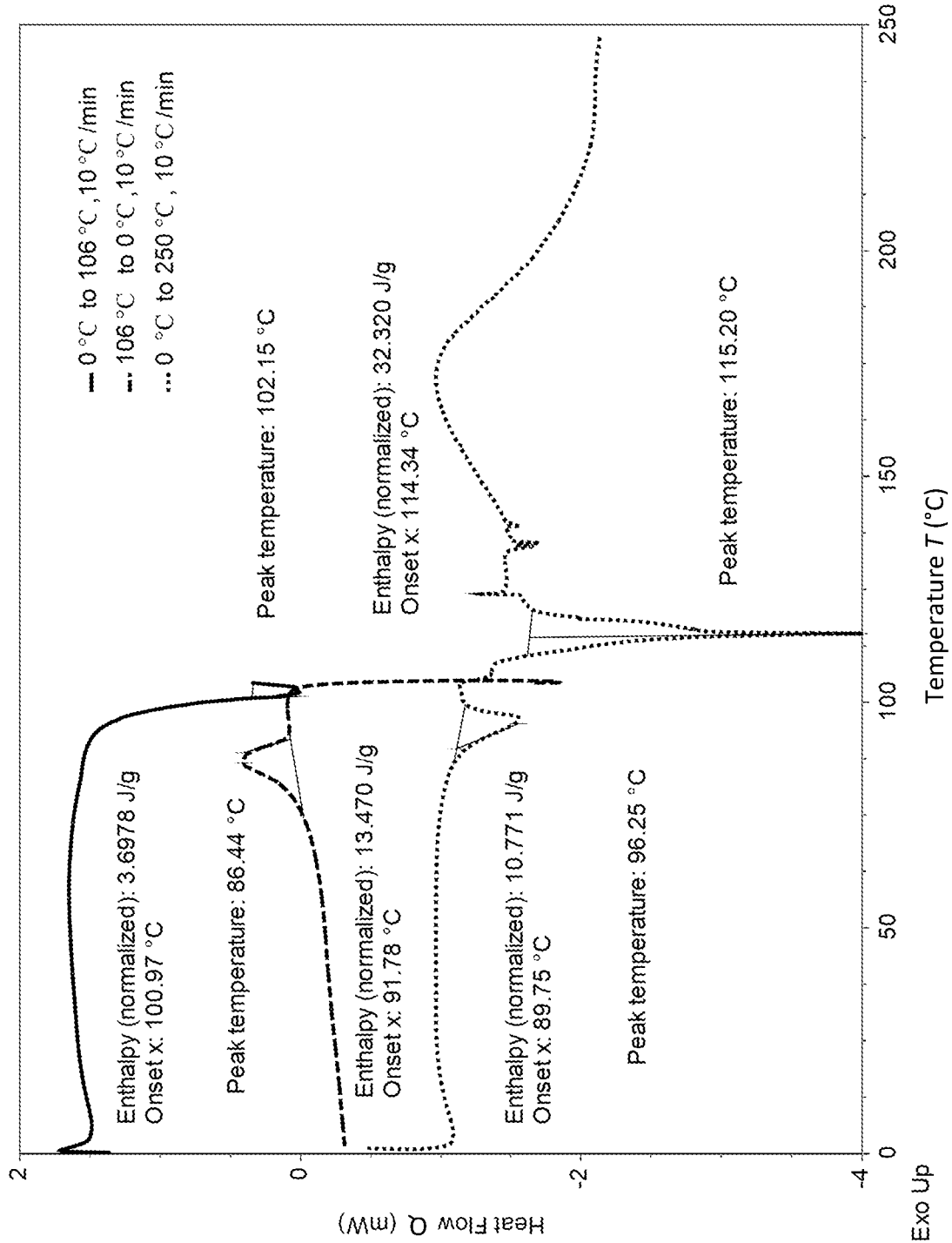
FIG. 69 is a heat-cool-heat DSC thermogram of Compound I monofumarate Pattern 1 (heating to 106° C.) (Example 12, Table 35)
Figure 70:
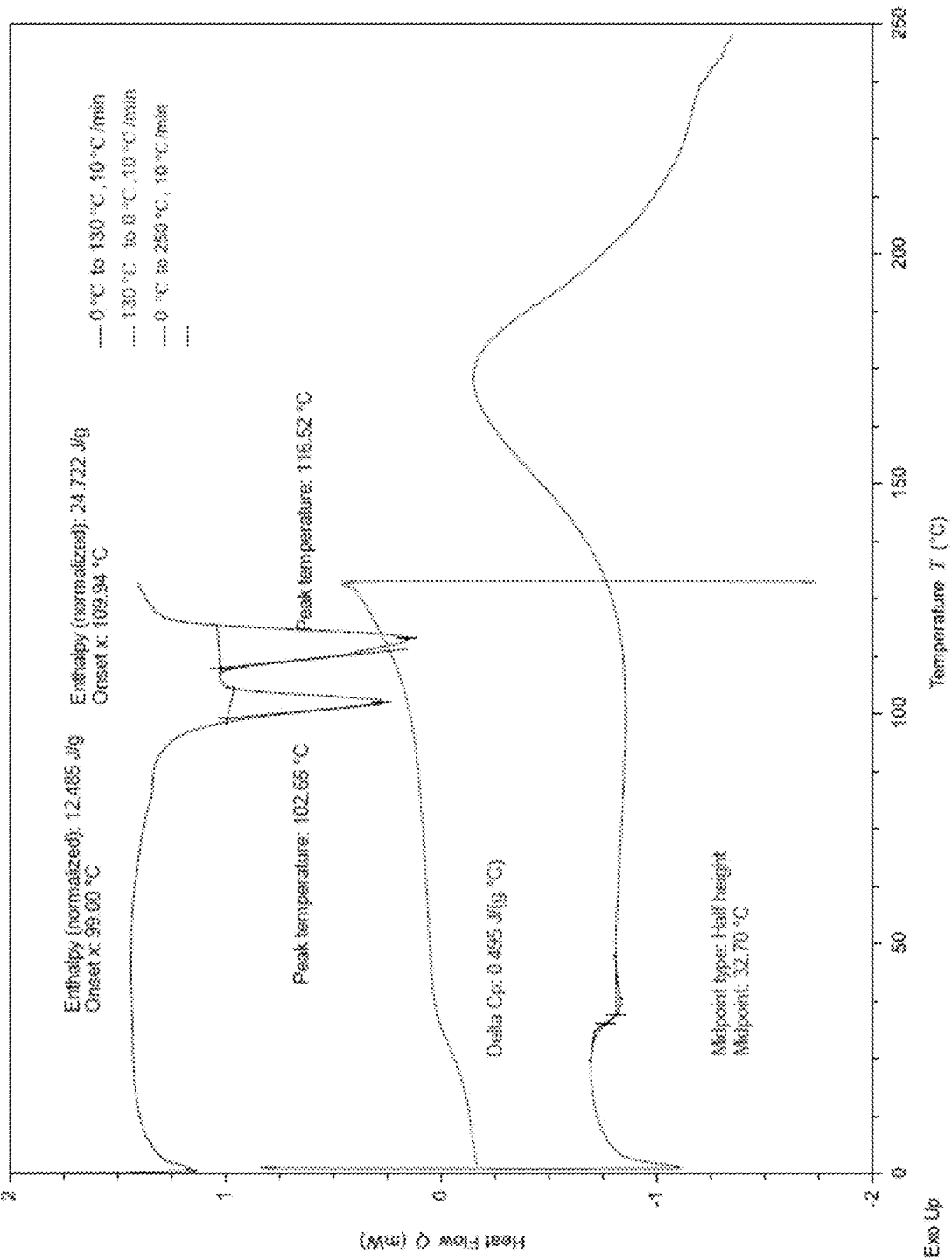
FIG. 70 is a heat-cool-heat DSC thermogram of Compound I monofumarate Pattern 1 (heating to 130° C.) (Example 12, Table 35)

The results are presented in Table 35 and in FIG. 69 and FIG. 70.

Behavior Under Compression

About 10 mg of Compound I monofumarate Pattern 1 (Example 7) was compressed for 5 minutes at 10 MPa with a hydraulic press. XRPD characterization was performed to investigate the polymorphic behavior under compression. According to the XRPD, no form change was observed.

Grinding Simulation Experiments

About 10 mg of Compound I monofumarate Pattern 1 (Example 7) was ground manually with a mortar and pestle for 5 min. Form transformation and degree of crystallinity was evaluated by XRPD. According to the XRPD, no form change was observed; crystallinity slightly decreased.

Granulation Simulation Experiments

Water or ethanol was added drop wise to about 10 mg of Compound I monofumarate Pattern 1 (Example 7) until solids were wetted sufficiently. The samples were ground manually with a mortar and pestle for 3 minutes. Samples are dried under ambient condition for 10 min. Form transformation and degree of crystallinity were evaluated by XRPD. According to the XRPD, neither in ethanol, nor in water form change was observed.

Summary of Identified Mono- and Hemi Fumarate Polymorphs

Compound I monofumarate Pattern 1 used in the study was prepared from Compound I free base according to Example 7. The initial form of monofumarate used in the polymorph study described below (Pattern 1) is an anhydrate of monofumarate with HPLC purity of about 99.3%. The ratio of free form and fumaric acid is about 1:0.96 by $^1$H

TABLE 35

Behavior of Compound I monofumarate Pattern 1 under heating and cooling

| Exp. | Heating rate | Thermal events |
|---|---|---|
| 1 | Cycle 1: 0° C. to 106° C. at 10° C./min; 106° C. to 0° C. at 10° C./min; reheat from 0° C. to 250° C. at 10° C./min. | Heating: Melting onset: 101.0° C., Enthalpy: 4 J/g; Cooling: Onset: exo 91.8° C., Enthalpy: 13 J/g; Heating: Onset: 89.8° C., Enthalpy: 11 J/g; Onset: 114.3° C., Enthalpy: 32 J/g |
| 2 | Cycle 1: 0° C. to 130° C. at 10° C./min; 130° to 0° C. at 10° C./min; reheat from 0° C. to 250° C. at 10° C./min | Heating: Onset: 99.0° C., Enthalpy: 12 J/g; Onset: 109.9° C., Enthalpy: 25 J/g Cooling: No obvious thermal event Heating: Thermal events: Tg: 32.7° C., Delta Cp: 0.5 J/(g. ° C.) |

NMR. It has two melting peaks with Tonset of about 98.5° C. with an enthalpy of about 14 J/g and 109.6° C. with an enthalpy of about 25 J/g, as measured by differential scanning calorimetry (DSC). By thermogravimetric analysis (TGA), Pattern 1 shows about 0.5% weight loss at about 98° C. and 0.6% weight loss from 98° C. to 140° C. About 1.0% (by weight) heptanes and 0.2% (by weight) IPA residue were detected by $^1$HNMR. Karl Fischer titration shows it contains about 1.3% water.

During the polymorph study, four new patterns were identified. Although monofumarate was used as initial physical form obtained new patterns showed different stoichiometric ratio. Pattern B, Pattern C and Pattern E are hemifumarate salts, and Pattern D is a degradation product.

Pattern B is an anhydrate of hemifumarate with HPLC purity of about 99.6%. With MEK, acetone, acetone/heptanes, MEK/heptanes and EtOH/MTBE as solvents, it can be obtained from equilibration experiment, addition of antisolvent, slow cooling and fast cooling experiments. The ratio of free base form to fumaric acid is about 1:0.52 by 1H-NMR.

Pattern E is an anhydrate of hemifumarate with HPLC purity of about 98.9%. It was obtained in acetone/toluene by equilibration experiment. The ratio of free base form to fumaric acid of the mixture is about 1:0.69 by $^1$H NMR. It has two thermal events with $T_{onset}$ of about 53.1° C. with an enthalpy of about 33 J/g and $T_{onset}$ of about 96.5° C. with an enthalpy of about 34 J/g. It shows about 1.0% weight loss at about 53° C. and 3.6% weight loss from 53° C. to 96° C. About 0.6% (by weight) acetone residue was detected by $^1$H NMR.

Results of the study on Compound I mono- and hemifumarate polymorphs are summarized in Table 36 below. The salt ratio is the ratio between Compound I free base and the salt counterion. "AS" indicates the form can be prepared by antisolvent addition, using the solvent/antisolvent pairs listed in the table. "EQ" indicates the form can be prepared through equilibration in the listed solvent. "SC" indicates the form can be prepared by slowly cooling a solution of Compound I monofumarate in the listed solvent. "FC" indicates t the form can be prepared by quickly cooling a solution of Compound I monofumarate in the listed solvent.

TABLE 36

Summary of identified Compound I fumarate salt Patterns A, B, C, and E

| Polymorph | Salt | Melting Temperatures (Enthalpy) | Salt ratio | Preparation |
| --- | --- | --- | --- | --- |
| Pattern 1 | Mono-fumarate | 98.5° C. (14 J/g) and 109.6° C. (25 J/g) | 1:0.96 | AS: IPA/heptanes |
| Pattern B | Hemi-fumarate anhydrate | 77.4° C. (71 J/g) and 88.4° C. (18 J/g) | 1:0.52 | EQ: MEK or acetone; AS: acetone/heptanes, MEK/heptanes, or EtOH/MTBE; SC: MEK or acetone; FC: MEK |
| Pattern C containing residual fumaric acid | Hemi-fumarate | 74.0° C. (89 J/g) and 90.6° C. (15 J/g) | 1:0.76 | EQ: ACN or ACN/water; SC: ACN; FC: CAN |
| Pattern E | Hemi-fumarate anhydrate | 53.1° C. (33 J/g) and 96.5° C. (34 J/g) | 1:0.69 | EQ: 1:1 acetone:toluene |

It has two thermal events with $T_{onset}$ of about 77.4° C. with an enthalpy of about 71 J/g and 88.4° C. with an enthalpy of about 18 J/g. It shows about 0.7% weight loss at about 77° C. and 4.2% weight loss from 77° C. to 130° C. About 4.6% (by weight) MEK residue was detected by $^1$H NMR.

With ACN and ACN/water as solvents, a mixture of Pattern C and fumaric acid was obtained by equilibration, slow cooling and fast cooling experiments. The ratio of free base form to fumaric acid of the mixture is about 1:0.95 by $^1$H NMR. After washing by water, the ratio decreased to about 1:0.76. This indicates that Pattern C is not a monofumarate. It has two thermal events with $T_{onset}$ of about 74.0° C. with an enthalpy of about 89 J/g and $T_{onset}$ of about 90.6° C. with an enthalpy of about 15 J/g. It shows about 0.4% weight loss at about 73° C. and 2.1% weight loss from 73° C. to 144° C. About 2.0% (by weight) ACN residue was detected by $^1$H NMR.

Pattern D is a degradation product with HPLC purity of about 0.2%. It was obtained in water by equilibration experiment. It has two thermal events with $T_{onset}$ of about 41.4° C. with an enthalpy of about 67 J/g and $T_{onset}$ of about 72.1° C. with an enthalpy of about 29 J/g. It shows about 0.6% weight loss at about 41° C. and 8.5% weight loss from 41° C. to 178° C.

Example 13: Preparation of Compound II Pattern 1

Figure 71:
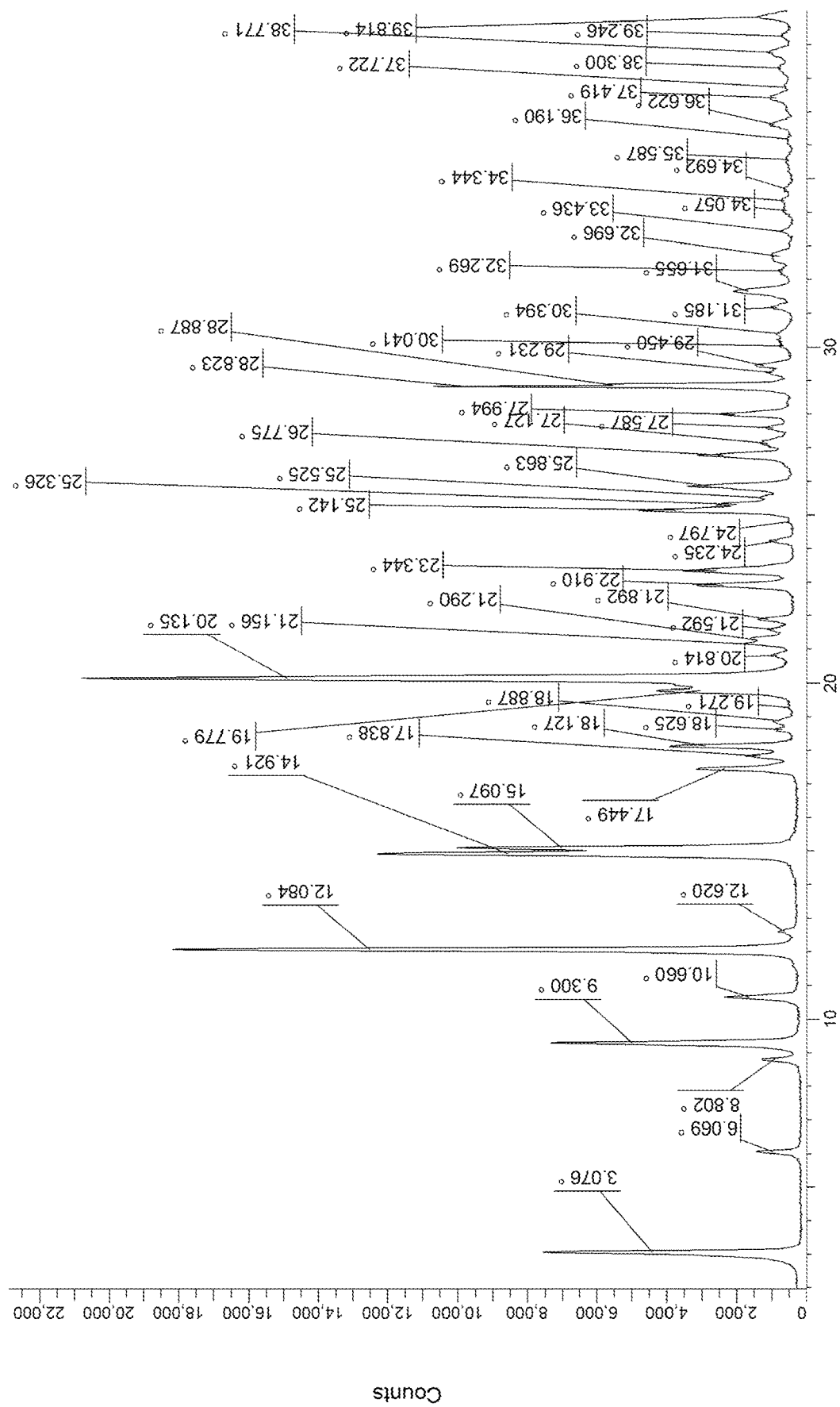
FIG. 71 is an XRPD diffractogram of Compound II Pattern 1 (Example 13).

Experiment 1. Small-Scale Synthesis and Preparation of Seeds 100 mg of $R_P$ Compound I free base and 0.3 mL of IPA were added into a glass vial. To it was added 1.0 equiv. of fumaric acid and the resulting mixture was stirred at 50° C. for 2 min, most of the material was precipitated out. To it 1.0 mL of heptanes was added. The sample was stirred at 50° C. for 1 h, then cooled to 3° C. with 0.1° C./min. After stirring at 3° C. for about 8 h, 0.4 mL of heptanes was added. Solids obtained was isolated by filtration and drying in vacuum oven at 40° C. for about 2 h to obtain Compound II Pattern 1. The characterization results are reported in Table 37. XRPD diffractogram of Compound II Pattern 1 is shown in FIG. 71.

TABLE 37

Properties of Compound II Pattern 1 (small scale preparation)

| Parameter | Method | Result |
| --- | --- | --- |
| X-ray diffraction | 3-40° (2 theta) | Compound II Pattern 1 |
| DSC melting onset | DSC, 10° C./min | Melting onset: 141.2° C., |

TABLE 37-continued

Properties of Compound II Pattern 1 (small scale preparation)

| Parameter | Method | Result |
|---|---|---|
| and enthalpy | | enthalpy: combined with decomposition |
| Thermogravimetry | TGA, 10° C./min | Weight loss: ~0.4% at 130° C. |
| Stoichiometry and residual solvent | $^1$H NMR | Free base:fumaric acid = 1:0.98; 0.2% (by weight) IPA residue |

Figure 72:
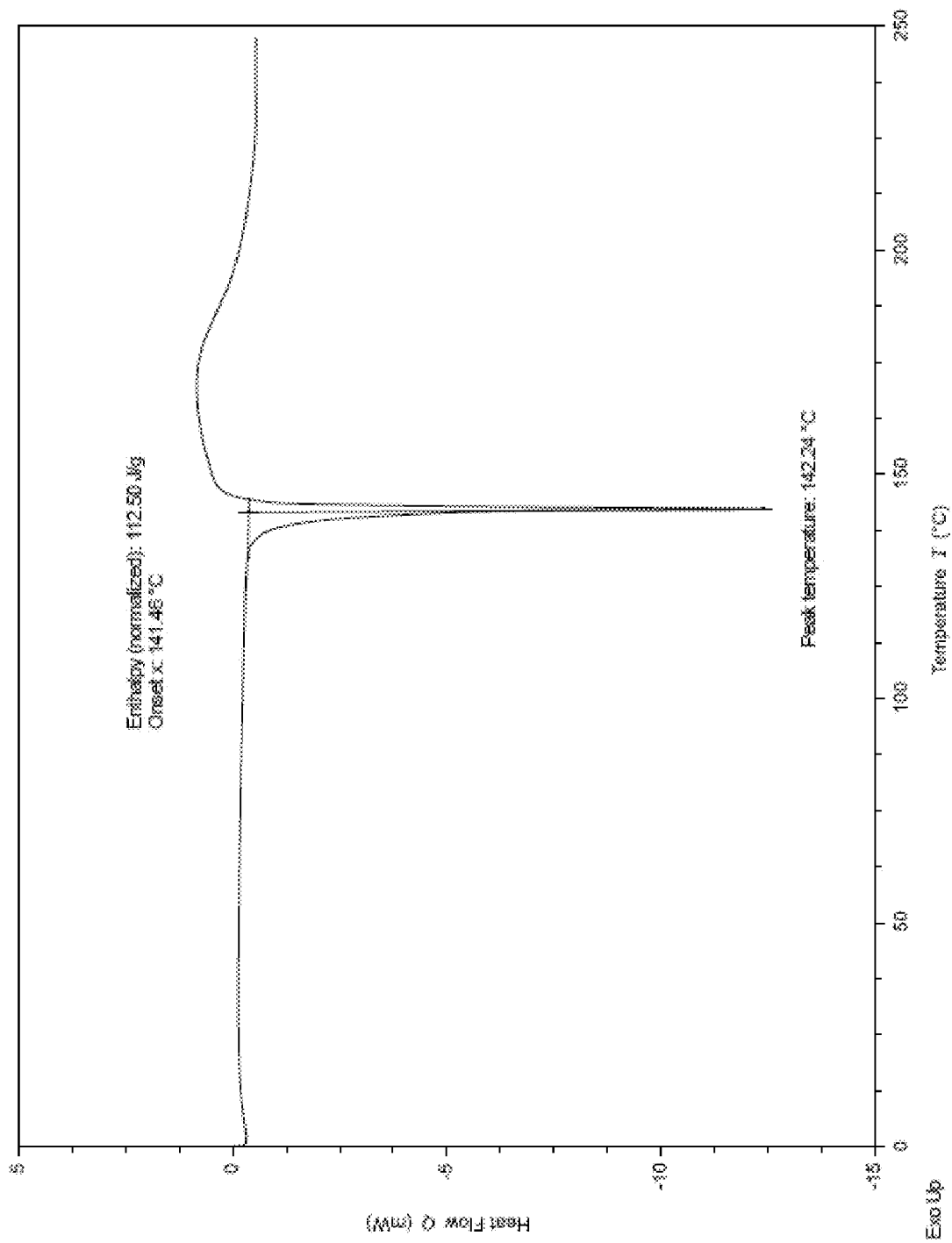
FIG. 72 is a DSC thermogram of Compound II Pattern 1 (Example 13).
Figure 73:
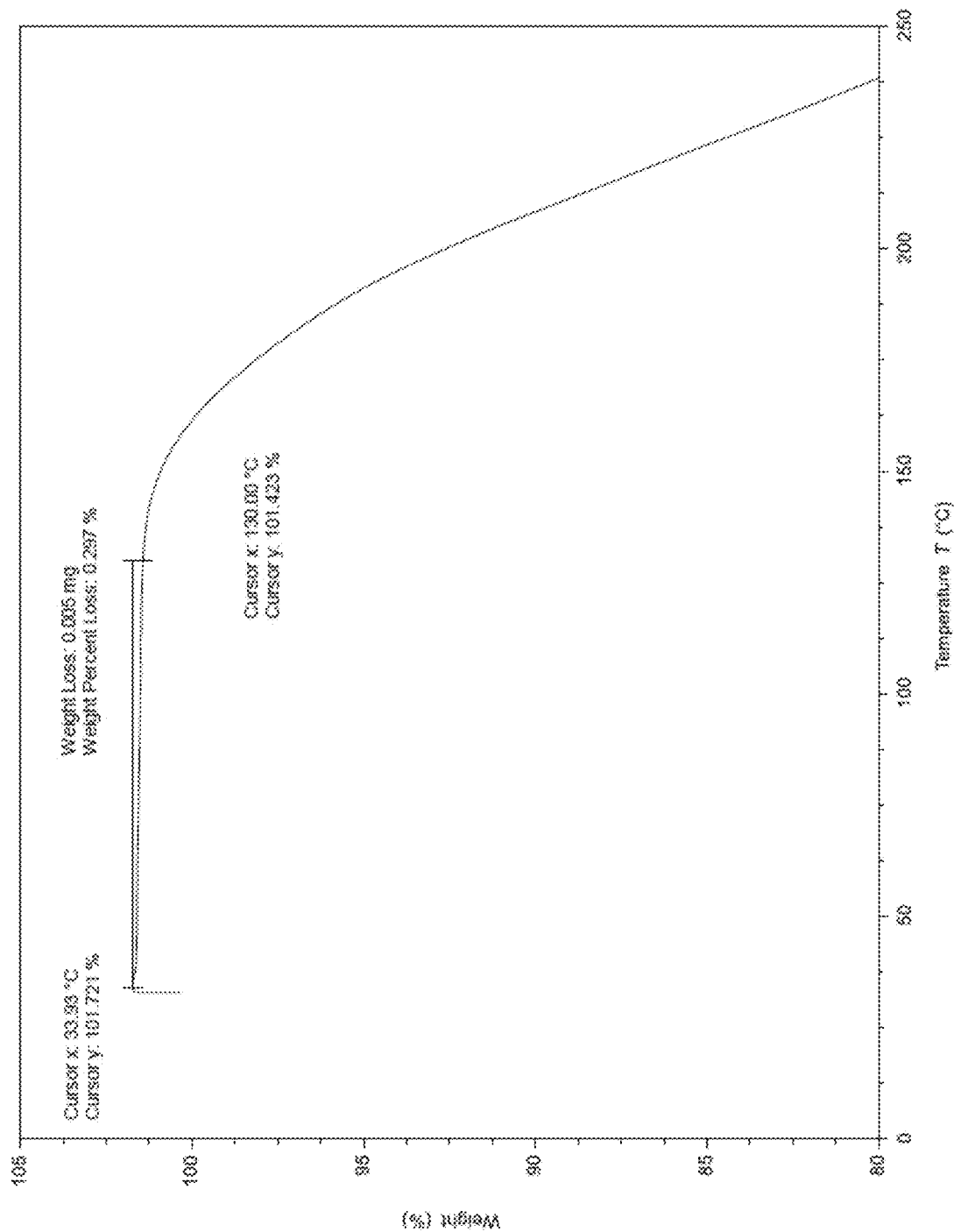
FIG. 73 is a TGA thermogram of Compound II Pattern 1 (Example 13).

Experiment 2. Large-Scale Preparation 3 g of $R_P$ Compound I free base and 9 mL of IPA were added into a glass vial. To it was added 1.0 equiv. of fumaric acid and the resulting mixture was stirred at 50° C. for 5 min. About 21 mg of Compound II Pattern 1 seeds from Experiment 1 were added into the mixture. 30 mL of heptanes was added into the mixture. The sample was stirred at 50° C. for 1 h then cooled to 3° C. with 0.1° C./min. After stirring at 3° C. for about 16 h, the solid obtained was isolated by filtration and drying in vacuum oven at 40° C. for about 4 h and at 50° C. for about 3 h. This resulted in 2.9 g of white solid Compound II Pattern 1 in a yield of 78.3%. XRPD diffractogram of Compound II Pattern 1 is shown in FIG. 71. DSC thermogram of Compound II Pattern 1 is shown in FIG. 72. TGA thermogram of Compound II Pattern 1 is shown in FIG. 73.

TABLE 38

Properties of Compound II Pattern 1 (large scale preparation)

| Parameter | Method | Result |
|---|---|---|
| Yield | | 78.3% |
| Purity | HPLC | 99.7%, (de = 98.4%) |
| X-ray diffraction | 3-40° (2 theta) | Mono fumarate Pattern 1 of Compound II |
| DSC melting onset and enthalpy | DSC, 10° C./min | Melting onset: 141.5° C., enthalpy: combined with decomposition |
| Thermogravimetry | TGA, 10° C./min | Weight loss: ~0.3% at 130° C. |
| Stoichiometry and residual solvent | $^1$H NMR | Free base:fumaric acid = 1:1.0; No residual solvent |
| Morphology | PLM | Irregular particles |

Compound II Pattern 1 is an anhydrate. The stoichiometry of free base:fumaric acid is about 1:1.0 based on $^1$H NMR result. It has a melting peak at $T_{onset}$ of 141.5° C. combined with decomposition. TGA shows about 0.3% weight loss at about 130° C. No residual solvent was detected by $^1$H NMR.

Example 14: Preparation of Compound IV Pattern 1

Figure 74:
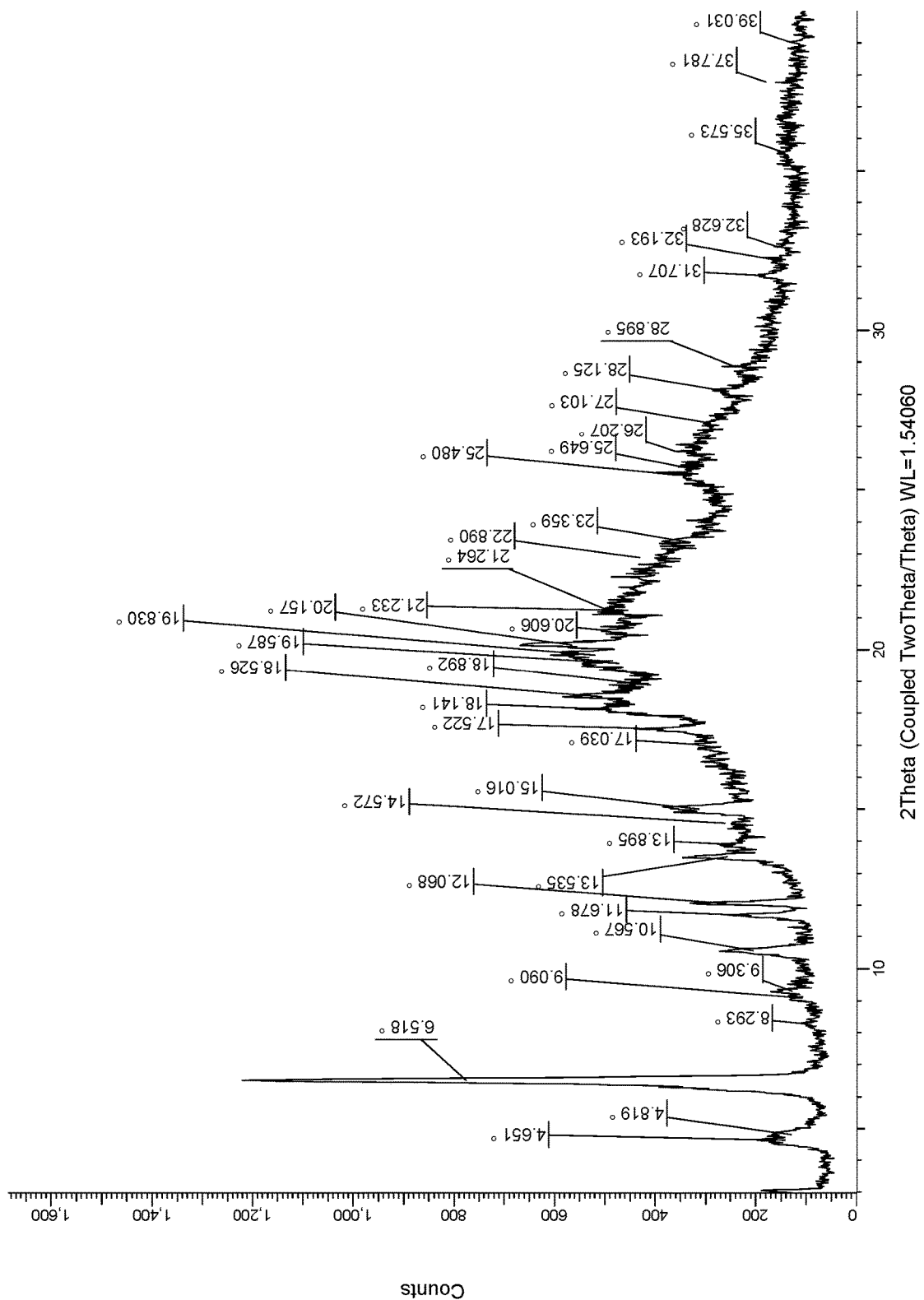
FIG. 74 is an XRPD diffractogram of Compound IV Pattern 1 (Example 14).
Figure 75:
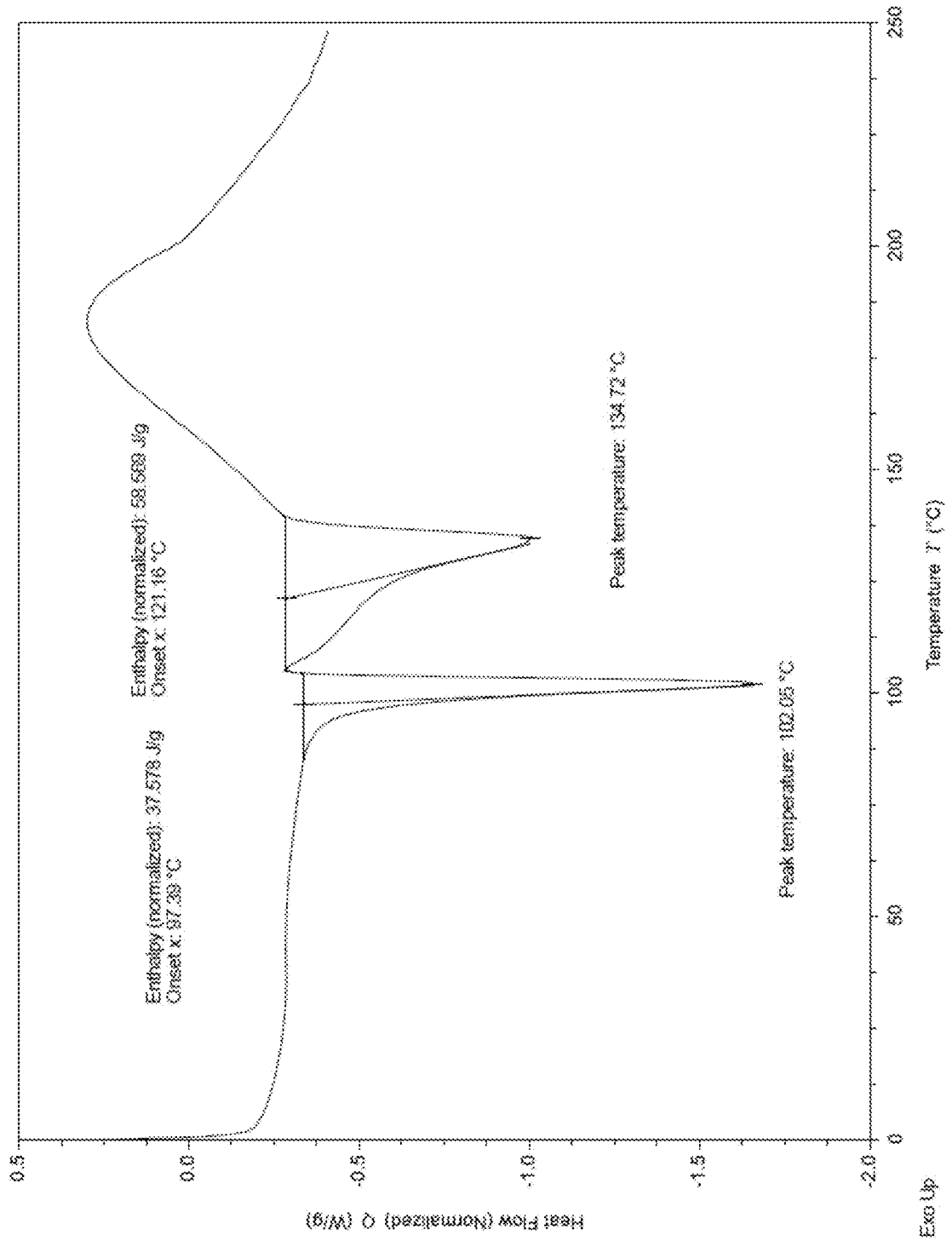
FIG. 75 is a DSC thermogram of Compound IV Pattern 1 (Example 14).
Figure 76:
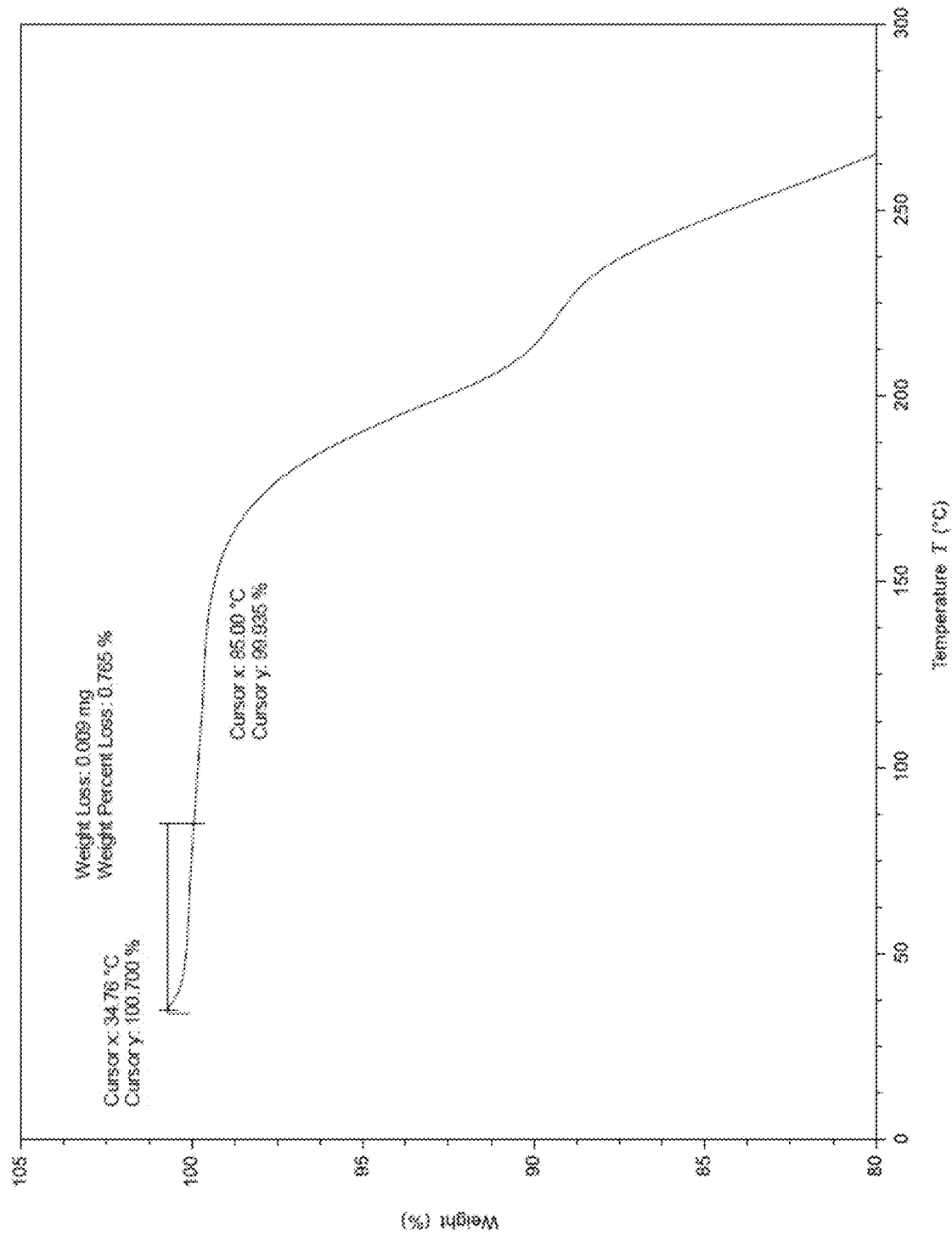
FIG. 76 is a TGA thermogram of Compound IV Pattern 1 (Example 14).

66 mg of $R_P$ Compound I free base and 0.2 mL of EtOH were added into a glass vial. To it was added 0.5 equiv. of fumaric acid and the resulting mixture was stirred at 50° C. for 2 h, then some solid precipitated out. To this suspension, 0.4 ml of heptanes was added and was stirred further at 25° C. for about 4 days. Solid was isolated by filtration and drying in vacuum oven at 50° C. for about 2 h. Compound IV Pattern 1 obtained was characterized as reported in Table 39. XRPD diffractogram of Compound IV Pattern 1 is shown in FIG. 74. DSC thermogram of Compound IV Pattern 1 is shown in FIG. 75. TGA thermogram of Compound IV Pattern 1 is shown in FIG. 76.

TABLE 39

Properties of Compound IV Pattern 1

| Parameter | Method | Result |
|---|---|---|
| X-ray diffraction | 3-40° (2 theta) | Compound IV Pattern 1 |
| DSC melting onset and enthalpy | DSC, 10° C./min | Melting onset: 97.4° C., enthalpy: 38 J/g; Melting onset: 121.2° C., enthalpy: combined with decomposition |
| Thermogravimetry | TGA, 10° C./min | Weight loss: ~0.8% at 85° C. |
| Stoichiometry and residual solvent | $^1$H NMR | Free base:fumaric acid = 1:0.5; No residual solvent |

Example 15: Preparation of Compound III Pattern 1

Figure 77:
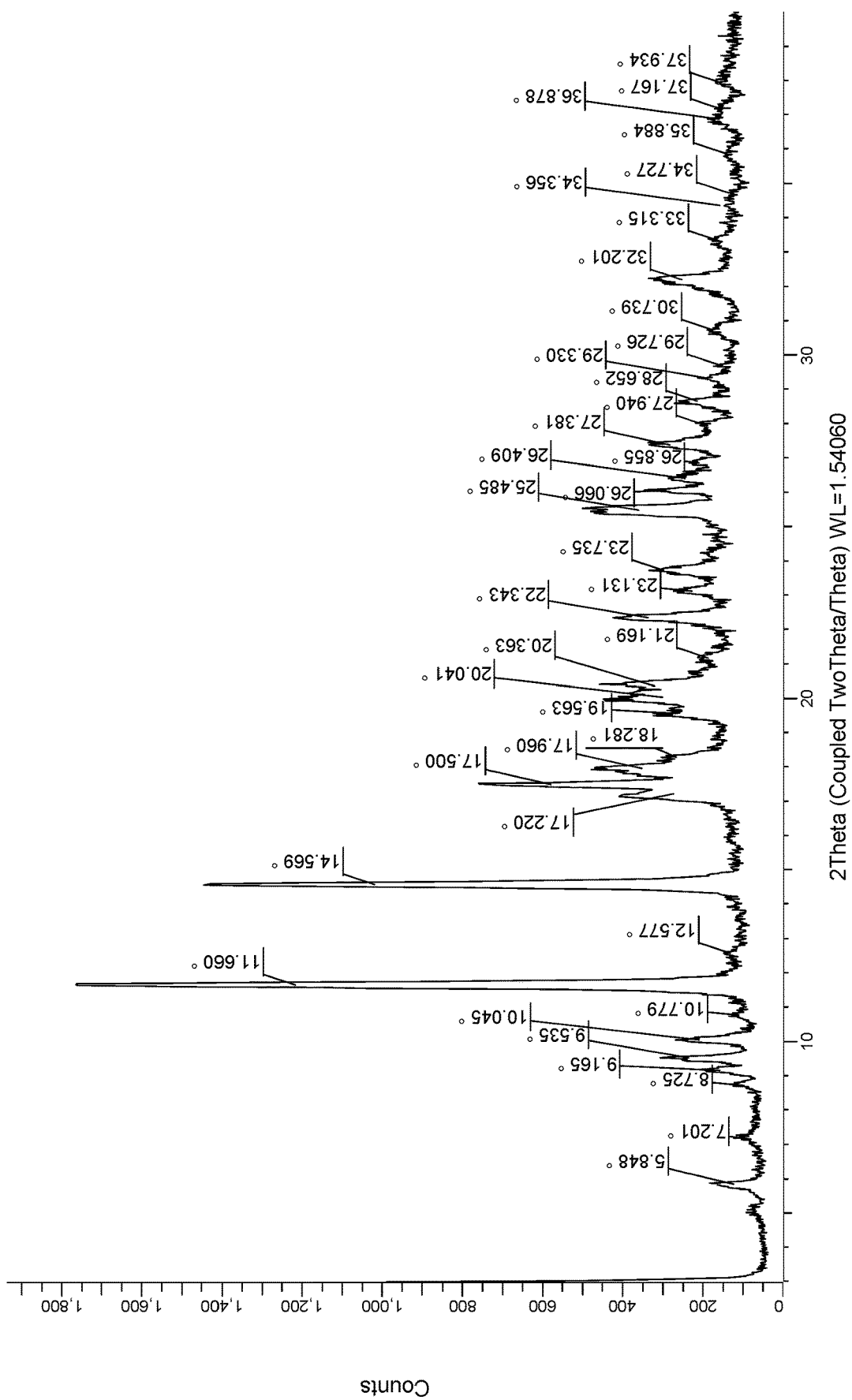
FIG. 77 is an XRPD diffractogram of Compound III Pattern 1 (Example 15).
Figure 78:
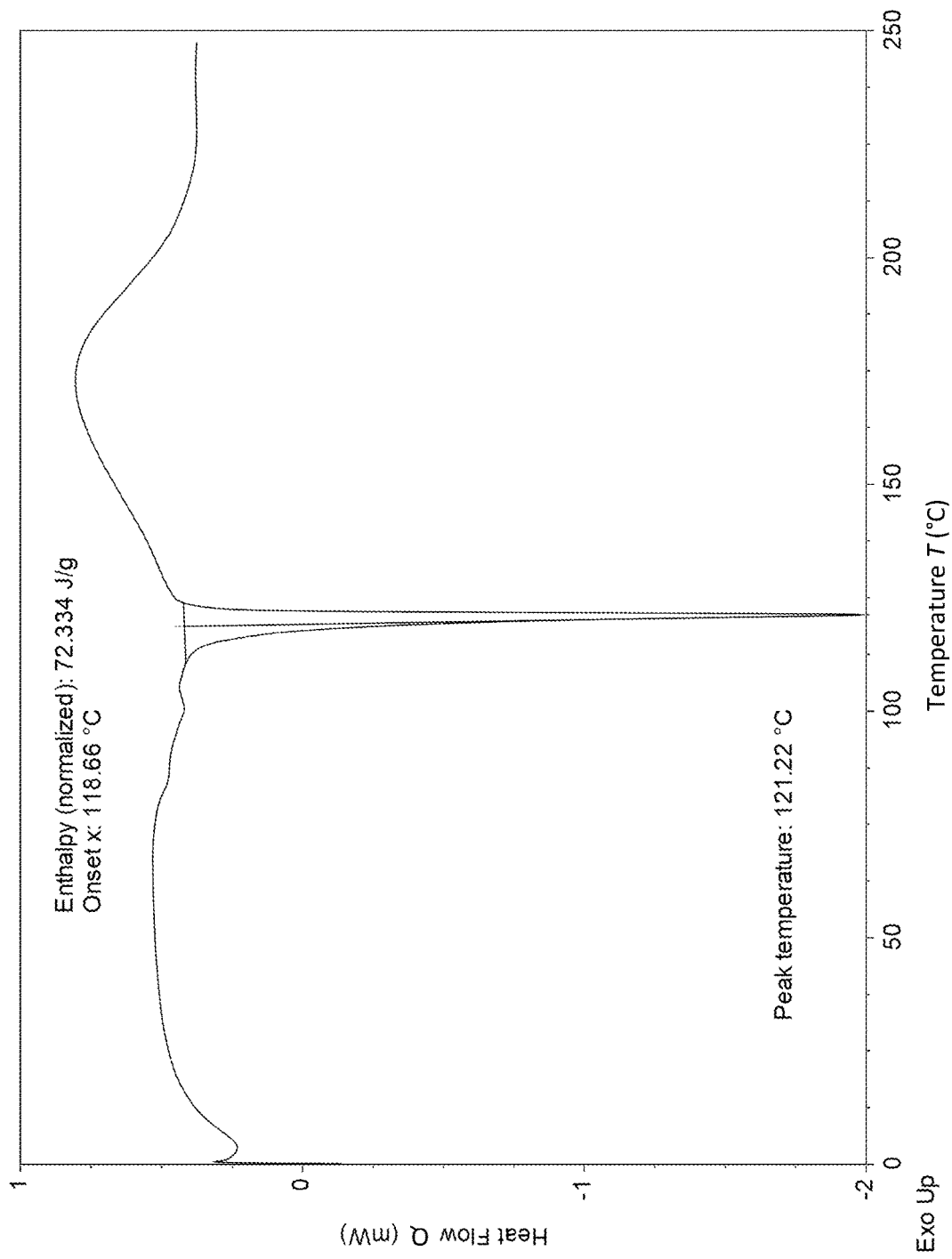
FIG. 78 is a DSC thermogram of Compound III Pattern 1 (Example 15).
Figure 79:
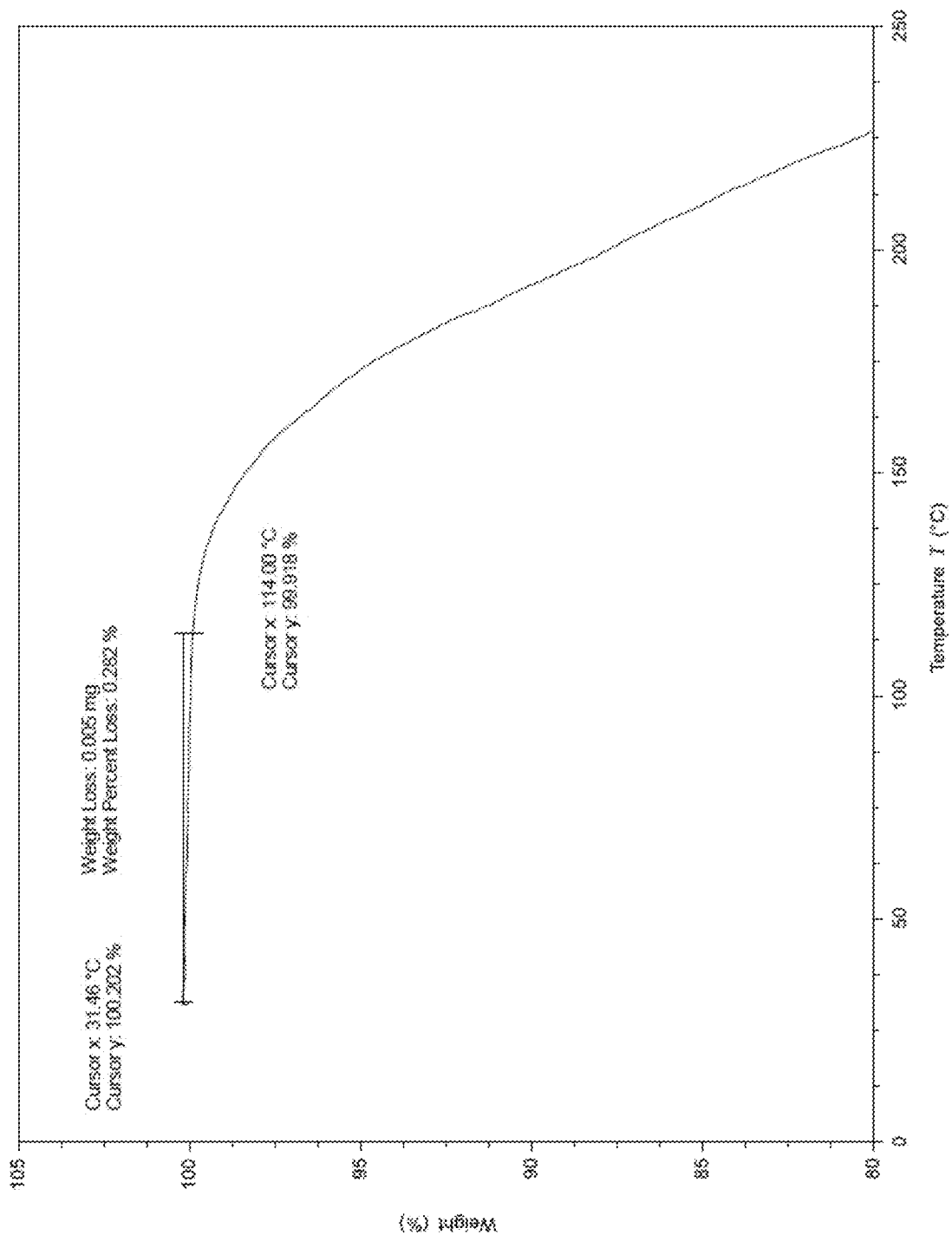
FIG. 79 is a TGA thermogram of Compound III Pattern 1 (Example 15).

100 mg of $S_P$ Compound I free base and 0.3 mL of IPA were added into a glass vial. To it was added 1.0 equiv. of fumaric acid and the mixture was stirred at 50° C. for 15 min, most of the material was precipitated out. After addition of 1.0 mL heptanes, the sample was stirred at 50° C. for 1 h, then cooled to 3° C. with 0.1° C./min. After stirring at 3° C. for about 8 h, 0.4 mL of heptanes was added into the mixture to get better suspension. White solid was isolated by filtration and drying in vacuum oven at 40° C. for about 2 h to yield Compound III Pattern 1. The characterization results are reported in Table 40. XRPD diffractogram of Compound III Pattern 1 is shown in FIG. 77. DSC thermogram of Compound III Pattern 1 is shown in FIG. 78. TGA thermogram of Compound III Pattern 1 is shown in FIG. 79.

TABLE 40

Properties of Compound III Pattern 1

| Parameter | Method | Result |
|---|---|---|
| X-ray diffraction | 3-40° (2 theta) | Compound III Pattern 1 |
| DSC melting onset and enthalpy | DSC, 10° C./min | Melting onset: 118.7° C., enthalpy: combined with decomposition |
| Thermogravimetry | TGA, 10° C./min | Weight loss: ~0.3% at 114° C. |
| Stoichiometry and residual solvent | $^1$H NMR | Free base:fumaric acid = 1:0.91; No residual solvent |

Example 16: Preparation of Compound III Pattern 2

Figure 80:
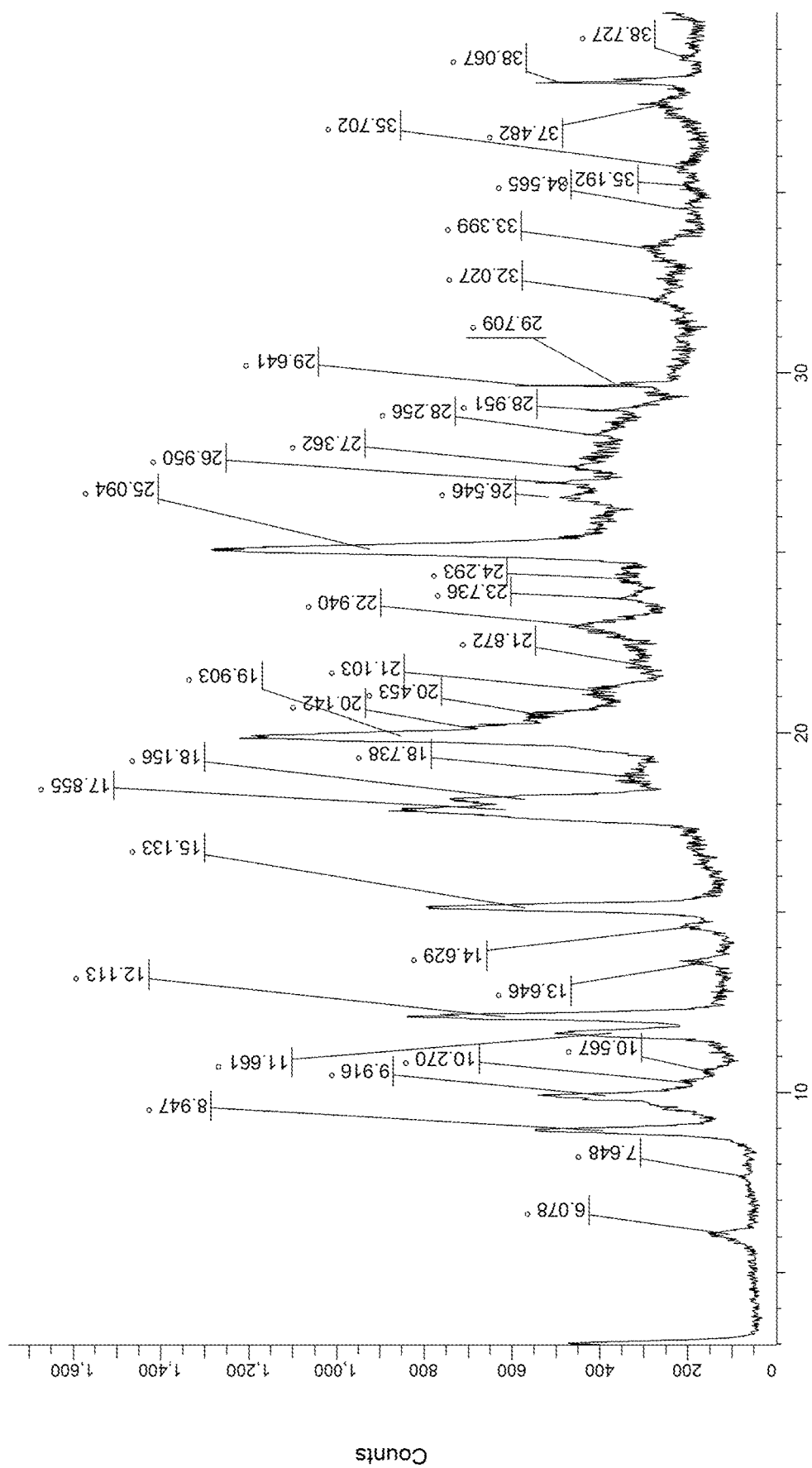
FIG. 80 is an XRPD diffractogram of Compound III Pattern 2 (Example 16).
Figure 81:
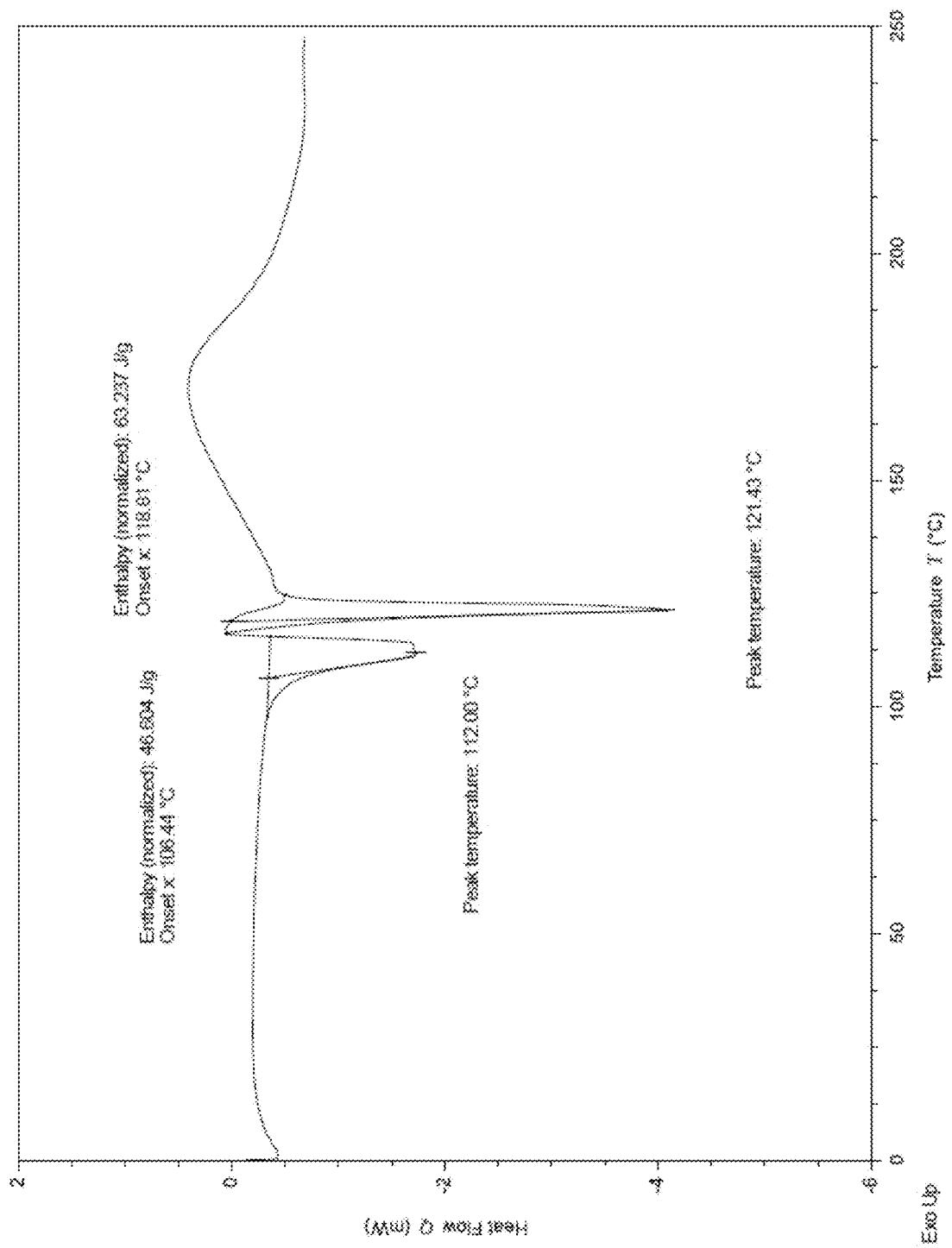
FIG. 81 is a DSC thermogram of Compound III Pattern 2 (Example 16).
Figure 82:
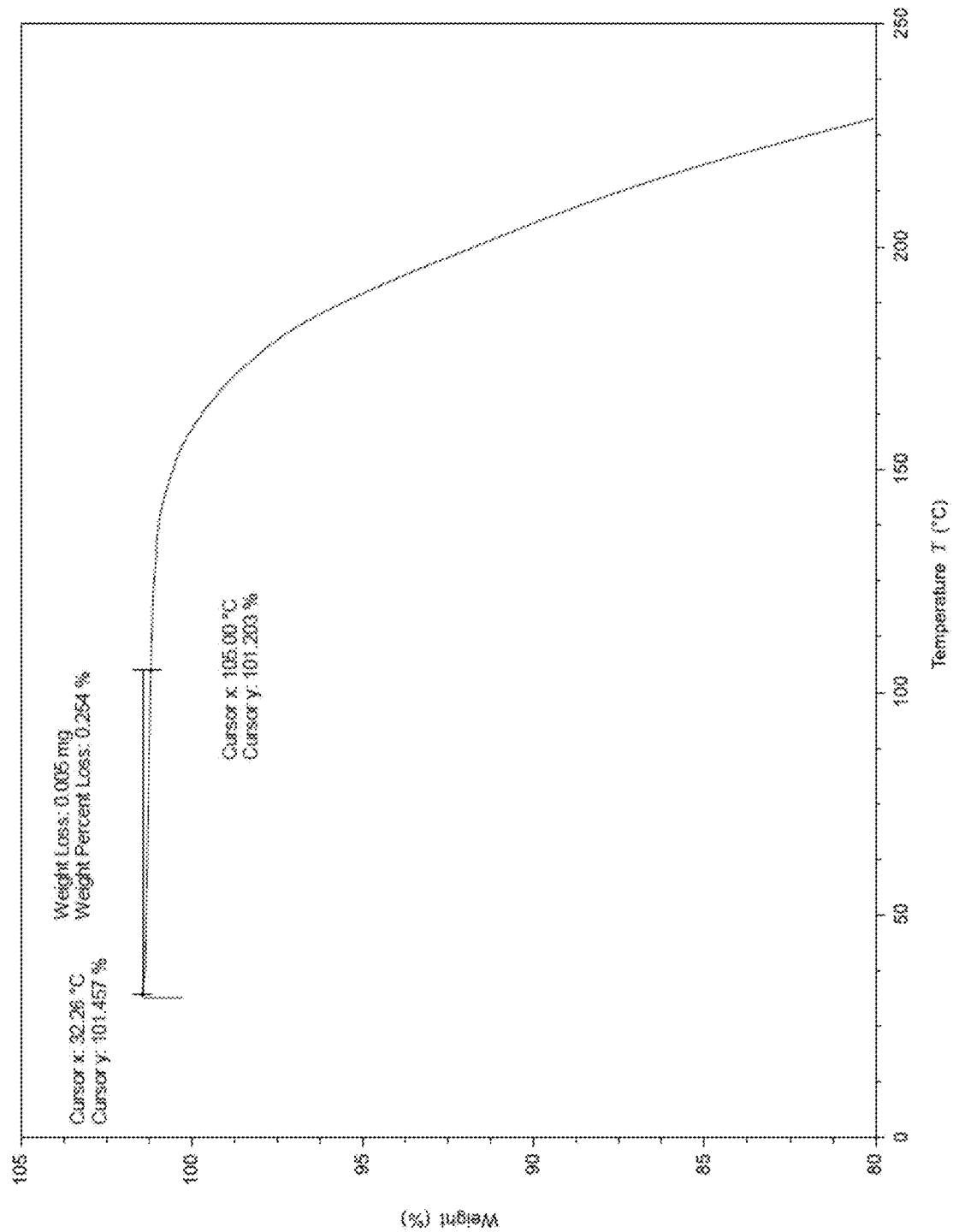
FIG. 82 is a TGA thermogram of Compound III Pattern 2 (Example 16).

3 g of $S_P$ Compound I free base and 9 mL of IPA were added into a glass vial. After the addition of 1.0 equiv. of fumaric acid, a lot of solid precipitated out immediately. 30 mL of heptanes was added into the mixture, then about 20 mg of Compound III Pattern 1 seeds were added into the mixture. The sample was stirred at 50° C. for 1 h, then cooled to 3° C. with 0.1° C./min. After stirring at 3° C. for about 20 h, the sample was heated from 3° C. to 50° C. within 20 mins, then 0.2 equiv. of fumaric acid and 1.5 ml of heptanes were added into the mixture. The resulting mixture was stirred at 50° C. for about 2 h then cooled to 3° C. with 0.1° C./min. After stirring at 3° C. for about 13 h, it was reheated to 50° C. within 20 mins and kept stirred at 50° C. for about 6 h. It was cooled to 3° C. with 0.1° C./min and stirred at 3° C. for about 2 days. The resulting solid was isolated by filtration and drying in vacuum oven at 50° C. for about 3 h to obtain 3.1 g of white solid in a yield of 83.6%. The results are reported in Table 41. XRPD diffractogram of Compound III Pattern 2 is shown in FIG. 80. DSC thermogram of Compound III Pattern 2 is shown in FIG. 81. TGA thermogram of Compound III Pattern 2 is shown in FIG. 82.

TABLE 41

Properties of Compound III Pattern 2

| Parameter | Method | Result |
| --- | --- | --- |
| Yield |  | 83.6% |
| Purity | HPLC | 98.8% |
| X-ray diffraction | 3-40° (2 theta) | Compound III Pattern 2 |
| DSC melting onset and enthalpy | DSC, 10° C./min | Melting onset: 106.4° C., enthalpy: 47 J/g; Melting onset: 118.8° C., enthalpy: 63 J/g |
| Thermogravimetry | TGA, 10° C./min | Weight loss: ~0.3% at 105° C. |
| Stoichiometry and residual solvent | $^1$H NMR | Free base:fumaric acid = 1:1.2; No residual solvent |
| Morphology | PLM | Irregular particles |

Compound III Pattern 2 is an anhydrate. The stoichiometry of free base: fumaric acid is about 1:1.2 based on $^1$H NMR result. It has two melting peaks at $T_{onset}$ of 106.4° C. with an enthalpy of about 47 J/g and $T_{onset}$ of 118.8° C. with an enthalpy of about 63 J/g. It shows about 0.3% weight loss at about 105° C. No residual solvent was detected by $^1$H NMR.

Example 17: Preparation of Compound V Pattern 1

Figure 83:
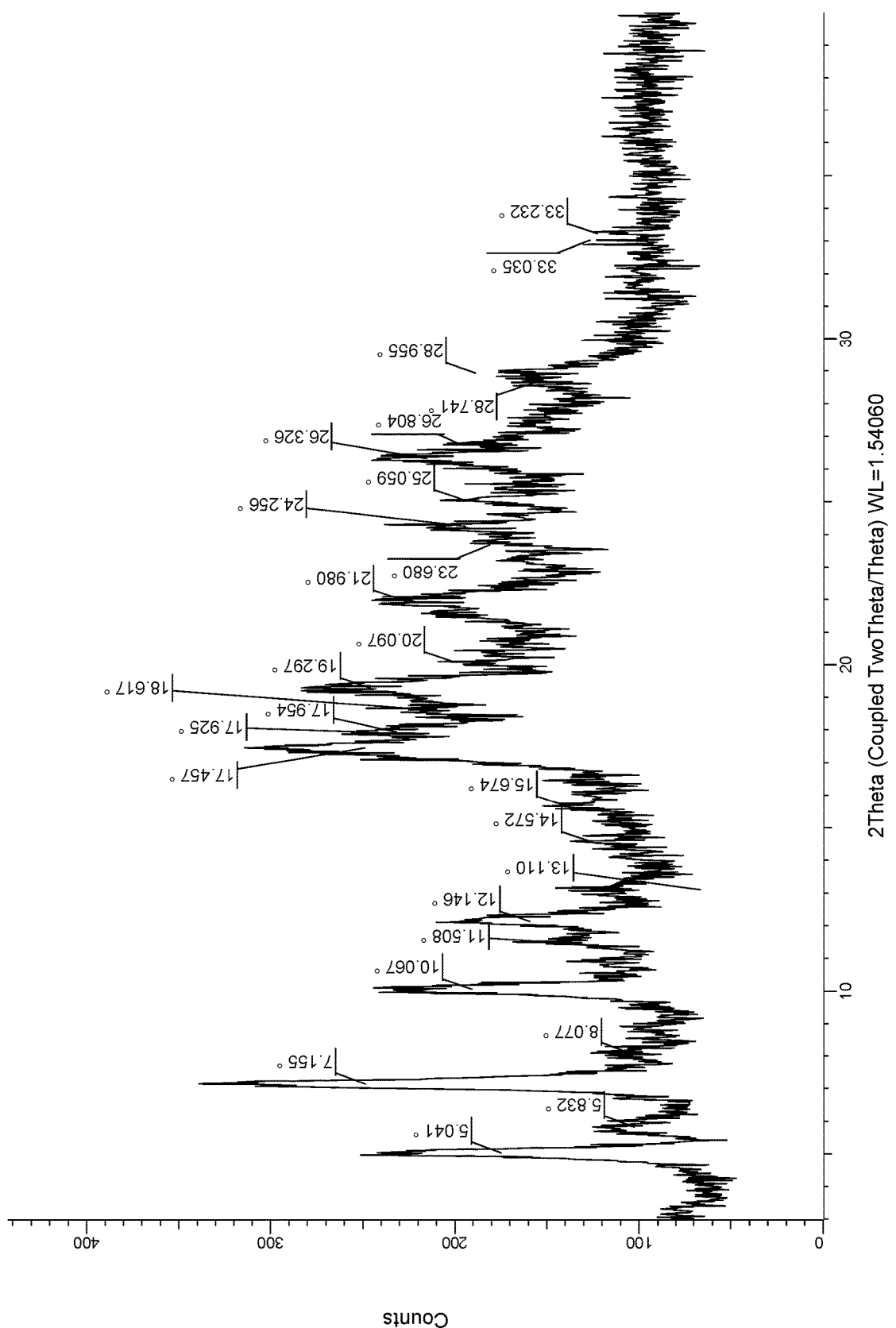
FIG. 83 is an XRPD diffractogram of Compound V Pattern 1 (Example 17).
Figure 84:
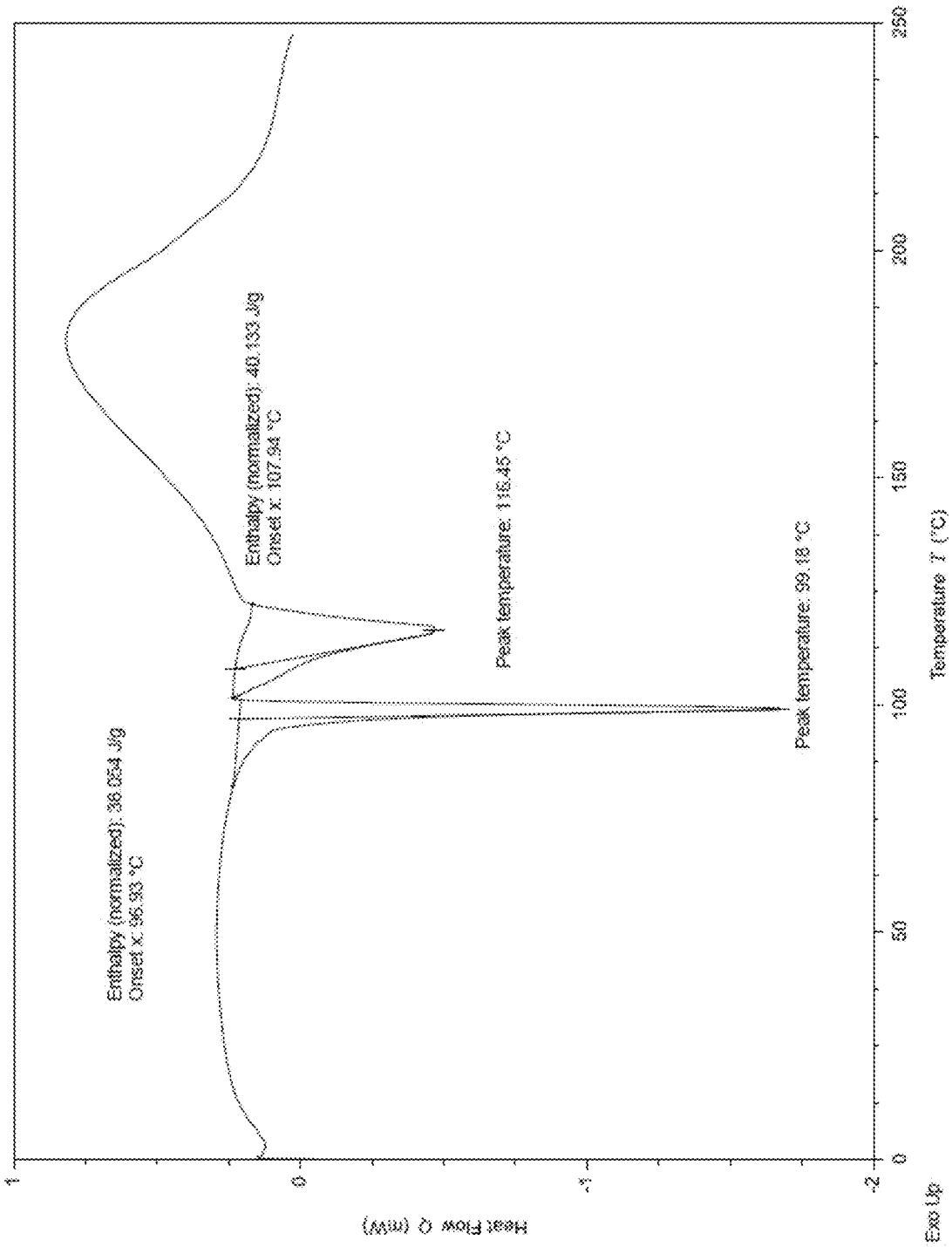
FIG. 84 is a DSC thermogram of Compound V Pattern 1 (Example 17).
Figure 85:
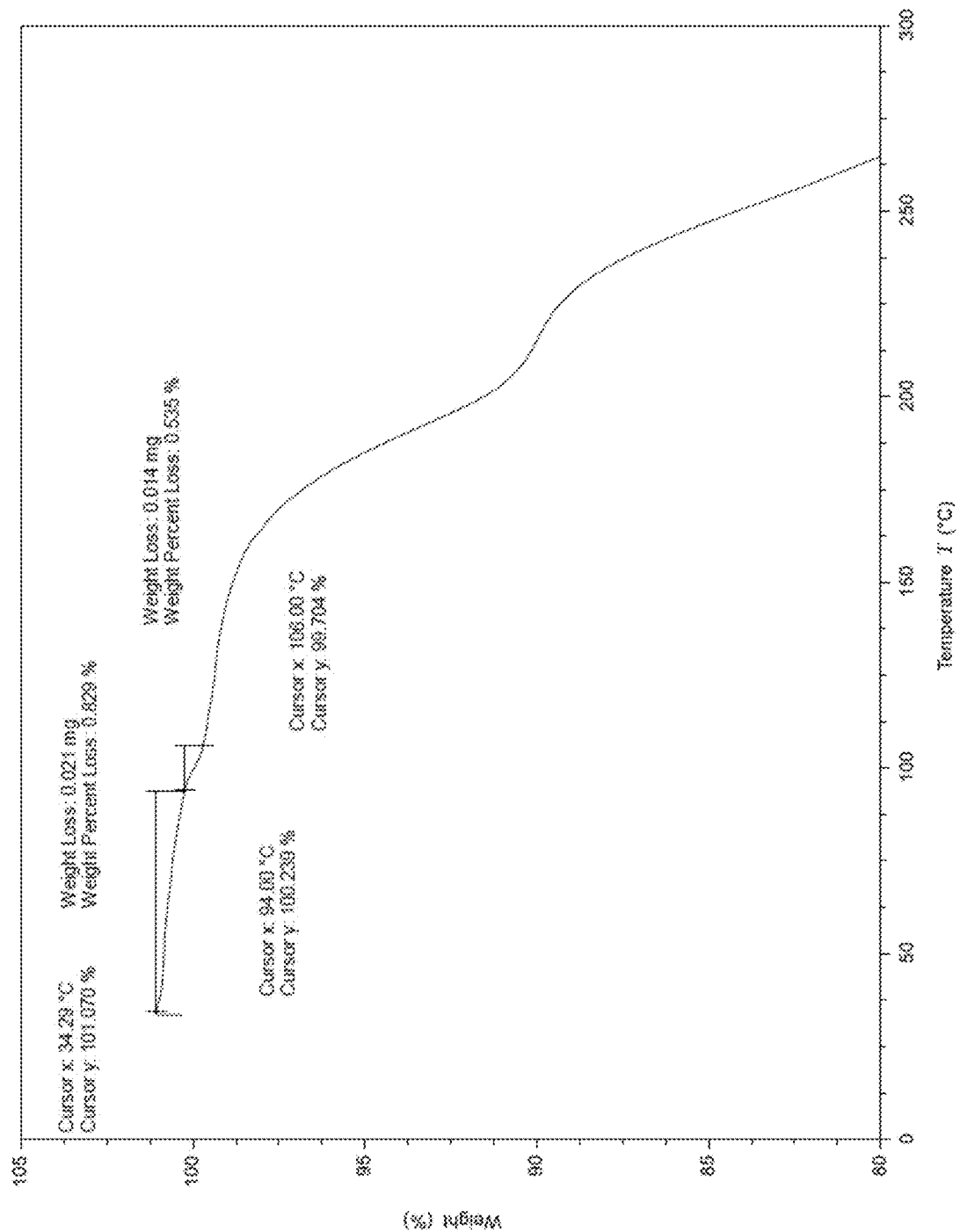
FIG. 85 is a TGA thermogram of Compound V Pattern 1 (Example 17).

100 mg of $S_P$ Compound I free base and 1.0 equiv. of fumaric acid was added into a glass vial followed by the addition of 0.8 mL of IPA. After stirring at 50° C. for about 1 h, a clear solution was obtained. About 2 mg Compound III Pattern 1 seeds were added into the mixture. After observing precipitation of some solid mass, 1 mL of heptanes was added into the mixture. The mixture was stirred at 50° C. for 2 h then cooled to 3° C. with 0.1° C./min. It was kept stirred at 3° C. for about 3 days. Solid was isolated by filtration and drying in vacuum oven at 50° C. for about 2 h to yield Compound V Pattern 1. The results are reported in Table 42. XRPD diffractogram of Compound V Pattern 1 is shown in FIG. 83. DSC thermogram of Compound V Pattern 1 is shown in FIG. 84. TGA thermogram of Compound V Pattern 1 is shown in FIG. 85.

TABLE 42

Properties of Compound V Pattern 1

| Parameter | Method | Result |
| --- | --- | --- |
| X-ray diffraction | 3-40° (2 theta) | Compound V Pattern 1 |
| DSC melting onset and enthalpy | DSC, 10° C./min | Melting onset: 96.9° C., enthalpy: 38 J/g; Melting onset: 107.9° C., enthalpy: 40 J/g |

TABLE 42-continued

Properties of Compound V Pattern 1

| Parameter | Method | Result |
| --- | --- | --- |
| Thermogravimetry | TGA, 10° C./min | Weight loss: ~0.8% at 94° C.; ~0.5% from 94° C. to 106° C. |
| Stoichiometry and residual solvent | $^1$H NMR | Free base:fumaric acid = 1:0.5; No residual solvent |

Example 18: Preparation of Compound V Pattern 2

Figure 86:
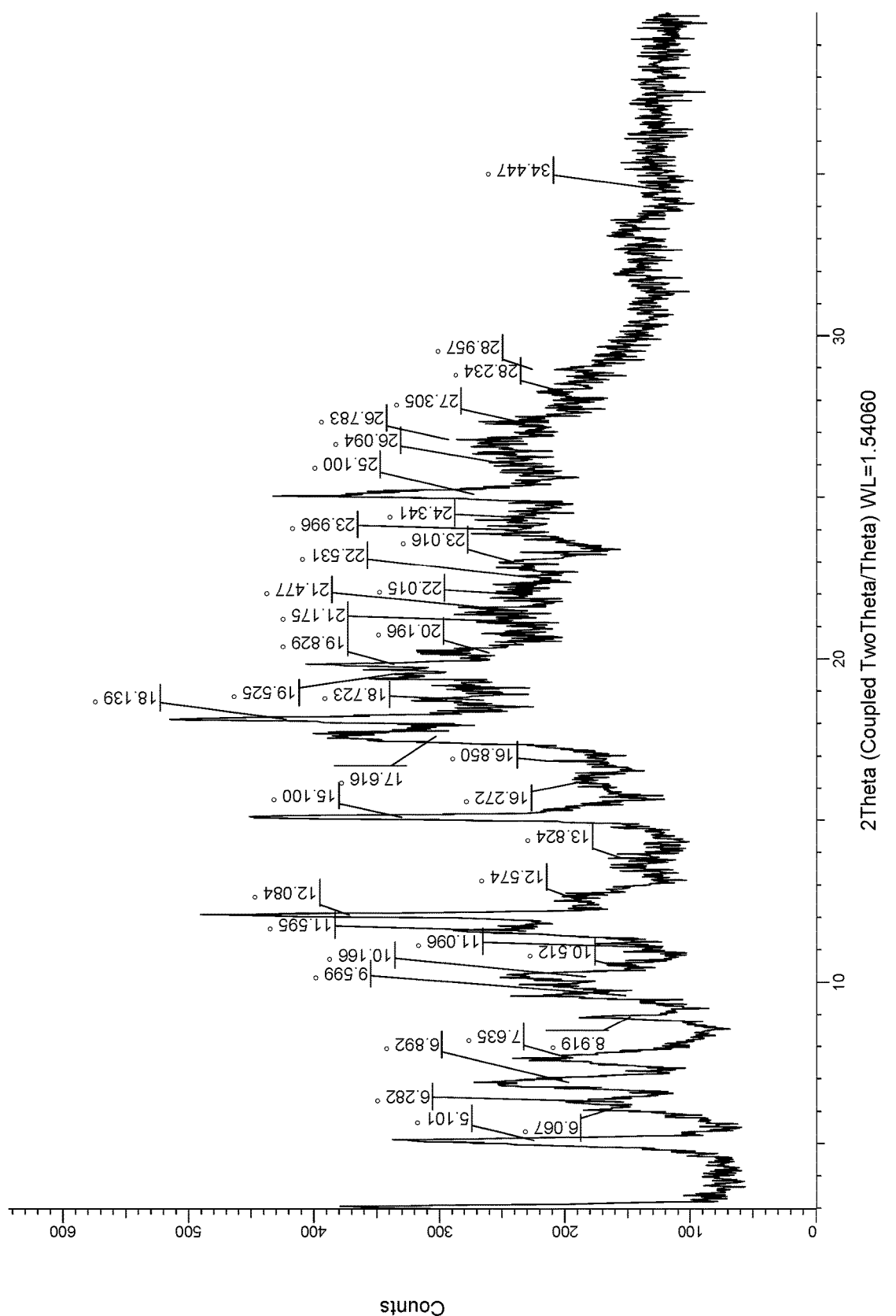
FIG. 86 is an XRPD diffractogram of Compound V Pattern 2 (Example 18).
Figure 87:
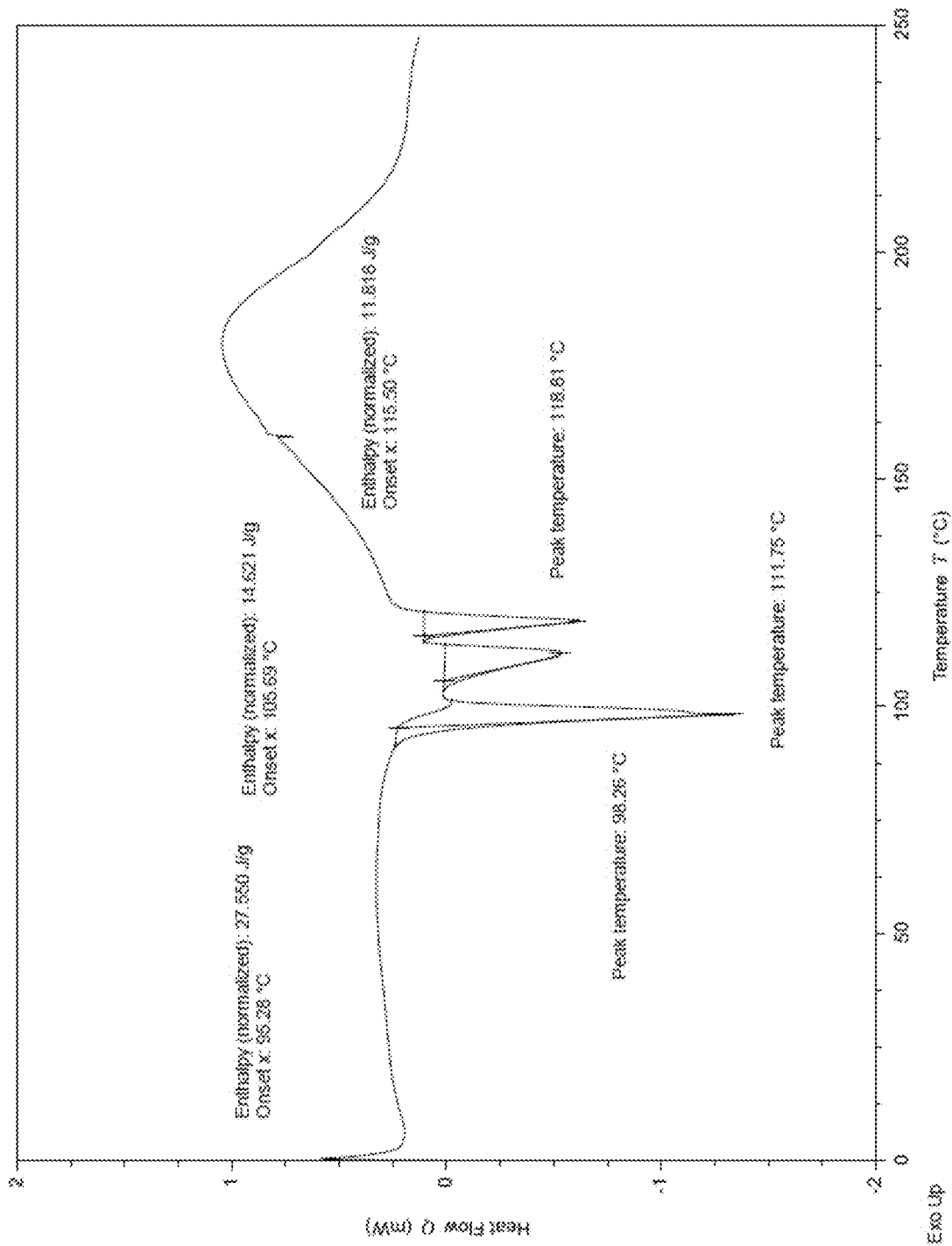
FIG. 87 is a DSC thermogram of Compound V Pattern 2 (Example 18).
Figure 88:
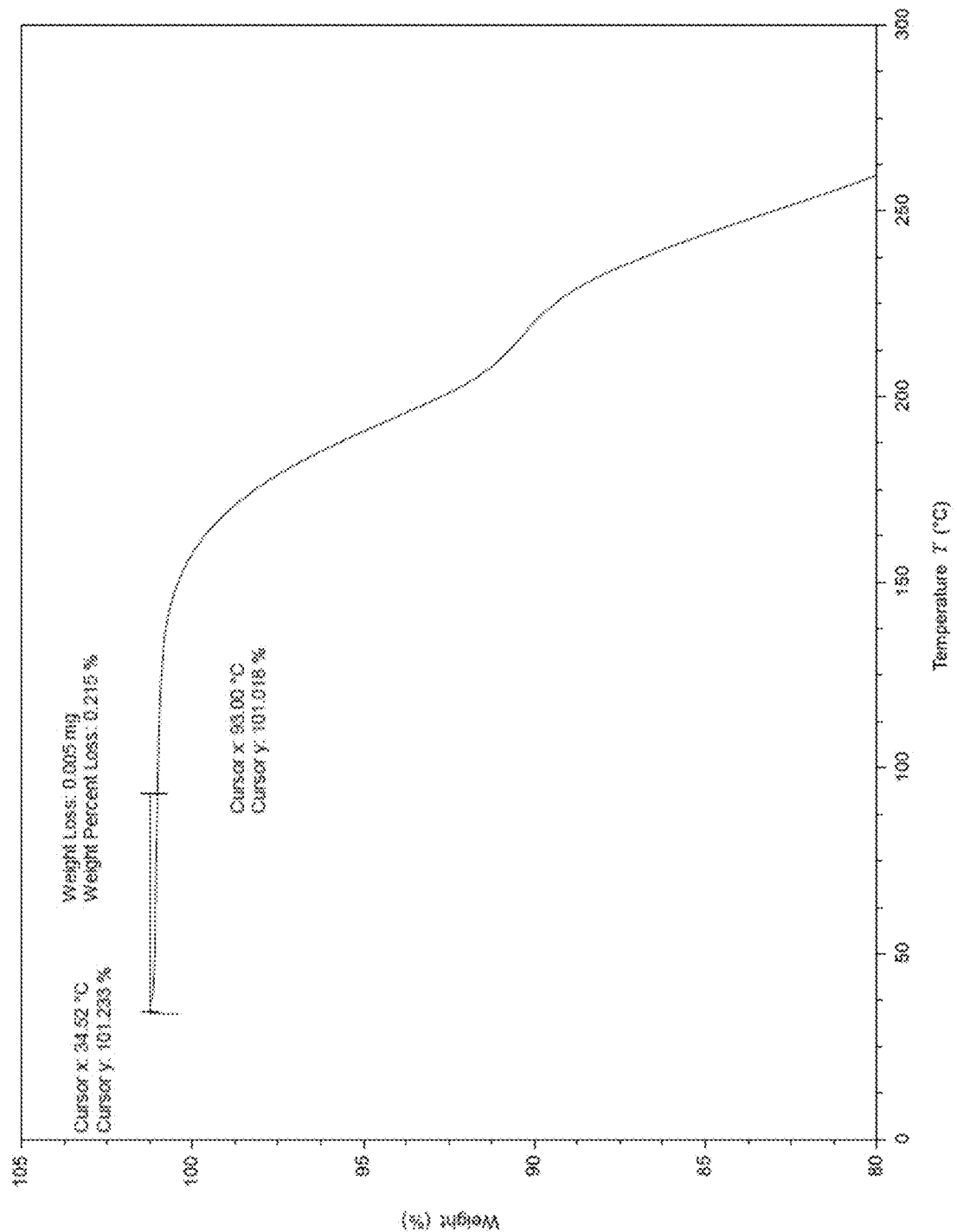
FIG. 88 is a TGA thermogram of Compound V Pattern 2 (Example 18).
Figure 89:
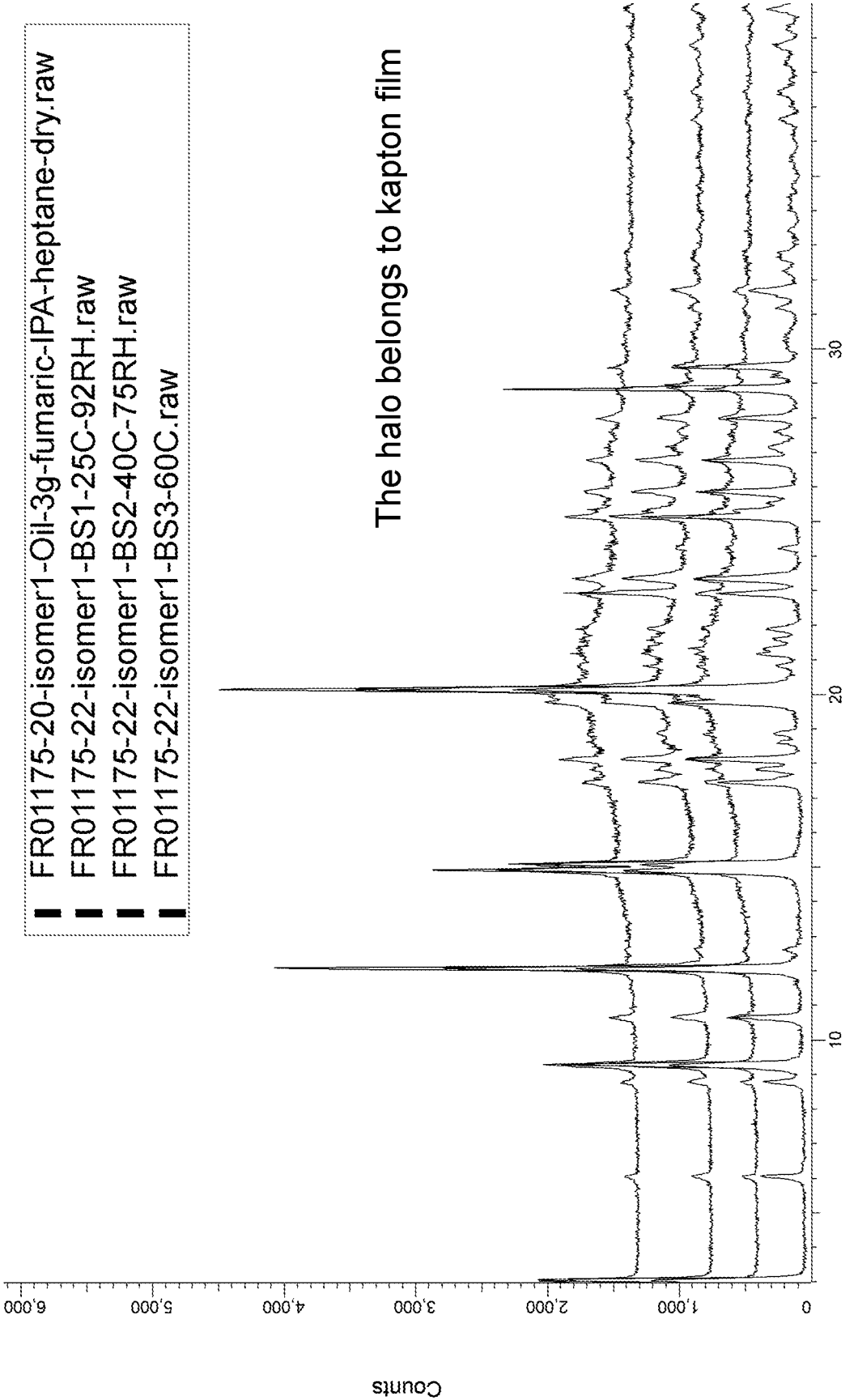
FIG. 89 is a comparison of XRPD diffractograms of Compound II Pattern 1 obtained from bulk stability study (Example 19).
Figure 90:
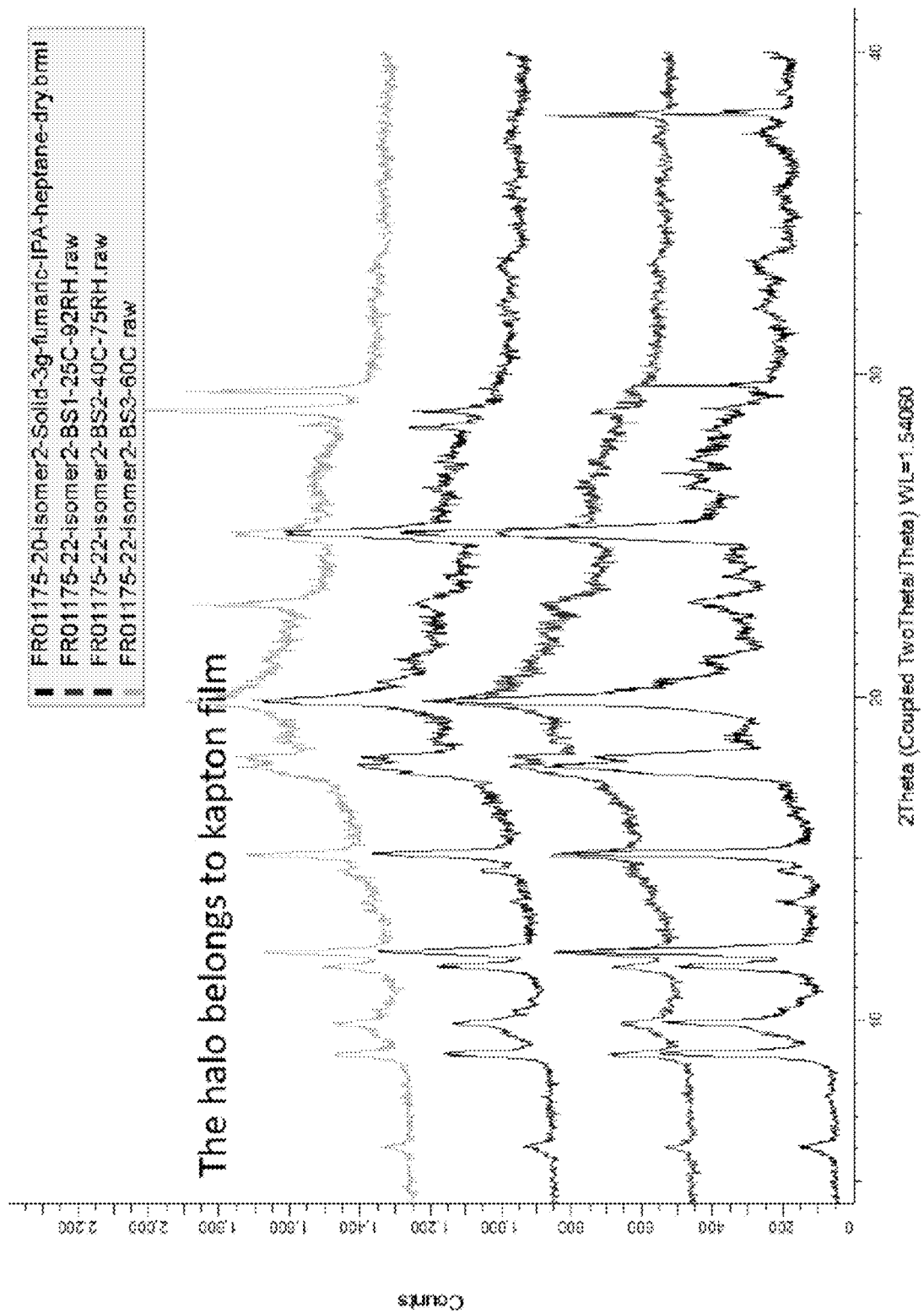
FIG. 90 is a comparison of XRPD diffractograms of Compound III Pattern 2 obtained from bulk stability study (Example 19).
Figure 91:
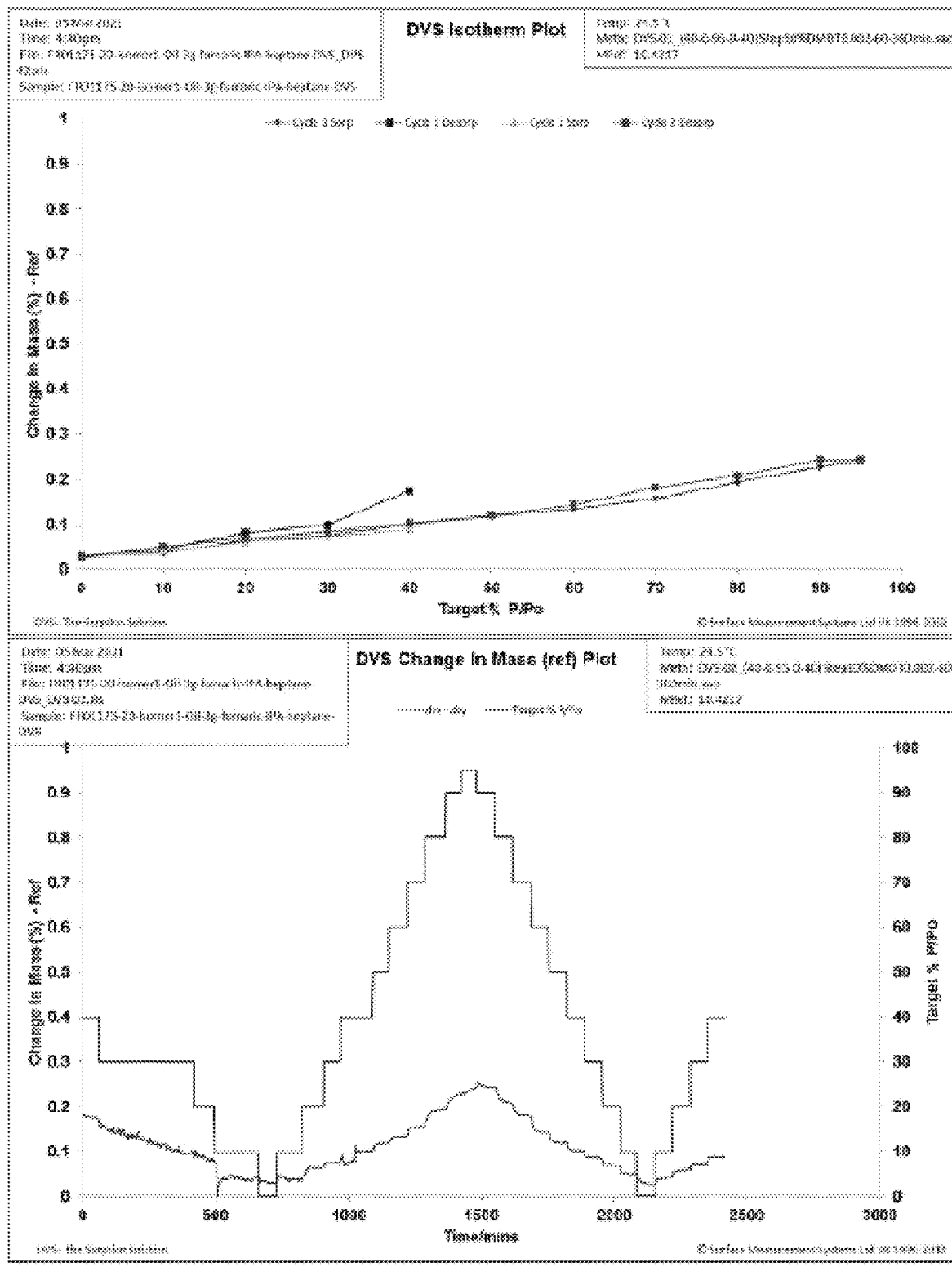
FIG. 91 is a Dynamic Vapor Sorption (DVS) plot and DVS change in mass plot for Compound II Pattern 1 (Example 21).
Figure 92:
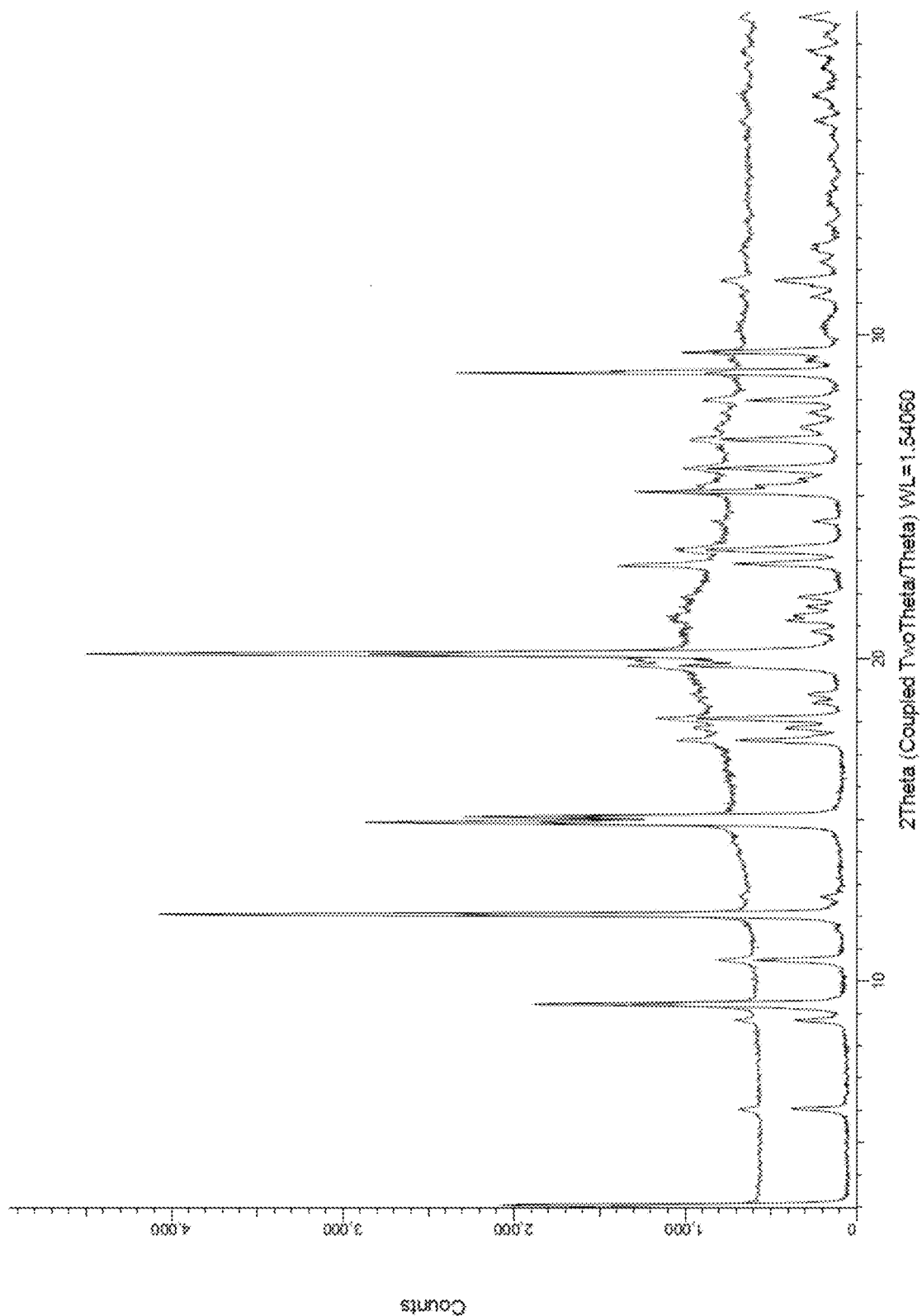
FIG. 92 is a comparison of XRPD diffractograms of Compound II Pattern 1 before and after DVS study (Example 21).
Figure 93:
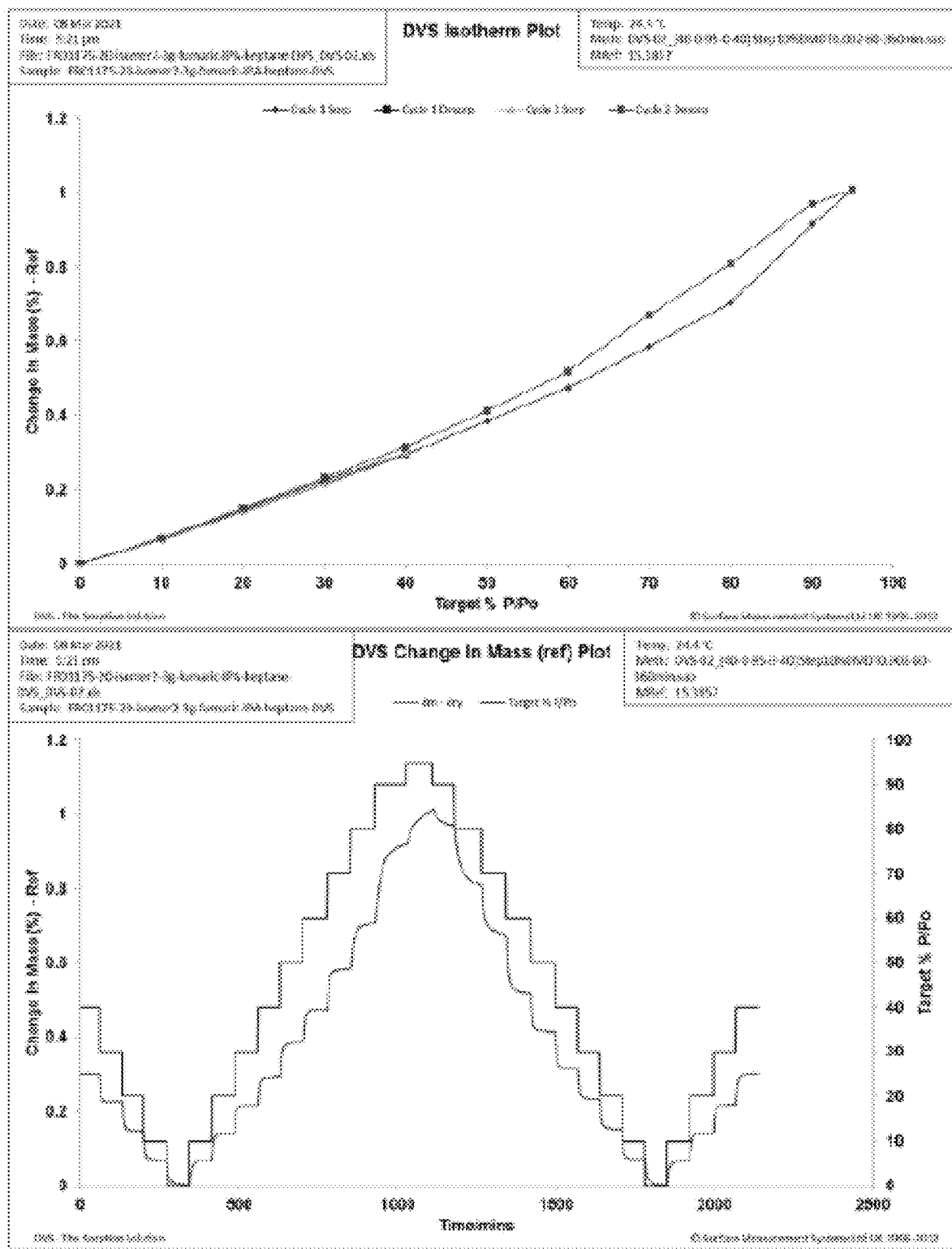
FIG. 93 is a Dynamic Vapor Sorption (DVS) plot and DVS change in mass plot for Compound III Pattern 2 (Example 21).
Figure 94:
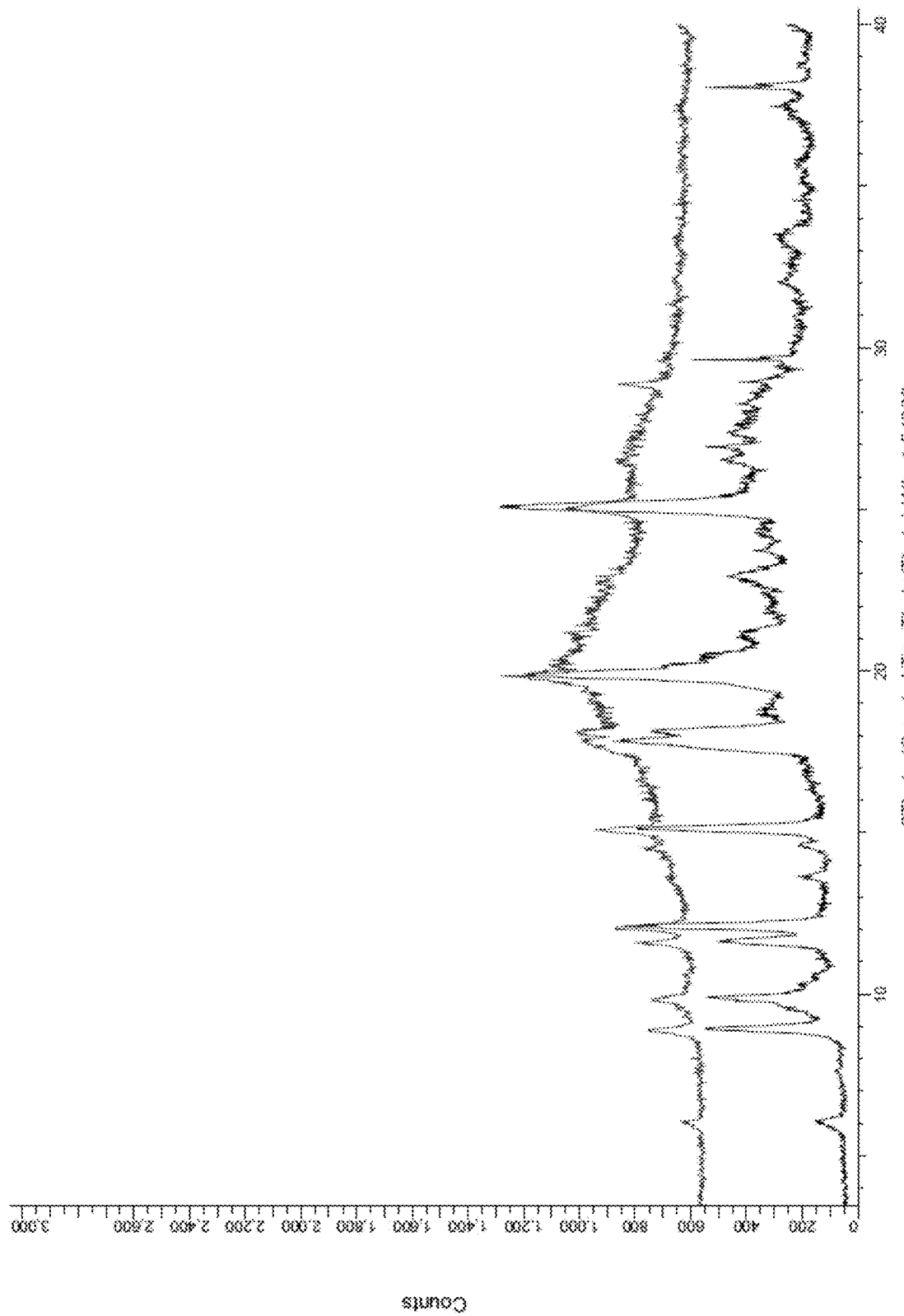
FIG. 94 is a comparison of XRPD diffractograms of Compound III Pattern 2 before and after DVS study (Example 21).
Figure 95:
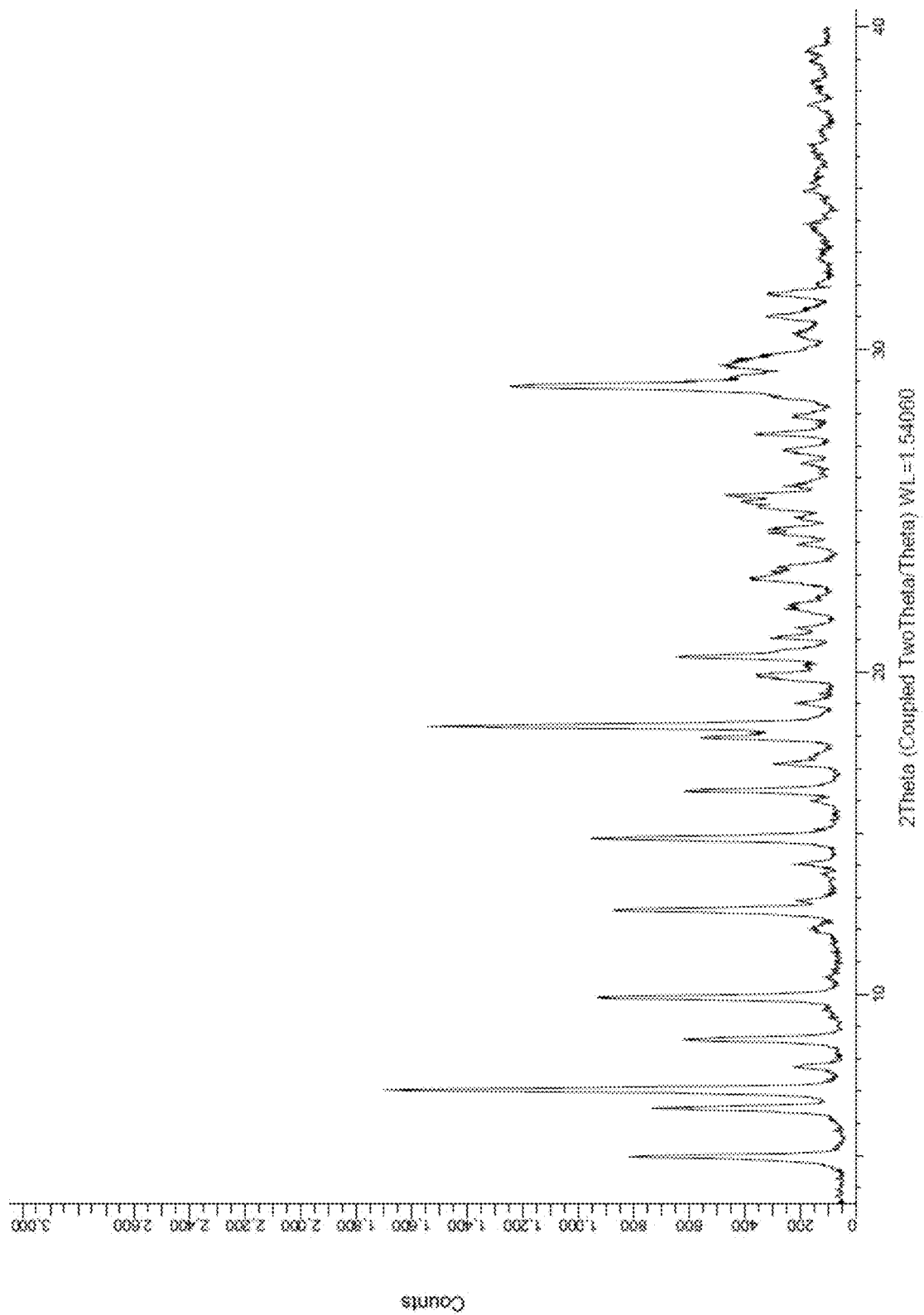
FIG. 95 is an XRPD diffractogram of Compound IV Pattern 1 obtained from Compound II Pattern 1 in Example 22 in Experiment PS4.
Figure 96:
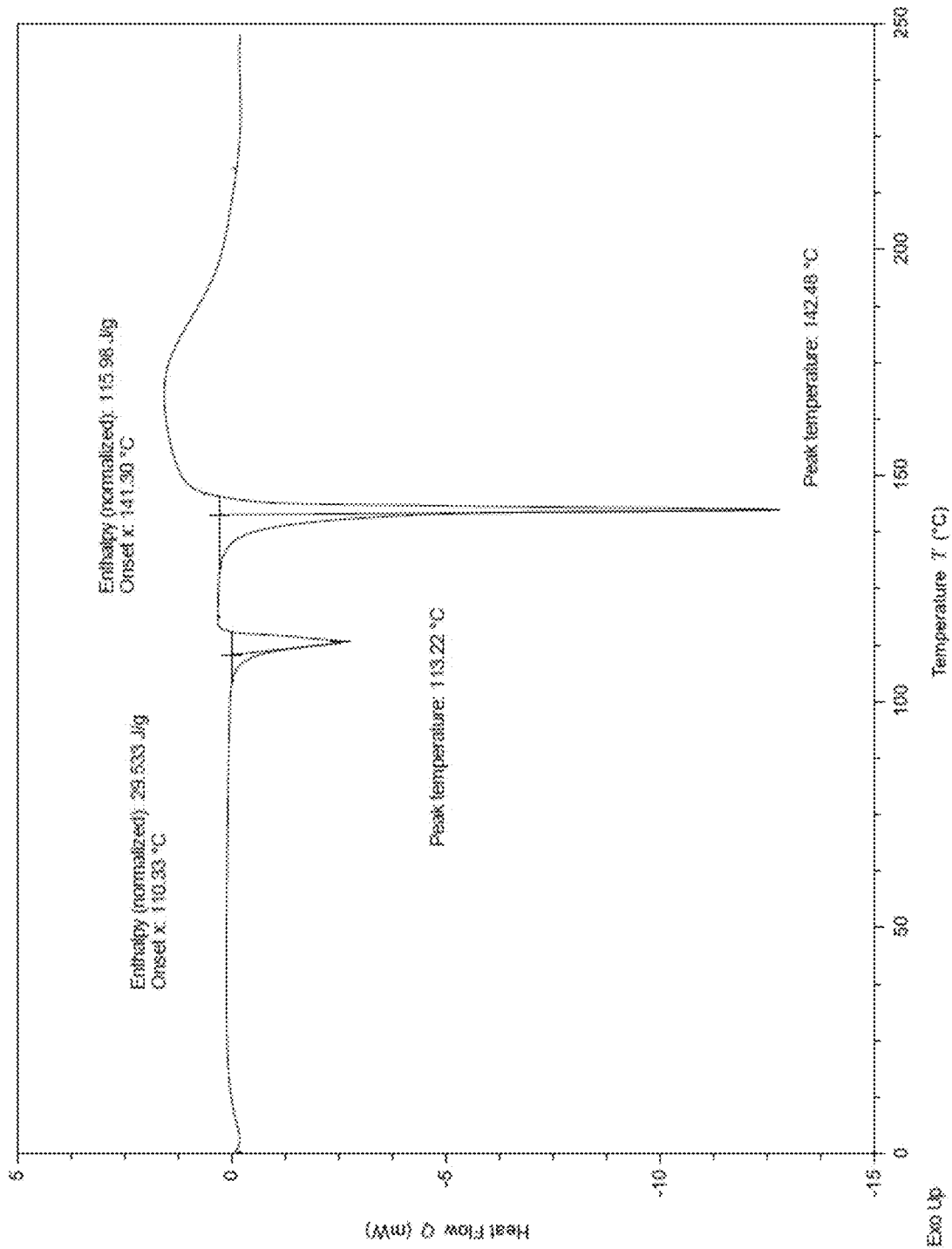
FIG. 96 is a DSC thermogram of Compound IV Pattern 1 obtained from Compound II Pattern 1 in Example 22 in Experiment PS4.
Figure 97:
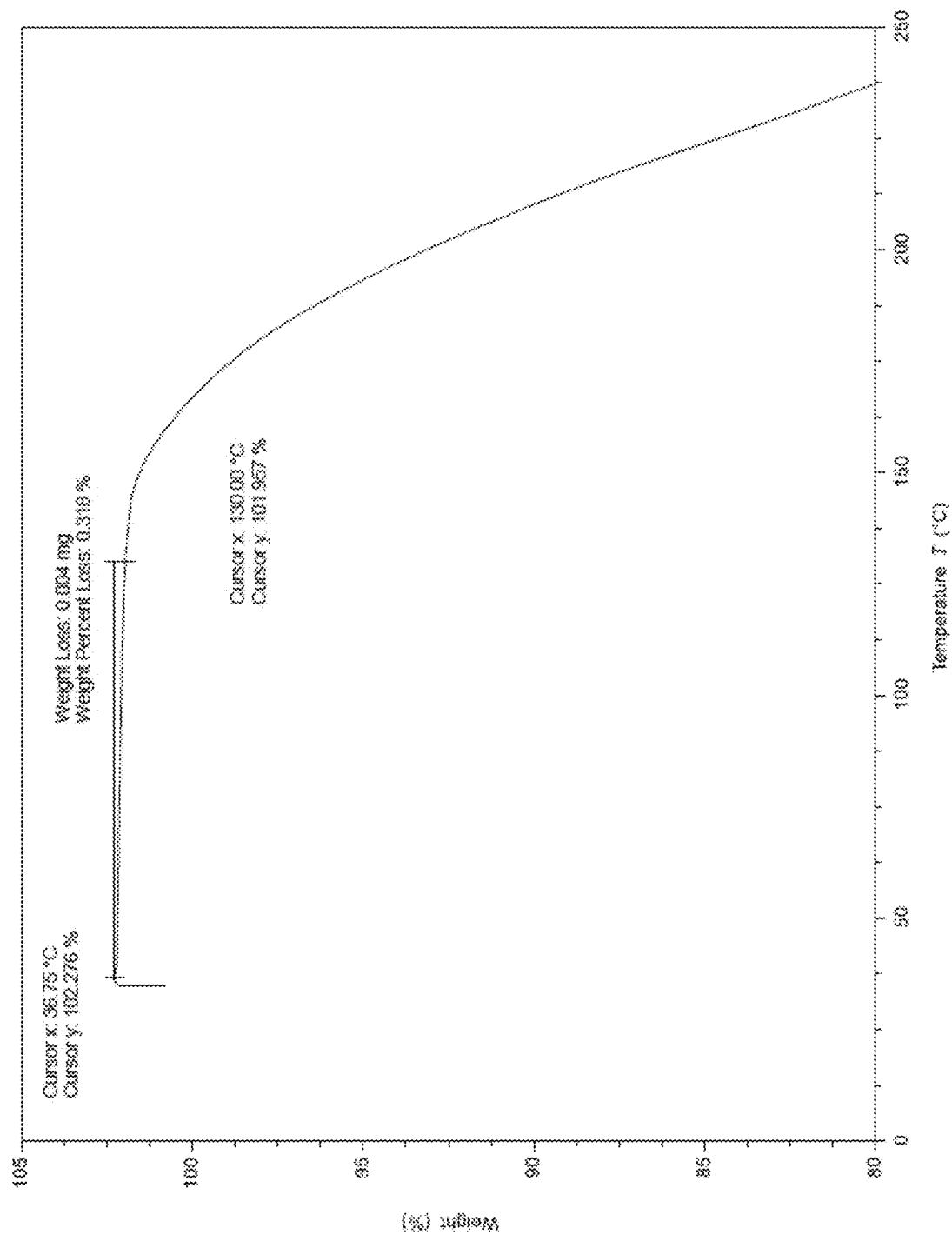
FIG. 97 is a TGA thermogram of Compound IV Pattern 1 obtained from Compound II Pattern 1 in Example 22 in Experiment PS4.
Figure 98:
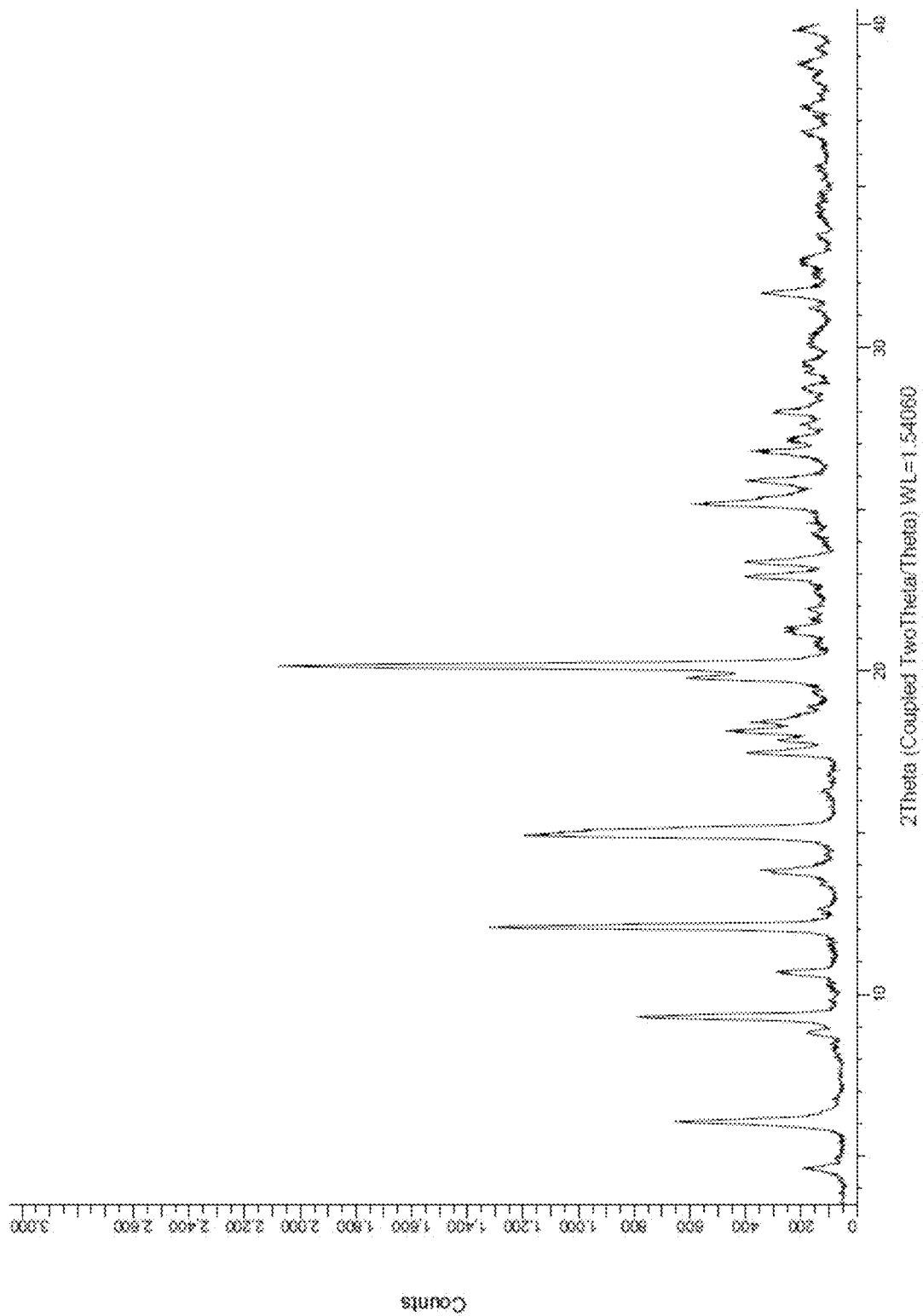
FIG. 98 is an XRPD diffractogram of Compound IV Pattern 2 obtained from Compound II Pattern 1 in Example 22 in Experiment PS5.
Figure 99:
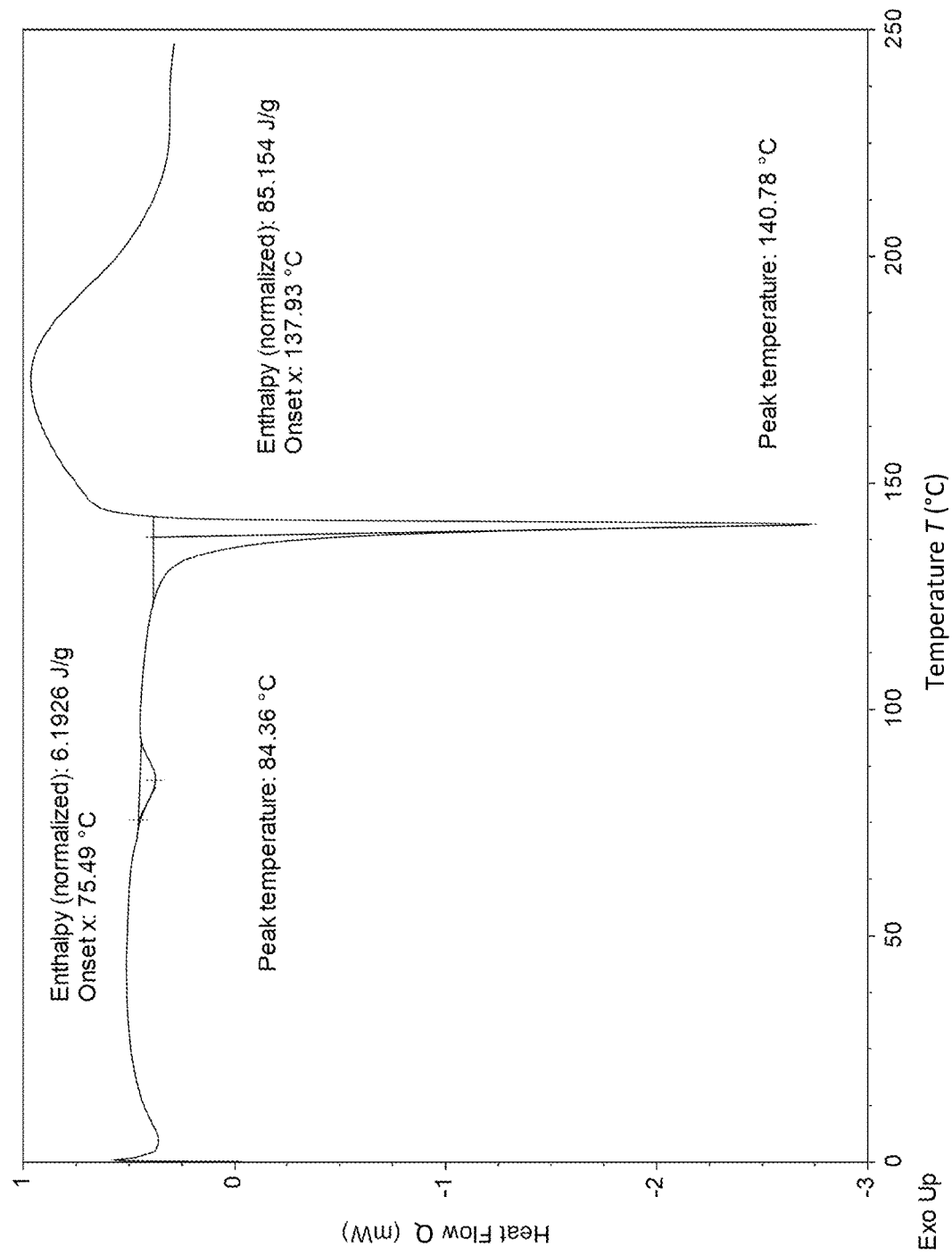
FIG. 99 is a DSC thermogram of Compound IV Pattern 2 obtained from Compound II Pattern 1 in Example 22 in Experiment PS5.
Figure 100:
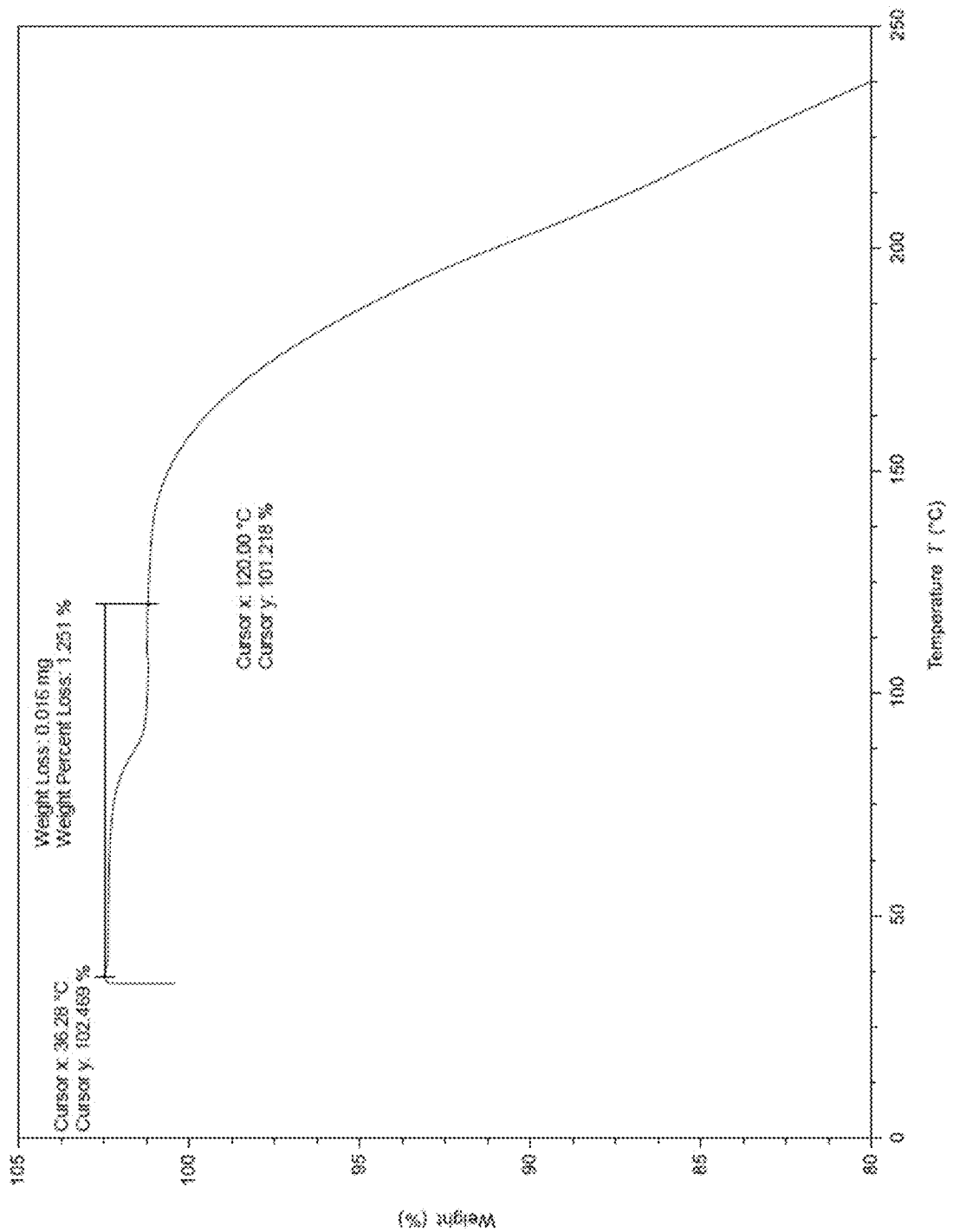
FIG. 100 is a TGA thermogram of Compound IV Pattern 2 obtained from Compound II Pattern 1 in Example 22 in Experiment PS5.
Figure 101:
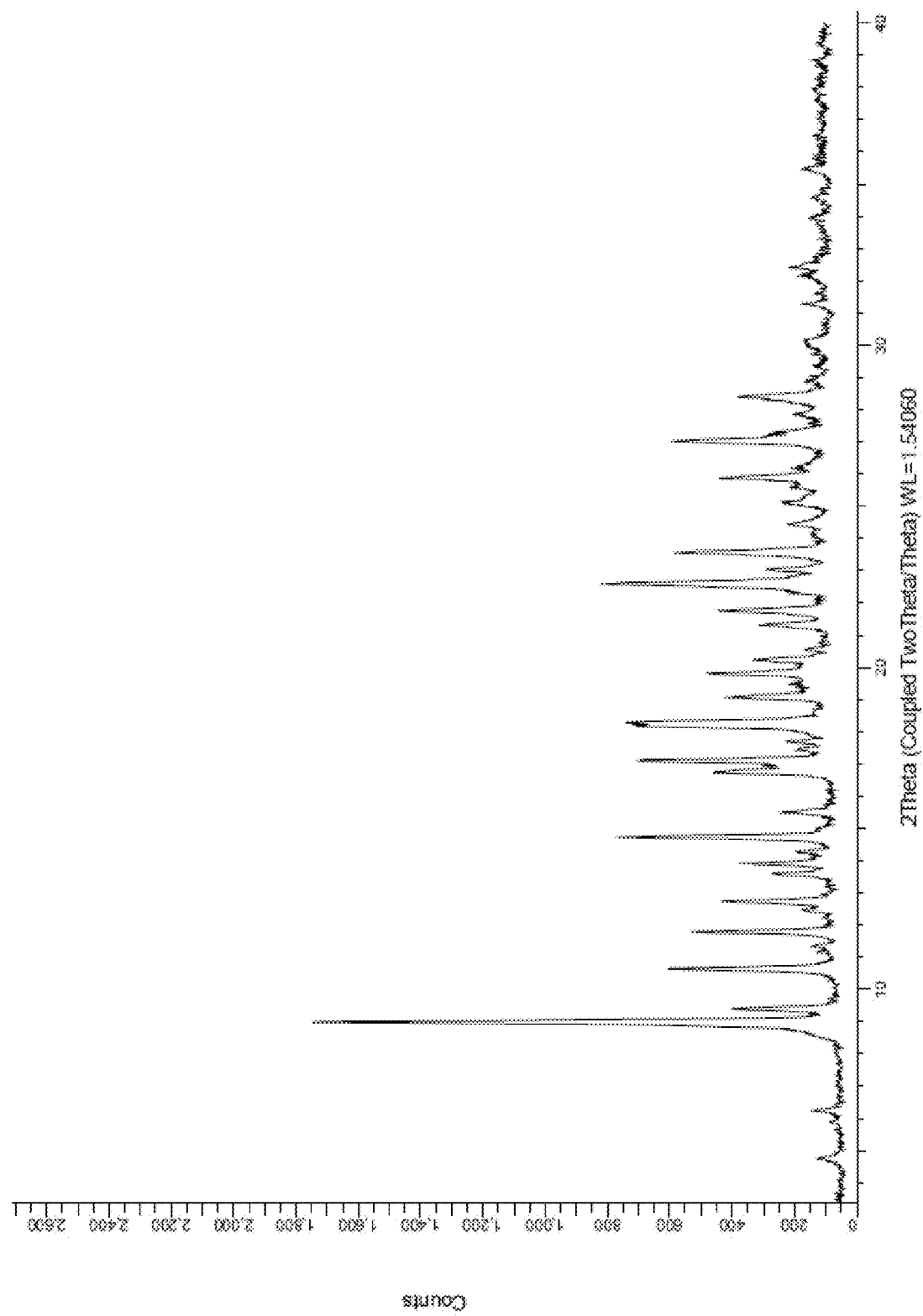
FIG. 101 is an XRPD diffractogram of Compound III Pattern 3 obtained from Compound III Pattern 2 in Example 22 in Experiment PS3.
Figure 102:
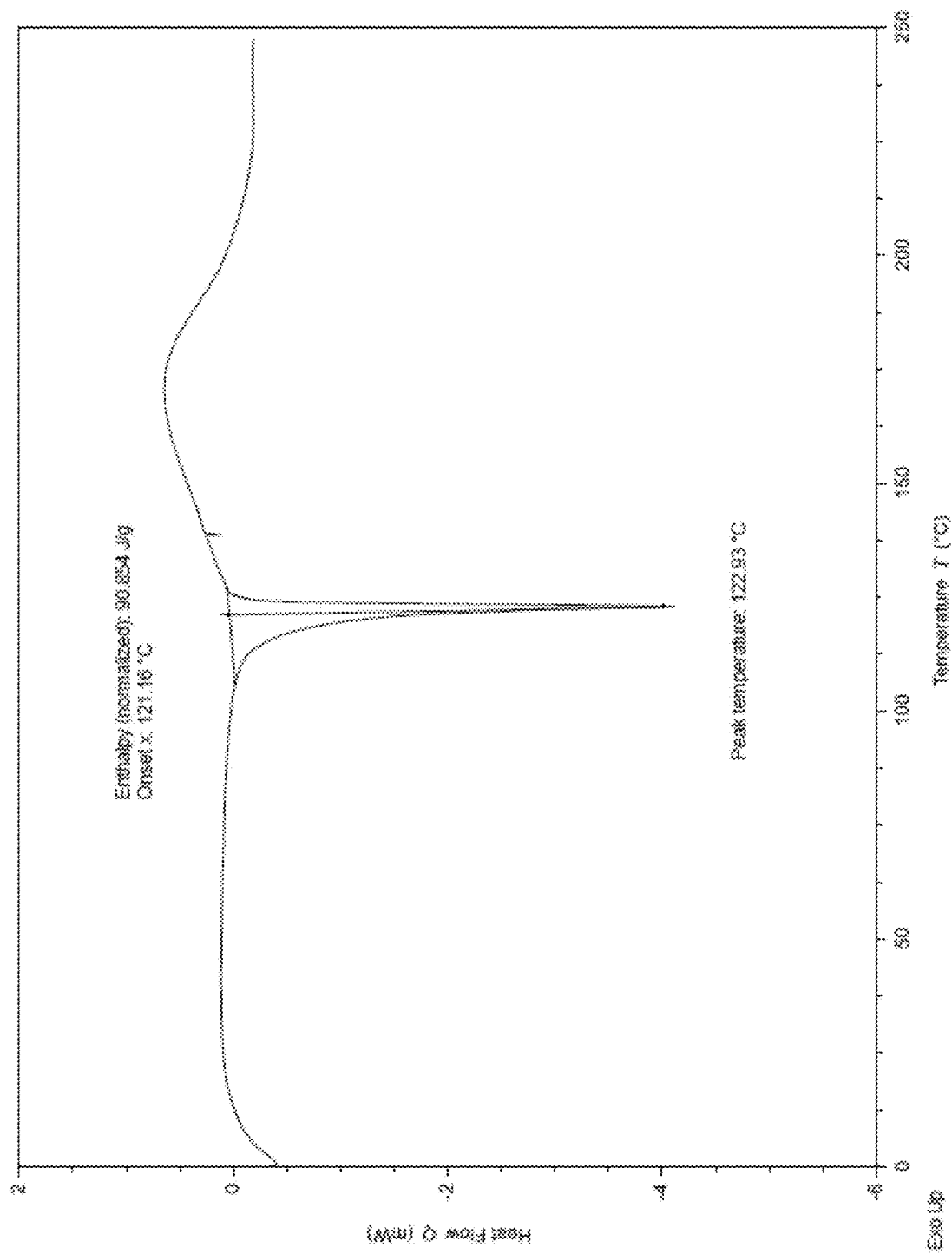
FIG. 102 is a DSC thermogram of Compound III Pattern 3 obtained from Compound III Pattern 2 in Example 22 in Experiment PS3.
Figure 103:
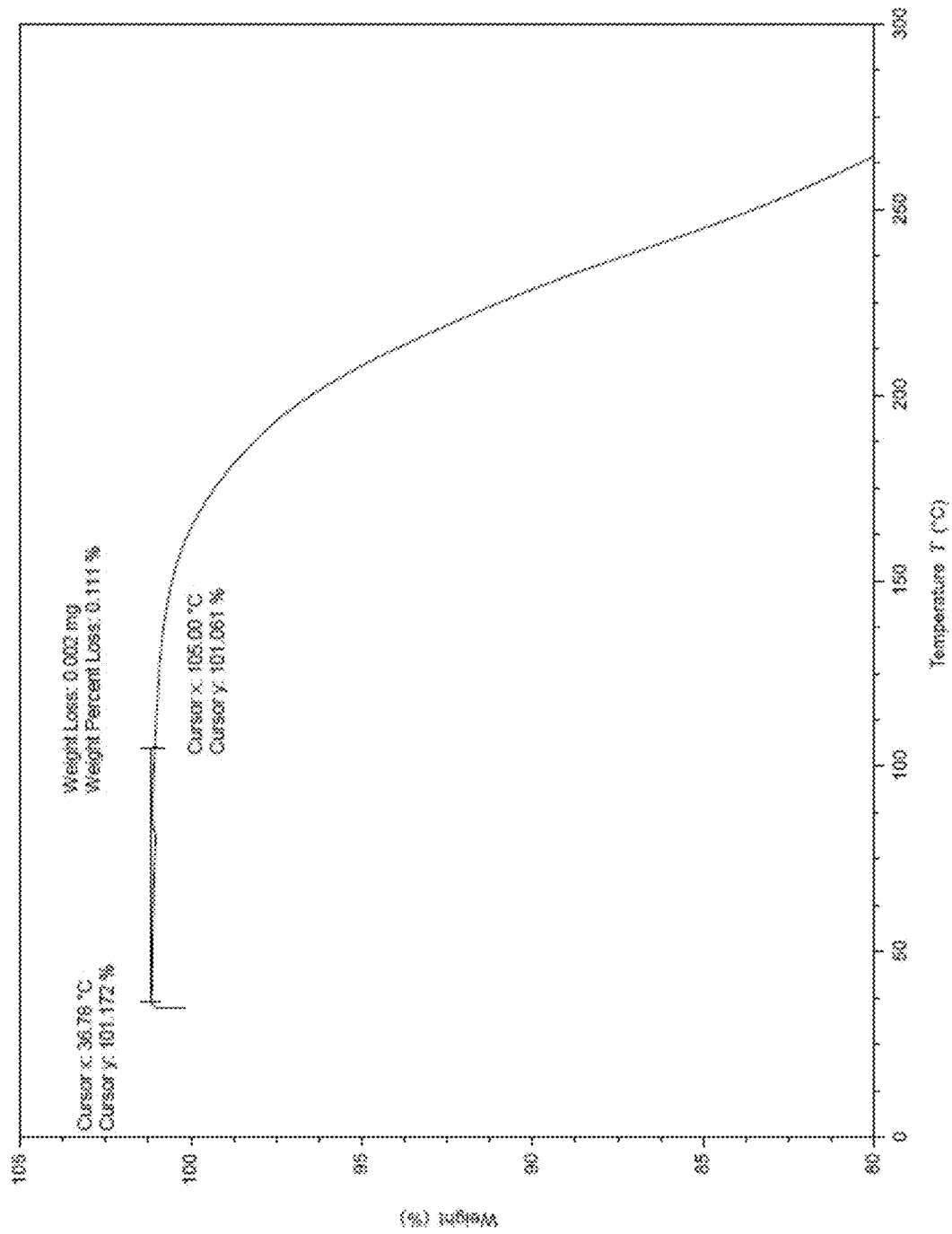
FIG. 103 is a TGA thermogram of Compound III Pattern 3 obtained from Compound III Pattern 2 in Example 22 in Experiment PS3.
Figure 104:
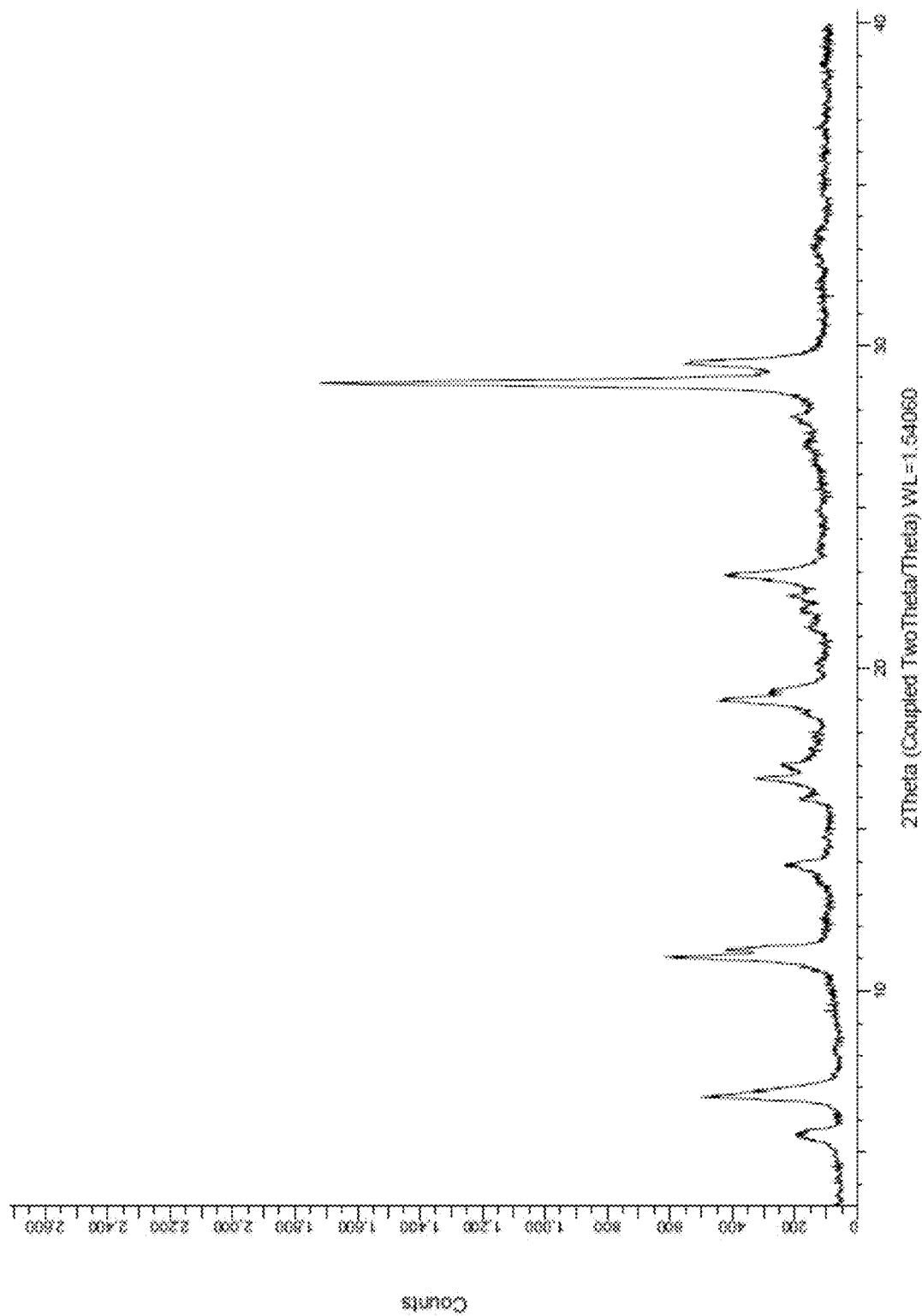
FIG. 104 is an XRPD diffractogram of Compound III Pattern 4 obtained from Compound III Pattern 2 in Example 22 in Experiment PS4.
Figure 105:
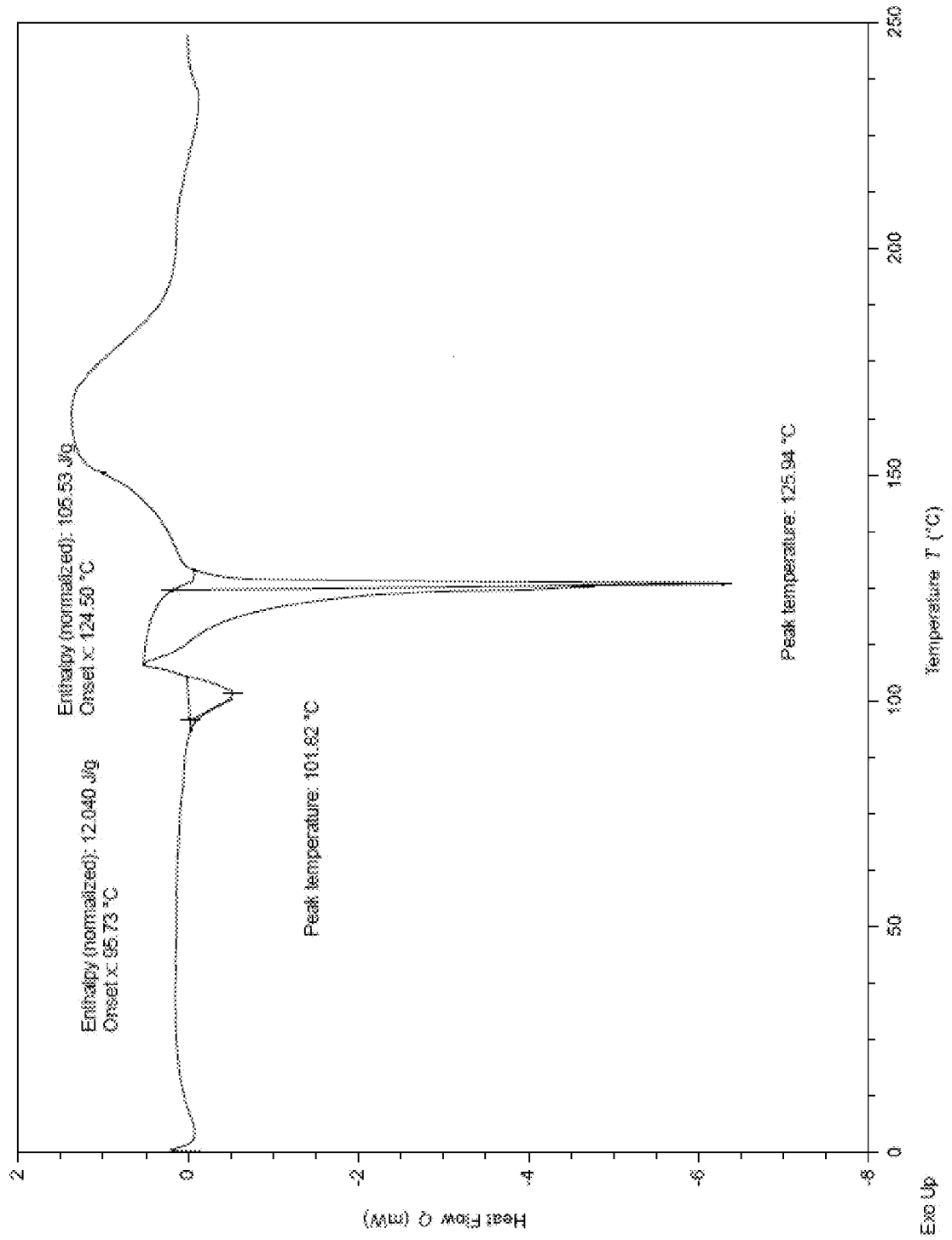
FIG. 105 is a DSC thermogram of Compound III Pattern 4 obtained from Compound III Pattern 2 in Example 22 in Experiment PS4.
Figure 106:
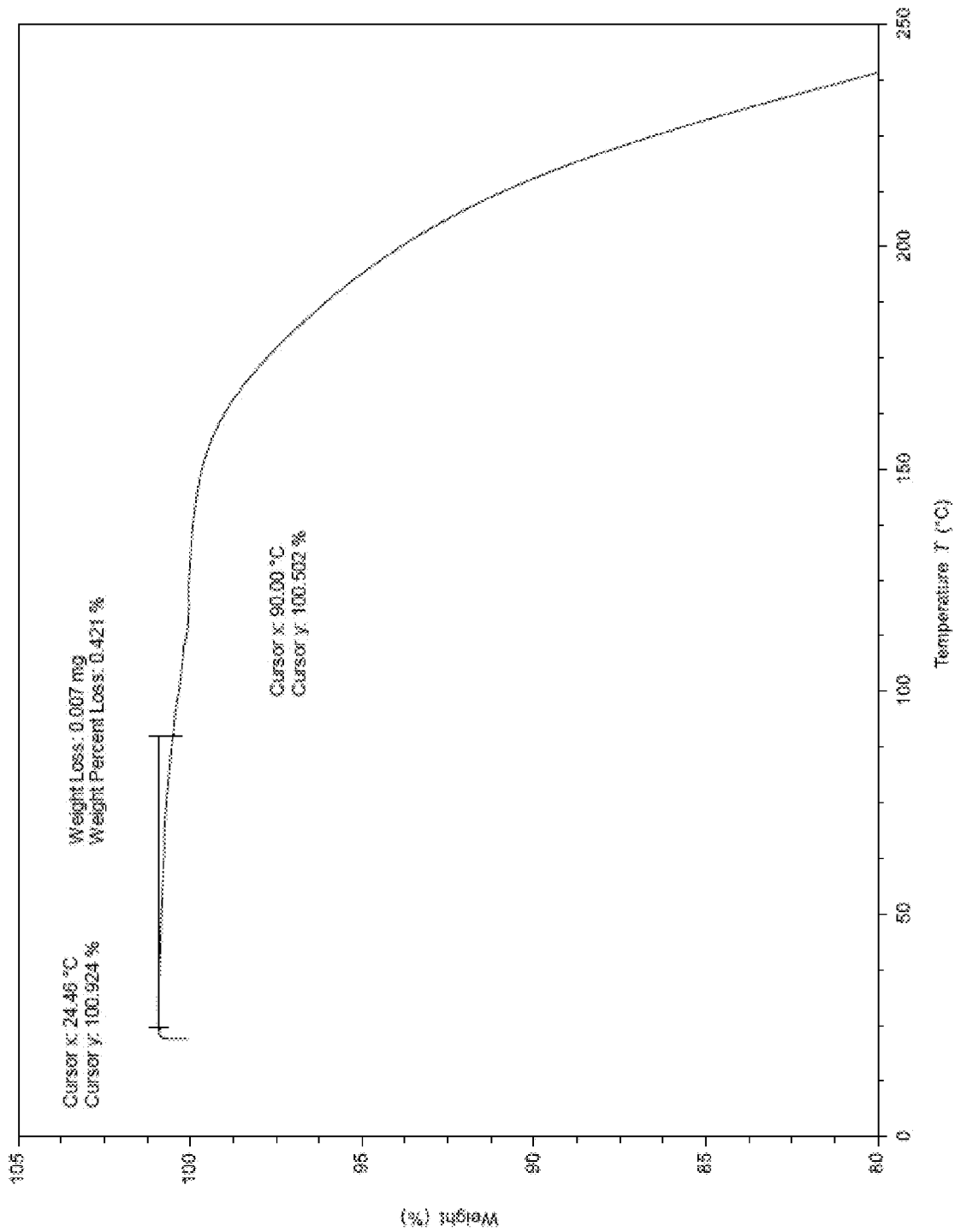
FIG. 106 is a TGA thermogram of Compound III Pattern 4 obtained from Compound III Pattern 2 in Example 22 in Experiment PS4.
Figure 107:
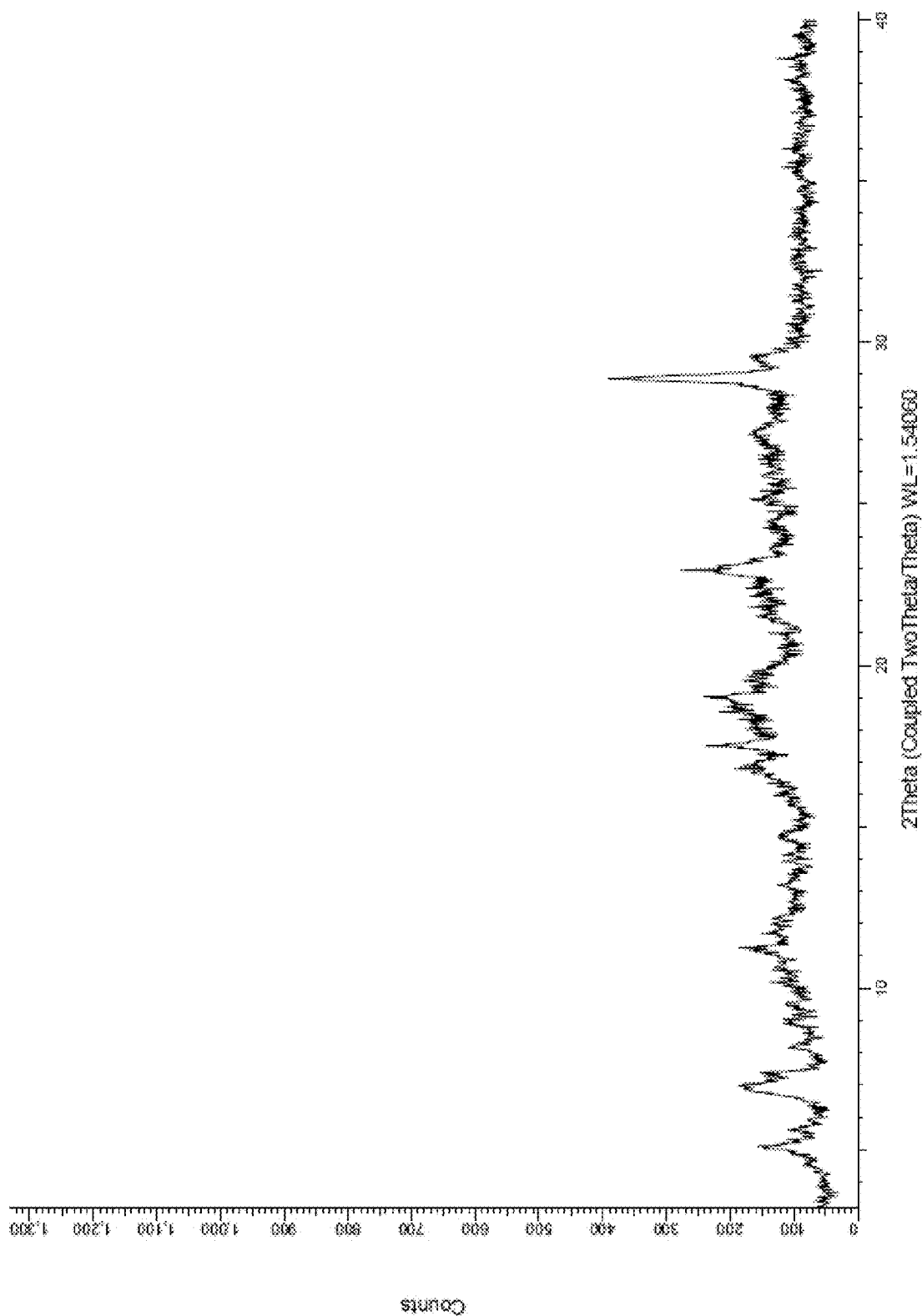
FIG. 107 is an XRPD diffractogram of Compound III Pattern 5 obtained from Compound III Pattern 2 in Example 22 in Experiment PS5.
Figure 108:
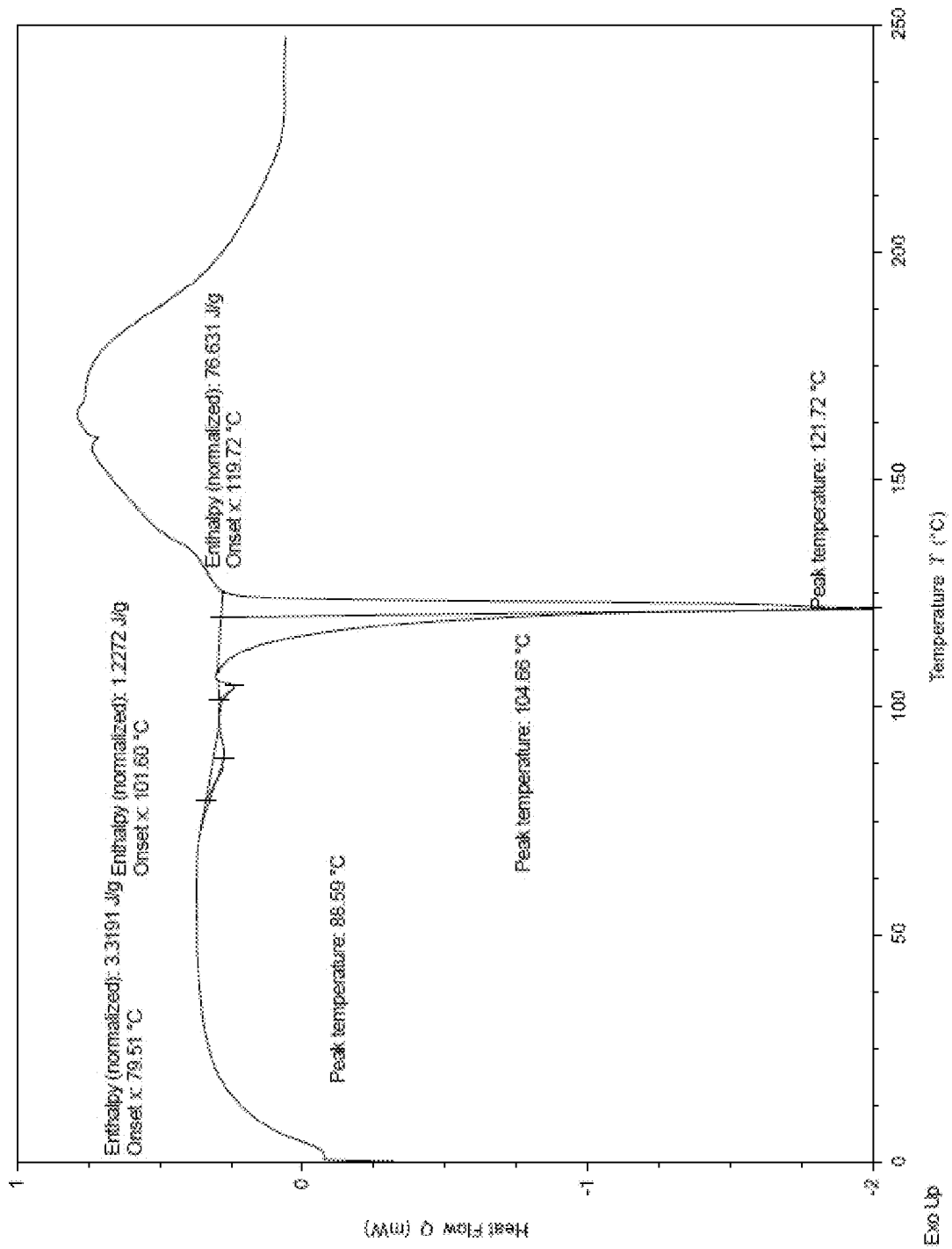
FIG. 108 is a DSC thermogram of Compound III Pattern 5 obtained from Compound III Pattern 2 in Example 22 in Experiment PS5.
Figure 109:
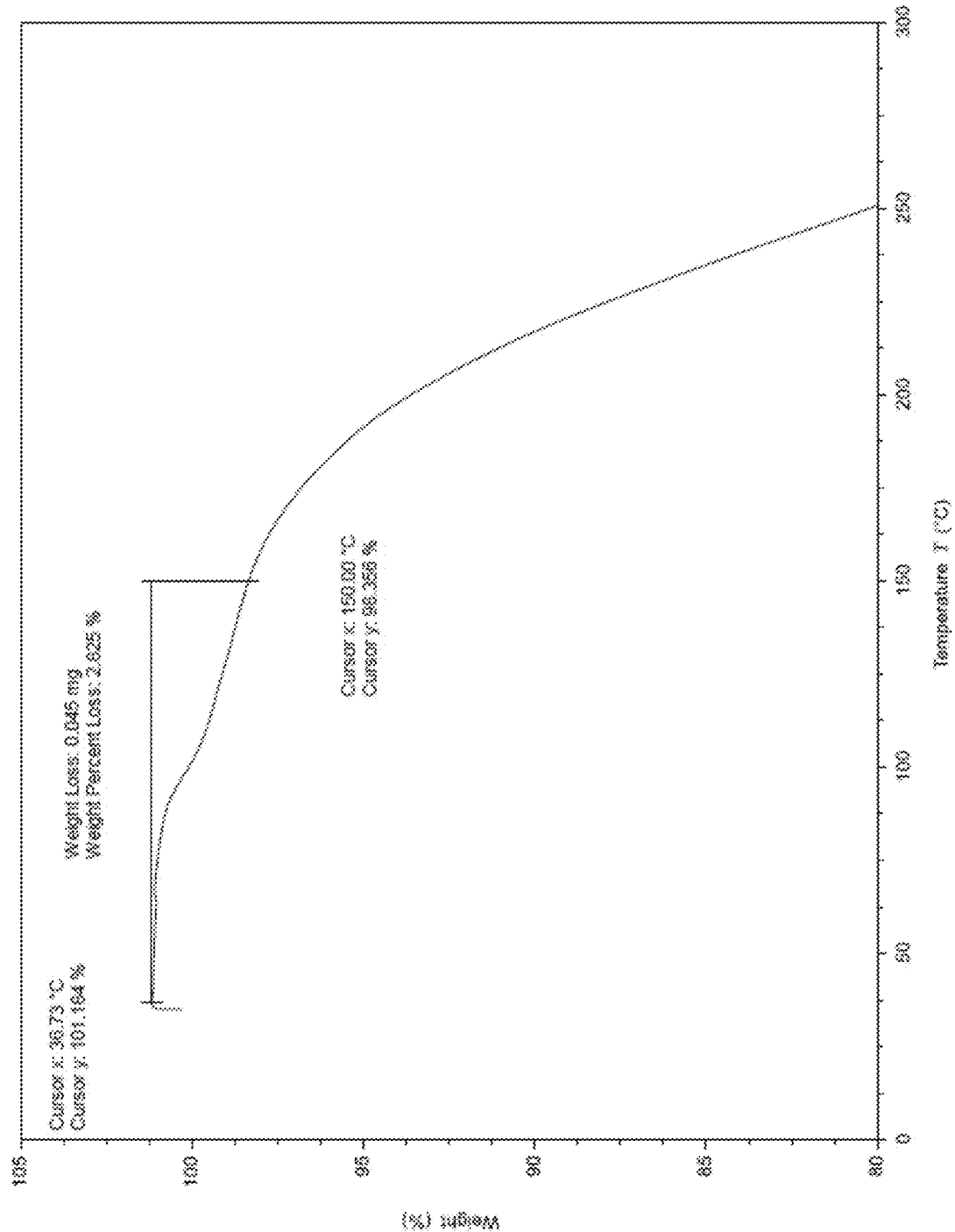
FIG. 109 is a TGA thermogram of Compound III Pattern 5 obtained from Compound III Pattern 2 in Example 22 in Experiment PS5.
Figure 110:
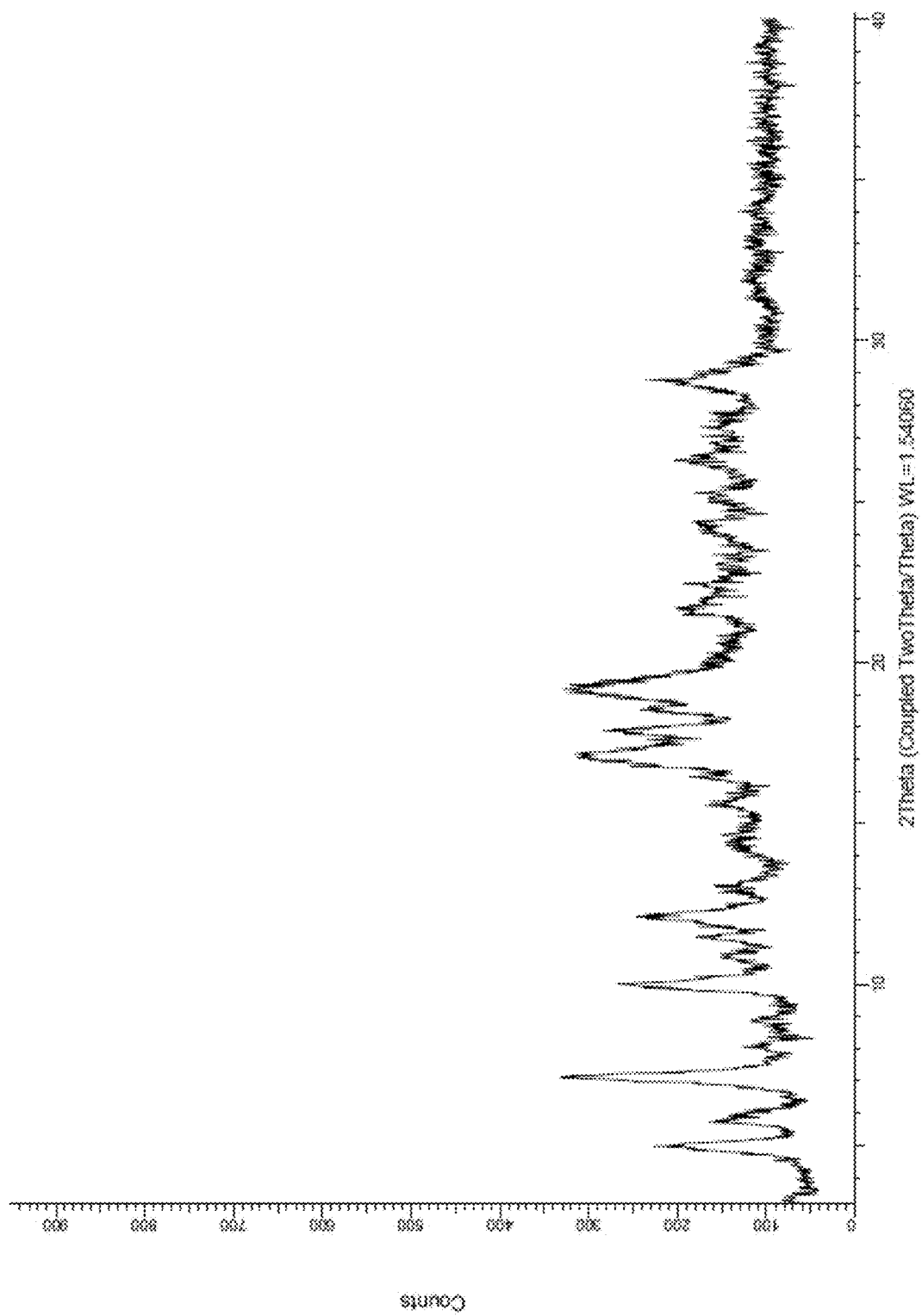
FIG. 110 is an XRPD diffractogram of Compound III Pattern 6 obtained from Compound III Pattern 2 in Example 22 in Experiment PS9.
Figure 111:
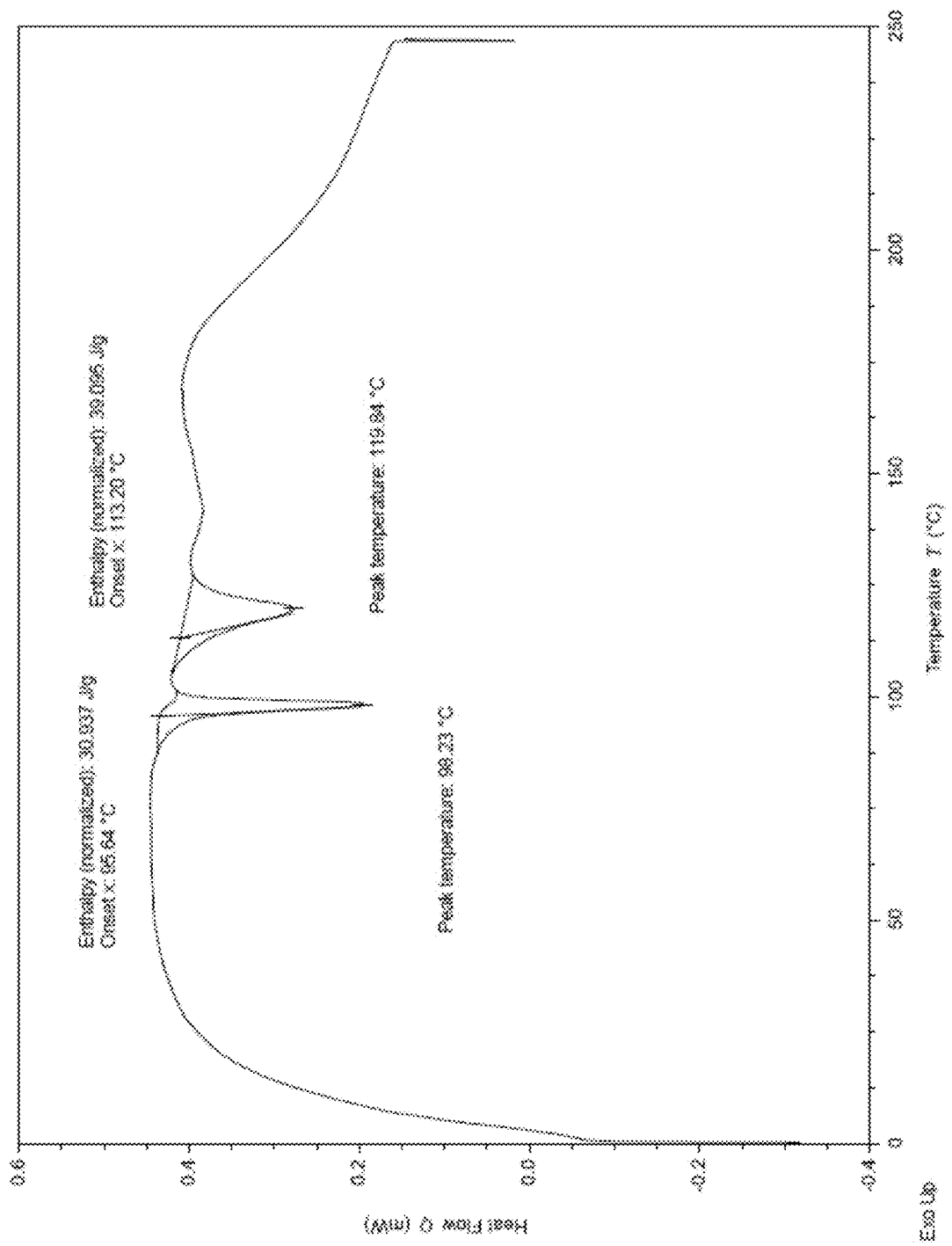
FIG. 111 is a DSC thermogram of Compound III Pattern 6 obtained from Compound III Pattern 2 in Example 22 in Experiment PS9.
Figure 112:
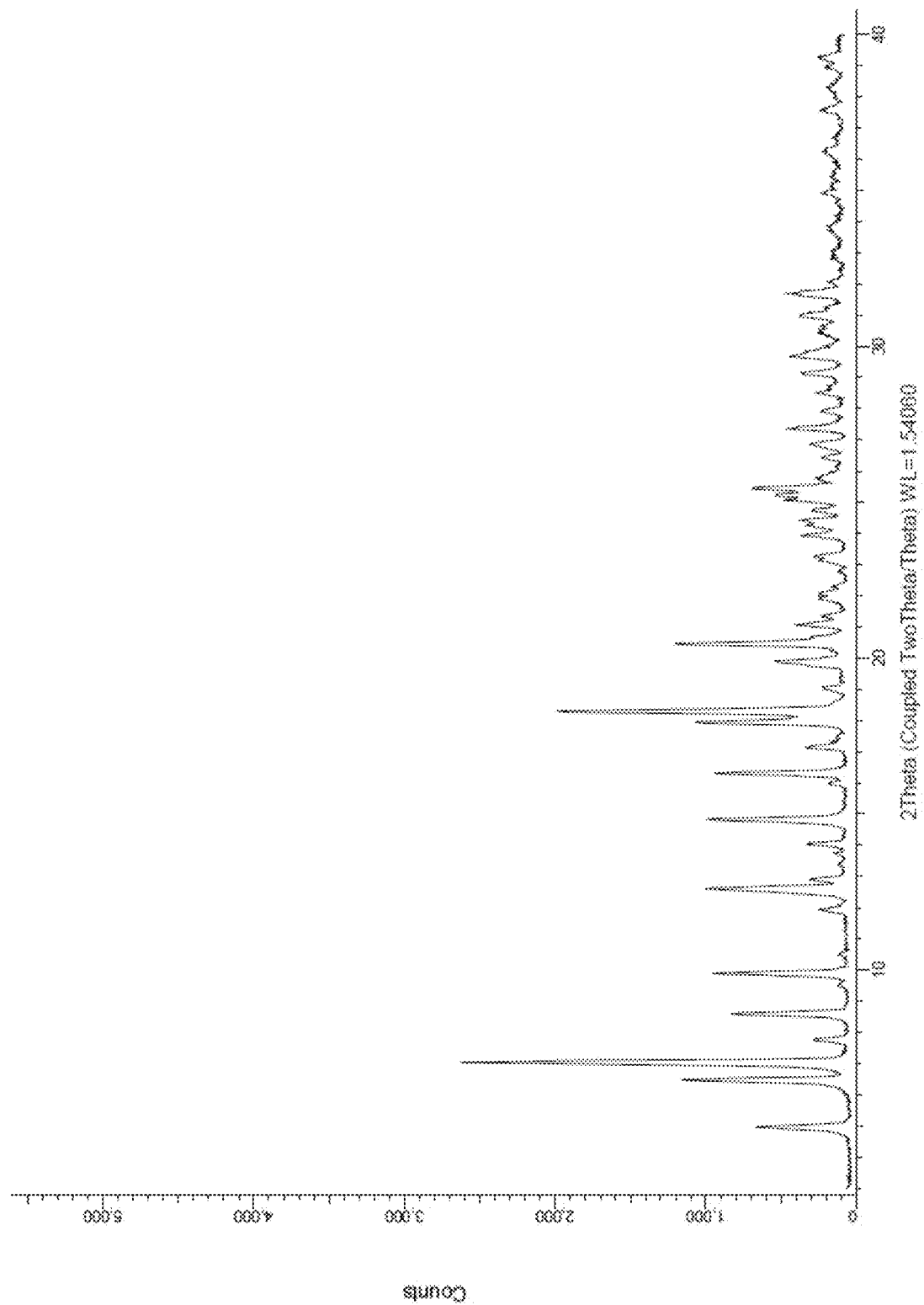
FIG. 112 is an XRPD diffractogram of Compound IV Pattern 1 obtained from Compound II Pattern 1 in Example 22 in Experiment PS8.
Figure 113:
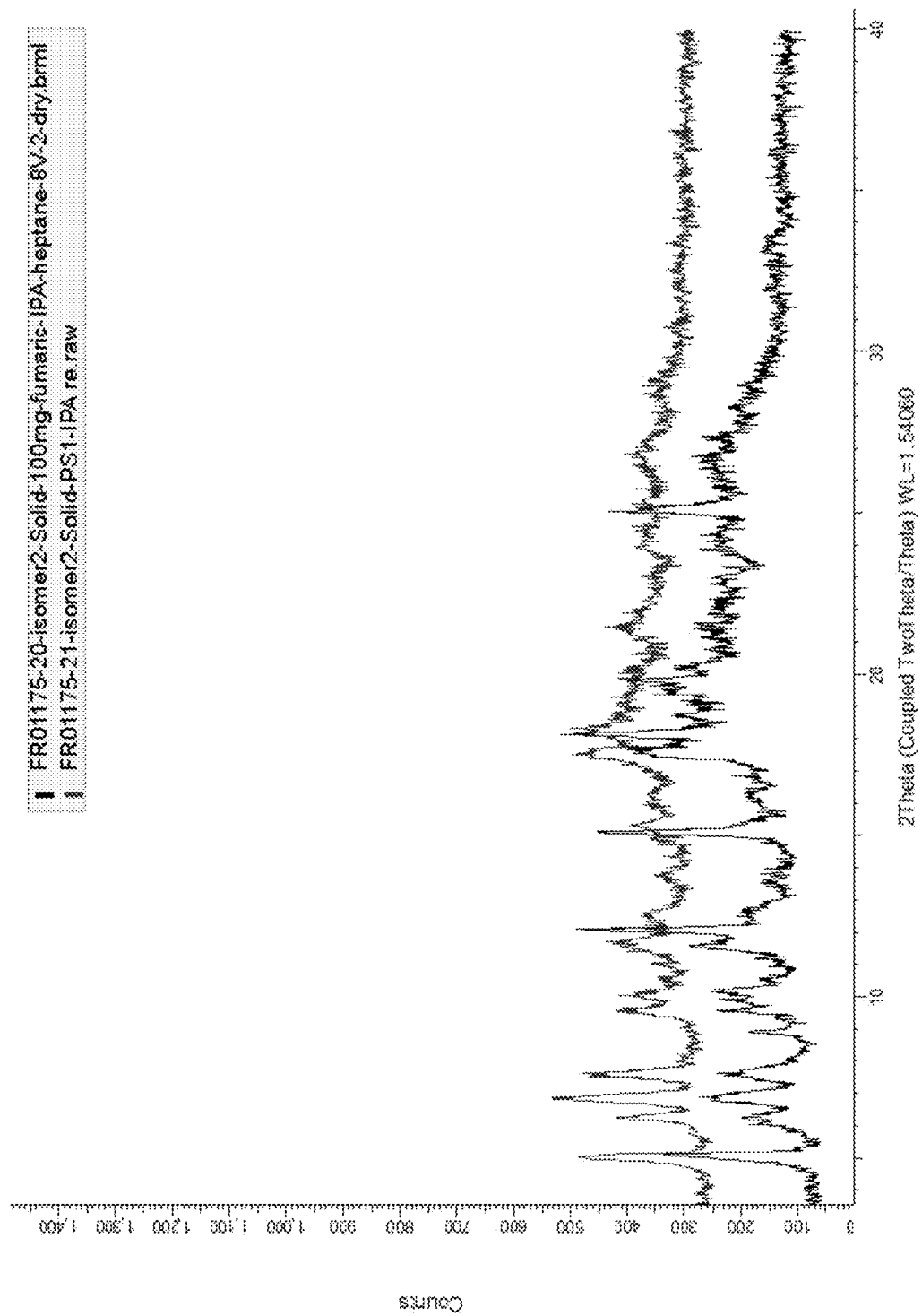
FIG. 113 a comparison of XRPD diffractograms of Compound V Pattern 1 obtained from Compound III Pattern 2 in Example 22 in Experiment PS1 and Compound V Pattern 1 obtained in Example 18.

100 mg of $S_P$ Compound I free base and 1.0 equiv. of fumaric acid was added into a glass vial followed by addition of 0.8 mL of IPA. To a resulting clear solution, 1 ml of heptanes was added, the mixture was stirred at 50° C. for 2 h then cooled to 3° C. with 0.1° C./min. It was kept stirred at 3° C. for about 3 days. Solids formed were isolated by filtration and drying in vacuum oven at 50° C. for about 2 h to obtain Compound V Pattern 2. The results are reported in Table 43. XRPD diffractogram of Compound V Pattern 2 is shown in FIG. 86. DSC thermogram of Compound V Pattern 2 is shown in FIG. 87. TGA thermogram of Compound V Pattern 2 is shown in FIG. 88.

TABLE 43

Properties of Compound V Pattern 2

| Parameter | Method | Result |
| --- | --- | --- |
| X-ray diffraction | 3-40° (2 theta) | Compound V Pattern 2 |
| DSC melting onset and enthalpy | DSC, 10° C./min | Melting onset: 95.3° C., enthalpy: 28 J/g; Onset: 105.7° C., enthalpy: 15 J/g; Onset: 115.5° C., enthalpy: 12 J/g |
| Thermogravimetry | TGA, 10° C./min | Weight loss: ~0.2% at 93° C. |
| Stoichiometry and residual solvent | $^1$H NMR | Free base:fumaric acid = 1:0.6; No residual solvent |

Example 19: Bulk Stability of Compound II Pattern 1 and Compound III Pattern 2

Compound II Pattern 1 and Compound III Pattern 2 were placed in an open container at 25° C./92% RH, in an open container at 40° C./75% RH, and in a closed container at 60° C. for 1 week. Samples were characterized by XRPD and HPLC and inspected for color change. The results are presented in Table 44.

TABLE 44

Stability: purity and appearance

| Exp. | Parameter | Compound II Pattern 1 | | Compound III Pattern 2 | |
|---|---|---|---|---|---|
| | Initial HPLC purity | 99.7% | | 98.8% | |
| | Initial color | White solids | | White solids | |
| | | Purity | Color | Purity | Color |
| Solid state, 25° C./92% RH, open container, 1 week | | | | | |
| BS1 | Bulk (HPLC) | 99.5% | No change | 98.7% | No change |
| | Bulk (XRPD) | No form change | | No form change | |
| Solid state, 40° C./75% RH, open container, 1 week | | | | | |
| BS2 | Bulk (HPLC) | 99.4% | No change | 97.2% | No change |
| | Bulk (XRPD) | No form change | | No form change (One peak disappeared) | |
| Solid state, 60° C., tight container, 1 week | | | | | |
| BS3 | Bulk (HPLC) | 99.7% | No change | 97.3% | No change |
| | Bulk (XRPD) | No form change | | No form change (One peak disappeared) | |

Initial Chemical and Chiral Purity

Initial chemical purity of Compound II Pattern 1 and Compound III Pattern 2 is 99.7% and 98.8%, respectively. Chiral purity (% de) of Compound II Pattern 1 is 98.4%.

Bulk Stability

Accelerated stability experiments were conducted at 25° C./92% RH in an open container, at 40° C./75% RH in an open container, and at 60° C. in a tight container for one week. Compound II Pattern 1 showed good physical and chemical stability after exposure to the three conditions. Compound III Pattern 2 showed good physical stability at the above mentioned three conditions. Degradation product increased by 1.6% and 1.5% after exposure to 40° C./75% RH in an open container and 60° C. in a tight container, respectively.

Example 20: Solubility Study of Compound II Pattern 1 and Compound III Pattern 2

Accurately 12 mg of Compound II Pattern 1, 12 mg of Compound III Pattern 2 were weighed into an 8 mL glass vial and to it 5 mL of solubility medium was added. The salt amount used is equivalent to 10 mg anhydrous free base. All the samples were clear solution in the media after 0.5 and 2 h at 37° C. The obtained clear solutions were analyzed by pH meter for pH, and solubility was determined by observation.

TABLE 45

Solubility at 37° C., target concentration 10 mg/5 mL, equilibration for 0.5 h and 2 h

| | | Compound II Pattern 1 | | Compound III Pattern 2 | |
|---|---|---|---|---|---|
| Exp. | Solvent media | Solubility 0.5 hours | Solubility (pH) 2 hours | Solubility 0.5 hours | Solubility (pH) 2 hours |
| ES1 | pH 3.0, 100 mM citrate buffer | >2 | >2 (2.85) | >2 | >2 (2.83) |
| ES2 | pH 4.5, 50 mM acetate buffer | >2 | >2 (4.2) | >2 | >2 (4.12) |
| ES3 | pH 6.8, 50 mM phosphate buffer | >2 | >2 (6.47) | >2 | >2 (6.44) |
| ES4 | Water | >2 | >2 (2.87) | >2 | >2 (2.78) |
| ES5 | Simulated vaginal fluid (pH adjusted by 0.1N NaOH) | >2 | >2 (5.79) | >2 | >2 (5.37) |

Solubility was tested in five media, pH 3.0 citrate buffer, pH 4.5 acetate buffer, pH 6.8 phosphate buffer, water, simulated vaginal fluid (pH 4.2) at 37° C. for 0.5 h and 2 h. The two candidates, Compound II Pattern 1 and Compound III Pattern 2, are highly soluble in the media (>2 mg/mL).

Example 21: Hygroscopicity of Compound II Pattern 1 and Compound III Pattern 2

Hygroscopicity was investigated by DVS at 25° C., using the following method:

Method: 40-0-95-0-40% RH, dm/dt=0.002

Both of Compound II Pattern 1 and Compound III Pattern 2 are slightly hygroscopic. Compound II Pattern 1 shows about 0.2% water uptake up to 95% RH. No form change after the DVS test was observed. Compound III Pattern 2 shows about 1.0% water uptake up to 95% RH. No form change after the DVS test was observed. Results are presented in Table 46.

TABLE 46

| | Compound II Pattern 1 | | | | Compound III Pattern 2 | | | |
|---|---|---|---|---|---|---|---|---|
| % RH | Desorp. (%) Cycle 1 | Sorp. (%) Cycle 1 | Desorp. (%) Cycle 2 | Sorp. (%) Cycle 2 | Desorp. (%) Cycle 1 | Sorp. (%) Cycle 1 | Desorp. (%) Cycle 2 | Sorp. (%) Cycle 2 |
| 0% | 0.03 | 0.03 | 0.03 | 0.03 | 0.00 | 0.00 | 0.00 | 0.00 |
| 10% | 0.05 | 0.04 | 0.05 | 0.04 | 0.07 | 0.07 | 0.07 | 0.07 |
| 20% | 0.08 | 0.06 | 0.07 | 0.06 | 0.15 | 0.14 | 0.15 | 0.14 |
| 30% | 0.10 | 0.08 | 0.08 | 0.07 | 0.23 | 0.22 | 0.23 | 0.22 |
| 40% | 0.17 | 0.10 | 0.10 | 0.09 | 0.30 | 0.29 | 0.32 | 0.30 |
| 50% | | 0.12 | 0.12 | | | 0.39 | 0.41 | |
| 60% | | 0.13 | 0.14 | | | 0.47 | 0.52 | |
| 70% | | 0.16 | 0.18 | | | 0.59 | 0.67 | |
| 80% | | 0.19 | 0.21 | | | 0.71 | 0.81 | |

TABLE 46-continued

|  | Compound II Pattern 1 | | | | Compound III Pattern 2 | | | |
| --- | --- | --- | --- | --- | --- | --- | --- | --- |
| % RH | Desorp. (%) Cycle 1 | Sorp. (%) Cycle 1 | Desorp. (%) Cycle 2 | Sorp. (%) Cycle 2 | Desorp. (%) Cycle 1 | Sorp. (%) Cycle 1 | Desorp. (%) Cycle 2 | Sorp. (%) Cycle 2 |
| 90% |  | 0.23 | 0.24 |  |  | 0.92 | 0.97 |  |
| 95% |  | 0.24 | 0.24 |  |  | 1.01 | 1.01 |  |
| XRPD after DVS test |  | No form change | | | | No form change (One peak disappeared) | | |

Example 22: Polymorph Screening of Compound II Pattern 1 and Compound III Pattern 2

50 mg of mono fumarate was equilibrated in suitable amount of solvent or solvent mixture. Obtained suspensions were equilibrated for 1 week. Solids were isolated by centrifugation filtration. Wet cakes obtained after equilibration were analyzed by XRPD to determine crystal form change.

TABLE 47

Mini-polymorph screening: Crystal modification after 1 week equilibration at 25° C. (salt ratio is defined as free base:fumaric acid ratio

| | | Parameter | |
| --- | --- | --- | --- |
| Exp. | Solvent | Compound II Pattern 1 Characterization results | Compound III Pattern 2 Characterization results |
| PS1 | IPA | Compound II Pattern 1<br>Melting onset: 143.7° C., enthalpy: combined with decomposition<br>Weight loss: ~0.4% at 130° C.;<br>Salt ratio = 1:1.0<br>Residual solvent: 5.3% (by weight) IPA | Compound V Pattern 2<br>Salt ratio = 1:0.5<br>Residual solvent: 1.1% (by weight) IPA |
| PS2 | Heptanes | Compound II Pattern 1 | Compound III Pattern 2<br>Salt ratio = 1:1.2<br>No solvent residue |
| PS3 | Water | Compound II Pattern 1<br>Melting onset: 139.8° C., enthalpy: combined with decomposition<br>Weight loss: ~0.5% at 130° C.<br>Salt ratio = 1:1.0<br>No solvent residue | Compound III Pattern 3<br>Melting onset: 121.2° C., enthalpy: 91 J/g<br>Weight loss: ~0.1% at 105° C.<br>Salt ratio = 1:1.0<br>No solvent residue |
| PS4 | ACN | Compound II Pattern 2<br>Melting onset: 110.3° C., enthalpy: 30 J/g;<br>Melting onset: 141.3° C., enthalpy: combined with decomposition<br>Weight loss: ~0.3% at 130° C.<br>Salt ratio = 1:1.0<br>Residual solvent: ACN 1.9% (by weight) | Compound III Pattern 4<br>Melting onset: 95.7° C., enthalpy: 12 J/g;<br>Melting onset: 124.5° C. enthalpy: 106 J/g<br>Weight loss: ~0.4% at 90° C.<br>Salt ratio = 1:1.4<br>Residual solvent: ACN 2.0% (by weight) |
| PS5 | MEK | Compound II Pattern 3<br>Desolvation onset: 75.5° C., enthalpy: 6 J/g;<br>Melting onset: 137.9° C., enthalpy: combined with decomposition<br>Weight loss: ~1.3% at 120° C.<br>KF: 0.3% (by weight) water<br>Salt ratio = 1:0.9<br>0.1 equiv. MEK residue<br>Chiral purity: 98.7% | Compound III Pattern 5<br>Desolvation onset: 79.5° C., enthalpy: 3 J/g;<br>Desolvation onset: 101.6° C., enthalpy: 1 J/g;<br>Melting onset: 119.7° C., enthalpy: combined with decomposition<br>Weight loss: ~2.8% at 150° C.<br>Salt ratio = 1:1.0<br>Residual solvent: 0.1 equiv. MEK |
| PS6 | Acetone | Compound II Pattern 1 | Similar to Compound III Pattern 5<br>Salt ratio = 1:0.7<br>0.9% (by weight) acetone residue |

Chiral purity: 99.3% appears under PS4 Compound II column.

TABLE 47-continued

Mini-polymorph screening: Crystal modification after 1 week equilibration at 25° C. (salt ratio is defined as free base:fumaric acid ratio

| Exp. | Solvent | Parameter Compound II Pattern 1 Characterization results | Compound III Pattern 2 Characterization results |
|---|---|---|---|
| PS7 | IPA/heptanes (3/10, v/v) | Compound II Pattern 1 | Compound III Pattern 2 |
| PS8 | water/ACN (2.9/97.1, v/v) | Compound II Pattern 2 | Compound III Pattern 4 |
| PS9 | IPA/MTBE (1/3, v/v) | Compound II Pattern 1 | Compound III Pattern 6 Onset: 95.6° C., enthalpy: 31 J/g; Onset: 113.2° C., enthalpy: 39 J/g; Salt ratio = 1:0.8 0.8% (by weight) IPA residue |
| PS10 | EA/toluene (1/3, v/v) | Compound II Pattern 1 | Compound III Pattern 2 |

Polymorphism Evaluation of Compound II Pattern 1

In this study, no dissociation was observed during equilibration experiments and 2 new potential polymorphs of the fumarate salts (Compound II Pattern 2 and Compound II Pattern 3) of Isomer I were obtained from acetonitrile and MEK, respectively. These both showed lower melting temperature than for Compound II Pattern 1. Both polymorphs of isomer 1 show unchanged high chiral purity.

Polymorphism Evaluation of Compound III Pattern 2

In this study, dissociation was observed during equilibration experiments, a hemifumarate (hemifumarate Pattern 2) of Isomer II was obtained. In addition, 4 new monofumarate salts (Compound III Pattern 3, Compound III Pattern 4, Compound III Pattern 5 and Compound III Pattern 6) of Isomer II were obtained.

Example 23: X-Ray Powder Diffraction (XRPD)

The XRPD analysis was carried out on a Bruker D8 Advance diffractometer.

Table 48 below provides the results of the XRPD performed on Compound II Pattern 1. The XRPD exhibited sharp peaks, indicating the sample was composed of crystalline material. Significant peaks were observed in the XRPD on Compound II Pattern 1 at about 3.1±0.2°, about 9.3±0.2°, about 12.1±0.2°, about 14.9±0.2°, about 15.1±0.2°, about 18.1±0.2°, about 19.8±0.2°, about 20.1±0.2°, about 25.1±0.2°, about 25.9±0.2°, and about 28.8±0.2°.

TABLE 48

XRPD Peak List For Compound II Pattern 1

| Pos. [°2θ] | d-spacing [Å] | Rel. Int. [%] |
|---|---|---|
| 3.076 | 28.69958 | 29.1 |
| 6.069 | 14.55143 | 5.6 |
| 8.802 | 10.03830 | 4.9 |
| 9.300 | 9.50181 | 33.0 |
| 10.660 | 8.29244 | 9.9 |
| 12.084 | 7.31818 | 84.6 |
| 12.620 | 7.00842 | 2.4 |
| 14.921 | 5.93274 | 57.1 |
| 15.097 | 5.86381 | 46.5 |
| 17.449 | 5.07828 | 13.9 |
| 17.838 | 4.96858 | 6.7 |
| 18.127 | 4.88980 | 17.5 |
| 18.625 | 4.76036 | 2.1 |
| 18.887 | 4.69491 | 2.5 |
| 19.779 | 4.48509 | 18.1 |
| 20.135 | 4.40651 | 100.0 |
| 20.814 | 4.26435 | 2.9 |
| 21.242 | 4.17924 | 3.9 |
| 21.592 | 4.11236 | 3.6 |
| 21.892 | 4.05666 | 4.9 |
| 22.910 | 3.87861 | 13.7 |
| 23.344 | 3.80762 | 15.3 |
| 24.235 | 3.66953 | 3.3 |
| 25.142 | 3.53913 | 23.0 |
| 25.326 | 3.51390 | 11.0 |
| 25.863 | 3.44216 | 15.8 |
| 26.775 | 3.32692 | 13.4 |
| 27.127 | 3.28453 | 4.2 |
| 27.587 | 3.23082 | 3.2 |
| 27.994 | 3.18474 | 10.6 |
| 28.824 | 3.09496 | 63.9 |
| 29.231 | 3.05278 | 3.4 |
| 29.450 | 3.03051 | 5.1 |
| 30.394 | 2.93851 | 2.2 |
| 31.185 | 2.86575 | 2.9 |
| 31.655 | 2.82427 | 8.5 |
| 32.269 | 2.77194 | 1.7 |
| 32.697 | 2.73666 | 2.3 |
| 33.436 | 2.67779 | 1.8 |
| 34.057 | 2.63038 | 1.0 |
| 34.344 | 2.60902 | 1.4 |
| 34.692 | 2.58370 | 1.1 |
| 35.587 | 2.52074 | 0.7 |
| 36.190 | 2.48010 | 0.5 |
| 36.622 | 2.45179 | 3.1 |
| 37.419 | 2.40142 | 2.7 |
| 38.300 | 2.34820 | 1.5 |
| 38.771 | 2.32073 | 3.0 |
| 39.246 | 2.29373 | 1.2 |

Table 49 below provides the results of the XRPD performed on Compound IV Pattern 1. Significant peaks were observed in the XRPD on Compound IV Pattern 1 at about 6.5±0.2°, about 12.1±0.2°, about 17.5±0.2°, about 18.1±0.2°, about 18.5±0.2°, about 19.6±0.2°, about 19.8±0.2°, about 20.2±0.2°, about 20.6±0.2°, and about 21.3±0.2.

TABLE 49

XRPD Peak List For Compound IV Pattern 1

| Pos. [°2θ] | d-spacing [Å] | Rel. Int. [%] |
|---|---|---|
| 4.651 | 18.98268 | 10.6 |
| 4.819 | 18.32057 | 8.6 |
| 6.518 | 13.54879 | 100.0 |
| 8.293 | 10.65357 | 3.0 |
| 9.090 | 9.72120 | 2.9 |
| 9.306 | 9.49597 | 5.4 |
| 10.567 | 8.36487 | 15.4 |
| 11.678 | 7.57151 | 14.6 |
| 12.068 | 7.32822 | 21.0 |
| 13.535 | 6.53691 | 13.8 |
| 13.895 | 6.36828 | 9.7 |
| 14.572 | 6.07384 | 5.1 |
| 15.016 | 5.89525 | 14.8 |
| 17.039 | 5.19961 | 4.9 |
| 17.522 | 5.05725 | 17.9 |
| 18.141 | 4.88628 | 28.5 |
| 18.526 | 4.78544 | 30.4 |
| 18.958 | 4.67734 | 17.3 |
| 19.587 | 4.52865 | 23.6 |
| 19.830 | 4.47357 | 30.2 |
| 20.157 | 4.40168 | 36.6 |
| 20.606 | 4.30684 | 19.8 |
| 21.264 | 4.17497 | 18.9 |
| 21.333 | 4.16178 | 15.3 |
| 22.890 | 3.88210 | 8.5 |
| 23.359 | 3.80519 | 6.2 |
| 25.619 | 3.47430 | 5.2 |
| 25.490 | 3.49164 | 11.2 |
| 26.207 | 3.39775 | 11.2 |
| 27.103 | 3.28744 | 5.4 |
| 28.125 | 3.17017 | 6.9 |
| 28.895 | 3.08746 | 6.8 |
| 31.707 | 2.81977 | 5.6 |
| 32.193 | 2.77826 | 2.8 |
| 32.628 | 2.74228 | 3.7 |
| 35.573 | 2.52168 | 3.2 |
| 37.781 | 2.37920 | 3.2 |
| 39.031 | 2.30587 | 4.7 |

Table 50 below provides the results of the XRPD performed on Compound III Pattern 1. Significant peaks were observed in the XRPD on Compound III Pattern 1 at about 9.5±0.2°, about 11.7±0.2°, about 14.6±0.2°, about 17.5±0.2°, about 18.0±0.2°, about 20.0±0.2°, about 20.4±0.2°, about 22.3±0.2°, about 23.7±0.2°, and about 25.5±0.2.

TABLE 50

XRPD Peak List For Compound III Pattern 1

| Pos. [°2θ] | d-spacing [Å] | Rel. Int. [%] |
|---|---|---|
| 5.848 | 15.10034 | 6.0 |
| 7.201 | 12.26565 | 3.4 |
| 8.725 | 10.12629 | 2.6 |
| 9.165 | 9.64191 | 7.5 |
| 9.535 | 9.26787 | 14.0 |
| 10.045 | 8.79898 | 11.4 |
| 10.779 | 8.2013 | 2.1 |
| 11.660 | 7.58362 | 100.0 |
| 12.577 | 7.03220 | 2.9 |
| 14.569 | 6.07529 | 81.0 |
| 17.220 | 5.14523 | 11.9 |
| 17.500 | 5.06368 | 38.8 |
| 17.960 | 4.93485 | 18.1 |
| 18.281 | 4.84914 | 10.2 |
| 19.563 | 4.53410 | 9.6 |
| 20.041 | 4.42710 | 12.8 |
| 20.363 | 4.35764 | 14.5 |
| 21.169 | 4.19367 | 3.0 |
| 22.343 | 3.97587 | 16.3 |
| 23.131 | 3.84211 | 6.3 |

TABLE 50-continued

XRPD Peak List For Compound III Pattern 1

| Pos. [°2θ] | d-spacing [Å] | Rel. Int. [%] |
|---|---|---|
| 23.735 | 3.74577 | 12.7 |
| 25.485 | 3.49233 | 18.1 |
| 26.066 | 3.41580 | 12.0 |
| 26.409 | 3.37219 | 7.8 |
| 26.855 | 3.31714 | 5.0 |
| 27.381 | 3.25470 | 11.9 |
| 27.940 | 3.19079 | 4.1 |
| 28.652 | 3.11305 | 6.9 |
| 29.330 | 3.0426 | 5.2 |
| 29.726 | 3.00304 | 2.7 |
| 30.739 | 2.90632 | 4.7 |
| 32.201 | 2.77762 | 11.1 |
| 33.315 | 2.68722 | 2.8 |
| 34.356 | 2.60814 | 2.0 |
| 34.727 | 2.58116 | 1.9 |
| 35.884 | 2.50055 | 1.9 |
| 36.878 | 2.43540 | 3.9 |
| 37.167 | 2.41713 | 3.0 |
| 37.934 | 2.36998 | 3.4 |

Table 51 below provides the results of the XRPD performed on Compound III Pattern 2. The XRPD exhibited sharp peaks, indicating the sample was composed of crystalline material. Significant peaks were observed in the XRPD on Compound III Pattern 2 at about 8.9±0.2°, about 9.9±0.2°, about 11.7±0.2°, about 12.1±0.2°, about 15.1±0.2°, about 17.9±0.2°, about 18.2±0.2°, about 19.9±0.2°, about 25.1±0.2°, about 29.6±0.2°, and about 38.1±0.2°.

TABLE 51

XRPD Peak List For Compound III Pattern 2

| Pos. [°2θ] | d-spacing [Å] | Rel. Int. [%] |
|---|---|---|
| 6.078 | 14.53063 | 8.6 |
| 7.648 | 11.54965 | 2.2 |
| 8.947 | 9.87613 | 50.4 |
| 9.891 | 8.93546 | 42.8 |
| 9.916 | 8.91288 | 46.2 |
| 10.321 | 8.56390 | 9.7 |
| 10.567 | 8.36489 | 7.4 |
| 11.661 | 7.58287 | 41.1 |
| 12.113 | 7.30075 | 79.0 |
| 13.646 | 6.48398 | 5.1 |
| 14.629 | 6.05032 | 9.0 |
| 15.133 | 5.84996 | 70.4 |
| 16.350 | 5.41721 | 4.0 |
| 16.820 | 5.26668 | 5.0 |
| 17.855 | 4.96384 | 65.3 |
| 18.156 | 4.88213 | 56.8 |
| 18.738 | 4.73179 | 11.4 |
| 18.874 | 4.69802 | 13.7 |
| 19.903 | 4.45746 | 94.1 |
| 20.382 | 4.35370 | 31.1 |
| 21.103 | 4.20648 | 14.7 |
| 21.924 | 4.05093 | 7.0 |
| 22.362 | 3.97249 | 8.0 |
| 22.881 | 3.88352 | 16.0 |
| 22.940 | 3.87365 | 22.2 |
| 23.736 | 3.74562 | 13.8 |
| 25.094 | 3.54590 | 100.0 |
| 26.065 | 3.41597 | 6.9 |
| 26.548 | 3.35484 | 21.7 |
| 26.901 | 3.31157 | 22.8 |
| 27.386 | 3.25410 | 20.3 |
| 27.936 | 3.19118 | 13.4 |
| 28.282 | 3.15297 | 19.0 |
| 28.951 | 3.08162 | 21.9 |
| 29.641 | 3.01144 | 51.6 |
| 32.027 | 2.79230 | 9.5 |
| 32.606 | 2.74402 | 5.5 |

TABLE 51-continued

XRPD Peak List For Compound III Pattern 2

| Pos. [°2θ] | d-spacing [Å] | Rel. Int. [%] |
|---|---|---|
| 33.389 | 2.68145 | 10.0 |
| 33.404 | 2.68026 | 7.8 |
| 35.702 | 2.51285 | 5.5 |
| 36.973 | 2.42933 | 5.3 |
| 37.224 | 2.41357 | 9.8 |
| 37.482 | 2.39750 | 11.1 |
| 38.067 | 2.36201 | 49.4 |

Table 52 below provides the results of the XRPD performed on Compound V Pattern 1. Significant peaks were observed in the XRPD on Compound V Pattern 1 at about 5.0±0.2°, about 7.2±0.2°, about 10.1±0.2°, about 12.1±0.2°, about 17.5±0.2°, about 17.9±0.2°, about 19.3±0.2°, about 22.0±0.2°, about 24.3±0.2°, about 25.1±0.2°, and about 26.3±0.2.

TABLE 52

XRPD Peak List For Compound V Pattern 1

| Pos. [°2θ] | d-spacing [Å] | Rel. Int. [%] |
|---|---|---|
| 5.041 | 17.51522 | 63.4 |
| 5.832 | 15.14207 | 17.6 |
| 7.155 | 12.34533 | 100.0 |
| 8.077 | 10.93821 | 12.9 |
| 10.067 | 8.77930 | 61.1 |
| 11.508 | 7.68306 | 31.4 |
| 12.146 | 7.28079 | 38.1 |
| 13.110 | 6.74798 | 11.2 |
| 14.572 | 6.07403 | 13.7 |
| 15.674 | 5.64928 | 17.0 |
| 17.625 | 5.02802 | 32.8 |
| 17.457 | 5.07608 | 69.6 |
| 17.954 | 4.93661 | 56.3 |
| 18.617 | 4.76222 | 27.0 |
| 19.297 | 4.59597 | 58.8 |
| 20.097 | 4.41478 | 30.2 |
| 21.980 | 4.04058 | 48.4 |
| 23.809 | 3.73417 | 20.6 |
| 24.256 | 3.66636 | 32.9 |
| 25.059 | 3.55066 | 32.7 |
| 26.326 | 3.38261 | 46.1 |
| 26.804 | 3.32340 | 28.6 |
| 28.741 | 3.10368 | 12.8 |
| 28.955 | 3.08118 | 25.5 |
| 33.035 | 2.70936 | 14.4 |
| 33.232 | 2.69374 | 16.6 |

Table 53 below provides the results of the XRPD performed on Compound V Pattern 2. Significant peaks were observed in the XRPD on Compound V Pattern 2 at about 5.1±0.2°, about 6.9±0.2°, about 7.6±0.2°, about 10.2±0.2°, about 11.6±0.2°, about 12.1±0.2°, about 15.1±0.2°, about 17.6±0.2°, about 18.1±0.2°, about 18.7±0.2°, about 19.5±0.2°, about 19.8±0.2°, and about 25.1±0.2°.

TABLE 53

XRPD Peak List For Compound V Pattern 2

| Pos. [°2θ] | d-spacing [Å] | Rel. Int. [%] |
|---|---|---|
| 5.101 | 17.31028 | 59.1 |
| 6.067 | 14.55584 | 17.0 |
| 6.282 | 14.05830 | 28.9 |
| 6.892 | 12.81562 | 45.6 |
| 7.635 | 11.56928 | 45.3 |
| 8.919 | 9.90658 | 25.4 |
| 9.599 | 9.20630 | 22.4 |

TABLE 53-continued

XRPD Peak List For Compound V Pattern 2

| Pos. [°2θ] | d-spacing [Å] | Rel. Int. [%] |
|---|---|---|
| 10.166 | 8.69465 | 31.9 |
| 10.512 | 8.40903 | 15.4 |
| 11.096 | 7.96777 | 8.4 |
| 11.595 | 7.62565 | 45.6 |
| 12.084 | 7.31802 | 100.0 |
| 12.574 | 7.03426 | 19.0 |
| 13.824 | 6.40081 | 17.8 |
| 15.101 | 5.86245 | 79.2 |
| 16.272 | 5.44285 | 11.7 |
| 16.850 | 5.25764 | 21.7 |
| 17.616 | 5.03067 | 53.1 |
| 18.139 | 4.88678 | 97.6 |
| 18.723 | 4.73547 | 33.2 |
| 19.525 | 4.54287 | 43.0 |
| 19.829 | 4.47390 | 59.0 |
| 20.196 | 4.39345 | 28.6 |
| 21.175 | 4.19247 | 16.9 |
| 21.477 | 4.13419 | 18.7 |
| 22.015 | 4.03426 | 20.5 |
| 22.531 | 3.94300 | 15.4 |
| 23.016 | 3.86108 | 21.0 |
| 23.996 | 3.70550 | 23.1 |
| 24.341 | 3.65378 | 16.1 |
| 25.100 | 3.54503 | 35.6 |
| 26.094 | 3.41222 | 23.0 |
| 26.783 | 3.32591 | 27.7 |
| 27.305 | 3.26355 | 22.1 |
| 28.234 | 3.15821 | 11.9 |
| 28.957 | 3.08103 | 14.2 |
| 33.447 | 2.67697 | 9.1 |

Example 24: Single-Crystal X-Ray Diffraction (SC-XRD) Study of Compound II Pattern 1

Single crystals of Compound II Pattern 1 suitable for SC-XRD study were obtained in a temperature cycling experiment in MeOH. X-ray diffraction data were collected on a D8 Venture diffractometer equipped with a CMOS area detector at 170(2) K using Cu-Kα radiation (λ=1.5418 Å); X-ray generator power: 50 kV, 1.4 mA; Distance from sample to area detector: 40 mm; Exposure time 150 seconds; Resolution: 0.81. Structure refinement: on $F^2$. Hydrogen site location: mixed. H atoms were treated by a mixture of independent and constrained refinement. X-ray diffraction data and crystal data are presented in Table 54.

TABLE 54

Crystallographic parameters and x-ray diffraction data

| | |
|---|---|
| Chemical Formula | $C_{21}H_{30}N_6O_6P\cdot C_4H_3O_4$ |
| Molecular weight | 608.54 |
| Temperature | 170 K |
| Crystal system | Monoclinic |
| Space group | $P2_1$ |
| a/Å | 10.0365(19) |
| b/Å | 4.9800(9) |
| c/Å | 28.827(6) |
| β/° | 90.658(7) |
| V/Å³ | 1440.7(5) |
| Z | 2 |
| Dcalc, g/cm³ | 1.403 |
| µ/mm⁻¹ | 0.16 |
| F(000) | 640 |
| Crystal size/mm³ | 0.08 × 0.04 × 0.02 |
| Crystal shape, color | Plate, colorless |
| Radiation | Mo Kα radiation (λ = 0.71073 Å) |
| Θ range/° | 2.5-24.9 |
| Index ranges | −11 ≤ h ≤ 11, −5 ≤ k ≤ 5, −33 ≤ l ≤ 29 |

TABLE 54-continued

Crystallographic parameters and x-ray diffraction data

| | |
|---|---|
| Absorption correction | multi-scan, SADABS2016/2 (Bruker, 2016/2) wR2 (int) was 0.1008 before and 0.0611 after correction. Ratio of minimum to maximum transmission is 0.8637. $T_{min} = 0.644$, $T_{max} = 0.745$ |
| Reflections collected | 11287 |
| Independent reflections | 4355 |
| Reflections with I > 2σ(I) | 3545 |
| $R_{int}$ | 0.057 |
| $R[F^2 > 2\sigma(F^2)]$ | 0.074 |
| $wR(F^2)$ | 0.195 |
| (Δ/σ)max | 0.541 |
| S | 1.15 |
| Restrains/Parameters | 2/392 |
| Absolute structure parameter | 0.16(10) |
| Largest diff. peak/hole/e Å$^{-3}$ | 0.35/−0.38 |

Crystalline form of Compound II Pattern 1 crystallized in monoclinic system, P2$_1$ space group with $R_{int}$=5.7% and the final R$_1$ [I>2σ(I)]=7.4%. The crystalline form did not contain solvent molecule. This crystalline form of Compound II Pattern 1 was found to have a free base to fumaric acid ratio of 1:1 and corresponds to monofumarate salt of Isomer I with Flack parameter (absolute structure parameter) of 0.16 (10). As shown in FIG. 115, protonated free base and fumaric acid anion are linked through a N$^+$(5)-H(5) . . . O(7) ionic bond in the single crystal structure. Proton transfer was observed from fumaric acid to the N(5)-nitrogen atom of purine.

Example 25. Tablet Stability Study

Tablets were prepared using the excipients and excipient ratios shown in the first column of the following tables. The tablets were then stored under the conditions indicated and periodically sampled and tested for purity by HPLC. The tablets produced from Compound I monofumarate degraded less than tablets produced from Compound I across a range of different formulations.

Tablets Produced with Compound I

| Excipients | 0 months | 1 month 25 C./60% RH | 1 month 40 C./75% RH |
|---|---|---|---|
| PC (49%) + Anhydrous Lactose (49%) | 99.40 | 95.98 | 41.3 |
| Carbomer (49%) + Mannitol (49%) | 98.87 | 91.54 | 6.75 |
| Carbomer (49%) + Hydrated Dextrose (49%) | 99.52 | 82.44 | 0.17 |
| PC (49%) + MCC (49%) | 98.64 | 97.16 | 46.11 |

Tablets Produced with Compound I Monofumarate

| Excipients | 0 months | 1 month 25 C./60% RH | 1 month 40 C./75% RH |
|---|---|---|---|
| PEO-15 (25%) + MCC (74%) + MgS (1%) | 99.03 | 97.76 | 83.13 |
| PEO-15 (25%) + Mannitol (74%) + MgS (1%) | 97.95 | 97.04 | 87.09 |
| PC (7.5%) + MCC (91.46%) + MgS (1%) | 99.81 | 98.04 | 84.92 |
| PC (7.5%) + Mannitol (91.46%) + MgS (1%) | 99.61 | 98.77 | 85.26 |

PEO: Polyethylene Oxide;
PC: Polycarbophil;
MCC: Microcrystalline cellulose;
MgS: magnesium stearate Example 26: Synthesis of Mixture of (R, S) and (S, S) ethyl-2-((((2-(2-amino-6-methoxy-9H-purin-9-yl)-ethoxy)-methyl)-(benzyloxy)-phosphoryl)-amino)-propionate (Compound I)

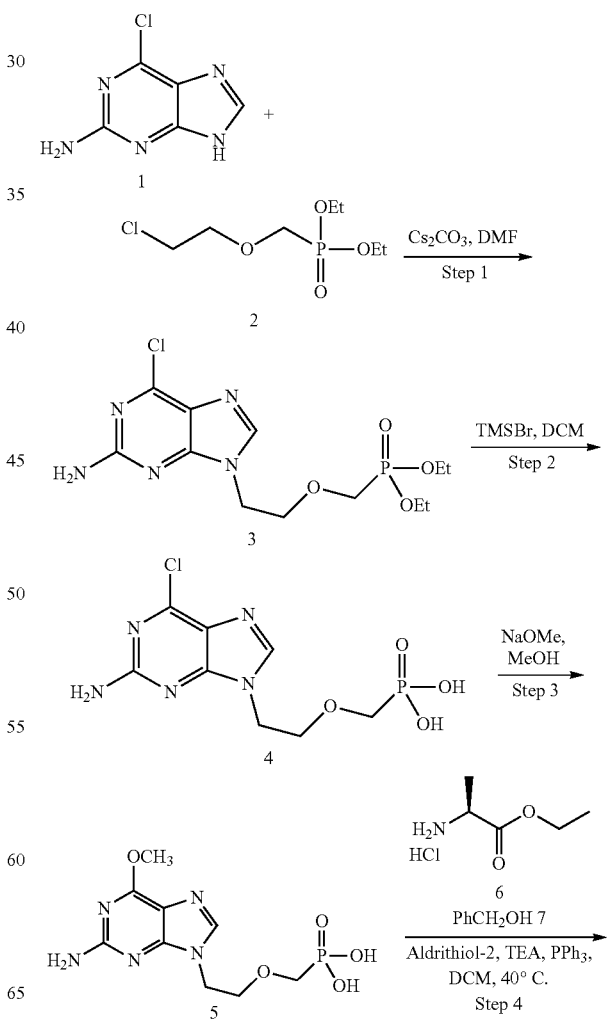

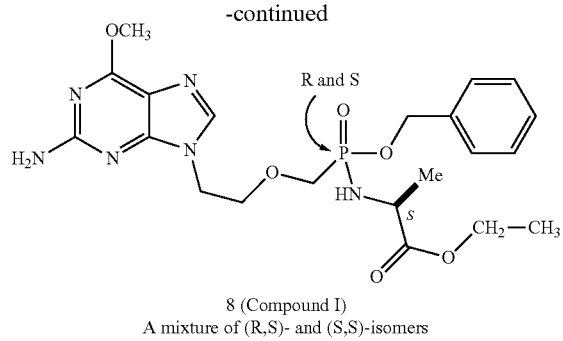

8 (Compound I)
A mixture of (R,S)- and (S,S)-isomers

Step 1: Preparation of diethyl-((2-(2-amino-6-chloro-9H-purin-9-yl)-ethoxy)-methyl)-phosphonate (3)

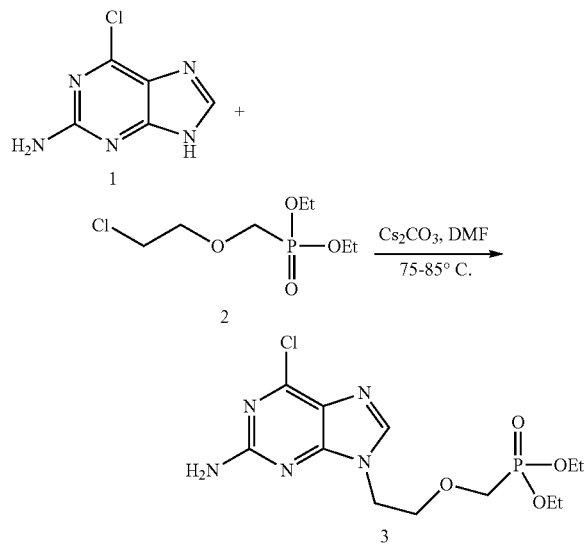

A dry reaction container was charged with 2-amino-6-chloropurine 1 (50 g, 0.296 mol, 1 equiv.), Cs$_2$CO$_3$ (96.37 g, 0.296 mol, 1 equiv.) and DMF (250 mL) under N$_2$ atmosphere at room temperature. To this at room temperature and under stirring was added diethyl 2-chloroethoxymethyl phosphonate 2 (74.85 g, 0.325 mol, 1.1 equiv.) in a drop-wise manner. The reaction was stirred at 40-50° C. for 0.5 to 1.5 hours, heated to 60-70° C. and stirred for 0.5-1.5 hours, and then stirred at 75 to 85° C. for 18-24 h. After bringing the reaction temperature to 20-30° C., the reaction mixture was filtered and the resulting cake was washed with DMF (100 mL×2). The combined filtrate was concentrated to a half volume below 70° C., diluted with n-heptane (250 mL) and again concentrated to a half volume below 75° C. The resulting solution was poured into DCM (1 L), stirred at 20 to 30° C. for 20-40 min., then aqueous 10% Na$_2$SO$_4$ solution (~100 mL) was added. The resulting bi-phasic solution was stirred for 20-40 minutes then filtered through diatomite and the wet cake was washed with DCM (~100 mL). From the filtrate, the aqueous phase was separated and the organic phase was again washed with aqueous 10% Na$_2$SO$_4$ solution (~100 mL). The combined aqueous phases upon washing (back extraction) with DCM (200-300 mL), the organic phases were combined and concentrated. The resulting crude product 3 was then purified by silica gel column chromatography using DCM to 1% MeOH in DCM. The fractions containing products were combined and the solvent was evaporated below 40° C. The solid product 3 was treated with the repeated dilution with MTBE and concentration (up to ⅓$^{rd}$ volume). The resulting slurry was then diluted with MTBE (400-500 mL) and agitated at 40-50° C. for 4-6 h and at 15-25° C. for 8-15 h. The suspension was filter and washed with MTBE and dried at 35-40° C. for 15-20 h to afford the desired product, diethyl-((2-(2-amino-6-chloro-9H-purin-9-yl)-ethoxy)-methyl)-phosphonate 3 in 43.4% (48.66 g) isolated yield with 91.8% purity by HPLC. $^1$H NMR (400 MHz, DMSO-d6), δ ppm: 8.08 (s, 1H), 6.91 (s, 2H), 4.24 (d, 2H, J=8 Hz), 3.92 (m, 4H), 3.86 (q, 4H, J=8 Hz), 1.14 (t, 6H, J=8 Hz). LCMS (m/z): 364.2 (MH+) and 366.2 (MH+).

Step 2: Preparation of ((2-(2-amino-6-chloro-9H-purin-9-yl)-ethoxy)-methyl)-phosphonic acid (4)

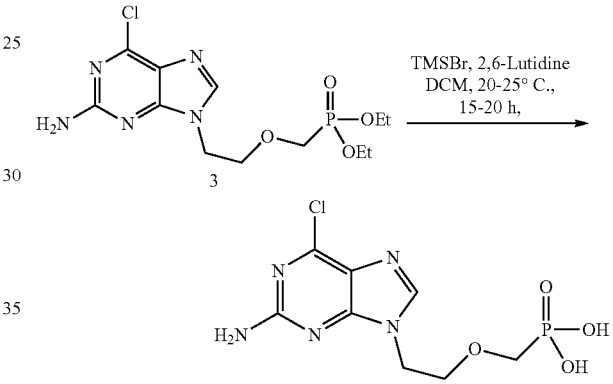

A dry reaction container containing DCM (1 L) under N$_2$ atmosphere was charged with diethyl-((2-(2-amino-6-chloro-9H-purin-9-yl)-ethoxy)-methyl)-phosphonate 3 (100 g, 0.275 mol) followed by 2,6-lutidine (147.33 g, 1.375 mol, 5 equiv.) and the temperature was adjusted to 0-5° C. To this was added TMSBr (167.47 g, 1.102 mol, 4.0 equiv.) in a drop-wise manner and stirred further for 0.5-1 h at 0-5° C. and 15-20 h at 20-25° C. After adjusting the reaction temperature at 0-5° C., a drop-wise addition of 1144 g aqueous 1N NaOH was performed. After maintaining the temperature at 20-30° C. for 1-2 h, the aqueous alkaline layer was separated and repeatedly washed with MTBE. An aqueous solution was acidified with a drop-wise addition of aqueous 2N HCl to pH=6-7 at 15-25° C. and charged with MeOH (10 Vol.). This resulting methanolic solution was further acidified with a drop-wise addition of aqueous 2N HCl to pH=3-4 at 35-45° C. After addition of seeds of product 4, the methanolic acidic solution was stirred at 35-45° C. for 3-5 h and acidified furthermore using a drop-wise addition of aqueous 2N HCl to pH=1.5-2.5 and stirred for 11-20 h at 15-20° C. The resulting solid was isolated by filtration, washing with MeOH (2×100 mL) and drying at 45-55° C. for 20-30 h to yield the desired product, ((2-(2-amino-6-chloro-9H-purin-9-yl)-ethoxy)-methyl)-phosphonic acid 4 in 96.5% (84.4 g) isolated yield with 99.8% purity by HPLC. $^1$H NMR (400 MHz, DMSO-d6), δ ppm: 8.1 (s, 1H), 6.92 (bs, 2H), 4.5-5.5 (bs, 2H), 4.22 (dd=t, 2H, J=8 Hz), 3.84 (t, 2H, J=8 Hz), 3.58 (t, 2H, J=8 Hz). LCMS (m/z): 308 (MH+) and 310 (MH+).

Step 3: Preparation of ((2-(2-amino-6-methoxy-9H-purin-9-yl)-ethoxy)-methyl)-phosphonic acid (5)

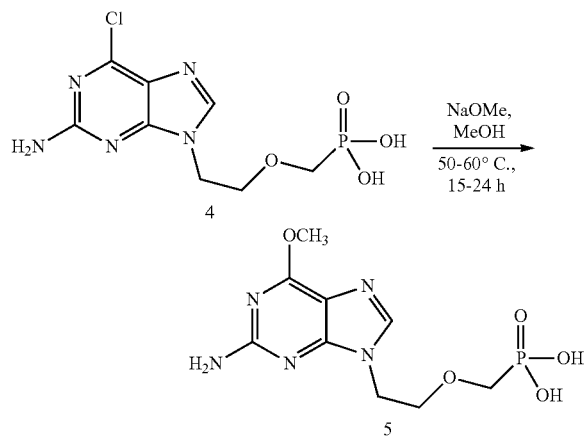

To a flask containing MeOH (350 mL) was charged ((2-(2-amino-6-chloro-9H-purin-9-yl)-ethoxy)-methyl)-phosphonic acid 4 (50 g, 0.162 mol) at 20-30° C., and stirred for 10-30 min. To this solution was added a 30 wt % NaOMe solution in MeOH (1.62 mol, 10 equiv.) in a drop-wise manner and then stirred at 50-60° C. for 15-24 h. The reaction was maintained at 20-30° C. for 20-40 min and then filtered. The filtrate was then acidified at 20-30° C. by a drop-wise addition of conc. HCl to adjust pH=6-7 and concentrated below 40° C. to one third of the volume. The temperature of the concentrated solution was raised to 35-45° C. and acidified to adjust the pH=3-4 by means of a drop-wise addition of conc. HCl. The resulting acidic solution was charged with the seeds of product 5, and stirred at 35-45° C. for 1.5-2.5 h. At this temperature, the addition of conc. HCl to adjust the pH=2-3 was done in a drop-wise rate, stirred for 3-5 h, cooled to -3° C. to 3° C. range and stirred for 8-15 h. The resulting solid was filtered, washed with MeOH (~100 mL) and n-heptane (~100 mL). The resulting cake was dried at 50-60° C. for 16-24 h under vacuum to afford the desired product, ((2-(2-amino-6-methoxy-9H-purin-9-yl)-ethoxy)-methyl)-phosphonic acid 5 in 89.3% (48.22 g) isolated yield with 99.5% purity by HPLC. $^1$H NMR (400 MHz, DMSO-d6), δ, ppm: 7.88 (s, 1H), 6.47 (bs, 4H), 4.18 (t, 2H, J=8 Hz), 3.96 (t, 2H, J=8 Hz), 3.60 (d, 2H, J=12 Hz). LCMS (m/z): 304.20 (MH+).

Step 4a: Preparation of a mixture of (R,S)- and (S,S)-ethyl-2-((((2-(2-amino-6-methoxy-9H-purin-9-yl)-ethoxy)-methyl)-(benzyloxy)-phosphoryl)-amino)-propionate (8)

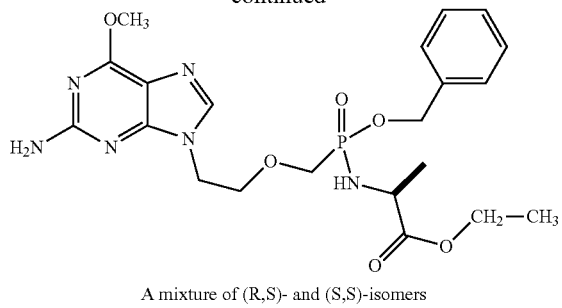

A mixture of (R,S)- and (S,S)-isomers

To a solution of ((2-(2-amino-6-methoxy-9H-purin-9-yl)-ethoxy)-methyl)-phosphonic acid 5 (40 g, 0.132 mol, 1 equiv.) in DCM (560 mL) at 20-30° C. under stirring was charged (S)-ethyl 2-aminopropionate hydrogen chloride salt 6 (20.19 g, 0.132 mol, 1 equiv.), benzyl alcohol 7 (71.28 g, 0.66 mol, 5 equiv.) and TEA (159.98 g, 1.58 mol, 12 equiv.), and the solution was stirred for 10-30 min. To this was added a solution prepared from Ph$_3$P (207.5 g, 0.792 mol, 6 equiv.) and 2,2'-dithiopyridine (Aldrithiol-2) (174.24 g, 0.792 mol, 6 equiv.) in DCM (320 mL) at 20-30° C. over 60 min. The resulting reaction mixture was stirred at 35-45° C. for 15-20 h and concentrated to remove ¾$^{th}$ of solvent under vacuum below 40° C. To the resulting residue were added MeOH (~120 mL), distilled water (~400 mL), toluene (~400 mL) and n-heptane (~400 mL) and stirred at 20-30° C. for 0.5-1 h. After allowing the reaction mixture to stand for 0.5 to 1 h at 20-30° C., the organic phase was separated and the aqueous phase was extracted few more times with a mixture 15 of toluene (~400 mL) and n-heptane (~400 ml) to remove maximum amount of remaining reagents and by-products. The remaining aqueous phase was then extracted with DCM (2×400 mL) and upon concentration of DCM under vacuum below 40° C., the crude product was purified by silica gel column chromatography with DCM to 2% MeOH in DCM as a mobile phase. The eluting fractions containing product were combined and solvent was removed under vacuum below 40° C. to give the desired product as a mixture of diastereoisomers namely, (R, S) and (S, S); (±) (2S)-ethyl-2-((((2-(2-amino-6-methoxy-9H-purin-9-yl)-ethoxy)-methyl)-(benzyloxy)-phosphoryl)-amino)-propionate 8 (Compound I) in 45.8% (29.74 g) isolated yield with 98.8% purity by HPLC. $^1$H NMR (400 MHz, DMSO-d6), δ, ppm: 7.85 (s, 1H), 7.34 (m, 5H), 6.44 (s, 2H), 5.36 (m, 1H), 4.90 (m, 2H), 4.17 (m, 2H), 4.07 (m, 2H), 3.95 (s, 3H), 3.82 (m, 5H), 1.18-1.24 (m, 6H). LCMS (m/z): 493.3 (MH+).

Step 4b: Preparation of a mixture of (R,R)- and (S,R)-ethyl-2-((((2-(2-amino-6-methoxy-9H-purin-9-yl)-ethoxy)-methyl)-(benzyloxy)-phosphoryl)-amino)-propionate

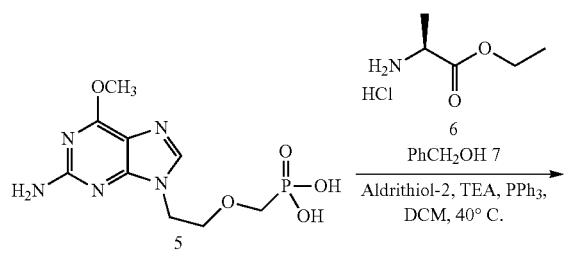

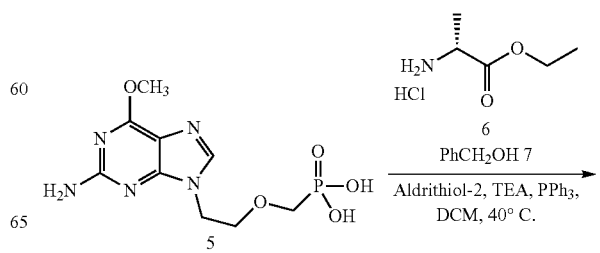

129

-continued

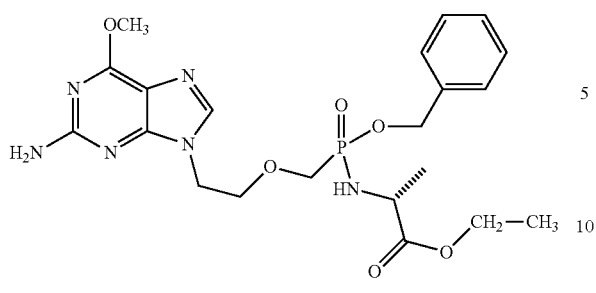

A mixture of (R,S)- and (S,S)-isomers

To synthesize the (R,R) and (S,R) mixture, the procedure of Step 4a can be performed substituting D-alanine ethyl ester ((R)-ethyl 2-aminopropionate hydrogen chloride salt) for the L-alanine ethyl ester ((S)-ethyl 2-aminopropionate hydrogen chloride salt).

Example 27: Preparation of (1)-Compound I Monofumarate ((±)-(2S)-Ethyl-2-((((2-(2-amino-6-methoxy-9H-purin-9-yl)-ethoxy)-methyl)-(benzyloxy)-phosphoryl)-amino)-propionate monofumarate) (9)

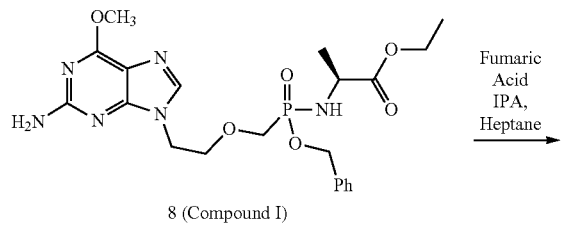

8 (Compound I)   Fumaric Acid IPA, Heptane →

130

-continued

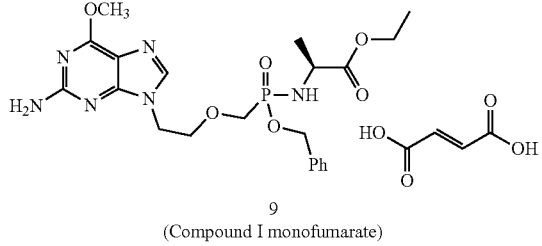

9
(Compound I monofumarate)

To a solution of (±)-(2S)-ethyl-2-((((2-(2-amino-6-methoxy-9H-purin-9-yl)-ethoxy)-methyl)-(benzyloxy)-phosphoryl)-amino)-propionate (Compound I) 8 (29.72 g, 0.06 mol, 1 equiv.) in IPA was added a solution of fumaric acid (7.66 mol, 1.1 equiv.) in IPA through a filter at 45-55° C. and stirring was continued for 1-2 h. The seeds of the compound 9 were added to the reaction mixture and stirring was continued for 1-2 h at 45-55° C. After allowing the reaction mixture to settle at 20-30° C. for 4-6 h, a drop-wise addition of n-heptane (~300 mL) was performed and stirring was continued for another 8-15 h at 20-30° C. and 0-5° C. for 8-15 h. The solid observed was filtered and the wet cake was washed with a mixture of IPA/n-heptane (⅓, v/v, ~50-60 mL). The solid cake was dried at 35-45° C. for 16-24 h under vacuum to afford the desired product, (±)-(2S)-ethyl-2-((((2-(2-amino-6-methoxy-9H-purin-9-yl)-ethoxy)-methyl)-(benzyloxy)-phosphoryl)-amino)-propionate monofumarate 9 (Compound I monofumarate) in 87.9% (32.74 g) isolated yield with 99.1% purity by HPLC. $^1$H NMR (DMSO-d6), δ, ppm: 1.14 (t, 3H, J=7.2 Hz), 1.22 (d, 3H, J=7.2 Hz), 3.82 (m, 2H; dd, 1H, J=4.0 Hz; bs, 2H), 3.95 (s, 3H), 4.06 (m, 2H), 4.17 (m, 2H), 4.87 (m, 2H), 5.38 (q, 1H, J=4 Hz), 6.44 (s, 2H), 6.64 (s, 2H), 7.33 (m, 5H), 7.82 (s, 1H), 13.18 (bs, 2H). LCMS (m/z): 493.20 (MH+).

Example 28: Chiral Separation of (R,S)- and (S,S)-Isomers of Compound I and Preparation of their Monofumarate Salts, Compound II and Compound III

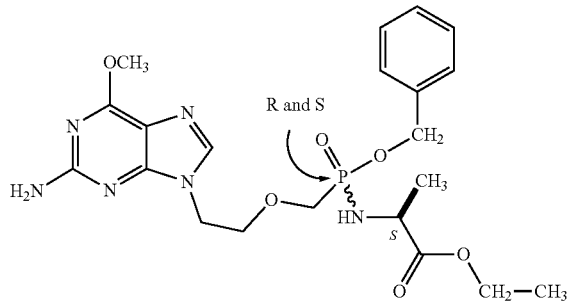

Compound I
Mixture of (R, S)- and (S, S)-
Diastereoisomers

Separation by
Chiral Column
Chromatography

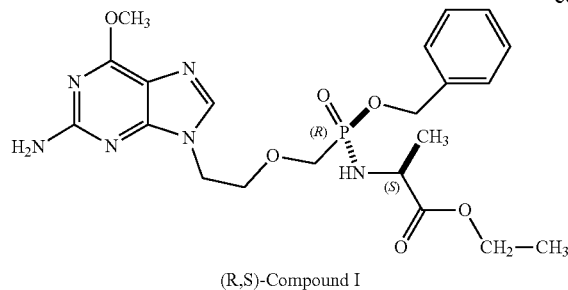

(R,S)-Compound I

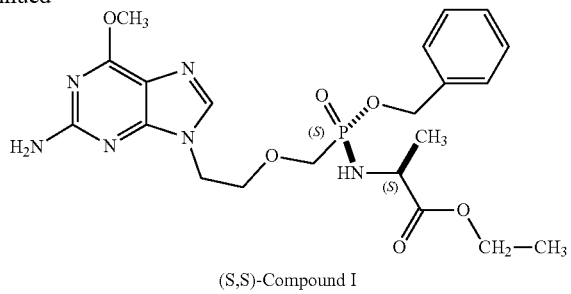

(S,S)-Compound I

Step 1a: Chiral Separation of (R,S)-ethyl-2-((((2-(2-amino-6-methoxy-9H-purin-9-yl)-ethoxy)-methyl)-(benzyloxy)-phosphoryl)-amino)-propionate and (S,S)-ethyl-2-((((2-(2-amino-6-methoxy-9H-purin-9-yl)-ethoxy)-methyl)-(benzyloxy)-phosphoryl)-amino)-propionate Compound I (a diastereoisomeric mixture of Isomers I and II) (22.50 g) was subjected to a chiral chromatography separation under SFC separation conditions as shown below to separate and obtain the 11.7 g of (R,S)-Isomer I (10) with 98.6% purity by HPLC and 9.1 g of (S,S)-Isomer II (11) with 95.6% purity by HPLC.

SFC Conditions:
Column: ChiralPak AD, 250×30 mm I.D., 10 μm;
Mobile phases: A: $CO_2$ and B: Ethanol (0.1% $NH_3H_2O$);
Gradient: B 45% isocratic;
Flow rate: 200 mL/min;
Wavelength: 310 nm;
Cycle time: ~6 min;
Back pressure: 100 bar;
Injection amount: ~1 g.

Characterization of (R,S)-ethyl-2-((((2-(2-amino-6-methoxy-9H-purin-9-yl)-ethoxy)-methyl)-(benzyloxy)-phosphoryl)-amino)-propionate (Isomer I) as a free base: Purity by HPLC: 98.6%; $^1$H NMR (DMSO-d6), δ, ppm: 7.82 (s, 1H), 7.30 (m, 5H), 6.38 (s, 2H), 5.30 (t, 1H), 4.83 (d, 2H), 4.18 (t, 2H), 4.05 (m, 2H), 3.95 (s, 3H), 3.84 (m, 2H), 3.60 (m, 5H), 1.20 (d, 3H), 1.15 (t, 3H); LCMS (m/z): 493 (MH+).

Characterization of (S,S)-ethyl-2-((((2-(2-amino-6-methoxy-9H-purin-9-yl)-ethoxy)-methyl)-(benzyloxy)-phosphoryl)-amino)-propionate (Isomer II) as a free base: Purity by HPLC: 95.6%; $^1$H NMR (DMSO-d6): δ ppm 7.82 (s, 1H), 7.35 (m, 5H), 6.45 (s, 2H), 5.30 (t, 1H), 4.80 (d, 2H), 4.18 (t, 2H), 4.05 (m, 2H), 3.95 (s, 3H), 3.80 (m, 3H), 3.70 (m, 2H), 1.20 (d, 3H), 1.15 (t, 3H); LCMS (m/z): 493 (MH+).

In certain nonlimiting embodiments, the stereoisomers are separated using HPLC or SFC with achiral or chiral stationary phases. Non limiting examples of chiral stationary phases which may be used include Chiralpak AD, Chiralpak AS, Chiralcel OG, and Chiralcel OJ.

In alternative non limiting embodiments, the individual isomers can be synthesized asymmetrically. For nonlimiting examples of asymmetric synthesis of phosphonamidates see Numan, A et al. "Asymmetric Synthesis of Stereogenic Phosphorus P(V) Centers Using Chiral Nucleophilic Catalysis", *Molecules* 2021, 26, 3661 and Ambrosi, A. et al. "Synthesis of Rovafovir Etalafenamide (Part III): Evolution of the Synthetic Process to the Phosphonamidate Fragment" 2021, *Org. Process Res. Dev.* 25, 5, 1247-1262.

Step 1b: Chiral Separation of (R,S)-ethyl-2-((((2-(2-amino-6-methoxy-9H-purin-9-yl)-ethoxy)-methyl)-(benzyloxy)-phosphoryl)-amino)-propionate and (S,S)-ethyl-2-((((2-(2-amino-6-methoxy-9H-purin-9-yl)-ethoxy)-methyl)-(benzyloxy)-phosphoryl)-amino)-propionate

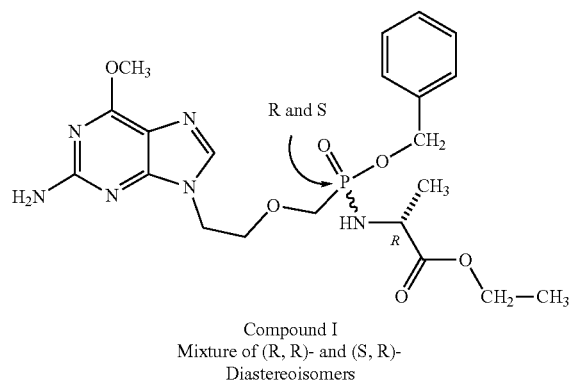

Compound I
Mixture of (R, R)- and (S, R)-Diastereoisomers

Separation by Chiral Column Chromatography | Step 1

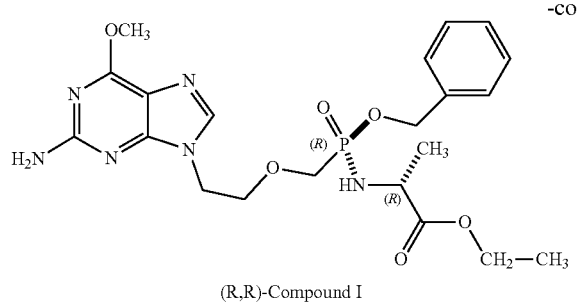

(R,R)-Compound I

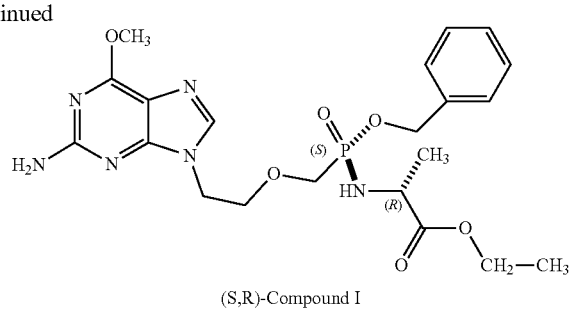

(S,R)-Compound I

Separation of (R,R)-ethyl-2-((((2-(2-amino-6-methoxy-9H-purin-9-yl)-ethoxy)-methyl)-(benzyloxy)-phosphoryl)-amino)-propionate and (S,R)-ethyl-2-((((2-(2-amino-6-methoxy-9H-purin-9-yl)-ethoxy)-methyl)-(benzyloxy)-phosphoryl)-amino)-propionate (synthesis described in Step 4b of Example 26) can be performed using same techniques for the (R,S) and (S,S) mixture as described above.

Step 2a: Preparation of (R,S)-ethyl-2-((((2-(2-amino-6-methoxy-9H-purin-9-yl)-ethoxy)-methyl)-(benzyloxy)-phosphoryl)-amino)-propionate monofumarate (Compound II)

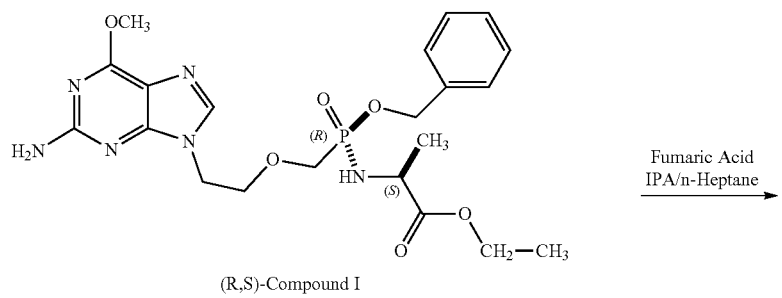

(R,S)-Compound I

Fumaric Acid
IPA/n-Heptane
→

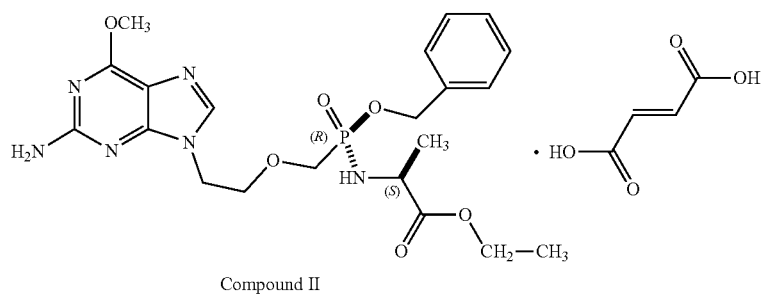

Compound II

To a solution of (R,S)-ethyl-2-((((2-(2-amino-6-methoxy-9H-purin-9-yl)-ethoxy)-methyl)-(benzyloxy)-phosphoryl)-amino)-propionate 10 (3 g, 6 mmol, 1 equiv.) in IPA was added a solution of fumaric acid (0.765 g, 6.6 mmol, 1.1 equiv.) in IPA through a filter at 45-55° C. and stirring was continued for 1-2. The seeds of the compound 12 were added to the reaction mixture and stirring was continued for 1-2 h at 45-55° C. After allowing the reaction mixture to settle at 20-30° C. for 4-6 h, a drop-wise addition of n-heptane (~30 mL) was performed and stirring was continued for another 8-15 h at 20-30° C. and 0-5° C. for 8-15 h. The solid observed was filtered and the wet cake was washed with a mixture of IPA/n-heptane (⅓, v/v, ~5 mL). The solid cake was dried at 35-45° C. for 16-24 h under vacuum to afford the desired product, (R,S)-ethyl-2-((((2-(2-amino-6-methoxy-9H-purin-9-yl)-ethoxy)-methyl)-(benzyloxy)-phosphoryl)-amino)-propionate monofumarate 12 (Isomer I monofumarate or Compound II) in 85% (3.1 g) isolated yield with 98.6% purity by HPLC. $^1$H NMR (DMSO-d6), δ, ppm: δ7.80 (s, 1H), 7.35 (m, 5H), 6.63 (s, 2H), 6.40 (s, 2H), 5.53 (t, 1H), 4.84 (d, 2H), 4.15 (t, 2H), 4.00 (m, 2H), 3.92 (s, 3H), 3.80 (m, 3H), 3.75 (m, 2H), 1.20 (d, 3H), 1.13 (t, 3H); Base (10): Fumaric acid ratio: 1:1.00 (by $^1$H NMR).

Step 2b: Preparation of (S,S)-ethyl-2-((((2-(2-amino-6-methoxy-9H-purin-9-yl)-ethoxy)-methyl)-(benzyloxy)-phosphoryl)-amino)-propionate monofumarate (13), also referred as Compound III

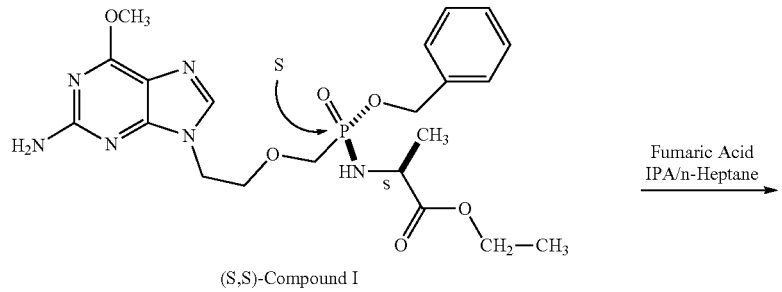

(S,S)-Compound I

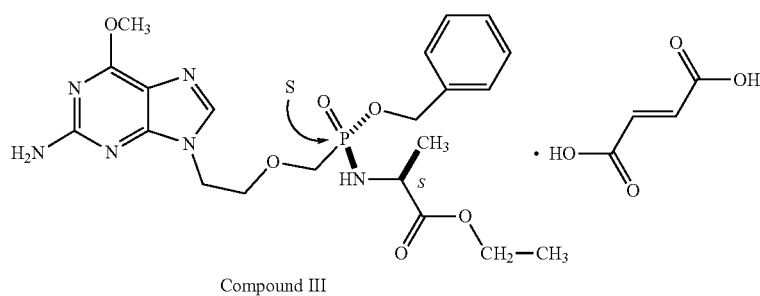

Compound III

To a solution of (R,S)-ethyl-2-((((2-(2-amino-6-methoxy-9H-purin-9-yl)-ethoxy)-methyl)-(benzyloxy)-phosphoryl)-amino)-propionate 11 (3 g, 6 mmol, 1 equiv.) in IPA was added a solution of fumaric acid (0.765 g, 6.6 mmol, 1.1 equiv.) in IPA through a filter at 45-55° C. and stirring was continued for 1-2. The seeds of the compound 13 were added to the reaction mixture and stirring was continued for 1-2 h at 45-55° C. After allowing the reaction mixture to settle at 20-30° C. for 4-6 h, a drop-wise addition of n-heptane (~30 mL) was performed and stirring was continued for another 8-15 h at 20-30° C. and 0-5° C. for 8-15 h. The solid observed was filtered and the wet cake was washed with a mixture of IPA/n-heptane (⅓, v/v, ~5 mL). The solid cake was dried at 35-45° C. for 16-24 h under vacuum to afford the desired product, (S,S)-ethyl-2-((((2-(2-amino-6-methoxy-9H-purin-9-yl)-ethoxy)-methyl)-(benzyloxy)- phosphoryl)-amino)-propionate monofumarate 13 (Isomer II monofumarate or Compound III) in 80% (2.9 g) isolated yield with 95.6% purity by HPLC. $^1$H NMR (DMSO-d6), δ, ppm: δ7.82 (s, 1H), 7.35 (m, 5H), 6.62 (s, 2H), 6.35 (s, 2H), 5.30 (t, 1H), 4.90 (d, 2H), 4.15 (t, 2H), 4.05 (m, 2H), 3.95 (s, 3H), 3.80 (m, 3H), 3.70 (m, 2H), 1.20 (d, 3H), 1.15 (t, 3H); Base (11): Fumaric acid ratio: 1:1.2 (by $^1$H NMR).

Step 2c: Preparation of (R,R)-ethyl-2-((((2-(2-amino-6-methoxy-9H-purin-9-yl)-ethoxy)-methyl)-(benzyloxy)-phosphoryl)-amino)-propionate monofumarate and (S,R)-ethyl-2-((((2-(2-amino-6-methoxy-9H-purin-9-yl)-ethoxy)-methyl)-(benzyloxy)-phosphoryl)-amino)-propionate monofumarate

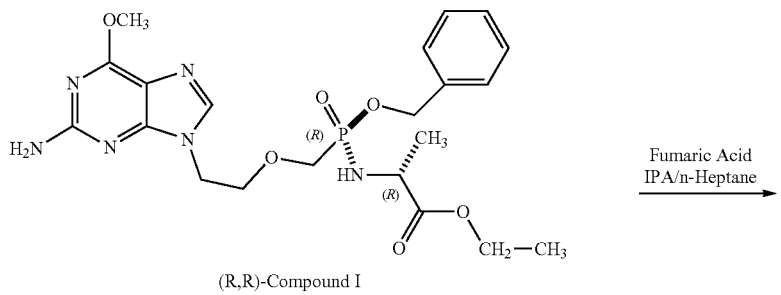

(R,R)-Compound I

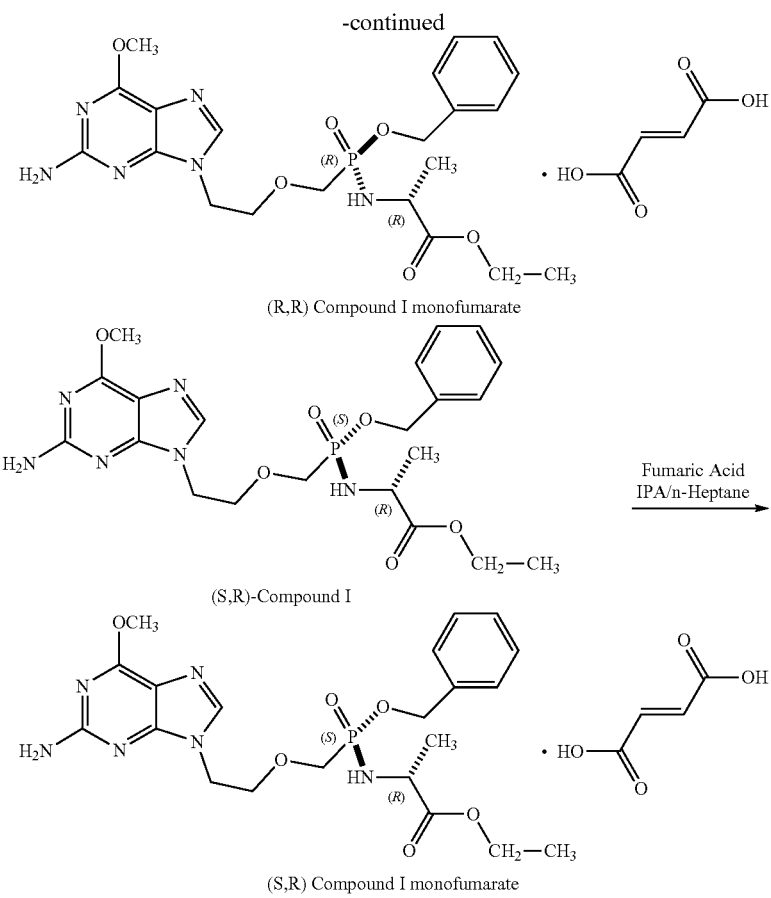

(R,R) Compound I monofumarate (S,R)-Compound I

Fumaric Acid
IPA/n-Heptane (S,R) Compound I monofumarate

Synthesis of (R,R)-ethyl-2-((((2-(2-amino-6-methoxy-9H-purin-9-yl)-ethoxy)-methyl)-(benzyloxy)-phosphoryl)-amino)-propionate monofumarate and (S,R)-ethyl-2-((((2-(2-amino-6-methoxy-9H-purin-9-yl)-ethoxy)-methyl)-(benzyloxy)-phosphoryl)-amino)-propionate monofumarate can be carried out as in Steps 2b and 2c for the (R,S) and (S,S) stereoisomers, substituting the starting materials in Steps 2b and 2c with the product of the chiral separation in Step 1b.

Example 29. Nonlimiting Examples of Preparation of Semisolid Formulations

A topical cream formulation can be prepared, for example, by emulsifying an oil phase and an aqueous phase along with an active pharmaceutical ingredient. In a nonlimiting embodiment, the oil phase of the cream was prepared by mixing light mineral oil, propylparaben and Tefose® 63. Next, the aqueous phase of the cream was prepared by mixing water, EDTA, methylparaben, and Carbopol® 974P. The oil and water phases were then emulsified. To the emulsified mixture was added the active pharmaceutical ingredient and propylene glycol. The mixture was pH adjusted and then filled into tubes.

A topical gel formulation can be prepared, for example, by mixing an aqueous gel carrier with an active pharmaceutical ingredient. In a non-limiting embodiment, the aqueous phase of the topical gel was prepared by mixing water, EDTA, methylparaben (or sorbic acid) and Carbopol® 974P. The active pharmaceutical ingredient and propylene glycol was added to this solution, mixed and pH adjusted, then filled into tubes.

In certain nonlimiting embodiments, from about 0.001% w/w to about 10% w/w active pharmaceutical ingredient is added to the semisolid formulation. For example, from about 0.0025% w/w to about 2.5% w/w, such as 0.003%, 0.01%, 0.03%, 0.1%, 0.3% or 1%.

Example 30. Preparation of Compound I Monofumarate Tablets

A nonlimiting example of the preparation of cervical tablets of Compound I monofumarate is provided below (See FIG. 119 for a flow diagram). Two or more of the excipients are combined, blended, and screened to make the excipient blend. Then the active pharmaceutical ingredient (such as Compound I monofumarate) is screened and added to a portion of the excipient blend. The resulting mixture is then blended and then more excipient blend is added. The mixture is thus gradually diluted with the excipient blend, with thorough mixing after each addition of excipient blend. Once the Excipient blend has been used up, the magnesium stearate is added and the mixture blended once more. The mixture is then compressed into tablets and packaged.

TABLE 57

Batch Formula for Compound I monofumarate Vaginal Tablets, 0.3 mg for batch size of 1.0 Kg

| Ingredient | % w/w | Qty/batch (g) |
| --- | --- | --- |
| Compound I monofumarate, Compound II or Compound III | 0.212 | 2.126 |

TABLE 57-continued

Batch Formula for Compound I monofumarate Vaginal Tablets, 0.3 mg for batch size of 1.0 Kg

| Ingredient | % w/w | Qty/batch (g) |
|---|---|---|
| Microcrystalline cellulose (PH 102) | 88.788 | 887.88 |
| Mannitol | 10.0 | 100.0 |
| Magnesium stearate | 1.0 | 10 |
| Total | 100.0 | 1000.0 |

Individual tablet weight: 175 mg

Compound I Monofumarate Vaginal Tablets, 0.3 mg

A non-limiting example of a process to prepare the vaginal tablet of Compound I monofumarate is provided below.

Dispensing
1. Weigh the materials as per the batch manufacturing formula and dispense in separate poly bags.

Screening
1. Sieve all excipients through a screen.

Blending of Active and Screening
1. Blend the screened excipients: microcrystalline cellulose and mannitol in a diffusion blender.
2. Take 49.5 grams of the excipients blend and add 2.12 grams of Compound I monofumarate
3. Blend the active and the excipients, and screen to remove chunks
4. To this blend add 148.5 grams of the excipients blend
5. Blend the active blend and the excipients and screen to remove chunks
6. To this blend add 247.5 grams of the excipients blend
7. Blend the active blend and the excipients and screen to remove chunks
8. To this blend add the remaining 495 grams of the excipients blend
9. Blend the active blend and the excipients and screen to remove chunks Final Blending
10. Add magnesium stearate to the diffusion blender and mix the contents.
11. Discharge and reconcile blend.

Compression
1. Compress the blend on a rotary tablet press using appropriate tooling (punches and die), to target weight. Check friability and disintegration at the beginning of the compression run, and check periodically for individual tablet weights, thickness and hardness.

Packaging
1. Package bulk tablets into double lined re-closable clear PE bags with desiccants between the bags and further into an aluminum foil pouch with desiccant and heat sealed.

Example 31. Illustrative Excipients for a Tablet Formulation

Tablet formulation are selected to display the properties of mucoadhesion and substantivity and include excipients that have solubilizing, erosion-generating (for disintegration), porosity (for water uptake) and viscosity enhancing (to keep the drug at the target site) properties. Examples of excipients that will cause rapid disintegration to cover the cervix, anal or vaginal areas include, but are not limited to mannitol, microcrystalline cellulose, lactose, sucrose, calcium phosphate, sodium phosphate, sodium bicarbonate, citric acid, maleic acid, adipic acid or fumaric acid. Examples of excipients that can enhance disintegration and coverage of the affected area include but are not limited to sodium starch glycollate, pregelatinized starch, crospovidone and croscarmellose sodium. Mucoadhesive excipients that are useful in the present invention include but are not limited to microcrystalline cellulose, polycarbophil, hydroxymethyl cellulose, hypromellose, hydroxypropyl cellulose, and PVP.

The table below lists combinations of excipients which have the desired properties for a tablet formulation. A tablet formulation comprises the active pharmaceutical ingredient, microcrystalline cellulose and may contain mannitol. In certain non-limiting embodiments, the tablet formulation comprises one or more excipients selected from the rapid disintegrant category (left column of Table 58). In certain non-limiting embodiments, the tablet formulation comprises one or more excipients selected from the disintegration enhancement category (middle column of Table 58). In certain non-limiting embodiments, the tablet formulation comprises one or more excipients selected from the mucoadhesive excipient category (right column of Table 58).

TABLE 58

| Excipients for Tablets | | |
|---|---|---|
| Rapidly disintegrating and covering target tissue with these excipients | To Enhance Disintegration and coverage of target tissue | Mucoadhesive polymers |
| Mannitol and/or Microcrystalline cellulose (0 to 99.9%) | | Microcrystalline cellulose (0.1% to 99.9%) |
| Additional Excipients | | |
| Lactose (0 to 70%) | Sodium starch glycollate (0 to 20%) | Polycarbophil (0 to 50%) |
| Sucrose (0 to 70%) | Pregelatinised starch (0 to 20%) | Polyethylene Oxide (0 to 50%) |
| Calcium Phosphate (0 to 70%) | Crospovidone (0 to 20%) | Hydroxyethylmethyl cellulose (0 to 50%) |
| Sodium Biocarbonate (0 to 50%) | Croscarmellose Na (0 to 20%) | Hydroxyethylcellulose (0 to 50%) |

TABLE 58-continued

Excipients for Tablets

| Rapidly disintegrating and covering target tissue with these excipients | To Enhance Disintegration and coverage of target tissue | Mucoadhesive polymers |
|---|---|---|
| Citric acid (0 to 50%) | | Hypromellose (0 to 50%) |
| Maleic acid (0 to 50%) | | Hydroxyproply cellulose (0 to 50%) |
| Adipic acid (0 to 50%) | | PVP (0 to 30%) |
| Fumaric acid (0 to 50%) | | |

(Percentages are given in a weight/weight %)

Example 32. Illustrative Excipients for a Reconstitution Powder or Dry Powder Formulation A reconstitution powder or dry powder formulation may improve the shelf stability of a pharmaceutical agent or formulation. In certain nonlimiting embodiments, the dry powder formulation may be mixed with saline, propylene glycol or other aqueous carrier shortly before it is administered, minimizing the time for degradation. In certain nonlimiting embodiments, the dry powder formulation is mixed with an oil, cream, or other nonaqueous carrier shortly before it is administered.

In certain embodiments, the reconstitution powder or dry powder formulation rapidly covers the infected or diseased tissue in the cervix, vulva, vagina, perianal region, penis or anus. Excipients which enhance the rapid coverage of the cervix, vulva, vagina, perianal region, penis or anus include but are not limited to mannitol, lactose, sucrose, calcium phosphate, and microcrystalline cellulose. In certain embodiments the excipient for rapid coverage of the cervix, vulva, vagina, perianal region, penis or anus is mannitol.

In certain embodiments, the reconstitution powder or dry powder formulation has good coverage of the cervix, vulva, vagina, perianal region, penis or anus. Nonlimiting examples of excipients which enhance the coverage of the cervix, vulva, vagina, perianal region, penis or anus include sodium starch glycollate, pregelatinized starch, crospovidone, and croscarmellose sodium.

In certain embodiments the reconstitution powder or dry powder formulation contains mucoadhesive properties once it has been reconstituted. This prevents smearing of the dosage form or otherwise exposing healthy tissues to the active pharmaceutical ingredient. Excipients which improve the mucoadhesive properties of the reconstituted powder or dry powder formulation include but are not limited to xanthan gum, polycarbophil, polyethylene oxide, hydroxyethylmethyl cellulose, hydroxyethyl cellulose, Hypromellose, hydroxypropyl cellulose, PVP, and microcrystalline cellulose. In certain embodiments, the excipient which improves mucoadhesion is xanthan gum.

The table below lists combinations of excipients which have the desired properties for a reconstitution powder or dry powder formulation. A dry powder or reconstitution powder formulation comprises the active pharmaceutical ingredient and may contain mannitol and/or xanthan gum. In certain non-limiting embodiments, the dry powder or reconstitution powder formulation comprises one or more excipients selected from the rapid coverage category (left column of Table 59). In certain non-limiting embodiments, the dry powder or reconstitution powder formulation comprises one or more excipients selected from the coverage enhancement category (middle column of Table 59). In certain non-limiting embodiments, the dry powder or reconstitution powder formulation comprises one or more excipients selected from the mucoadhesive excipient category (right column of Table 58).

TABLE 59

Excipients for Reconstitution Powders of Dry Powder Dosage Forms

| Rapidly covering target tissue with these excipients | To Enhance coverage of target tissue | Mucoadhesive polymers |
|---|---|---|
| Mannitol (0 to 70%) | | Xanthan Gum (0 to 50%) |
| | Alternative excipients | |
| Lactose (0 to 70%) | Sodium starch glycollate (0 to 20%) | Polycarbophil (0 to 50%) |
| Sucrose (0 to 70%) | Pregelatinized starch (0 to 20%) | Polyethylene Oxide (0 to 50%) |
| Calcium Phosphate (0 to 70%) | Crospovidone (0 to 20%) | Hydroxyethylmethyl cellulose (0 to 50%) |
| Microcrystalline cellulose (0 to 70%) | Croscarmellose Na (0 to 20%) | Hydroxyethylcellulose (0 to 50%) |
| | | Hypromellose (0 to 50%) |
| | | Hydroxypropyl cellulose (0 to 50%) |
| | | PVP (0 to 50%) |
| | | Microcrystalline Cellulose (0 to 50%) |

(Percentages are given in a weight/weight %)

Example 33. Illustrative Excipients for a Semisolid Formulation

Semisolid formulations are selected to display the properties of mucoadhesion and assist in the drug penetration into the tissue. Semisolid formulations may include excipients that have solubilizing, lipophilic (to assist in solubilizing lipophilic compound), penetration enhancing (for higher activity) and mucoadhesive (to keep the drug at the target site) properties.

In certain embodiments, the semisolid formulation is mucoadhesive. Excipients which contribute to the mucoadhesive properties include but are not limited to carbomer, polyethylene glycol, crospovidone, polycarbophil, Hypromellose, and hyroxyethyl cellulose.

In certain embodiments, the semisolid formulation enhances the penetration and/or solubility of the active pharmaceutical ingredient. Excipients which enhance the penetration and/or solubility of the active pharmaceutical ingredient include but are not limited to polyoxyl 6 stearate type I, ethylene glycol stearate, polyoxyl 32 stearate type I, and propylene glycol.

The table below lists combinations of excipients which have the desired properties for a semisolid formulation. A semisolid formulation comprises the active pharmaceutical ingredient and one or more excipients from each column of Table 60. In certain non-limiting embodiments, the semisolid formulation comprises one or more excipients selected from the mucoadhesive polymer category (left column of Table 60). In certain non-limiting embodiments, the tablet formulation comprises one or more excipients selected from the solubility and penetration enhancers category (second column of Table 60). In certain non-limiting embodiments, the semisolid formulation comprises one or more excipients selected from the lipophilic solubilizer category (third column of Table 60). In certain non-limiting embodiments, the semisolid formulation comprises one or more excipients selected from the penetration enhancer category (right column of Table 60).

TABLE 60

| | Excipients for semisolid dosage forms | | |
| --- | --- | --- | --- |
| Mucoadhesive polymer | Solubility and penetration enhancers | Lipophilic solubilizers | Penetration Enhancer |
| Carbomer (0 to 10%) | Mixture of Polyoxyl 6 Stearate Type I, Ethylene Glycol Stearates and Polyoxyl 32 Stearate Type I (0 to 15%) | Light Mineral Oil (0 to 20%) | Propylene Glycol (0 to 20%) |
| Polyethylene Glycol (0 to 10%) | Cetyl alcohol (0 to 20%) | Mineral oil (0 to 20%) | Transcutol P (0 to 20%) |
| Crospovidone (0 to 10%) | Stearyl alcohol (0 to 25%) | White Wax (0 to 99.9%) | Oleic acid (0 to 20%) |
| Polycarbophil (0 to 10%) | Polysorbate 80 (0 to 25%) | Silicone Fluid (0 to 20%) | Isopropyl myristate (0 to 20%) |
| Hypromellose (0 to 10%) | Sodium Lauryl Sulphate (0 to 25%) | | Propylene Glycol dicaprylate/dicaprate (0 to 20%) |
| Hydroxyethyl cellulose (0 to 10%) | Mono and diglycerides (0 to 25%) | | Glyceryl monooleate (0 to 20%) |
| | Sorbitan Monostearate (0 to 25%) | | propylene glycol monocaprylate (0 to 20%) |
| | Glyceryl isostearate (0 to 25%) | | PEG-8 Bees wax (0 to 20%) |
| | Polyoxyl 15 hydroxystearate (0 to 25%) | | Cetyl alcohol (0 to 20%) |
| | Polyoxyl 40 hydrogenated castor oil (0 to 25%) | | Stearic acid (0 to 20%) |
| | Octyl dodecanol (0 to 25%) | | Cetyl Palmitate (0 to 20%) |
| | Soybean Lecithin | | Cetostearyl Alcohol (0 to 20%) |

(Percentages are given in a weight/weight %)

Example 34. Illustrative Excipients for a Semisolid Formulation

Pessary and film forming formulations are selected to be solid at room temperature but soften to release the active pharmaceutical ingredient at body temperature. This allows for easy handling and storage of the formulation as well as achieving desired tissue coverage at the cervix, vulva, vagina, perianal region, penis or anus. In a non-limiting embodiment of a film forming formulation, one or more excipients from the left column of Table 61 provide the desired properties. In a non-limiting embodiment of a pessary formulation, one or more excipients from the right column of Table 61 provide the desired properties.

TABLE 61

Excipients for films and pessaries

| Films (Film Formers) | Pessaries (Vaginal Suppositories) |
| --- | --- |
| Hypromellose (0 to 99.9%) | Hard Fat (e.g., of brands Ovucire, Witepsol, Supposi-Base) (0 to 99.9%) |
| Polyethylene Glycol (0 to 99.9%) | PEG (0 to 99.9%) |
| Polymethacrylates (0 to 99.9%) | Macrogols (0 to 99.9%) |
| Microcrystalline Cellulose (0 to 99.9%) | Cocoa butter (0 to 99.9%) |
| Guar Gum (0 to 99.9%) | Glycerol (0 to 60%) |
| Xanthan Gum (0 to 99.9%) | |
| Polyvinylpyrrolidone (0 to 99.9%) | |

(Percentages are given in a weight/weight %)

Example 35. Illustrative Tablet Formulations

In certain non-limiting embodiments, the formulation for a tablet dosage form comprises the ingredients in Table 62. In certain non-limiting embodiments, the formulation for a tablet dosage form comprises the ingredients in Table 63. An illustrative process for combining these ingredients into a tablet dosage form can be found in Example 29.

TABLE 62

Example Tablet Formulation

| Material | Amount in tablet |
| --- | --- |
| Active pharmaceutical ingredient | 0.05 mg to 5 mg (for example 0.1 mg to 2.5 mg, such as 0.1 mg, 0.3 mg or 1.0 mg) |
| Microcrystalline cellulose | 250 mg |
| Crospovidone | 20 mg |
| Magnesium Stearate | 5 mg |
| Silicon dioxide | 5 mg |
| Polyethylene oxide | 5 mg |
| Mannitol | 100 mg |

TABLE 63

Example Tablet Formulation

| Material | Amount in tablet |
| --- | --- |
| Active pharmaceutical ingredient | 0.05 mg to 5 mg (for example 0.1 mg to 2.5 mg, such as 0.1 mg, 0.3 mg or 1.0 mg) |
| Microcrystalline cellulose | 155 mg |
| Magnesium Stearate | 1.75 mg |
| Mannitol | 17.5 mg |

Example 36. Illustrative Semisolid Formulations

In certain non-limiting embodiments, the formulation for a cream semisolid dosage form comprises the ingredients in Table 64. In certain non-limiting embodiments, the formulation for a gel semisolid dosage form comprises the ingredients in Table 65. An illustrative process for combining these ingredients into a cream or gel semisolid dosage form can be found in Example 27.

TABLE 64

Example semisolid formulation (cream)

| Material | Amount per Gram |
| --- | --- |
| Active pharmaceutical ingredient | 0.025 mg to 25 mg (for example 0.03 mg to 10 mg, such as 0.03, 0.1 mg, 0.3 mg, 1.0 mg, 3 mg or 10 mg) |
| Carbomer | 15 mg |
| Propylene glycol | 50 mg |
| Sorbic acid | 10 mg |
| EDTA | 5 mg |
| Water | 920 mg |

TABLE 65

Example semisolid formulation (gel)

| Material | Amount per Gram |
| --- | --- |
| Active pharmaceutical ingredient | 0.025 mg to 25 mg (for example 0.03 mg to 10 mg, such as 0.03, 0.1 mg, 0.3 mg, 1.0 mg, 3 mg or 10 mg) |
| Carbomer | 20 mg |
| Mineral oil | 70 mg |
| Mixture of Polyoxyl 6 Stearate Type I, Ethylene Glycol Stearates and Polyoxyl 32 Stearate Type I | 80 mg |
| Parabens | 5 mg |
| Propylene glycol | 60 mg |
| EDTA | 5 mg |
| Water | 760 mg |

Example 37. Illustrative Film Forming Formulation

A film dosage form can be prepared by solvent casting or hot melt extrusion. To prepare the film dosage form, for example, the active pharmaceutical ingredient is dissolved into a solution of the excipients and water. This solution is then optionally de-aerated and cast into a thin film and dried in an oven. The film dosage form can also be prepared by hot melt extrusion. In certain embodiments, the active pharmaceutical ingredient is mixed with the excipient(s) in a hopper. The components are then mixed, grinded and kneaded into a homogeneous mixture. The mixture is heated until it flows and is extruded through a die onto a roller where it is cooled. In certain embodiments, the ingredients for a film dosage form can be found in Table 66.

TABLE 66

Example formulation of a film

| Film Excipients | Amount per 1 Gram of Film |
| --- | --- |
| Active pharmaceutical ingredient | 0.025 mg to 25 mg (for example 0.03 mg to 10 mg, such as 0.03, 0.1 mg, 0.3 mg, 1.0 mg, 3 mg or 10 mg) |
| Hypromellose | Up to 999.9 mg |

Example 38. Illustrative Dry Powder or Reconstitution Powder Formulation

In certain non-limiting embodiments, the dry powder or reconstitution powder formulation comprises the ingredients listed in Table 67. These ingredients can be mixed in a suitable apparatus, for example a V blender, and then portioned into sterile vials for reconstitution.

TABLE 67

Example formulation of a dry powder or powder for reconstitution

| Dry Powder Excipients | Amount per Gram |
| --- | --- |
| Active pharmaceutical ingredient | 0.025 mg to 25 mg (for example 0.03 mg to 10 mg, such as 0.03, 0.1 mg, 0.3 mg, 1.0 mg, 3 mg or 10 mg) |
| Xanthan Gum | 15 mg |
| Mannitol | 19.8 mg |
| Silicon dioxide | 5 mg |
| Sodium benzoate | 0.5 mg |

Example 39. Illustrative Pessary Formulation

In certain non-limiting embodiments, the pessary formulation comprises the ingredients listed in Table 68 or Table 69. The pessary dosage form can be prepared, for example, by mixing the active pharmaceutical ingredient with the excipient. In one non-limiting embodiment, the excipient is heated in a mixing apparatus while stirring until it has softened or melted, then the active pharmaceutical ingredient is added portionwise. The temperature, stirring speed, and rate of addition are controlled to ensure an even distribution of active pharmaceutical ingredient. The mixture is then mixed until homogeneous and placed into pessary or suppository molds to solidify.

TABLE 68

Example formulation for a pessary

| Pessary Excipients | Amount per Gram |
| --- | --- |
| Active pharmaceutical ingredient | 0.025 mg to 25 mg (for example 0.03 mg to 10 mg, such as 0.03, 0.1 mg, 0.3 mg, 1.0 mg, 3 mg or 10 mg) |
| Witepsol H 15 | Up to 999.9 mg |

TABLE 69

Example formulation for a pessary

| Pessary Excipients | Amount per Gram |
| --- | --- |
| Active pharmaceutical ingredient | 0.025 mg to 25 mg (for example 0.03 mg to 10 mg, such as 0.03, 0.1 mg, 0.3 mg, 1.0 mg, 3 mg or 10 mg) |
| Ovucire WL 3264 | Up to 999.9 mg |

Example 40. In-Vitro Cytotoxicity Testing

Compounds:

Three compounds (Compound I, Compound II and Compound III) were solubilized at 40 mM in DMSO and stored at −20° C. The test compounds were evaluated using a high test concentration of 50 µM. Serial half-logarithmic dilutions were performed for the in vitro cytotoxicity assays. Tamoxifen citrate was purchased from Sigma-Aldrich (St. Louis, MO). Tamoxifen citrate was solubilized in DMSO at 40 mM and used as a positive control compound at a high test concentration of 100 µM for the cytotoxicity assays.

In Vitro Cytotoxicity Evaluations:

Cells listed in Table 70 were enumerated by Trypan Blue Dye exclusion method and seeded in the interior wells of a 96 well flat bottom microtiter plate at 100 µL/well. Proliferating cells were incubated overnight at 37° C./5% $CO_2$ to allow the cells to adhere to the plates at approximately 70% confluency. Tissue culture medium was removed and replaced with 100 µL/well of fresh medium. One-hundred microliters (100 µL) of each compound at six concentrations was transferred to the 96-well plate containing the cells in triplicate. Table 70 lists the cell line, type of cell, source of cell stock, base tissue culture medium supplemented with 10% fetal bovine serum, 2 mM L-glutamine, 100 U/mL penicillin and 100 µg/mL streptomycin, and microtiter plate seeding density.

TABLE 70

| Cell Line | Cell Type | Cell Source | Cell Culture | Seeding Density |
| --- | --- | --- | --- | --- |
| Hs27 | Normal human foreskin fibroblasts | ATCC CRL1634 | DMEM | $1 \times 10^4$ |
| HeLa | HPV18+ cervical epithelial adenocarcinoma | ATCC CCL2 | DMEM | $1 \times 10^4$ |
| C33A | HPV− cervical carcinoma | ATCC HTB31 | DMEM | $2 \times 10^4$ |
| HEK293 | Human embryonic kidney | ATCC CRL1573 | DMEM | $1.5 \times 10^4$ |

Cytotoxicity XTT:

Following incubation at 37° C. in a 5% $CO_2$ incubator for five days, the test plates were stained with the tetrazolium dye XTT (2,3-bis(2-methoxy-4-nitro-5-sulfophenyl)-5-[(phenylamino)carbonyl]-2H-tetrazolium hydroxide). XTT-tetrazolium was metabolized by the mitochondrial enzymes of metabolically active cells to a soluble formazan product. XTT solution was prepared daily as a stock of 1 mg/ml in RPMI1640. Phenazine methosulfate (PMS) solution was prepared at 0.15 mg/ml in PBS and stored in the dark at −20° C. XTT/PMS stock was prepared immediately before use by adding 40 μL of PMS per ml of XTT solution. Fifty microliters of XTT/PMS were added to each well of the plate and the plate was reincubated for 4 hours at 37° C. Plates were sealed with adhesive plate sealers and shaken gently or inverted several times to mix the soluble formazan product and the plate was read spectrophotometrically at 450/650 nm with a Molecular Devices Vmax plate reader.

Data Analysis and Evaluation:

Microsoft Excel 2010 was used to analyze and graph the raw data. $CC_{50}$ (50% reduction in cell viability) values are tabulated and provided. Raw data for cytotoxicity with a graphic representation of the data are provided in a printout summarizing the compound effect on cell viability.

In Vitro Cytotoxicity Evaluations:

Compounds I, II, and III were evaluated for cytotoxicity to proliferating Hs27, HeLa, C33A and HEK293 cells by measuring cell viability using XTI tetrazolium dye following five days in culture (Table 71). The $CC_{50}$ values calculated from these assays are summarized in the below tables.

Tamoxifen citrate was evaluated in parallel as a control compound. The $CC_{50}$ value for tamoxifen citrate in proliferating C33A, HeLa, Hs27, and HEK293 cells was 17.2, 19.9, 21.2 and 21.3 μM, respectively. Compound I and its two isomers were similarly cytotoxic when evaluated in parallel against each of the four cell lines. $CC_{50}$ values for the three test compounds ranged from approximately 0.1 to 0.28 μM in C33A cells. In HeLa cells, $CC_{50}$ values for the three test compounds ranged from 15.1 to 18.6 μM. The $CC_{50}$ values for the three test compounds ranged from approximately 7.62 to 23.2 μM in Hs27 cells. In HEK293 cells, $CC_{50}$ values for the three test compounds was approximately 0.1 μM.

TABLE 71

In vitro cytotoxicity

| Compound | C33A $CC_{50}$ (μM) | HeLa $CC_{50}$ (μM) | Hs27 $CC_{50}$ (μM) | HEK293 $CC_{50}$ (μM) |
|---|---|---|---|---|
| AB12280 | 0.28 | 18.6 | 22.9 | <0.16 |
| AB12280 Isomer 1 | 0.20 | 15.1 | 23.2 | <0.16 |
| AB12280 Isomer 2 | <0.16 | 16.9 | 7.62 | <0.16 |
| Tamoxifen | 17.2 | 19.9 | 21.2 | 21.3 |

Example 41. Ex Vivo Permeation and Penetration of Antiviral Drugs Across Porcine Vaginal Tissue Preparation of Porcine Vaginal Tissue Freshly harvested porcine vaginal tissue was procured from local slaughterhouse in an ice box. The vaginal tissue was cut open to expose the mucosal surface and tissue was cleaned by gentle flow of PBS pH 7.4. The porcine vaginal tissue was cut into circular portions (approximately 2 cm²) with help of a telemetric punch.

Mounting Porcine Vaginal Tissue on Franz Diffusion Cells

The circular portion of tissue was sandwiched between two chambers of a Franz diffusion cell with an active diffusion area of 1 cm², and the mucosal layer was exposed to the donor chambers. The resistance across porcine vaginal tissue was measured using a wave form generator to ensure the integrity of the tissue segment used for the permeation study. Porcine vaginal tissue with resistance of ≥3 KΩ·cm² was used for study. The receiver chamber was filled with 8 ml of 5% solutol PBS 7.4 pH, which was stirred at 600 rpm with a 3 mm magnetic stir bar and the temperature was maintained at 37° C. with a circulating water bath.

Loading of Formulation in the Donor Chamber

The ~200 mg of gel was filled into tared 1 mL syringe and gel was dispensed to donor chamber. The gel was spread on to mucosal surface with pre weighed applicator. After loading and spreading of the gel onto surface of mucosal surface, the weight of 1 mL syringe and applicator was noted to determine the exact amount of gel loaded into donor chamber.

Permeation and Penetration Study

Time course (2 h, 4 h and 8 h) porcine vaginal permeation studies were performed. After loading gel, 500 μL samples were withdrawn from the receiver compartment at different time intervals and each time an equal volume of fresh receiver media was used to replace withdrawn samples. The sample withdrawn at each time interval were stored immediately in −20° C. until analysis. After 2, 4 and 8 h, the formulation was removed from the donor chamber with help of syringe and cleaned with cotton swab. The tissue was removed and washed gently with wash solution (50% methanol in water) 5 times and alternatively cleaning with cotton swab.

TABLE 72

Time course IVPT study design

| Study | Receptor fluid sampling time points | Study Period |
|---|---|---|
| 2 h IVPT | 0 and 2 h | 2 h |
| 4 h IVPT | 0, 2 and 4 h | 4 h |
| 8 h IVPT | 0, 2, 4, 6 and 8 h | 8 h |

Mincing the Porcine Vaginal Tissue (Active Diffusion Area) after IVPT

An 8 mm punch of active diffusion area of washed porcine vaginal tissue was removed, weighed and transferred into a tube. This tube was immediately placed into dry ice for ~15 min. After specified time, tissue was removed and placed in precooled dish. The tissue was minced into smaller pieces on a dish with a precooled surgical blade. The minced tissue was transferred to sample tubes and dish was rinsed with 1 ml of 5% solutol in PBS 7.4 pH and transferred to same tissue sample tube. These tubes were stored in −70° C. until analysis.

Preparation of Receptor Fluid for Analysis

The samples stored at −20° C. was removed and thawed at room temperature for 30 min. The drug from receptor fluid was centrifuged at 13000 rpm for 5 min and to 200 μL of supernatant equal volume of extraction solvent was added. These samples were centrifuged at 13000 rpm for 5 min and supernatant was transferred into vials for analysis.

Extraction of Drug from Porcine Vaginal Tissue

The minced tissue samples stored at −70° C. were removed and thawed at room temperature for ~90 min. The samples were kept for shaking at room temperature for 4 h in BioShaker. After 4 h, samples were centrifuged at 13000 rpm for 5 min. To 100 µL of supernatant, 400 µL of extraction solvent was added and vortexed for 2 min. These samples were centrifuged at 13000 rpm for 5 min and supernatant was transferred into vials for analysis.

All publications and patent applications cited in this specification are herein incorporated by reference as if each individual publication or patent application were specifically and individually indicated to be incorporated by referenced.

Although the foregoing invention has been described in some detail by way of illustration and example for the purposes of clarity of understanding, it will be readily apparent to one of ordinary skill in the art in light of the teaching of this invention that certain changes and modifications may be made thereto without departing from the spirit or scope of the invention as defined in the embodiments and/or claims.

We claim:

1. A compound salt of the formula:

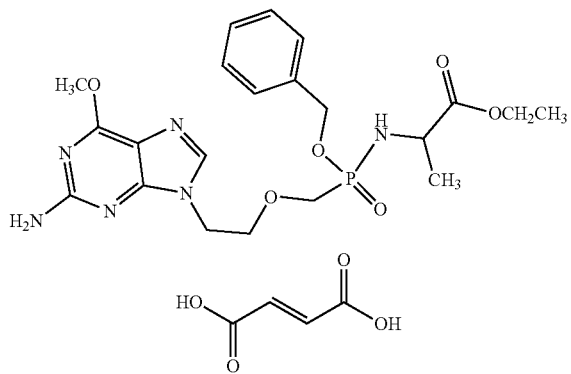

wherein the compound salt is isomerically enriched by greater than 50% by weight with R chirality at the phosphorus atom.

2. A compound salt of claim 1, of the formula:

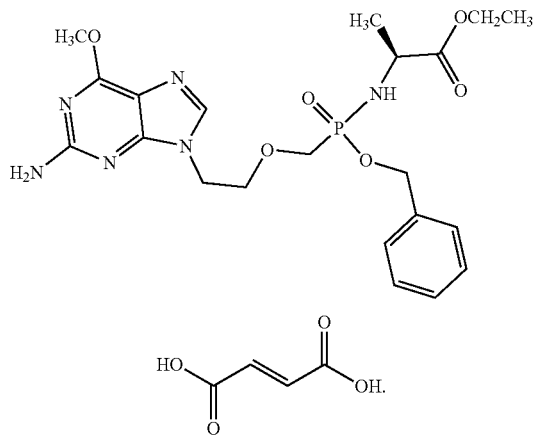

3. A compound salt of the formula:

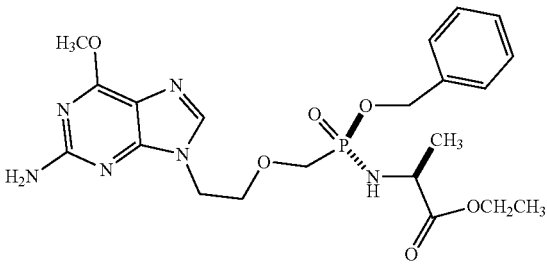

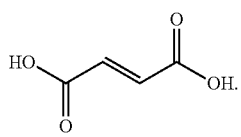

4. The compound salt of claim 1, wherein the compound salt is crystalline.

5. The compound salt of claim 2, wherein the compound salt is crystalline.

6. The compound salt of claim 3, wherein the compound salt is crystalline.

7. A compound salt of the formula:

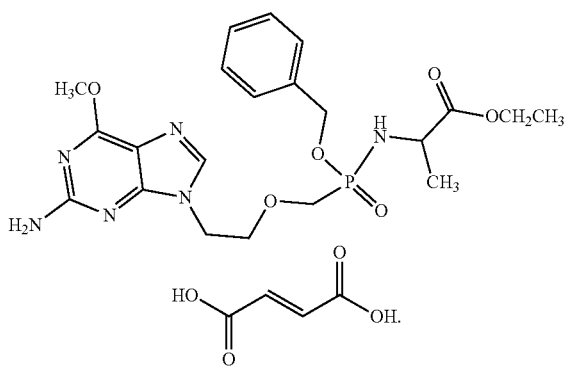

8. The compound salt of claim 7, wherein the compound salt is crystalline.

9. A compound salt of the formula:

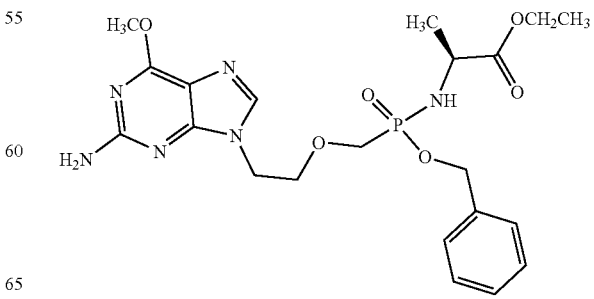

-continued
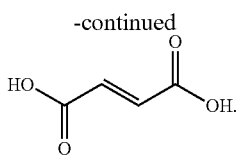
10. The compound salt of claim 9, wherein the compound salt is crystalline.
* * * * *